(12) United States Patent
Haber et al.

(10) Patent No.: US 12,227,578 B2
(45) Date of Patent: Feb. 18, 2025

(54) MODULATION OF INTESTINAL EPITHELIAL CELL DIFFERENTIATION, MAINTENANCE AND/OR FUNCTION THROUGH T CELL ACTION

(71) Applicants: The Broad Institute, Inc., Cambridge, MA (US); Massachusetts Institute of Technology, Cambridge, MA (US); The General Hospital Corporation, Boston, MA (US)

(72) Inventors: Adam Haber, Cambridge, MA (US); Moshe Biton, Cambridge, MA (US); Rebecca H. Herbst, Cambridge, MA (US); Karthik Shekhar, Cambridge, MA (US); Christopher Smillie, Cambridge, MA (US); Orit Rozenblatt-Rosen, Cambridge, MA (US); Ramnik Xavier, Boston, MA (US); Aviv Regev, Cambridge, MA (US); Jose Ordovas-Montanes, Cambridge, MA (US); Alexander K. Shalek, Cambridge, MA (US); Noga Rogel, Cambridge, MA (US)

(73) Assignees: The Broad Institute, Inc., Cambridge, MA (US); Massachussetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 629 days.

(21) Appl. No.: 16/348,911

(22) PCT Filed: Nov. 7, 2017

(86) PCT No.: PCT/US2017/060469
§ 371 (c)(1),
(2) Date: May 10, 2019

(87) PCT Pub. No.: WO2018/089386
PCT Pub. Date: May 17, 2018

(65) Prior Publication Data
US 2019/0263912 A1    Aug. 29, 2019

Related U.S. Application Data

(60) Provisional application No. 62/421,204, filed on Nov. 11, 2016, provisional application No. 62/533,653, filed on Jul. 17, 2017.

(51) Int. Cl.
| | | |
|---|---|---|
| *G01N 33/50* | (2006.01) | |
| *A61K 35/17* | (2015.01) | |
| *A61P 1/04* | (2006.01) | |
| *A61P 1/14* | (2006.01) | |
| *A61P 31/04* | (2006.01) | |

(Continued)

(52) U.S. Cl.
CPC .......... *C07K 16/2833* (2013.01); *A61K 35/17* (2013.01); *A61P 1/04* (2018.01); *A61P 1/14* (2018.01); *A61P 31/04* (2018.01); *A61P 33/00* (2018.01); *C07K 14/47* (2013.01); *C07K 14/52* (2013.01); *C07K 14/71* (2013.01); *C12N 5/0636* (2013.01); *C12N 5/0637* (2013.01); *C12N 5/0679* (2013.01); *G01N 33/5044* (2013.01);
(Continued)

(58) Field of Classification Search
CPC .... A61K 45/06; A61K 39/3955; A61K 38/00; A61K 38/1709; A61K 2039/505; A61K 39/00; A61K 35/17; A61K 39/4611; C07K 2317/76; C07K 16/2896; C07K 2317/75; C07K 16/18; C07K 14/00; C07K 14/435; C07K 16/244; C07K 16/249; C07K 14/5428; C07K 14/5437; C07K 14/54; C07K 14/57; C12N 5/0679; C12N 5/0636; C12N 5/0637; C12N 2502/1114; G01N 33/5044; G01N 33/505; G01N 33/56966; G01N 33/56972
See application file for complete search history.

(56) References Cited

U.S. PATENT DOCUMENTS

| 4,816,567 A | 3/1989 | Cabilly et al. |
| 5,270,163 A | 12/1993 | Gold et al. |

(Continued)

FOREIGN PATENT DOCUMENTS

| EP | 2 784 162 A1 | 10/2014 |
| EP | 2 771 468 B1 | 2/2015 |

(Continued)

OTHER PUBLICATIONS

Li et al. The response of intestinal stem cells and epithelium after alemtuzumab administration. Cell Mol Immunol 8: 325-332, 2011.*

(Continued)

*Primary Examiner* — Bridget E Bunner
(74) *Attorney, Agent, or Firm* — Foley & Lardner LLP; Sunit Talapatra

(57) ABSTRACT

An atlas of intestinal epithelial cells, intestinal epithelial stem cells and intestinal immune cells identifies new cell populations, markers, networks, and responses to stimuli. Intestinal T cells drive intestinal epithelial cell differentiation and activity. Accordingly, disclosed are methods of modulating intestinal epithelial cell differentiation, maintenance and/or function, related methods for the treatment of disease, including IBD. Also disclosed are methods and kits for identifying cell types, their differentiation, homeostasis and activation.

18 Claims, 157 Drawing Sheets

(51) Int. Cl.
  *A61P 33/00* (2006.01)
  *C07K 14/47* (2006.01)
  *C07K 14/52* (2006.01)
  *C07K 14/71* (2006.01)
  *C07K 16/28* (2006.01)
  *C12N 5/071* (2010.01)
  *C12N 5/0783* (2010.01)
  *G01N 33/569* (2006.01)

(52) U.S. Cl.
  CPC . *G01N 33/56966* (2013.01); *G01N 33/56972* (2013.01); *G01N 2800/26* (2013.01)

(56) References Cited

U.S. PATENT DOCUMENTS

| | | |
|---|---|---|
| 5,686,281 A | 11/1997 | Roberts |
| 5,843,728 A | 12/1998 | Seed et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,507,272 B2 | 8/2013 | Zhang et al. |
| 8,637,307 B2 | 1/2014 | June et al. |
| 8,697,359 B1 | 4/2014 | Zhang |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 2004/0224402 A1 | 11/2004 | Bonyhadi et al. |
| 2012/0244133 A1 | 9/2012 | Rosenberg et al. |
| 2013/0071414 A1 | 3/2013 | Dotti et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199700 A1 | 7/2014 | Kume et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2014/0342456 A1 | 11/2014 | Mali et al. |
| 2014/0356959 A1 | 12/2014 | Church et al. |
| 2015/0031132 A1 | 1/2015 | Church et al. |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |

FOREIGN PATENT DOCUMENTS

| | | |
|---|---|---|
| EP | 2 764 103 B1 | 8/2015 |
| WO | 92/15322 A1 | 9/1992 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004055052 A2 | 7/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |

(56) References Cited

FOREIGN PATENT DOCUMENTS

| | | |
|---|---|---|
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2016/000304 A1 | 1/2016 |
| WO | 2016/011210 A2 | 1/2016 |
| WO | 2016/049258 A2 | 3/2016 |
| WO | 2016/070061 A1 | 5/2016 |
| WO | 2016/094867 A1 | 6/2016 |
| WO | 2016/094872 A1 | 6/2016 |
| WO | 2016/094874 A1 | 6/2016 |
| WO | 2016/106244 A1 | 6/2016 |
| WO | 2018/089386 A1 | 5/2018 |

OTHER PUBLICATIONS

Bergstrom et al. Goblet cell derived RELM-beta recruits CD4+ T cells during infectious colitis to promote protective intestinal epithelial cell proliferation. PLoS Pathogens 11(8): e1005108, 2015.*
Denning et al. Expression of IL-10 receptors on epithelial cells from the murine small and large intestine. Int Immunol 12(2): 133-139, 2000.*
Maynard et al. Intestinal effector T cells in health and disease. Immunity 31: 389-400, 2009.*
Parr et al. Demonstration of Ia antigens on mouse intestinal epithelial cells by immunoferritin labeling. Immunogenetics 8: 499-508, 1979.*
Peterson et al. Intestinal epithelial cells: regulators of barrier function and immune homeostasis. Nature Rev 14: 141-153, 2014.*
R&D Systems illustration titled "The IL-12 family of cytokines & mechanisms of intestinal inflammation", 2015 (1 page); https://www.rndsystems.com/resources/posters/il-12-family-cytokines-mechanisms-intestinal-inflammation.*
Wallace et al. Immunopathology of inflammatory bowel disease. World J Gastroenterol 20(1): 6-21, 2014.*
Zanello et al. The cytosolic microbial receptor Nod2 regulates small intesting crypt damage and epithelial regeneration following T cell-induced enteropathy. J Immunol 197: 345-355, May 2016.*
Chen et al. Cytokine Networks and T-Cell Subsets in Inflammatory Bowel Diseases. Inflamm Bowel Dis 22: 1157-1167, 2016.*
Denning et al. Lamina propria macrophages and dendritic cells differentially induce regulatory and interleukin 17-producing T cell responses. Nature Immunol 8(10): 1086-1094, 2007.*
Henderson et al. Function of the Intestinal Epithelium and Its Dysregulation in Inflammatory Bowel Disease. Inflamm Bowel Dis 17: 382-395, 2011.*
Jarry et al. Mucosal IL-10 and TGF-β play crucial roles in preventing LPS-driven, IFN-γ-mediated epithelial damage in human colon explants. J Clin Invest 118(3): 1132-1142, 2008.*
Nishikawa et al. The protective role of endogenous cytokines in host resistance against an intragastric infection with Listeria monocytogenes in mice. FEMS Immunol Med Microbiol 16: 291-298, 1996.*
Pan et al. Interleukin-10 prevents epithelial cell apoptosis by regulating IFNgamma and TNFa expression in rhesus macaque colon explants. Cytokine 64: 30-34, 2013.*
Powrie et al. Inhibition of Th1 Responses Prevents Inflammatory Bowel Disease in scid Mice Reconstituted with CD45RBhi CD4+ T Cells. Immunity 1: 553-562, 1994.*
Przemioslo et al. Histological changes in small bowel mucosa induced by gliadin sensitive T lymphocytes can be blocked by anti-interferon γ antibody. Gut 36: 874-879, 1995.*
Qiu et al. Effects of Intraepithelial Lymphocyte-Derived Cytokines on Intestinal Mucosal Barrier Function. J Interferon Cytokine Res 33(10): 551-562, 2013.*
Shibahara et al. Alteration of intestinal epithelial function by intraepithelial lymphocyte homing. J Gastroenterol 40: 878-886, 2005.*
Tsao et al. HuZAF, a humanized anti-IFN-y antibody, inhibits chemokine production by activated T cell and intestinal epithelial cells and blocks chemotaxis of activated CXCR3+ lymphocytes. Gastroenterol 124(4 Suppl): A332, 2003.*
Van Wijk et al. Intestinal T cells: Facing the mucosal immune dilemma with synergy and diversity. Sem Immunol 21: 130-138, 2009.*
Golubovskaya et al. Different Subsets of T Cells, Memory, Effector Functions, and CAR-T Immunotherapy. Cancers 8: 36, Mar. 2016 (12 total pages).*
Lozano-Ojavlo et al. "PBMC-Derived T Cells" in Impact Food Bio-Actives Gut Health: in vitro and ex vivo models. Cham (CH): Springer, 2015, Chapter 16 (pp. 169-180).*
Wang et al. Modeling the effects of inflammatory stress on human intestinal epithelial cells in 3D enteroid co-culture. Cancer Res 76 (14 Suppl): 4253, Jul. 15, 2016.*
Zachos et al. Human Enteroids/Colonoids and Intestinal Organoids Functionally Recapitulate Normal Intestinal Physiology. J Biol Chem 291(8): 3759-3766, Feb. 19, 2016.*
Golubovskaya (Year: 2016).*
Lozano-Ojalvo (Year: 2015).*
Wang et al. (Year: 2016).*
Zachos et al. (Year: 2016).*
"GenBank Accession NM_001205011.2 Mus Musculus Mucosal Pentraxin 2 (Mptx2), mRNA", www.ncbi.nlm.nih.gov/nuccore/354459074?sat=4&satkey=135324733, Feb. 25, 2018, 1 page.
Bonnardel, et al., "Innate and Adaptive Immune Functions of Peyer's Patch Monocyte-Derived Cells", Cell Rep, vol. 11, No. 5, 2015, pp. 770-784.
Jessup, et al., "Intradermal Administration of Thymic Stromal Lymphopoietin Induces a T Cell- and Eosinophil-Dependent Systemic Th2 Inflammatory Response", J. Immunol., vol. 181, 2008, pp. 4311-4319.
Umesaki, et al., "Segmented Filamentous Bacteria are Indigenous Intestinal Bacteria that Activate Intraepithelial Lymphocytes and Induce MHC class II Molecules and Fucosyl Asialo GM1 Glycolipids

(56) References Cited

OTHER PUBLICATIONS on the Small Intestinal Epithelial Cells in the Ex-Germ-Free Mouse", Microbiol. Immune., vol. 39, No. 8, 1995, pp. 555-562.
The Broad Institute, Inc., "PCT International Search Report and Written Opinion issued in PCT/US2017/060469", Apr. 23, 2018, 13 pages.
Barriga, et al., "Mex3a Marks a Slowly Dividing Subpopulation of Lgr5+ Intestinal Stem Cells", Cell Stem Cell, vol. 20, No. 6, Jun. 1, 2017, 801-816.
Basak, et al., "Induced Quiescence of Lgr5+ Stem Cells in Intestinal Organoids Enables Differentiation of Hormone-Producing Enteroendocrine Cells", Cell Stem Cell, vol. 20, No. 2, Feb. 2, 2017, 177-190.
Bezencon, et al., "Murine Intestinal Cells Expressing Trpm5 are Mostly Brush Cells and Express Markers of Neuronal and Inflammatory Cells", Journal of Comparative Neurology, vol. 509, No. 5, Aug. 10, 2008, 514-525.
Bland, Paul "MHC Class II Expression by the Gut Epithelium", Immunology Today, vol. 9, No. 6, 1988, 174-178.
Cheng, et al., "Origin, Differentiation and Renewal of the Four Main Epithelial Cell Types in the Mouse Small Intestine III. Entero-Endocrine Cells", The American Journal of Anatomy, vol. 141, 1974, 503-519.
Egerod, et al., "A Major Lineage of Enteroendocrine Cells Coexpress CCK, Secretin, GIP, GLP-1, PYY, and Neurotensin but not Somatostatin", Endocrinology, vol. 153, No. 12, Dec. 2012, 5782-5795.
Grun, et al., "Single-Cell Messenger RNA Sequencing Reveals Rare Intestinal Cell Types", Nature, vol. 525, No. 7568, Sep. 10, 2015, 251-255.
Jang, et al., "Intestinal Villous M Cells: an Antigen Entry Site in The Mucosal Epithelium", Proceedings of the National Academy of Sciences of the United States of America, vol. 101, No. 16, Apr. 20, 2004, 6110-6115.
Kambayashi, et al., "Atypical MHC Class II-Expressing Antigen-presenting Cells: Can Anything Replace a Dendritic Cell?", Nature Reviews Immunology, vol. 14, 2014, 719-730.
Kim, et al., "Single-Cell Transcript Profiles Reveal Multilineage Priming in Early Progenitors Derived from Lgr5(+) Intestinal Stem Cells", Cell Reports, vol. 16, No. 8, Aug. 23, 2016, 14 pages.
Kowalczyk, et al., "Single Cell RNA-Seq Reveals Changes in Cell Cycle and Differentiation Programs Upon Aging of Hematopoietic Stem Cell", Genome Research , vol. 25, No. 12, Dec. 2015, 1860-1872.
Rodenburg, et al., "*Salmonella* Induces Prominent Gene Expression in The Rat Colon", BMC Microbiology, vol. 7, Sep. 12, 2007, 16 pages.
Salomon, et al., "The Expression and Regulation of Class Ii Antigens in Normal and Inflammatory Bowel Disease Peripheral Blood Monocytes and Intestinal Epithelium", Autoimmunity, 1991, vol. 9, 1991, 141-149.
Sjölund, et al., "Endocrine Cells in Human Intestine: an Immunocytochemical Study", Gastroenterology, Nov. 1983, vol. 85, No. 5, 1983, 1120-1130.
Terahara, et al., "Comprehensive Gene Expression Profiling of Peyer's Patch M Cells, Villous M-Like Cells, and Intestinal Epithelial Cells", Journal of Immunology, vol. 180, No. 12, Jun. 15, 2008, 7840-7846.
Tetteh, et al., "Replacement of Lost Lgr5-Positive Stem Cells through Plasticity of Their Enterocyte-Lineage Daughters", Cell Stem Cell, vol. 18, No. 2, Feb. 4, 2016, 203-213.
The Broad Institute, Inc., et al., "International Preliminary Report on Patentability issued in International Application No. PCT/US2017/060469", May 23, 2019, 9 pages.
Thelemann, et al., "Interferon-$\gamma$ Induces Expression of MHC Class II on Intestinal Epithelial Cells and Protects Mice from Colitis", PLos One, 2014 , vol. 9. No. 1, Jan. 2014, 10 pages.
Yan, et al., "Non-Equivalence of Wnt and R-Spondin Ligands During Lgr5+ Intestinal Stem Cell Self-renewal", Nature, vol. 545, No. 7653, May 11, 2017, 36 pages.

Biton, et al. T Helper Cell Cytokines Modulate Intestinal Stem Cell Renewal and Differentiation. Cell. 2018;175 (5):1307-1320.e22.
Ali et al., "Regulatory T Cells in Skin Facilitate Epithelial Stem Cell Differentiation," Cell, Jun. 2017, vol. 169, No. 6 (pp. 1119-1129).
Altman et al., "Phenotypic Analysis of Antigen-specific T Lymphocytes," Science, Oct. 4, 1996, vol. 274, No. 5284 (pp. 94-96).
Amir et al., "viSNE Enables Visualization of High Dimensional Single-Cell Data and Reveals Phenotypic Heterogeneity of Leukemia," Nature Biotechnology, Jun. 2013, vol. 31, No. 6 (25 pages).
Arpaia et al., "A Distinct Function of Regulatory T Cells in Tissue Protection," Cell, Aug. 27, 2015, vol. 162, No. 5 (pp. 1078-1089).
Artis et al., "RELMbeta/FIZZ2 is a Goblet Cell-Specific Immune-Effector Molecule in the Gastrointestinal Tract," Proceedings of the National Academy of Sciences, USA Sep. 14, 2004, vol. 101, No. 37 (p. 13596-13600).
Aurora et al., "Immune modulation of stem cells and regeneration," Cell Stem Cell, Jul. 3, 2014, vol. 15, No. 1 (pp. 14-25).
Banaszynski et al., "A rapid, reversible, and tunable method to regulate protein function in living cells using synthetic small molecules," Cell, Sep. 8, 2006 Vol. 126, No. 5 (pp. 995-1004).
Banaszynski et al., "Chemical control of protein stability and function in living mice," Nature Medicine, Oct. 2008, vol. 14, No. 10 (pp. 1123-1127).
Barker et al., "Identifying the stem cell of the intestinal crypt: strategies and pitfalls," Cell Stem Cell, Oct. 5, 2012, vol. 11 (pp. 452-460).
Barker et al. "Identification of stem cells in small intestine and colon by marker gene Lgr5," Nature, Oct. 25, 2007, vol. 449, No. 7165 (pp. 1003-1007).
Barker et al., "Adult Intestinal Stem Cells: Critical Drivers of Epithelial Homeostasis and Regeneration," Nature Reviews Molecular Cell Biology, Jan. 2014, vol. 15, No. 1 (pp. 19-33).
Bartel et al., "MicroRNAs: Genomics, Biogenesis, Mechanism, and Function," Cell, Jan. 23, 2004, vol. 116, No. 2 (pp. 281-297).
Basak et al., "Mapping Early Fate Determination in Lgr5 Crypt Stem Cells Using A Novel Ki67-RFP Allele," The EMBO Journal, Sep. 17, 2014, vol. 33, No. 18 (pp. 2057-2068).
Battle et al., "GATA4 is Essential for Jejunal Function in Mice," Gastroenterology, Nov. 2008, vol. 135, No. 5 (pp. 1676-1686).
Bendall et al., "Single-cell Trajectory Detection Uncovers Progression and Regulatory Coordination in Human B Cell Development", Cell, Apr. 24, 2014, vol. 157, No. 3 (pp. 714-725).
Benjamin et al., "Controlling the False Discovery Rate: A Practical and Powerful Approach to Multiple Testing," Journal of the Royal Statistical Society, 1995 Series B, vol. 57, No. 1 (pp. 289-300).
Besser et al., "Clinical responses in a phase II study using adoptive transfer of short-term cultured tumor infiltration lymphocytes in metastatic melanoma patients," Clinical Cancer Research, May 1, 2010, vol. 16, No. 9 (pp. 2646-2655).
Beuling et al., "GATA Factors Regulate Proliferation, Differentiation, and Gene Expression in Small Intestine of Mature Mice," Gastroenterology, Apr. 2011, vol. 140, No. 4 (pp. 1219-1229).
Beyaz et al., "High-fat diet enhances stemness and tumorigenicity of intestinal progenitors," Nature, 2016, vol. 531, No. 7592 (pp. 53-58).
Birchenough et al., "New Developments in Goblet Cell Mucus Secretion and Function," Mucosal Immunology, Jul. 2015, vol. 8, No. 4 (pp. 712-719).
Biton et al., "Epithelial microRNAs regulate gut mucosal immunity via epithelium T cell crosstalk," Nature Immunology, Mar. 2011, vol. 12, No. 3 (pp. 239-246).
Boch et al., "Breaking The Code Of DNA Binding Specificity Of T AL-Type III Effectors," Science, Dec. 11, 2009 vol. 326, No. 5959 (pp. 1509-1512).
Boes et al., "T-cell engagement of dendritic cells rapidly rearranges MHC class II transport," Nature, Aug. 29, 2002, vol. 418 (pp. 983-988).
Boni et al., "Adoptive transfer of allogeneic tumor-specific T cells mediates effective regression of large tumors across major histocompatibility barriers," Blood, Dec. 1, 2008, vol. 112, No. 12 (pp. 4746-4754).

(56) References Cited

OTHER PUBLICATIONS

Bosse et al., "Gata4 is essential for the maintenance of jejunal-ileal identities in the adult mouse small intestine," Molecular and Cellular Biology, Dec. 2006, vol. 26, No. 23 (pp. 9060-9070).
Brennecke et al., "Accounting for Technical Noise in Single-Cell RNA-seq Experiments," Nature Methods, Sep. 22, 2013, vol. 10, No. 11 (pp. 1093-1095).
Buczacki et al., "Intestinal label-retaining cells are secretory precursors expressing Lgr5," Nature, Mar. 7, 2013, vol. 495, No. 7439 (pp. 65-96).
Budde et al., "Combining a CD20 Chimeric Antigen Receptor and an Inducible Caspase 9 Suicide Switch to Improve the Efficacy and Safety of T Cell Adoptive Immunotherapy for Lymphoma," Plos One, 2013, vol. 8, No. 12, e82742 (10 pages).
Buja et al., "Remarks on Parallel Analysis," published in: Multivariate Behavioral Research, 1992, vol. 27, No. 4 (26 pages).
Burzyn et al., "A special population of regulatory T cells potentiates muscle repair," Cell, Dec. 5, 2013, vol. 155 (pp. 1282-1295).
Cermak et al., "Efficient Design and Assembly of Custom Talen and Other Tal Effector-Based Constructs for DNA Targeting", Nucleic Acids Research, 2011, vol. 39, No. 12 (pp. 1-11).
Charman, "Lipids, Lipophilic Drugs, and Oral Drug Delivery-Some Emerging Concepts," Journal of Pharmaceutical Sciences, 2000, vol. 89, No. 8 (pp. 967-978).
Clackson et al., "Making antibody fragments using phage display libraries," Nature, Aug. 1991, vol. 352 (pp. 624-628).
Clevers et al., "Wnt/beta-catenin signaling in development and disease," Cell, Nov. 3, 2006, vol. 127 (pp. 469-480).
Clevers, H., "The intestinal crypt, a prototype stem cell compartment," Cell, Jul. 18, 2013, vol. 154 (pp. 274-284).
Coburn et al., "Salmonella, the host and disease: a brief review," Immunology and Cell Biology, 2007, vol. 85 (pp. 112-118).
Coifman et al., "Geometric diffusions as a tool for harmonic analysis and structure definition of data: diffusion maps," Proceedings of the National Academy of Sciences, USA, May 24, 2005, vol. 102, No. 21 (pp. 7426-7431).
Cong et al., "CRISPR-Assisted Mammalian Genome Engineering," published as "Multiplex Genome Engineering Using CRISPR-Cas Systems," Science, Oct. 5, 2012, vol. 339 (pp. 819-823) [Manuscript including Supplementary Materials—36 pages].
Cook et al., "Characterization and development of RGD-peptide-modified poly(lactic acid-co-lysine) as an interactive, resorbable biomaterial," Journal of Biomedical Materials Research, Jun. 15, 1997 (pp. 513-523).
Cordier et al., "Development of thymus, parathyroids, and ultimobranchial bodies in NMRI and nude mice," The American Journal of Anatomy, 1980, vol. 157 (pp. 227-263).
Darwin et al., "Molecular basis of the interaction of Salmonella with the intestinal mucosa," Clinical Microbiology Review, Jul. 1999, vol. 12, No. 3 (pp. 505-428).
Datta et al., "Identification of Novel Genes in Intestinal Tissue that are Regulated after Infection with an Intestinal Nematode Parasite," Infection and Immunity, Jul. 2005, vol. 73, No. 7 (pp. 4025-4033).
Di Stasi et al., "Inducible apoptosis as a safety switch for adoptive cell therapy," Clinical Trial, New England Journal of Medicine, Nov. 3, 2011, vol. 365, No. 18 (pp. 1673-1683).
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].
Dombrowski et al., "Regulatory T cells promote myelin regeneration in the central nervous system," Nature Neuroscience, May 2017, vol. 20, No. 5 (pp. 674-680).
Doyon et al., "Heritable targeted gene disruption in zebrafish using designed zinc-finger nucleases," Nature Biotechnology, Jun. 2008, vol. 26, No. 6 (pp. 702-708).
Du Clos," Pentraxins: structure, function, and role in inflammation," ISRN Inflammation, Sep. 14, 2013, vol. 2013, Article ID 379040 (pp. 1-22).
Duboc et al., "The Bile Acid TGR5 Membrane Receptor: From Basic Research to Clinical Application," Digestive and Liver Disease, Apr. 2014, vol. 46, No. 4 (pp. 302-312).
Dudley et al., "Adoptive Cell Transfer Therapy Following Non-Myeloablative but Lymphodepleting Chemotherapy for the Treatment of Patients with Refractory Metastatic Melanoma," Journal of Clinical Oncology, Apr. 1, 2005, vol. 23, No. 10 (pp. 2346-2357).
Dudley et al., "Cancer regression and autoimmunity in patients after clonal repopulation with antitumor lymphocytes," Science, 2002, vol. 298, No. 5594 (pp. 850-854).
Eckhardt et al., "Intestinal Epithelial Serum Amyloid a Modulates Bacterial Growth in Vitro and Pro-Inflammatory Responses in Mouse Experimental Colitis," BMC Gastroenterology, Nov. 10, 2010, vol. 10 (pp. 1-9).
Ellington et al., "In vitro selection of RNA molecules that bind specific ligands," Nature, 1990, vol. 346, No. 6287 (pp. 818-822).
Erichson et al., "Randomized Matrix Decompositions using R," Journal of Statistical Software, May 2019, vol. 89, Issue 11 (47 pages).
Esplugues et al., "Control of TH 17 cells occurs in the small intestine," Nature, 2012, vol. 475, No. 7357 (pp. 514-518).
Ester et al., "A density-based algorithm for discovering clusters a density-based algorithm for discovering clusters in large spatial databases with noise," Proceedings of the Second International Conference on Knowledge Discovery and Data Mining, 1996 (pp. 226-231).
Farin et al., "Paneth cell extrusion and release of antimicrobial products is directly controlled by immune cell-derived IFN-gamma," Journal of Experimental Medicine, 2014, vol. 211, No. 7 (pp. 1393-1405).
Ferraris et al., "Regulation of Brush-Border Enzyme Activities and Enterocyte Migration Rates in Mouse Small Intestine," The American Journal of Physiology, Jun. 1992, vol. 262 (pp. G1047-G1059).
Finak et al., "MAST: a flexible statistical framework for assessing transcriptional changes and characterizing heterogeneity in single-cell RNA sequencing data," Genome Biology, Dec. 10, 2015, vol. 16 (pp. 1-13).
Furness et al., "The gut as a sensory organ," Nature reviews, Gastroenterology & hepatology, 2013, vol. 10 (pp. 729-740).
Garabedian et al., "Examining the Role of Paneth Cells in The Small Intestine by Lineage Ablation in Transgenic Mice," The Journal of Biological Chemistry, Sep. 19, 1997, vol. 272, No. 38 (pp. 23729-23740).
Gerbe et al., "Intestinal Epithelial Tuft Cells Initiate Type 2 Mucosal Immunity to Helminth Parasites," Nature, Jan. 14, 2016, vol. 529, No. 7585 (pp. 226-230).
Gerbe et al., "The intestinal epithelium tuft cells: specification and function," Cellular and Molecular Life Sciences, 2012, vol. 69 (pp. 2907-2917).
Gershon et al., "The serotonin signaling system: from basic understanding to drug development for functional GI disorders," Gastroenterology, Jan. 2007, vol. 132, No. 1 (pp. 397-414).
Graham et al., "From Genetics of Inflammatory Bowel Disease Towards Mechanistic Insights," Trends in Immunology Aug. 2013, vol. 34, No. 8 (pp. 371-378).
Graham et al., "Functional genomics identifies negative regulatory nodes controlling phagocyte oxidative burst," Nature Communications, 2015, vol. 6, No. 7838 (pp. 1-12).
Greco et al., "Improving the safety of cell therapy with the TK-suicide gene," Frontiers in Pharmacology, May 5, 2015, vol. 6, No. 95 (13 pages).
Gribble et al., "Enteroendocrine Cells: Chemosensors in the Intestinal Epithelium," Annual Review of physiology, 2016, vol. 78, (pp. 277-299).
Griffin et al., "Development of protective immunity to Salmonella, a mucosal pathogen with a systemic agenda," Mucosal Immunol Jul. 2011, vol. 4, No. 4 (pp. 371-382).
Habib et al., "Co-localisation and secretion of glucagon-like peptide 1 and peptide YY from primary cultured human L cells," Diabetologia, 2013, 56 (pp. 1413-1416).
Habib et al., "Div-Seq: Single-nucleus RNA-Seq reveals dynamics of rare adult newborn neurons," Science, Aug. 26, 2016, vol. 353, No. 6302 (pp. 925-928).

(56) References Cited

OTHER PUBLICATIONS

Haghverdi et al., "Diffusion maps for high-dimensional single-cell analysis of differentiation data," Bioinformatics, 2015, vol. 31, No. 18 (pp. 2989-2998).
Hashimoto et al., "A conditional null allele of the major histocompatibility IA-beta chain gene," Genesis, 2002, vol. 32 (pp. 152-153).
Hayami et al., "Overexpression of the JmjC histone demethylase KDM5B in human carcinogenesis: involvement in the proliferation of cancer cells through the E2F/RB pathway," Molecular Cancer, Mar. 13, 2010, vol. 9, No. 59 (pp. 1-14).
Heinz et al., "The selection and function of cell type-specific enhancers," Nature Reviews Molecular Cell Biology, Mar. 2015, vol. 16, No. 3 (pp. 144-154).
Hicke et al., "Escort aptamers: a delivery service for diagnosis and therapy," The Journal of Clinical Investigation, Oct. 2000, vol. 106, No. 8 (pp. 923-928).
Horwell et al., "The 'peptoid' approach to the design of non-peptide, small molecule agonists and antagonists of neuropeptides," Trends in Biotechnology, Apr. 1995, vol. 13, No. 4 (pp. 132-134).
Howie et al., "Secreted and Transmembrane 1A Is a Novel Co-Stimulatory Ligand," PLOS One, Sep. 2013, vol. 8, No. 9 (pp. 1-9).
Howitt et al., "Tuft Cells, Taste-Chemosensory Cells, Orchestrate Parasite Type 2 Immunity in the Gut," Science, Mar. 18, 2016, vol. 361 (pp. 1329-1333.
Hsu et al., "Development and Applications of CRISPR-Cas9 for Genome Engineering," Cell, 2014, vol. 157 (pp. 1262-1278).
Hsu et al., "DNA targeting specificity of RNA-guided Cas9 nucleases," Nature Biotechnology, Sep. 2013, vol. 31, No. 9 (pp. 827-832).
Huch et al., "In vitro Expansion of Single Lgr5 Liver Stem Cells Induced by Wnt-driven Regeneration," Nature, Feb. 2013, vol. 494 (pp. 247-250).
Ichimura et al., "Free Fatty Acid Receptors Act as Nutrient Sensors to Regulate Energy Homeostasis," Journal - Elsevier, Sep. 2009, vol. 89, No. 3-4 (pp. 82-88).
Ivanov et al., "Induction of intestinal Th17 cells by segmented filamentous bacteria," Cell, Oct. 30, 2009, vol. 139, No. 3 (pp. 485-498).
Iwata et al., "Retinoic acid imprints gut-homing specificity on T cells," Immunity, Oct. 2004, vol. 21, No. 4 (pp. 527-538).
Jager et al., "Th1, Th17, and Th9 effector cells induce experimental autoimmune encephalomyelitis with different pathological phenotypes," The Journal of Immunology, Nov. 2009, vol. 183 (pp. 7169-7177).
Jensen et al., "Design and Implementation of Adoptive Therapy with Chimeric Antigen Receptor- Modified T Cells," Immunological Reviews, Jan. 2014, vol. 257, No. 1 (32 pages).
Jiang et al., "RNA-guided editing of bacterial genomes using CRISPR-Cas systems," Nature Biotechnology, Mar. 2013, vol. 31 [30 pages, including supplementary information] (pp. 233-239).
Johnson et al., "Adjusting batch effects in microarray expression data using empirical Bayes methods," Biostatistics, Jan. 2007, vol. 8, No. 1 (pp. 118-127).
Johnson et al., "Gene therapy with human and mouse T-cell receptors mediates cancer regression and targets normal tissues expressing cognate antigen," Blood, Jul. 2009, vol. 114, No. 3 (pp. 535-546).
Kalos et al., "T Cells with Chimeric Antigen Receptors Have Potent Antitumor Effects and Can Establish Memory in Patients with Advanced Leukemia," Science Translational Medicine, Aug. 10, 2011, vol. 3, No. 95 (12 pages).
Karra et al., "The role of peptide YY in appetite regulation and obesity," The Journal of Physiology, Jan. 15, 2009, vol. 587, No. 1 (pp. 19-25).
Kaser et al., "XBP1 Links Er Stress to Intestinal Inflammation and Confers Genetic Risk for Human Inflammatory Bowel Disease", Cell, Sep. 5, 2008, vol. 134, No. 5 (pp. 743-756).
Katz et al., "The zinc-finger transcription factor Klf4 is required for terminal differentiation of goblet cells in the colon," Development, Jun. 2002, vol. 129, No. 11 (pp. 2619-2628).
Keefe et al., "Aptamers as therapeutics," Nature Reviews, Jul. 2010, vol. 9 (pp. 537-550).
Kim et al., "Chimeric restriction endonuclease," Proceedings of the National Academy of Sciences, USA, Biochemistry, Feb. 1994, vol. 91 (pp. 883-887).
Kim et al., "Regulatory T cells prevent catastrophic autoimmunity throughout the lifespan of mice," Nature Immunology, Feb. 2007, vol. 8, No. 2 (pp. 191-197).
Kim et al., "Hybrid restriction enzymes: zinc finger fusions to Fok I cleavage domain," Proceedings of the National Academy of Sciences, USA, Feb. 6, 1996, vol. 93, No. 3 (pp. 1156-1160).
Klein et al., "Droplet barcoding for single-cell transcriptomics applied to embryonic stem cells," Cell, May 21, 2015, vol. 161 (pp. 1187-1201).
Kleinstiver et al., "Engineered CRISPR-Cas9 nucleases with altered PAM specificities," Nature, Jul. 23, 2015, vol. 523, No. 7561 (pp. 481-485).
Klok et al., "The role of leptin and ghrelin in the regulation of food intake and body weight in humans: a review," Obesity Reviews, Jan. 2007, vol. 8, No. 1 (pp. 21-34).
Kobayashi et al., "Identification of Novel Genes Selectively Expressed in the Follicle-associated Epithelium from the Meta-Analysis of Transcriptomics Data from Multiple Mouse Cell and Tissue Populations," DNA Research: An International Journal for Rapid Publication of Reports on Genes and Genomes, Oct. 2012, vol. 19, No. 5 (pp. 407-422).
Kohler et al., "Continuous cultures of fused cells secreting antibody of predefined specificity," Nature, 1975, vol. 256 (pp. 495-497).
Kohlnhofer et al., "GATA4 Regulates Epithelial Cell Proliferation to Control Intestinal Growth and Development in Mice," Cellular and Molecular Gastroenterology and Hepatology, Mar. 2016, vol. 2, No. 2 (pp. 189-209).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).
Kurreck et al., "Antisense technologies. Improvement through novel chemical modifications," European Journal of Biochemistry, Apr. 2003, vol. 270, No. 8 (pp. 1628-1644).
Lagos-Quintana et al., "Identification of Novel Genes Coding for Small Expressed RNAs," Science, Oct. 26, 2001, vol. 294 (pp. 853-858).
Lagos-Quintana et al., "Identification of tissue-specific microRNAs from mouse," Current Biology, Apr. 30, 2002, vol. 12, (pp. 735-739).
Lagos-Quintana et al., "New microRNAs from mouse and human," RNA, 2003, vol. 9 (pp. 175-179).
Langmead et al., "Ultrafast and memory-efficient alignment of short DNA sequences to the human genome", Genome Biology, Mar. 4, 2009, vol. 10, No. 3 (pp. 1-10).
Lau et al., "An abundant class of tiny RNAs with probable regulatory roles in Caenorhabditis elegans," Science, Oct. 26, 2001, vol. 294 (pp. 858-862).
Lau et al., "Peyer's patch M cells derived from Lgr5(+) stem cells require SpiB and are induced by RankL in cultured 'miniguts'," Molecular and cellular biology, 2012, 32, 3639-3647.
Le Mercier et al., "Beyond CTLA-4 and PD-1, the generation Z of negative checkpoint regulators," Frontiers in Immunology, Aug. 21, 2015, vol. 6, Article 418 (15 pages).
Lee et al., "An Extensive Class of Small RNAs in Caenorhabditis elegans," Science, Oct. 26, 2001, vol. 294 (pp. 862-864).
Leek et al., "The sva package for removing batch effects and other unwanted variation in high- throughput experiments," Bioinformatics, Mar. 15, 2012, vol. 28, No. 6 (pp. 882-883).
Lei et al., "Intestinal Subepithelial Myofibroblasts Support the Growth of Intestinal Epithelial Stem Cells," PLOS One, Jan. 6, 2014 Vol. 9, No. 1 (11 pages).
Levine et al., "Data-Driven Phenotypic Dissection of AML Reveals Progenitor-like Cells that Correlate with Prognosis," Cell, 2015, vol. 162, No. 1 (pp. 184-197).

(56) References Cited

OTHER PUBLICATIONS

Levy-Nissenbaum et al., Nanotechnology and aptamers: applications in drug delivery, Trends in Biotechnology, Aug. 2008, vol. 26, No. 8 (pp. 442-449).
Li et al., "RSEM: accurate transcript quantification from RNA-Seq data with or without a reference genome," BMC Bioinformatics, 2011, vol. 12 No. 323 (16 pages).
Liberzon et al., "Molecular signatures database (MSigDB) 3.0," Bioinformatics Jun. 15, 2011, vol. 27, No. 12 (pp. 1739-1740).
Lim et al., "The microRNAs of Caenorhabditis elegans," Genes & Development, Apr. 15, 2003, vol. 17, No. 8 (pp. 991-1008).
Lim et al., "Vertebrate microRNA genes," Science, Mar. 7, 2003, vol. 299, No. 5612 (p. 1540).
Lindemans et al., "Interleukin-22 Promotes Intestinal-Stem-Cell-Mediated Epithelial Regeneration," Nature, Dec. 24, 2015, vol. 528 (pp. 560-564).
Loonen et al., "REG3-gamma-deficient mice have altered mucus distribution and increased mucosal inflammatory responses to the microbiota and enteric pathogens in the ileum," Mucosal Immunology, Jul. 2014, vol. 7, No. 4 (pp. 939-947).
Mabbott et al., "Microfold (M) Cells: Important Immunosurveillance Posts in The Intestinal Epithelium," Mucosal Immunology, Jul. 2013, vol. 6, No. 4 (pp. 666-677).
Macosko et al., "Highly Parallel Genome-wide Expression Profiling of Individual Cells Using Nanoliter Droplets," Cell, May 21, 2015, vol. 161 (pp. 1202-1214).
Madsen et al., "Mice lacking all conventional MHC class II genes," Proceeding of the National Academy of Sciences, USA, Aug. 1999, vol. 96 (pp. 10338-10343).
Mali et al., "RNA-Guided Human Genome Engineering Via Cas9" Science, dated Feb. 15, 2013 vol. 339 (pp. 823-826, 41 pages—Includes Supplemental Information).
Man et al., "Salmonella infection induces recruitment of Caspase-8 to the inflammasome to modulate IL-1 beta production," Journal of Immunology, Nov. 15, 2013, vol. 191, No. 10 (pp. 5239-5246).
Marasco et al., Design, intracellular expression, and activity of a human anti-human immunodeficiency virus type 1 gp120 single-chain antibody, Proceedings of the National Academy of Sciences, Aug. 15, 1993, vol. 90 (pp. 7889-7893).
Marjou et al., "Tissue-specific and inducible Cre-mediated recombination in the gut epithelium," Genesis, Jul. 2004 Vol. 39, No. 3 (pp. 186-193).
Marks et al., "By-passing immunization. Human antibodies from V-gene libraries displayed on phage," Journal of Molecular Biology, 1991, vol. 222, No. 3 (pp. 581-597).
Martinez Rodriguez, et al., "Expansion of Paneth Cell Population in Response to Enteric Salmonella Enterica Serovar Typhimurium Infection," Infection and immunity, vol. 80, No. 1, Jan. 2012, (pp. 266-275).
Matsumoto et al., "Retinal Promotes In Vitro Growth of Proximal Colon Organoids through a Retinoic Acid-Independent Mechanism," PLOS One, Aug. 26, 2016, vol. 11, No. 8 (pp. 1-15).
Maus et al., "Adoptive immunotherapy for cancer or viruses," Annual Review of Immunology, 2014, vol. 32 (pp. 189-225).
Maynard et al., "A directed approach for engineering conditional protein stability using biologically silent small molecules," Journal of Biological Chemistry, Sep. 2007, vol. 282, No. 34 (p. 24866-24872).
Mikos et al., "Laminated three-dimensional biodegradable foams for use in tissue engineering," Biomaterials, Apr. 1993, vol. 14, No. 5 (pp. 323-330).
Mikos et al., "Preparation and characterization of poly(L-lactic acid) foams," Polymer, 1994, vol. 35, No. 5 (pp. 1068-1077).
Miyazaki et al., Destabilizing Domains Derived from the Human Estrogen Receptor:, Journal of the American Chemical Society, Mar. 7, 2012, vol. 134 (pp. 3942-3945).
Mombaerts et al. "Spontaneous Development of Inflammatory Bowel Disease In T Cell Receptor Mutant Mice," Cell, Oct. 22, 1993, vol. 75, No. 2 (pp. 274-282).

Mombaerts et al., "Mutations in T-cell antigen receptor genes alpha and beta block thymocyte development at different stages," Nature, Nov. 19, 1992, vol. 360 (pp. 225-231).
Morgan et al., "Cancer Regression in Patients After Transfer of Genetically Engineered Lymphocytes," Science, Oct. 6, 2006, vol. 314, No. 5796 (pp. 126-129).
Moscou et al., "A Simple Cipher Governs DNA Recognition by TAL Effectors", Science, Dec. 11, 2009, vol. 326 (p. 1501).
Mukherjee et al., "Antimicrobial Defense of the Intestine," Immunity, vol. 42, No. 1, Jan. 20, 2015 (pp. 28-39).
Munoz et al., "The LGR5 Intestinal Stem Cell Signature: Robust Expression of Proposed Quiescent ' 4' Cell Markers," The EMBO Journal, vol. 31, No. 14, Jun. 12, 2012 (pp. 3079-3091).
Nakamura, et al., "Codon usage tabulated from international DNA sequence databases: status for the year 2000" Nucleic Acids Research, 2000, vol. 28 (p. 292).
Ng et al., "Human leucine-rich repeat proteins: a genome-wide bioinformatic categorization and functional analysis in innate immunity," Proceedings of the National Academy of Sciences, USA, Mar. 15, 2011, vol. 108, Suppl. 1 (pp. 4631-4638).
Nishimasu et al., "Crystal Structure of Cas9 in Complex with Guide RNA and Target DNA," Cell, Feb. 27, 2014, vol. 156 (pp. 935-949).
Noah et al., "Intestinal Development and Differentiation," Experimental Cell Research, Nov. 15, 2011, vol. 317, No. 19 (pp. 2702-2710).
Nozaki et al., "Co-culture with intestinal epithelial organoids allows efficient expansion and motility analysis of intraepithelial lymphocytes," Journal of Gastroenterology, Mar. 2016, vol. 51, No. 3 (pp. 206-213).
Oki et al., "A novel cell-cycle-indicator, mVenus-p27K-identifies quiescent cells and visualizes G0-G1 transition," Scientific Reports, Feb. 6, 2014, vol. 4 (pp. 1-10).
Overton et al., "GPR119 A Novel G Protein-Coupled Receptor Target for the Treatment of Type 2 Diabetes and Obesity," British Journal of Pharmacology, Mar. 2008, vol. 153 (pages S76-S81).
Paige et al., "RNA mimics of green fluorescent protein," Science, Jul. 29, 2011, vol. 333, No. 6042 (pp. 642-646).
Parker et al., "Scheme for ranking potential HLA-A2 binding peptides based on independent binding of individual peptide side-chains," The Journal of Immunology, Jan. 1, 1994, vol. 152, No. 1 (pp. 163-175).
Pashine et al., "Th1 dominance in the immune response to live Salmonella typhimurium requires bacterial invasiveness but not persistence," International Immunology, Apr. 1999, vol. 11, No. 4, (pp. 481-489).
Patel et al., "Single-cell RNA-seq highlights intratumoral heterogeneity m primary glioblastoma," Science, Jun. 20, 2014, vol. 344, No. 6190 (pp. 1396-1401).
Pelaseyed et al., "The Mucus and Mucins of the Goblet Cells and Enterocytes Provide the First Defense Line of the Gastrointestinal Tract and Interact with the Immune System," Immunological Reviews, Jul. 2014, vol. 260, No. 1 (pp. 8-20).
Picelli et al. "Full-length RNA-seq from single cells using Smart-seq2," Nature Protocols, Jan. 2014, vol. 9, No. 1 (pp. 171-181).
Platt et al., "CRISPR-Cas9 Knockin Mice for Genome Editing and Cancer Modeling," Cell, 2014, vol. 159 (pp. 440-455).
Poirot et al., "Multiplex genome edited T-cell manufacturing platform for 'off-the-shelf' adoptive T-cell immunotherapies," Cancer Research, Sep. 15, 2015, vol. 75, No. 18 (pp. 3853-3864).
Potten et al., "Intestinal stem cells protect their genome by selective segregation of template DNA strands," Journal of Cell Science, 2002, vol. 115, No. 11 (pp. 2381-2388).
Powell et al. "Compendium of Excipients for Parenteral Formulations," PDA Journal of Pharmaceutical Science and Technology, Sep./Oct. 1998, vol. 52, No. 2 (pp. 238-311).
Ramage et al., "5-hydroxytryptamine and cardiovascular regulation," Trends in Pharmacological Sciences, Sep. 2008, vol. 29, No. 9 (pp. 472-481).
Ramilowski et al., " A draft network of ligand-receptor-mediated multicellular signalling in human," Nature Communications, 2016, vol. 6, No. 7866 (pp. 1-11).

(56) References Cited

OTHER PUBLICATIONS

Ramos et al., "An inducible caspase 9 suicide gene to improve the safety of mesenchymal stromal cell therapies," Stem Cells, Jun. 2010, vol. 28, No. 6 (pp. 1107-1115).
Ran et al., "Double Nicking by RNA-guided CRISPR Cas9 for enhanced genome editing specificity", Cell, Sep. 12, 2013, vol. 154 (pp. 1380-1389).
Ran et al., "Genome engineering using the CRISPR-Cas9 system," Nature Protocols, 2013, vol. 8 (pp. 2281-2308).
Reigstad et al., "Gut microbes promote colonic serotonin production through an effect of short-chain fatty acids on enterochromaffin cells," The Journal of the federation of American Societies for Experimental Biology, Apr. 2015, vol. 29, No. 4 (pp. 1395-1403).
Restifo et al., "Adoptive Immunotherapy for Cancer: Harnessing the T Cell Response", Nature Reviews Immunology, Mar. 22, 2012, vol. 12, No. 4 (pp. 269-281).
Reynolds et al., "Immunity to the model intestinal helminth parasite Heligmosomoides polygyrus", Seminars in immunopathology, 2012, vol. 34 (pp. 829-846).
Ritsma et al., "Intestinal crypt homeostasis revealed at single-stem-cell level by in vivo live imaging," Nature, Mar. 20, 2014, vol. 507, No. 7492 (pp. 362-365).
Rodriguez et al., "Machine learning. Clustering by fast search and find of density peaks," Science, Jun. 27, 2014, vol. 344, No. 6191 (pp. 1492-1496).
Rodriguez et al., "Targeted Chemical-Genetic Regulation of Protein Stability In Vivo," Chemistry & Biology, Mar. 23, 2012, vol. 19 (pp. 391-398).
Roesch et al., "Temporarily Distinct Subpopulation of Slow-Cycling Melanoma Cells is Required for Continuous Tumor Growth," Cell, May 14, 2010, vol. 141 (pp. 583-594).
Rosenberg et al., "Adoptive cell transfer as personalized immunotherapy for human cancer," Cancer Immunology and Immunotherapy, Apr. 2015, vol. 348, Issue 6230 (pp. 62-69).
Rosvall et al., "Maps of Random Walks on Complex Networks Reveal Community Structure," Proceedings of the National Academy of Sciences, USA, Jan. 29, 2008, vol. 105, No. 4 (pp. 1118-1123).
Rubin," The Bayesian Bootstrap," The Annals of Statistics, 1981, vol. 9, No. 1 (pp. 130-134).
Sadelain et al., "Eliminating Cells Gone Astray," New England Journal of Medicine, Nov. 3, 2011, vol. 365, No. 18 (pp. 1735-1737).
Saha et al., "Macrophage-derived extracellular vesicle-packaged WNTs rescue intestinal stem cells and enhance survival after radiation injury," Nature Communications, Oct. 13, 2016, vol. 7 (pp. 1-16).
Salzman et al., "Protection Against Enteric Salmonellosis in Transgenic Mice Expressing a Human Intestinal Defensin," Nature, Apr. 3, 2003, vol. 422, No. 6931 (pp. 522-526).
Sangiorgi et al., " Bmi1 is expressed in vivo in intestinal stem cells," Nature Genetics, Jul. 2008, vol. 40, No. 7 (pp. 915-920).
Sato et al., "Growing self-organizing mini-guts from a single intestinal stem cell: mechanism and applications," Science, Jun. 7, 2013, vol. 340, No. 6137 (pp. 1190-1194).
Sato et al., "Single Lgr5 Stem Cells Build Crypt-Villus Structures In Vitro without a Mesenchymal Niche," Nature, May 14, 2009, vol. 159, No. 7244 (pp. 262-265).
Schneider et al., "NIH Image to ImageJ: 25 years of image analysis," Nature Methods, Jul. 2012, vol. 9, No. 7 (pp. 671-675).
Shale et al., "CD4(+) T-cell subsets in intestinal inflammation," Immunological Reviews, 2013, vol. 252 (pp. 164-182).
Shalek et al., "Single-Cell RNA-Seq Reveals Dynamic Paracrine Control of Cellular Variation," Nature, Jun. 19, 2014, vol. 510 (pp. 363-369).
Shalem et al., "Genome-Scale CRISPR-Cas9 Knockout Screening in Human Cells," Science, Jan. 3, 2014, vol. 343 (pp. 84-87).
Shekhar et al., "Comprehensive Classification of Retinal Bipolar Neurons by Single-Cell Transcriptomics," Cell, Aug. 25, 2016, vol. 166, No. 5 (pp. 1308-1323).
Shields et al., "Microfluidic cell sorting: a review of the advances in the separation of cells from debulking to rare cell isolation," Lab Chip, Mar. 7, 2015, vol. 15, No. 5 (pp. 1230-1249).
Shmakov et al., "Discovery and Functional Characterization of Diverse Class 2 CRISPR-Cas Systems," Molecular Cell, Nov. 1, 2015, vol. 60, No. 3 (pp. 385-397).
Slaymaker et al., "Rationally engineered Cas9 nucleases with improved specificity," Science, Dec. 1, 2015, vol. 351, No. 6268 (pp. 84-88).
Snippert et al., "Intestinal crypt homeostasis results from neutral competition between symmetrically dividing Lgr5 stem cells," Cell, Oct. 1, 2010 Vol. 143, No. 1 (pp. 134-144).
Sokol et al., "Basophils function as antigen-presenting cells for an allergen-induced T helper type 2 response," Nature Immunology, Jul. 2009, vol. 10, No. 7 (pp. 713-720).
Stappenbeck et al., "The Role of Stromal Stem Cells in Tissue Regeneration and Wound Repair," Science, Jun. 26, 2009, vol. 324, No. 5935 (5 pages).
Strober et al., "Chronic Intestinal Inflammation: An Unexpected Outcome in Cytokine or T Cell Receptor Mutant Mice," Cell, Oct. 22, 1993, vol. 75, No. 2 (pp. 203-205).
Su et al., "Coinfection with an intestinal helminth impairs host innate immunity against Salmonella enterica serovar Typhimurium and exacerbates intestinal inflammation in mice," Infection and Immunity, Sep. 2014, vol. 82, No. 9 (pp. 3855-3866).
Su et al., "Development of fatal intestinal inflammation in MyD88 deficient mice co-infected with helminth and bacterial," PLOS Neglected Tropical Diseases, Jul. 2014, vol. 8, No. 7 (pp. 1-13).
Swiech et al., "In vivo interrogation of gene function in the mammalian brain using CRISPR-Cas9," Nature Biotechnology, 2014, vol. 33 (pp. 102-106) [Including Supplemental information, 4 pages].
Tanoue et al., "Development and maintenance of intestinal regulatory T cells," Nature Reviews Immunology, May 2016, vol. 16, No. 5 (pp. 295-309).
Tirosh et al., "Dissecting The Multicellular Ecosystem of Metastatic Melanoma By Single-Cell RNA- Seq," Science, Apr. 8, 2016, vol. 352, No. 6282 (23 pages).
Trapnell et al., "The Dynamics and Regulators of Cell Fate Decisions are Revealed by Pseudotemporal Ordering of Single Cells," Nature Biotechnology, Apr. 2014, vol. 32, No. 4 (pp. 381-386).
Tuerk et al., "Systematic evolution of ligands by exponential enrichment: RNA ligands to bacteriophage T4 Dna polymerase," Science, Aug. 3, 1990, vol. 249, No. 4968 (pp. 505-510).
Van Ampting et al., "Intestinally secreted C-type lectin Reg3b attenuates salmonellosis but not listeriosis in mice," Infection and Immunity, Mar. 2012, vol. 80, No. 3 (pp. 1115-1120).
Van Der Flier et al., "Stem Cells, Self-Renewal, and Differentiation in the Intestinal Epithelium," Annual Review of Physiology, 2009, vol. 71 (pp. 241-260).
Van Der Maaten et al., "Visualizing Data Using t-SNE," Journal of Machine Learning Research, Nov. 2008, vol. 9 (pp. 2579-2605).
Van Der Maaten, "Accelerating t-SNE using Tree-Based Algorithms", Journal of Machine Learning Research, Oct. 2014, vol. 15, No. 1 (pp. 3221-3245).
Van Der Meer Van-Kraaj et al., "Dietary modulation and structure prediction of rat mucosal pentraxin (Mptx) protein and loss of function in humans," Genes and Nutrition, Dec. 2007, vol. 2, No. 3 (pp. 275-285).
Van Es et al., "Notch/gamma-secretase inhibition turns proliferative cells in intestinal crypts and adenomas into goblet cells," Nature, Jun. 16, 2005, vol. 435 (pp. 959-963).
Vassen et al., "Gfi1b:green fluorescent protein knock-in mice reveal a dynamic expression pattern of Gfi1b during hematopoiesis that is largely complementary to Gfi1," Blood, Mar. 15, 2007, vol. 109, No. 6 (pp. 2356-2364).
Von Essen, "Constitutive and ligand-induced TCR degradation," Journal of Immunology, vol. 173, No. 1 (pp. 384-393).
Von Moltke et al., Tuft-cell-derived IL-25 regulates an intestinal ILC2-epithelial response circuit, Nature, Jan. 14, 2016, vol. 529, No. 785 (pp. 221-225).

(56) References Cited

OTHER PUBLICATIONS

Wagner et al., "Revealing the vectors of cellular identity with single-cell genomics," Nature Biotechnology, Nov. 8, 2016, vol. 34, No. 11 (pp. 1145-1160).

Wang et al., "Genetic screens in human cells using the CRISPR/Cas9 system," Science, Jan. 3, 2014, vol. 343 No. 6166 (pp. 80-84).

Wang et al., "One-Step Generation Of Mice Carrying Mutations In Multiple Genes By CRISPR/Cas- Mediated Genome Engineering," Cell, May 9, 2013, vol. 153 (pp. 910-918).

Wang, Wei, "Lyophilization and development of solid protein pharmaceuticals", International Journal of Pharmaceutics, Aug. 2000, vol. 203, Issues 1-2 (pp. 1-60).

Watson et al., "SHP-1: the next checkpoint target for cancer immunotherapy?" Biochemical Society Transactions, Apr. 15, 2016, vol. 44, No. 2 (pp. 356-362).

Wlodarska et al., "NLRP6 inflammasome orchestrates the colonic host-microbial interface by regulating goblet cell mucus secretion," Cell, Feb. 27, 2014 (vol. 156, No. 5 (pp. 1045-1059).

Worthington, et al., "Enteroendocrine Cells-Sensory Sentinels of the Intestinal Environment and Orchestrators of Mucosal Immunity," Mucosal Immunology, vol. 11, No. 1, Jan. 2018, 3-20.

Wu et al., "Remote control of therapeutic T cells through a small molecule-gated chimeric receptor," Science, Oct. 16, 2015, vol. 350, No. 6258 (pp. 1-21).

Wu et al., "Genome-wide binding of the CRISPR endonuclease Cas9 in mammalian cells," Nature Biotechnology, 2014, Including Supplemental information, 2 pages (pp. 1-9).

Yan et al., "Intestinal Enteroendocrine Lineage Cells Possess Homeostatic and Injury-Inducible Stem Cell Activity," Cell Stem Cell, Jul. 6, 2017, vol. 21, No. 1 (pp. 78-90).

Young et al., "Expression of Taste Molecules in the Upper Gastrointestinal Tract in Humans with and Without Type 2 Diabetes," Gut, Mar. 2009, vol. 58, No. 3, (pp. 337-346).

Young et al., "Gene ontology analysis for RNA-seq: accounting for selection bias," Genome Biology, 2010, vol. 11, No. R14 (pp. 1-12).

Zeisel et al., Brain Strcuture: "Cell Types in The Mouse Cortex and Hippocampus Revealed by Single-cell RNA-seq," Science, Mar. 6, 2015, vol. 347, No. 6226 (pp. 1138-1142).

Zetsche et al., "A split-Cas9 architecture for inducible genome editing and transcription modulation", Nature Biotechnology, Feb. 2015, vol. 33, No. 2 (pp. 139-142).

Zetsche et al., "Cpf1 is a single RNA-guided endonuclease of a class 2 CRISPR-Cas system," Cell, Oct. 22, 2015, vol. 163 (pp. 759-771).

Zhang et al., "AnimalTFDB: a comprehensive animal transcription factor database," Nucleic Acids Research, 2012, vol. 40 (pp. 1-6).

Zhang et al., "Efficient Construction Of Sequence-Specific TAL Effectors For Modulating Mammalian Transcription," Nature Biotechnology, Feb. 2011 (published on-line Jan. 19, 2011), vol. 29, No. 2 (pp. 149-153).

Zheng et al. "Haplotyping germline and cancer genomes with high-throughput linked-read sequencing" Nature Biotechnology, Feb. 1, 2016, vol. 34, No. 3 (pp. 303-311) [with Supplemental Material].

Zhou et al., "Aptamer-targeted cell-specific RNA interference," Silence, Feb. 1, 2010, vol. 1, No. 4 (10 pages).

Zhou et al., "Long-term outcome after haploidentical stem cell transplant and infusion of T cells expressing the inducible caspase 9 safety transgene," Blood, Jun. 19, 2014, vol. 123, No. 25 (pp. 3895-3905).

Ziegler et al., "Sensing the Outside World: TSLP Regulates Barrier Immunity," Nature Immunology, Apr. 2010, vol. 11, No. 4 (pp. 289-293).

* cited by examiner

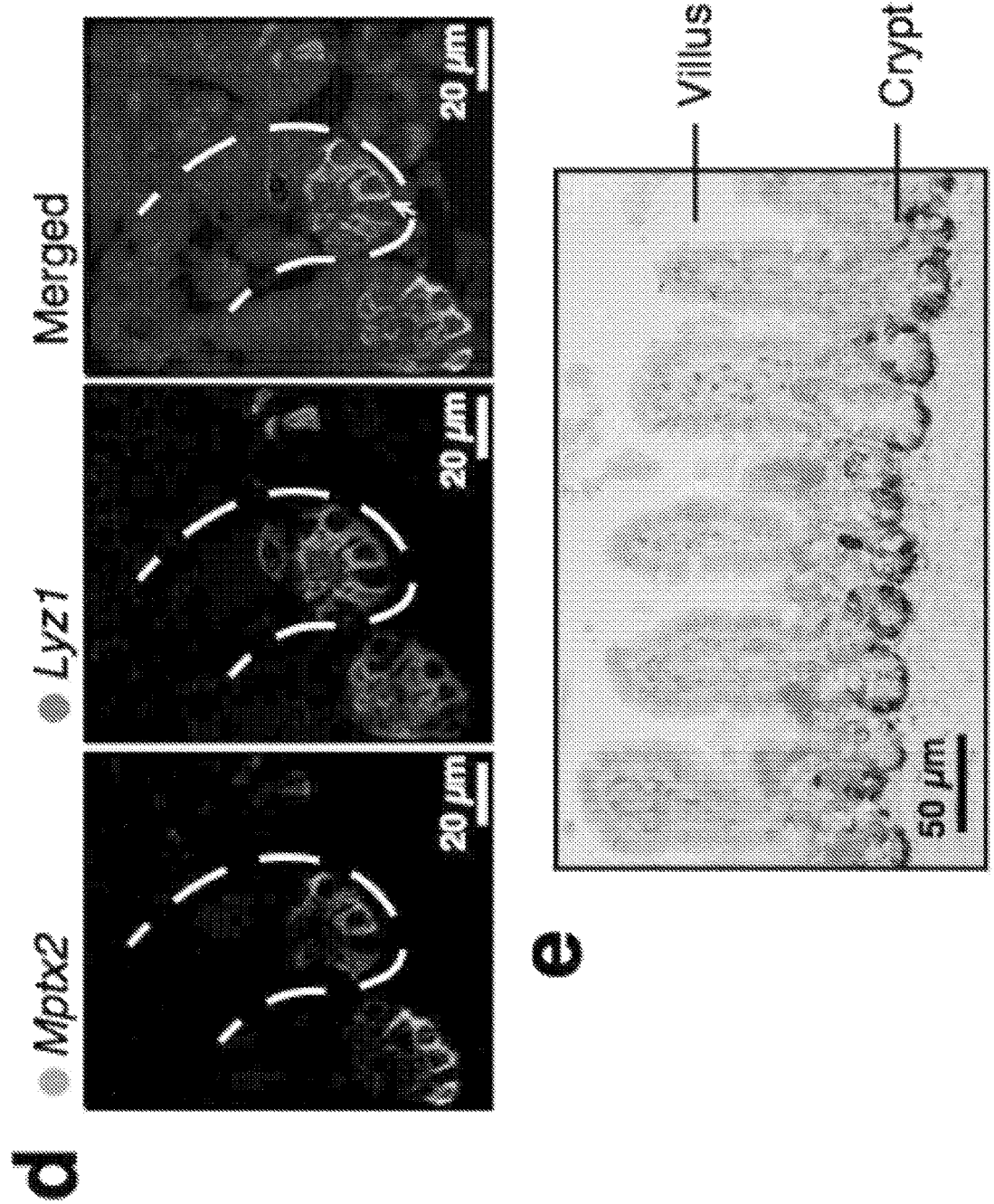
FIG. 1D-E

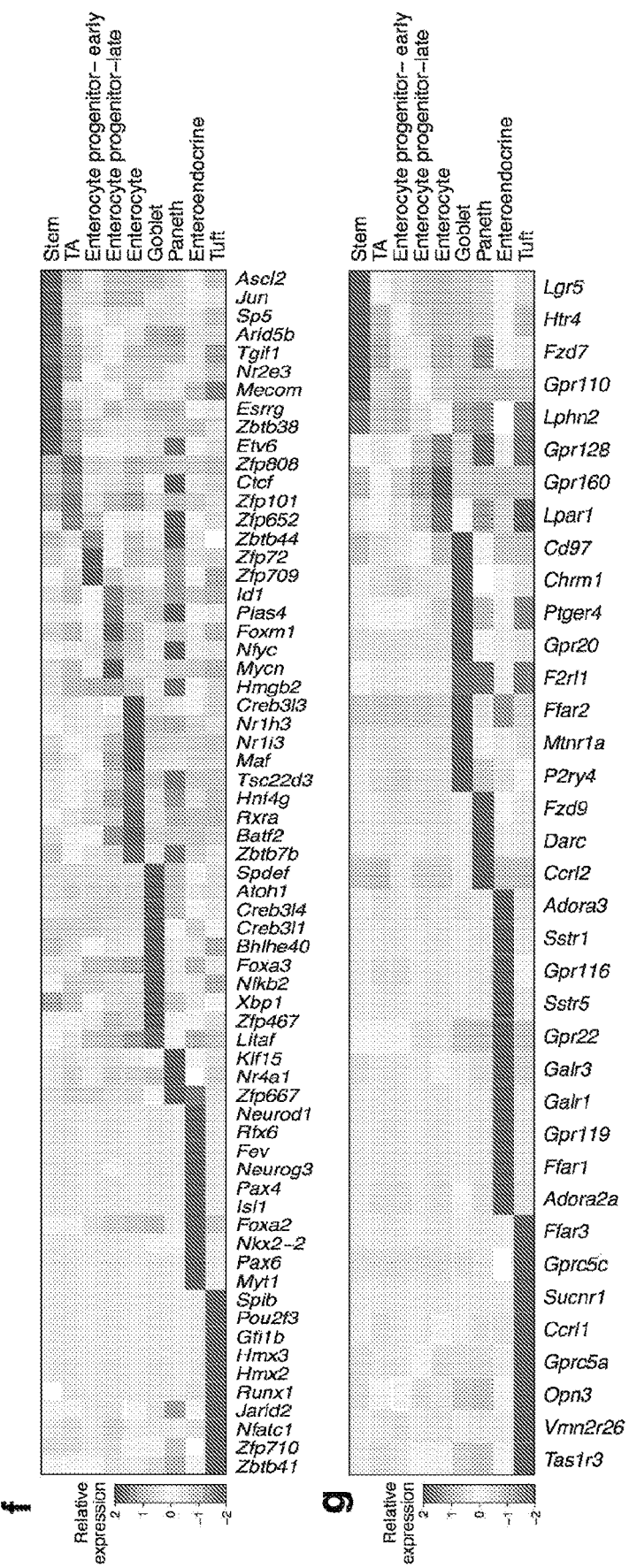
FIG. 1 F-G

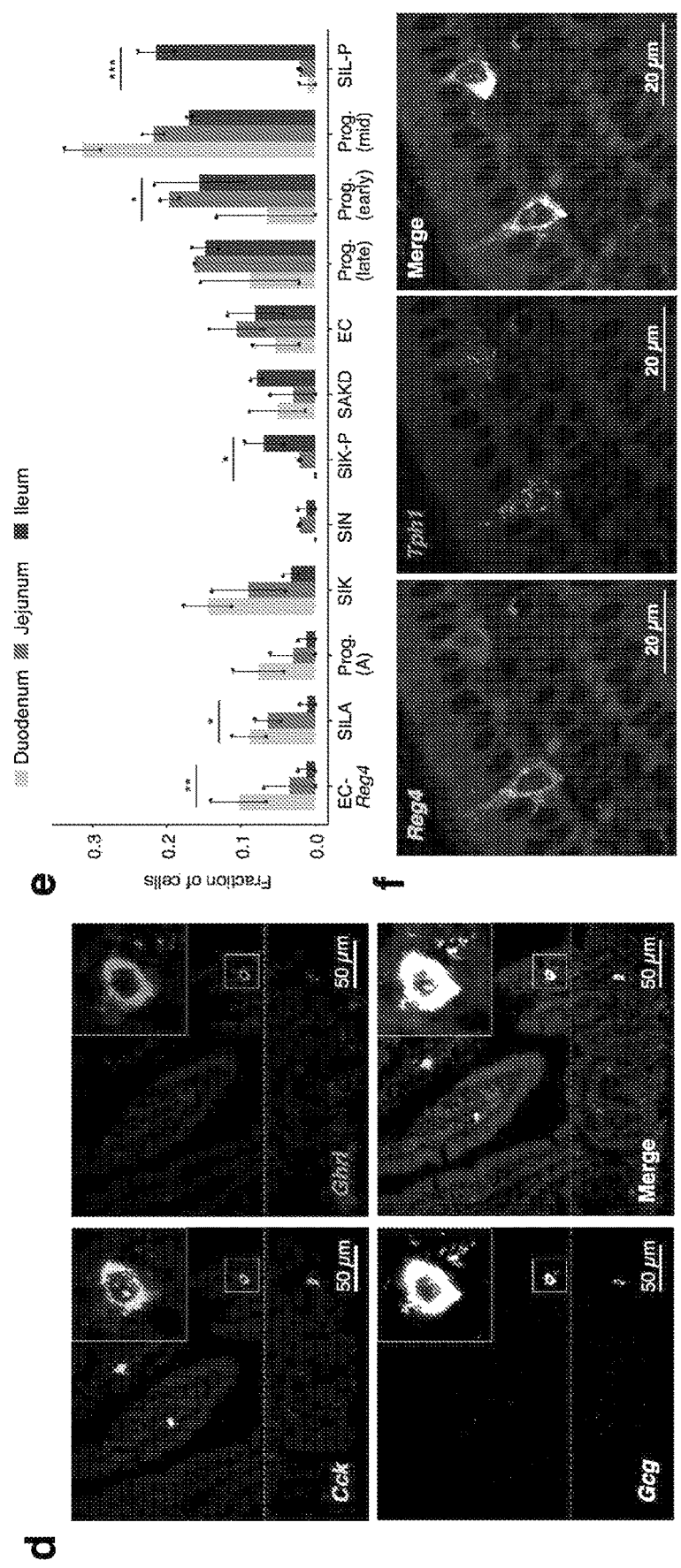
FIG. 3 D-F

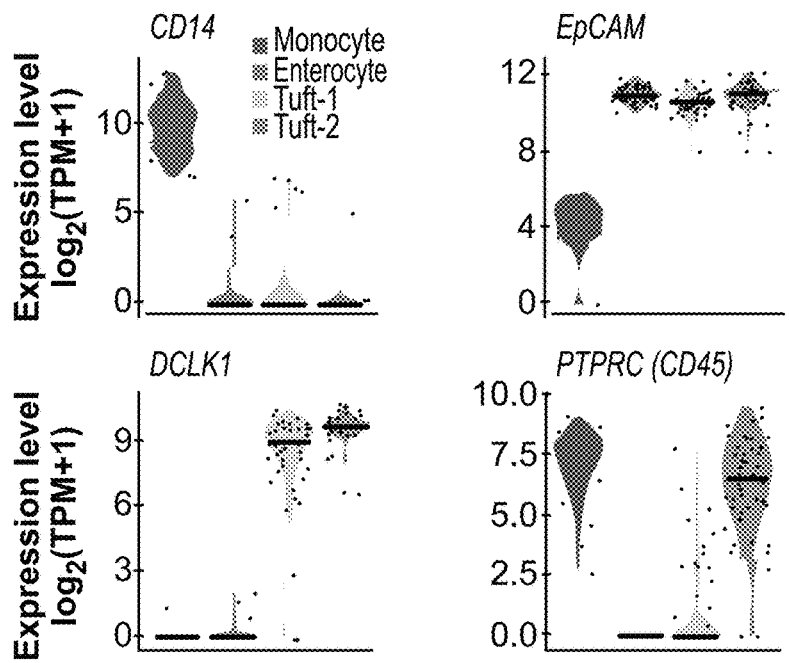
FIG. 4F
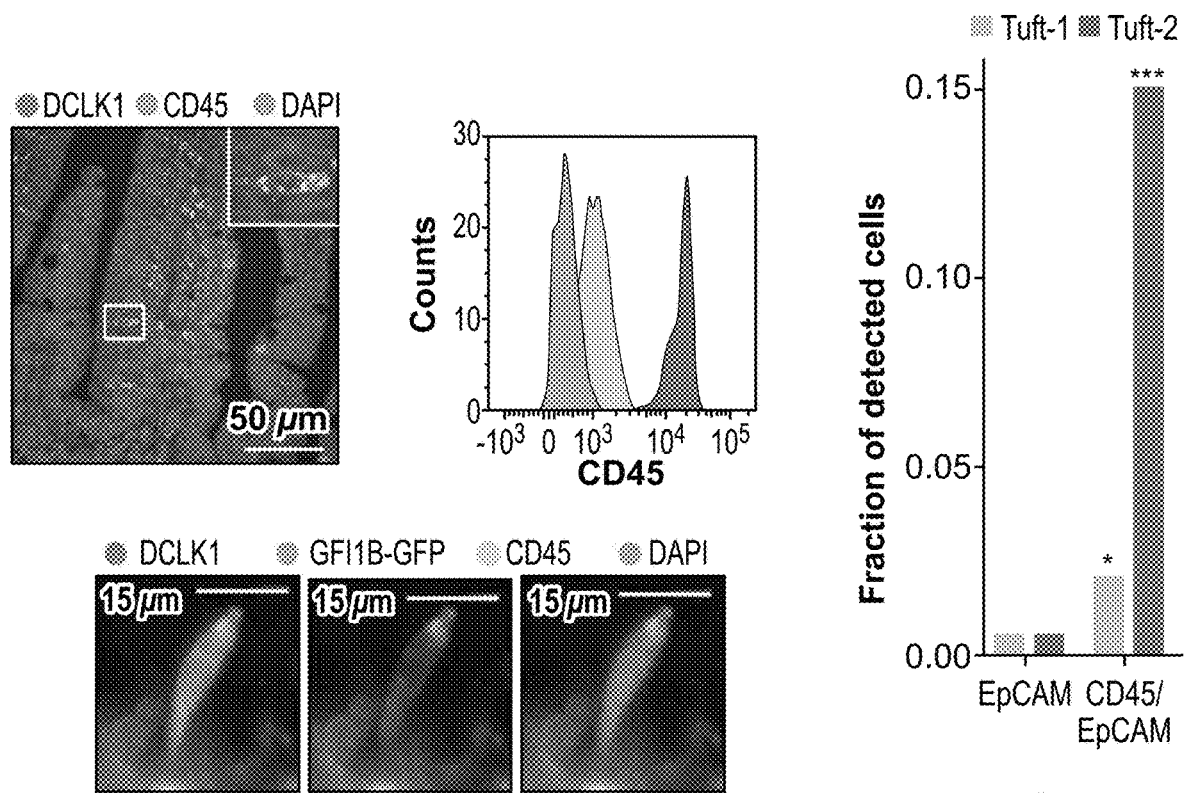
FIG. 4G
FIG. 4H

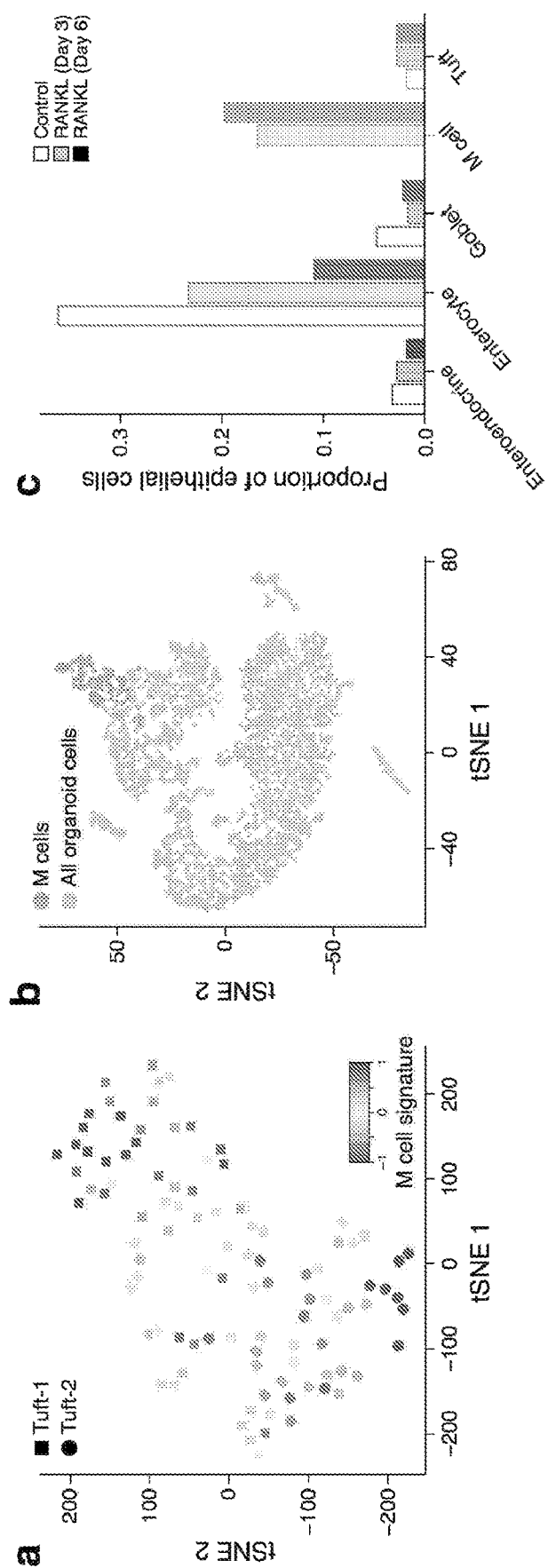
FIG. 5 A-C

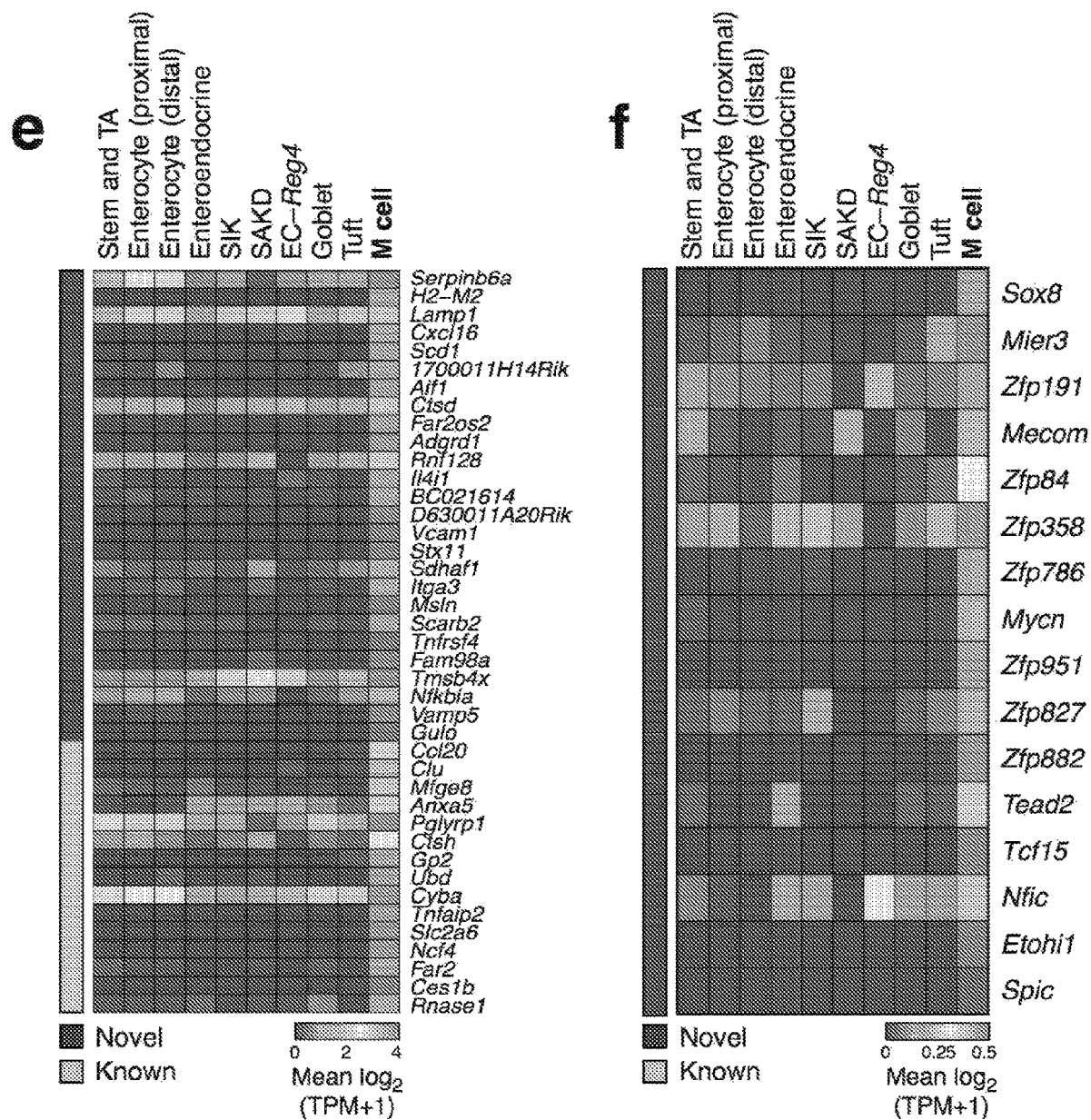
FIG. 5 E-F

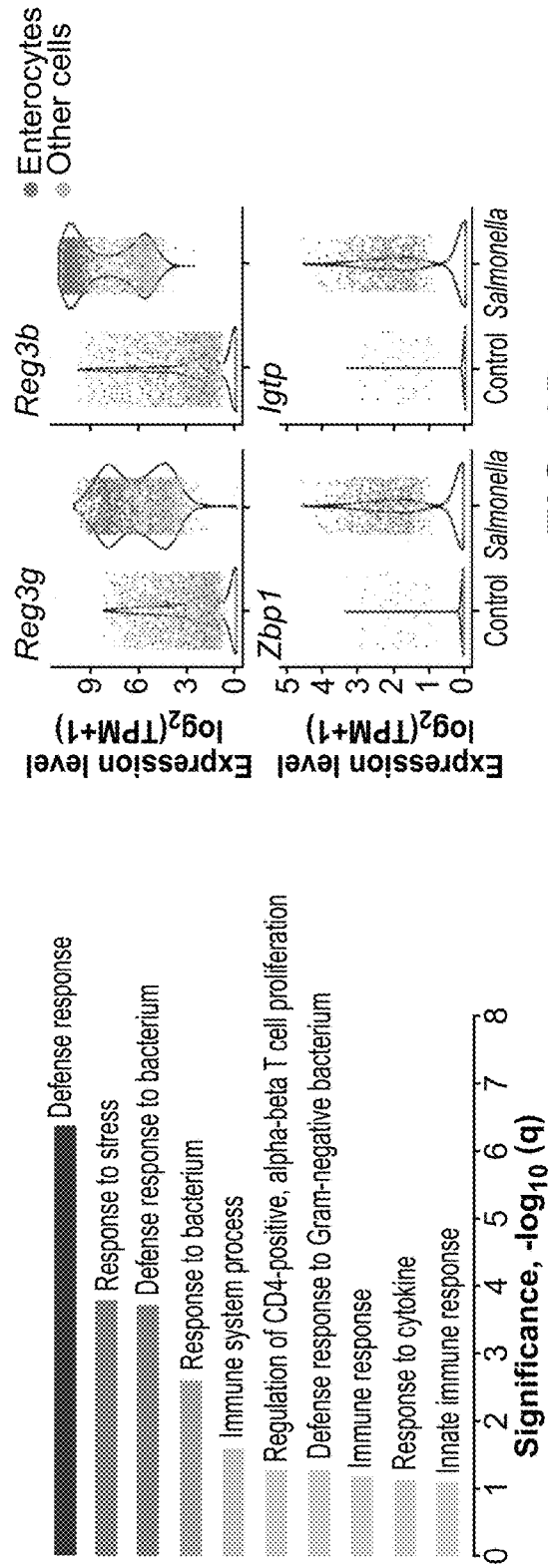
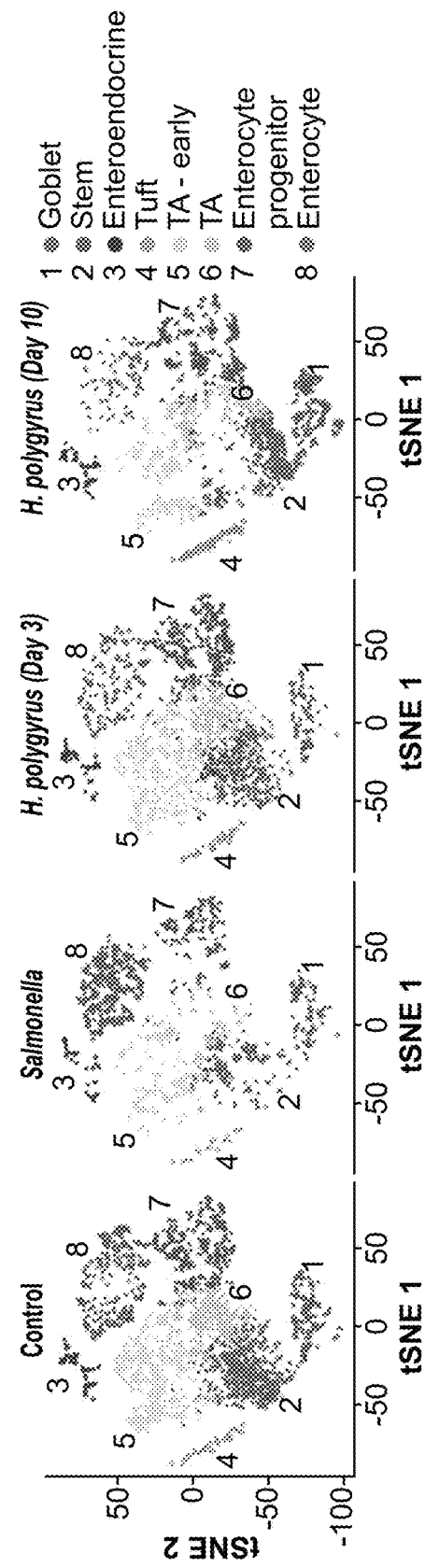
FIG. 6A
FIG. 6B
FIG. 6C

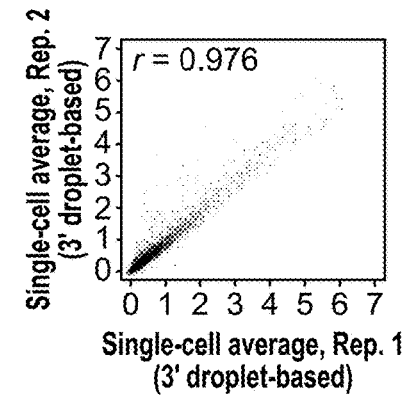
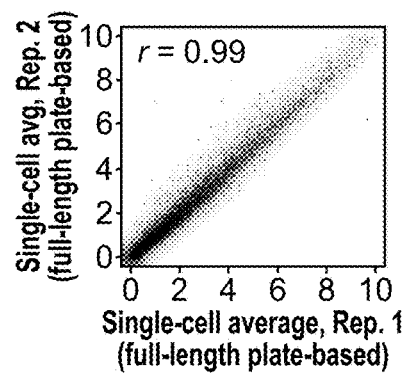
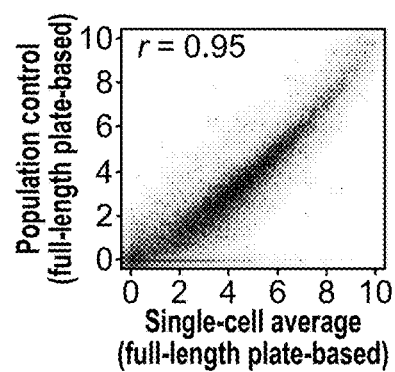
FIG. 7F
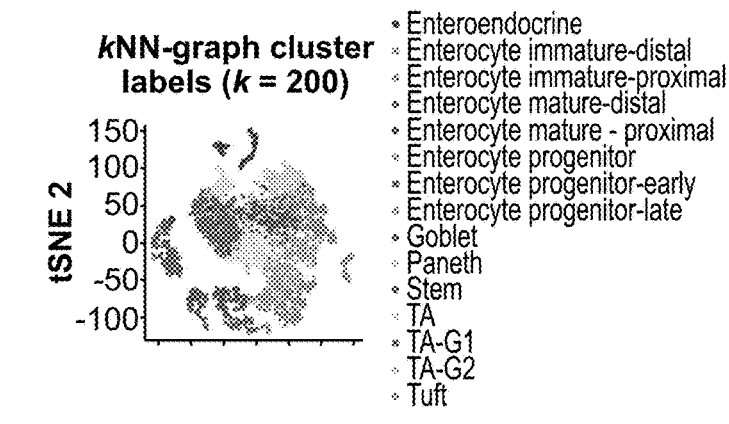
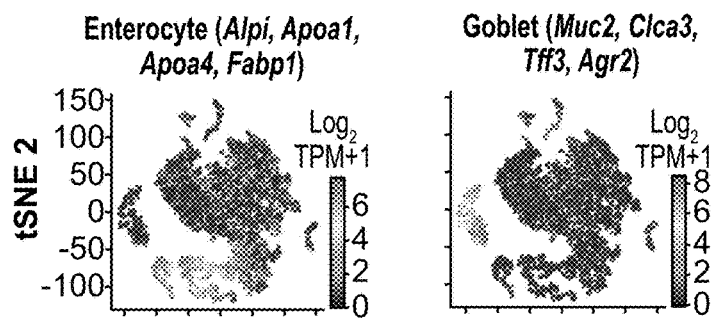
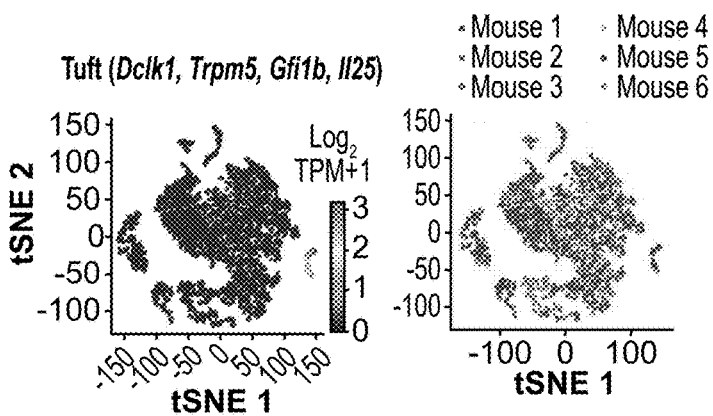
FIG. 7G

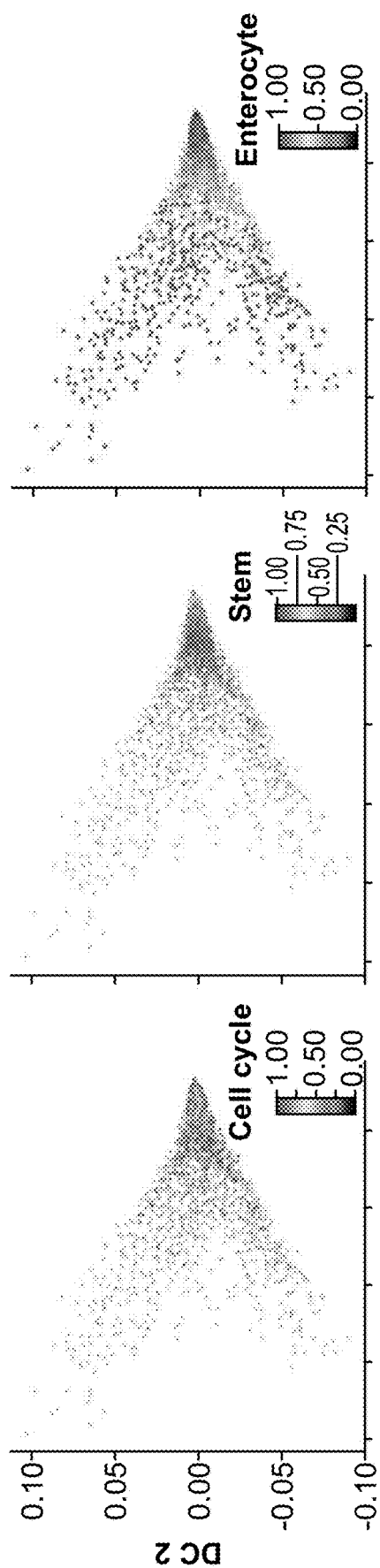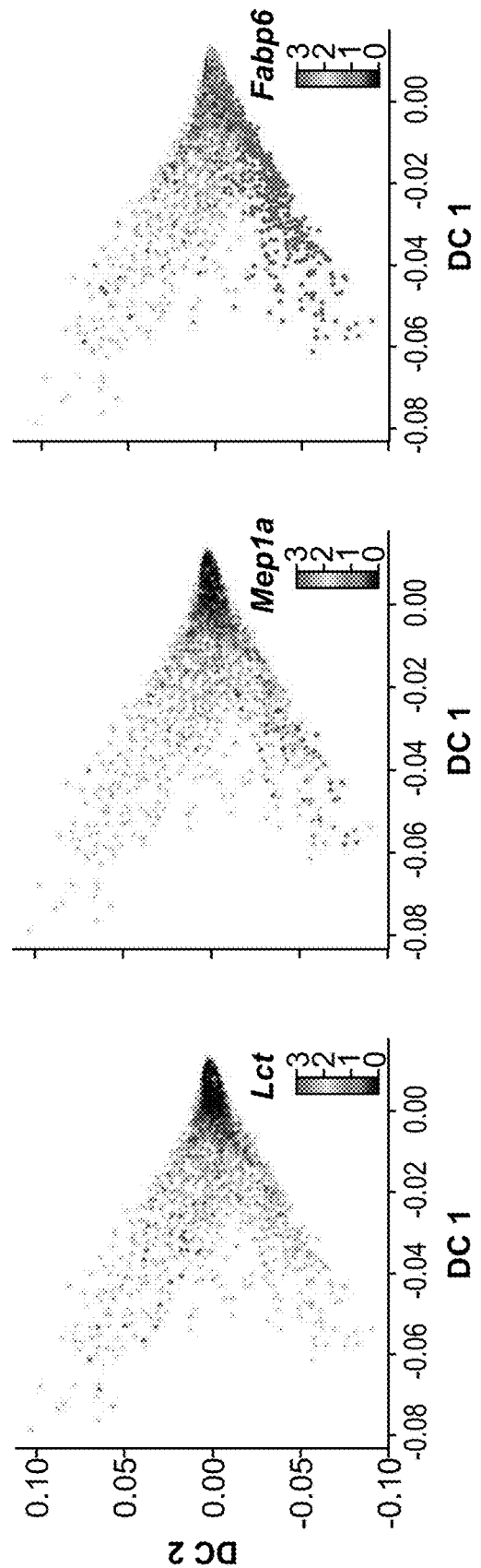
FIG. 10A  FIG. 10B  FIG. 10C
FIG. 10D  FIG. 10E  FIG. 10F

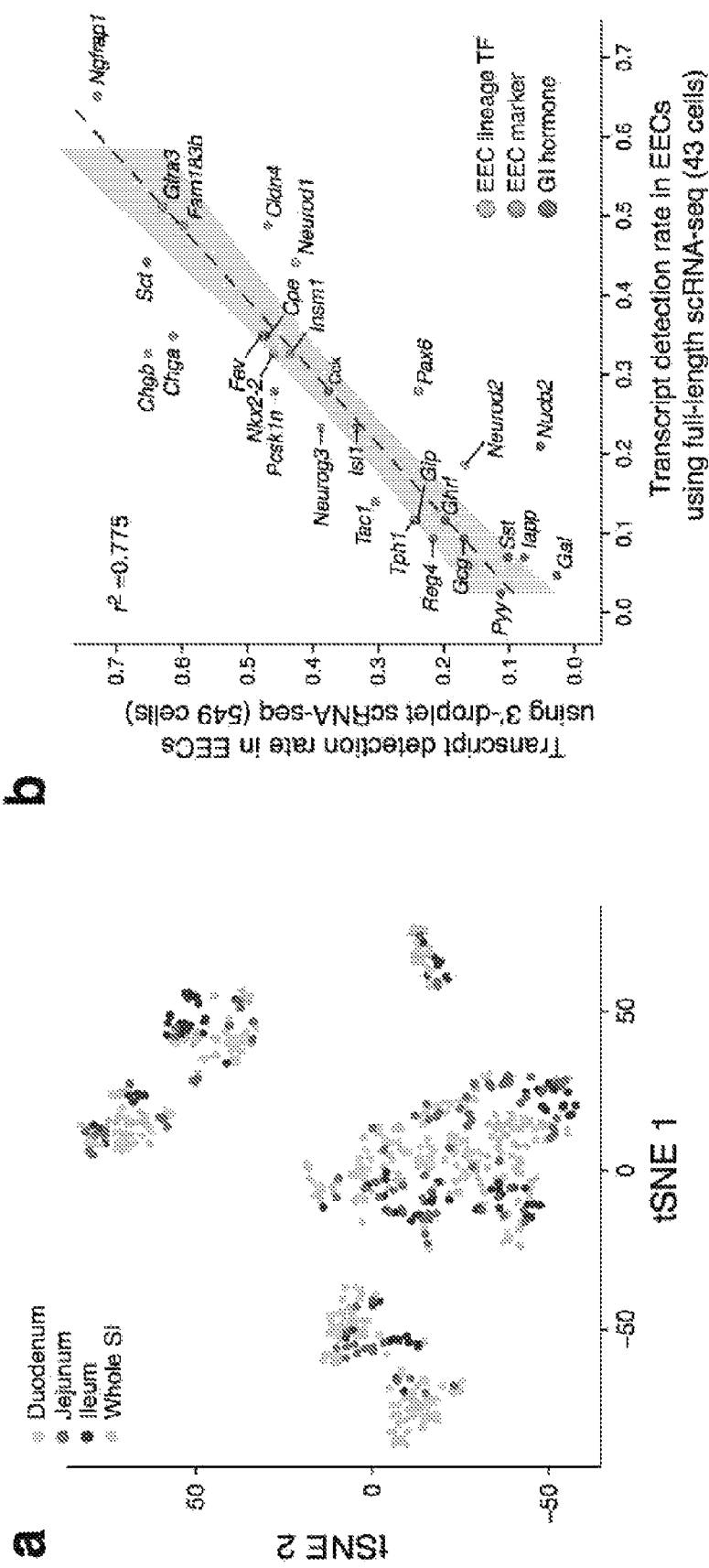
FIG. 11 A-B

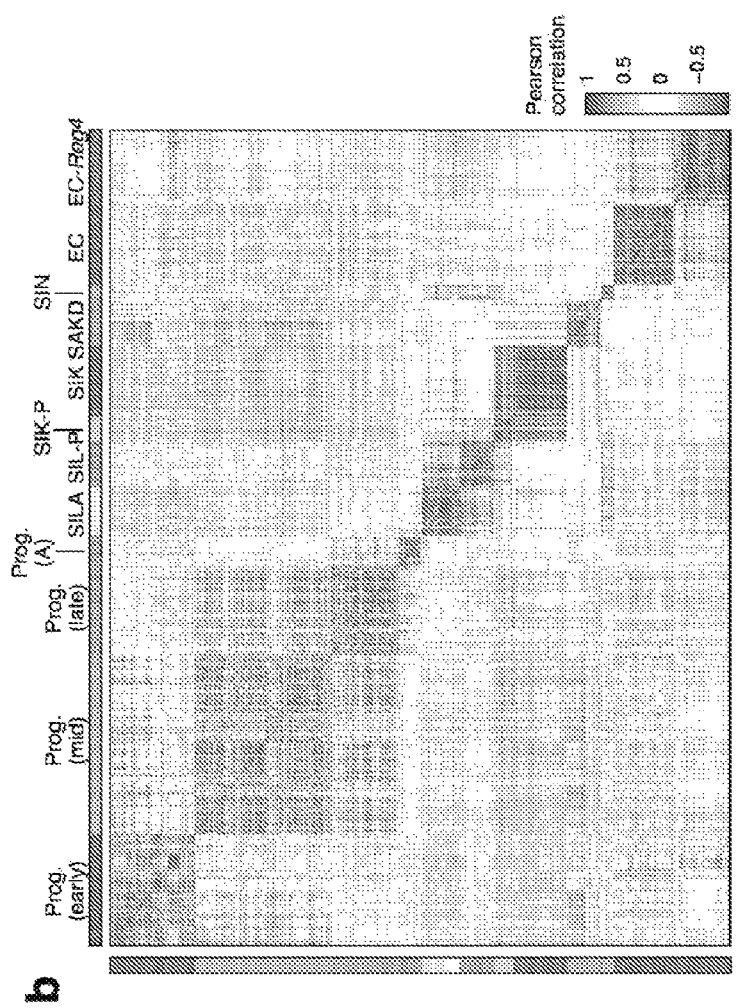
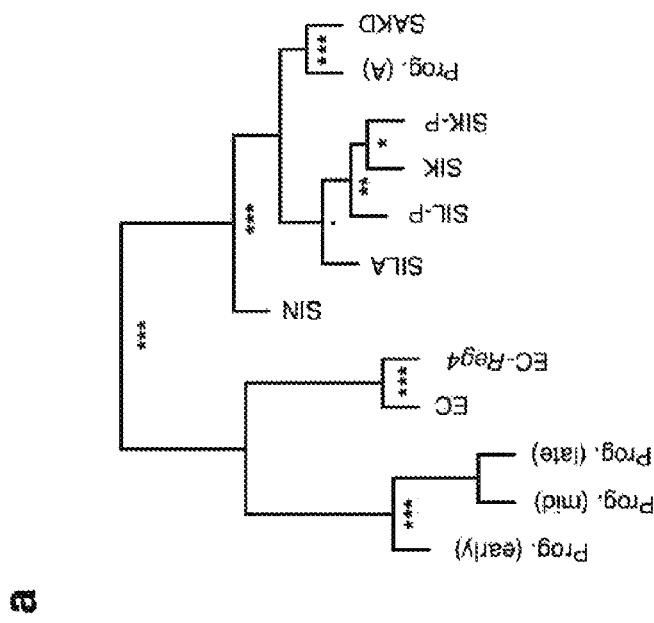
FIG. 12 A-B

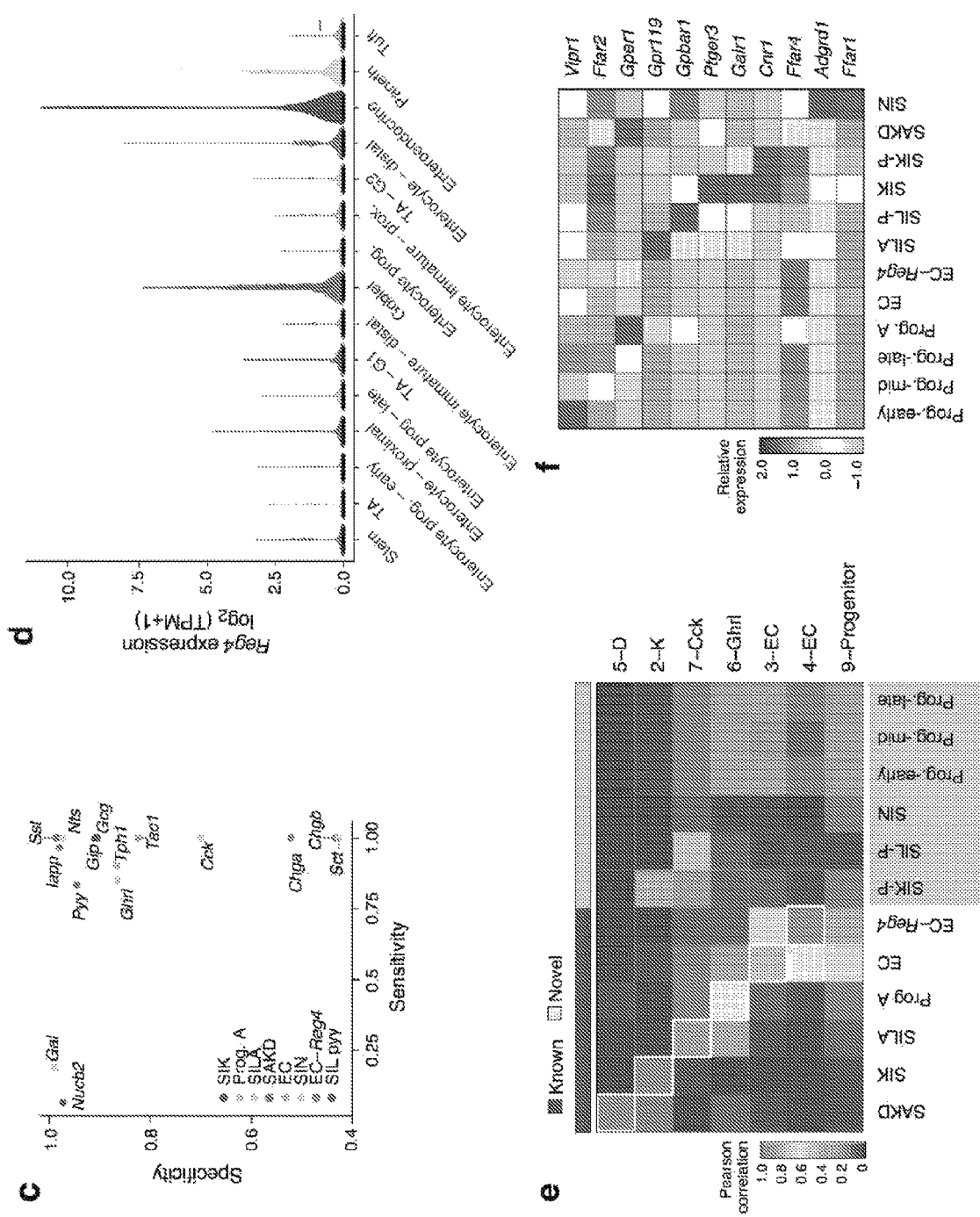
FIG. 12 C-F

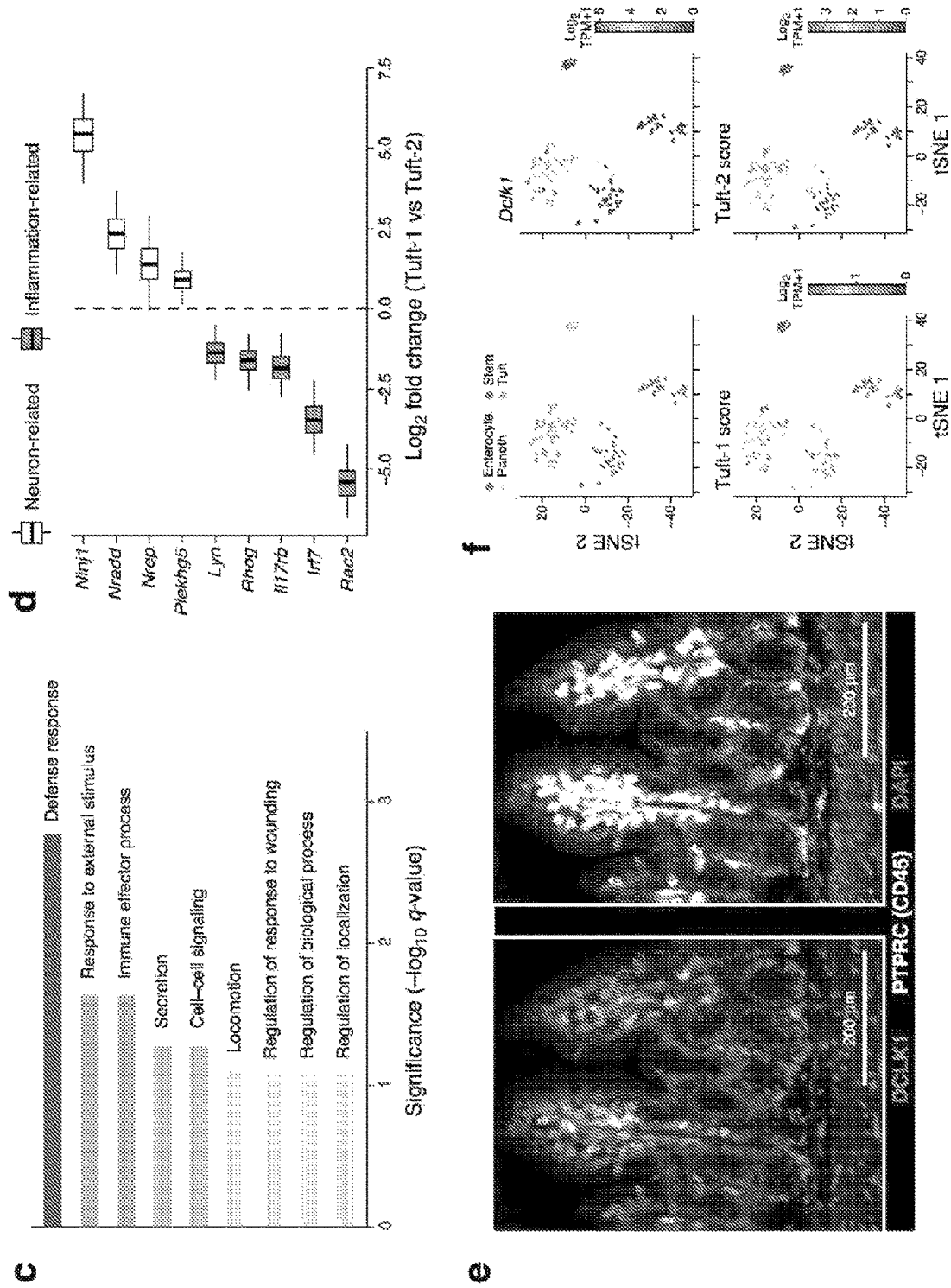
FIG. 13 C-F

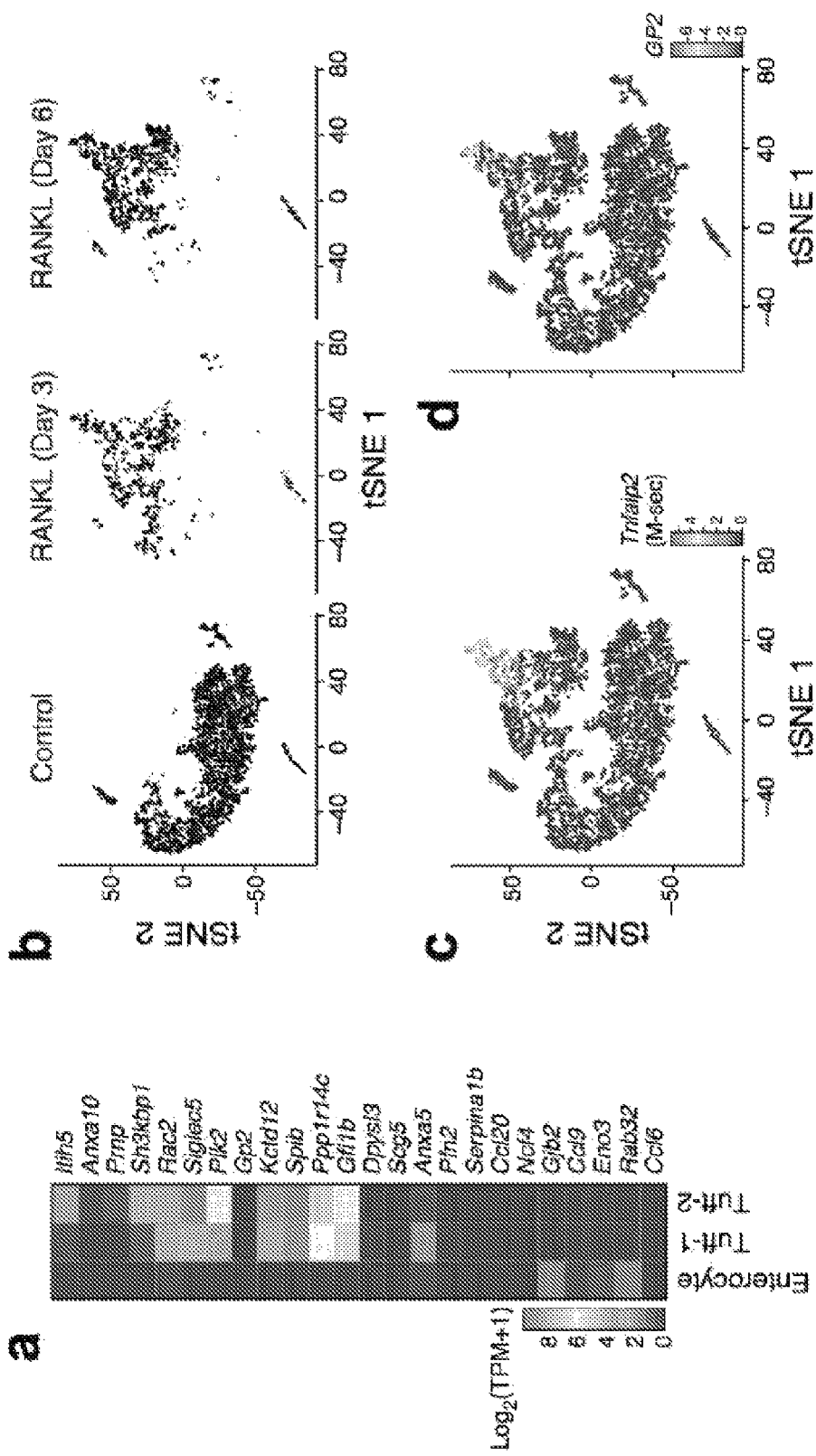
FIG. 14 A-D

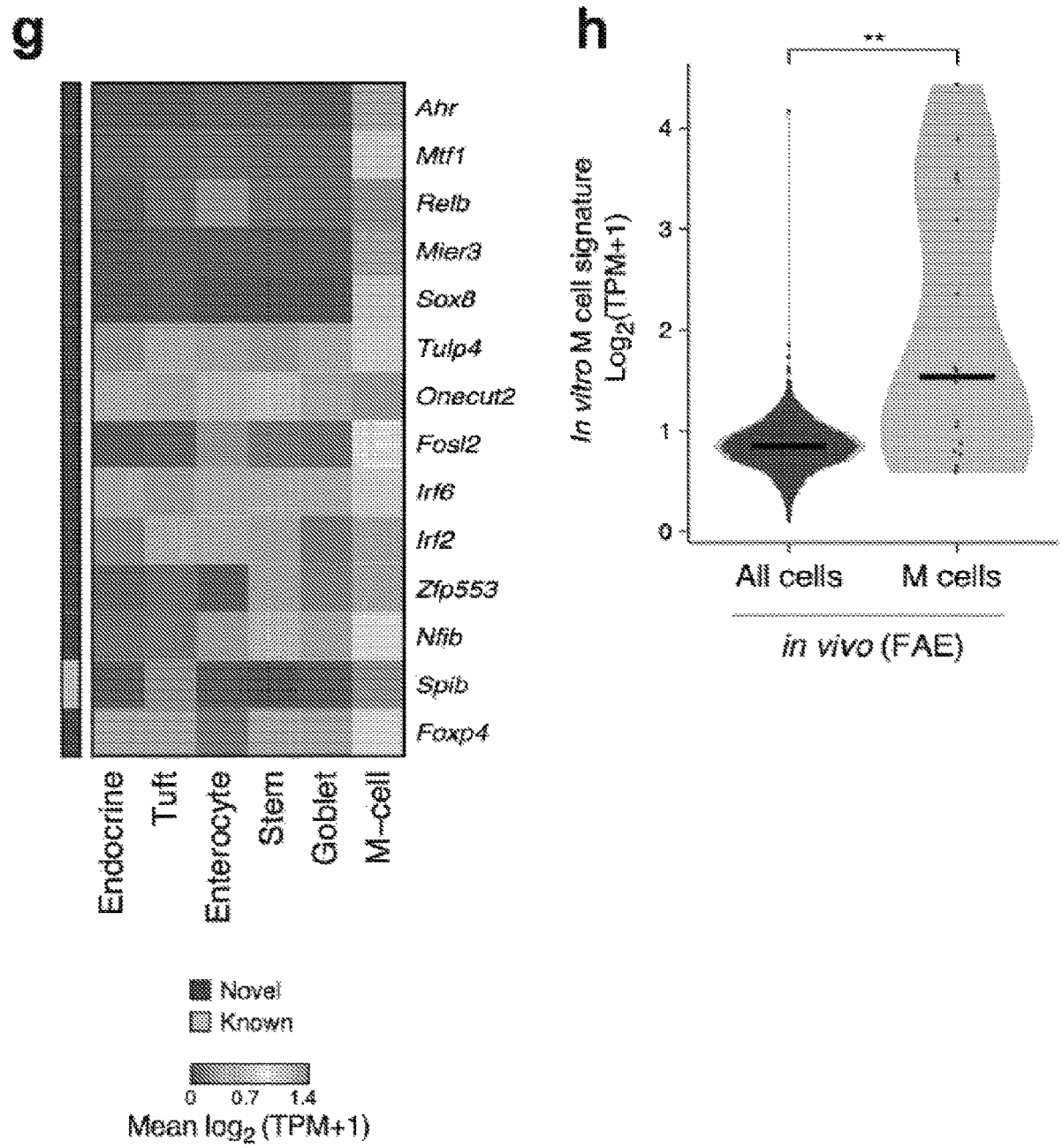
FIG. 14 G-H

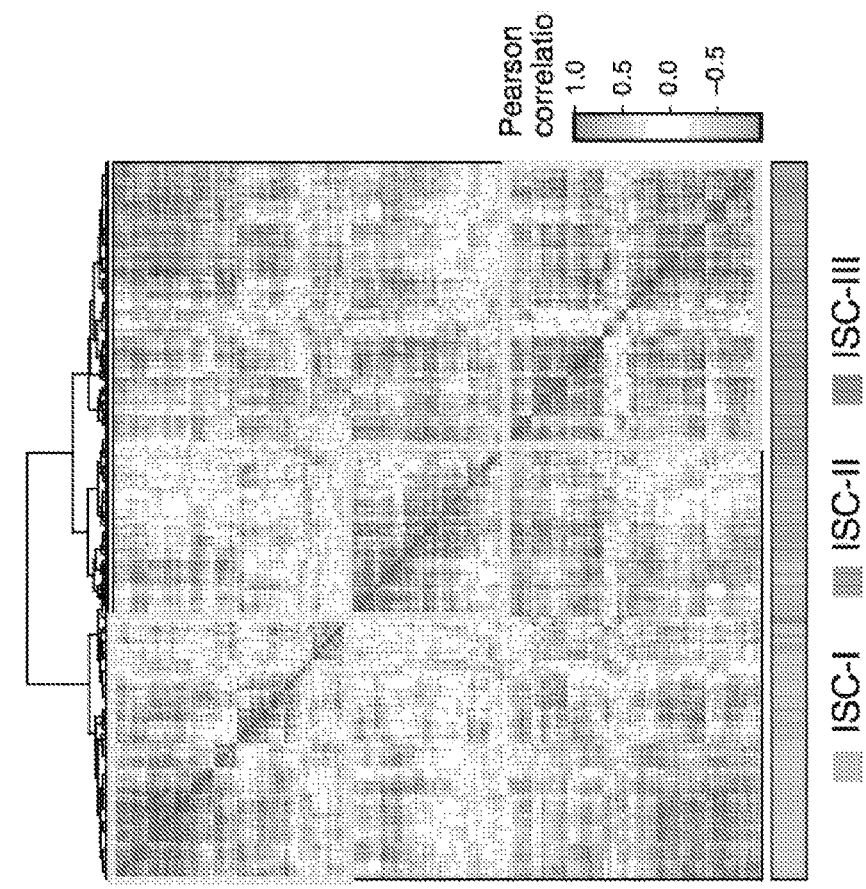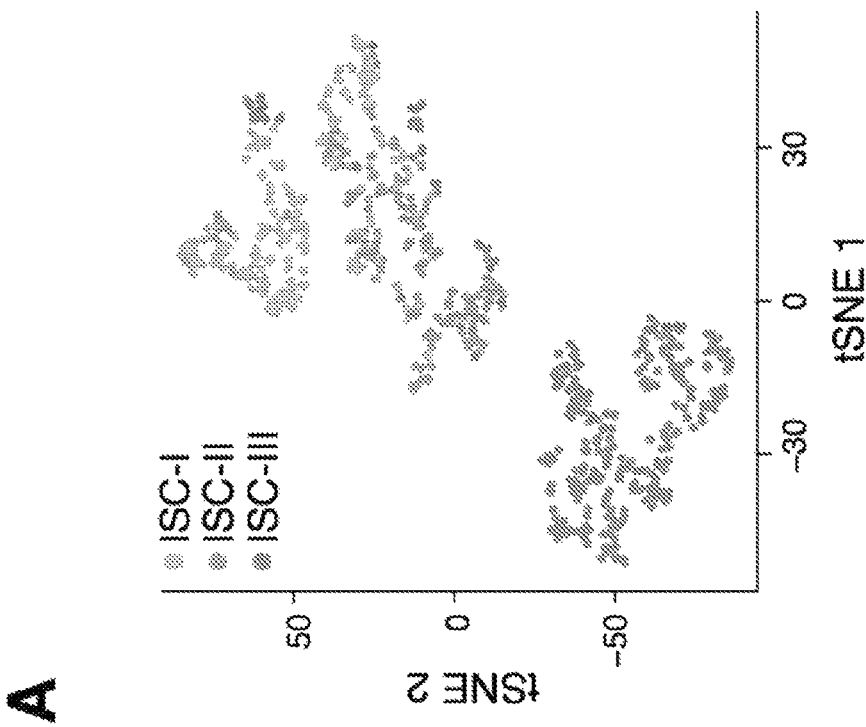
FIG. 17 A-B

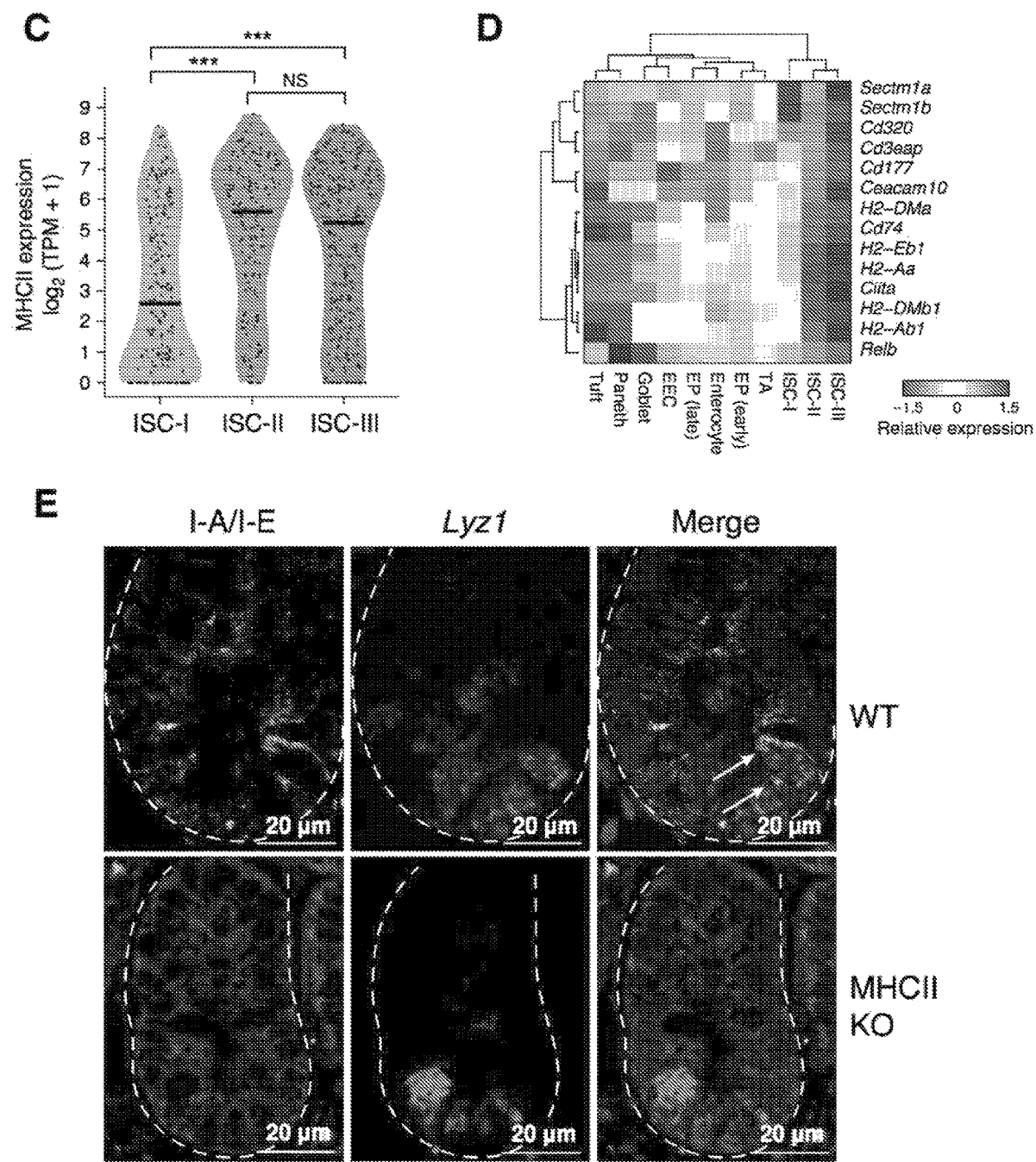
FIG. 17C-E

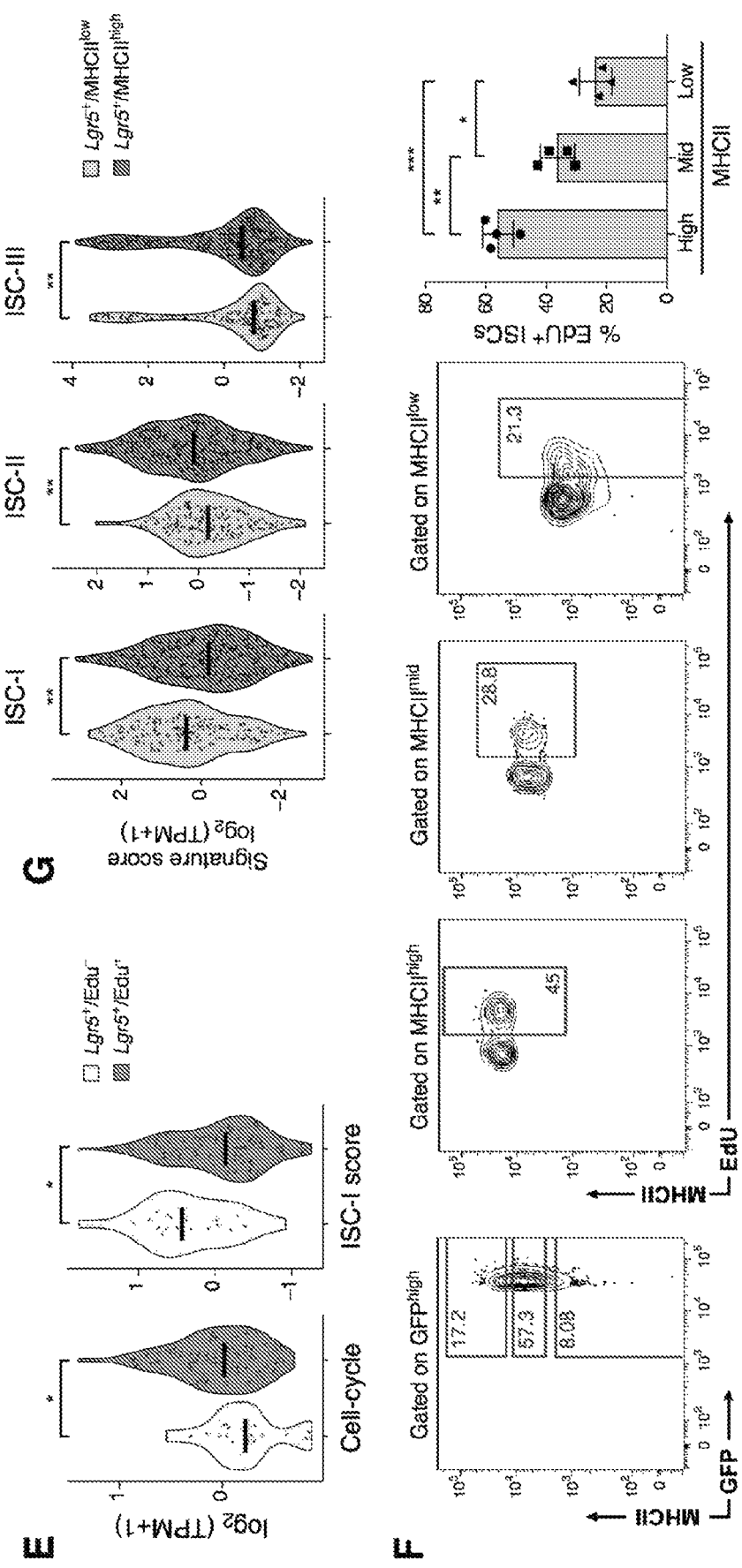
FIG. 18E-F

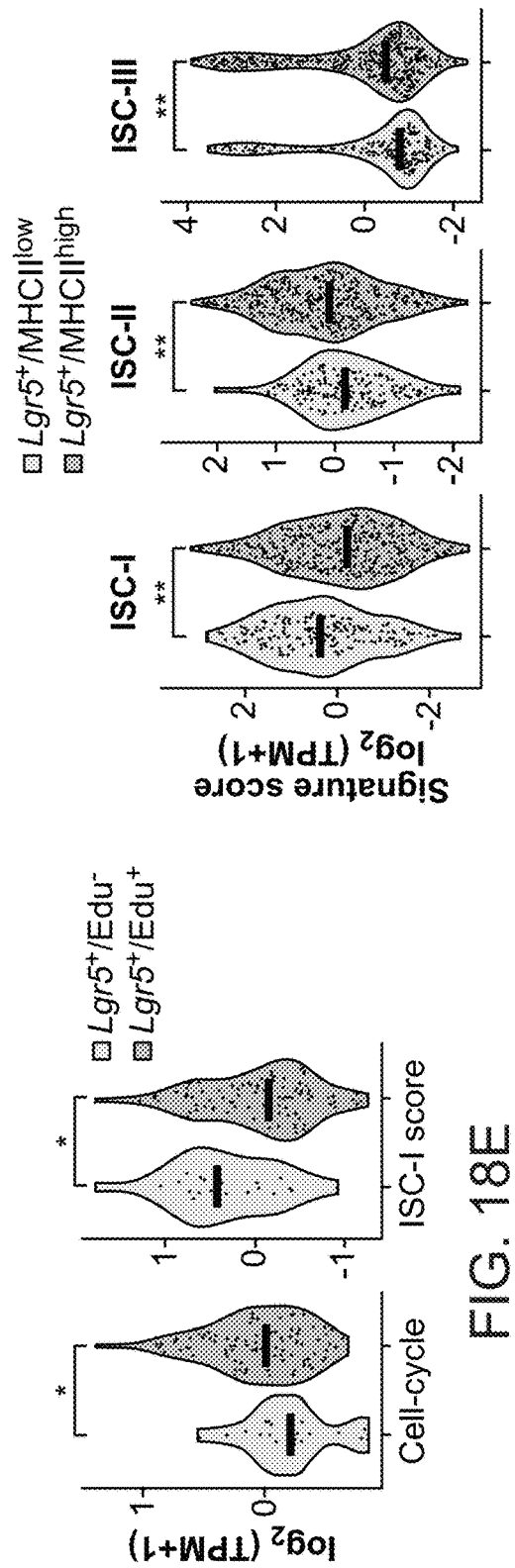
FIG. 18E
FIG. 18G
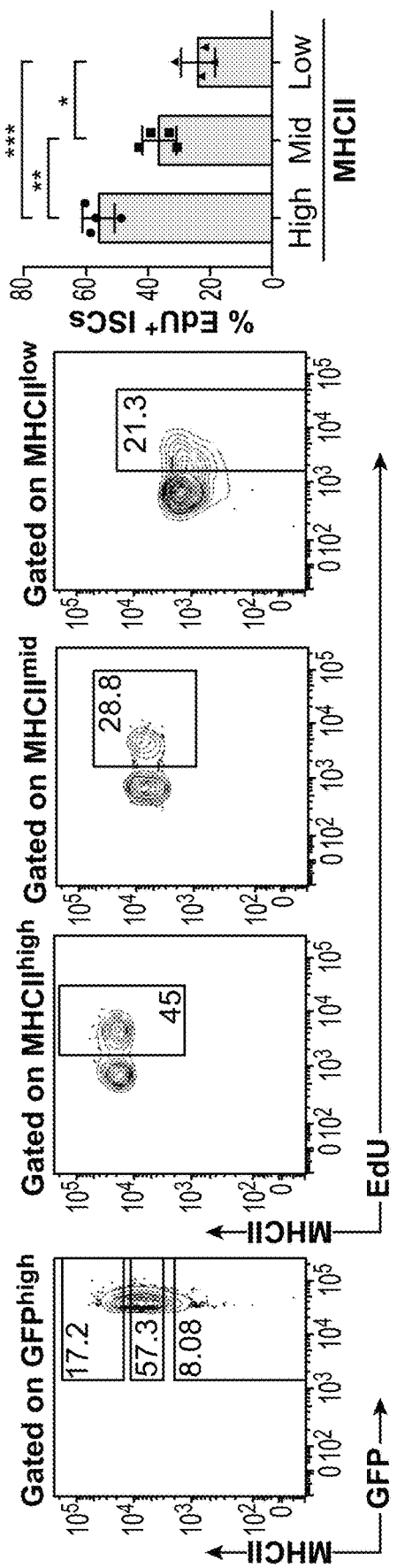
FIG. 18F

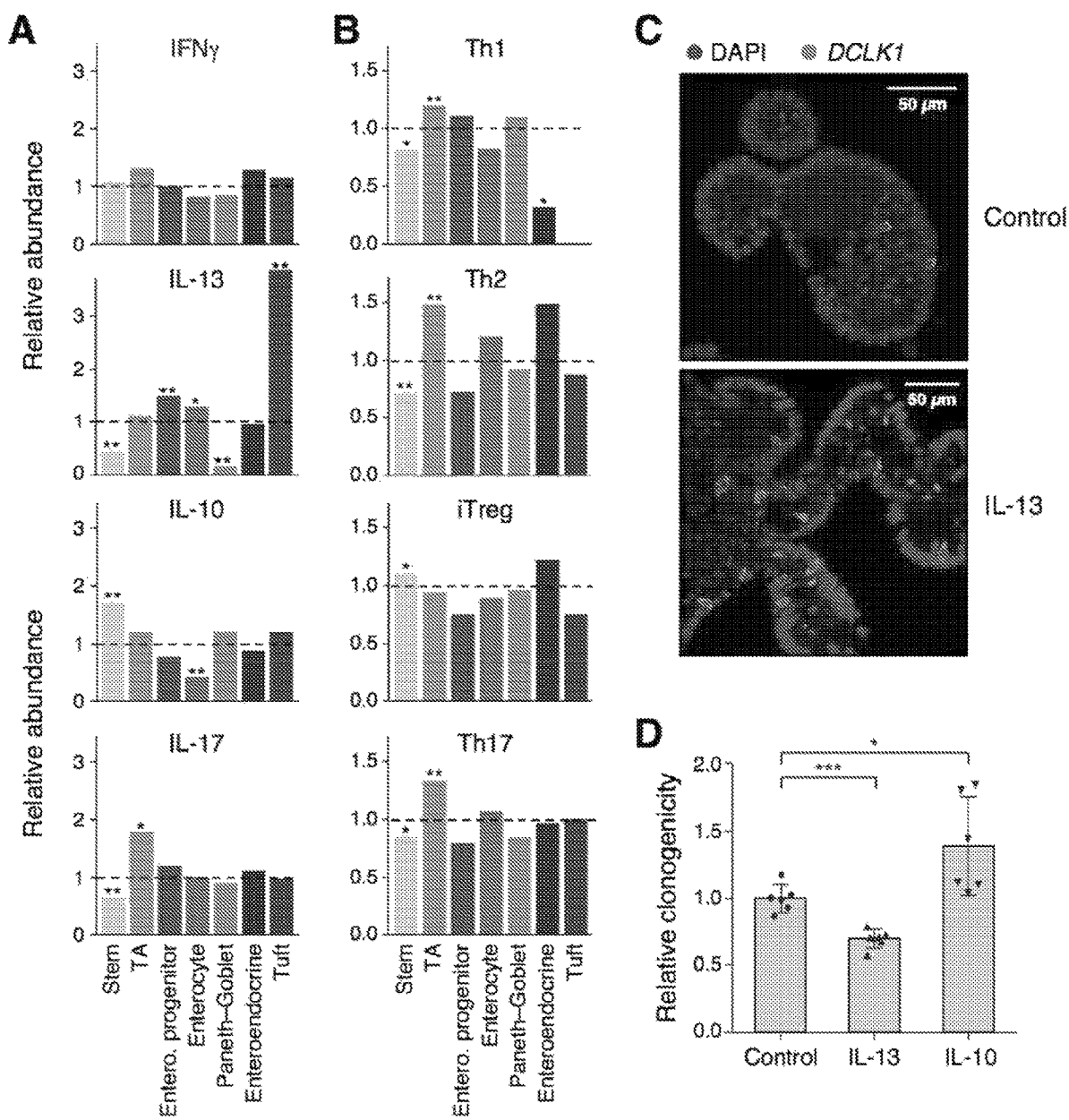
FIG. 19A-D

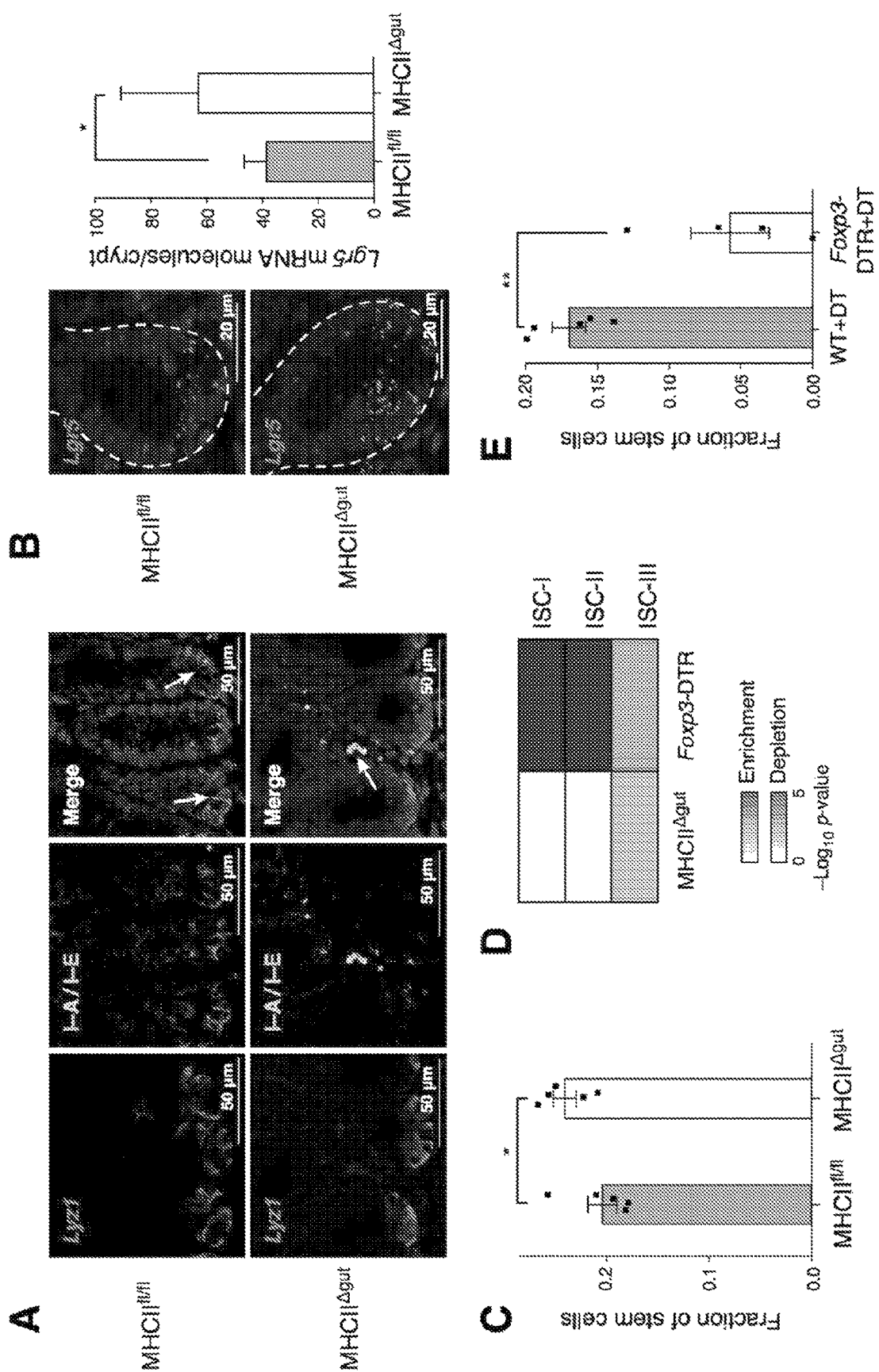
FIG. 20A-E

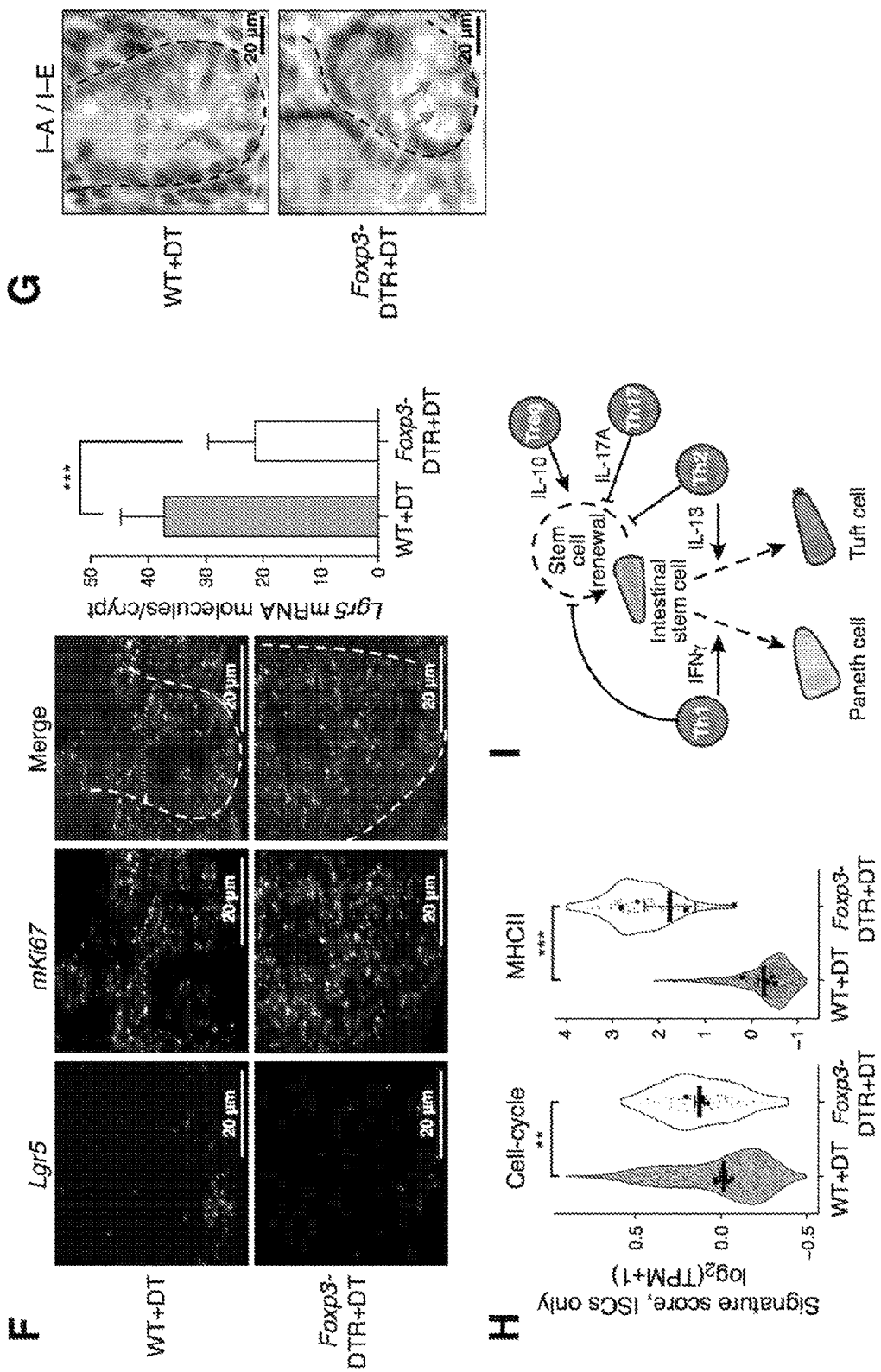
FIG. 20F-I

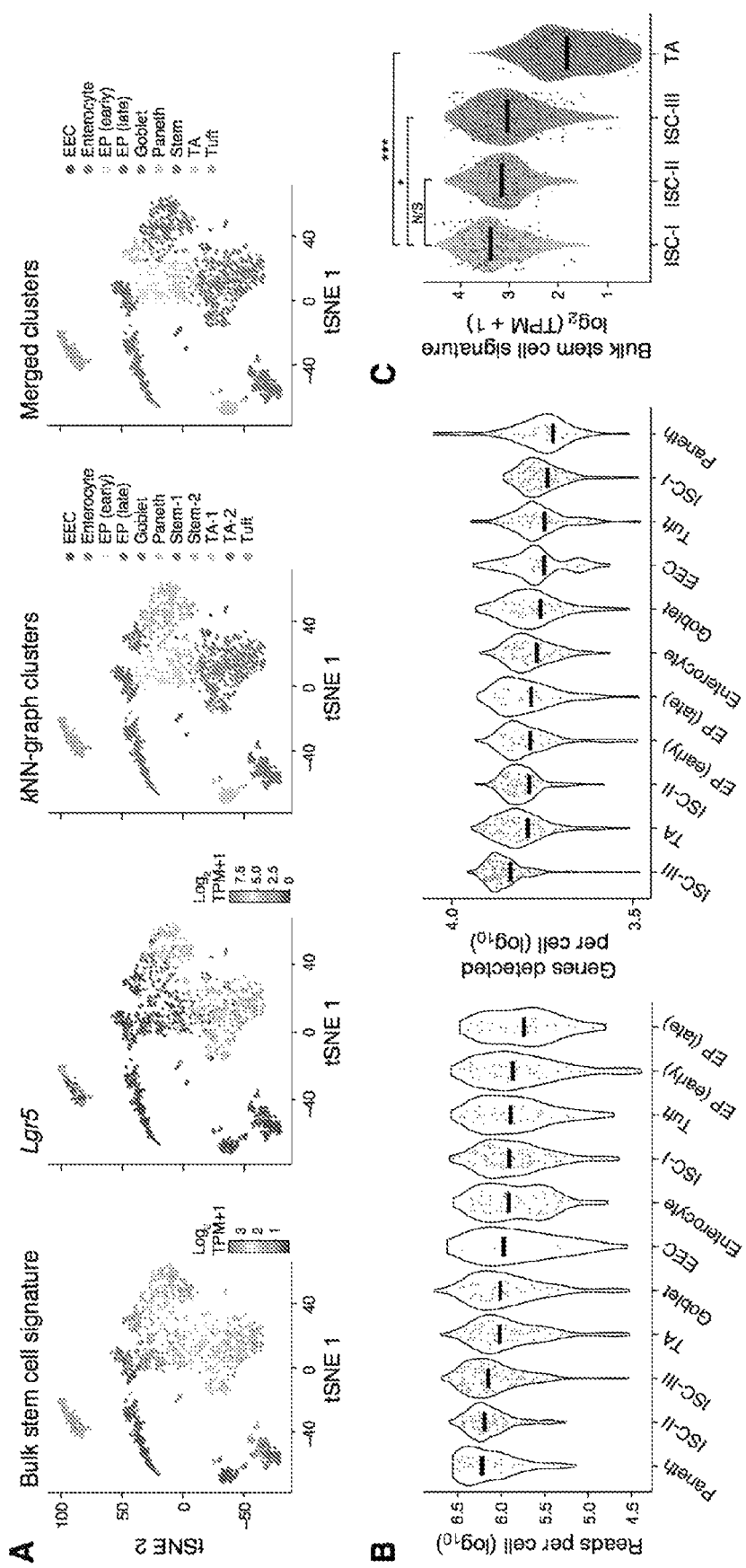
FIG. 21A-C

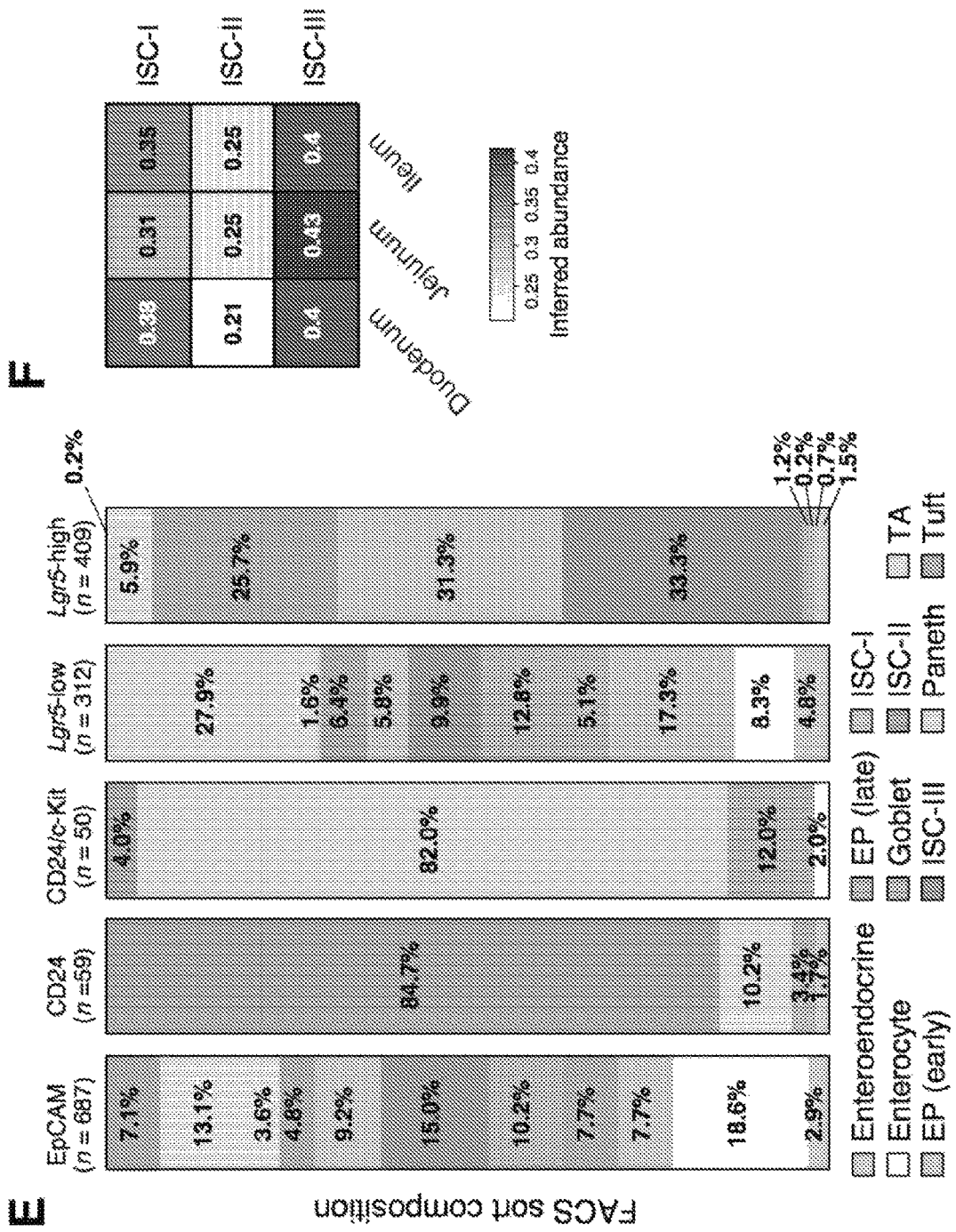
FIG. 21E-F

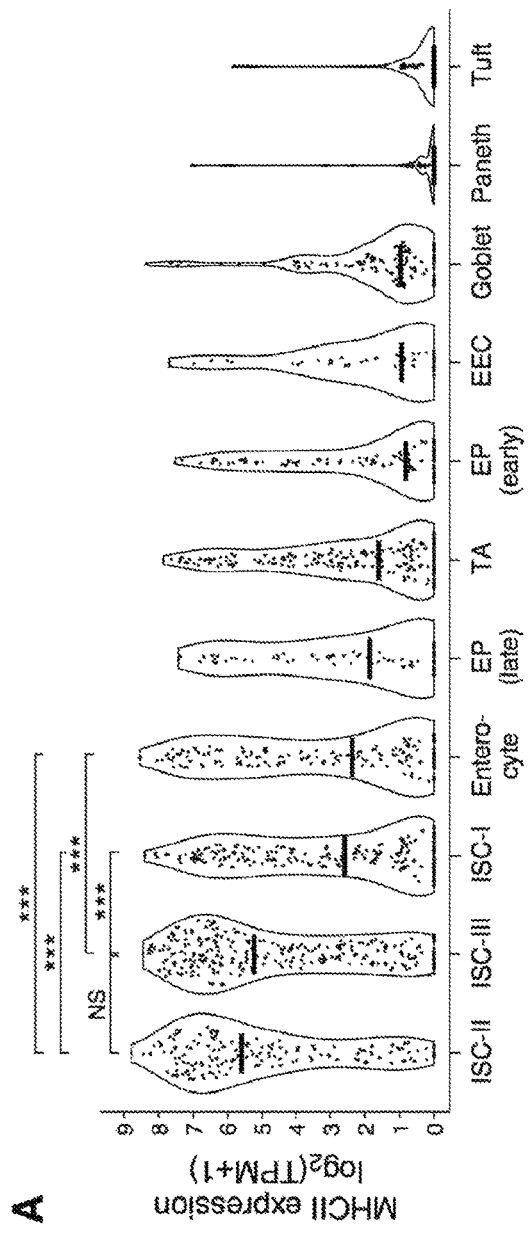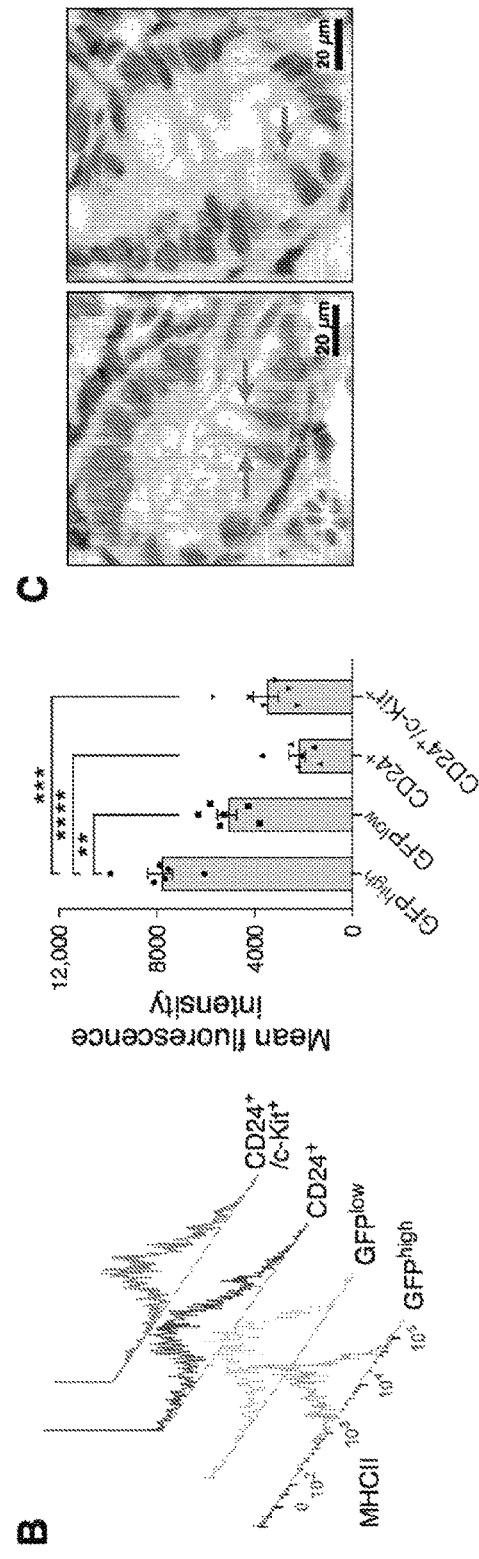
FIG. 22A-C

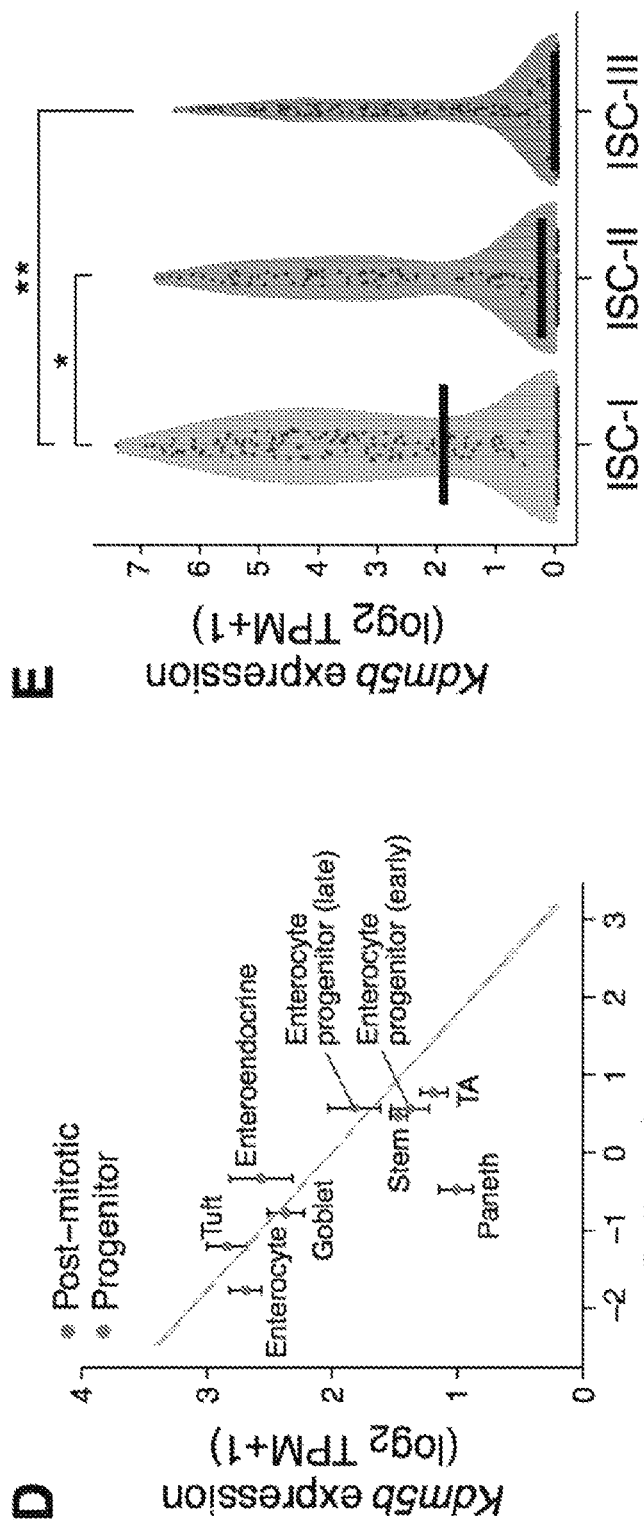
FIG. 22D-E

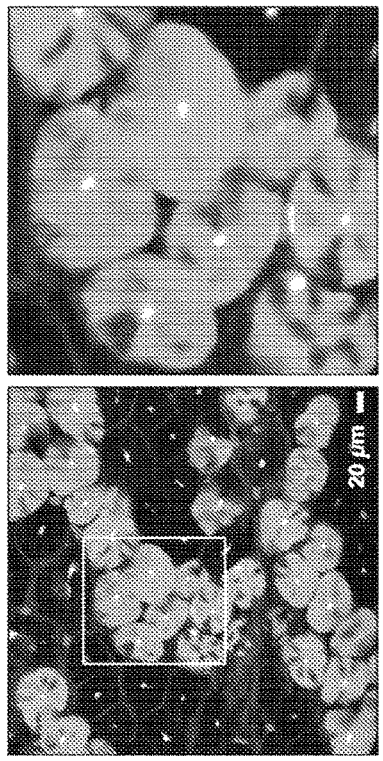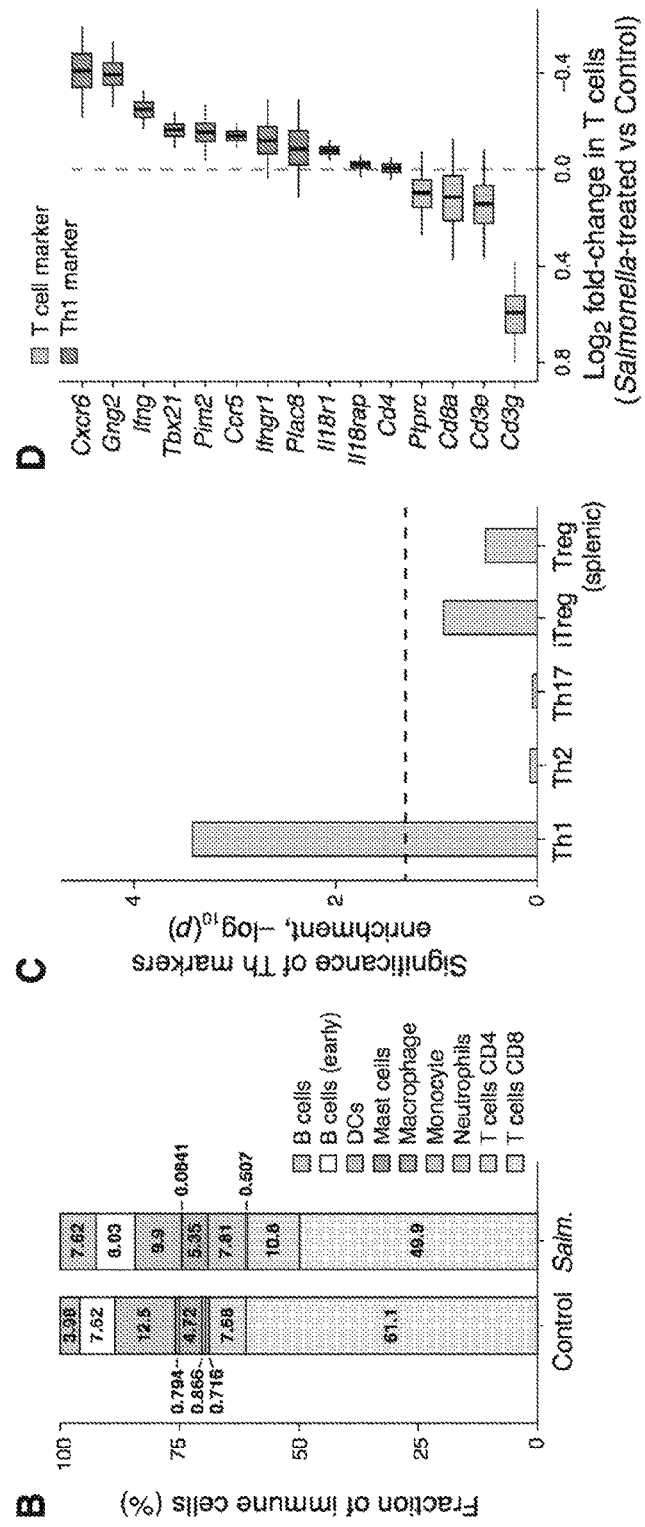
FIG. 24A-D

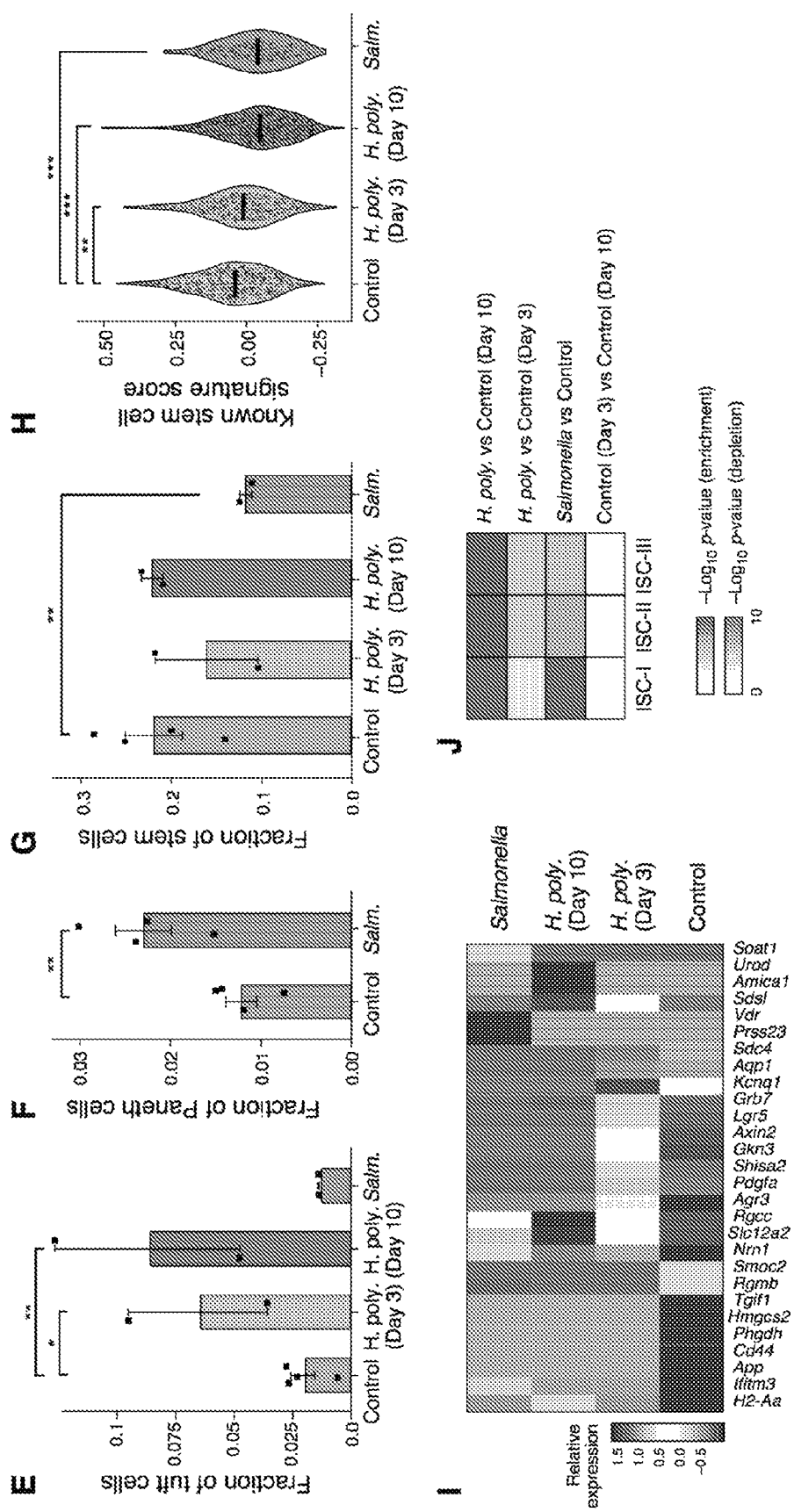
FIG. 24E-J

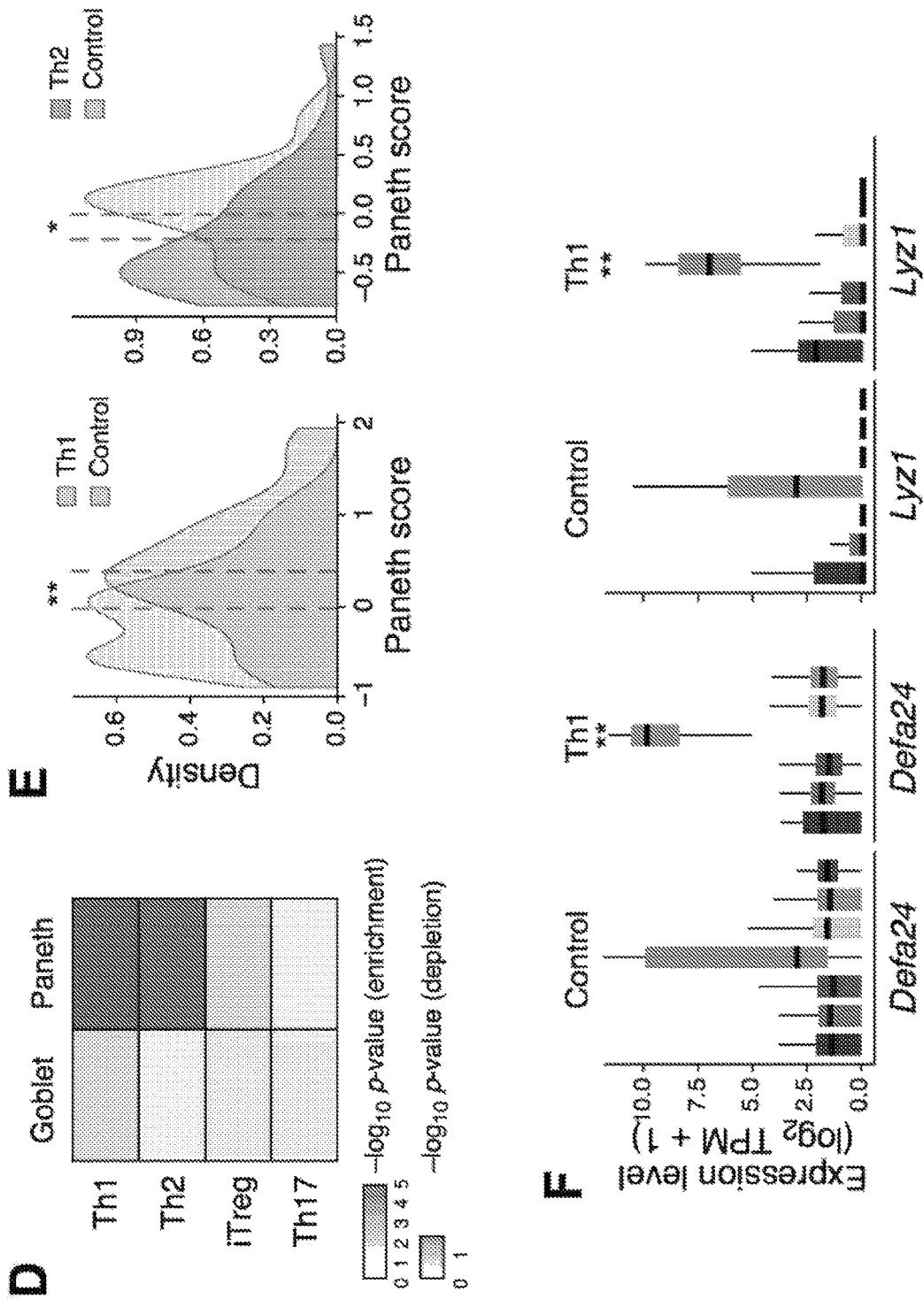
FIG. 26D-F

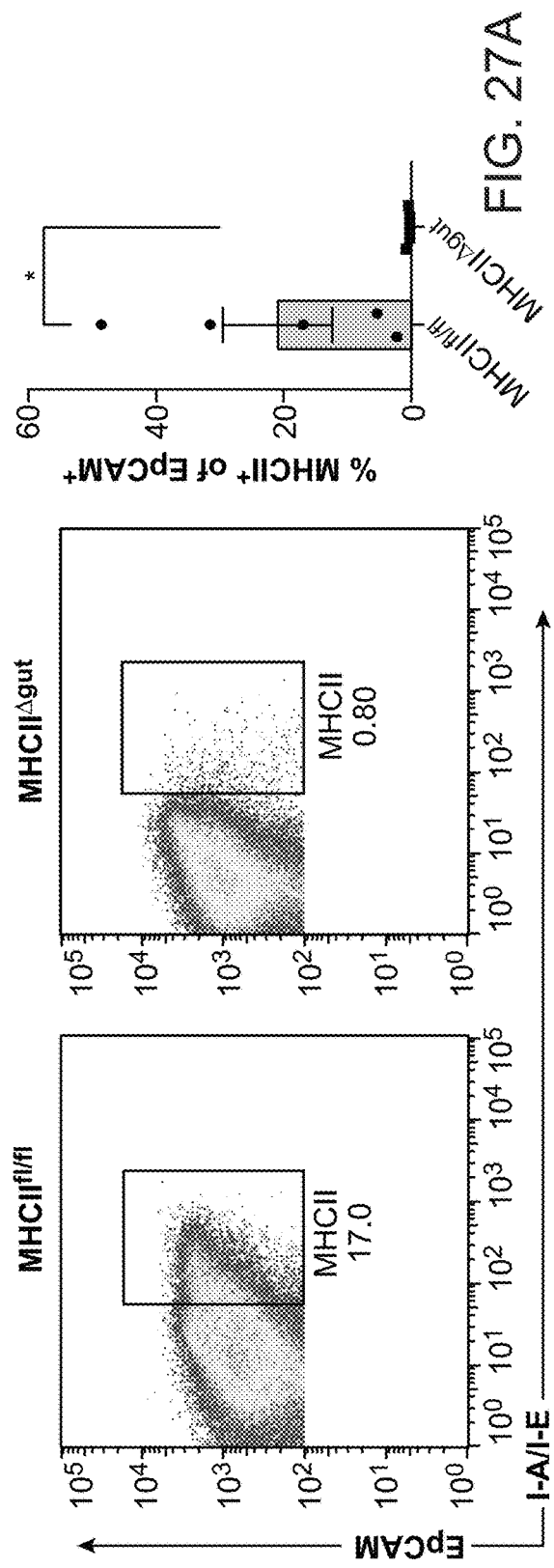
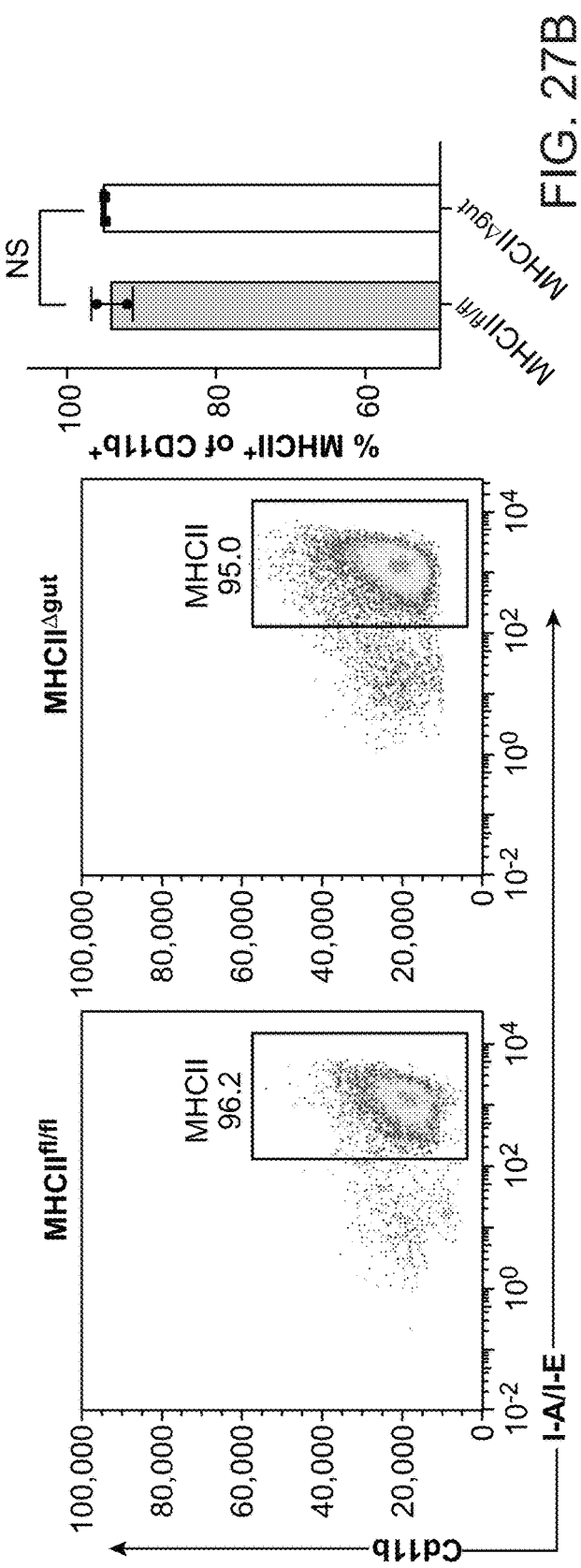
FIG. 27A
FIG. 27B

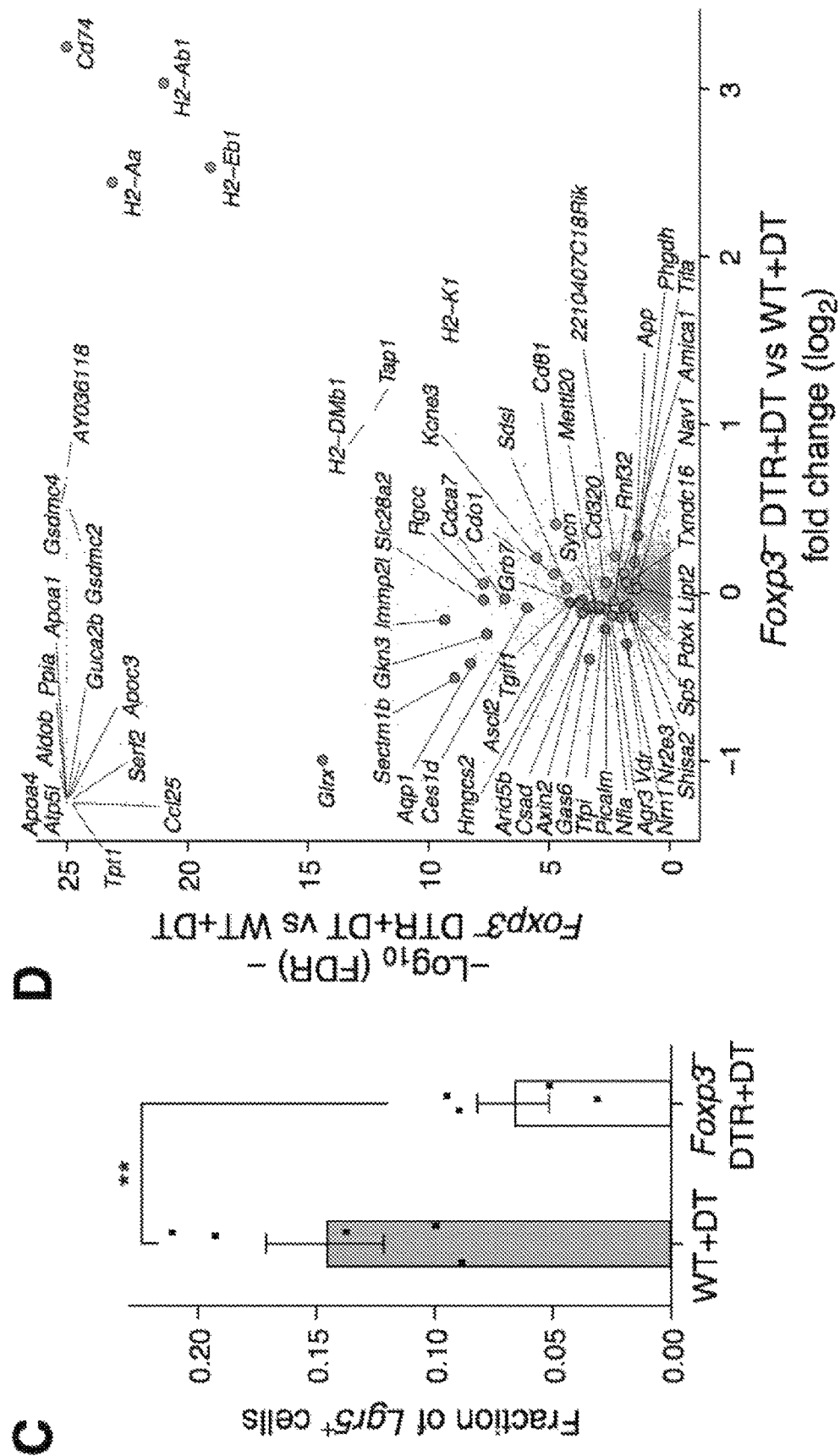
FIG. 30C-D

F
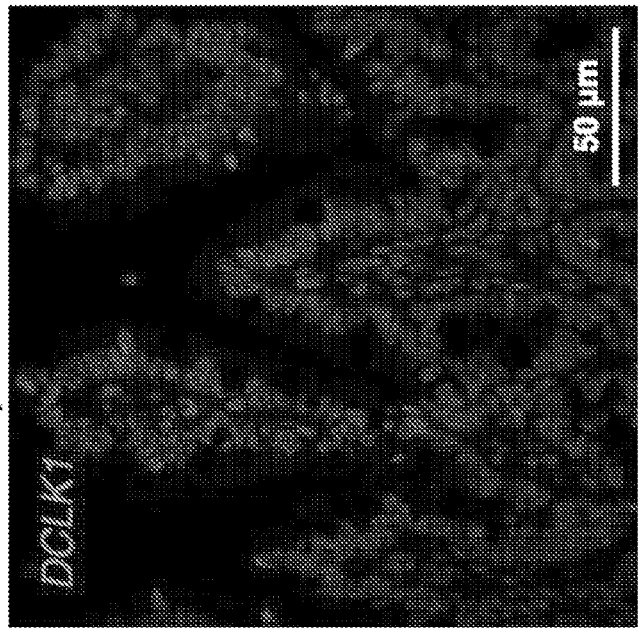
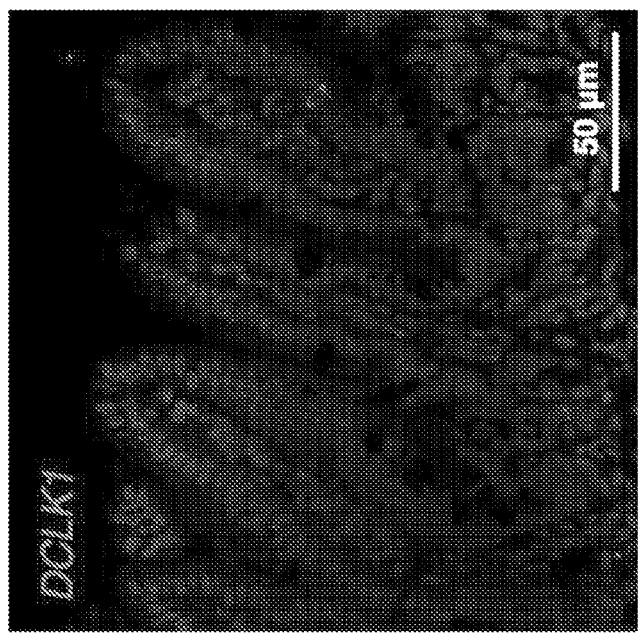
FIG. 30F

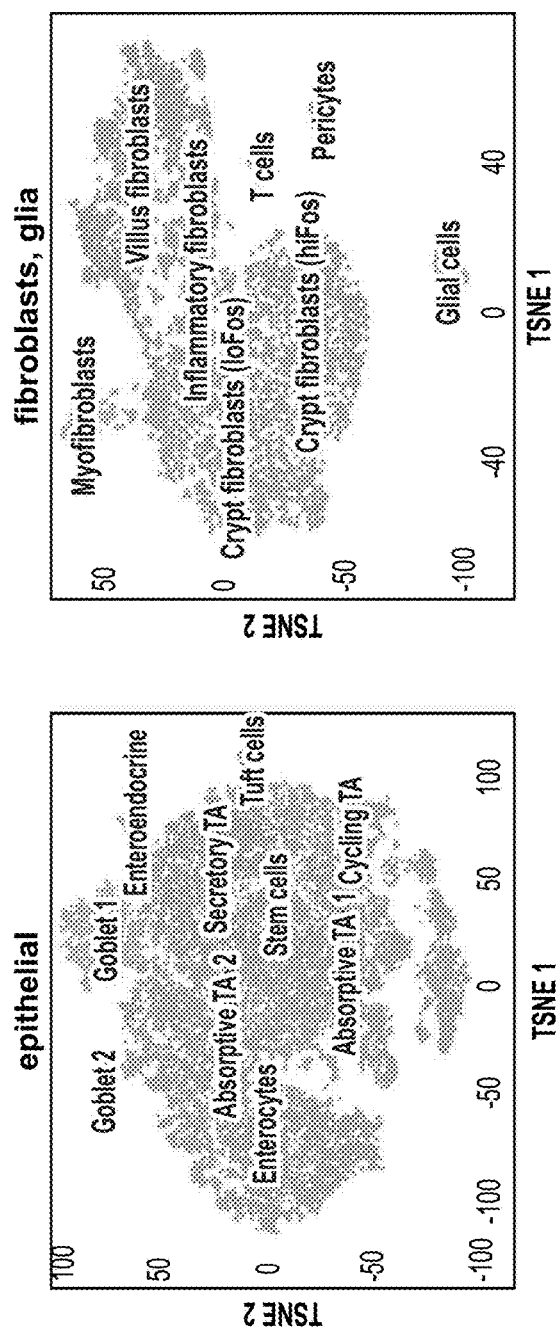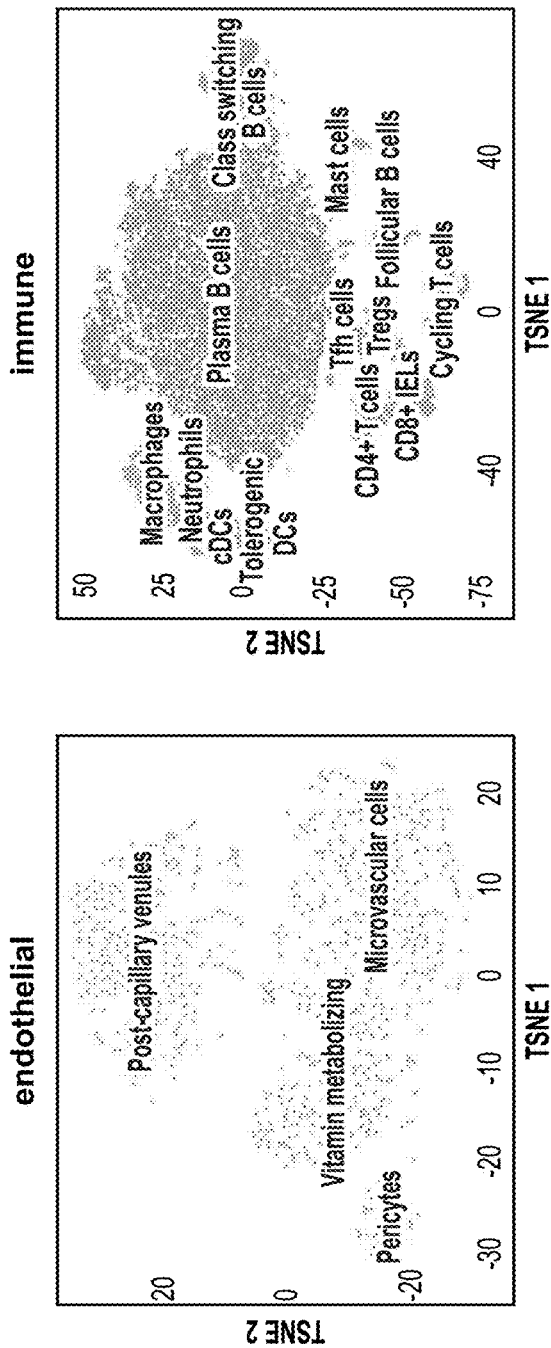
FIG. 39 enrichment of GWAS genes in each cell type; adjusted *P*<0.05

MODULATION OF INTESTINAL EPITHELIAL CELL DIFFERENTIATION, MAINTENANCE AND/OR FUNCTION THROUGH T CELL ACTION

CROSS-REFERENCE TO RELATED APPLICATIONS

This application is the U.S. National Stage of International Application No. PCT/US2017/060469., filed Nov. 7, 2017 published in English under PCT Article 21(2), which claims the benefit of U.S. Provisional Application numbers 62/421,204, filed Nov. 11, 2016 and 62/533,653, filed Jul. 17, 2017. The entire contents of the above-identified priority applications are hereby fully incorporated herein by reference.

STATEMENT REGARDING FEDERALLY SPONSORED RESEARCH

This invention was made with government support under Grant Nos. OD020839, DK114784, DK043351 and DK097485 awarded by the National Institutes of Health. The government has certain rights in the invention.

TECHNICAL FIELD

The subject matter disclosed herein is generally directed to compositions and methods for modulating, controlling or otherwise influencing enteric cell differentiation, homeostasis and activation. Manipulation of T cell balance and activity drives intestinal epithelial cell (IEC) differentiation and activity. This invention also relates generally to identifying and exploiting target genes and/or target gene products that modulate, control or otherwise influence T cell balance and enteric cell balance in a variety of therapeutic and/or diagnostic indications. This invention also relates generally to a gut atlas identifying novel cell types and markers for detecting, quantitating and isolating said cell types.

BACKGROUND

The functional balance between the epithelium and the constituents within the lumen plays a central role in both maintaining the normal mucosa and in disease. Intestinal epithelial cells (IECs) of the small intestinal epithelium comprise two major lineages—absorptive and secretory[1]—reflecting its dual roles to absorb nutrients and form a flexible barrier, monitoring and titrating responses to a variety of noxious substances or pathogens[2]. Enterocytes of the absorptive lineage comprise approximately 80% of the epithelium and are specialized for digestion and transport of nutrients[3]. The secretory lineage comprises five further terminally differentiated types of IECs: goblet, Paneth, enteroendocrine, tuft and microfold (M) cells[4-6]—each with distinct and specialized sensory and effector functions.

The epithelium is organized in a repeating structure of villi, which project toward the lumen, and nearby crypts (FIG. 1a). The crypts of the small intestine are the proliferative part of the epithelium, in which intestinal stem cells (ISCs) and progenitors, termed transit-amplifying cells (TAs), reside[6,7]. In contrast, only fully differentiated cells are found on the villi[2,7]. The crypt also contains Paneth cells, which secrete anti-microbial peptides (AMPs), such as defensins and lysozyme, into the lumen to keep the microbiota in check[8,9]. The highly proliferative TA cells migrate along the crypt-villus axis and differentiate into functionally distinct epithelial cell types that subsequently reach the tip of the villus, where mature cells undergo apoptosis and shed to the lumenl.

Epithelial tissue turns over rapidly (~5 days)[8], allowing it to dynamically shift its composition in response to stress or pathogens. For example, parasitic infection typically induces hyperplasia of goblet cells, which produce and secrete mucins to prevent pathogen attachment, strengthening the epithelial barrier and facilitating parasite expulsion[10]. Rare (0.5-1%) enteroendocrine cells (EECs) secrete over 20 individual hormones and are key mediators of intestinal response to nutrients[11,12] by directly detecting fluctuations in luminal nutrient concentrations via G-protein-coupled receptors (GPCRs)[11]. Finally, IECs communicate with immune cells to initiate either inflammatory responses or tolerance in response to lumen signals[2,13] Tuft cells[5], a rare IEC population, promote type-2 immunity in response to intestinal parasites by expressing interleukin-25 (Il25), which in turn mediates the recruitment of group 2 of innate lymphoid cells (ILC2s) that initiate the expansion of T-helper type 2 (Th2) cells upon parasite infection[14-16]. M cells, which reside exclusively in follicle-associated epithelia (FAE)[17], play an important role in immune sensing by transporting luminal content to immune cells found directly below them[18] in Peyer's patches, gut associated lymphoid follicles. Disruption in any of the major innate immune sensors and proximity effector functions of IECs may result in increased antigenic load through weakening of the epithelial barrier, and may lead to the onset of acute or chronic inflammation.

Despite this extensive knowledge, given the complexity of the epithelial cellular ecosystem, many questions remain open. First, do we know all the discrete epithelial cell types of the gut, or are there additional types, or new sub-types that have eluded previous studies. Second, what are the molecular characteristics of each type. For example, mapping the GPCRs and hormones expressed by EECs has important therapeutic applications; charting known and new specific cell surface markers would provide handles for specific cell isolation, and help assess the validity of legacy ones; and finding differentially expressed transcription factors (TFs) will open the way to study the molecular processes that accompany the differentiation of IECs, such as tuft or enteroendocrine cells. Third, we still know little about the response of individual cell populations to pathogenic insult, both in terms of changes in cellular proportions and cell-intrinsic responses.

A systematic atlas of single-cell RNA profiles can help address these questions, as the gene-expression program of a given cell closely reflects both its identity and function[19,20]. Most previous studies have examined the gene-expression profiles of IECs, but relied on known markers to purify cell populations[6,15,21,22], which may isolate either a mixed population if marker expression is more promiscuous than assumed, or a subset of a larger group if overly specific. They may further fail to detect rare cellular populations or intermediate, transient states on a continuum. A recent study[23] attempted to overcome these limitations using single-cell RNAseq (scRNA-seq), but analyzed only several hundred single cells, which may be insufficient to address the diversity of IECs, especially for subtypes that occur at a frequency of less than 0.1%[11,12]. Additional, studies[53,30,145] also attempted to overcome these limitations using single-cell RNAseq (scRNA-seq). All of these studies have not yet extensively characterized intestinal epithelial cellular diversity.

The intestinal mucosa maintains a functional equilibrium with the complex luminal milieu, which is dominated by a spectrum of gut microbial species and their products. The functional balance between the epithelium and the lumen plays a central role in maintaining the normal mucosa and in the pathophysiology of many gastrointestinal disorders[2]. To maintain barrier integrity and tissue homeostasis in response to immune signals and luminal contents[2], the gut epithelium constantly regenerates by rapid proliferation and differentiation[149]. This process is initiated by intestinal stem cells (ISCs), which give rise to committed progenitors that in turn differentiate to specific IEC types[103,39].

ISC differentiation depends on external signals from an ecosystem of non-epithelial cells in the gut niche. In particular, canonical signal transduction pathways, such as Wnt and Notch[113,114], are essential to ISC maintenance and differentiation, and rely on signals from stromal cells[11,51,50]. The intestinal tract is also densely populated by innate and adaptive immune cells, which maintain the balance between immune activation and tolerance[2,151]. However, it is unknown if and how immune cells and the adjacent ISCs interact.

Several studies suggest an important role for immune cells in tissue homeostasis. Tissue-resident innate immune cells, such as macrophages and type 3 innate lymphoid cells (ILC3s), can play a role in regeneration of the gut[111,116] and other tissues[117,119]. Among adaptive immune cells, recent studies have implicated T regulatory cells ($T_{regs}$) in regeneration within muscles, lungs, and the central nervous system[111,152,153]. Skin-resident $T_{regs}$ were very recently shown to be involved in maintaining hair follicle stem cell (HFSC) renewal through Jagged1-mediated Notch signaling[154]. In the gut, mouse models of intestinal infection, T cell depletion, and inflammatory bowel disease (IBD) all display aberrant epithelial cell composition, such as goblet cell hypoplasia or tuft cell expansion 14,155. These phenotypes have been primarily interpreted as reflecting intestinal epithelial cell dysfunction and changes in gut microbial populations[13,151,156,157]

The small intestinal mucosa is a complex system. The mucosa comprises multiple cell types involved in absorption, defense, secretion and more. These cell types are rapidly renewed from intestinal stem cells. The types of cells, their differentiation, and signals controlling differentiation and activation are poorly understood. The small intestinal mucosa also possesses a large and active immune system, poised to detect antigens and bacteria at the mucosal surface and to drive appropriate responses of tolerance or an active immune response. Finally, there is complex luminal milieu which comprises a combination of diverse microbial species and their products as well as derivative products of the diet. It is increasingly clear that a functional balance between the epithelium and the constituents within the lumen plays a central role in both maintaining the normal mucosa and the pathophysiology of many gastrointestinal disorders. Many disorders, such as irritable bowel disease, Crohn's disease, and food allergies, have proven difficult to treat. The manner in which these multiple factors interact remains unclear.

SUMMARY

Applicants have identified novel markers and networks driving the regulation and differentiation of stem cells and intestinal epithelial cells, have identified markers capable of identifying new subpopulations of cells, have developed an atlas of the cells in the small intestine, and identified the crucial role of intestinal T cells in controlling epithelial stem cell differentiation and regulation. The present invention provides methods for modulating intestinal cells for the treatment gastrointestinal disorders, such as irritable bowel disease, Crohn's disease, and food allergies.

In some embodiments, the invention provides a method of modulating intestinal epithelial cell differentiation, maintenance and/or function, the method comprising contacting an intestinal T cell or a population of intestinal T cells with a T cell modulating agent in an amount sufficient to modify differentiation, maintenance and/or function of the T cell or population of T cells as compared to differentiation, maintenance and/or function of the T cell or population of T cells in the absence of the T cell modulating agent, whereby the differentiation, maintenance and/or function of the T cell directly influences intestinal epithelial cell differentiation, maintenance and/or function.

In some embodiments, such modulating of intestinal epithelial cell differentiation, maintenance and/or function modulates inflammation of the gut. In other embodiments, modulating can increase the immune response, or shape the immune response to treat disease.

In another embodiment, provided is a method of modulating intestinal epithelial cell differentiation, maintenance and/or function by administering an agent that modulates MHCII. In a related embodiment, provided is method of modulating differentiation, maintenance and/or function of MHC II-expressing cells in the intestines, particularly of MHC II-expressing intestinal epithelial cells, comprising administering to a subject in need thereof an agent that modulates differentiation, maintenance and/or function of T cells. In the foregoing, the T cell or population of T cells includes, without limitation, Th1 cells, Th2 cells, Th17 cells, and regulatory T cells (Tregs).

In other embodiments, provided is method of modulating intestinal epithelial cell differentiation, maintenance and/or function by administering an agent that modulates one or more of H2-Abl, H2-DMb1, H2-DMa, H2-Aa, H2-Eb1, Cd74, Sectm1a, Sectm1b, Defa17, Defa24, Lyz1, It/n1, Mmp7, Ang4, Tslp, CD45, Rntlb, Wars, Pnlipr2, Muc2, Mptx1, Mptx2, Reg3b, Reg3g, Gfra3, Gpbar1, Gpr119 Neurog3, Sox4, Sct, Cck, Klf15, Grm4, Gal, Nts, Nucb2, Iapp, Sst, Nr1h4, Nr1h3, Nr1i2, Nr1i, Ffar, Ffar2, Ffar4, Ghrl, GIP, Gcg, Ghrl, Cd24a, Batf2, Mxd3, Foxa3, Gata5, Creb3l3, Osr2, Nfe2/2, Gata4, mKi67, Lgr5, Cyp2e1, Psrc1, and Kdm5

In related embodiments the invention is a method of proliferating intestinal stem cells comprising contacting the stem cells with an agent that increases expression of MHC II genes. Such a method of regulating the proliferation rate of intestinal stem cells may, in some embodiments, comprise contacting the stem cells with (i) an agent that regulates expression of MHC II genes and/or proteins, and/or (ii) an agent that binds to MHC II proteins. Such an agent may be an MHC II blocking antibody or an infectious agent.

In the foregoing, the expression of MHC genes includes, without limitation, one or more of H2-Abl, H2-DMb1, H2-DMa, H2-Aa, H2-Eb1, Cd74, Sectm1a, and Sectm1b.

In further embodiments, provided is a method of enhancing expression of one or more of Defa7, Defa24, Lyz1, Itln1, Mmp7, and Ang4 in intestinal cells, comprising administering to a subject in need thereof an agent that increases the presence of Th1 cells in the intestines.

In further embodiments, provided is a method of enhancing Th2 cell responses, comprising administering an agent that increases enteric levels of at least one of Tslp, CD45, Rntlb, Wars, Pnlipr2, and Muc2 protein and/or mRNA; preferably Tslp and/or CD45 protein and/or mRNA.

In further embodiments, provided is a method of treating an enteric condition, comprising inducing enterocyte and Paneth cell differentiation.

In an additional embodiment, provided is a method of treating an enteric condition, comprising administering Mptx2 protein and/or an agent that increases Mptx2 expression to a subject in need thereof. Such a method may further comprise administering at least one treatment selected from
a) Mptx1 and/or an agent that increases Mptx1 expression;
b) CRP and/or an agent that increases CRP expression;
c) Reg3b and/or an agent that increases Reg3b expression; and
d) Reg3g and/or an agent that increases Reg3g expression.

In view of the identification of the role of T cells in gut differentiation and modulation, provide also is a method of inducing intestinal stem cell differentiation comprising incubating stem cells in the presence of T cells (such as Th1, Th17 and Treg) or a cytokine selected from T-bet, FNγ, IL-13, IL-17A, and IL-10. Such a method may be in vitro or in vivo. Also encompassed is a stem cell produced by foregoing stimulation by T cells or T cell cytokines.

The foregoing method is useful for the modulation of gut function and in the related treatment of an enteric disease or condition. Such diseases include cancer, an infection (such as caused by a bacterial or parasitic infection, such as *Salmonella*), inflammation (such as inflammatory bowel disease, Crohn's disease, ulcerative colitis, and food allergies) or an immune dysfunction.

The inventors have identified a number of markers to identify disease. In some embodiments, provided is a method of diagnosing enteric bacterial infection in a subject comprising detecting protein or mRNA of at least one of Mptx1, Mptx2, Reg3b and Reg3g in an intestinal or fecal sample, wherein expression, such as elevated expression indicates bacterial infection.

Another embodiment comprises a method of diagnosing an enteric parasitic infection in a subject comprising detecting expression of Tslp and CD45 protein and/or mRNA in an intestinal or fecal sample, wherein expression, such as an elevated level thereof indicates parasitic infection. The method may further comprise detecting expression of protein and/or mRNA for Rntlb, Wars, Pnlipr2, and Muc2, wherein the expression, such as an elevated level thereof, indicates parasitic infection.

The inventors have also identified markers to identify cell types, metabolic state, age, and the like. A method for identifying Paneth cells in a sample, comprising detecting expression of protein or mRNA of one or more of Klfl5, Mptx1 or Mptx2, wherein the expression, such as elevated expression, indicates Paneth cells.

Accordingly, in some embodiments provided is a method for identifying gut enteroendocrine cells in a sample, comprising detecting expression of protein or mRNA of one or more of Gfra3 protein or mRNA wherein the expression, such as elevated expression, indicates enteroendocrine cells.

In another embodiment provided is a method for identifying gut enteroendocrine cells in a sample, comprising detecting expression of protein or mRNA of at least 2 of Gfra3 Gpbar1, Gpr119 Neurog3, Sox4, Sct, and Cck, wherein expression, such as elevated expression, indicates enteroendocrine cells.

In another embodiment provided is a method for identifying gut enterochromaffin cells in a sample, comprising detecting expression of protein or mRNA of any one or more of Grm4 or Chrm4, wherein expression, such as elevated expression, indicates enterochromaffin cells.

In another embodiment provided is a method for identifying enteroendocrine cell subtypes, comprising detecting expression of one or more protein or mRNA selected from Galanin (Gal), Neurotensin (Nts), Nesfatin-1 (Nucb2), Amylin (Iapp) and Somatostatin (Sst).

In another embodiment provided is a method for identifying gut enterocytes in a sample, comprising detecting expression of protein or mRNA of any one or more of Nr1h4, Nr1h3, Nr1i2, or Nr1i in the sample, wherein expression thereof, such as elevated expression, indicates enterocytes. Such a method may be further comprising detecting the expression of at least one of Ffar, Ffar2, Ffar4, Ghrl, GIP, Gcg, Ghrl and Cd24a.

In another embodiment provided is a method for identifying the developmental lineage of an enteric cell, particularly of an enterocyte, comprising measuring the expression of mRNA or protein of any one or more of Batf2 or Mxd3. Such a method may further comprisie measuring any one or more of Sox4, or Foxa3.

In another embodiment provided is a method for identifying the proximal or distal (in terms of location in the intestinal tract) identity of an enteric cell, particularly of an enterocyte, comprising measuring the levels of mRNA or protein of any one or more of Gata5, Creb313, Osr2, or Nfe212, optionally further comprising measuring any one or more of Gata4 or Nr1h4.

In another embodiment provided is a method of identifying the cell cycle state in an intestinal stem cell, comprising detecting the expression of protein or mRNA of one or more of Cyp2e1 and Psrc1 and optionally also mKi67, Lgr5, in a cell.

In another embodiment provided is a method of decreasing cell cycle rate in an intestinal stem cell comprising administering to a subject in need thereof an agent that increases the expression of Kdm5b protein or mRNA.

In another embodiment provided is a method for identifying tuft cells in a sample, comprising detecting expression of any one or more of Cd24a, Tas1r3, Ffar3, Sucnrl, Gabbrl or Drd3 protein or mRNA, wherein the expression indicates tuft cells. Such a method may further comprise detecting expression of any one or more of Ptprc or Tslp protein or mRNA, wherein the expression indicates a subset of tuft cells, and may further comprise detecting expression of any one or more of Nrep, Nradd, Ninj 1, and Plekhg5 protein or mRNA, wherein the expression indicates a subset of tuft cells.

In another embodiment provided is a method for identifying enteroendocrine cell subtypes in a sample, comprising detecting expression of a gene or gene product signature, the signature comprising or consisting of one or more genes or gene products as set forth in this application.

In another embodiment provided is a method for identifying enterochromaffin cell subtypes in a sample, comprising detecting expression, such as elevated expression, of protein or mRNA of Reg4.

In another embodiment provided is an isolated gastrointestinal tract cell characterized by expression of one or markers for a cell type selected from any of Tables 3 to 10 or 15 A to D.

In another embodiment provided is a method for detecting or quantifying gastrointestinal tract cells in a biological sample of a subject, the method comprising detecting or quantifying in the biological sample gastrointestinal tract cells as defined in herein. The gastrointestinal tract cell may be detected or quantified using one or more markers for a cell type selected from any of Tables 3 to 10 or 15 A to D.

In another embodiment provided is a method of isolating a gastrointestinal tract cell from a biological sample of a subject, the method comprising isolating from the biological sample gastrointestinal tract cells as defined herein. The gastrointestinal tract cell may be isolated using one or more surface markers for a cell type selected from any of Tables 3 to 10 or 15 A to D.

The gastrointestinal tract cells may be isolated, detected or quantified using a technique selected from the group consisting of RT-PCR, RNA-seq, single cell RNA-seq, western blot, ELISA, flow cytometry, mass cytometry, fluorescence activated cell sorting, fluorescence microscopy, affinity separation, magnetic cell separation, microfluidic separation, and combinations thereof.

The ability to identify cell types, metabolic state, cycling state and the like has many utilities—for example, identifying the source of a cancer cell type; identifying disease states; screening for drug effects; and applied and basic research.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 1A-1G—A single-cell expression atlas of intestinal epithelial cells. FIG. 1a. Schematic overview. Two complementary scRNA-seq methods used to create a high-resolution atlas of the mouse small intestinal epithelium. FIG. 1b. Cell type clusters. t-distributed stochastic nearest-neighbor embedding (tSNE) visualization of 7,216 single cells. Individual points correspond to single cells colored by their assignment to clusters using a k-nearest neighbor (kNN) graph-based algorithm (see Methods). Although EECs are classified as a single group by clustering, the tSNE embedding separates out the enterochromaffin subset (small left-hand cluster, top of figure). This heterogeneity is fully characterized in (FIG. 3). Legend shows the cluster post-hoc annotation to cell types. FIG. 1c. Cell type-specific signatures. Heatmap shows the relative expression level (row-wise Z-score of $\log_2(TPM+1)$ expression values, color bar) of genes (rows) in high confidence cell-type-specific signatures based on both full-length and 3' scRNA-seq data, across the individual post-mitotic IECs (columns). Color code marks the cell types and their associated signatures. FIG. 1d-FIG. 1e.Mptx2 is a novel Paneth cell marker. (d) Shown is combined single-molecule fluorescence in situ hybridization (smFISH) with immunofluorescence assay (IFA) of FFPE sections of Mptx2 (green) co-stained with the canonical Paneth cell Lyz1 protein marker (red). Scale bar, 20 μm. (e) In situ hybridization (ISH) of Mptx2 (red) at lower magnification. Scale bar, 50 μm. FIG. if-FIG. 1g. Cell type-specific transcription factors (TFs) and G protein-coupled receptors (GPCRs). Heatmaps depict the average relative expression (Z-score of mean $\log_2(TPM+1)$, color bar) of the top 10 TFs (f) and GPCRs (g) (columns) that are specifically expressed in the cells of each IEC type (rows) based on the higher depth, full-length scRNA-seq data.

FIG. 2a. Gene signature-based embedding of the IEC lineage. Shown are 7,216 single IECs (see main text and Methods) positioned by signature scores for key cell types: the difference between the signature scores for tuft and enteroendocrine cells (x-axis); between enterocyte and goblet cell scores (y-axis), and the stem cell score (z-axis). Each signature score was computed using 50 genes (Methods). Cells are colored by expression levels of the stem cell marker Lgr5 (left), cell-cycle gene set (center), and the enterocyte marker Alpi (right). FIG. 2b-FIG. 2e. Diffusion-map embedding of 5,282 cells progressing through stages of enterocyte differentiation (Methods). (FIG. 2b-FIG. 2c) Cells are colored by their cluster assignment (FIG. 1b). Diffusion component 1 and 3 (DC-1 and DC-3) are associated with the transition from stem cells to progenitors (FIG. 2b), while DC-2 distinguishes between proximal and distal enterocyte fate commitment (FIG. 2c). (FIG. 2d-FIG. 2e) Cells are colored by the expression ($\log_2(TPM+1)$, color bar) of known and novel TFs associated with stages of differentiation (FIG. 2d), or with proximal or distal enterocyte differentiation (FIG. 2e). FIG. 2f. Top 10 markers for absorptive and secretory IECs. Heatmap shows the mean expression level (color bar, $\log_2(TPM+1)$) for genes (rows) in cells in the two subsets (columns).

FIG. 3A-3F—Novel classification of rare enteroendocrine subtypes. FIG. 3a. Type discovery by unsupervised clustering. Shown is a tSNE embedding of the 533 enteroendocrine cells (EECs) from the droplet-based dataset. Cells are numbered and shaded based on the 12 clusters determined through kNN-graph based clustering (Methods), and labeled by post-hoc analysis based on known genes (b-c). FIG. 3b. EEC subtype signatures. Heatmap of the relative expression level (row-wise Z-scores, color bar) of the most specific (FDR<0.01, log 2(fold change)>0.1) genes (rows) for the cells (columns) in each of the 12 detected clusters (color coded as in a). FIG. 3c. Marker based classification of EECs. Violin plots show the distribution of expression ($\log_2(TPM+1)$) of genes (columns) encoding major EEC TFs, markers genes, and hormones in the cells (dots) from each of the 12 subtype clusters (rows), color coded as in a. Grey bars indicate traditional nomenclature for EEC subtypes based on hormone expression (S, I, L, K, A). FIG. 3d. smFISH of the co-expression of gut hormones Cck (green, "I"), Ghrl (red, "A") and Gcg (white, "L") by individual EECs. Scale bar, 50 μm. Inset (x5) of triple positive SILA cell FIG. 3e. Distribution of EEC subtypes in different SI regions. Proportion (y axis) of each EEC subset in cells sampled from each of three regions of the small intestine, duodenum, jejunum and ileum (color legend) in each mouse (dots, n=2 mice per region). Error bars: standard error of the mean (SEM). (* FDR<0.25, ** FDR<0.1, * ** FDR<0.01, x test, Methods) FIG. 3f. Combined smFISH and IFA of enterochromaffin cells with Reg4 (green, left) and Tphl (red, middle) co-stained with ChgA antibody (white, right). Scale bar, 20 μm.

FIG. 4A-4H—A CD45-positive subset of tuft cells expresses the epithelial cytokine TSLP. FIG. 4a. Tuft cell subsets. tSNE embedding of 166 tuft cells from the droplet-based dataset (FIG. 1b). Cells are colored by their subtype assignment based on kNN-graph-clustering (Methods), and annotated post-hoc (legend, top right). FIG. 4b. Gene signatures for Tuft-1 and Tuft-2 cells. Heatmap shows the relative expression (row-wise Z-scores, color bar) of the consensus marker genes for Tuft-1 and Tuft-2 cells (rows) across single cells from the droplet-based dataset (columns) assigned to Tuft-1 and Tuft-2 cell clusters (orange and brown, respectively). The top 25 genes are shown, all FDR<0.01 and log 2fold change>0.1 in both plate- and droplet-based datasets). FIG. 4c. TSLP expression in Tuft-2 cells. Violin plots show the distribution of expression of epithelial cytokines (1125, left; 1133, middle; TSLP: right) in the cells (dots) in enterocytes (blue), Tuft-1 (orange) and Tuft-2 (brown) subsets, in full-length scRNA-seq data. Both tuft cell subsets express 1125, but TSLP is enriched in the Tuft-2 subset. (* FDR<0.1, *** FDR<0.0001, Mann-Whitney U-test). FIG. 4d-FIG. 4e. Validation of high TSLP expression by Tuft-2 cells. (FIG. 4d) Combined smFISH and IFA of TSLP (green) co-stained with DCLK1 (red), scale bar 10 µm. (FIG. 4e) qPCR (y axis, relative quantification compared to Tuft-2 group) of Alpi (enterocyte marker), TSLP and Dclk1 (tuft cell markers) from cells defined as Tuft-1, Tuft-2 or randomly selected single cells from processed plates of the full-length scRNA-seq data (16 cells per group). (* p<0.05, **p<0.005, t-test). FIG. 4f. High expression of Ptprc (CD45) by Tuft-2 cells. Violin plots show the distribution of expression of Cd14 (top-left), EpCAM (top-right), Dclk1 (bottom-left) and Ptprc (CD45; bottom-right) in the cells (dots) of enterocyte (blue), Tuft-1 (orange), and Tuft-2 (brown) subsets as well as monocytes (brown) based on the deeper-coverage full-length scRNA-seq data. FIG. 4g. Validation of CD45 expression by tuft cells. Top left: smFISH imaging of Ptprc (encoding CD45, green) co-stained with DCLK1 antibody (red). Scale bar 50 µm. Top right: Distribution of CD45 protein levels within Gfi1b-GFP labeled cells (green), compared to background (light grey) and monocytes (dark grey) based on FACS. Bottom: IFA co-staining of DCLK1 (red), Gfi1b-GFP (green) and CD45 (white) within the same tuft cell. Scale bar 15 µm. FIG. 4h. Isolation of Tuft-2 cells using FACS based on CD45 expression. Proportion (y axis) of detected Tuft-1 and Tuft-2 cells (colored as in a-f) in 3' droplet scRNAseq data (n=3 pooled mice) from cells sorted using EpCAM alone (left) or using EpCAM and CD45 (right) (* p<0.05, * * * p<0.0005, hypergeometric test).

FIG. 5A-5F—Microfold (M) cell-specific gene signatures. FIG. 5a. Tuft-2 cells express a higher level of known M cell genes. tSNE embedding of 101 tuft cells (squares: Tuft-1; circles: Tuft-2) extracted from full-length scRNA-seq data (FIGS. 8a and 8b). Cells are colored by their relative score (color bar, Methods) for the expression of 20 known M cell genes[17]. FIG. 5b-FIG. 5c. RANKL-mediated in-vitro differentiation of M cells. (FIG. 5b) tSNE embedding of 5,434 epithelial cells profiled from intestinal organoids with and without treatment of RANKL. Blue: 384 differentiated M cells, identified by unsupervised clustering (FIG. 14e). (FIG. 5c) Shown are the proportions of epithelial cells (y axis) in each cell subset (x axis; subsets identified by graph-clustering and labeled post-hoc; Methods) from organoids grown under control conditions (white bars) or treated with RANKL for 3 days (light shaded bars) or 6 days (dark shaded bars). FIG. 5d-FIG. 5f. M cells from follicular-associated epithelium (FAE) in vivo. (FIG. 5d) M cell cluster. Heatmap shows the Pearson correlation coefficient (color bar) between expression profiles from each pair of cells (rows, columns), for 4,700 FAE derived epithelial cells (n=5 mice). Cells are ordered by unsupervised clustering (Methods), with large clusters down-sampled to a maximum of 250 cells for visualization only. Arrow marks a group of 18 M cells. (FIG. 5e-FIG. 5f). Gene signatures of in vivo M cells. Heat maps show the mean expression (color bar) in each FAE cell type cluster (columns) of genes (rows) for known (grey bars) or novel (black bars) cell surface markers (FIG. 5e) or transcription factors (FIG. 5f), identified as specific (FDR<0.05, Mann-Whitney U-test) to M cells in vivo.

FIG. 6A-6I—Tailored remodeling of the proportion and transcriptional programs of intestinal epithelial cells in response to different infections. FIG. 6a. Functional changes in IEC transcriptional programs in Salmonella infection. Shown are the significance ($-\log_{10}(q)$, x axis) for the top 10 enriched GO terms among genes in Salmonella-treated IECs compared to control IECs. FIG. 6b. Up-regulation of Reg3b and Reg3b expression in both enterocytes and other epithelial cells during Salmonella infection. Violin plots show the distribution of expression levels ($\log_2(TPM+1)$, y axis) of antimicrobial C-type lectins Reg3g (top left) and Reg3b (top right), and interferon inducible and regulatory proteins Zbp1 (bottom left) and Igtp (bottom right) in control and Salmonella-treated enterocytes (red) and all other cells (grey). FIG. 6c-FIG. 6d. Changes in cell composition during Salmonella and helminth infection. (FIG. 6c) tSNE visualization of IECs subsets (numbered and shaded according to their assignment to cell-type clusters using unsupervised clustering; color legend) in controls (left; n=4 mice), Salmonella infected mice (n=2, center left), and mice infected with the intestinal parasite H. Polygyrus for 3 (n=2, center right) or 10 (n=2, right) days. FIG. 6d. Frequencies (y axis) of cells of each subtype (as in FIG. 6c) in each mouse (dots) under each infection condition (* FDR<$1\times10^{-5}$; ** FDR<$1\times10^{-10}$, Wald test). Error bars: standard error of the mean (SEM). FIG. 6e. Cell-intrinsic changes in enterocyte transcriptional programs following Salmonella infection. Heatmap shows the relative expression (row-wise Z-scores, color bar) of 104 genes (left panel, rows) of which 58 (right panel) are specific to Salmonella infection (Methods), significantly up-regulated (FDR<0.05, Mann-Whitney U-test, log 2fold-change>0.1) in individual enterocytes (columns) from the Salmonella infected mice (green) compared to controls (grey). Enterocytes from H. polygyrus-treated mice (pink: 3 days; red: 10 days) are shown (right panel) for comparison. Labels indicate 10 representative up-regulated genes. FIG. 6f. Shifts in composition of tuft cell subsets in response to H. polygyrus infection. Frequencies (y axis) of cells in each subset (FIG. 16b-c) after 3 (left) and 10 (days) of infection in each mouse (dots, n=2 mice). Error bars: standard error of the mean (SEM). (* FDR<0.25; ** FDR<0.05, Wald test). FIG. 6g. Up-regulation of anti-parasitic genes by goblet cells in response to H. polygyrus infection. Violin plots show the distribution of expression levels (log 2 (TPM+1), y axis) of three genes, previously implicated in anti-parasitic immunity?°, which are up-regulated by goblet cells from control mice (grey) and mice infected by H. polygyrus for 3 and 10 days (light and dark red, respectively) (FDR<0.05, Mann-Whitney U-test, 3' scRNA-seq dataset). FIG. 6h. Cell intrinsic changes in enterocyte transcriptional programs following Salmonella infection. Heatmap shows the relative expression (row-wise Z-scores, color bar) of 104 (left) genes (rows) of which 58 are specific to Salmonella infection (right, Methods) significantly up-regulated (FDR<0.05, Mann-Whitney U-test, $\log_2$ fold-change>0.1) in individual enterocytes (columns) from the Salmonella infected mice (green) compared to controls (grey). Enterocytes from H. polygyrus-treated mice (pink: 3 days; red: 10 days) are shown (right) for comparison, labels indicate 10 representative up-regulated genes. FIG. 6i. Cell intrinsic changes in goblet cell transcriptional programs following helminth infection. Heatmap shows the relative expression (row-wise Z-scores, color bar) of 20 genes (left panel, rows) of which 14 are specific to H. polygyrus infection (right panel, Methods) significantly up-regulated in individual goblet cells (columns, FDR<0.05, Mann-Whitney U-test, $\log_2$ fold-change>0.1) from H. Polygyrus infected mice (pink: 3 days; red: 10 days) compared to control (grey). Goblet cells from Salmonella-treated mice (green) are shown (right) for comparison, labels indicate 10 representative up-regulated genes.

FIG. 7A-7H—Identifying intestinal epithelial cell-types in scRNA-seq data by unsupervised clustering, related to FIG. 1. FIG. 7a-FIG. 7b. Quality metrics for scRNA-seq data. Shown are distributions of the number of reads per cell (left), the number of genes detected with non-zero transcript counts per cell (center) and the fraction of reads mapping to the mm10 mouse transcriptome per cell (right) in the droplet-based 3' scRNA-seq data (FIG. 7a) and the plate-based full-length scRNA-Seq data (FIG. 7b). FIG. 7c-FIG. 7f. Agreement across batches. (c) Contribution of batches to each cluster. Each pie chart shows the batch composition (color coded legend) of each detected cluster (post-hoc annotation and number of cells are marked on top) in the droplet-based 3' scRNA-seq dataset. All 10 biological replicates contribute to all clusters, and no major batch effect is observed. (n=6 mice). (FIG. 7d) Contribution of each mouse to each cluster. Shown is the proportion of detected cells (y axis) in each major cell type (x axis) in the droplet-based 3' scRNA-seq dataset in each of six mice (dots). Grey bar: mean; error bars: standard error of the mean (SEM). (FIG. 7e) Agreement in expression profiles across mice. Box and whisker plot shows the Pearson correlation coefficients (x axis) in average expression profiles (average $\log_2(TPM+1)$) for cells in each cluster (y axis), across all pairs of mice. Black bar indicates median value, box edges correspond to the 25th and 75th percentiles, while whiskers indicate a further 1.5*IQR where IQR is the interquartile range. Note that clusters with additional sub-types (e.g., Tuft, enteroendocrine cells) show more variation, as expected. (FIG. 7f) Scatter plots compare the average $\log_2(TPM+1)$ gene expression values between two scRNA-seq experiments from the droplet-based 3' scRNA-seq dataset (top, x and y axis), two scRNA-seq experiments from the plate-based full length scRNA-seq dataset (center, x and y axis), or between the average of a plate-based full-length scRNA-seq (x axis) and a population control (y axis) (bottom). Pearson correlation is marked top left. FIGS. 7g and 7h. Additional QC metrics and post-hoc cluster annotation by the expression of known cell-type markers. tSNE visualization of 7,216 single cells, where individual points correspond to single cells. Top left corner to bottom right corner, in order: Cells are colored by their assignment to clusters (top left, identical to FIG. 1b), mean expression ($\log_2(TPM+1)$, color bar) of several known marker genes for a particular cell type or state (indicated on top), the mouse from which they originate (color legend), the number of reads per cell (color bar), the number of genes detected per cell (color bar) and the number of transcripts as measured by unique molecular identifiers (UMIs) per cell.

FIGS. 8a and 8b. QC metrics andpost-hoc cluster annotation by the expression of known cell-type markers. tSNE visualization of 1,522 single cells where individual points correspond to single cells. Top left corner to bottom right corner, in order: Cells are numbered and shaded by their assignment to clusters, using a k-nearest neighbor (kNN) graph-based algorithm (Methods; Legend shows the cluster post-hoc annotation to cell types); mean expression ($\log_2(TPM+1)$, color bar) of several known marker genes for a particular cell type or state (indicated on top; same as in FIGS. 7g and 7h); the mouse from which they originate (color legend) and its genotype, the FACS gate used to sort them (color legend), the number of reads per cell (color bar) and the number of genes detected per cell (color bar). FIG. 8c. Cell-type-specific signatures. Heatmap shows the relative expression level (row-wise Z-scores, color bar) of genes (rows) in consensus cell-type-specific signatures (same genes as FIG. 1c, with the exception of enterocytes), across the individual post-mitotic IECs (columns) in the full-length scRNA-seq data. Color code marks the cell types and their associated signatures. FIG. 8d. Mptx2, a novel Paneth cell marker. tSNE of the cells from the droplet-based 3' scRNA-seq (left, as in FIG. 1b) and plate-based full-length scRNA-seq (right, as in a) datasets, colored by expression ($\log_2(TPM+1)$, color bar) of the mucosal pentraxin Mptx2. FIGS. 8e-8g. Cell-type-enriched GPCRs. Heatmap shows the relative expression (row-wise Z-scores, color bar) of genes encoding GPCRs (rows) that are significantly (FDR<0.001, Mann-Whitney U-test) up- or down-regulated in the cells (columns) in a given cell-type (top, color coded as in a) compared to all other cells, in the plate-based full-length scRNA-seq data. FIG. 8h. Cell type specific Leucine-rich repeat (LRR) proteins. Heatmap depicts the mean relative expression (column-wise Z-score of mean $\log_2(TPM+1)$ values, color bar) of genes (columns) encoding LRR proteins that are significantly (FDR<0.001, Mann-Whitney U-test) up- or down-regulated in a given cell-type (rows) compared to all other cells, in the plate-based full length scRNA-seq data. FIG. 8i. Expression of marker genes in absorptive and secretory lineages.

FIG. 9b. Gene signature-based embedding of the IEC lineage. Shown are 7,216 single IECs positioned by signature scores for key cell types: the difference between the signature scores for enterocyte and enteroendocrine cells (x axis); the difference between goblet and tuft cell scores (y axis), and the stem cell score (z axis) (as in FIG. 2b). Each signature score was computed using 50 genes (Methods). Cells are colored by $\log_2(TPM+1)$ expression (color bar) of the goblet cell marker Muc2 (left), the tuft cell marker Dclk1 (middle), and the enteroendocrine marker Chgb (right). FIG. 9c-FIG. 9e. DC-3 reflects the distinction between stem cells and enterocyte progenitors. Diffusion-map embedding of 5,282 cells progressing through stages of enterocyte differentiation (see also FIG. 2c). Shown are DC-1 (x axis) and DC-3 (y axis) with cells (points) colored by the score (color bar, Methods) for gene signatures of the cell-cycle (FIG. 9c), stem cells (FIG. 9d), and enterocytes (FIG. 9e).

FIG. 10A-10R—Enterocyte differentiation toward proximal and distal fates, related to FIG. 2. FIG. 10a-FIG. 10f. DC-1 is driven by enterocyte differentiation and DC-2 distinguished proximal and distal enterocytes. Diffusion-map embedding of 5,282 cells through stages of enterocyte differentiation. Shown are DC-1 (x axis) and DC-2 (y axis) with cells (points) colored by the score (color bar, Methods) for gene signatures of the cell cycle (FIG. 10a), stem cells (FIG. 10b), enterocytes (FIG. 10c), or by the expression levels ($\log_2(TPM+1)$, color bar) of the proximal enterocyte marker Lct (FIG. 10d), and the distal markers Mep1a (FIG. 10e) and Fabp6 (FIG. 10f). FIG. 10l. Regional enterocyte signatures. Relative expression of genes (rows) across cells (columns), sorted by region. FIG. 10n, FIG. 10o. Paneth cell subsets. (FIG. 10n) tSNE of 10,396 single cells (points) obtained using a large cell-enriched protocol (Methods), numbered and shaded by clusters annotated post-hoc. n=2 mice. FIG. 10o-FIG. 10p. Paneth cell subset markers. (FIG. 10o) Expression (row-wise Z-score, color bar) of genes specific (FDR<0.05, Mann-Whitney U-test, log 2 fold-change>0.5) to each of the two Paneth cell subsets (average of 724.5 cells per subtype, down-sampled to 500 for visualization) shown in (FIG. 10n). FIG. 10p. Two Paneth subsets reflect regional diversity. Expression of the same genes (rows) as in (FIG. 10o) but in Paneth cells from each of three small intestinal regions (176.3 cells obtained per each of the regions on average, columns; FIG. 10h); 11 of 11 Paneth-1 markers are enriched in the ileal Paneth cells, while 7/10 Paneth-2 markers are enriched in duodenal or jejunal Paneth cells (FDR<0.05, Mann-Whitney U-test). FIG. 10q. Regional variation of intestinal stem cells. Expression (row-wise Z-score) of genes specific to stem cells from each intestinal region (FDR<0.05, Mann-Whitney U-test, log 2 fold-change>0.5). There are 1,226.3 obtained cells per each of the three regions on average, down-sampled to 500 for visualization. FIG. 10r. Novel regional stem cell markers (FIG. 10q) identify distinct populations in diffusion map space. Close-up of stem-cell region of diffusion space (FIG. 2c) colored by expression level ($\log_2$(TPM+1), color bars) pan-ISC marker Lgr5 (left), proximal ISC marker Gkn3 (center) and distal ISC marker (Bex1). Dashed line is a visual guide.

FIG. 11A-11E—Heterogeneity within EECs, related to FIG. 3. FIG. 11a. EEC subset discovery and spatial location. Shown is a tSNE embedding of the 533 enteroendocrine cells (EECs) identified from the droplet-based datasets for whole SI and regional samples (Methods). FIG. 11b. Agreement in hormone detection rates between 3' droplet and full-length scRNA-seq. Scatter plot shows the detection rate (fraction of cells with non-zero expression of a given transcript) for a set of known EEC hormones, TFs and marker genes (color legend) in EECs from the full-length dataset (x axis), and from the 3' droplet-based dataset (y axis). Linear fit (dashed line) and 95% confidence interval (shaded) are shown. FIG. 11c. Expression of key genes across subset clusters. tSNE plot shows cells numbered and shaded by either by their assignment to 12 clusters (top left plot; identical to FIG. 3a) or by the expression ($\log_2$(TPM+1), color bar) of genes encoding either gut hormones (Sct, Sst, Cck, Gcg, Ghrl, GIP, Nts), or markers of immature EECs (Neurog3), mature EECs (Chgb) or enterochromaffin cells (Tac1, Reg4). FIG. 11d. Co-expression of GI hormones by individual cells. Left: Heatmap shows the expression (color bar) of canonical gut hormone genes (rows) in each of 533 individual EECs (columns), ordered by their assignment to the clusters in a (color bar, top). Right: Heatmap shows for each cluster (columns) the percentage of cells (color bar, inset text) in which the transcript for each hormone (rows) is detected. FIG. 11e. Potential markers for the enteroendocrine (EEC) lineage. Shown is a Volcano plot of the differential expression of each gene (dot) between 310 of the EECs and 6,906 remaining IECs (x axis), and the significance ($-\log_{10}$(Q value)) of each such test (y axis). Genes (points) are colored by their expression level ($\log_2$(TPM+1), color bar)). The names of known lineage TFs are in blue and of gut hormone genes in green.

FIG. 12A-12F—Classification and specificity of enteroendocrine subsets related to FIG. 3. FIG. 12a-FIG. 12b. Relationships between EEC subsets. Dendrogram shows the relationship between EEC clusters as defined by hierarchical clustering of mean expression profiles of all the cells in a subset (Methods). Estimates for the significance of each split are derived from 100,000 bootstrap iterations using the R package pvclust (* p<0.05; ** p<0.01, p<0.001, x test). Heat map (FIG. 12b) shows cell-cell Pearson correlations (r, color bar) between the scores across 11 significant PCs (p<0.05, Methods) across the 533 EECs (rows, columns). Rows and columns are ordered using cluster labels obtained using unsupervised clustering (Methods). FIG. 12c. Subset specificity of gut hormones and related genes. Scatter plot shows for each gene its specificity to its marked cell subset (y axis; defined as the proportion of cells not in a given subset which do not express a given gene) and its sensitivity in that subset (defined as the fraction of cells of a given type which do express the gene, Methods). Subsets are color coded as in the legend. Genes are assigned to the subset where they are most highly expressed on average. Genes were chosen based on their known annotation as gut hormones (Cck, Gal, Gcg, Ghrl, GIP, Iapp, Nucb2, Nts, Pyy, Sct, Sst), enterochromaffin markers (Tph1, Tac1) and canonical EEC markers (Chga, Chgb). FIG. 12d. The enteroendocrine marker Reg4 is substantially expressed in enteroendocrine, goblet and Paneth cells. Violin plots show the distribution of expression ($\log_2$(TPM+1), y axis) of Reg4 in each of the IEC subsets (x axis). FIG. 12e. Mapping the in vivo-identified EEC subsets to EEC subsets in organoid[51]. Heatmap shows the Pearson correlation (color bar) between average expression profiles of the cells of each of 12 subsets in the study (columns), and seven recently reported clusters (rows) from organoids[53]. Cluster-pairs that are maximal across both a row and a column are highlighted (white border). FIG. 12f. GPCRs enriched in different EEC subtypes. Heatmap shows the expression levels (row-wise Z-score, color bar) averaged across the cells in each of the EEC sub-types (columns) of 11 GPCR-encoding genes (rows) that are differentially expressed (FDR<0.25, Mann-Whitney U-test) in one of the EEC subtype clusters.

FIG. 13A-13F—Characterization of tuft cell heterogeneity and identification of hematopoietic lineage marker Ptprc (CD45) in a subset of tuft cells, related to FIG. 4. FIG. 13a. Tuft-1 and Tuft-2 cells. tSNE visualization of 102 tuft cells (points) from the plate-based full-length scRNA-seq dataset (FIG. 7f), labeled by their sub-clustering into Tuft-1 (orange)

and Tuft-2 (brown) subtypes. FIG. 13b. Gene signatures for Tuft-1 and Tuft-2 cells. Heatmap shows the relative expression (row-wise Z-scores, color bar) of the consensus Tuft-1 and Tuft-2 marker genes (rows; orange and brown, respectively), across single cells from the plate-based dataset (columns) assigned to Tuft-1 and Tuft-2 cell clusters (orange and brown, respectively). Top 25 genes shown for each subtype (all FDR<0.01 and log 2 fold change>0.1 in both plate- and droplet-based datasets). FIG. 13c. Tuft-2 signature genes are enriched in immune functions. Shown are the significantly enriched (Methods, FDR<0.1, $-\log_{10}$(Q-value), x axis) GO terms (y axis) in the gene signature for the Tuft-2 subset. FIG. 13d. Expression of neuron- and immune-related genes in Tuft-1 and Tuft-2 subsets, respectively. Plot shows for each gene (y axis) its differential expression (x axis) between Tuft-1 and Tuft-2 cells. Bar indicates Bayesian bootstrap[74] estimates of log 2 (fold change), and hinges and whiskers indicate 25% and 95% confidence intervals, respectively. FIG. 13e. Validation of CD45 expression in some Tuft cells. IFA showing co-expression of a specific tuft cell marker, DCLKl (red) and CD45 (white). Scale bar, 200 μm. FIG. 13f. Isolation of Tuft-2 cells using FACS based on CD45 expression. tSNE embedding of 332 EpCAM*/CD45+FACS-sorted single cells (points, n=3 pooled mice), colored by unsupervised clustering (top left), the expression of the Tuft cell marker Dclkl (top right), or the signature scores for Tuft-1 and Tuft-2 cells (bottom left and right, respectively).

FIG. 14A-14I—Microfold (M) cells from RANKL-treated intestinal organoids and in vivo, related to FIG. 5. FIG. 14a. Previously reported[17] M cell signature genes expressed in Tuft-2 cells. Heat map shows the mean expression level ($\log_2$(TPM+1), color bar) of M cell signature genes[17] (rows) in cells from the Tuft-1 and Tuft-2 subsets (columns) and in mature enterocytes, shown for comparison, based on the high-coverage full-length scRNA-seq data. Cells in the Tuft-2 subset express a significantly higher level of these genes on average ($p<1\times10^{-5}$, Mann-Whitney U-test). FIG. 14b-FIG. 14e. scRNA-seq identifies M cells in RANKL treated organoids. tSNE embedding of 5,434 single cells (dots) from organoids, highlighting (FIG. 14b) those from control (left) or RANKL-treated (middle, right) intestinal organoids; or coloring each cell (c-d) by the expression ($\log_2$(TPM+1), color bar) of the canonical M cell markers TNF-alpha induced protein 2 (Tnfaip2, M-sec, c) and glycoprotein 2 (Gp2, d). FIG. 14e. Expression of M cell marker genes[17,51,75] in each of the organoid cell clusters. Violin plots show the distribution of expression levels ($\log_2$(TPM+1)) for each of 10 previously reported M cell marker genes[58] (columns), in the cells (dots) in each of 13 clusters identified by k-NN clustering of the 5,434 scRNA-seq profiles from organoids. FIG. 14f-FIG. 14g. M cell gene signature in vitro. Heat maps show for each cell type cluster of organoid-derived intestinal epithelial cells (columns) the mean expression (color bar) of genes (rows) for known (grey bars) or novel (black bars) M cell markers (FIG. 14f) or transcription factors (FIG. 14g), identified as specific (FDR<0.05, Mann-Whitney U-test) to M cells both in vitro and in vivo (Methods). FIG. 14h. Congruence of in vitro and in vivo-derived M cell gene signatures. Violin plot shows the distribution of the mean expression of the in vitro-derived signature genes (y-axis) across the in vivo M cells (blue) and all other cells derived from the FAE (grey). FIG. 14i. In vivo expression of the M cell signature genes from organoids. Heatmaps show the mean expression level ($\log_2$(TPM+1), color bar) each of the genes specific to M cells (FDR<0.05, Mann-Whitney U-test, $\log_2$ fold change>0.5) in the organoid data (rows), in the cells from each of the cell type clusters (columns) from the organoids (left) or from in vivo IECs (right). Known and novel M cell markers are marked by red and pink (left). Genes that are specific to M cells in vitro but expressed by IECs in vivo (grey) are filtered out, and a refined set of 18 specific M cell markers (black) that are not expressed by in vivo IECs is retained.

FIGS. 15a and 15b. Generalized and pathogen-specific response genes. Volcano plots show for each gene (dot) the differential expression (DE, x axis), and its associated significance (y axis; ($-\log_{10}$(Q value); Likelihood-ratio test) in response to either Salmonella (top) or H. polygyrus (bottom). Genes strongly up-regulated in Salmonella (FDR<$10^{-6}$) or H. polygyrus (FDR<$5\times10^{-3}$) are highlighted in green or red, respectively. (All highlighted genes were significantly differentially expressed (FDR<0.05) in both the 3' scRNA-seq and the higher depth full-length scRNA-seq datasets.) Left panels: all genes differentially expressed in the noted parasite infection vs. uninfected controls; middle panels: the subset differentially expressed in both parasites vs. control; right panels: the subset differentially expressed only in the noted parasite but not the other (Methods). FIG. 15c. Global induction of enterocyte-specific genes across cells during Salmonella infection. tSNE embedding of 9,842 single IECs from control wild-type mice (left) and mice infected with Salmonella (right). Cells are colored by the expression of the indicated genes, all specific to enterocytes in control mice (Tables 3-5) and strongly up-regulated by infection (FDR<$10^{-10}$ in both the 3' scRNA-seq datasets and in the higher depth full length scRNA-seq dataset). FIG. 15d. Up-regulation of pro-inflammatory apolipoproteins Serum Amyloid A 1 and 2 (Saal and Saa2) in distal enterocytes under Salmonella infection. Violin plot shows $\log_2$(TPM+1) expression level (y axis) of Saa1 (top) and Saa2 (bottom) across all post-mitotic cell-types from control and Salmonella-treated mice (n=4 mice, sample identity shown by color legend) (* FDR<0.01; ** FDR<0.0001, Mann-Whitney U-test). FIG. 15e. Up-regulation of antimicrobial peptides by Paneth cells following Salmonella infection. Violin plots show log 2 (TPM+1) expression levels (y axis) of genes encoding antimicrobial peptides (panels, marked on top left) and the mucosal pentraxin Mptx2 (bottom right) in the cells (dots) from control and Salmonella-infected mice (n=4 mice, sample identity shown by color legend) (* FDR<0.1;  FDR<0.01,  FDR<0.0001, Mann-Whitney U-test). FIG. 15f. Paneth cell numbers detected (using graph-clustering, Methods) after Salmonella. Frequencies (y-axis) of Paneth cells in each mouse (dots) under each condition (color legend). Error bars: standard error of the mean (SEM). (** FDR<0.01, Wald test).

FIG. 16a. Genes significantly induced in response to H. polygyrus infection in a non-cell-type specific manner. tSNE visualization of 9,842 single IECs (dots) from control wild-type mice (left) and mice infected with H. polygyrus for three (middle) or ten (right) days. Cells are colored by the expression ($\log_2$(TPM+1), color bar) of the indicated genes. Genes were selected as significantly differentially expressed in response to infection in a non-cell-type specific manner (FDR<0.001 in both the 3' scRNA-seq and full-length scRNA-seq datasets). Ifitm3 is specific to H. polygyrus infection, while others are up-regulated in both pathogenic infections. FIG. 16b-FIG. 16c. Expression of the Tuft-1 signature (left), Tuft-2 signature (middle) and Dclkl (right)

in the combined dataset of control, *Salmonella* and *H. polygyrus* infected cells in tuft cell subgroups defined by cluster analysis. (FIG. 16b) Violin plots of the distribution of the respective signature scores (left and middle) and the expression of Dclk1 (right, log 2 (TPM+1, y axis) in cells (dots) in each of the tuft subsets (x axis). (FIG. 16c) tSNE mapping of the 409 tuft progenitor, Tuft-1 and Tuft-2 cells, colored by the scores for each signature (color bar, left and middle) and their assignment to subtype clusters via kNN-graph clustering (right). FIG. 16d. Anti-parasitic protein secretion by goblet cells during *H. polygyrus* infection. Immunofluorescence assay (IFA) of FFPE sections of RELMb (top-left, red), E-cadherin (Bottom left, green) and their merged view (right) after 10 days of helminth infection. White arrow: sections of *H. polygyrus*. Scale bar, 200 μm.

FIG. 17A-E—Single-cell RNA-seq reveals MHCII expression in subsets of Lgr5* intestinal stem cells. FIG. 17A, FIG. 17B. Three subsets of intestinal stem cells (ISCs). Shown are a t-distributed stochastic neighbor (tSNE) embedding (FIG. 17A) and correlation matrix (FIG. 17B) of 637 intestinal stem cells identified by unsupervised clustering from 1,522 full-length scRNA-seq profiles (FIG. 21A, Methods). Individual points in the tSNE embedding (FIG. 17A) correspond to single cells colored by their assignment based on kNN-graph-clustering (Methods) and post-hoc annotation (legend, top left). Heatmap (FIG. 17B) shows the Pearson correlation coefficient (r, color bar) between scores of individual cells (rows and columns) along the first 10 principal components (PCs). Color code marks ISC subsets, (bottom, Methods) FIG. 17C. MHCII expression in Lgr5$^+$ ISCs. Violin plot of the distribution of the mean expression levels ($\log_2$(TPM+1), y-axis) of MHCII genes (H2-Abl, H2-Aa, Ciita, Cd74, H2-DMa, H2-DMb1) in each of the three ISC groups. FIG. 17D. Antigen presentation genes are enriched in Lgr5$^+$ ISCs. Heatmap shows the relative mean expression (row-wise Z-score of $\log_2$(TPM+1) values, color bar) of MHCII-related genes (rows) in each of the IEC types (columns) as defined by clustering of the 1,522 full-length scRNA-seq profiles. EP: Enterocyte progenitor, EEC: enteroendocrine cell. FIG. 17E. Validation of MHCII expression by ISCs. IFA of MHCII (I-A/I-E; green) co-stained with Paneth cell marker, Lyz1 (red) within the intestinal crypt of a wild type (WT, top row) and MHCII constitutive knockout (MHCII KO, bottom row) mouse. Yellow arrows: MHCII-expressing ISCs adjacent to Lyz1$^+$ Paneth cells at the bottom of the crypt. Scale bar, 20 μm.

FIG. 18A-18F—MHCII expression is correlated with ISC proliferation. FIG. 18A, FIG. 18B. Distinct cell-cycle characteristics in the three ISC subsets. (FIG. 18A) Violin plot shows the distribution of expression scores (y-axis) for a signature of cell-cycle genes (Methods) in each stem cell subset (x-axis).  $p<10^{-5}$, * $p<10^{-7}$ (Mann-Whitney U-test). (FIG. 18B) Scatter plots show the signature score for 637 ISCs (points, Methods) for G1/S genes (x-axis) and G2/M genes (y-axis). Cells are colored by their cluster assignment to ISC subsets. FIG. 18C. Gene signatures of ISC subsets. Heatmap shows relative expression level (row-wise Z-score of $\log_2$(TPM+1) values, color bar) of ten representative genes from each ISC subset signature and a pan-stem signature (rows, right color bar) in 637 individual stem cells and 201 TA progenitors (columns, bottom color bar as in (A)) identified from 1,522 scRNA-seq profiles. Gene signatures are identified based on our analysis as well as from a previously published signature of stem cell genes of a bulk dataset [3]. FIG. 18D. Identification of proliferating stem cells in intestinal crypts. Upper panels: Combined single-molecule fluorescence in situ hybridization (smFISH) with immunofluorescence (IFA) of FFPE sections of intestinal tissue from wild type mice, showing the pan-stem cell marker Lgr5 (upper left), ISC-I marker Cyp2e1 (upper middle) and ISC-III marker Psrc1 (upper right) all in red and mKi67 in white. Cell borders were assessed with E-cadherin (green); scale bar, 20 m. Bottom left: Schematic of the lower crypt fraction ('stem cell zone'), in which co-expression of stem cell markers (Lgr5 and Cyp2e1 or Psrc1) and the proliferation marker mKi67 was quantified. Bottom right: Bar plot showing the fraction (y-axis) of cells which are positive for mKi67 out of all cells positive for each stem cell marker (lower right panel). n=4 mice, 10 crypts on average per mouse (** $p<0.0025$, t-test; error bars: SEM). FIG. 18E. Enrichment of ISC-I in EdU$^-$cells. Violin plots show the distribution of signature scores for the cell-cycle (left, signature as in (A)) and ISC-I (right, signature as in (C)) from FACS sorted EdU$^-$ Lgr5$^+$ ISCs (light green) or EdU$^+$ Lgr5$^+$ ISCs (dark green) after in vivo EdU labeling and profiled using single-nucleus RNA-seq (Div-Seq). FIG. 18F. Higher proliferation of ISCs with high MHCII expression. FACS plots of ISCs gated on GFP-high (Lgr5$^+$, left) binned into subsets with low, intermediate and high MHCII expression (middle panels, y-axis), and then gated on EdU incorporation (middle panels, x-axis). Bar plot (right) shows the fraction (percentage, y-axis) of EdU$^+$ cells within each MHCII expression level (n=4 mice, * $p<0.05$,  $p<0.005$, * $p<0.0005$, t-test, error bars: SEM). G. ISC subset signatures across MHCII expression. Violin plots show the distribution of signature scores (as in (C)) for ISC-I, ISC-II, and ISC-III subsets (left to right), across scRNA-seq profiles from 326 Lgr5$^+$ MHCII$^{high}$ (light blue) and 177 Lgr5$^+$ MHCII$^{low}$ (dark blue) cells (individual black dots). Horizontal black line denotes the median ( $p<0.005$, * $p<0.0005$, Mann-Whitney U-test).

FIG. 19A-19D—T helper cells and their key cytokines impact ISC number and differentiation in intestinal organoids. FIG. 19A, FIG. 19B. Shifts in cell type composition within organoids treated with CD4+Th signature cytokines (FIG. 19A) or co-cultured with Th cells (FIG. 19B). relative abundance (y-axis) of each IEC-type under each condition relative to their proportions in control organoids (dashed line). Subsets were identified by unsupervised clustering of 23,177 single cells obtained from the Th co-culture and cytokine conditions and annotated post-hoc (FIG. S5D, Methods). * $p<0.01$, ** $p<10-4$ (hypergeometric test, Methods) FIG. 19C. DCLK1+ tuft cell expansion following IL-13 treatment. IFA of DCLK1 (red) in control organoids (top) and IL-13-treated organoids (bottom). Scale bar, 50 μm. FIG. 19D. Altered clonogenicity following pre-treatment with different cytokines. Bar plot shows the relative clonogenicity of organoid cultures (y-axis, relative to the mean value of control organoids) defined by the number of organoids in cultures re-seeded after treatment with IL-10 or IL-13 (x-axis). Dots: technical replicates. Error bars: SD, * $p<0.05$, *** $p<0.0005$, t-test.

FIG. 20A-20I—MHCII depletion leads to increased ISC numbers while $T_{reg}$ ablation results in reduced ISC pool. FIG. 20A FIG. 20D. Expansion of the ISC pool following epithelial specific ablation of MHCII. (FIG. 20A) Validation of epithelial-specific MHCII-KO (MHCII$^{\Delta gut}$) mouse. IFA of Lyz1 (red) and MHCII (I-A/I-E, green) in MHCII$^{fl/fl}$ (top row) and MHCII$^{\Delta gut}$ mice (bottom row). Yellow arrow: MHCII$^+$ epithelial cell, white arrow: MHCII$^+$ non-epithelial cell. (FIG. 20B) smFISH of the expression of Lgr5 (red) within intestinal crypts from MHCII$^{fl/fl}$ controls (n=5, top left) and MHCII$^{\Delta gut\ t}$ mice (n=5, bottom left). Bar plot (right) shows the number of Lgr5 mRNA molecules per crypt (y-axis) in MHCII$^{fl/fl}$ and MHCII$^{\Delta gut}$ mice (x-axis). n=2 mice and 8 fields per group. Error bars: SD (* p<0.05, t-test). (FIG. 20C) Bar plot shows the fraction of ISCs (y-axis, determined by unsupervised clustering) in MHCII$^{\Delta gut}$ and MHCII$^{\Delta gut}$ mice (points, x-axis). Error bars are SEM. (* FDR<0.05, likelihood-ratio test, Methods). (FIG. 20D) Heatmap shows the significance of changes in signature scores (–log$_{10}$(p-value), Mann-Whitney U-test, of enrichment (red) and depletion (blue), Methods) of MHCII$^{\Delta gut}$ or T$_{reg}$ ablation compared to control mice (columns) for signatures (rows) associated with the three ISC subsets. E-H. Reduction in ISC numbers and shifts toward ISC-II and ISC-III states in T$_{reg}$ depleted mouse model. (FIG. 20E) Bar plot shows the fraction of ISCs (y-axis) detected by unsupervised clustering in WT and Foxp3-DTR mice both treated with DT). Error bars are SEM. ( FDR<0.005, likelihood-ratio test, Methods). (FIG. 20F) smFISH of FFPE sections of intestinal tissue from wild type mice (top) or Foxp3-DTR mice (bottom) both treated with DT, showing from left to right, the stem cell marker Lgr5 (red), mKi67 (white) and a merge; scale bar, 20 m. Bar plot (right) shows the number of Lgr5 mRNA molecules per crypt (y-axis) in WT and Foxp3-DTR mice treated with DT (x-axis). n=2 mice and 8 fields per group, error bars are SD (* p<0.001, t-test). (FIG. 20G) Immunohistochemistry (IHC) of MHCII (I-A/I-E; brown) co-stained with hematoxylin (blue) within the intestinal crypt of wild type (top) and Foxp3-DTR (bottom) mice both treated with DT. Red arrows indicate MHCII$^+$ ISCs. (FIG. 20H) A shift towards proliferative ISC states following T$_{reg}$ depletion. Violin plots of the distribution of scores (Methods) for the cell-cycle (left; as in FIG. 2) and MHCII genes (right; as in FIG. 17) in ISCs (small points) from WT (n=5; 2,572 cells) and Foxp3-DTR (n=4, 815 cells) mice. Squares: mean score per mouse; thick bar: overall mean; error bars: SEM. (* p<0.05, ** p<0.005, * * * p<5×10-4, likelihood-ratio test). FIG. 20I. Proposed model of a novel interaction between CD4+T helper cells and ISCs mediated by MHCII. T helper cell subsets (blue nodes) modulate (solid arrows) the differentiation (dashed arrows) of ISCs (green). T$_{regs}$ and their key cytokine IL-10 promote stem cell renewal, while Th17 cells and their cytokine IL-17a reduce stem cell renewal and promote differentiation. Both Th1 and Th2 suppress stem cell renewal and promote specific differentiation towards Paneth cells (tan) and tuft cells (orange), respectively.

FIG. 21A-21G—Identification of Lgr5$^+$ stem cells by single cell RNA-seq, FIG. 21A. Intestinal stem cells (ISCs) identified from scRNA-seq data by unsupervised clustering and post-hoc annotation. tSNE visualization of 1,522 single cells (points) profiled by full-length scRNA-seq. Cells are colored by the mean expression (mean Log$_2$(TPM+1), color bar) of a previously published[103] ISC gene signature (left), the marker gene Lgr5 (log$_2$(TPM+1), color bar, center left), or by a color code of clusters from kNN-graph clustering (center right), which identifies two clusters (Stem-1 and Stem-2, dark green and cyan, respectively) both of which are positive for the ISC signature genes and express Lgr5. The union of these two clusters (dark green, right) forms a set of 637 ISCs, which were used for further analyses. EP: Enterocyte progenitor, EEC: enteroendocrine cell. FIG. 21B. Quality control. Violin plots show the distributions of reads per cell (y-axis, left) and genes detected per cell (y-axis, right) in each IEC-type (x-axis, as defined in (A)). Horizontal bars: median. FIG. 21C. All ISC subsets express a stemness signature. Violin plot showing mean expression (log$_2$(TPM+ 1), y-axis) of stem cell signature genes[103], in each of the three ISC subsets as well as in the cluster of 201 TA progenitors (FIG. 21A) (x-axis). * p<0.001,  p<1×10$^{-5}$, * p<1×10$^{-7}$ (Mann-Whitney U-test). D,E. Validation of in silico cell type identification using FACS. (FIG. 21D) Proportion (percentage, y-axis) of cells from FACS sorted EpCAM$^+$, Lgr5$^{Low}$, Lgr5$^{High}$ CD24$^+$ and CD24$^+$/c-Kit$^+$ fractions (color legend) in each of the cell type clusters (bars), identified in the 1,522 IECs sequenced using full-length scRNA-seq (as in (A), Methods). At least 50% of the cells in each of the ISC subsets are Lgr5$^{High}$, while less than 15% of the cells in any other subset are Lgr5$^{High}$. (FIG. 21E) Proportion (percentage, y-axis) of cells from each identified cluster (color legend) in each of the FACS fractions (bars). 90.3% of cells in the Lgr5$^{High}$ fraction are assigned to one of the three ISC states. FIG. 21F. Three ISC subsets are similarly represented along the small intestine. Heatmap shows the fraction (color legend) of cells in each of the detected ISC states (rows) among the ISC isolated from each of three spatial regions (columns), as inferred using a random forest classifier trained on 2,965 ISCs, extracted from each of the respective gut regions (Methods). FIG. 21G. Cell type-enriched ligands and receptors. Average relative expression (Z-score of mean log$_2$(TPM+1), color bar) of the top 10 receptors (left) and ligands (right, columns) enriched (FDR<0.05, Mann-Whitney U-test) in each cell type (rows). The invariant chain of MHCII, Cd74, is highlighted in red (left).

FIG. 22A-22E—Identification and characterization of MHCII-expressing Lgr5$^+$ stem cells. FIG. 22A. MHCII signature is largely restricted to ISCs. Violin plot shows the distribution of mean expression levels (log$_2$(TPM+1), y-axis, bar: median) of MHCII genes (H2-Ab, H2-Aa, Ciita, Cd74, H2-DMa, H2-DMb1) in IEC types (FIG. S1A) from the 1,522 IECs profiled by full-length scRNA-seq. EP: Enterocyte progenitor, EEC: enteroendocrine cell. FIG. 22B. Protein-level quantification via FACS of MHCII expression in IECs from Lgr5-GFP mouse. Distribution (left) and mean (bar plot, right) of detected fluorescence corresponding to MHCII protein expression in populations sorted for GFP-high, GFP-low, CD24+ or CD24+/c-kit*. Error bars: SEM. n=6 mice. FIG. 22C. MHCII is expressed in intestinal crypts of wild type mice. IHC images show MHCII expression (I-A/I-E, brown) within crypts of WT mice (n=2 mice). Red arrow, MHCII$^+$ cell. Scale bar, 20 µm. FIG. 22D, FIG. 22E. Known quiescence marker Kdm5b identifies post-mitotic cells and low-cycling ISC-I subset. (FIG. 22D) Scatter plot shows the negative relationship between cell-cycle score (x-axis) and the mean expression of the putative quiescence marker Kdm5b$^{98-102}$ (log$_2$(TPM+1), y-axis) in each IEC-type (dots) for both proliferating (blue) and post-mitotic (red) cells. Trend line shows the random-effects linear model fit to all 1,522 cells. Error bars: SEM. (FIG. 22E) Violin plot of the distribution of expression level of Kdm5b (log$_2$ (TPM+1), y-axis) in ISC-I, ISC-II, and ISC-III clusters (x axis) (* p<0.05, ** p<0.005, Mann-Whitney U test).

FIG. 23A. Distinct signatures of the three ISC subsets. Shown are cumulative distribution functions (CDF) of signature scores (x-axis) in the cells from each of the three subsets of ISCs (colored curves) of a published ISC signature from bulk data[103] (left), or signatures of 25 genes defined by differential expression testing in each subset (Methods). FIG. 23B. Two ISC subsets found in GO are varying by MHCII expression. Top left: Scatter plot of the G1/S (x-axis) and G2/M (y-axis) signature scores for 637 Lgr5$^+$ ISCs (points). A subset of 183 Lgr5$^+$ ISCs that are likely in GO is marked in purple. Other panels: PCA of these 183 ISCs, where cells (dots; density marked by contours) are colored by the expression ($\log_2$(TPM+1), color bar) of MHCII (top right panel) or by three ISC-I markers (bottom panels). FIG. 23C. Two subsets of cells are separated by PC-1: one is MHCII$^{low}$ and positive for ISC-I markers and the other is MHCII$^{high}$. C. MHCII$^{high}$ ISCs sorted by FACS express higher levels of MHCII mRNA. Violin plot shows the distribution of the mean expression level (y-axis, ($\log_2$(TPM+1)) of the MHCII gene signature (Methods) in each cell (dot) in Lgr5$^{high}$ cells sorted on MHCII$^{low}$ and MHCII$^{high}$ (x-axis) (*** $p<0.0005$, Mann-Whitney U test).

FIG. 24A-24J Changes in immune cells, IEC cell-type composition and ISC gene expression in response to pathogen infection in vivo. FIG. 24A. CD4$^+$ T cells interact with stem cells in vivo. Two-photon microscopy image of the small intestine from Lgr5-GFP (green) knock-in mouse engrafted with RFP$^+$ CD4$^+$ T cells (red). CD4$^+$ T cells are visible in close proximity to Lgr5$^+$ ISCs (inset and right). Scale bar, 20 µm. FIG. 24B-FIG. 24D. *Salmonella enterica* infection induces Th1 polarization in the gut. (FIG. 24B) Changes in immune cell proportions. Stacked bar plots show the percentage (y-axis) of different immune cell subsets (color legend), as determined by scRNA-seq of 5,122 CD45+ cells from the lamina propria of control and *Salmonella*-infected mice. (FIG. 24C) Bar plot shows the significance of the enrichment ($-\log_{10}$(p-value), y-axis, hypergeometric test) of marker genes for different T helper subsets (x-axis) among the genes induced (FDR<0.05, likelihood-ratio test) in T cells from *Salmonella* infected vs. control mice. Dashed line: p=0.05. (FIG. 24D) Plot shows differential expression (x-axis) for each gene (y-axis) across 824 T cells from *Salmonella*-infected mice (n=4) and 543 T cells from control mice (n=5). Bar indicates Bayesian bootstrap[74] estimates of log 2(fold-change), and hinges and whiskers indicate 25% and 95% confidence intervals, respectively. Th1 cell markers are labeled in green. Dashed line: no differential expression. FIG. 24E, FIG. 24F. Changes in fractions of tuft and Paneth cells within the intestinal epithelium after infection. Bar plots show the frequencies of tuft (E) and Paneth (F) cells (y-axis), as determined by unsupervised clustering of droplet-based scRNA-seq data in mice under different conditions (x-axis), n=2 and 4 mice (points) per group, in (FIG. 24E) and (FIG. 24F), respectively. * FDR<10-5;  FDR<10-10, likelihood-ratio test, Methods. FIG. 24G. Fraction of ISCs within the intestinal epithelium after infection. Cell-type frequencies (y-axis) determined by unsupervised clustering of droplet-based scRNA-seq data in each infection model and control mice (x-axis, n=2 mice (points) per infection group, n=4 for control;  FDR<$10^{-10}$ likelihood-ratio test, Methods). FIG. 24H. Reduced stemness scores in ISCs during pathogenic infection in vivo. Violin plot shows the distribution of the bulk stemness signature score (y-axis, Methods) of 1,857 ISCs identified by clustering (Methods) of 9,842 cells sequenced using droplet-based scRNA-seq from *Salmonella enterica*- or *H. polygyrus*-treated mice and controls (x-axis). * $p<0.01$, ** $p<10-5$ (Mann-Whitney U-test). FIG. 24I. Pathogenic infection reduces the expression of ISC marker genes. Heatmap shows the mean expression (column-wise Z-score of mean $\log_2$(TPM+1) values, color bar) of all of the known ISC marker genes[103] (columns) that are differentially expressed (FDR<0.05) by 1,857 ISCs, as determined by unsupervised clustering from a total of 9,842 cells profiled by droplet-based scRNA-seq, in control and pathogen-infected mice (rows). FIG. 24J. Shifts in the three ISC subsets under infection in vivo. Heatmap shows the significance of changes of expression scores ($\log_{10}$(p-value), Mann-Whitney U-test, color bar, of enrichment (red) and depletion (blue)) within 1,857 ISCs. ISCs in each condition were scored for expression of each ISC subset gene signature (columns, sets and signatures as in FIG. 18), and the distribution of scores was compared to that in ISCs from control mice (top three rows). Bottom row: comparison between control mice on day 3 and 10 of the *H. polygyrus* infection course.

FIG. 25A. Intestinal organoid co-cultured with T cells. Images of organoid and T$_{reg}$ co-cultures at x4 magnification. Lines mark T$_{regs}$ and organoids. FIG. 25B, FIG. 25C. Validation of in vitro-polarized Th cell populations. FACS plots for each of the four subsets of Th cells. Top panels: quantification of the viability dye 7-AAD (y-axis) and the Th cell marker CD4 (x-axis). Bottom panels: quantification of relevant marker proteins for each Th subset (x- and y-axes, bottom panels). (FIG. 25C). Heatmap shows the mean relative expression (row-wise Z-score of mean $\log_2$(TPM+1) values, color bar) of canonical marker genes (rows) in the cells from each in vitro-differentiated Th cell subset (columns), identified by droplet-based scRNA-seq of co-cultures (Methods). FIG. 25D. IEC type identification within intestinal organoid cultures. tSNE embeddings of 17,755 single IECs (individual points) isolated from control, cytokine-treated and Th cell co-cultured intestinal organoids and sequenced using droplet-based scRNA-seq. Most cells were merged into a single dataset to maximize the statistical power of clustering (Methods). Top left panel: cells numbered and shaded by cluster assignment from unsupervised kNN-graph clustering (Methods). Top middle panel: cells numbered and shaded by post-hoc annotations using cell-type signatures derived from in vivo scRNA-seq data (clusters that expressed high levels of the same signatures were merged to a final set of seven clusters). All other panels: cells colored by the mean expression (color bar, $\log_2$(TPM+1)) of the noted cell-type specific signatures. FIG. 25E. Organoid-derived secretory IECs co-express markers for goblet and Paneth cells. Scatter plots show the expression levels (top three rows, $\log_2$(TPM+1)) of canonical markers for goblet cells (Spink4, Agr2, Tff3, y-axis) and for Paneth cells (Defa24, Itlnl, Lyz1, x-axis) or signature scores for goblet and Paneth cells (bottom row, 50 genes), for in vivo goblet cells (left), cells in the Paneth-goblet cluster from control organoids (middle) and in vivo Paneth cells (right). FIG. 25F. Reanalysis of published scRNA-seq data confirms Paneth and goblet cell marker co-expression in organoids. tSNE embeddings of 161 Reg4+ cells sorted from intestinal organoid cultures in an independent study[160]. Top left: Cell types were identified using the RaceID clustering algorithm, as in the original publication[160] (colored and numbered nodes). Remaining plots: cells are colored by the expression (log 2(normalized transcript count), color bars) of canonical markers of Paneth and goblet cells. A group of Paneth-goblet-like cells is clearly observed, where individual cells are double-positive for markers of both cell types. FIG. 25G. Induction of MHCII expression in organoids co-cultured with Th1 cells. Violin plot shows the distribution of mean expression levels ($\log_2$(TPM+1), y-axis, bar denotes the median value) of six MHCII genes (H2-Abl, H2-Aa, Ciita, Cd74, H2-DMa, H2-DMb1) in IECs profiled by droplet-based scRNA-seq from control organoids and those co-cultured with each subset of Th cells (total of 6,234 cells, x-axis). *** $p<10^{-10}$, (Mann-Whitney U-test).

FIG. 26A-26F—Changes in cell proportions and ISC expression programs in organoids co-cultured with Th subsets or their signature cytokines. FIG. 26A-FIG. 26C.

Changes in proportion of cells expressing stem cell marker genes after co-culture with $iT_{regs}$ or treatment with IL-10. FIG. 26A, FIG. 26B. Scatter plots compare the fraction of cells showing non-zero expression (a, y-axis) of each gene (dot) in organoids (FIG. 26A) co-cultured with $iT_{reg}$-cells or (FIG. 26B) treated with IL-10, compared to the fraction in matching control organoids (a, x-axis). All genes up-regulated (FDR<0.05) are shown, sized relative to their significance ($-\log_{10}$(FDR), legend top left). Several key ISC marker genes (Methods) are labeled. The diagonal line indicates no change relative to the control organoid. (FIG. 26C) Heatmap shows the fraction of cells with non-zero expression (a, color bar) of 10 selected stem cell marker genes (columns) within organoids co-cultured with $T_{regs}$ or Th1 cells (top, rows) or treated with IL-13 or IL-10 cytokines (bottom, rows). All genes are expressed at a larger proportion of cells (FDR<0.05, Mann-Whitney U-test) in organoids co-cultured with $iT_{reg}$ cells (top) or treated with IL-10 (bottom), compared to control organoids. FIG. 26D-FIG. 26F. Th1 co-culture up-regulates Paneth cell-related gene expression in organoids. (FIG. 26D) Heatmap of the significance of change of the Paneth cell signature score in 'Paneth-goblet' cells between different Th co-cultures (rows) and control organoids ($-\log_{10}$(p-value), Mann-Whitney U-test, color bar, of enrichment (red) and depletion (blue). (FIG. 26E) Density histograms of the distribution of Paneth cell signature scores in 'Paneth-goblet' cells in organoids co-cultured with either Th1 (red, left) or Th2 (red, right) cells compared to their matching control organoids (blue). Dashed lines denote the mean score. * p<0.05,  p<$10^{-5}$ (Mann-Whitney U-test). (FIG. 26F) Box plots of the distribution of expression levels ($\log_2$(TPM+1), y-axis) of canonical Paneth cell markers Defa24 (left) and Lyz1 (right) in the IEC-type cluster (x-axis) from organoids co-cultured with Th1 cells (right part of each panel) compared to control organoids (left part).  p<$10^{-5}$ (Mann-Whitney U-test).

FIG. 27A-27B—Validation of MHCII knockout in intestinal epithelial cells. A,B. Validation of epithelial-specific MHCII knockout by FACS quantification of MHCII-expressing IECs in small intestine (FIG. 27A) and mesenteric lymph node (FIG. 27B). Scatter plots (left) and bar plots (right) show the fraction of EpCAM*/MHCII+ (A) or CD11b+/MHCII+ (B) cells in $MHCII^{fl/fl}$ and MHCII knockout mice ($MHCII^{\Delta gut}$). (A) n=5 mice, * p<0.05. (B) n=2 mice, NS: not statistically significant.

FIG. 28A. Increased proportion of Lgr5+ cells in $MHCII^{\Delta gut}$ mice. Bar plot shows the fraction of cells (y-axis) in which the transcript for Lgr5 is detected, amongst the 1,559 cells profiled from $MHCII^{\Delta gut}$ mice (n=5) and 1,617 cells profiled from matched $MHCII^{\Delta gut}$ controls (n=5). Error bars: SEM, * p<0.05, likelihood-ratio test. FIG. 28B. scRNA-seq of IECs from $MHCII^{\Delta gut}$ and matched controls. tSNE embedding of 3,176 cells colored by their genotype (numbered and shaded as in legend, left), assignment to cell types by unsupervised clustering (middle, Methods) and stemness score (right; score as in FIG. 21A). FIG. 28C, FIG. 28D. Expansion of ISCs following KO of MHCII specifically in gut epithelial cells. Bar plot (FIG. 28C) and volcano plot (FIG. 28D) based on all 1,559 cells in $MHCII^{\Delta gut}$ mice (n=5) vs. 1,617 cells from matched $MHCII^{fl/fl}$ controls (n=5). Green dots in (FIG. 28D): up-regulated ISC genes, red dots: down-regulated ISC genes (FDR<0.05, likelihood-ratio test), grey dots: non-DE genes. FIG. 28E. Higher stemness signatures in ISCs from $MHCII^{\Delta gut}$ mice. Violin plots of the distribution of the signature scores for the cell-cycle (as in FIG. 18A), MHCII genes and stemness[103] (as in FIG. 17C), in ISCs from $MHCII^{fl/fl}$ mice (n=5, grey) and from $MHCII^{\Delta gut}$ mice (n=5, white), when including either all 381 ISCs (top left), only the 173 ISCs that still have detectable mRNA for H2-Ab1 (bottom left), or only the 208 ISCs that are a confirmed KO: do not have detectable mRNA for H2-Ab1 (bottom right). Expression of H2-Ab1 mRNA is also shown in these two groups (top right). Small dots: individual cells; squares: mean per mouse; * p<0.05, likelihood-ratio test.

FIG. 29E, FIG. 29F. ISC expansion in two T cell-depleted mouse models. (FIG. 29E) Bar plot shows the fraction of epithelial cells which are stem cells (y-axis), as determined by unsupervised clustering of scRNA-seq profiles, from WT (7,216 cells, n=6), nude (2,967 cells, n=2), and TCRβ-KO mice (9,488 cells, n=2). Dots correspond to individual mice. Error bars are SEM. (* p<0.05, p<$10^{-3}$, * p<$10^{-5}$, likelihood-ratio test, Methods). (FIG. 29F) smFISH of Lgr5+ cells in the crypt. Left: Lgr5 expression (red) in intestinal crypts of wild type (left), TCRβ-KO (center), and nude (right) mice. Right: bar plot shows the number of Lgr5 molecules detected per crypt (y-axis) in each of the three models (x-axis). n=2 mice and 8 fields per group. Error bars: SD (* p<0.05, **p<0.005, t-test, Methods).

FIG. 30A-30F—Impact of $T_{reg}$ depletion on ISC pool in vivo. FIG. 30A FIG. 30E. Reduction of the ISC pool following $T_{reg}$ depletion in Foxp3-DTR mice. FIG. 30A. Representative FACS plot (left) and quantified mean proportion (bar plot, right) of TCRβ+ Foxp3+ $T_{regs}$ out of all CD4+ TCRβ+ cells in the small intestine of WT and Foxp3-DTR mice (y-axis) after 7 days of DT treatment. Dots: individual mice. Error bars: SEM (n=3 mice, * p<0.0005 t-test). FIG. 30B. IHC images of FFPE sections stained for H&E (left), cleaved Caspase-3 (brown, middle) and Ki67 (brown, right) in WT (top row) and Foxp3-DTR mice (bottom row) after 7 days of DT treatment. Inset is 3× magnification showing $T_{reg}$ depletion results in proliferation at the bottom of the crypts, where stem cells reside, with no signs of apoptosis. Scale bar, 50 μm. FIG. 30C. Bar plot of the frequency of cells in which Lgr5 mRNA is detected (y-axis) in WT and Foxp3-DTR mice both treated with DT. (Error bars: SEM, p<0.005 likelihood-ratio test). FIG. 30D. Volcano plot shows mean log 2 (fold-change, x-axis) and significance ($-\log_{10}$(FDR), Methods) of differential expression between 815 cells from Foxp3-DTR mice (n=4) vs. 2,572 cells from matched WT controls (n=5) both treated with DT. Green dots: upregulated ISC genes, Red dot: downregulated ISC genes (FDR<0.05, likelihood-ratio test, grey dots: non-DE genes. FIG. 30E. Bar plot shows frequency (y-axis) of IEC-types, as determined by unsupervised clustering (Methods), in 815 cells from Foxp3-DTR mice (n=4, white) vs. 2,572 cells from matched WT controls (n=5, grey) both treated with DT. Individual mice marked by points. Error bars: SEM. ( FDR<0.005, * FDR<10-5 likelihood-ratio test). FIG. 30F. Expansion of tuft cells following $T_{reg}$ depletion in Foxp3-DTR mice. IFA image of DCLK1+(red) tuft cells in the epithelia of wild type (WT, left) and Foxp3-DTR mice (right) both treated with DT. Scale bar, 50 m.

FIG. 31b. show expression (row-wise Z-scores of mean $Log_2$(TPM+1) values, color bar) of a subset of genes (rows) from either published (Munoz et al., 2012) or data-driven (see Methods intestinal stem cell signatures which are also up-regulated (FDR<0.05, Mann-Whitney U-test) after co-culture with iTregs. FIG. 31c. Organoids co-cultured with Th1 cells. FIG. 31d. show expression (row-wise Z-scores of mean $Log_2$ (TPM+1) values, color bar) of a subset of genes (rows) from either published (Munoz et al., 2012) or data-driven (see Methods intestinal stem cell signatures which are also up-regulated (FDR<0.05, Mann-Whitney U-test) after stimulation with IL-10.

FIG. 32a-FIG. 32d. A biopsy from a human patient with ulcerative colitis was processed as above. Shading: Light Shade:Uninflamed, Dark shade:Inflamed.

FIG. 33a-FIG. 33d. A biopsy from a human patient without disease was processed as above. Color code Blue Uninflamed, Green: Uninflamed.

FIG. 34a-FIG. 34d. Single cell sequencing of a small intestinal epithelium demonstrates a highly diverse stem cell population; FIG. 34A sets forth a t-distributed stochastic nearest-neighbor embedding (tSNE) visualization of 1,600 single cells and about 6000 genes; Cell cycle signatures show three distinct stem cell subpopulations associated with high-cycling ISC (FIG. 34B), primed SC (FIG. 34C), and low-cycling ISC (FIG. 34D) states.

FIG. 35 sets forth a diagram demonstrating that, in accordance with some embodiments, stem cells directly communicate with immune cells. For example, the stem cell extracellular peptide can engage immune cells that lead to stem cell proliferation and/or differentiation (e.g., the immune synapse may govern intestinal proliferation and/or differentiation by comminucation and/or sampling of the stem cell lumen content).

FIG. 36a-FIG. 36d. FIG. 36A sets forth data showing that IL-13 programs organoid differentiation toward the secretory lineage of goblet and tuft/microfold cells (e.g., leading to an upregulation of goblet and tuft cells and a downregulation of Paneth and enteroendocrine cells); FIG. 36B sets forth expression and lineage markers determined by RNA-seq; FIG. 36C shows that co-culturing of organoids with Th1 derived T cells skews cell populations toward Paneth cells; FIG. 36D shows three distinct states of intestinal stem cells, from low cycling to highly proliferative ISCs, from low cycling to highly proliferative ISCs, determined in bulk populations and in single cells.

FIG. 37 sets forth data showing that *H. Polygyrus* infection results in goblet and tuft cell expansion, while *Salmonella* results in enterocyte and Paneth cell expansion.

FIG. 39 illustrates that the atlas uncovers almost all cell types and subtypes in the colon.

DETAILED DESCRIPTION OF THE EXAMPLE EMBODIMENTS

General Definitions

Figure 1A:
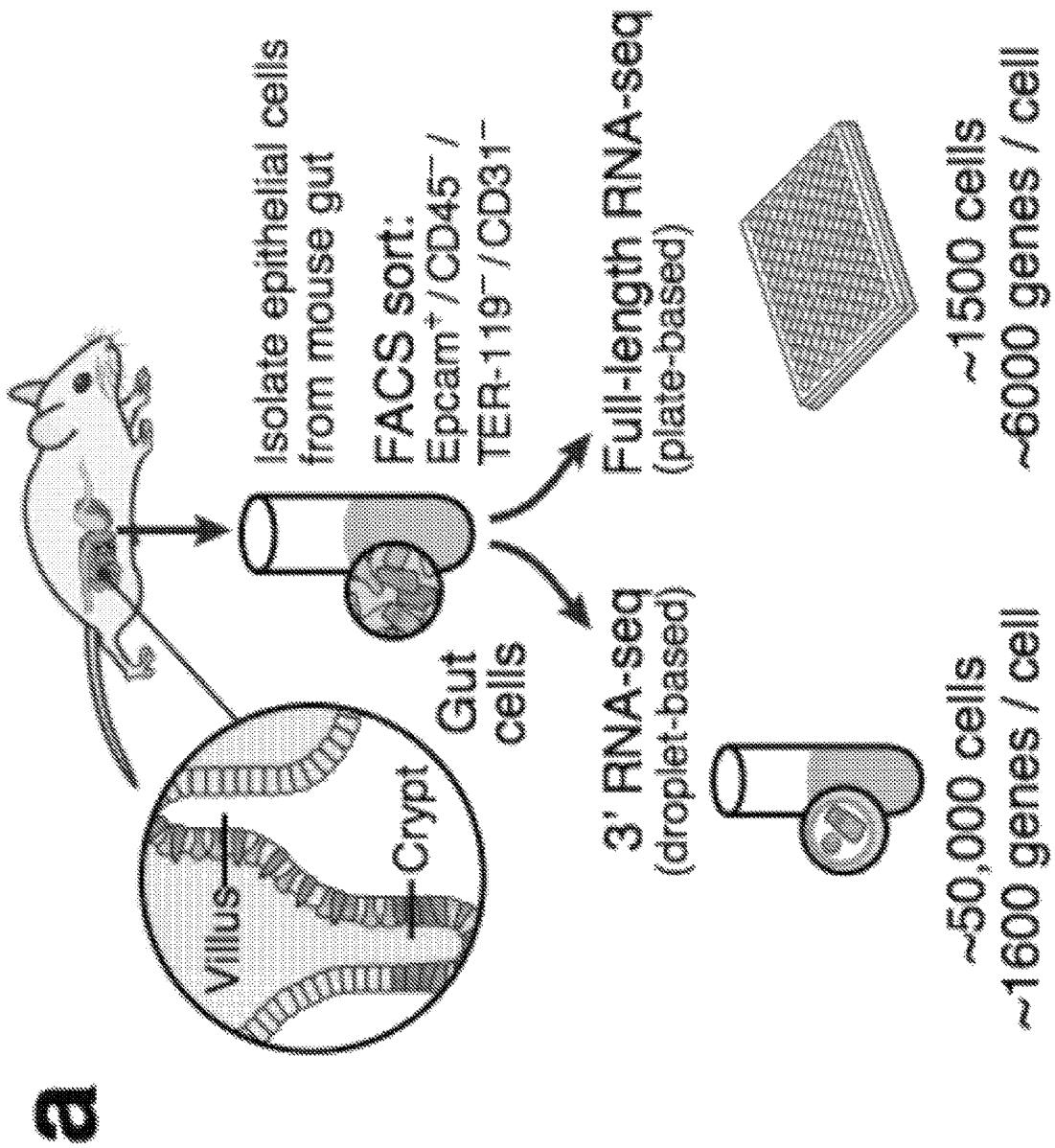

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints. The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Whereas the terms "one or more" or "at least one", such as one or more members or at least one member of a group of members, is clear per se, by means of further exemplification, the term encompasses inter alia a reference to any one of the members, or to any two or more of the members, such as, e.g., any≥3, ≥4, ≥5, ≥6 or ≥7 etc. of the members, and up to all members. In another example, "one or more" or "at least one" may refer to 1, 2, 3, 4, 5, 6, 7 or more.

The term "optional" or "optionally" means that the subsequent described event, circumstance or substituent may or may not occur, and that the description includes instances where the event or circumstance occurs and instances where it does not.

The term "isolated" as used throughout this specification with reference to a particular component generally denotes that such component exists in separation from—for example, has been separated from or prepared and/or maintained in separation from—one or more other components of its natural environment. More particularly, the term "isolated" as used herein in relation to a cell or cell population denotes that such cell or cell population does not form part of an animal or human body.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide markers and gene signatures for identifying, isolating and modulating cells for the treatment of diseases and disorders associated with the gut. Understanding the development, differentiation and function of an organ, such as the intestine, requires the identification and characterization of all of its component cell types. In the small bowel, intestinal epithelial cells (IECs) sense and respond to microbial stimuli and noxious substances, provide crucial barrier function and participate in the coordination of immune responses. Here, Applicants profiled 53,193 individual IECs from mouse small intestine and intestinal organoid cultures. Using unsupervised clustering, Applicants defined specific gene signatures for major IEC lineages, including the identification of Mptx2, a mucosal pentraxin, as a novel Paneth cell marker. In addition, Applicants identified unexpected diversity of hormone-secreting enteroendocrine populations, revealing co-expression programs of gut hormone genes, previously thought to represent different enteroendocrine subtypes, and constructed a novel hierarchical taxonomy of these cells. Applicants also distinguished two subtypes of Dclk1-positive tuft cells, one of which (Tuft-2) expresses both the epithelial cytokine Tslp and the pan-immune cell marker Ptprc (CD45), which has not been previously associated with any non-hematopoietic cell type. Finally, Applicants characterized how the intrinsic states and proportions of these cell types are reshaped in response to *Salmonella enterica* and *Heligmosomoides polygyrus* infections. *Salmonella* infection led to an increased number of Paneth cells and enterocytes, and Paneth cell-specific up-regulation of both defensins and Mptx2. In addition, an absorptive enterocyte-specific antimicrobial program was broadly activated across all IEC types, demonstrating previously uncharacterized cellular response to pathogens. In contrast, *H. polygyrus* led to expansion of goblet and tuft cell populations, with a particular expansion of the Cd45+ Tuft-2 group. The high-resolution atlas highlights new markers and transcriptional programs, novel allocation of sensory molecules to cell types and organizational principles of gut homeostasis and physiology.

Here, Applicants use scRNA-seq to chart a comprehensive atlas of the epithelial cells of the small intestine. Applicants identified gene signatures, key TFs and specific GPCRs for each of the major small intestinal differentiated cell types, and traced their differentiation from ISCs. Applicants identified and characterized cellular heterogeneity within specific cell-types, and validated individual genes and signatures in situ. Applicants found a transcriptional signature distinguishing proximal and distal enterocytes, established a novel classification of the different subtypes of the enteroendocrine cells and their differential deployment at different locations, and identified a previously unrecognized separation of tuft cells to two sub-types, one with a neuron-like and one with an immune-like gene signature, expressing Ptprc (CD45) and TSLP, a pan-immune cell marker and epithelial cytokine, respectively. Finally, Applicants demonstrated how these cell types and states change dynamically as the small intestine adapts to infection by distinct classes of pathogens. The high resolution cell atlas better defines the composition of the gut, highlights novel key molecules, TFs and GPCRs that can impact gut function and shows how changes in gut composition can play a key role in maintaining homeostasis in response to pathogens.

In the small intestine, a cellular niche of diverse accessory cell types supports the rapid generation of mature epithelial cell types through self-renewal, proliferation, and differentiation of intestinal stem cells (ISCs). However, not much is known about interactions between immune cells and ISCs, and it is unclear if and how immune cell dynamics affect eventual ISC fate or the balance between self-renewal and differentiation. Here, Applicants used single-cell RNA-seq (scRNA-Seq) of intestinal epithelial cells (IECs) to identify new mechanisms for ISC-immune cell interactions. Surprisingly, MHC class II (MHCII) is enriched in two distinct subsets of Lgr5' crypt base columnar ISCs, which are also distinguished by higher proliferation rates. Using co-culture of T cells with intestinal organoids, cytokine stimulations, and in vivo mouse models, Applicants confirm that CD4+T helper (Th) cells communicate with ISCs and affect their differentiation, in a manner specific to the Th subtypes and their signature cytokines and dependent on MHCII expression by ISCs. Specific inducible knockout of MHCII in intestinal epithelial cells in mice in vivo results in expansion of the ISC pool. Mice lacking T cells have expanded ISC pools, whereas specific depletion of $T_{reg}$ cells in vivo results in substantial reduction of ISC numbers. The findings show that interactions between Th cells and ISCs mediated via MHCII expressed in intestinal epithelial stem cells help orchestrate tissue-wide responses to external signals. The mechanisms discovered can be leveraged to treat disease in the gut.

Inflammatory Diseases of the Gut

Inflammatory bowel disease (IBD) is a group of inflammatory conditions of the colon and small intestine, principally including Crohn's disease and ulcerative colitis, with other forms of IBD representing far fewer cases (e.g., collagenous colitis, lymphocytic colitis, diversion colitis, Beçet's disease and indeterminate colitis). Pathologically, Crohn's disease affects the full thickness of the bowel wall (e.g., transmural lesions) and can affect any part of the gastrointestinal tract, while ulcerative colitis is restricted to the mucosa (epithelial lining) of the colon and rectum.

Graft-versus-host disease (GVHD) is an immune-related disease that can occur following an allogeneic tissue transplant. It is commonly associated with stem cell or bone marrow transplants, but GVHD also applies to other forms of tissue graft. In GVHD immune cells of the tissue graft recognize the recipient host as foreign and attack the host's cells.

It has long been recognized that IBD and GVHD are diseases associated with increased immune activity. The causes of IBD, while not well understood, may be related to an aberrant immune response to the microbiota in genetically susceptible individuals. IBD affects over 1.4 million people in the United States and over 2.2 million in Europe and is on the increase. With both environmental and genetic factors playing a role in the development and progression of IBD, response to current treatments (e.g., anti-inflammatory drugs, immune system suppressors, antibiotics, surgery, and other symptom specific medications) are unpredictable.

Similarly, a fundamental feature of GVHD is increased immune activity. As yet, the pathophysiology underlying GVHD is not well understood. It is a significant cause of morbidity and mortality following allogenic haematopoietic stem-cell transplantation and thus the focus of much ongoing research. Despite the advances in understanding the pathophysiology (e.g., predisposing factors), a standardized therapeutic strategy is still lacking. Currently both acute and chronic forms of GVHD are treated using corticosteroids (e.g., anti-inflammatory treatments). There is a need for new approaches to treating IBD and GVHD.

Some of the genetic factors predisposing one to IBD are known, as explored in Daniel B. Graham and Ramnik J. Xavier "From Genetics of Inflammatory Bowel Disease Towards Mechanistic Insights" Trends Immunol. 2013 August; 34(8): 371-378 (incorporated herein). This disclosure provides a rationale for modulating intestinal epithelial cell balance, function, differentiation and/or activity for the treatment of both IBD and GVHD, and other disorders.

In certain embodiments, the IBD is Crohn's disease or ulcerative colitis. In certain embodiments, the IBD is collagenous colitis, lymphocytic colitis, diversion colitis, Behçet's disease, or indeterminate colitis.

In other embodiments, the GVHD is acute graft-versus-host disease (aGVHD) or chronic graft-versus-host disease (cGVHD).

In yet other embodiments, the methods of the disclosure include administering to a subject in need thereof an effective amount (e.g., therapeutically effective amount or prophylactically effective amount) of the treatments provided herein. Such treatment may be supplemented with other known treatments, such as surgery on the subject. In certain embodiments, the surgery is strictureplasty, resection (e.g., bowel resection, colon resection), colectomy, surgery for abscesses and fistulas, proctocolectomy, restorative proctocolectomy, vaginal surgery, cataract surgery, or a combination thereof.

Atlas of the Small Intestinal Epithelium During Homeostasis and Pathogenic Infection The small intestinal mucosa is at equipoise with a complex luminal milieu which comprises a combination of diverse microbial species and their products as well as derivative products of the diet. It is increasingly clear that the functional balance between the epithelium and the constituents within the lumen plays a central role in both maintaining the normal mucosa and the pathophysiology of many gastrointestinal disorders. The barrier function is part fulfilled by anatomic features that partly impede penetration of macromolecules and diverse set of specialized cells that monitor and titrate responses to a variety of noxious substances or pathogens (Peterson and Artis, 2014). The underlying mucosal immune system is poised to detect antigens and bacteria at the mucosal surface and to drive appropriate responses of tolerance or an active immune response.

IECs of the small intestinal epithelium comprise two major lineages—absorptive and secretory (Clevers, 2006)—reflecting its dual roles. Enterocytes of the absorptive lineage comprise approximately 80% of the epithelium and are specialized for digestion and transport of nutrients (Ferraris et al., 1992). The secretory lineage comprises five further terminally differentiated types of IECs: goblet, Paneth, enteroendocrine, tuft and microfold (M) cells (Barker et al., 2007; Gerbe et al., 2012; Sato et al., 2009)—each with distinct and specialized sensory and effector functions.

The epithelium is organized in a repeating structure of villi, which project toward the lumen, and nearby crypts (FIG. 1a). The crypts of the small intestine are the proliferative part of the epithelium, in which intestinal stem cells (ISCs) and progenitors, termed transit-amplifying cells (TAs), reside (Barker et al., 2007; Barker et al., 2012; Miyoshi and Stappenbeck, 2013). In contrast, only fully differentiated cells are found on the villi (Barker, 2014; Clevers, 2013; Peterson and Artis, 2014). The crypt also contains Paneth cells, which secrete anti-microbial peptides (AMPs), such as defensins and lysozyme, into the lumen to keep the microbiota in check (Cheng and Leblond, 1974b; Clevers, 2013; Salzman et al., 2003). The highly proliferative TA cells migrate along the crypt-villus axis and differentiate into functionally distinct epithelial cell types that subsequently reach the tip of the villus, where mature cells undergo apoptosis and shed to the lumen (Clevers, 2006). Epithelial tissue turns over rapidly (~5 days) (Barker, 2014; Clevers, 2013; van der Flier et al., 2009), allowing it to dynamically shift its composition in response to stress or pathogens.

For example, parasitic infection typically induces hyperplasia of goblet cells, which produce and secrete mucins to prevent pathogen attachment, strengthening the epithelial barrier and facilitating parasite expulsion (Pelaseyed et al., 2014). Rare (0.5-1%) enteroendocrine cells (EECs) secrete over 20 individual hormones and are key mediators of intestinal response to nutrients (Furness et al., 2013; Gribble and Reimann, 2016) by directly detecting fluctuations in luminal nutrient concentrations via G-protein-coupled receptors (GPCRs)(Gribble and Reimann, 2016). Mapping these GPCRs and hormones has important therapeutic applications. Finally, IECs communicate with immune cells to initiate either inflammatory responses or tolerance in response to lumen signals (Biton et al., 2011; Peterson and Artis, 2014).

A rare IEC population, tuft cells (Gerbe et al., 2012) promote type-2 immunity in response to intestinal parasites by expressing interleukin-25 (1125), which in turn mediates the recruitment of group 2 of innate lymphoid cells (ILC2s) that initiate the expansion of T-helper type 2 cells upon parasite infection (Gerbe et al., 2016; Howitt et al., 2016; von Moltke et al., 2016). Furthermore, M cells reside exclusively in follicle-associated epithelia found only above Peyer's patches, which are gut associated lymphoid follicles (de Lau et al., 2012). M cells play an important role in immune sensing by transporting luminal content to immune cells found directly below them (Mabbott et al., 2013). Disruption in any of the major innate immune sensors and proximity effector functions of IECs may result in increased antigenic load through weakening of the epithelial barrier, and may lead to the onset of acute or chronic inflammation. Despite this extensive knowledge, given the complexity of the epithelial cellular ecosystem, many questions remain open.

It is an objective of the present invention to determine all the discrete epithelial cell types of the gut, additional types, or new sub-types that have eluded previous studies. It is another objective of the present invention to determine the molecular characteristics of each type. For example, mapping the GPCRs and hormones expressed by EECs has important therapeutic applications; charting known and new specific cell surface markers can provide handles for specific cell isolation, and help assess the validity of legacy ones; and finding differentially expressed transcription factors (TFs) can open the way to study the molecular processes that accompany the differentiation of IECs, such as tuft or enteroendocrine cells. It is another objective of the present invention to understand the response of individual cell populations to pathogenic insult, both in terms of changes in cellular proportions and cell-intrinsic responses. IDENTIFYING CELLS In some aspects the present disclosure refers to a method of identifying a cell or cell marker, comprising: a) isolating target cells based on a marker specifically expressed in or on the cell or by label-free imaging flow cytometry; b) quantifying gene expression in the target cells by single cell sequencing, and c) clustering the target cells based on the gene expression by application of one or more algorithms, d) optionally determining a transcription signature for each cluster based at least in part on identifying differentially expressed genes between two or more clusters and between each cluster and the remaining cells as background, and e) optionally validating gene expression against cellular morphology.

In some examples of the present disclosure identifying differentially expressed transcripts comprises application of a supervised or unsupervised machine-learning model. A supervised machine learning model is for example selected from the group consisting of an analytical learning model, an artificial neural network model, a back propagation model, a boosting model, a Bayesian statistics model, a case-based model, a decision tree learning model, an inductive logic programming model, a Gaussian process regression model, a group method of data handling model, a kernel estimator model, a learning automata model, a minimum message length model, a multilinear subspace learning, a naive bayes classifier model, a nearest neighbor model, a probably approximately correct (PAC) learning model, a ripple down rules model, a symbolic machine learning model, a subsymbolic machine learning model, a support vector machine learning model, a minimum complexity machine model, a random forest model, an ensemble of classifiers model, an ordinal classification model, a data pre-processing model, a handling imbalanced datasets model, a statistical relational learning model, a Proaftn model. An unsupervised machine learning model is for example selected from the group consisting of a k-means model, a mixture model, a hierarchical clustering model, an anomaly detection model, a neural network model, an expectation-maximization (EM) model, a method of moments model, or a blind signal separation technique.

These models are used separately or in combination with each other or in combination with any other machine-learning model, wherein a supervised model is combined with a supervised model, or an unsupervised model is combined with an unsupervised model or a supervised model is combined with an unsupervised model.

In other examples of the previous aspects (optional) validating gene expression against cellular morphology comprises sparse labeling the cell to enhance the expression of a fluorescent protein in the cell and combining the sparse labeling with fluorescent in situ hybridization (FISH) to validate the marker against cellular morphology in step e). In examples of the previous aspects FISH is for example combined with a specific antibody, double FISH or a transgenic reporter mouse line directed to a previously identified marker in the cell. For example an enhancer element is inserted into a lentivirus or an adeno-associated virus (AAV) vector upstream of the fluorescent protein to enhance its expression.

Marker

The term "marker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification.

Preferably, markers as intended herein may be peptide-, polypeptide- and/or protein-based, or may be nucleic acid-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or copy DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilisation of the cells.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis corresponding native proteins, such as, e.g., amino acid deletions, additions and/or substitutions. The term contemplates both full-length proteins and protein parts or fragments, e.g., naturally-occurring protein parts that ensue from processing of such full-length proteins.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "nucleic acid" as used throughout this specification typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and 0-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-0,4'-C-alkylene-linked, e.g., 2'-0,4'-C-methylene-linked or 2'-0,4'-C-ethylene-linked sugars such as ribose; 2'-fluoro-arabinose, etc.).

Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone inter-nucleoside linkages. Preferably, inter-nucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof.

A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

Unless otherwise apparent from the context, reference herein to any marker, such as a peptide, polypeptide, protein, or nucleic acid, may generally also encompass modified forms of the marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

Orthologs and Homologs

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Thus, when reference is made to mouse genes and proteins, it is understood that the same is believed to apply to the corresponding ortholog in humans or other species. Likewise, when referencing Cas9 and other proteins, it is understood to likewise apply to orthologs and homologs.

The CRISPR-CRISPR associated (Cas) systems of bacterial and archaeal adaptive immunity are some such systems that show extreme diversity of protein composition and genomic loci architecture. The CRISPR-Cas system loci has more than 50 gene families and there is no strictly universal genes indicating fast evolution and extreme diversity of loci architecture. So far, adopting a multi-pronged approach, there is comprehensive cas gene identification of about 395 profiles for 93 Cas proteins. Classification includes signature gene profiles plus signatures of locus architecture. A new classification of CRISPR-Cas systems is proposed in which these systems are broadly divided into two classes, Class 1 with multisubunit effector complexes and Class 2 with single-subunit effector modules exemplified by the Cas9 protein. Novel effector proteins associated with Class 2 CRISPR-Cas systems may be developed as powerful genome engineering tools and the prediction of putative novel effector proteins and their engineering and optimization is important.

The effector protein may comprise a chimeric effector protein comprising a first fragment from a first effector protein ortholog and a second fragment from a second effector protein ortholog, and wherein the first and second effector protein orthologs are different. At least one of the first and second effector protein orthologs may comprise an effector protein from an organism comprising *Bergeyella, Prevotella, Porphyromonas, Bacteroides, Alistipes, Riemerella, Myroides, Flavobacterium, Capnocytophaga, Chryseobacterium, Paludibacter, Phaeodactylibacter* or *Psychroflexus*.

In certain embodiments, the effector protein, particularly a Group 29 or Group 30 effector protein effector protein may be at least 700 amino acids long. In preferred embodiments, the effector protein may be about 1100 to about 1500 amino acids long, e.g., about 1100 to about 1200 amino acids long, or about 1200 to about 1300 amino acids long, or about 1300 to about 1400 amino acids long, or about 1400 to about 1500 amino acids long, e.g., about 900, about 1000, about 1100, about 1200, about 1300, about 1400, about 1500, about 1600, about 1700, or about 1800 amino acids long.

In certain embodiments, the Group 29 or Group 30 effector proteins as intended herein may be associated with a locus comprising short CRISPR repeats between 30 and 40 bp long, more typically between 34 and 38 bp long, even more typically between 36 and 37 bp long, e.g., 30, 31, 32, 33, 34, 35, 36, 37, 38, 39, or 40 bp long. In certain embodiments the CRISPR repeats are long or dual repeats between 80 and 350 bp long such as between 80 and 200 bp long, even more typically between 86 and 88 bp long, e.g., 80, 81, 82, 83, 84, 85, 86, 87, 88, 89, or 90 bp long.

Orthologous proteins may but need not be structurally related, or are only partially structurally related. In particular embodiments, the homologue or orthologue of a Group 29 or Group 30 protein as referred to herein has a sequence homology or identity of at least 80%, more preferably at least 85%, even more preferably at least 90%, such as for instance at least 95% with the Group 29 or Group 30 effector protein. In a preferred embodiment, the Group 29 or Group 30 effector protein may be an ortholog of an organism of a genus which includes but is not limited to *Bergeyella, Prevotella, Porphyromonas, Bacteroides, Alistipes, Riemerella, Myroides, Flavobacterium, Capnocytophaga, Chryseobacterium, Phaeodactylibacter, Paludibacter* or *Psychroflexus*. Some methods of identifying orthologs of CRISPR system enzymes may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes but is not limited to *Bergeyella, Prevotella, Porphyromonas, Bacteroides, Alistipes, Riemerella, Myroides, Flavobacterium, Capnocytophaga, Chryseobacterium, Phaeodactylibacter, Paludibacter* or *Psychroflexus*. A chimeric enzyme can comprise a first fragment and a second fragment, and the fragments can be of CRISPR enzyme orthologs of organisms of genuses herein mentioned or of species herein mentioned; advantageously the fragments are from CRISPR enzyme orthologs of different species.

TABLE 1

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Paludibacter propionicigenes* WB4 (NC_014734.1) | WP_013446107.1 | NA | 8 | N | N | N | 1155 |
| *Prevotella* sp. P5-60 (NZ_JXQJ01000080.1) | WP_044074780.1 | NA | 5 | Y | ? | ? | 1091 |
| *Prevotella* sp. P4-76 (NZ_JXQI01000021.1) | WP_044072147.1 | NA | 0 | ? | ? | ? | 1091 |
| *Prevotella* sp. P5-125 (NZ_JXQL01000055.1) | WP_044065294.1 | NA | 11 | ? | ? | ? | 1091 |
| *Prevotella* sp. P5-119 (NZ_JXQK01000043.1) | WP_042518169.1 | NA | 11 | ? | ? | ? | 1091 |
| *Capnocytophaga canimorsus* Cc5 (NC_015846.1) | WP_013997271.1 | WP_013997274.1 | 51 | Y | Y | Y | 1200 |
| *Phaeodactylibacter xiamenensis* (NZ_JPOS01000018.1) | WP_044218239.1 | WP_044218241.1 | 19 | ? | ? | ? | 1132 |
| *Porphyromonas gingivalis* W83 (NC_002950.2) | WP_005873511.1 | WP_005873518.1 | 7 | Y | Y | Y | 1136 |
| *Porphyromonas gingivalis* F0570 (NZ_KI259168.1) | WP_021665475.1 | WP_021665476.1 | 3 | ? | ? | ? | 1136 |
| *Porphyromonas gingivalis* ATCC 33277 (NC_010729.1) | WP_012458151.1 | WP_012458152.1 | 12 | Y | Y | Y | 1136 |
| *Porphyromonas gingivalis* F0185 (AWVC01000122.1) | ERJ81987.1 | ERJ81988.1 | 0 | ? | ? | ? | 1136 |
| *Porphyromonas gingivalis* F0185 (NZ_KI259960.1) | WP_021677657.1 | WP_021677658.1 | 6 | ? | ? | ? | 1136 |
| *Porphyromonas gingivalis* SJD2 (NZ_KI629875.1) | WP_023846767.1 | WP_005873518.1 | 4 | ? | ? | ? | 1136 |
| *Porphyromonas gingivalis* F0568 (AWUU01000145.1) | ERJ65637.1 | ERJ65638.1 | 3 | ? | ? | ? | 1136 |
| *Porphyromonas gingivalis* W4087 (AWVE01000130.1) | ERJ87335.1 | ERJ87336.1 | 2 | ? | ? | ? | 1136 |
| *Porphyromonas gingivalis* W4087 (NZ_KI260263.1) | WP_021680012.1 | WP_005873518.1 | 4 | ? | ? | ? | 1136 |
| *Porphyromonas gingivalis* F0568 (NZ_KI258981.1) | WP_021663197.1 | WP_021663198.1 | 6 | ? | ? | ? | 1136 |
| *Porphyromonas gingivalis* (NZ_LOEL01000010.1) | WP_061156637.1 | WP_005873518.1 | 11 | ? | ? | ? | 1136 |
| *Porphyromonas gulae* (NZ_JRAQ01000019.1) | WP_039445055.1 | WP_039445052.1 | 10 | ? | ? | ? | 1136 |
| *Bacteroides pyogenes* F0041 (KE993153.1) | ERI81700.1 | ERI81699.1 | 5 | ? | ? | ? | 1116 |
| *Bacteroides pyogenes* JCM 10003 (NZ_BAIU01000001.1) | WP_034542281.1 | WP_034542279.1 | 18 | ? | ? | ? | 1116 |
| *Alistipes* sp. ZOR0009 (NZ_JTLD01000029.1) | WP_047447901.1 | NA | 7 | ? | ? | ? | 954 |
| *Flavobacterium branchiophilum* FL-15 (NC_016001.1) | WP_014084666.1 | WP_014084665.1 | 19 | Y | N | Y | 1151 |
| *Prevotella* sp. MA2016 (NZ_JHUW01000010.1) | WP_036929175.1 | NA | 7 | ? | ? | ? | 1323 |
| *Myroides odoratimimus* CCUG 10230 (AGEC02000017.1) | EHO06562.1 | EHO06560.1 | 2 | ? | ? | ? | 1160 |
| *Myroides odoratimimus* CCUG 3837 (AGZK01000016.1) | EKB06014.1 | EKB06015.1 | 0 | ? | ? | ? | 1158 |
| *Myroides odoratimimus* CCUG 3837 (NZ_JH815535.1) | WP_006265509.1 | WP_006265510.1 | 0 | ? | ? | ? | 1158 |

TABLE 1-continued

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Myroides odoratimimus* CCUG 12901 (NZ_JH590834.1) | WP_006261414.1 | WP_006261415.1 | 0 | ? | ? | ? | 1158 |
| *Myroides odoratimimus* CCUG 12901 (AGED01000033.1) | EHO08761.1 | EHO08762.1 | 0 | ? | ? | ? | 1158 |
| *Myroides odoratimimus* (NZ_CP013690.1) | WP_058700060.1 | WP_006261415.1 | 10 | Y | Y | Y | 1160 |
| *Bergeyella zoohelcum* ATCC 43767 (AGYA01000037.1) | EKB54193.1 | EKB54194.1 | 9 | ? | ? | ? | 1225 |
| *Capnocytophaga cynodegmi* (NZ_CDOD01000002.1) | WP_041989581.1 | WP_041989578.1 | 7 | ? | ? | ? | 1219 |
| *Bergeyella zoohelcum* ATCC 43767 (NZ_JH932293.1) | WP_002664492.1 | WP_034985946.1 | 8 | Y | Y | Y | 1225 |
| *Flavobacterium* sp. 316 (NZ_JYGZ01000003.1) | WP_045968377.1 | NA | 0 | ? | ? | ? | 1156 |
| *Psychroflexus torquis* ATCC 700755 (NC_018721.1) | WP_015024765.1 | NA | 16 | Y | Y | Y | 1146 |
| *Flavobacterium columnare* ATCC 49512 (NC_016510.2) | WP_014165541.1 | NA | 7 | Y | Y | Y | 1180 |
| *Flavobacterium columnare* (NZ_CP013992.1) | WP_060381855.1 | NA | 5 | Y | Y | Y | 1214 |
| *Flavobacterium columnare* (NZ_CP015107.1) | WP_063744070.1 | NA | 3 | Y | Y | Y | 1214 |
| *Flavobacterium columnare* (NZ_CP016277.1) | WP_065213424.1 | NA | 14 | Y | Y | Y | 1215 |
| *Chryseobacterium* sp. YR477 (NZ_KN549099.1) | WP_047431796.1 | NA | 0 | ? | ? | ? | 1146 |
| *Riemerella anatipestifer* ATCC 11845 = DSM 15868 (NC_014738.1) | WP_004919755.1 | WP_004919758.1 | 12 | Y | Y | Y | 1096 |
| *Riemerella anatipestifer* RA-CH-2 (NC_020125.1) | WP_015345620.1 | WP_004919758.1 | 12 | Y | Y | Y | 949 |
| *Riemerella anatipestifer* (NZ_CP007504.1) | WP_049354263.1 | WP_004919758.1 | 11 | Y | Y | Y | 949 |
| *Riemerella anatipestifer* (NZ_LUDU01000012.1) | WP_061710138.1 | WP_061710139.1 | 13 | ? | ? | ? | 951 |
| *Riemerella anatipestifer* (NZ_LUDI01000010.1) | WP_064970887.1 | WP_064970885.1 | 4 | ? | ? | ? | 1096 |
| *Prevotella saccharolytica* F0055 (AMEP01000091.1) | EKY00089.1 | EKY00090.1 | 0 | ? | ? | ? | 1151 |
| *Prevotella saccharolytica* JCM 17484 (NZ_BAKN01000001.1) | WP_051522484.1 | NA | 5 | Y | Y | Y | 1152 |
| *Prevotella buccae* ATCC 33574 (AEPD01000005.1) | EFU31981.1 | EFU31982.1 | 16 | ? | ? | ? | 1128 |
| *Prevotella buccae* ATCC 33574 (NZ_GL586311.1) | WP_004343973.1 | WP_004343974.1 | 16 | Y | Y | Y | 1128 |
| *Prevotella buccae* D17 (NZ_GG739967.1) | WP_004343581.1 | WP_004343582.1 | 8 | ? | ? | ? | 1128 |
| *Prevotella* sp. MSX73 (NZ_ALJQ01000043.1) | WP_007412163.1 | WP_036927782.1 | 13 | ? | ? | ? | 1128 |
| *Prevotella pallens* ATCC 700821 (AFPY01000052.1) | EGQ18444.1 | EGQ18443.1 | 4 | ? | ? | ? | 1126 |
| *Prevotella pallens* ATCC 700821 (NZ_GL982513.1) | WP_006044833.1 | WP_050795200.1 | 4 | ? | ? | ? | 1126 |
| *Prevotella intermedia* ATCC 25611 = DSM 20706 (NZ_JAEZ01000017.1) | WP_036860899.1 | WP_050795200.1 | 11 | ? | ? | ? | 1127 |
| *Prevotella intermedia* (NZ_LBGT01000010.1) | WP_061868553.1 | NA | 27 | ? | ? | ? | 1121 |
| *Prevotella intermedia* 17 (CP003502.1) | AFJ07523.1 | AFJ07898.1 | 16 | N | N | N | 1135 |
| *Prevotella intermedia* (NZ_AP014926.1) | WP_050955369.1 | WP_014708440.1 | 16 | N | N | N | 1133 |
| *Prevotella intermedia* (AP014598.1) | BAU18623.1 | BAU18624.1 | 6 | N | N | N | 1134 |
| *Prevotella intermedia* ZT (ATMK01000017.1) | KJJ86756.1 | KJJ86755.1 | 2 | ? | ? | ? | 1126 |
| *Prevotella aurantiaca* JCM 15754 (NZ_BAKF01000019.1) | WP_025000926.1 | WP_036889078.1 | 5 | ? | ? | ? | 1125 |
| *Prevotella pleuritidis* F0068 (NZ_AWET01000045.1) | WP_021584635.1 | WP_021584705.1 | 6 | ? | ? | ? | 1140 |
| *Prevotella pleuritidis* JCM 14110 (NZ_BAJN01000005.1) | WP_036931485.1 | WP_024991772.1 | 7 | ? | ? | ? | 1117 |

TABLE 1-continued

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Prevotella falsenii* DSM 22864 = JCM 15124 (NZ_BAJY01000004.1) | WP_036884929.1 | WP_051527348.1 | 10 | ? | ? | ? | 1134 |
| *Porphyromonas gulae* (NZ_JRAT01000012.1) | WP_039418912.1 | WP_052073447.1 | 11 | Y | Y | Y | 1176 |
| *Porphyromonas* sp. COT-052 OH4946 (NZ_JQZY01000014.1) | WP_039428968.1 | WP_050563578.1 | 12 | ? | ? | ? | 1176 |
| *Porphyromonas gulae* (NZ_JRFD01000046.1) | WP_039442171.1 | WP_050563578.1 | 9 | ? | ? | ? | 1175 |
| *Porphyromonas gulae* (NZ_JRAJ01000010.1) | WP_039431778.1 | WP_046201041.1 | 2 | ? | ? | ? | 1176 |
| *Porphyromonas gulae* (NZ_KQ040500.1) | WP_046201018.1 | WP_046201041.1 | 4 | ? | ? | ? | 1176 |
| *Porphyromonas gulae* (NZ_JRAL01000022.1) | WP_039434803.1 | WP_039434800.1 | 20 | ? | ? | ? | 1176 |
| *Porphyromonas gulae* (NZ_JRAI01000002.1) | WP_039419792.1 | WP_052078041.1 | 9 | ? | ? | ? | 1120 |
| *Porphyromonas gulae* (NZ_JRAK01000129.1) | WP_039426176.1 | WP_039426172.1 | 6 | ? | ? | ? | 1120 |
| *Porphyromonas gulae* (NZ_KN294104.1) | WP_039437199.1 | WP_052102013.1 | 0 | ? | ? | ? | 1120 |
| *Porphyromonas gingivalis* TDC60 (NC_015571.1) | WP_013816155.1 | WP_043890185.1 | 2 | Y | Y | Y | 1120 |
| *Porphyromonas gingivalis* ATCC 33277 (NC_010729.1) | WP_012458414.1 | WP_012458413.1 | 4 | Y | Y | Y | 1120 |
| *Porphyromonas gingivalis* A7A1-28 (NZ_CP013131.1) | WP_058019250.1 | WP_043898408.1 | 6 | Y | Y | Y | 1176 |
| *Porphyromonas gingivalis* JCVI SC001 (APMB01000175.1) | EOA10535.1 | EOA10563.1 | 5 | ? | ? | ? | 1176 |
| *Porphyromonas gingivalis* W50 (NZ_AJZS01000051.1) | WP_005874195.1 | WP_010955981.1 | 2 | ? | ? | ? | 1176 |
| *Porphyromonas gingivalis* (NZ_CP011995.1) | WP_052912312.1 | WP_010955981.1 | 7 | Y | Y | Y | 1176 |
| *Porphyromonas gingivalis* AJW4 (NZ_CP011996.1) | WP_053444417.1 | WP_043898408.1 | 11 | N | N | N | 1120 |
| *Porphyromonas gingivalis* (NZ_CP007756.1) | WP_039417390.1 | WP_021665928.1 | 5 | Y | Y | Y | 1120 |
| *Porphyromonas gingivalis* (NZ_LOEL01000001.1) | WP_061156470.1 | WP_021663076.1 | 5 | ? | ? | ? | 1120 |

Fragment

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of the peptide, polypeptide, or protein. For example, insofar not exceeding the length of the full-length peptide, polypeptide, or protein, a fragment may include a sequence of >5 consecutive amino acids, or >10 consecutive amino acids, or >20 consecutive amino acids, or >30 consecutive amino acids, e.g., >40 consecutive amino acids, such as for example >50 consecutive amino acids, e.g., >60, >70, >80, >90, >100, >200, >300, >400, >500 or >600 consecutive amino acids of the corresponding full-length peptide, polypeptide, or protein.

The term "fragment" with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of the nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis. The phrase "gene or gene product signature" as intended throughout this specification refers to a set, group or collection of one or more, preferably two or more markers, such as genes or gene products, the expression status or profile of which is associated with or identifies a specific cell type, cell subtype, or cell state of a specific cell type or subtype. Such gene or gene product signatures can be used for example to indicate the presence of a specific cell type, cell subtype, or cell state of a specific cell type or subtype in a population of cells, and/or the overall cell type composition or status of an entire cell population. Such gene or gene product signatures may be indicative of cells within a population of cells in vivo. Preferably, a reference herein to a gene or gene product signature comprising or consisting of one or more genes or gene products from a discrete list of genes or gene products may denote that the genes or gene products said to be comprised by or constituting the signature are expressed in a specific cell type, cell subtype, or cell state of a specific cell type or subtype, i.e., that cells of the specific cell type, cell subtype, or cell state of the specific cell type or subtype are positive for the genes or gene products comprised by the signature.

Gene Signatures

Typically, a gene signature may comprise or consist of two or more, three or more, four or more, five or more, six or more, seven or more, eight or more, nine or more, ten or more, 15 or more, 20 or more, 25 or more, 30 or more, 35 or more, 40 or more, 45 or more, 50 or more, 60 or more, 70 or more, 80 or more, 90 or more, or 100 or more, or 200 or more, or 300 or more, or 400 or more, or 500 or more genes or gene products. Where the present specification refers to a signature as comprising or consisting of one or more genes set forth in a given Table, the signature may comprise of consist of, by means of example and without limitation, one, or two or more, three or more, four or more, five or more, six or more, seven or more, eight or more, nine or more, ten or more, 15 or more, 20 or more, 25 or more, 30 or more, 35 or more, 40 or more, 45 or more, 50 or more, 60 or more, 70 or more, 80 or more, 90 or more, or 100 or more (provided that the recited number does not exceed the number of genes or gene products listed in the Table) or substantially all or all genes or gene products as set forth in the Table. In certain embodiments, the signature may comprise or consist of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or at least 95%, e.g., 96%, 97%, 98%, 99%, or up to 100% (by number) of the genes or gene products set forth in the Table (rounded up or down as conventional to the closest integer).

As used herein a signature may encompass any gene or genes, or protein or proteins, whose expression profile or whose occurrence is associated with a specific cell type, subtype, or cell state of a specific cell type or subtype within a population of cells. Increased or decreased expression or activity or prevalence may be compared between different cells in order to characterize or identify for instance specific cell (sub)populations. A gene signature as used herein, may thus refer to any set of up- and down-regulated genes between different cells or cell (sub)populations derived from a gene-expression profile. For example, a gene signature may comprise a list of genes differentially expressed in a distinction of interest. It is to be understood that also when referring to proteins (e.g. differentially expressed proteins), such may fall within the definition of "gene" signature.

The signatures as defined herein (be it a gene signature, protein signature or other genetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to further modulate intestinal epithelial cells. The signatures of the present invention may be discovered by analysis of expression profiles of single-cells within a population of cells from isolated samples (e.g. biopsy), thus allowing the discovery of novel cell subtypes or cell states that were previously invisible or unrecognized.

The presence of subtypes or cell states may be determined by subtype specific or cell state specific signatures. The presence of these specific cell (sub)types or cell states may be determined by applying the signature genes to bulk sequencing data in a sample. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular pathological condition (e.g. cancer), or linked to a particular outcome or progression of the disease, or linked to a particular response to treatment of the disease.

The signature according to certain embodiments of the present invention may comprise or consist of one or more genes and/or proteins, such as for instance 1, 2, 3, 4, 5, 6, 7, 8, 9, 10 or more. In certain embodiments, the signature may comprise or consist of two or more genes and/or proteins, such as for instance 2, 3, 4, 5, 6, 7, 8, 9, 10 or more. In certain embodiments, the signature may comprise or consist of three or more genes and/or proteins, such as for instance 3, 4, 5, 6, 7, 8, 9, 10 or more. In certain embodiments, the signature may comprise or consist of four or more genes and/or proteins, such as for instance 4, 5, 6, 7, 8, 9, 10 or more. In certain embodiments, the signature may comprise or consist of five or more genes and/or proteins, such as for instance 5, 6, 7, 8, 9, 10 or more. In certain embodiments, the signature may comprise or consist of six or more genes and/or proteins, such as for instance 6, 7, 8, 9, 10 or more. In certain embodiments, the signature may comprise or consist of seven or more genes and/or proteins, such as for instance 7, 8, 9, 10 or more. In certain embodiments, the signature may comprise or consist of eight or more genes and/or proteins, such as for instance 8, 9, 10 or more. In certain embodiments, the signature may comprise or consist of nine or more genes and/or proteins, such as for instance 9, 10 or more. In certain embodiments, the signature may comprise or consist of ten or more genes and/or proteins, such as for instance 10, 11, 12, 13, 14, 15, or more. It is to be understood that a signature according to the invention may for instance also include a combination of genes or proteins.

It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins may be differentially expressed on a single cell level, or may be differentially expressed on a cell population level. Preferably, the differentially expressed genes/proteins as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein of the signature, such as for instance at least to, at least three, at least four, at least five, at least six, or all genes/proteins of the signature.

Signatures may be functionally validated as being uniquely associated with a particular phenotype of an intestinal epithelial cell, intestinal epithelial stem cell, or intestinal immune cell. Induction or suppression of a particular signature may consequentially be associated with or causally drive a particular phenotype.

Various aspects and embodiments of the invention may involve analyzing gene signature(s), protein signature(s), and/or other genetic signature(s) based on single cell analyses (e.g. single cell RNA sequencing) or alternatively based on cell population analyses, as is defined herein elsewhere.

As used herein the term "signature gene" means any gene or genes whose expression profile is associated with a specific cell type, subtype, or cell state of a specific cell type or subtype within a population of cells. The signature gene can be used to indicate the presence of a cell type, a subtype of the cell type, the state of the microenvironment of a population of cells, and/or the overall status of the entire cell population. Furthermore, the signature genes may be indicative of cells within a population of cells in vivo. Not being bound by a theory, the signature genes can be used to deconvolute the cells present in a tumor based on comparing them to data from bulk analysis of a tumor sample. The signature gene may indicate the presence of one particular cell type. Markers as taught herein or genes or gene products comprised by or constituting gene or gene product signatures as taught herein, or the gene or gene product signatures as taught herein, may display AUC (area under the receiver-operating curve (ROC) as well-established in the art) value of 0.70 or more, e.g., 0.75 or more, preferably 0.80 or more, more preferably 0.85 or more, even more preferably 0.90 or more, and still more preferably 0.95 or more, e.g., 0.96, 0.97, 0.98, 0.99, or 1.00. An AUC value of 1 implies that the marker, gene, gene product or signature is a perfect classifier for a given outcome (e.g., a cell type or cluster). An AUC value of 0.50 implies no predictive value for the outcome.

A marker, for example a gene or gene product, for example a peptide, polypeptide, protein, or nucleic acid, or a group of two or more markers, is "measured" in a tested object (e.g., in or on a cell, cell population, tissue, organ, or organism, e.g., in a biological sample of a subject) when the presence or absence and/or quantity of the marker or the group of markers is detected or determined in the tested object, preferably substantially to the exclusion of other molecules and analytes, e.g., other genes or gene products.

Depending on factors that can be evaluated and decided on by a skilled person, such as inter alia the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to another value, such as relative to a reference value. Performing a relative comparison between first and second variables (e.g., first and second quantities) may but need not require determining first the absolute values of the first and second variables. For example, a measurement method may produce quantifiable readouts (such as, e.g., signal intensities) for the first and second variables, wherein the readouts are a function of the value of the variables, and wherein the readouts may be directly compared to produce a relative value for the first variable vs. the second variable, without the actual need to first convert the readouts to absolute values of the respective variables.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/ "intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed for example as a percentage or fraction (by number) of cells comprised in the population that are positive for the marker, or as percentages or fractions (by number) of cells comprised in the population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of markers in a tested object (e.g., in or on a cell, cell population, tissue, organ, or organism, e.g., in a biological sample of a subject).

In certain examples, such methods may include biochemical assay methods, including inter alia assays of enzymatic activity, membrane channel activity, substance-binding activity, gene regulatory activity, or cell signalling activity of a marker, e.g., peptide, polypeptide, protein, or nucleic acid.

In other examples, such methods may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In further examples, such methods may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-knownper se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/$(MS)^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-$(MS)^n$; atmospheric pressure photoionization mass spectrometry (APPI-MS); APPI-MS/MS; and APPI-$(MS)^n$. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other examples, such methods may include chromatography methods. The term "chromatography" encompasses methods for separating substances, such as chemical or biological substances, e.g., markers, such as preferably peptides, polypeptides, or proteins, referred to as such and vastly available in the art. In a preferred approach, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between the mobile phase and the stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

Further techniques for separating, detecting and/or quantifying markers, such as preferably peptides, polypeptides, or proteins, may be used, optionally in conjunction with any of the above described analysis methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridisation-based analysis, microarray expression analysis, digital gene expression profiling (DGE), RNA-in-situ hybridisation (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. In particular, methods of Macosko et al. (Cell. 2015, vol. 161, 1202-1214) and Klein et al. (Cell. 2015, vol. 161, 1187-1201) are contemplated for the present invention.

In further examples, any combinations of methods such as discussed herein may be employed.

A further aspect of the invention thus relates to a method for detecting or quantifying intestinal epithelial cells, intestinal epithelial stem cells, or intestinal immune cells in a biological sample of a subject, or for isolating such cells from a biological sample of a subject, the method comprising: a) providing a biological sample of a subject; and b) detecting or quantifying in the biological sample intestinal epithelial cells, intestinal epithelial stem cells, or preferably intestinal epithelial cells as disclosed herein, or isolating from the biological sample such cells as disclosed herein.

The terms "subject", "individual" or "patient" are used interchangeably throughout this specification, and typically and preferably denote humans, but may also encompass reference to non-human animals, preferably warm-blooded animals, even more preferably mammals, such as, e.g., non-human primates, rodents, canines, felines, equines, ovines, porcines, and the like. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is a non-human mammal. In another embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The terms "sample" or "biological sample" as used throughout this specification include any biological specimen obtained from a subject. Particularly preferred are samples from the intestinal tissue, but may also include samples from intestinal lumen, faeces, or blood. The term "tissue" as used throughout this specification refers to any animal tissue types, but particularly preferred is intestinal tissue. The tissue may be healthy or affected by pathological alterations. The tissue may be from a living subject or may be cadaveric tissue. The tissue may be autologous tissue or syngeneic tissue or may be allograft or xenograft tissue.

The method may allow to detect or conclude the presence or absence of the specified intestinal epithelial cells, intestinal epithelial stem cells, or intestinal immune cells (preferably intestinal epithelial cells) in a tested object (e.g., in a cell population, tissue, organ, organism, or in a biological sample of a subject). The method may also allow to quantify the specified intestinal epithelial cells, intestinal epithelial stem cells, or intestinal immune cells (preferably intestinal epithelial cells) in a tested object (e.g., in a cell population, tissue, organ, organism, or in a biological sample of a subject). The quantity of the specified cells in the tested object such as the biological sample may be suitably expressed for example as the number (count) of the specified cells per standard unit of volume (e.g., ml, µl or nl) or weight (e.g., g or mg or ng) of the tested object such as the biological sample or may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) intestinal epithelial cells, intestinal epithelial stem cells, or intestinal immune cells (preferably intestinal epithelial cells), and of different (sub) types comprised in the tested object such as the biological sample. The quantity of the specified cells in the tested object such as the biological sample may also be suitably represented by an absolute or relative quantity of a suitable surrogate analyte, such as a peptide, polypeptide, protein, or nucleic acid expressed or comprised by the specified cells.

The method may allow to isolate or purify the specified intestinal epithelial cells, intestinal epithelial stem cells, or intestinal immune cells (preferably intestinal epithelial cells) from the tested object such as the biological sample. The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc.

Isolating or purifying the specified intestinal epithelial cells, intestinal epithelial stem cells, or intestinal immune cells from the tested object such as the biological sample may increase the abundance of the specified cells relative to all other cells comprised in the tested object such as the biological sample, or relative to other cells of a select subset of the cells comprised in the tested object such as the biological sample.

By means of example, isolating or purifying the specified cells from the tested object such as the biological sample may yield a cell population, in which the specified cells constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The intestinal epithelial cells, intestinal epithelial stem cells, or intestinal immune cells (preferably intestinal epithelial cells) disclosed herein are generally described or characterised with reference to certain marker(s) or combination(s) of markers (such as genes or gene products, e.g., peptides, polypeptides, proteins, or nucleic acids) expressed or not expressed by the cells, or with reference to certain gene or gene product signature(s) comprised by the cells. Accordingly, the present methods for detecting, quantifying or isolating the specified cells may be marker-based or gene or gene product signature-based, i.e., may involve detection, quantification or isolation of cells expressing or not expressing marker(s) or combination(s) of markers the expression or lack of expression of which is taught herein as typifying or characterising the specified cells, or may involve detection, quantification or isolation of cells comprising gene or gene product signature(s) taught herein as typifying or characterising the specified cells.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the specified intestinal epithelial cells, intestinal epithelial stem cells, or intestinal immune cells (preferably intestinal epithelial cells) in, or to isolate the specified cells from, a tested object (e.g., a cell population, tissue, organ, organism, or a biological sample of a subject). Such methods allow to detect, quantify or isolate the specified cells in or from the tested object (e.g., a cell population, tissue, organ, organism, or a biological sample of a subject) substantially to the exclusion of other cells comprised in the tested object.

Such methods may allow to detect, quantify or isolate the specified cells with sensitivity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified cells.

In certain embodiments, methods for detecting, quantifying or isolating the specified cells may comprise treatment(s) or step(s) which diminish or eliminate the viability of the cells. For example, methods which comprise measuring intracellular marker(s) typically necessitate permeabilisation of the cell membrane and possibly fixation of the cells; and methods which comprise measuring nucleic acid marker(s) may typically necessitate obtaining nucleic acids (such as particularly RNA, more particularly mRNA) from the cells. In certain other embodiments, methods for detecting, quantifying or isolating the specified cells may substantially preserve the viability of the cells. For example, methods which comprise measuring extracellular or cell surface marker(s) need not disturb the integrity of the cell membrane and may not require fixation /permeabilisation of the cells. By means of an example, methods for detecting, quantifying or isolating the specified cells may be configured such that at least 40% (by number), for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of the detected, quantified or isolated cells remain viable. The term "viable cells" as used throughout this specification refers to cells that can be qualified as viable by tests and assays known per se. For instance, the viability of cells may be measured using conventional dye exclusion assays, such as Trypan Blue exclusion assay or propidium iodide exclusion assay. In such assays, viable cells exclude the dye and hence remain unstained, while non-viable cells take up the dye and are stained. The cells and their uptake of the dye can be visualised and revealed by suitable techniques (e.g., conventional light microscopy, fluorescence microscopy, or flow cytometry), and viable (unstained) and non-viable (stained) cells in the tested sample can be counted.

In certain embodiments, methods for detecting, quantifying or isolating the specified intestinal epithelial cells, intestinal epithelial stem cells, or intestinal immune cells (preferably intestinal epithelial cells) may be single-cell-based, i.e., may allow to discretely detect, quantify or isolate the specified cells as individual cells. In other embodiments, methods for detecting, quantifying or isolating the specified cells may be cell population-based, i.e., may only allow to detect, quantify or isolate the specified cells as a group or collection of cells, without providing information on or allowing to isolate individual cells.

Methods for detecting, quantifying or isolating the specified intestinal epithelial cells, intestinal epithelial stem cells, or intestinal immune cells (preferably intestinal epithelial cells) may employ any of the above-described techniques for measuring markers, insofar the separation or the qualitative and/or quantitative measurement of the marker(s) can be correlated with or translated into detection, quantification or isolation of the specified cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the specified cells.

In certain embodiments, the intestinal epithelial cells, intestinal epithelial stem cells, or intestinal immune cells (preferably intestinal epithelial cells) are detected, quantified or isolated using a technique selected from the group consisting of flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analysed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyse cells by replacing fluorochrome-labelled binding reagents with mass tagged binding reagents, i.e., tagged with an element or isotope having a defined mass. In these methods, labelled particles are introduced into a mass cytometer, where they are individually atomised and ionised. The individual particles are then subjected to elemental analysis, which identifies and measures the abundance of the mass tags used. The identities and the amounts of the isotopic elements associated with each particle are then stored and analysed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analysed by their fluorescence properties. Fluorescence microscopy approaches may be manual or preferably automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 µm, more preferably less than 400 µm, more preferably less than 300 µm, more preferably less than 200 µm, e.g., 100 µm or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

In certain embodiments, the aforementioned methods and techniques may employ agent(s) capable of specifically binding to one or more gene products, e.g., peptides, polypeptides, proteins, or nucleic acids, expressed or not expressed by the intestinal epithelial cells, intestinal epithelial stem cells, or intestinal immune cells (preferably intestinal epithelial cells) as taught herein. In certain preferred embodiments, such one or more gene products, e.g., peptides, polypeptides, or proteins, may be expressed on the cell surface (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridisation probes or amplification or sequencing primers and primer pairs), small molecules, or combinations thereof.

Binding agents may be in various forms, e.g., lyophilised, free in solution, or immobilised on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about $10^4$-fold, or at least about $10^5$-fold, or at least about $10^6$-fold or more greater, than its affinity for a non-target molecule, such as for a suitable control molecule (e.g., bovine serum albumin, casein).

Preferably, the specific binding agent may bind to its intended target(s) with affinity constant (KA) of such binding $K_A \geq 1 \times 10^6$ M$^{-1}$, more preferably $K_A \geq 1 \times 10^7$ M$^{-1}$, yet more preferably $K_A \geq 1 \times 108$ M$^{-1}$, even more preferably $K_A \geq 1 \times 10^7$ M$^{-1}$, and still more preferably $K_A \geq 1 \times 10^{10}$ M$^{-1}$ or $K_A \geq 1 \times 10^{11}$ M$^{-1}$ or $K_A \geq 1 \times 10^{12}$ M$^{-1}$, wherein $K_A$=[SBA_T]/[SBA][T], SBA denotes the specific-binding agent, T denotes the intended target. Determination of $K_A$ can be carried out by methods known in the art, such as for example, using equilibrium dialysis and Scatchard plot analysis.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos, Lama glama* or *Lama vicugna*) or horse. An antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbor Laboratory, New York, 1988; Harlow and Lane, "Using Antibodies: A Laboratory Manual", Cold Spring Harbor Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., $K_A$ in the order $1 \times 10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

The term "oligonucleotide" as used throughout this specification refers to a nucleic acid (including nucleic acid analogues and mimetics) oligomer or polymer as defined herein. Preferably, an oligonucleotide, such as more particularly an antisense oligonucleotide, is (substantially) single-stranded. Oligonucleotides as intended herein may be preferably between about 10 and about 100 nucleoside units (i.e., nucleotides or nucleotide analogues) in length, preferably between about 15 and about 50, more preferably between about 20 and about 40, also preferably between about 20 and about 30. Oligonucleotides as intended herein may comprise one or more or all non-naturally occurring heterocyclic bases and/or one or more or all non-naturally occurring sugar groups and/or one or more or all non-naturally occurring inter-nucleoside linkages, the inclusion of which may improve properties such as, for example, increased stability in the presence of nucleases and increased hybridization affinity, increased tolerance for mismatches, etc. The reference to oligonucleotides may in particular but without limitation include hybridisation probes and/or amplification primers and/or sequencing primers, etc., as commonly used in nucleic acid detection technologies.

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to the target nucleic acid sequence. Antisense agents suitable for use herein, such as hybridisation probes or amplification or sequencing primers and primer pairs) may typically be capable of annealing with (hybridizing to) the respective target nucleic acid sequences at high stringency conditions, and capable of hybridizing specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In certain embodiments, the one or more binding agents may be one or more antibodies. In other embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., $Ni^{2+}$), maltose:maltose binding protein, etc. In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof. In certain embodiments, the one or more binding agents are one or more antibodies.

A marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

Kit

The terms "kit" and "kit of parts" as used throughout this specification refer to a product containing components necessary for carrying out the specified methods (e.g., methods for detecting, quantifying or isolating intestinal epithelial cells, intestinal epithelial stem cells, or intestinal immune cells (preferably intestinal epithelial cells) as taught herein), packed so as to allow their transport and storage. Materials suitable for packing the components comprised in a kit include crystal, plastic (e.g., polyethylene, polypropylene, polycarbonate), bottles, flasks, vials, ampules, paper, envelopes, or other types of containers, carriers or supports. Where a kit comprises a plurality of components, at least a subset of the components (e.g., two or more of the plurality of components) or all of the components may be physically separated, e.g., comprised in or on separate containers, carriers or supports. The components comprised in a kit may be sufficient or may not be sufficient for carrying out the specified methods, such that external reagents or substances may not be necessary or may be necessary for performing the methods, respectively.

Typically, kits and kit of parts are employed in conjunction with standard laboratory equipment, such as liquid handling equipment, environment (e.g., temperature) controlling equipment, analytical instruments, etc. In addition to the recited binding agents(s) as taught herein, such as for example, antibodies, hybridisation probes, amplification and/or sequencing primers, optionally provided on arrays or microarrays, the present kits may also include some or all of solvents, buffers (such as for example but without limitation histidine-buffers, citrate-buffers, succinate-buffers, acetate-buffers, phosphate-buffers, formate buffers, benzoate buffers, TRIS (Tris(hydroxymethyl)-aminomethane) buffers or maleate buffers, or mixtures thereof), enzymes (such as for example but without limitation thermostable DNA polymerase), detectable labels, detection reagents, and control formulations (positive and/or negative), useful in the specified methods. Typically, the kits and kit of parts may also include instructions for use thereof, such as on a printed insert or on a computer readable medium. The terms may be used interchangeably with the term "article of manufacture", which broadly encompasses any man-made tangible structural product, when used in the present context.

In certain embodiments, the kit of parts or article of manufacture may comprise a microfluidic system.

Pharmaceuticals

Another aspect of the invention provides a composition, pharmaceutical composition or vaccine comprising the intestinal epithelial cells, intestinal epithelial stem cells, or intestinal immune cells (preferably intestinal epithelial cells) or populations thereof as taught herein.

A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., modulants, immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating the support with a liquid suspension containing the cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types (e.g. differentiation) or cell states. The cells or cell populations may be grafted to or may migrate to and engraft within the intended organ.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified intestinal epithelial cells, intestinal epithelial stem cells, or intestinal immune cells (preferably intestinal epithelial cells) and/or other active components. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

A further aspect of the invention provides a population of the intestinal epithelial cells, intestinal epithelial stem cells, or intestinal immune cells (preferably intestinal epithelial cells) as taught herein. The terms "cell population" or "population" denote a set of cells having characteristics in common. The characteristics may include in particular the one or more marker(s) or gene or gene product signature(s) as taught herein. The intestinal epithelial cells, intestinal epithelial stem cells, or intestinal immune cells (preferably intestinal epithelial cells) cells as taught herein may be comprised in a cell population. By means of example, the specified cells may constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The isolated intestinal epithelial cells, intestinal epithelial stem cells, or intestinal immune cells (preferably intestinal epithelial cells) of populations thereof as disclosed throughout this specification may be suitably cultured or cultivated in vitro. The term "in vitro" generally denotes outside, or external to, a body, e.g., an animal or human body. The term encompasses "ex vivo".

The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Differentiation

Within the present specification, the terms "differentiation", "differentiating" or derivatives thereof, denote the process by which an unspecialised or relatively less specialised cell becomes relatively more specialised. In the context of cell ontogeny, the adjective "differentiated" is a relative term. Hence, a "differentiated cell" is a cell that has progressed further down a certain developmental pathway than the cell it is being compared with. The differentiated cell may, for example, be a terminally differentiated cell, i.e., a fully specialised cell capable of taking up specialised functions in various tissues or organs of an organism, which may but need not be post-mitotic; or the differentiated cell may itself be a progenitor cell within a particular differentiation lineage which can further proliferate and/or differentiate.

A relatively more specialised cell may differ from an unspecialised or relatively less specialised cell in one or more demonstrable phenotypic characteristics, such as, for example, the presence, absence or level of expression of particular cellular components or products, e.g., RNA, proteins or other substances, activity of certain biochemical pathways, morphological appearance, proliferation capacity and/or kinetics, differentiation potential and/or response to differentiation signals, electrophysiological behaviour, etc., wherein such characteristics signify the progression of the relatively more specialised cell further along the developmental pathway. Non-limiting examples of differentiation may include, e.g., the change of a pluripotent stem cell into a given type of multipotent progenitor or stem cell, the change of a multipotent progenitor or stem cell into a given type of unipotent progenitor or stem cell, or the change of a unipotent progenitor or stem cell to more specialised cell types or to terminally specialised cells within a given cell lineage.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having the disease or condition. For example, a prediction of a disease or condition in a subject may indicate a probability, chance or risk that the subject will develop the disease or condition, for example within a certain time period or by a certain age. The probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

As used throughout this specification, the terms "treat", "treating" and "treatment" refer to the alleviation or measurable lessening of one or more symptoms or measurable markers of a pathological condition such as a disease or disorder. Measurable lessening includes any statistically significant decline in a measurable marker or symptom. Generally, the terms encompass both curative treatments and treatments directed to reduce symptoms and/or slow progression of the disease. The terms encompass both the therapeutic treatment of an already developed pathological condition, as well as prophylactic or preventative measures, wherein the aim is to prevent or lessen the chances of incidence of a pathological condition. In certain embodiments, the terms may relate to therapeutic treatments. In certain other embodiments, the terms may relate to preventative treatments. Treatment of a chronic pathological condition during the period of remission may also be deemed to constitute a therapeutic treatment. The term may encompass ex vivo or in vivo treatments as appropriate in the context of the present invention.

As used throughout this specification, the terms "prevent", "preventing" and "prevention" refer to the avoidance or delay in manifestation of one or more symptoms or measurable markers of a pathological condition, such as a disease or disorder. A delay in the manifestation of a symptom or marker is a delay relative to the time at which such symptom or marker manifests in a control or untreated subject with a similar likelihood or susceptibility of developing the pathological condition. The terms "prevent", "preventing" and "prevention" include not only the avoidance or prevention of a symptom or marker of the pathological condition, but also a reduced severity or degree of any one of the symptoms or markers of the pathological condition, relative to those symptoms or markers in a control or non-treated individual with a similar likelihood or susceptibility of developing the pathological condition, or relative to symptoms or markers likely to arise based on historical or statistical measures of populations affected by the disease or disorder. By "reduced severity" is meant at least a 10% reduction in the severity or degree of a symptom or measurable marker relative to a control or reference, e.g., at least 15%, 20%, 30%, 40%, 50%, 60%, 70%, 80%, 90%, 95%, 99% or even 100% (i.e., no symptoms or measurable markers).

The terms "disease" or "disorder" are used interchangeably throughout this specification, and refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, indisposition, or affliction.

In certain embodiments, the pathological condition may be an infection, inflammation, proliferative disease, autoimmune disease, or allergy.

The term "infection" as used herein refers to presence of an infective agent, such as a pathogen, e.g., a microorganism, in or on a subject, which, if its presence or growth were inhibited, would result in a benefit to the subject. Hence, the term refers to the state produced by the establishment, more particularly invasion and multiplication, of an infective agent, such as a pathogen, e.g., a microorganism, in or on a suitable host. An infection may produce tissue injury and progress to overt disease through a variety of cellular and toxic mechanisms.

The term "inflammation" generally refers to a response in vasculated tissues to cellular or tissue injury usually caused by physical, chemical and/or biological agents, that is marked in the acute form by the classical sequences of pain, heat, redness, swelling, and loss of function, and serves as a mechanism initiating the elimination, dilution or walling-off of noxious agents and/or of damaged tissue. Inflammation histologically involves a complex series of events, including dilation of the arterioles, capillaries, and venules with increased permeability and blood flow, exudation of fluids including plasma proteins, and leukocyte migration into the inflammatory focus.

Further, the term encompasses inflammation caused by extraneous physical or chemical injury or by biological agents, e.g., viruses, bacteria, fungi, protozoan or metazoan parasite infections, as well as inflammation which is seemingly unprovoked, e.g., which occurs in the absence of demonstrable injury or infection, inflammation responses to self-antigens (auto-immune inflammation), inflammation responses to engrafted xenogeneic or allogeneic cells, tissues or organs, inflammation responses to allergens, etc. The term covers both acute inflammation and chronic inflammation. Also, the term includes both local or localised inflammation, as well as systemic inflammation, i.e., where one or more inflammatory processes are not confined to a particular tissue but occur generally in the endothelium and/or other organ systems.

Systemic inflammatory conditions may particularly encompass systemic inflammatory response syndrome (SIRS) or sepsis. "SIRS" is a systemic inflammatory response syndrome with no signs of infection. It can be characterised by the presence of at least two of the four following clinical criteria: fever or hypothermia (temperature of 38.0° C.) or more, or temperature of 36.0° C. or less); tachycardia (at least 90 beats per minute); tachypnea (at least 20 breaths per minute or $PaCO_2$ less than 4.3 kPa (32.0 mm Hg) or the need for mechanical ventilation); and an altered white blood cell (WBC) count of $12 \times 10^6$ cells/mL or more, or an altered WBC count of $4 \times 10^6$ cells/mL or less, or the presence of more than 10% band forms. "Sepsis" can generally be defined as SIRS with a documented infection, such as for example a bacterial infection. Infection can be diagnosed by standard textbook criteria or, in case of uncertainty, by an infectious disease specialist. Bacteraemia is defined as sepsis where bacteria can be cultured from blood. Sepsis may be characterised or staged as mild sepsis, severe sepsis (sepsis with acute organ dysfunction), septic shock (sepsis with refractory arterial hypotension), organ failure, multiple organ dysfunction syndrome and death.

The term "proliferative disease" generally refers to any disease or disorder characterised by neoplastic cell growth and proliferation, whether benign, pre-malignant, or malignant. The term proliferative disease generally includes all transformed cells and tissues and all cancerous cells and tissues. Proliferative diseases or disorders include, but are not limited to abnormal cell growth, benign tumours, pre-malignant or precancerous lesions, malignant tumors, and cancer.

The terms "tumor" or "tumor tissue" refer to an abnormal mass of tissue resulting from excessive cell division. A tumor or tumor tissue comprises "tumor cells" which are neoplastic cells with abnormal growth properties and no useful bodily function. Tumors, tumor tissue and tumor cells may be benign, pre-malignant or malignant, or may represent a lesion without any cancerous potential. A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

The term "cancer" refers to a malignant neoplasm characterised by deregulated or unregulated cell growth. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor. The term "metastatic" or "metastasis" generally refers to the spread of a cancer from one organ or tissue to another non-adjacent organ or tissue. The occurrence of the proliferative disease in the other non-adjacent organ or tissue is referred to as metastasis.

As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

"Activation" generally refers to the state of a cell, such as preferably T cell, following sufficient cell surface moiety ligation (e.g., interaction between the T cell receptor on the surface of a T cell (such as naturally-occurring TCR or genetically engineered TCR, e.g., chimeric antigen receptor, CAR) and MHC-bound antigen peptide presented on the surface of the immune cell as taught herein) to induce a noticeable biochemical or morphological change of the cell, such as preferably T cell. In particular, "activation" may refer to the state of a T cell that has been sufficiently stimulated to induce detectable cellular proliferation of the T cell. Activation can also encompass induced cytokine production, and detectable T cell effector functions, e.g., regulatory or cytolytic effector functions. The T cells and immune cells may be may be suitably contacted by admixing the T cells and immune cells in an aqueous composition, e.g., in a culture medium, in sufficient numbers and for a sufficient duration of time to produce the desired T cell activation.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein. The term "abolish" or "abolished" may in particular refer to a decrease by 100%, i.e., absent level as compared to a reference sample.

Any one or more of the several successive molecular mechanisms involved in the expression of a given gene or polypeptide may be targeted by the intestinal epithelial cells, intestinal epithelial stem cells, or intestinal immune cells (preferably intestinal epithelial cells) cell modification as intended herein. Without limitation, these may include targeting the gene sequence (e.g., targeting the polypeptide-encoding, non-coding and/or regulatory portions of the gene sequence), the transcription of the gene into RNA, the polyadenylation and where applicable splicing and/or other post-transcriptional modifications of the RNA into mRNA, the localisation of the mRNA into cell cytoplasm, where applicable other post-transcriptional modifications of the mRNA, the translation of the mRNA into a polypeptide chain, where applicable post-translational modifications of the polypeptide, and/or folding of the polypeptide chain into the mature conformation of the polypeptide. For compartmentalised polypeptides, such as secreted polypeptides and transmembrane polypeptides, this may further include targeting trafficking of the polypeptides, i.e., the cellular mechanism by which polypeptides are transported to the appropriate sub-cellular compartment or organelle, membrane, e.g. the plasma membrane, or outside the cell. Functional genomics can be used to modify cells for therapeutic purposes, and identify networks and pathways. For example, Graham et al ("Functional genomics identifies negative regulatory nodes controlling phagocyte oxidative burst," Nature Communications 6, Article number: 7838 (2015)) describes functional genetic screens to identify the phagocytic oxidative burst. With the rapid advancement of genomic technology, it is now possible to associate genetic variation with phenotypes of intestinal epithelial cells, intestinal epithelial stem cells, or intestinal immune cells (preferably intestinal epithelial cells) at the population level. In particular, genome-wide association studies (GWAS) have implicated genetic loci associated with risk for IBD and allowed for inference of new biological processes that contribute to disease. These studies highlight innate defense mechanisms such as antibacterial autophagy, superoxide generation during oxidative burst and reactive nitrogen species produced by iNOS. However GWAS requires functional analysis to unlock new insights. For example, many risk loci are densely populated with coding genes, which complicates identification of causal genes. Even when fine mapping clearly identifies key genes, a majority have poorly defined functions in host immunity. Moreover, any given gene may have multiple functions depending on the cell type in which it is expressed as well as environmental cues. Such context-specific functions of regulatory genes are largely unexplored. Thus, human genetics offers an opportunity to leverage insight from large amounts of genetic variation within healthy and patient populations to interrogate mechanisms of immunity. Irrespective of their putative roles in IBD pathology, genes within risk loci are likely to be highly enriched for genes controlling signalling pathways.

With respect to general information on CRISPR-Cas Systems, components thereof, the DNA binding protein is a (endo)nuclease or a variant thereof having altered or modified activity (i.e. a modified nuclease, as described herein elsewhere). In certain embodiments, the nuclease is a targeted or site-specific or homing nuclease or a variant thereof having altered or modified activity. In certain embodiments, the nuclease or targeted/site-specific/homing nuclease is, comprises, consists essentially of, or consists of a (modified) CRISPR/Cas system or complex, a (modified) Cas protein, a (modified) zinc finger, a (modified) zinc finger nuclease (ZFN), a (modified) transcription factor-like effector (TALE), a (modified) transcription factor-like effector nuclease (TALEN), or a (modified) meganuclease.

In certain embodiments, the (modified) nuclease or targeted/site-specific/homing nuclease is, comprises, consists essentially of, or consists of a (modified) RNA-guided nuclease. As used herein, the term "Cas" generally refers to a (modified) effector protein of the CRISPR/Cas system or complex, and can be without limitation a (modified) Cas9, or other enzymes such as Cpf1, The term "Cas" may be used herein interchangeably with the terms "CRISPR" protein, "CRISPR/Cas protein", "CRISPR effector", "CRISPR/Cas effector", "CRISPR enzyme", "CRISPR/Cas enzyme" and the like, unless otherwise apparent, such as by specific and exclusive reference to Cas9. It is to be understood that the term "CRISPR protein" may be used interchangeably with "CRISPR enzyme", irrespective of whether the CRISPR protein has altered, such as increased or decreased (or no) enzymatic activity, compared to the wild type CRISPR protein. Likewise, as used herein, in certain embodiments, where appropriate and which will be apparent to the skilled person, the term "nuclease" may refer to a modified nuclease wherein catalytic activity has been altered, such as having increased or decreased nuclease activity, or no nuclease activity at all, as well as nickase activity, as well as otherwise modified nuclease as defined herein elsewhere, unless otherwise apparent, such as by specific and exclusive reference to unmodified nuclease.

As used herein, the term "targeting" of a selected nucleic acid sequence means that a nuclease or nuclease complex is acting in a nucleotide sequence specific manner. For instance, in the context of the CRISPR/Cas system, the guide RNA is capable of hybridizing with a selected nucleic acid sequence. As uses herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

In certain embodiments, the DNA binding protein is a (modified) transcription activator-like effector nuclease (TALEN) system. Transcription activator-like effectors (TALEs) can be engineered to bind practically any desired DNA sequence. Exemplary methods of genome editing using the TALEN system can be found for example in Cermak T. Doyle EL. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church GM. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference. By means of further guidance, and without limitation, naturally occurring TALEs or "wild type zincs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X1-11-(X12\times13)-X14-33$ or 34 or 35, where the subscript indicates the amino acid position and X represents any amino acid. $X12\times13$ indicate the RVDs. In some polypeptide monomers, the variable amino acid at position 13 is missing or absent and in such polypeptide monomers, the RVD consists of a single amino acid. In such cases the RVD may be alternatively represented as $X^*$, where X represents X12 and (*) indicates that X13 is absent. The DNA binding domain comprises several repeats of TALE monomers and this may be represented as $(X1-11-(X12\times13)-X14-33$ or 34 or 35)z, where in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

In certain embodiments, the nucleic acid modification is effected by a (modified) zinc-finger nuclease (ZFN) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference. By means of further guidance, and without limitation, artificial zinc-finger (ZF) technology involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In certain embodiments, the nucleic acid modification is effected by a (modified) meganuclease, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

In certain embodiments, the nucleic acid modification is effected by a (modified) CRISPR/Cas complex or system. With respect to general information on CRISPR/Cas Systems, components thereof, and delivery of such components, including methods, materials, delivery vehicles, vectors, particles, and making and using thereof, including as to amounts and formulations, as well as Cas9CRISPR/Cas-expressing eukaryotic cells, Cas-9 CRISPR/Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310930 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), WO2015/058052 (PCT/US2014/061077), WO2015070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO/2016/04925 (PCT/US2015/051830), WO/2016/094867 (PCT/US2015/065385), WO/2016/094872 (PCT/US2015/065393), WO/2016/094874 (PCT/US2015/065396), WO/2016/106244 (PCT/US2015/067177).

Reference is further made to Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science Feb 15; 339 (6121):819-23 (2013); RNA-guided editing of bacterial genomes using CRISPR-Cas systems. Jiang W., Bikard D., Cox D., Zhang F, Marraffini LA. Nat Biotechnol March; 31(3):233-9 (2013); One-Step Generation of Mice Carrying Mutations in Multiple Genes by CRISPR/Cas-Mediated Genome Engineering. Wang H., Yang H., Shivalila CS., Dawlaty MM., Cheng AW., Zhang F., Jaenisch R. Cell May 9; 153(4):910-8 (2013); Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23; Double Nicking by RNA-Guided CRISPR Cas9 for Enhanced Genome Editing Specificity. Ran, F A., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13)01015-5. (2013); DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, 0., Cradick, TJ., Marraffini, LA., Bao, G., & Zhang, F. Nat Biotechnol doi:10.1038/nbt.2647 (2013); Genome engineering using the CRISPR-Cas9 system. Ran, FA., Hsu, PD., Wright, J., Agarwala, V., Scott, DA., Zhang, F. Nature Protocols November; 8(11):2281-308. (2013); Genome-Scale CRISPR-Cas9 Knockout Screening in Human Cells. Shalem, 0., Sanjana, NE., Hartenian, E., Shi, X., Scott, DA., Mikkelson, T., Heckl, D., Ebert, BL., Root, DE., Doench, JG., Zhang, F. Science December 12. (2013). [Epub ahead of print]; Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27. (2014). 156(5):935-49; Genome-wide binding of the CRISPR endonuclease Cas9 in mammalian cells. Wu X., Scott DA., Kriz AJ., Chiu AC., Hsu PD., Dadon DB., Cheng AW., Trevino AE., Konermann S., Chen S., Jaenisch R., Zhang F., Sharp PA. Nat Biotechnol. (2014) April 20. doi: 10.1038/nbt.2889; CRISPR-Cas9 Knockin Mice for Genome Editing and Cancer Modeling, Platt et al., Cell 159(2): 440-455 (2014) DOI: 10.1016/j.cell.2014.09.014; Development and Applications of CRISPR-Cas9 for Genome Engineering, Hsu et al, Cell 157, 1262-1278 (Jun. 5, 2014) (Hsu 2014); Genetic screens in human cells using the CRISPR/Cas9 system, Wang et al., Science. 2014 Jan. 3; 343(6166): 80-84. doi:10.1126/science.1246981; Rational design of highly active sgRNAs for CRISPR-Cas9-mediated gene inactivation, Doench et al., Nature Biotechnology 32(12):1262-7 (2014) published online 3 Sep. 2014; doi:10.1038/nbt.3026, and In vivo interrogation of gene function in the mammalian brain using CRISPR-Cas9, Swiech et al, Nature Biotechnology 33, 102-106 (2015) published online 19 Oct. 2014; doi:10.1038/nbt.3055, Cpf1 Is a Single RNA-Guided Endonuclease of a Class 2 CRISPR-Cas System, Zetsche et al., Cell 163, 1-13 (2015); Discovery and Functional Characterization of Diverse Class 2 CRISPR-Cas Systems, Shmakov et al., Mol Cell 60(3): 385-397 (2015); Each of these publications, patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Preferred DNA binding proteins are CRISPR/Cas enzymes or variants thereof. In certain embodiments, the CRISPR/Cas protein is a class 2 CRISPR/Cas protein. In certain embodiments, the CRISPR/Cas protein is a type II, type V, or type VI CRISPR/Cas protein. The CRISPR/Cas system does not require the generation of customized proteins to target specific sequences but rather a single Cas protein can be programmed by an RNA guide (gRNA) to recognize a specific nucleic acid target, in other words the Cas enzyme protein can be recruited to a specific nucleic acid target locus (which may comprise or consist of RNA and/or DNA) of interest using the short RNA guide.

In general, the CRISPR/Cas or CRISPR system is as used herein foregoing documents refers collectively to elements involved in the expression of or directing the activity of CRISPR-associated ("Cas") proteins or genes, including sequences encoding a Cas protein and a guide RNA. In this context of the guide RNA this may include one or more of, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), In general, a CRISPR system is characterized by elements that promote the formation of a CRISPR complex at the site of a target sequence. In the context of formation of a CRISPR complex, "target sequence" refers to a sequence to which a guide sequence is designed to have complementarity, where hybridization between a target DNA sequence and a guide sequence promotes the formation of a CRISPR complex.

In certain embodiments, the gRNA comprises a guide sequence fused to a tracr mate sequence (or direct repeat), and a tracr sequence. In particular embodiments, the guide sequence fused to the tracr mate and the tracr sequence are provided or expressed as discrete RNA sequences. In preferred embodiments, the gRNA is a chimeric guide RNA or single guide RNA (sgRNA), comprising a guide sequence fused to the tracr mate which is itself linked to the tracr sequence. In particular embodiments, the CRISPR/Cas system or complex as described herein does not comprise and/or does not rely on the presence of a tracr sequence (e.g. if the Cas protein is Cpf1).

As used herein, the term "guide sequence" in the context of a CRISPR/Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay.

A guide sequence, and hence a nucleic acid-targeting guide RNA may be selected to target any target nucleic acid sequence. The target sequence may be DNA. The target sequence may be genomic DNA. The target sequence may be mitochondrial DNA.

In certain embodiments, the gRNA comprises a stem loop, preferably a single stem loop. In certain embodiments, the direct repeat sequence forms a stem loop, preferably a single stem loop. In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In particular embodiments, the CRISPR/Cas system requires a tracrRNA. The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and gRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop may correspond to the tracr mate sequence, and the portion of the sequence 3' of the loop then corresponds to the tracr sequence. In a hairpin structure the portion of the sequence 5' of the final "N" and upstream of the loop may alternatively correspond to the tracr sequence, and the portion of the sequence 3' of the loop corresponds to the tracr mate sequence. In alternative embodiments, the CRISPR/Cas system does not require a tracrRNA, as is known by the skilled person.

In certain embodiments, the guide RNA (capable of guiding Cas to a target locus) may comprise (1) a guide sequence capable of hybridizing to a target locus and (2) a tracr mate or direct repeat sequence (in 5' to 3' orientation, or alternatively in 3' to 5' orientation, depending on the type of Cas protein, as is known by the skilled person). In particular embodiments, the CRISPR/Cas protein is characterized in that it makes use of a guide RNA comprising a guide sequence capable of hybridizing to a target locus and a direct repeat sequence, and does not require a tracrRNA. In particular embodiments, where the CRISPR/Cas protein is characterized in that it makes use of a tracrRNA, the guide sequence, tracr mate, and tracr sequence may reside in a single RNA, i.e. an sgRNA (arranged in a 5' to 3' orientation or alternatively arranged in a 3' to 5' orientation), or the tracr RNA may be a different RNA than the RNA containing the guide and tracr mate sequence. In these embodiments, the tracr hybridizes to the tracr mate sequence and directs the CRISPR/Cas complex to the target sequence.

In particular embodiments, the DNA binding protein is a catalytically active protein. In these embodiments, the formation of a nucleic acid-targeting complex (comprising a guide RNA hybridized to a target sequence results in modification (such as cleavage) of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest). The skilled person will be aware of specific cut sites for selected CRISPR/Cas systems, relative to the target sequence, which as is known in the art may be within the target sequence or alternatively 3' or 5' of the target sequence.

Accordingly, in particular embodiments, the DNA binding protein has nucleic acid cleavage activity. In some embodiments, the nuclease as described herein may direct cleavage of one or both nucleic acid (DNA, RNA, or hybrids, which may be single or double stranded) strands at the location of or near a target sequence, such as within the target sequence and/or within the complement of the target sequence or at sequences associated with the target sequence. In some embodiments, the nucleic acid-targeting effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be blunt (e.g. for Cas9, such as SaCas9 or SpCas9). In some embodiments, the cleavage may be staggered (e.g. for Cpf1), i.e. generating sticky ends. In some embodiments, the cleavage is a staggered cut with a 5' overhang. In some embodiments, the cleavage is a staggered cut with a 5' overhang of 1 to 5 nucleotides, preferably of 4 or 5 nucleotides. In some embodiments, the cleavage site is upstream of the PAM. In some embodiments, the cleavage site is downstream of the PAM.

In certain embodiments, the target sequence should be associated with a PAM (protospacer adjacent motif) or PFS (protospacer flanking sequence or site); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. Further, engineering of the PAM Interacting (PI) domain may allow programing of PAM specificity, improve target site recognition fidelity, and increase the versatility of the Cas, e.g. Cas9, genome engineering platform. Cas proteins, such as Cas9 proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/nature14592. In some embodiments, the method comprises allowing a CRISPR complex to bind to the target polynucleotide to effect cleavage of the target polynucleotide thereby modifying the target polynucleotide, wherein the CRISPR complex comprises a CRISPR enzyme complexed with a guide sequence hybridized to a target sequence within the target polynucleotide, wherein the guide sequence is linked to a tracr mate sequence which in turn hybridizes to a tracr sequence. The skilled person will understand that other Cas proteins may be modified analogously.

In some embodiments, the nucleic acid-targeting effector protein may be mutated with respect to a corresponding wild-type enzyme such that the mutated nucleic acid-targeting effector protein lacks the ability to cleave one or both DNA strands of a target polynucleotide containing a target sequence. As a further example, two or more catalytic domains of a Cas protein (e.g. RuvC I, RuvC II, and RuvC III or the HNH domain of a Cas9 protein) may be mutated to produce a mutated Cas protein which cleaves only one DNA strand of a target sequence.

In particular embodiments, the nucleic acid-targeting effector protein may be mutated with respect to a corresponding wild-type enzyme such that the mutated nucleic acid-targeting effector protein lacks substantially all DNA cleavage activity. In some embodiments, a nucleic acid-targeting effector protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

As used herein, the term "modified" Cas generally refers to a Cas protein having one or more modifications or mutations (including point mutations, truncations, insertions, deletions, chimeras, fusion proteins, etc.) compared to the wild type Cas protein from which it is derived. By derived is meant that the derived enzyme is largely based, in the sense of having a high degree of sequence homology with, a wildtype enzyme, but that it has been mutated (modified) in some way as known in the art or as described herein.

As detailed above, in certain embodiments, the nuclease as referred to herein is modified. As used herein, the term "modified" refers to which may or may not have an altered functionality. By means of example, and in particular with reference to Cas proteins, modifications which do not result in an altered functionality include for instance codon optimization for expression into a particular host, or providing the nuclease with a particular marker (e.g. for visualization). Modifications with may result in altered functionality may also include mutations, including point mutations, insertions, deletions, truncations (including split nucleases), etc., as well as chimeric nucleases (e.g. comprising domains from different orthologues or homologues) or fusion proteins. Fusion proteins may without limitation include for instance fusions with heterologous domains or functional domains (e.g. localization signals, catalytic domains, etc.). Accordingly, in certain embodiments, the modified nuclease may be used as a generic nucleic acid binding protein with fusion to or being operably linked to a functional domain. In certain embodiments, various different modifications may be combined (e.g. a mutated nuclease which is catalytically inactive and which further is fused to a functional domain, such as for instance to induce DNA methylation or another nucleic acid modification, such as including without limitation a break (e.g. by a different nuclease (domain)), a mutation, a deletion, an insertion, a replacement, a ligation, a digestion, a break or a recombination). As used herein, "altered functionality" includes without limitation an altered specificity (e.g. altered target recognition, increased (e.g. "enhanced" Cas proteins) or decreased specificity, or altered PAM recognition), altered activity (e.g. increased or decreased catalytic activity, including catalytically inactive nucleases or nickases), and/or altered stability (e.g. fusions with destabilization domains). Suitable heterologous domains include without limitation a nuclease, a ligase, a repair protein, a methyltransferase, (viral) integrase, a recombinase, a transposase, an argonaute, a cytidine deaminase, a retron, a group II intron, a phosphatase, a phosphorylase, a sulfurylase, a kinase, a polymerase, an exonuclease, etc. Examples of all these modifications are known in the art. It will be understood that a "modified" nuclease as referred to herein, and in particular a "modified" Cas or "modified" CRISPR/Cas system or complex preferably still has the capacity to interact with or bind to the polynucleic acid (e.g. in complex with the gRNA).

By means of further guidance and without limitation, in certain embodiments, the nuclease may be modified as detailed below. As already indicated, more than one of the indicated modifications may be combined. For instance, codon optimization may be combined with NLS or NES fusions, catalytically inactive nuclease modifications or nickase mutants may be combined with fusions to functional (heterologous) domains, etc.

In certain embodiments, the nuclease, and in particular the Cas proteins of prokaryotic origin, may be codon optimized for expression into a particular host (cell). An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid. Codon optimization may be for expression into any desired host (cell), including mammalian, plant, algae, or yeast.

In certain embodiments, the nuclease, in particular the Cas protein, may comprise one or more modifications resulting in enhanced activity and/or specificity, such as including mutating residues that stabilize the targeted or non-targeted strand (e.g. eCas9; "Rationally engineered Cas9 nucleases with improved specificity", Slaymaker et al. (2016), Science, 351(6268):84-88, incorporated herewith in its entirety by reference). In certain embodiments, the altered or modified activity of the engineered CRISPR protein comprises increased targeting efficiency or decreased off-target binding. In certain embodiments, the altered activity of the engineered CRISPR protein comprises modified cleavage activity. In certain embodiments, the altered activity comprises increased cleavage activity as to the target polynucleotide loci. In certain embodiments, the altered activity comprises decreased cleavage activity as to the target polynucleotide loci. In certain embodiments, the altered activity comprises decreased cleavage activity as to off-target polynucleotide loci. In certain embodiments, the altered or modified activity of the modified nuclease comprises altered helicase kinetics. In certain embodiments, the modified nuclease comprises a modification that alters association of the protein with the nucleic acid molecule comprising RNA (in the case of a Cas protein), or a strand of the target polynucleotide loci, or a strand of off-target polynucleotide loci. In an aspect of the invention, the engineered CRISPR protein comprises a modification that alters formation of the CRISPR complex. In certain embodiments, the altered activity comprises increased cleavage activity as to off-target polynucleotide loci. Accordingly, in certain embodiments, there is increased specificity for target polynucleotide loci as compared to off-target polynucleotide loci. In other embodiments, there is reduced specificity for target polynucleotide loci as compared to off-target polynucleotide loci. In certain embodiments, the mutations result in decreased off-target effects (e.g. cleavage or binding properties, activity, or kinetics), such as in case for Cas proteins for instance resulting in a lower tolerance for mismatches between target and gRNA. Other mutations may lead to increased off-target effects (e.g. cleavage or binding properties, activity, or kinetics). Other mutations may lead to increased or decreased on-target effects (e.g. cleavage or binding properties, activity, or kinetics). In certain embodiments, the mutations result in altered (e.g. increased or decreased) helicase activity, association or formation of the functional nuclease complex (e.g. CRISPR/Cas complex). In certain embodiments, the mutations result in an altered PAM recognition, i.e. a different PAM may be (in addition or in the alternative) be recognized, compared to the unmodified Cas protein (see e.g. "Engineered CRISPR-Cas9 nucleases with altered PAM specificities", Kleinstiver et al. (2015), Nature, 523(7561):481-485, incorporated herein by reference in its entirety). Particularly preferred mutations include positively charged residues and/or (evolutionary) conserved residues, such as conserved positively charged residues, in order to enhance specificity. In certain embodiments, such residues may be mutated to uncharged residues, such as alanine.

In certain embodiments, the nuclease, in particular the Cas protein, may comprise one or more modifications resulting in a nuclease that has reduced or no catalytic activity, or alternatively (in case of nucleases that target double stranded nucleic acids) resulting in a nuclease that only cleaves one strand, i.e. a nickase. By means of further guidance, and without limitation, for example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As further guidance, where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a Cas is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Thus, the Cas may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the Cas or has a mutation as otherwise as discussed herein.

In certain embodiments, the nuclease is a split nuclease (see e.g. "A split-Cas9 architecture for inducible genome editing and transcription modulation", Zetsche et al. (2015), Nat Biotechnol. 33(2):139-42, incorporated herein by reference in its entirety). In a split nuclease, the activity (which may be a modified activity, as described herein elsewhere), relies on the two halves of the split nuclease to be joined, i.e. each half of the split nuclease does not possess the required activity, until joined. As further guidance, and without limitation, with specific reference to Cas9, a split Cas9 may result from splitting the Cas9 at any one of the following split points, according or with reference to SpCas9: a split position between 202A/203S; a split position between 255F/256D; a split position between 310E/311I; a split position between 534R/535K; a split position between 572E/573C; a split position between 713S/714G; a split position between 1003L/104E; a split position between 1054G/1055E; a split position between 1114N/1115S; a split position between 1152K/1153S; a split position between 1245K/1246G; or a split between 1098 and 1099. Identifying potential split sides is most simply done with the help of a crystal structure. For Sp mutants, it should be readily apparent what the corresponding position for, for example, a sequence alignment. For non-Sp enzymes one can use the crystal structure of an ortholog if a relatively high degree of homology exists between the ortholog and the intended Cas9. Ideally, the split position should be located within a region or loop. Preferably, the split position occurs where an interruption of the amino acid sequence does not result in the partial or full destruction of a structural feature (e.g. alpha-helixes or beta-sheets). Unstructured regions (regions that did not show up in the crystal structure because these regions are not structured enough to be "frozen" in a crystal) are often preferred options. In certain embodiments, a functional domain may be provided on each of the split halves, thereby allowing the formation of homodimers or heterodimers. The functional domains may be (inducible) interact, thereby joining the split halves, and reconstituting (modified) nuclease activity. By means of example, an inducer energy source may inducibly allow dimerization of the split halves, through appropriate fusion partners. An inducer energy source may be considered to be simply an inducer or a dimerizing agent. The term 'inducer energy source' is used herein throughout for consistency. The inducer energy source (or inducer) acts to reconstitute the Cas9. In some embodiments, the inducer energy source brings the two parts of the Cas9 together through the action of the two halves of the inducible dimer. The two halves of the inducible dimer therefore are brought tougher in the presence of the inducer energy source. The two halves of the dimer will not form into the dimer (dimerize) without the inducer energy source.

Thus, the two halves of the inducible dimer cooperate with the inducer energy source to dimerize the dimer. This in turn reconstitutes the Cas9 by bringing the first and second parts of the Cas9 together. The CRISPR enzyme fusion constructs each comprise one part of the split Cas9. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer. The Cas9 is split in the sense that the two parts of the Cas9 enzyme substantially comprise a functioning Cas9. That Cas9 may function as a genome editing enzyme (when forming a complex with the target DNA and the guide), such as a nickase or a nuclease (cleaving both strands of the DNA), or it may be a dead Cas9 which is essentially a DNA-binding protein with very little or no catalytic activity, due to typically two or more mutations in its catalytic domains as described herein further.

In certain embodiments, the nuclease may comprise one or more additional (heterologous) functional domains, i.e. the modified nuclease is a fusion protein comprising the nuclease itself and one or more additional domains, which may be fused C-terminally or N-terminally to the nuclease, or alternatively inserted at suitable and appropriate sited internally within the nuclease (preferably without perturbing its function, which may be an otherwise modified function, such as including reduced or absent catalytic activity, nickase activity, etc.). any type of functional domain may suitably be used, such as without limitation including functional domains having one or more of the following activities: (DNA or RNA) methyltransferase activity, methylase activity, demethylase activity, DNA hydroxylmethylase domain, histone acetylase domain, histone deacetylases domain, transcription or translation activation activity, transcription or translation repression activity, transcription or translation release factor activity, histone modification activity, nuclease activity, single-strand RNA cleavage activity, double-strand RNA cleavage activity, single-strand DNA cleavage activity, double-strand DNA cleavage activity, nucleic acid binding activity, a protein acetyltransferase, a protein deacetylase, a protein methyltransferase, a protein deaminase, a protein kinase, a protein phosphatase, transposase domain, integrase domain, recombinase domain, resolvase domain, invertase domain, protease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase, histone tail protease, HDACs, histone methyltransferases (HMTs), and histone acetyltransferase (HAT) inhibitors, as well as HDAC and HMT recruiting proteins, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains. In some embodiments, the functional domain is an epigenetic regulator; see, e.g., Zhang et al., U.S. Pat. No. 8,507,272 (incorporated herein by reference in its entirety). In some embodiments, the functional domain is a transcriptional activation domain, such as VP64, p65, MyoD1, HSF1, RTA, SET7/9 or a histone acetyltransferase. In some embodiments, the functional domain is a transcription repression domain, such as KRAB. In some embodiments, the transcription repression domain is SID, or concatemers of SID (eg SID4X), NuE, or NcoR. In some embodiments, the functional domain is an epigenetic modifying domain, such that an epigenetic modifying enzyme is provided. In some embodiments, the functional domain is an activation domain, which may be the P65 activation domain. In some embodiments, the functional domain comprises nuclease activity. In one such embodiment, the functional domain may comprise FokI. Mention is made of U.S. Pat. Pub. 2014/0356959, U.S. Pat. Pub. 2014/0342456, U.S. Pat. Pub. 2015/0031132, and Mali, P. et al., 2013, Science 339(6121):823-6, doi: 10.1126/science.1232033, published online 3 Jan. 2013 and through the teachings herein the invention comprehends methods and materials of these documents applied in conjunction with the teachings herein. It is to be understood that also destabilization domains or localization domains as described herein elsewhere are encompassed by the generic term "functional domain". In certain embodiments, one or more functional domains are associated with the nuclease itself. In some embodiments, one or more functional domains are associated with an adaptor protein, for example as used with the modified guides of Konnerman et al. (Nature 517(7536): 583-588, 2015; incorporated herein by reference in its entirety), and hene form part of a Synergistic activator mediator (SAM) complex. The adaptor proteins may include but are not limited to orthogonal RNA-binding protein/aptamer combinations that exist within the diversity of bacteriophage coat proteins. A list of such coat proteins includes, but is not limited to: QP, F2, GA, fr, JP501, M12, R17, BZ13, JP34, JP500, KUl, M11, MX1, TW18, VK, SP, FI, ID2, NL95, TW19, AP205, #Cb5, #Cb8r, #Cbl2r, #Cb23r, 7s and PRR1. These adaptor proteins or orthogonal RNA binding proteins can further recruit effector proteins or fusions which comprise one or more functional domains.

In certain embodiments, the nuclease, in particular the Cas protein, may comprise one or more modifications resulting in a destabilized nuclease when expressed in a host (cell). Such may be achieved by fusion of the nuclease with a destabilization domain (DD). Destabilizing domains have general utility to confer instability to a wide range of proteins; see, e.g., Miyazaki, J Am Chem Soc. Mar. 7, 2012; 134(9): 3942-3945, incorporated herein by reference. CMP8 or 4-hydroxytamoxifen can be destabilizing domains. More generally, A temperature-sensitive mutant of mammalian DIFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β.6,7 This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with a CRISPR enzyme confers to the CRISPR protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to a CRISPR enzyme and its stability can be regulated or perturbed using a ligand, whereby the CRISPR enzyme has a DD. Another DD can be a 12-kDa (107-amino-acid) tag based on a mutated FKBP protein, stabilized by Shield1 ligand; see, e.g., Nature Methods 5, (2008). For instance a DD can be a modified FK506 binding protein 12 (FKBP12) that binds to and is reversibly stabilized by a synthetic, biologically inert small molecule, Shield-1; see, e.g., Banaszynski LA, Chen LC, Maynard-Smith LA, Ooi AG, Wandless TJ. A rapid, reversible, and tunable method to regulate protein function in living cells using synthetic small molecules. Cell. 2006; 126:995-1004; Banaszynski LA, Sellmyer MA, Contag CH, Wandless TJ, Thorne SH. Chemical control of protein stability and function in living mice. Nat Med. 2008; 14:1123-1127; Maynard-Smith LA, Chen LC, Banaszynski LA, Ooi AG, Wandless TJ. A directed approach for engineering conditional protein stability using biologically silent small molecules. The Journal of biological chemistry. 2007; 282: 24866-24872; and Rodriguez, Chem Biol. Mar. 23, 2012; 19(3): 391-398-all of which are incorporated herein by reference and may be employed in the practice of the invention in selected a DD to associate with a CRISPR enzyme in the practice of this invention. As can be seen, the knowledge in the art includes a number of DDs, and the DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the CRISPR enzyme and hence the CRISPR-Cas complex or system to be regulated or controlled-turned on or off so to speak, to thereby provide means for regulation or control of the system, e.g., in an in vivo or in vitro environment. For instance, when a protein of interest is expressed as a fusion with the DD tag, it is destabilized and rapidly degraded in the cell, e.g., by proteasomes. Thus, absence of stabilizing ligand leads to a D associated Cas being degraded. When a new DD is fused to a protein of interest, its instability is conferred to the protein of interest, resulting in the rapid degradation of the entire fusion protein. Peak activity for Cas is sometimes beneficial to reduce off-target effects. Thus, short bursts of high activity are preferred. The present invention is able to provide such peaks. In some senses the system is inducible. In some other senses, the system repressed in the absence of stabilizing ligand and de-repressed in the presence of stabilizing ligand. By means of example, and without limitation, in some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT. More than one (the same or different) DD may be present, and may be fused for instance C-terminally, or N-terminally, or even internally at suitable locations. Having two or more DDs which are heterologous may be advantageous as it would provide a greater level of degradation control.

In some embodiments, the fusion protein as described herein may comprise a linker between the nuclease and the fusion partner (e.g. functional domain). In some embodiments, the linker is a GlySer linker.

In some embodiments, the nuclease is fused to one or more localization signals, such as nuclear localization sequences (NLSs), such as about or more than about 1, 2, 3, 4, 5, 6, 7, 8, 9, 10, or more NLSs. In some embodiments, the nuclease comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the nuclease comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen; the NLS from nucleoplasmin (e.g. the nucleoplasmin bipartite NLS; the c-myc NLS; the hRNPA1 M9 NLS; or the IBB domain from importin-alpha.

With particular reference to the CRISPR/Cas system as described herein, besides the Cas protein, in addition or in the alternative, the gRNA and/or tracr (where applicable) and/or tracr mate (or direct repeat) may be modified. Suitable modifications include, without limitation dead guides, escorted guides, protected guides, or guides provided with aptamers, suitable for ligating to, binding or recruiting functional domains (see e.g. also elsewhere herein the reference to synergistic activator mediators (SAM)). Mention is also made of WO/2016/049258 (FUNCTIONAL SCREENING WITH OPTIMIZED FUNCTIONAL CRISPR-CAS SYSTEMS (SAM)), WO/2016/094867

(PROTECTED GUIDE RNAS (PGRNAS); WO/2016/094872 (DEAD GUIDES FOR CRISPR TRANSCRIPTION FACTORS); WO/2016/094874 (ESCORTED AND FUNCTIONALIZED GUIDES FOR CRISPR-CAS SYSTEMS); all incorporated herein by reference. In certain embodiments, the tracr sequence (where appropriate) and/or tracr mate sequence (direct repeat), may comprise one or more protein-interacting RNA aptamers. The one or more aptamers may be located in the tetraloop and/or stemloop 2 of the tracr sequence. The one or more aptamers may be capable of binding MS2 bacteriophage coat protein. In certain embodiments, the gRNA (or trace or tracr mate) is modified by truncations, and/or incorporation of one or more mismatches vis-à-vis the intended target sequence or sequence to hybridize with.

By means of further guidance, and without limitation, in certain embodiments, the gRNA is a dead gRNA (dgRNA), which are guide sequences which are modified in a manner which allows for formation of the CRISPR complex and successful binding to the target, while at the same time, not allowing for successful nuclease activity (i.e. without nuclease activity/without indel activity). These dead guides or dead guide sequences can be thought of as catalytically inactive or conformationally inactive with regard to nuclease activity. Several structural parameters allow for a proper framework to arrive at such dead guides. Dead guide sequences are shorter than respective guide sequences which result in active Cas-specific indel formation. Dead guides are 5%, 10%, 20%, 30%, 40%, 50%, shorter than respective guides directed to the same Cas protein leading to active Cas-specific indel formation. Guide RNA comprising a dead guide may be modified to further include elements in a manner which allow for activation or repression of gene activity, in particular protein adaptors (e.g. aptamers) as described herein elsewhere allowing for functional placement of gene effectors (e.g. activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g. an activator or repressor; dimerized MS2 bacteriophage coat proteins as fusion proteins with an activator or repressor), or a protein which itself binds an effector (e.g. activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

By means of further guidance, and without limitation, in certain embodiments, the gRNA is an escorted gRNA (egRNA). By "escorted" is meant that the CRISPR-Cas system or complex or guide is delivered to a selected time or place within a cell, so that activity of the CRISPR-Cas system or complex or guide is spatially or temporally controlled. For example, the activity and destination of the CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time. The escorted Cpf1 CRISPR-Cas systems or complexes have a gRNA with a functional structure designed to improve gRNA structure, architecture, stability, genetic expression, or any combination thereof. Such a structure can include an aptamer. Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke BJ, Stephens AW. "Escort aptamers: a delivery service for diagnosis and therapy." J Clin Invest 2000, 106: 923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

By means of further guidance, and without limitation, in certain embodiments, the gRNA is a protected guide. Protected guides are designed to enhance the specificity of a Cas protein given individual guide RNAs through thermodynamic tuning of the binding specificity of the guide RNA to target nucleic acid. This is a general approach of introducing mismatches, elongation or truncation of the guide sequence to increase/decrease the number of complimentary bases vs. mismatched bases shared between a target and its potential off-target loci, in order to give thermodynamic advantage to targeted genomic loci over genomic off-targets. In certain embodiments, the guide sequence is modified by secondary structure to increase the specificity of the CRISPR-Cas system and whereby the secondary structure can protect against exonuclease activity and allow for 3' additions to the guide sequence. In certain embodiments, a "protector RNA" is hybridized to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target binding to the mismatched basepairs at the 3' end. In certain embodiments, additional sequences comprising an extented length may also be present.

Guide RNA (gRNA) extensions matching the genomic target provide gRNA protection and enhance specificity.

Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region. Thermodynamic prediction can be used to predict completely matching or partially matching guide extensions that result in protected gRNA states. This extends the concept of protected gRNAs to interaction between X and Z, where X will generally be of length 17-20 nt and Z is of length 1-30 nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and EL are used interchangeably to correspond to the term extended length (ExL) which represents the number of nucleotides by which the target sequence is extended. An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nuleotides in length. In a more preferred embodiment the ExL is 4 nuleotides in length. The extension sequence may or may not be complementary to the target sequence. An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence. Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

In certain embodiments, any of the nucleases, including the modified nucleases as described herein, may be used in the methods, compositions, and kits according to the invention. In particular embodiments, nuclease activity of an unmodified nuclease may be compared with nuclease activity of any of the modified nucleases as described herein, e.g. to compare for instance off-target or on-target effects. Alternatively, nuclease activity (or a modified activity as described herein) of different modified nucleases may be compared, e.g. to compare for instance off-target or on-target effects.

Also provided herein are compositions for use in carrying out the methods of the invention. More particularly, non-naturally occurring or engineered compositions are provided which comprise one or more of the elements required to ensure genomic perturbation. In particular embodiments, the compositions comprise one or more of the (modified) DNA binding protein, and/or a guide RNA. In particular embodiments, the composition comprises a vector. In further particular embodiments, the vector comprises a polynucleotide encoding a gRNA. In particular embodiments, the vector comprises two or more guide RNAs. The two or more guide RNAs may target a different target (so as to ensure multiplex targeting) or the same target, in which case the different guide RNAs will target different sequences within the same target sequence. Where provided in a vector the different guide RNAs may be under common control of the same promotor, or may be each be under control of the same or different promoters.

In certain embodiments, a modulant may comprise silencing one or more endogenous genes.

As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

In certain embodiments, a modulant may comprise (i) a DNA-binding portion configured to specifically bind to the endogenous gene and (ii) an effector domain mediating a biological activity.

In certain embodiments, the DNA-binding portion may comprises a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In some embodiments the effector domain may be a transcriptional inhibitor (i.e., a repressor domain), such as an mSin interaction domain (SID). SID4X domain or a Kruppel-associated box (KRAB) or fragments of the KRAB domain. In some embodiments the effector domain may be an enhancer of transcription (i.e. an activation domain), such as the VP16, VP64 or p65 activation domain. In some embodiments, the nucleic acid binding portion may be linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.In certain embodiments, a modulant may comprise introducing one or more endogenous genes and/or one or more exogenous genes in expressible format into the immune cell, in accordance with the practice of transgenesis as taught elsewhere in this specification.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T cells (including, e.g., thymocytes, Th or Tc; Th1, Th2, Th17, Thap, CD4+, CD8+, effector Th, memory Th, regulatory Th, CD4+/CD8+ thymocytes, CD4-/CD8-thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

The invention provides compositions and methods for modulating T cell and intestinal epithelial cell balance. As used herein, the term "modulating" includes up-regulation of, or otherwise increasing, the expression of one or more genes, down-regulation of, or otherwise decreasing, the expression of one or more genes, inhibiting or otherwise decreasing the expression, activity and/or function of one or more gene products, and/or enhancing or otherwise increasing the expression, activity and/or function of one or more gene products. The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without the modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without the modulation. Preferably, modulation may be specific or selective, hence, one or more desired phenotypic aspects of a cell or cell population may be modulated without substantially altering other (unintended, undesired) phenotypic aspect(s).

In certain embodiments, an modulant may comprise altering expression and/or activity of one or more endogenous genes of the cell. The term "altered expression" denotes that the modification of the cell alters, i.e., changes or modulates, the expression of the recited gene(s) or polypeptides(s). The term "altered expression" encompasses any direction and any extent of the alteration. Hence, "altered expression" may reflect qualitative and/or quantitative change(s) of expression, and specifically encompasses both increase (e.g., activation or stimulation) or decrease (e.g., inhibition) of expression.

As used herein, the term "modulating T cell balance" includes the modulation of any of a variety of T cell-related functions and/or activities, including by way of non-limiting example, controlling or otherwise influencing the networks that regulate T cell differentiation; controlling or otherwise influencing the networks that regulate T cell maintenance, for example, over the lifespan of a T cell; controlling or otherwise influencing the networks that regulate T cell function; controlling or otherwise influencing the networks that regulate helper T cell (Th cell) differentiation; controlling or otherwise influencing the networks that regulate Th cell maintenance, for example, over the lifespan of a Th cell; controlling or otherwise influencing the networks that regulate Th cell function; controlling or otherwise influencing the networks that regulate Th17 cell differentiation; controlling or otherwise influencing the networks that regulate Th17 cell maintenance, for example, over the lifespan of a Th17 cell; controlling or otherwise influencing the networks that regulate Th17 cell function; controlling or otherwise influencing the networks that regulate regulatory T cell (Treg) differentiation; controlling or otherwise influencing the networks that regulate Treg cell maintenance, for example, over the lifespan of a Treg cell; controlling or otherwise influencing the networks that regulate Treg cell function; controlling or otherwise influencing the networks that regulate other CD4$^+$ T cell differentiation; controlling or otherwise influencing the networks that regulate other CD4$^+$ T cell maintenance; controlling or otherwise influencing the networks that regulate other CD4$^+$ T cell function; manipulating or otherwise influencing the ratio of T cells such as, for example, manipulating or otherwise influencing the ratio of Th17 cells to other T cell types such as Tregs or other CD4$^+$ T cells; manipulating or otherwise influencing the ratio of different types of Th17 cells such as, for example, pathogenic Th17 cells and non-pathogenic Th17 cells; manipulating or otherwise influencing at least one function or biological activity of a T cell; manipulating or otherwise influencing at least one function or biological activity of Th cell; manipulating or otherwise influencing at least one function or biological activity of a Treg cell; manipulating or otherwise influencing at least one function or biological activity of a Th17 cell; and/or manipulating or otherwise influencing at least one function or biological activity of another CD4$^+$ T cell.

As used herein, the term "modulating enteric cell balance" comprises cell differentiation types, rates, activity levels, death rate, and more.

The invention provides T cell modulating agents that modulate T cell balance. For example, in some embodiments, the invention provides T cell modulating agents and methods of using these T cell modulating agents to regulate, influence or otherwise impact the level(s) of and/or balance between T cell types, e.g., between Th17 and other T cell types, for example, regulatory T cells (Tregs), and/or Th17 activity and inflammatory potential.

As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

For example, in some embodiments, the invention provides T cell modulating agents and methods of using these T cell modulating agents to regulate, influence or otherwise impact the level of and/or balance between Th17 phenotypes, and/or Th17 activity and inflammatory potential. Suitable T cell modulating agents include an antibody, a soluble polypeptide, a polypeptide agent, a peptide agent, a nucleic acid agent, a nucleic acid ligand, or a small molecule agent.

For example, in some embodiments, the invention provides T cell modulating agents and methods of using these T cell modulating agents to regulate, influence or otherwise impact the level of and/or balance between Th17 cell types, e.g., between pathogenic and non-pathogenic Th17 cells. For example, in some embodiments, the invention provides T cell modulating agents and methods of using these T cell modulating agents to regulate, influence or otherwise impact the level of and/or balance between pathogenic and non-pathogenic Th17 activity.

For example, in some embodiments, the invention provides T cell modulating agents and methods of using these T cell modulating agents to influence or otherwise impact the differentiation of a population of T cells, for example toward Th17 cells, with or without a specific pathogenic distinction, or away from Th17 cells, with or without a specific pathogenic distinction.

For example, in some embodiments, the invention provides T cell modulating agents and methods of using these T cell modulating agents to influence or otherwise impact the differentiation of a population of T cells, for example toward a non-Th17 T cell subset or away from a non-Th17 cell subset. For example, in some embodiments, the invention provides T cell modulating agents and methods of using these T cell modulating agents to induce T cell plasticity, i.e., converting Th17 cells into a different subtype, or into a new state.

For example, in some embodiments, the invention provides T cell modulating agents and methods of using these T cell modulating agents to induce T cell plasticity, e.g., converting Th17 cells into a different subtype, or into a new state.

For example, in some embodiments, the invention provides T cell modulating agents and methods of using these T cell modulating agents to achieve any combination of the above.

The terms "pathogenic" or "non-pathogenic" as used herein are not to be construed as implying that one cell phenotype is more desirable than the other.

In some embodiments, the invention provides a method of activating therapeutic immunity by exploiting the blockade of immune checkpoints. The progression of a productive immune response requires that a number of immunological checkpoints be passed. Immunity response is regulated by the counterbalancing of stimulatory and inhibitory signal. One skilled in the art will appreciate that the T cell modulating agents have a variety of uses. For example, the T cell modulating agents are used as therapeutic agents as described herein. The T cell modulating agents can be used as reagents in screening assays, diagnostic kits or as diagnostic tools, or these T cell modulating agents can be used in competition assays to generate therapeutic reagents.

Adoptive Cell Transfer (Act)

Given the linkage between T cells and intestinal epithelial cell differentiation, function and activity, the invention also contemplates the adoptive cell transfer for the modulation of epithelial cells. Adoptive cell therapy or adoptive cell transfer (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may, for example, be employed to genetically modify T cells by altering the specificity of the T cell receptor (TCR), for example, by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fe domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CD5, CD9, CD 16, CD22, CD33, CD37, CD64, CD80, CD86, CD 134, CD137, CD 154, TCR. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a $V_L$ linked to a VH of a specific antibody, linked by a flexible linker, for example by a CD8a hinge domain and a CD8a transmembrane domain, to the transmembrane and intracellular signaling domains of either CD3(or FcRy (scFv-CD3 (or scFv-FcRy; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3(; see U.S. Pat. Nos. 8,911,993; 8,916,381; 8,975,071; 9,101,584; 9,102,760; 9,102,761).

Third-generation CARs include a combination of costimulatory endodomains, such a CD3ζ-chain, CD97, GDI 1a-CD18, CD2, ICOS, CD27, CD2, CD7, LIGHT, LFA-1, NKG2C, B7-H3, CD30, CD40, PD-1, CD154, CDS, OX40, 4-1BB, or CD28 signaling domains (for example scFv-CD28-4-1BB-CD3(or scFv-CD28-OX40-CD3(; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native apTCR, for example by antigen on professional antigen-presenting cells, with attendant costimulation. In addition, additional engineered receptors may be provided on the immunoresponsive cells, for example to improve targeting of a T cell attack and/or minimize side effects.

Alternatively, T cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may be eliminated using RNA interference (e.g., shRNA, siRNA, miRNA, etc.), CRISPR, or other methods that target the nucleic acids encoding specific TCRs (e.g., TCR-a and TCR-0) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T cell response. Some CARs may also comprise a "suicide switch" to induce cell death of the CAR T cells following treatment (Buddee et al., PLoS One, 2013) or to downregulate expression of the CAR following binding to the target antigen (WO 2016/011210).

Various techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3(and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with y-irradiated activating and propagating cells (AaPC), which co-express the cancer antigen and co-stimulatory molecules. The engineered CAR T cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-y). CAR T cells of this kind may for example be used in animal models, for example to treat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of 104-10 cells per kg body weight, preferably 10 to $10^6$ cells/kg body weight including all integer values of cell numbers within those ranges. Dosing in CAR T cell therapies may for example involve administration of from 106 to 10 cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T cell manufacturing platform for "off-the-shelf" adoptive T cell immunotherapies, Cancer Res 75 (18): 3853). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T cell receptors (TCR), disrupt the target of a chemotherapeutic agent, block an immune checkpoint, activate a T cell, and/or increase the differentiation and/or proliferation of functionally exhausted or dysfunctional CD8+ T cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system can specifically catalyze cleavage in one targeted gene thereby inactivating the targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via NHEJ often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, a and 3, which assemble to form a heterodimer and associates with the CD3-transducing subunits to form the T cell receptor complex present on the cell surface. Each a and p chain of the TCR consists of an immunoglobulin-like N-terminal variable (V) and constant (C) region, a hydrophobic transmembrane domain, and a short cytoplasmic region. As for immunoglobulin molecules, the variable region of the a and p chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRa or TCRP can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor a-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCDI). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MTi and/or MTi inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT. In preferred embodiments, the novel genes or gene combinations described herein are targeted or modulated.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment T cells that have infiltrated a tumor are isolated. T cells may be removed during surgery. T cells may be isolated after removal of tumor tissue by biopsy. T cells may be isolated by any means known in the art. In one embodiment the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., $3\chi^{28}$)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8+ T cells in dilute concentrations. In one embodiment, the concentration of cells used is $5×10^6$/ml. In other embodiments, the concentration used can be from about $1×10^5$/ml to $1×10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation And Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one T cells are isolated by contacting the T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

Use of Biomarkers

The invention provides biomarkers for the identification, diagnosis and manipulation of cell properties, for use in a variety of diagnostic and/or therapeutic indications. Biomarkers in the context of the present invention encompasses, without limitation nucleic acids, together with their polymorphisms, mutations, variants, modifications, subunits, fragments, and other analytes or sample-derived measures.

Biomarkers are useful in methods of diagnosing, prognosing and/or staging an immune response in a subject by detecting a first level of expression, activity and/or function of one or more biomarker and comparing the detected level to a control of level wherein a difference in the detected level and the control level indicates that the presence of an immune response in the subject.

These biomarkers are useful in methods of identifying patient populations at risk or suffering from an immune response based on a detected level of expression, activity and/or function of one or more biomarkers. These biomarkers are also useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The biomarkers provided herein are useful for selecting a group of patients at a specific state of a disease with accuracy that facilitates selection of treatments.

The present invention also may comprise a kit with a detection reagent that binds to one or more biomarkers.

Use of T Cell Modulating Agents

Suitable T cell modulating agent(s) for use in any of the compositions and methods provided herein include an antibody, a soluble polypeptide, a polypeptide agent, a peptide agent, a nucleic acid agent, a nucleic acid ligand, or a small molecule agent. By way of non-limiting example, suitable T cell modulating agents or agents for use in combination with one or more T cell modulating agents are shown below in Table 1.

TABLE 1

T cell Modulating Agents

| Target | Agent |
|---|---|
| CCR6 | prostaglandin E2, lipopolysaccharide, mip-3alpha, vegf, rantes, calcium, bortezomib, ccl4, larc, tarc, lipid, E. coli B5 lipopolysaccharide |
| CCR5 | cholesterol, cyclosporin a, glutamine, methionine, guanine, simvastatin, threonine, indinavir, lipoxin A4, cysteine, prostaglandin E2, zinc, dapta, 17-alpha-ethinylestradiol, polyacrylamide, progesterone, zidovudine, rapamycin, rantes, glutamate, alanine, valine, ccl4, quinine, NSC 651016, methadone, pyrrolidine dithiocarbamate, palmitate, nor-binaltorphimine, interferon beta-1a, vitamin-e, tak779, lipopolysaccharide, cisplatin, albuterol, fluvoxamine, vicriviroc, bevirimat, carbon tetrachloride, galactosylceramide, ATP-gamma-S, cytochalasin d, hemozoin, CP 96345, tyrosine, etravirine, vitamin d, mip 1alpha, ammonium, tyrosine sulfate, isoleucine, isopentenyl diphosphate, il 10, serine, N-acetyl-L-cysteine, histamine, cocaine, ritonavir, tipranavir, aspartate, atazanavir, tretinoin, ATP, ribavirin, butyrate, N-nitro-L-arginine methyl ester, larc, buthionine sulfoximine, DAPTA, aminooxypentane-rantes, triamcinolone acetonide, shikonin, actinomycin d, bucladesine, aplaviroc, nevirapine, N-formyl-Met-Leu-Phe, cyclosporin A, lipoarabinomannan, nucleoside, sirolimus, morphine, mannose, calcium, heparin, c-d4i, pge2, beta-estradiol, mdms, dextran sulfate, dexamethasone, arginine, ivig, mcp 2, cyclic amp, U 50488H, N-methyl-D-aspartate, hydrogen peroxide, 8-carboxamidocyclazocine, latex, groalpha, xanthine, ccl3, retinoic acid, Maraviroc, sdf 1, opiate, efavirenz, estrogen, bicyclam, enfuvirtide, filipin, bleomycin, polysaccharide, tarc, pentoxifylline, E. coli B5 lipopolysaccharide, methylcellulose, maraviroc |
| ITGA3 | SP600125, paclitaxel, decitabine, e7820, retinoid, U0126, serine, retinoic acid, tyrosine, forskolin, Ca2+ |
| IRF4 | prostaglandin E2, phorbol myristate acetate, lipopolysaccharide, A23187, tacrolimus, trichostatin A, stallimycin, imatinib, cyclosporin A, tretinoin, bromodeoxyuridine, ATP-gamma-S, ionomycin |
| BATF | Cyclic AMP, serine, tacrolimus, beta-estradiol, cyclosporin A, leucine |
| RBPJ | zinc, tretinoin |
| PROCR | lipopolysaccharide, cisplatin, fibrinogen, 1, 10-phenanthroline, 5-N-ethylcarboxamido adenosine, cystathionine, hirudin, phospholipid, Drotrecogin alfa, vegf, Phosphatidylethanolamine, serine, gamma-carboxyglutamic acid, calcium, warfarin, endotoxin, curcumin, lipid, nitric oxide |
| ZEB1 | resveratrol, zinc, sulforafan, sorafenib, progesterone, PD-0332991, dihydrotestosterone, silibinin, LY294002, 4-hydroxytamoxifen, valproic acid, beta-estradiol, forskolin, losartan potassium, fulvestrant, vitamin d |
| POU2AF1 | terbutaline, phorbol myristate acetate, bucladesine, tyrosine, ionomycin, KT5720, H89 |
| EGR1 | ghrelin, ly294002, silicone, sodium, propofol, 1, 25 dihydroxy vitamin d3, tetrodotoxin, threonine, cyclopiazonic acid, urea, quercetin, ionomycin, 12-o-tetradecanoylphorbol 13-acetate, fulvestrant, phenylephrine, formaldehyde, cysteine, leukotriene C4, prazosin, LY379196, vegf, rapamycin, leupeptin, pd 98, 059, ruboxistaurin, pCPT-cAMP, methamphetamine, nitroprusside, H-7, Ro31-8220, phosphoinositide, lysophosphatidylcholine, bufalin, calcitriol, leuprolide, isobutylmethylxanthine, potassium chloride, acetic acid, cyclothiazide, quinolinic acid, tyrosine, adenylate, resveratrol, topotecan, genistein, thymidine, D-glucose, mifepristone, lysophosphatidic acid, leukotriene D4, carbon monoxide, poly rI:rC-RNA, sp 600125, agar, cocaine, 4- |

TABLE 1-continued

T cell Modulating Agents

| Target | Agent |
|---|---|
| | nitroquinoline-1-oxide, tamoxifen, lead, fibrinogen, tretinoin, atropine, mithramycin, K+, epigallocatechin-gallate, ethylenediaminetetraacetic acid, h2o2, carbachol, sphingosine-1-phosphate, iron, 5-hydroxytryptamine, amphetamine, SP600125, actinomycin d, SB203580, cyclosporin A, norepinephrine, okadaic acid, ornithine, LY294002, pge2, beta-estradiol, glucose, erlotinib, arginine, 1-alpha, 25-dihydroxy vitamin D3, dexamethasone, pranlukast, phorbol myristate acetate, nimodipine, desipramine, cyclic amp, N-methyl-D-aspartate, atipamezole, acadesine, losartan, salvin, methylnitronitrosoguanidine, EGTA, gf 109203x, nitroarginine, 5-N-ethylcarboxamido adenosine, 15-deoxy-delta-12, 14-PGJ 2, dbc-amp, manganese superoxide, di(2-ethylhexyl) phthalate, egcg, mitomycin C, 6, 7-dinitroquinoxaline-2, 3-dione, GnRH-A, estrogen, ribonucleic acid, imipramine, bapta, L-triiodothyronine, prostaglandin, forskolin, nogalamycin, losartan potassium, lipid, vincristine, 2-amino-3-phosphonopropionic acid, prostacyclin, methylnitrosourea, cyclosporin a, vitamin K3, thyroid hormone, diethylstilbestrol, D-tubocurarine, tunicamycin, caffeine, phorbol, guanine, bisindolylmaleimide, apomorphine, arachidonic acid, SU6656, prostaglandin E2, zinc, ptx1, progesterone, cyclosporin H, phosphatidylinositol, U0126, hydroxyapatite, epoprostenol, glutamate, 5fluorouracil, indomethacin, 5-fluorouracil, RP 73401, Ca2+, superoxide, trifluoperazine, nitric oxide, lipopolysaccharide, cisplatin, diazoxide, tgf beta1, calmidazolium, anisomycin, paclitaxel, sulindac sulfide, ganciclovir, gemcitabine, testosterone, ag 1478, glutamyl-Se-methylselenocysteine, doxorubicin, tolbutamide, cytochalasin d, PD98059, leucine, SR 144528, cyclic AMP, matrigel, haloperidol, serine, sb 203580, triiodothyronine, reverse, N-acetyl-L-cysteine, ethanol, s-nitroso-n-acetylpenicillamine, curcumin, l-nmma, H89, tpck, calyculin a, chloramphenicol, A23187, dopamine, platelet activating factor, arsenite, selenomethylselenocysteine, ropinirole, saralasin, methylphenidate, gentamicin, reserpine, triamcinolone acetonide, methyl methanesulfonate, wortmannin, thapsigargin, deferoxamine, calyculin A, peptidoglycan, dihydrotestosterone, calcium, phorbol-12-myristate, ceramide, nmda, 6-cyano-7-nitroquinoxaline-2, 3-dione, hydrogen peroxide, carrageenan, sch 23390, linsidomine, oxygen, clonidine, fluoxetine, retinoid, troglitazone, retinoic acid, epinephrine, n acetylcysteine, KN-62, carbamylcholine, 2-amino-5-phosphonovaleric acid, oligonucleotide, gnrh, rasagiline, 8-bromo-cAMP, muscarine, tacrolimus, kainic acid, chelerythrine, inositol 1, 4, 5 trisphosphate, yohimbine, acetylcholine, atp, 15-deoxy-delta-12, 14-prostaglandin j2, ryanodine, CpG oligonucleotide, cycloheximide, BAPTA-AM, phenylalanine |
| ETV6 | lipopolysaccharide, retinoic acid, prednisolone, valproic acid, tyrosine, cerivastatin, vegf, agar, imatinib, tretinoin |
| IL17RA | rantes, lipopolysaccharide, 17-alpha-ethinylestradiol, camptothecin, E. coli B5 lipopolysaccharide |
| EGR2 | phorbol myristate acetate, lipopolysaccharide, platelet activating factor, carrageenan, edratide, 5-N-ethylcarboxamido adenosine, potassium chloride, dbc-amp, tyrosine, PD98059, camptothecin, formaldehyde, prostaglandin E2, leukotriene C4, zinc, cyclic AMP, GnRH-A, bucladesine, thapsigargin, kainic acid, cyclosporin A, mifepristone, leukotriene D4, LY294002, L-triiodothyronine, calcium, beta-estradiol, H89, dexamethasone, cocaine |
| SP4 | betulinic acid, zinc, phorbol myristate acetate, LY294002, methyl 2-cyano-3, 12-dioxoolean-1, 9-dien-28-oate, beta-estradiol, Ca2+ |
| IRF8 | oligonucleotide, chloramphenicol, lipopolysaccharide, estrogen, wortmannin, pirinixic acid, carbon monoxide, retinoic acid, tyrosine |
| NFKB1 | Bay 11-7085, Luteolin, Triflusal, Bay 11-7821, Thalidomide, Caffeic acid phenethyl ester, Pranlukast |
| TSC22D3 | phorbol myristate acetate, prednisolone, sodium, dsip, tretinoin, 3-deazaneplanocin, gaba, PD98059, leucine, triamcinolone acetonide, prostaglandin E2, steroid, norepinephrine, U0126, acth, calcium, ethanol, beta-estradiol, lipid, chloropromazine, arginine, dexamethasone |
| PML | lipopolysaccharide, glutamine, thyroid hormone, cadmium, lysine, tretinoin, bromodeoxyuridine, etoposide, retinoid, pic 1, arsenite, arsenic trioxide, butyrate, retinoic acid, alpha-retinoic acid, h2o2, camptothecin, cysteine, leucine, zinc, actinomycin d, proline, stallimycin, U0126 |
| IL12RB1 | prostaglandin E2, phorbol myristate acetate, lipopolysaccharide, bucladesine, 8-bromo-cAMP, gp 130, AGN194204, galactosylceramide-alpha, tyrosine, ionomycin, dexamethasone, il-12 |
| IL21R | azathioprine, lipopolysaccharide, okadaic acid, E. coli B5 lipopolysaccharide, calyculin A |
| NOTCH1 | interferon beta-1a, lipopolysaccharide, cisplatin, tretinoin, oxygen, vitamin B12, epigallocatechin-gallate, isobutylmethylxanthine, threonine, apomorphine, matrigel, trichostatin A, vegf, 2-acetylaminofluorene, rapamycin, dihydrotestosterone, poly rI:rC-RNA, hesperetin, valproic acid, asparagine, lipid, curcumin, dexamethasone, glycogen, CpG oligonucleotide, nitric oxide |
| ETS2 | oligonucleotide |
| MINA | phorbol myristate acetate, 4-hydroxytamoxifen |

TABLE 1-continued

T cell Modulating Agents

| Target | Agent |
|---|---|
| SMARCA4 | cyclic amp, cadmium, lysine, tretinoin, latex, androstane, testosterone, sucrose, tyrosine, cysteine, zinc, oligonucleotide, estrogen, steroid, trichostatin A, tpmp, progesterone, histidine, atp, trypsinogen, glucose, agar, lipid, arginine, vancomycin, dihydrofolate |
| FAS | hoechst 33342, ly294002, 2-chlorodeoxyadenosine, glutamine, cd 437, tetrodotoxin, cyclopiazonic acid, arsenic trioxide, phosphatidylserine, niflumic acid, gliadin, ionomycin, safrole oxide, methotrexate, rubitecan, cysteine, propentofylline, vegf, boswellic acids, rapamycin, pd 98, 059, captopril, methamphetamine, vesnarinone, tetrapeptide, oridonin, raltitrexed, pirinixic acid, nitroprusside, H-7, beta-boswellic acid, adriamycin, concanamycin a, etoposide, trastuzumab, cyclophosphamide, ifn-alpha, tyrosine, rituximab, selenodiglutathione, chitosan, omega-N-methylarginine, creatinine, resveratrol, topotecan, genistein, trichostatin A, decitabine, thymidine, D-glucose, mifepristone, tetracycline, Sn50 peptide, poly rI:rC-RNA, actinomycin D, sp 600125, doxifluridine, agar, ascorbic acid, acetaminophen, aspirin, tamoxifen, okt3, edelfosine, sulforafan, aspartate, antide, n, n-dimethylsphingosine, epigallocatechin-gallate, N-nitro-L-arginine methyl ester, h2o2, cerulenin, sphingosine-1-phosphate, SP600125, sodium nitroprusside, glycochenodeoxycholic acid, ceramides, actinomycin d, SB203580, cyclosporin A, morphine, LY294002, n(g)-nitro-l-arginine methyl ester, 4-hydroxynonenal, piceatannol, valproic acid, beta-estradiol, 1-alpha, 25-dihydroxy vitamin D3, arginine, dexamethasone, sulfadoxine, phorbol myristate acetate, beta-lapachone, nitrofurantoin, chlorambucil, methylnitronitrosoguanidine, CD 437, opiate, egcg, mitomycin C, estrogen, ribonucleic acid, fontolizumab, tanshinone iia, recombinant human endostatin, fluoride, L-triiodothyronine, bleomycin, forskolin, nonylphenol, zymosan A, vincristine, daunorubicin, prednisolone, cyclosporin a, vitamin K3, diethylstilbestrol, deoxyribonucleotide, suberoylanilide hydroxamic acid, orlistat, 3-(4, 5-dimethylthiazol-2-yl)-2, 5-diphenyltetrazolium bromide, rottlerin, arachidonic acid, ibuprofen, prostaglandin E2, toremifene, depsipeptide, ochratoxin A, (glc)4, phosphatidylinositol, mitomycin c, rantes, sphingosine, indomethacin, 5fluorouracil, phosphatidylcholine, 5-fluorouracil, mg 132, thymidylate, trans-cinnamaldehyde, sterol, polyadenosine diphosphate ribose, nitric oxide, vitamin e succinate, lipopolysaccharide, cisplatin, herbimycin a, 5-aza-2'deoxycytidine, proteasome inhibitor PSI, 2, 5-hexanedione, epothilone B, caffeic acid phenethyl ester, glycerol 3-phosphate, tgf beta1, anisomycin, paclitaxel, gemcitabine, medroxyprogesterone acetate, hymecromone, testosterone, ag 1478, doxorubicin, S-nitroso-N-acetylpenicillamine, adpribose, sulforaphane, vitamin d, annexin-v, lactate, reactive oxygen species, sb 203580, serine, N-acetyl-L-cysteine, dutp, infliximab, ethanol, curcumin, cytarabine, tpck, calyculin a, dopamine, gp 130, bromocriptine, apicidin, fatty acid, citrate, glucocorticoid, arsenite, butyrate, peplomycin, oxaliplatin, camptothecin, benzyloxycarbonyl-Leu-Leu-Leu aldehyde, clofibrate, carbon, wortmannin, fludarabine, N-(3-(aminomethyl)benzyl)acetamidine, sirolimus, peptidoglycan, c2 ceramide, dihydrotestosterone, 7-aminoactinomycin d, carmustine, heparin, ceramide, paraffin, mitoxantrone, docosahexaenoic acid, vitamin a, ivig, hydrogen peroxide, 7-ethyl-10-hydroxy-camptothecin, oxygen, pydrin, bortezomib, retinoic acid, 1, 4-phenylenebis(methylene)selenocyanate, teriflunomide, epinephrine, n acetylcysteine, noxa, irinotecan, oligonucleotide, d-api, rasagiline, 8-bromo-cAMP, atpo, agarose, fansidar, clobetasol propionate, teniposide, aurintricarboxylic acid, polysaccharide, CpG oligonucleotide, cycloheximide |
| IRF1 | tamoxifen, chloramphenicol, polyinosinic-polycytidylic acid, inosine monophosphate, suberoylanilide hydroxamic acid, butyrate, iron, gliadin, zinc, actinomycin d, deferoxamine, phosphatidylinositol, adenine, ornithine, rantes, calcium, 2',5'-oligoadenylate, pge2, poly(i-c), indoleamine, arginine, estradiol, nitric oxide, etoposide, adriamycin, oxygen, retinoid, guanylate, troglitazone, ifn-alpha, retinoic acid, tyrosine, adenylate, am 580, guanosine, oligonucleotide, estrogen, thymidine, tetracycline, serine, sb 203580, pdtc, lipid, cycloheximide |
| MYC | cd 437, 1, 25 dihydroxy vitamin d3, phenethyl isothiocyanate, threonine, arsenic trioxide, salicylic acid, quercetin, prostaglandin E1, ionomycin, 12-o-tetradecanoylphorbol 13-acetate, fulvestrant, phenylephrine, fisetin, 4-coumaric acid, dihydroartemisinin, 3-deazaadenosine, nitroprusside, pregna-4, 17-diene-3, 16-dione, adriamycin, bromodeoxyuridine, AGN194204, STA-9090, isobutylmethylxanthine, potassium chloride, docetaxel, quinolinic acid, 5, 6, 7, 8-tetrahydrobiopterin, propranolol, delta 7-pga1, topotecan, AVI-4126, trichostatin A, decitabine, thymidine, D-glucose, mifepristone, poly rI:rC-RNA, letrozole, L-threonine, 5-hydroxytryptamine, bucladesine, SB203580, 1'-acetoxychavicol acetate, cyclosporin A, okadaic acid, dfmo, LY294002, hmba, piceatannol, 2',5'-oligoadenylate, 4-hydroxytamoxifen, butylbenzyl phthalate, dexamethasone, ec 109, phosphatidic acid, grape seed extract, phorbol myristate acetate, coumermycin, tosylphenylalanyl chloromethyl ketone, CD 437, di(2-ethylhexyl) phthalate, butyrine, cytidine, sodium arsenite, tanshinone iia, L-triiodothyronine, niacinamide, glycogen, daunorubicin, |

TABLE 1-continued

T cell Modulating Agents

| Target | Agent |
|---|---|
| | vincristine, carvedilol, bizelesin, 3-deazaneplanocin, phorbol, neplanocin a, panobinostat, [aid], phosphatidylinositol, U0126, dichlororibofuranosylbenzimidazole, flavopiridol, 5-fluorouracil, verapamil, cyclopamine, nitric oxide, cisplatin, hrgbeta1, 5, 6-dichloro-1-beta-d-ribofuranosylbenzimidazole, amsacrine, gemcitabine, aristeromycin, medroxyprogesterone acetate, gambogic acid, leucine, alpha-naphthyl acetate, cyclic AMP, reactive oxygen species, PD 180970, curcumin, chloramphenicol, A23187, crocidolite asbestos, 6-hydroxydopamine, cb 33, arsenite, gentamicin, benzyloxycarbonyl-Leu-Leu-Leu aldehyde, clofibrate, wortmannin, sirolimus, ceramide, melphalan, 3M-001, linsidomine, CP-55940, hyaluronic acid, ethionine, clonidine, retinoid, bortezomib, oligonucleotide, methyl 2-cyano-3, 12-dioxoolean-1, 9-dien-28-oate, tacrolimus, embelin, methyl-beta-cyclodextrin, 3M-011, folate, 1y294002, PP1, hydroxyurea, aclarubicin, phenylbutyrate, PD 0325901, methotrexate, Cd2+, prazosin, vegf, rapamycin, alanine, phenobarbital, pd 98, 059, trapoxin, 4-hydroperoxycyclophosphamide, methamphetamine, s-(1, 2-dichlorovinyl)-l-cysteine, aphidicolin, vesnarinone, ADI PEG20, pirinixic acid, wp631, H-7, carbon tetrachloride, bufalin, 2, 2-dimethylbutyric acid, etoposide, calcitriol, trastuzumab, cyclophosphamide, harringtonine, tyrosine, N(6)-(3-iodobenzyl)-5'-N-methylcarboxamidoadenosine, resveratrol, thioguanine, genistein, S-nitroso-N-acetyl-DL-penicillamine, zearalenone, lysophosphatidic acid, Sn50 peptide, roscovitine, actinomycin D, propanil, agar, tamoxifen, acetaminophen, imatinib, tretinoin, mithramycin, ATP, epigallocatechin-gallate, ferric ammonium citrate, acyclic retinoid, L-cysteine, nitroblue tetrazolium, actinomycin d, sodium nitroprusside, 1, 2-dimethylhydrazine, dibutyl phthalate, ornithine, 4-hydroxynonenal, beta-estradiol, 1-alpha, 25-dihydroxy vitamin D3, cyproterone acetate, nimodipine, nitrofurantoin, temsirolimus, 15-deoxy-delta-12, 14-PGJ 2, estrogen, ribonucleic acid, ciprofibrate, alpha-amanitin, SB 216763, bleomycin, forskolin, prednisolone, cyclosporin a, thyroid hormone, tunicamycin, phosphorothioate, suberoylanilide hydroxamic acid, pga2, 3-(4, 5-dimethylthiazol-2-yl)-2, 5-diphenyltetrazolium bromide, benzamide riboside, bisindolylmaleimide, SU6656, prostaglandin E2, depsipeptide, zidovudine, cerivastatin, progesterone, sethoxydim, indomethacin, mg 132, mezerein, pyrrolidine dithiocarbamate, vitamin e succinate, herbimycin a, 5-aza-2'deoxycytidine, lipopolysaccharide, diazoxide, anisomycin, paclitaxel, sodium dodecylsulfate, nilotinib, oxysterol, doxorubicin, lipofectamine, PD98059, steroid, delta-12-pgj2, serine, H-8, N-acetyl-L-cysteine, ethanol, n-(4-hydroxyphenyl)retinamide, tiazofurin, cytarabine, H89, 10-hydroxycamptothecin, everolimus, lactacystin, n(1), n(12)-bis(ethyl)spermine, silibinin, glucocorticoid, butyrate, camptothecin, triamcinolone acetonide, tocotrienol, n-ethylmaleimide, phorbol 12, 13-didecanoate, thapsigargin, deferoxamine, R59949, bryostatin 1, paraffin, romidepsin, vitamin a, docosahexaenoic acid, hydrogen peroxide, droloxifene, saikosaponin, fluoxetine, retinoic acid, n acetylcysteine, dithiothreitol, cordycepin, agarose, 8-bromo-cAMP, D-galactosamine, tachyplesin i, theophylline, metoprolol, SU6657, 15-deoxy-delta-12, 14-prostaglandin j2, dmso, 2-amino-5-azotoluene, cycloheximide |

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman WN "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Diseases that may be treated by the foregoing include, without limitation, infection, inflammation, immune-related disorders or aberrant immune responses.

Diseases with an aberrant or pathologic immune response include, for example, Acquired Immunodeficiency Syndrome (AIDS, which is a viral disease with an autoimmune component), Crohn's disease, systemic lupus erythematosus, ulcerative colitis, multiple sclerosis (MS), inflammatory bowel disease and chronic and acute inflammatory disorders. Examples of inflammatory disorders include asthma, atopic allergy, allergy, eczema, glomerulonephritis, graft vs. host disease.

Administration of a modulating agent to a patient suffering from a disorder or aberrant or condition considered successful if any of a variety of laboratory or clinical objectives is achieved, such as if symptoms associated with the disorder or condition is alleviated, reduced, inhibited or does not progress to a further, i.e., worse, state.

A therapeutically effective amount of an agent relates generally to the amount needed to achieve a therapeutic objective, and will depend on the specificity of agent for its specific target, the rate and route of administration, and the like. Where polypeptide-based agents are used, the smallest fragment that specifically binds to the target and retains therapeutic function is preferred. Such fragments can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other.

The invention having now been described by way of written description, those of skill in the art will recognize that the invention can be practiced in a variety of embodiments and that the foregoing description and examples below are for purposes of illustration and not limitation of the claims that follow.

Although the present invention and its advantages have been described in detail, it should be understood that various changes, substitutions and alterations can be made herein without departing from the spirit and scope of the invention as defined in the appended claims.

The invention is further described in the following examples, which do not limit the scope of the invention described in the claims.

EXAMPLES

Example 1—A Single-Cell Atlas Identifies all Known Populations of Epithelial Cells in the Small Intestine Here, Applicants performed an scRNA-seq survey of 53,193 epithelial cells of the small intestine (SI) in homeostasis and during infection. Applicants identified gene signatures, key transcription factors (TFs) and specific G protein-coupled receptors (GPCRs) for each major small intestinal differentiated cell type. Applicants distinguished proximal and distal enterocytes and their stem cells, established a novel classification of different enteroendocrine subtypes, and identified previously unrecognized heterogeneity within both Paneth and tuft cells. Finally, Applicants demonstrated how these cell types and states adaptively change is response to different infections.

Applicants profiled a total of 53,193 individual cells across this study (Table 2). Applicants estimated the required cell numbers using a general statistical model based on the negative binomial distribution for random sampling (Methods). There are seven known cell-types in the intestinal epithelium, and in order to provide an unbiased estimate, Applicants arbitrarily allow for as many as twice this number. The statistical framework suggested that to achieve a 99% probability of sampling at least 50 cells from each of 14 expected cell types, where the rarest cell type is present at a fraction of 1%, Applicants needed to sequence 7,500 cells (Methods).

TABLE 2

| Dataset | Number of cells | Single-cell platform |
|---|---|---|
| Atlas (droplet) | 7216 | 3'-droplet |
| Atlas (plate) | 1522 | Full-length plate |
| Infection models (10X) | 9842 | 3'-droplet |
| Salmonella infection | 2,029 | 3'-droplet |
| Infection models (SS2) | 389 | Full-length plate |
| RANKL-treated organoids | 5434 | 3'-droplet |
| Follicle-associated epithelium (FAE) | 4700 | 3'-droplet |
| Spatial regions | 11665 | 3'-droplet |
| Paneth cell enrichment | 10396 | 3'-droplet |
| Total | 53193 | |

Figure 7A:
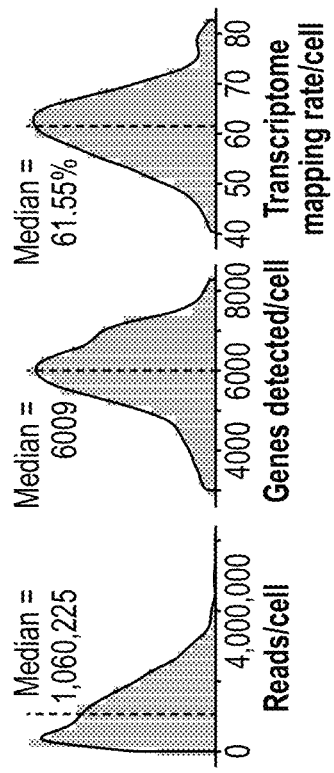

Applicants used droplet-based massively-parallel single cell RNA-Seq[24] (Methods) to transcriptionally profile EpCAM$^+$ epithelial cells from the small intestine of C57BL/6 wild-type and Lgr5-GFP knock-in mice[6] (FIG. 1a). Applicants measured 8,882 single-cell profiles, removed 1,402 low quality cells (<800 genes detected; Methods) and 264 contaminating immune cells (Methods), retaining 7,216 cells for all subsequent analyses (median 42,697 transcripts per cell, median 1,659 genes detected per cell; FIG. 7a), with excellent reproducibility between replicates (n=6 mice, mean r=0.95, FIG. 7c-f).

Unsupervised clustering of the data partitioned the cells into 15 distinct groups. First, Applicants built a k-nearest neighbor graph on a low-dimensional representation of the cellular expression data using principal component analysis (PCA), and partitioned this graph into 15 discrete clusters using the Infomap algorithm[25,26], each comprising transcriptionally similar cells (Methods). The clusters, each of which contained cells from all mice and replicate experiments (FIG. 7c,g), were visualized using t-stochastic neighborhood embedding[26-28] (tSNE) (FIG. 1b).

Figure 1B:
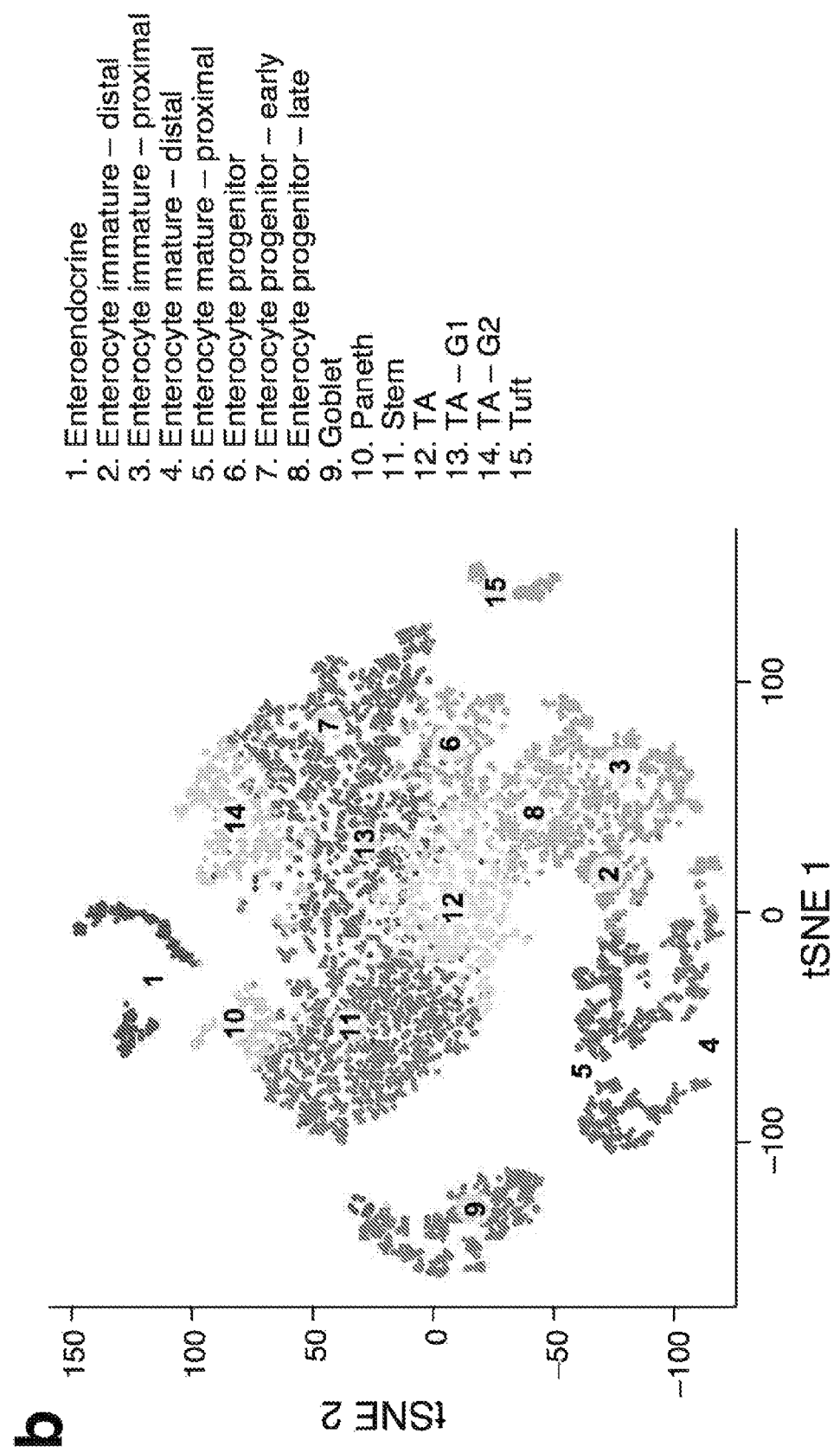

Applicants labeled the 15 clusters post hoc based on the expression of signatures of known marker genes (7 FIGS. 7g and 7h), showing that each is associated with a distinct cell type or state, including the major post-mitotic cell-types: enterocyte, goblet, Paneth, enteroendocrine and tuft cells (FIG. 1b). Applicants scored proliferating cells with a cell-cycle signature that Applicants previously developed from single-cell profiles[29] to distinguish between dividing stem or progenitor cells and fully differentiated, post-mitotic cells. To enrich for M cells, found only above Peyer's patches, Applicants isolated and analyzed the follicle associated epithelium (FAE) in a separate set of experiments (below). The enteroendocrine, Paneth, goblet, stem and tuft cells were each represented by a single (1:1 matching) cluster (FIG. 1b and FIGS. 7g and 7h). While the term 'enterocytes' is occasionally used to refer to all intestinal epithelial cells, in this study Applicants use the term to refer exclusively to absorptive enterocytes, which are the most abundant cell type in the intestinal epithelium[1]. This subset of cells was partitioned across seven clusters representing distinct stages of maturation (FIG. 1b, FIGS. 7g and 7h). Of note, a recent study[30] identified the same major cell-type clusters of IECs without these distinctions between various stages of enterocyte differentiation. The proportions of common differentiated IEC types, such as goblet cells (7.1%) and enterocyte (44.6%), were consistent with their expected abundances given the crypt-enriched isolation protocol Applicants used (Methods, FIG. 7d), with the exception of Paneth cells, which were under-represented in the data (3.6% compared to the expected 5%[31]). Conversely, the proportions of enteroendocrine and tuft cells were 4.3% and 2.3%, respectively, significantly higher than current estimates[11,12,14]. To improve Paneth cell capture, Applicants devised a sorting strategy to better capture large cells. Profiling an additional 10,396 epithelial cells identified 1,449 Paneth cells (13.9%) in two distinct clusters (FIG. 10N), but no additional novel cell-types. Applicants thus expect that all cell-types with >0.75% prevalence were detected in the survey at 99% confidence.

Figure 2A:
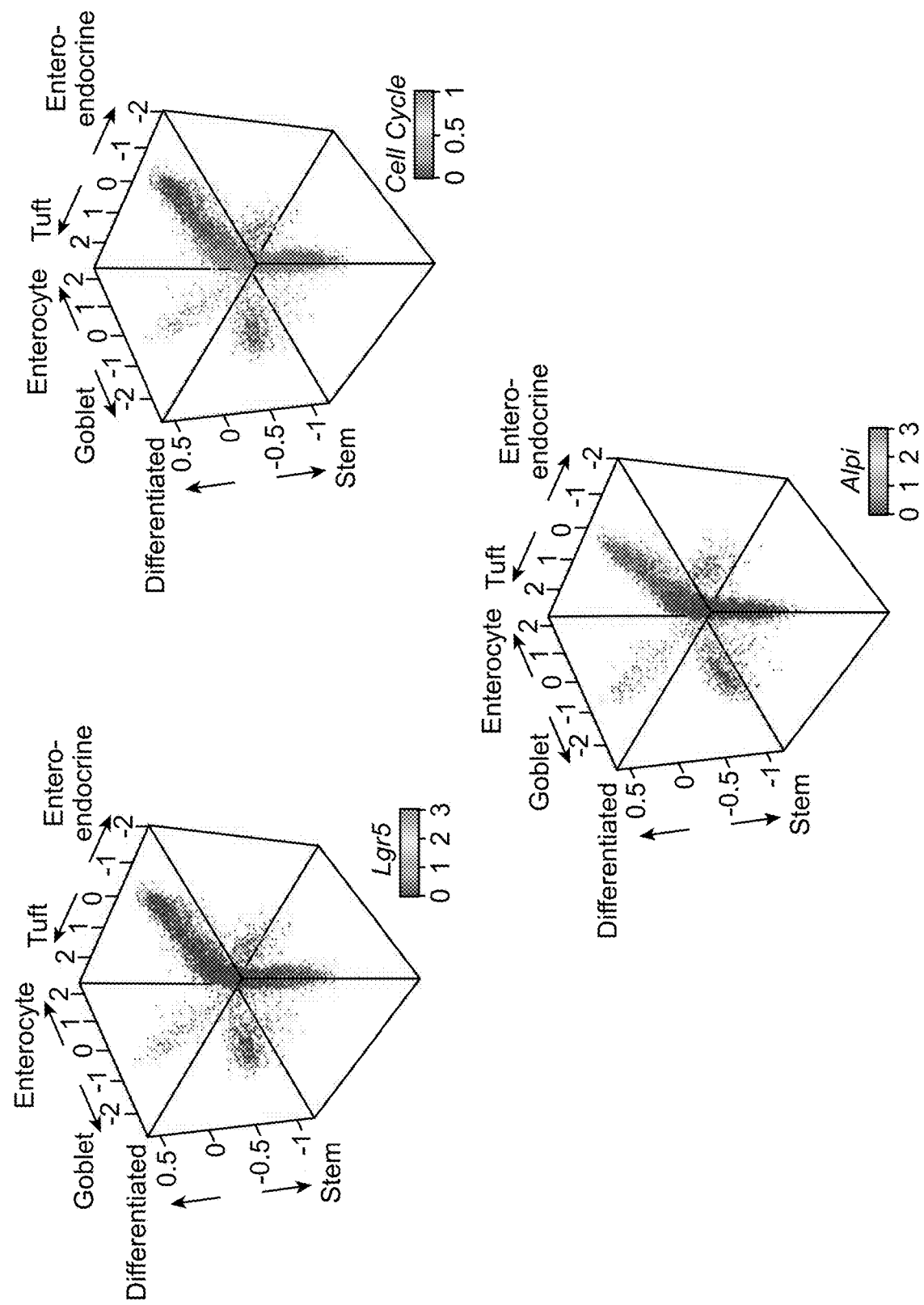
FIG. 2A-2F—Differentiation from stem cells to mature enterocytes.
Figure 2B:
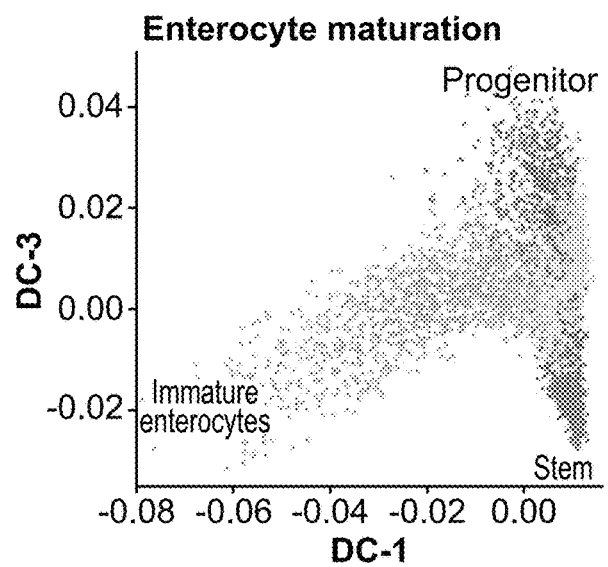
Figure 2C:
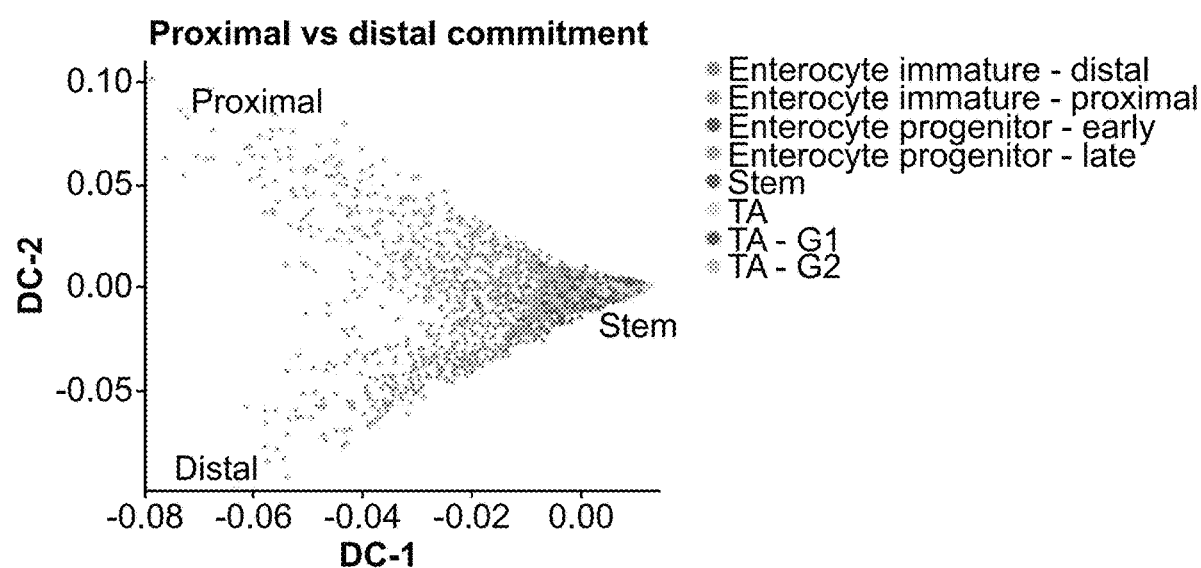
Figure 7B:
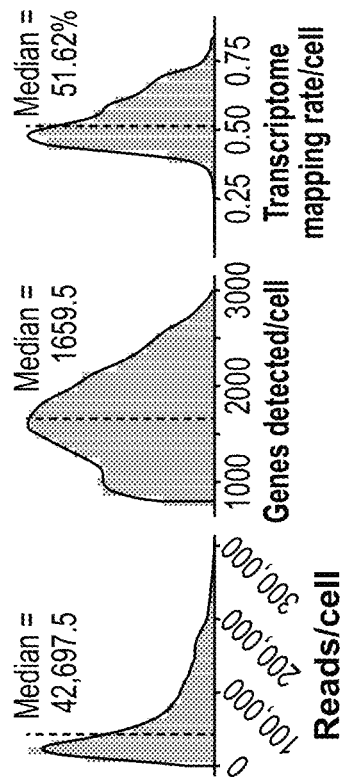
Figure 7C:
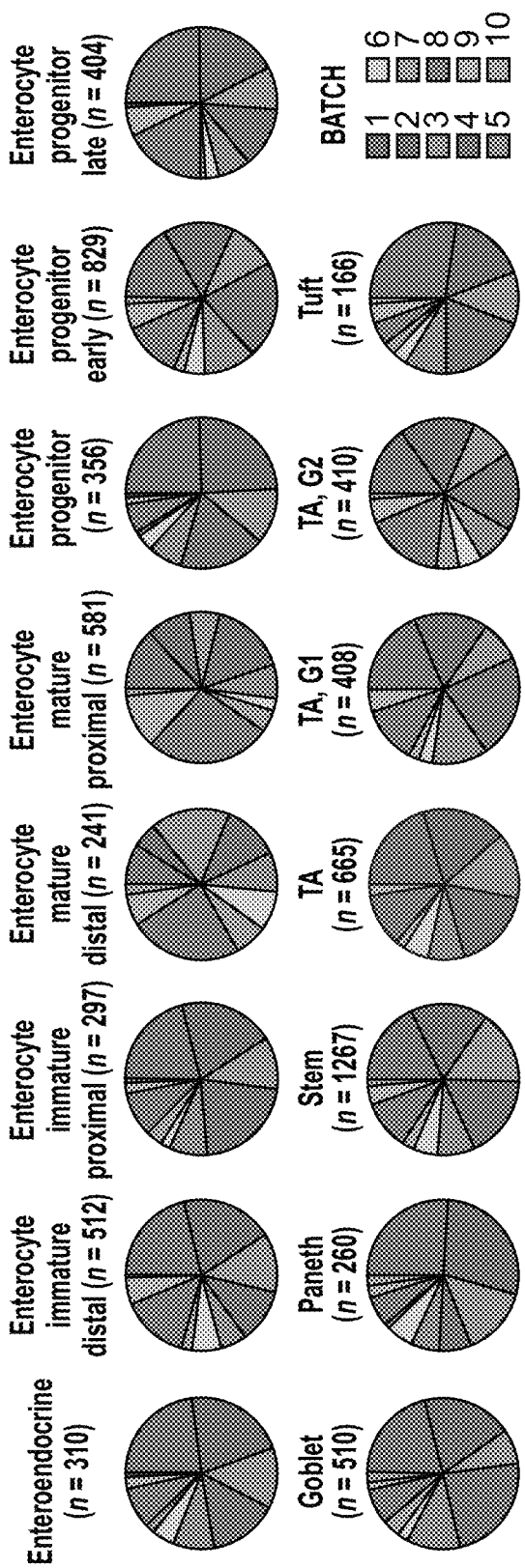
Figure 7D:
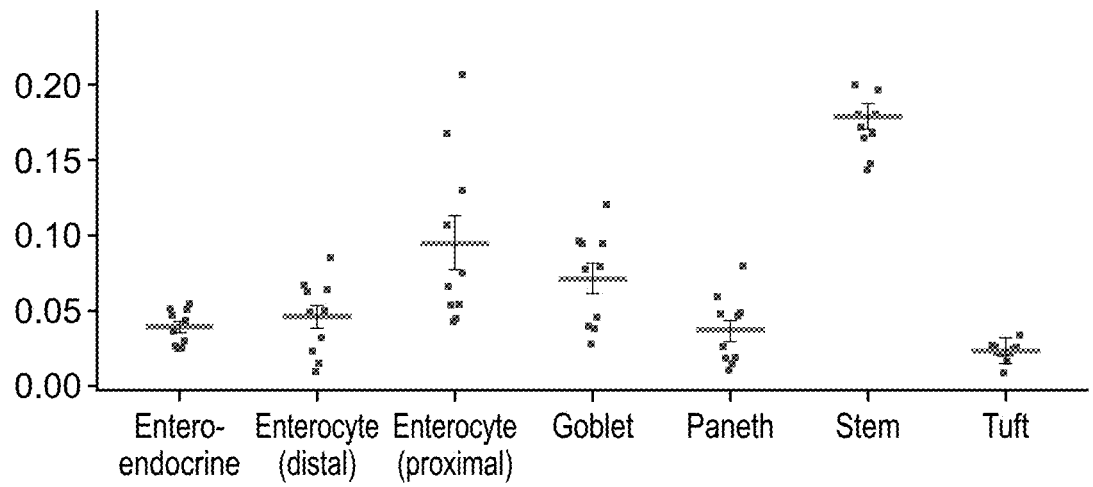
Figure 7E:
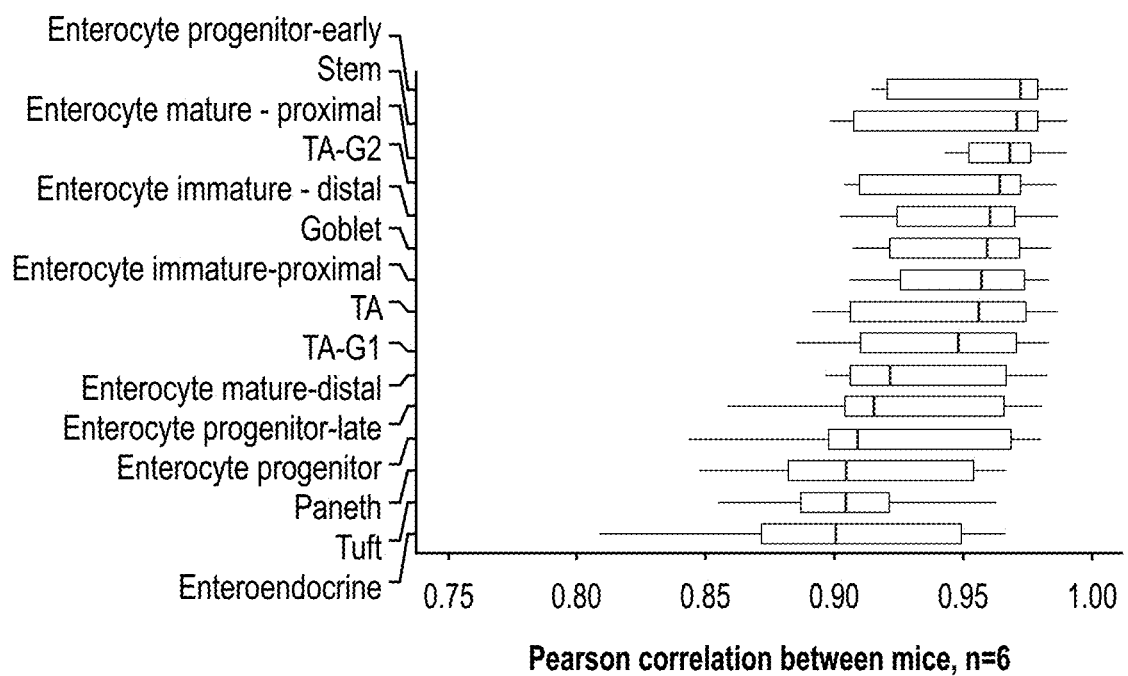
Figure 7H:
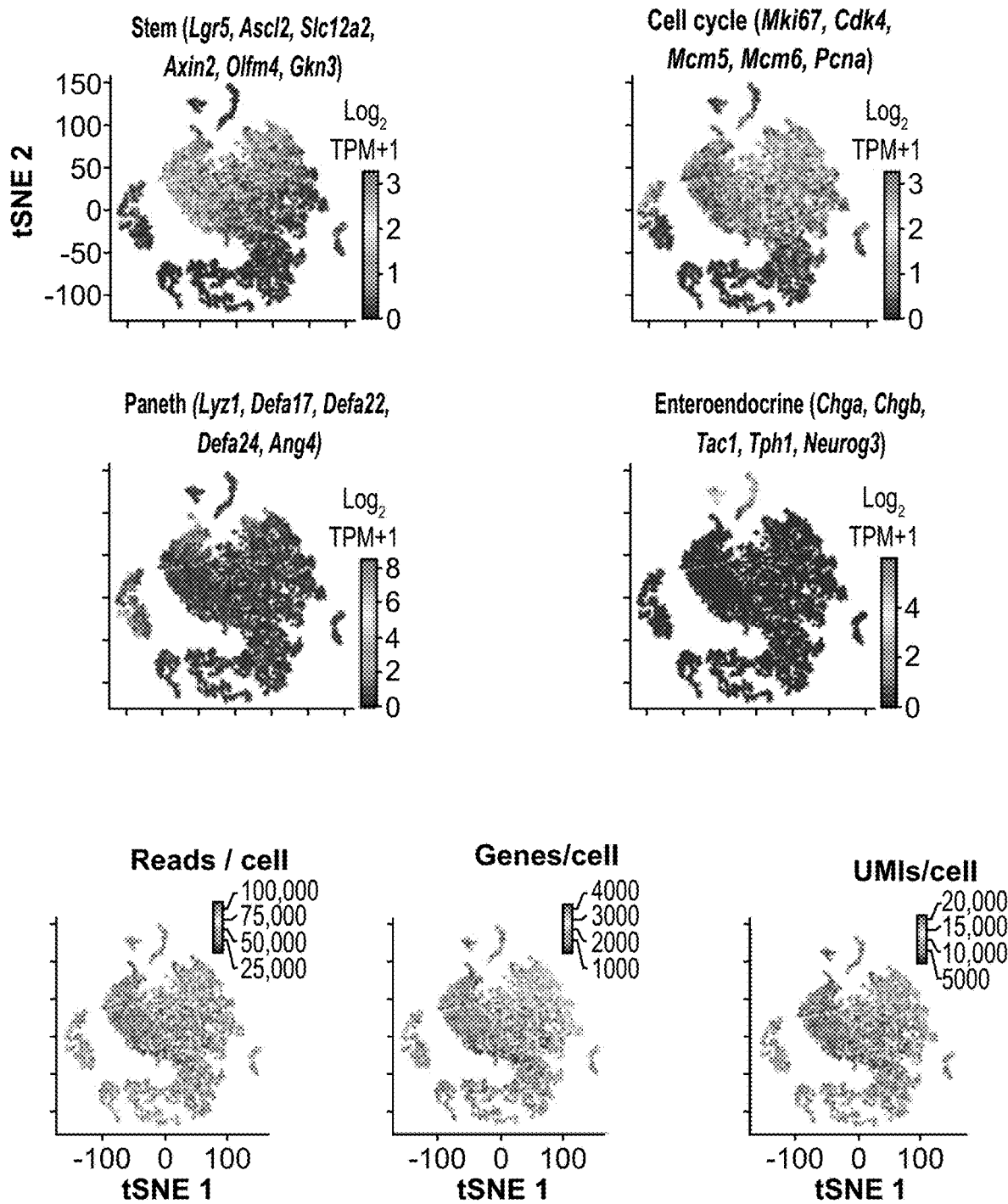

Applicants validated the atlas by independently profiling single epithelial cells that were sorted by FACS followed by an established full-length scRNA-seq protocol[32] (FIG. 1a and FIGS. 7b and 2a). Applicants profiled 1,853 single cells, filtered isolated immune cells and lower quality cells (<3,000 genes per cell; Methods), and retained a high-quality subset of 1,522 single cells for analysis, with high reproducibility across mice (n=10 mice, FIGS. 8a and 8b). The measured cell profiles had much higher coverage (median 1.06 million reads per cell, median of 6,009 genes per cell; FIG. 7b). The same clustering procedure (using the 15 significant PCs in this data; Methods) identified 8 clusters, and overall recapitulated the same post-mitotic cluster groups (FIG. 8a and 8b), but without finer distinctions by maturity and location among the enterocytes (below), as expected given the much smaller cell number. This highlights the importance of collecting a large number of scRNA-seq profiles to make finer distinctions[26].

Figure 1C:
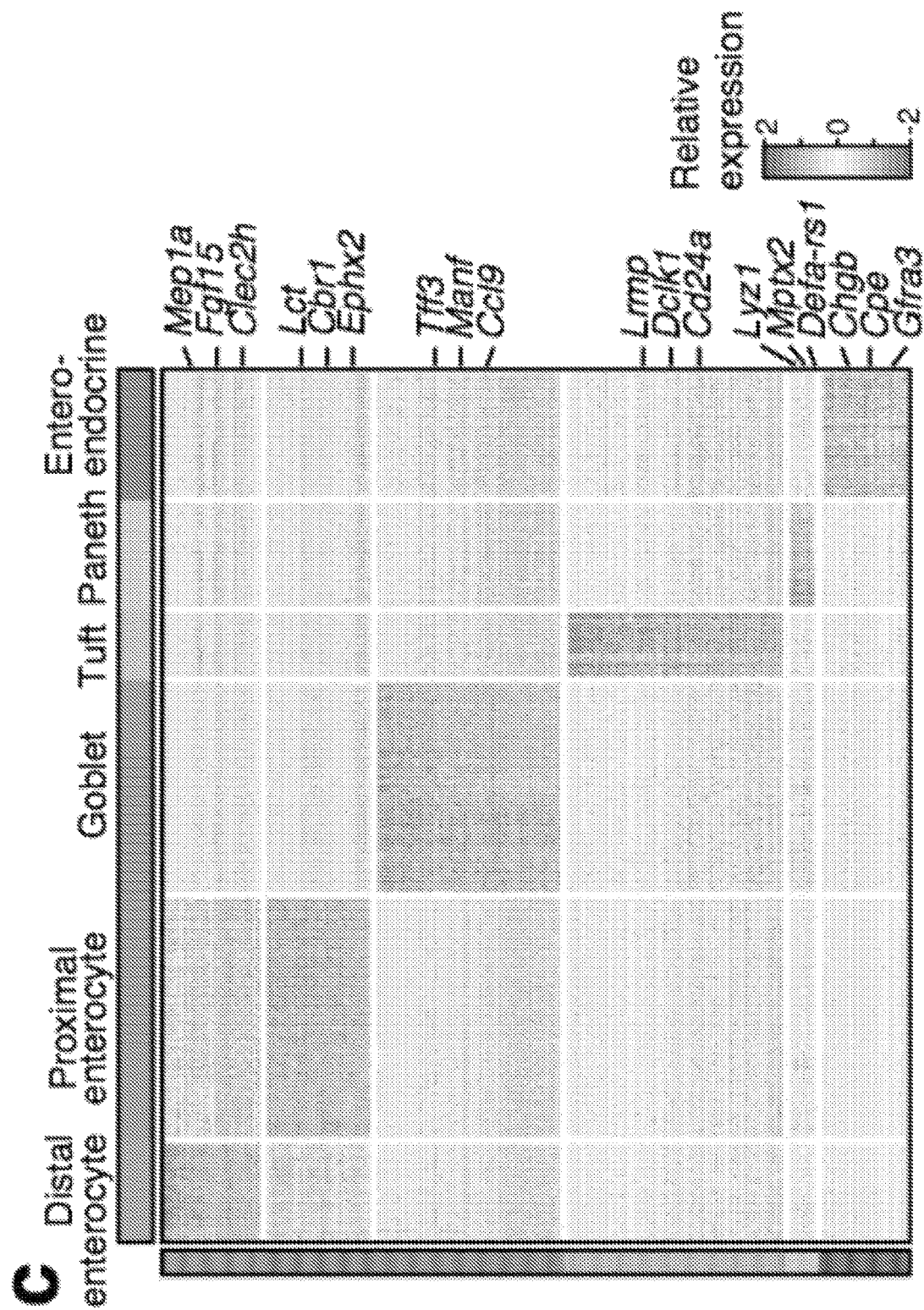
Figure 8A:
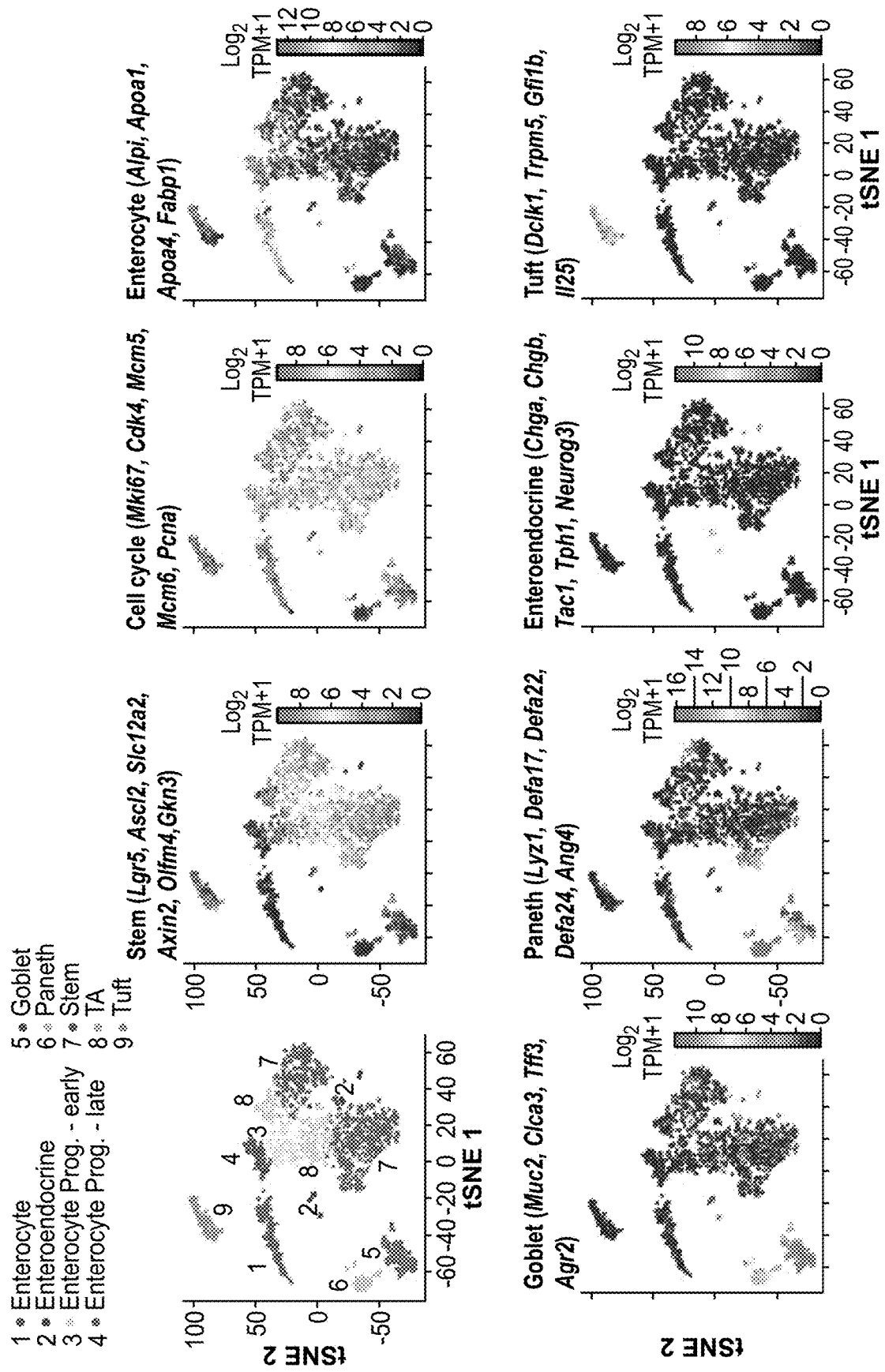
FIG. 8A-8I—Identification and characterization of intestinal epithelial cell-types in plate-based full-length scRNA-seq data by unsupervised clustering, related to FIG. 1.
Figure 8B:
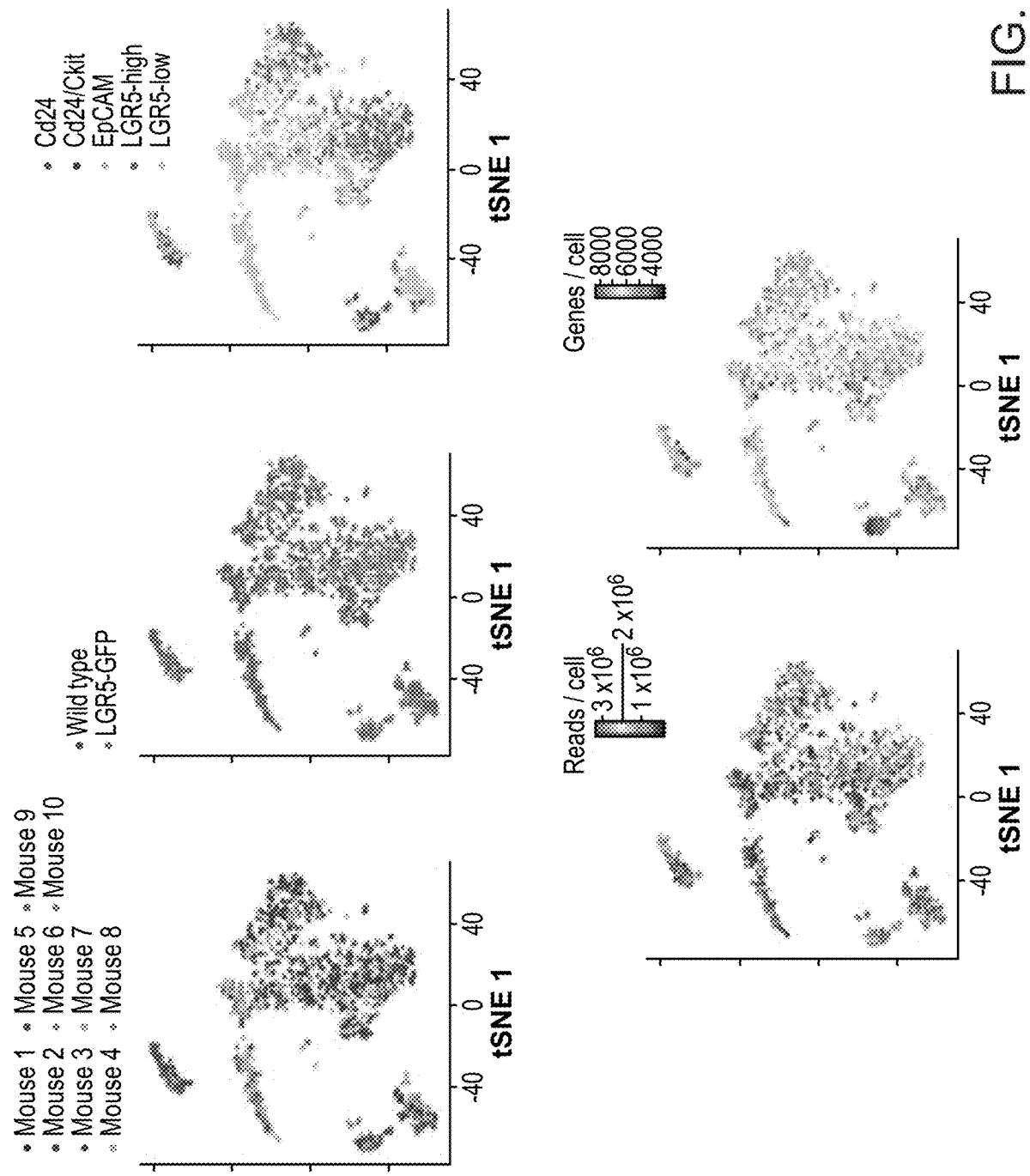
Figure 8C:
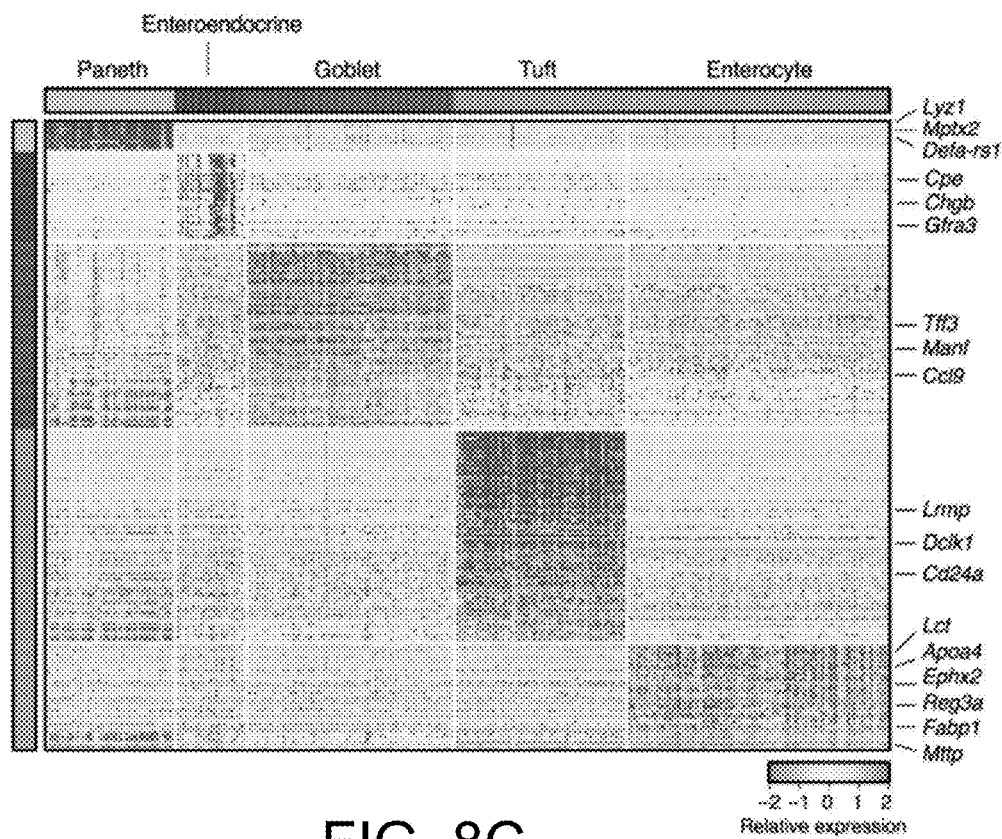
Figure 8D:
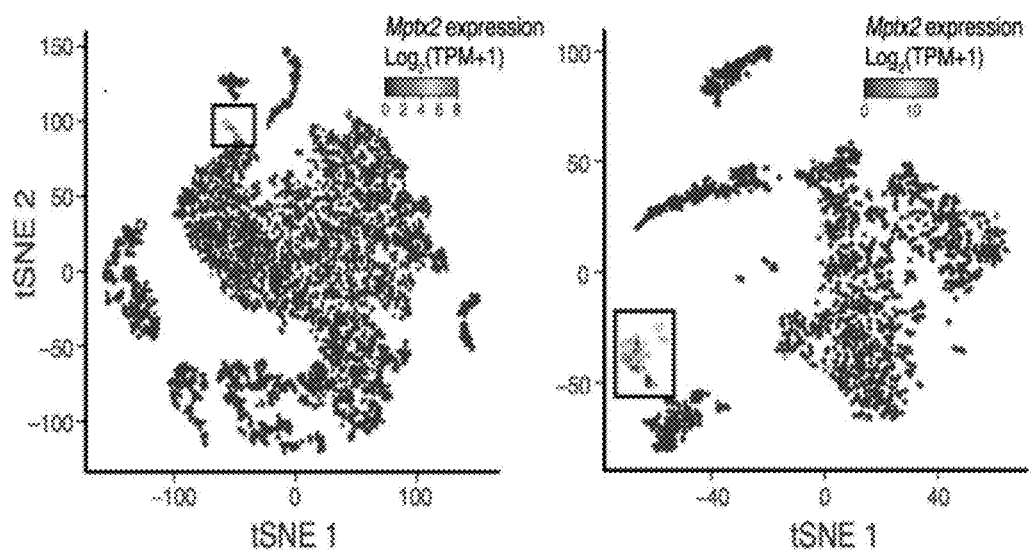
Figure 8E:
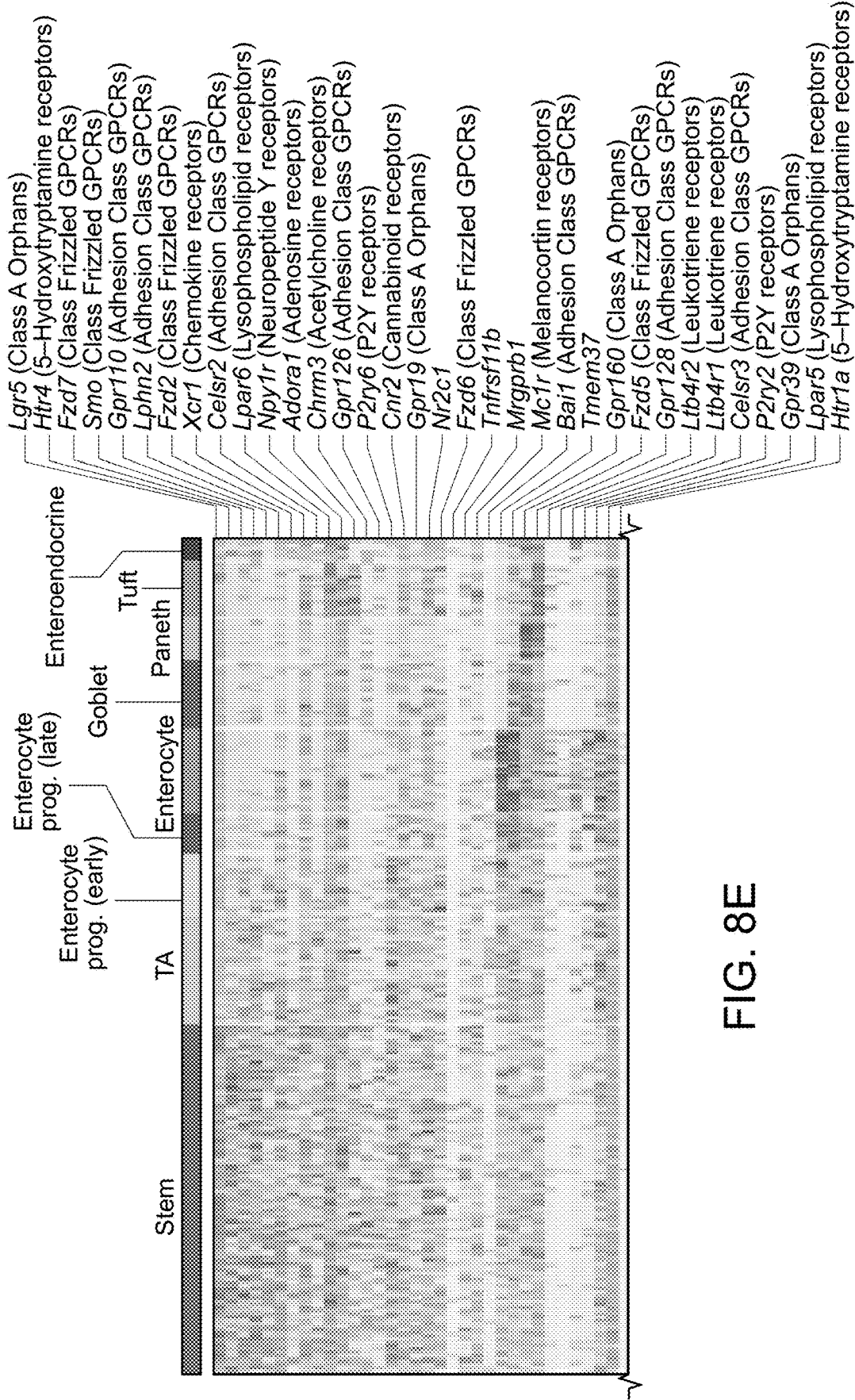
Figure 8F:
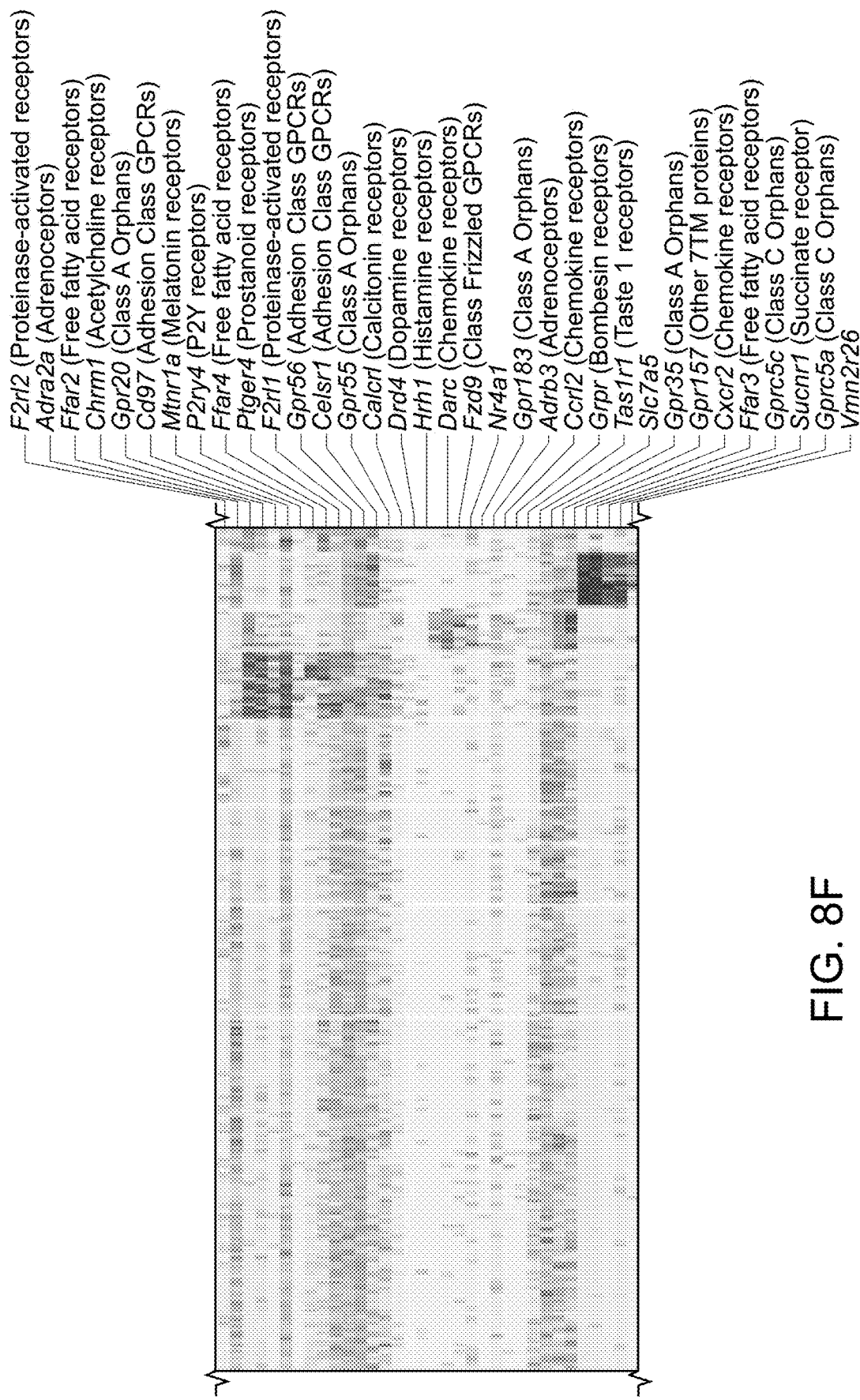
Figure 8G:
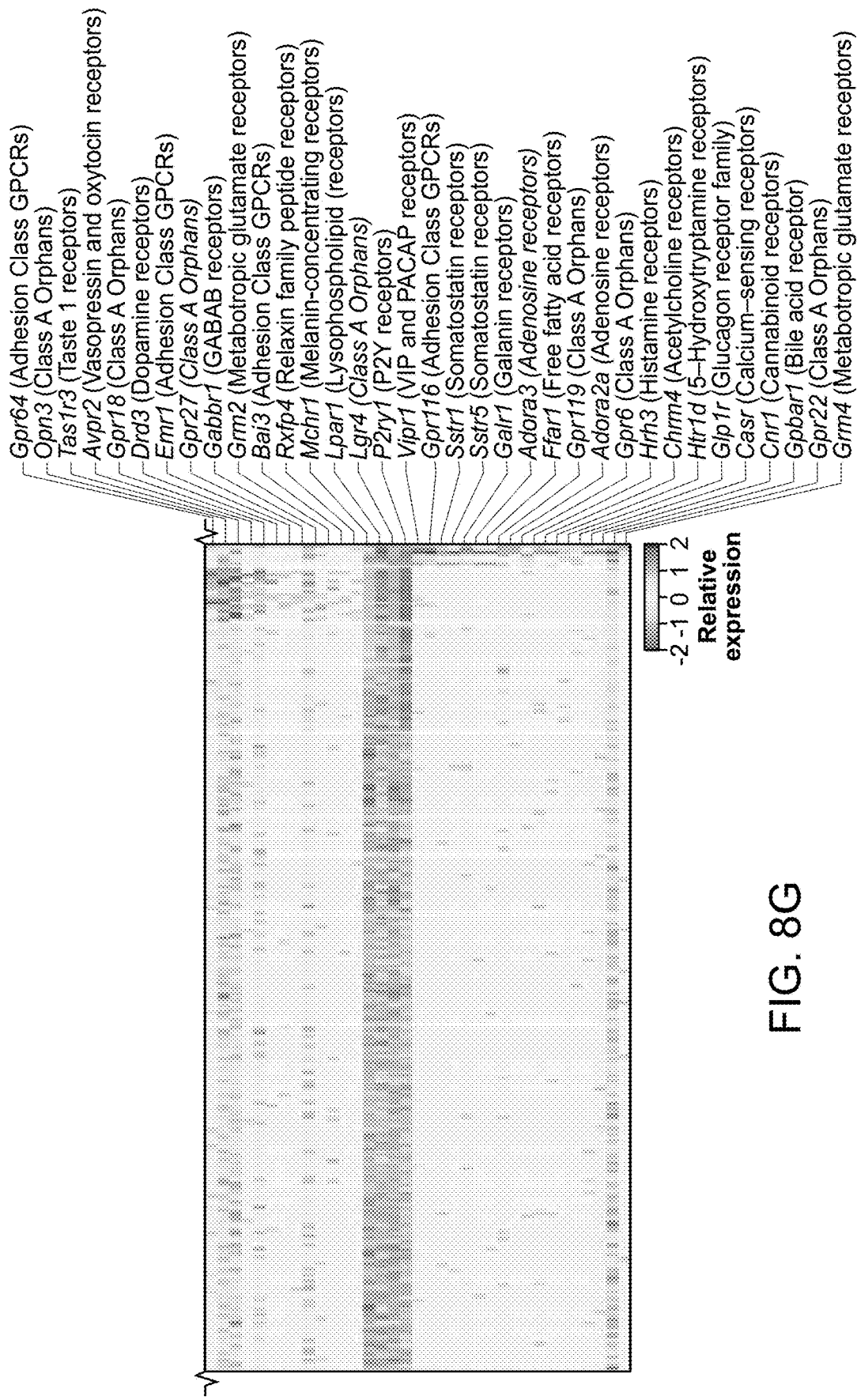
Figure 10G:
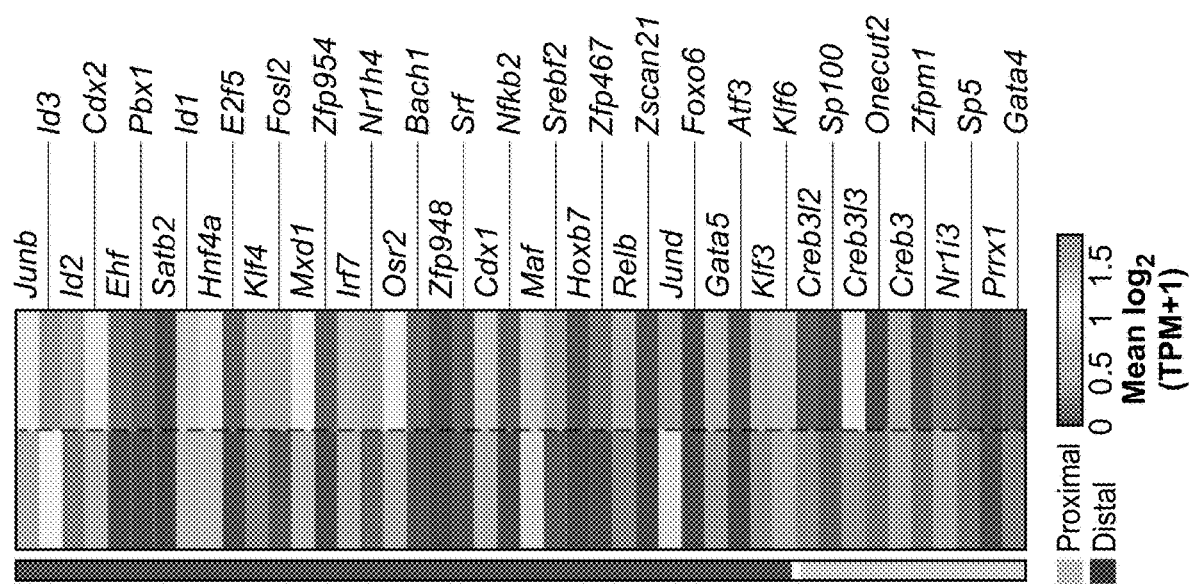
FIG. 10g. TF genes differentially expressed between proximal and distal cell fate. Heatmap shows the mean expression level (color bar) of 44 TFs differentially expressed between the proximal and distal (color legend) enterocyte clusters of FIG. 1b (FDR<0.05, Mann-Whitney U-test).
Figure 10H:
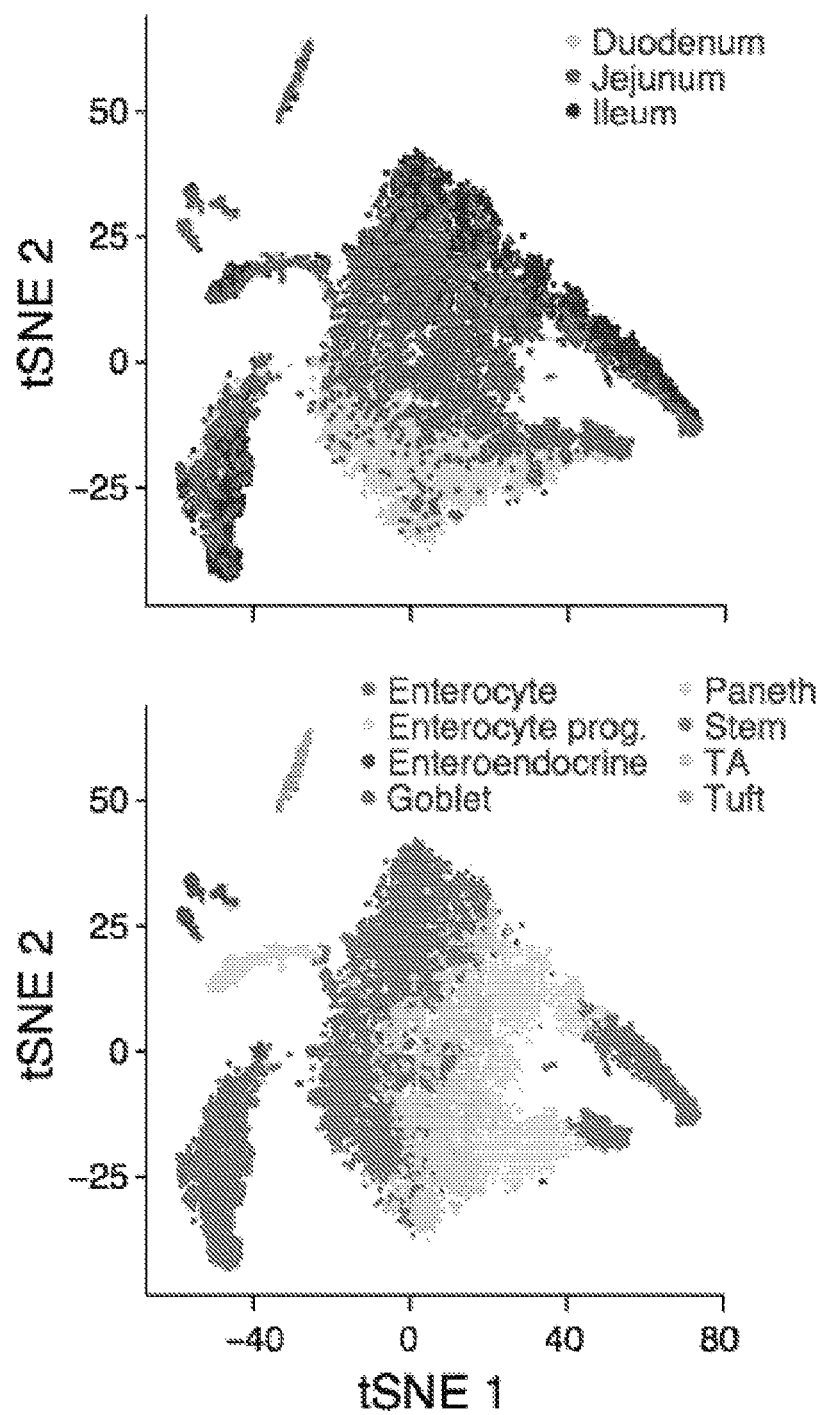
FIG. 10h. Single-cell profiles from regional sites of the small intestine. tSNE embedding of 11,665 single cells extracted from three regions of the small intestine (duodenum, jejunum and ileum), colored by the region of origin (top, color legend) or their assignment to cell-type by unsupervised clustering (bottom, color legend). n=2 mice.
Figure 10I:
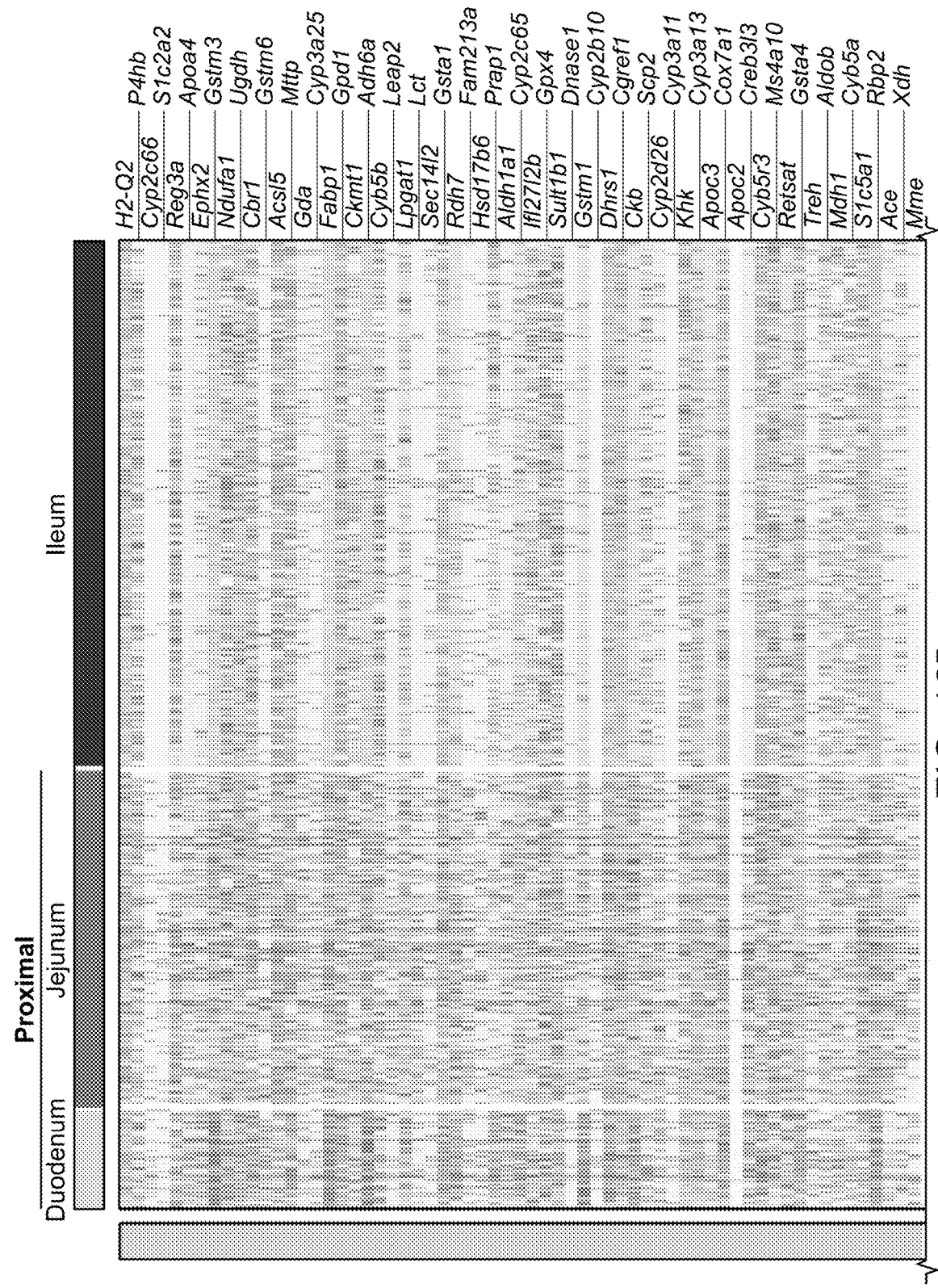
Figure 10J:
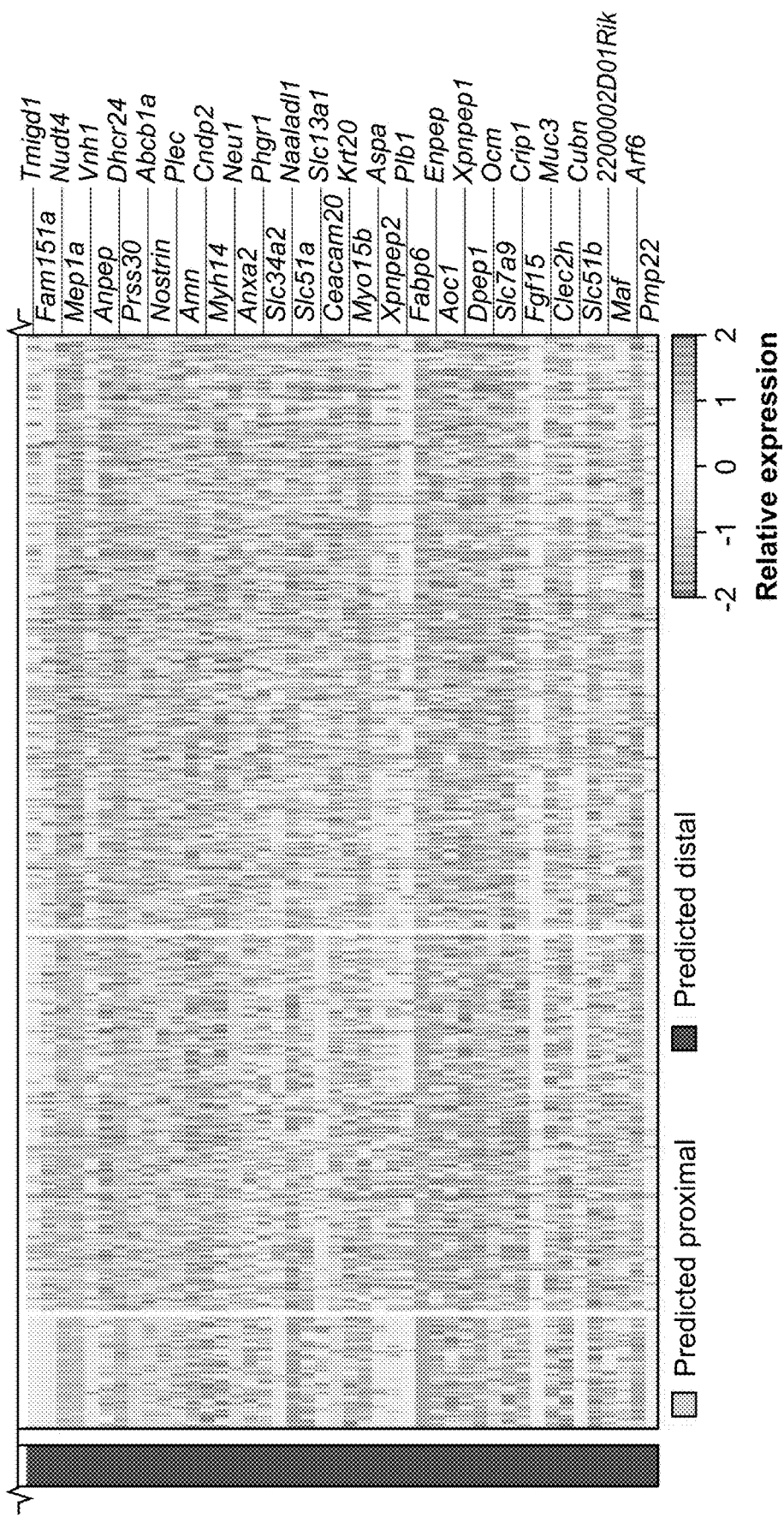
FIGS. 10l and 10j. Validation of predicted regional markers. Heatmap shows the expression level (row-wise Z-score, color bar) in each of the 1,041 enterocytes (columns) analyzed from three regions of the small intestine (duodenum, jejunum and ileum; color bar, top) of 108 genes (rows) predicted to be markers of proximal (light grey) and distal (dark grey) enterocytes (color bar, left) using unsupervised cluster analysis (FIG. 1b,c).
Figure 10K:
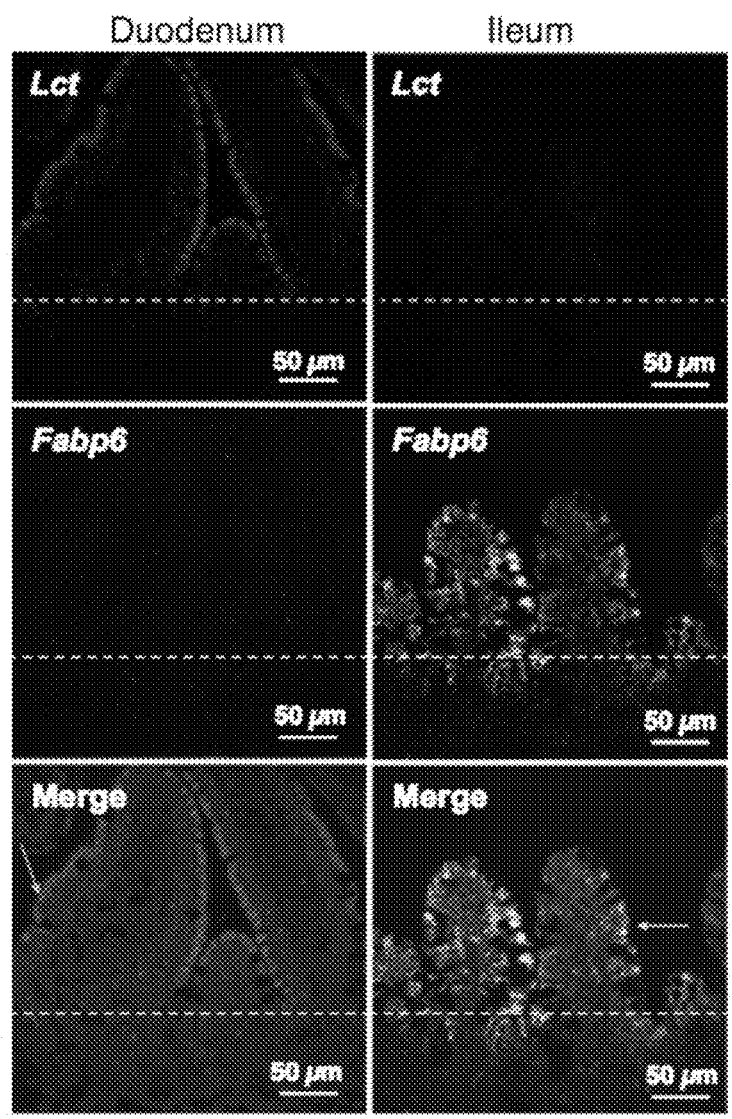
FIG. 10k. Validation of proximal and distal enterocyte markers. smFISH of Lct (red) and Fabp6 (white) in the duodenum (proximal small intestine, top) and the ileum (distal small intestine, bottom). Dotted line indicates the boundary between the crypt region (below) and the villi (above). Scale bar, 50 μm.
Figure 10L:
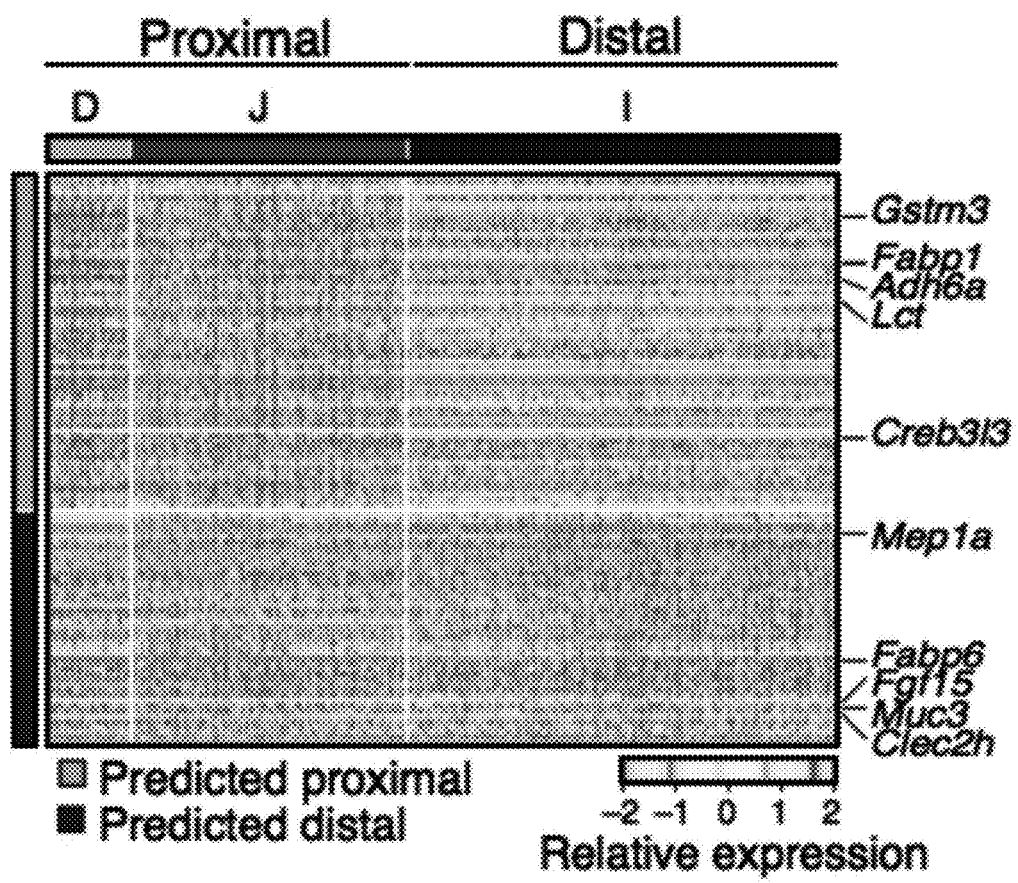
Figure 10M:
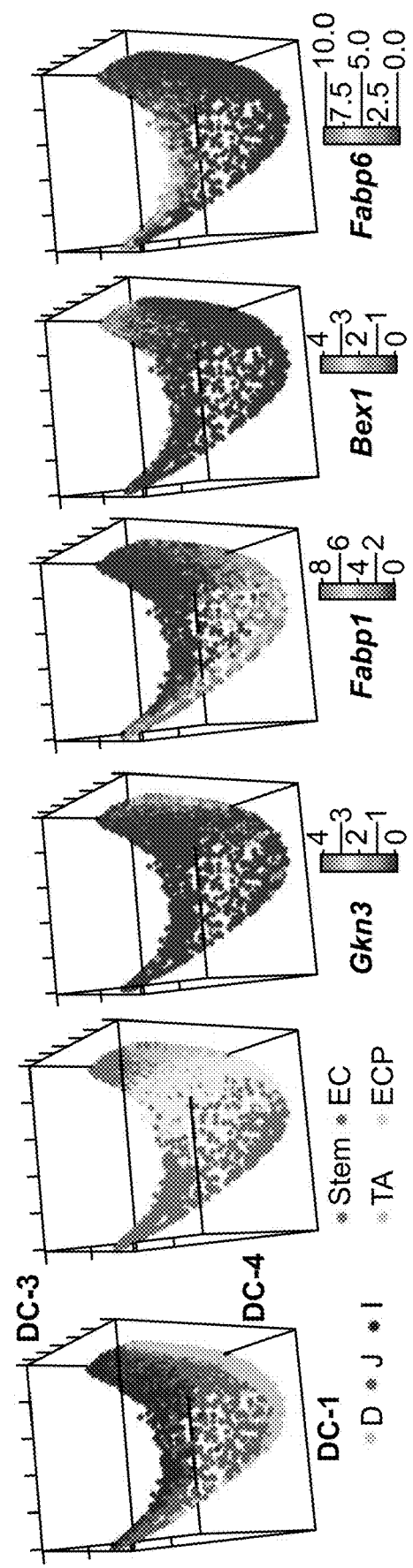
FIG. 10m. Regional differences in ISC differentiation. Diffusion-map embedding of 8,988 cells colored by region (left), cluster (center left), or expression of novel regional markers of ISCs (Gkn3, Bex1) or enterocytes (Fabp1, Fabp6).
Figure 10N:
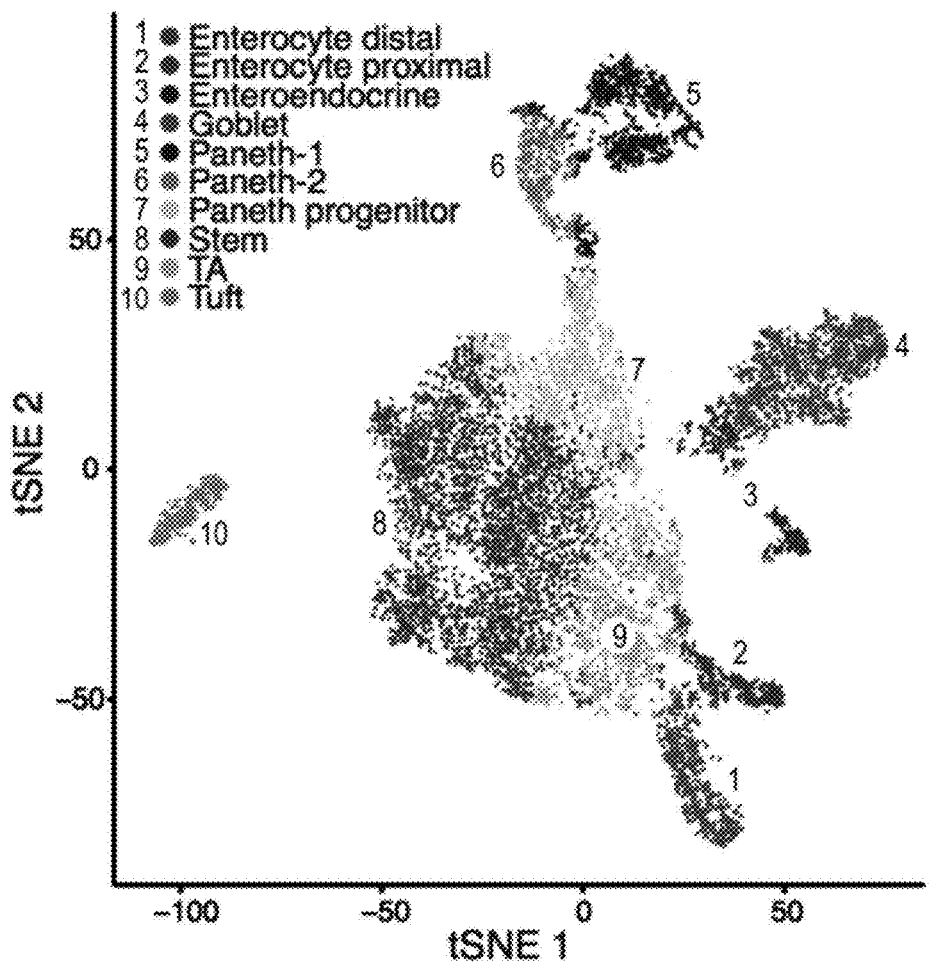
FIG. 10n-FIG. 10q. Regional variation in Paneth cell sub-types and stem cell markers.
Figure 10O:
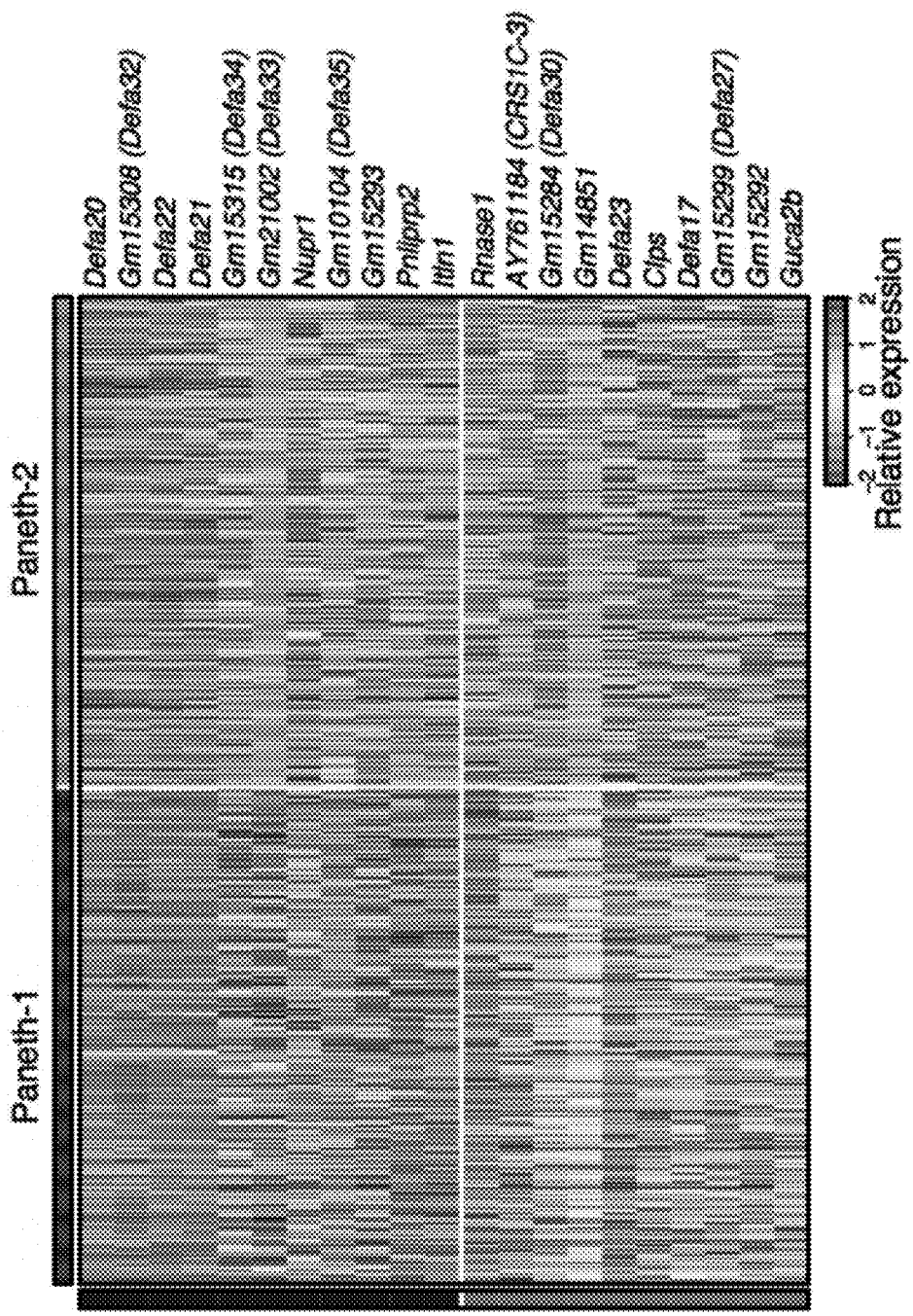

Example 2—Distinct Cell Types are Characterized by Specific Signatures, TFs and Receptors Relying on the high congruence between the two approaches, Applicants defined high-confidence consensus expression signatures for each cell type (Methods), highlighting known markers (corroborating the labels) and novel ones suggesting specific functions (FIG. 1c, FIG. 8c and Tables 3-5). For example, the Paneth cell consensus signature identified Mptx2, a mucosal pentraxin, with unknown function[33], (FIG. 1c, FIGS. 8c and 8d, Table 5), which Applicants validated using single-molecule fluorescence in situ hybridization (smFISH, Methods) (FIG. 1d,e). From the deeper, full length RNA-seq dataset, Applicants also identified Mptx1, another mucosal pentraxin, as specific to Paneth cells (FDR<0.001, Mann-Whitney U-test, Table 4). Other Pentraxins include C reactive protein (CRP) and serum amyloid P component protein (SAP), secreted proteins that play a role in host defense against pathogenic bacteria[34]. In addition, the two Paneth cell subsets expressed distinct panels of anti-microbial alpha-defensins (FIG. 10o).

TABLE 3

Marker genes (3' droplet-based data) for intestinal epithelial cell-types

| Enteroendocrine | Enterocyte Immature Distal | Enterocyte Immature Proximal | Enterocyte Mature Distal | Enterocyte Mature Proximal | Goblet | Paneth | Stem | TA (G2) | Tuft |
|---|---|---|---|---|---|---|---|---|---|
| ChRb | Reg3g | Casp6 | Tmigd1 | Apoa4 | Agr2 | Gm15284 | Gkn3 | Stmn1 | Lrmp |
| Chga | Gsdmc4 | | Fabp6 | Fabp1 | Spink4 | Gm14851 | | Tubb5 | Alox5ap |
| Gfra3 | Prss32 | | Slc51b | Apoc2 | Fcgbp | Defa21 | | | Rgs13 |
| Cpe | Krt8 | | Slc51a | Rbp2 | Tff3 | Defa22 | | | Sh2d6 |
| Tac1 | | | Mep1a | Apoc3 | Muc2 | AY761184 | | | Ltc4s |
| Fam183b | | | Fam151a | Leap2 | Zg16 | Defa24 | | | Avil |
| Hmgn3 | | | Naaladl1 | Cyp2b10 | Clca1 | Defa17 | | | Hck |
| Cck | | | Slc34a2 | Cyp3a11 | Ccl6 | Lyz1 | | | Dclk1 |
| Fev | | | Plb1 | Lct | Klk1 | Defa-rs1 | | | Snrnp25 |
| Gch1 | | | Nudt4 | Gsta1 | Tpsg1 | Defa3 | | | Cd24a |
| Pcsk1n | | | Dpep1 | Gstm1 | Ccl9 | Mptx2 | | | Trpm5 |
| Bex2 | | | Pmp22 | Gstm3 | Txndc5 | Ang4 | | | Kctd12 |
| Neurog3 | | | Xpnpep2 | Ephx2 | Smim14_EN-SMUSG0000-0037822 | Defa26 | | | Aldh2 |
| Ngfrap1 | | | Muc3 | Ms4a10 | Tspan13 | Gm15292 | | | Il13ra1 |
| Vwa5b2 | | | Neu1 | Fam213a | Atoh1 | | | | Gng13 |
| Resp18 | | | Clec2h | Cbr1 | Lrrc26 | | | | Tmem176a |
| Sct | | | Phgr1 | Adh6a | Ramp1 | | | | Skap2 |
| Aplp1 | | | 2200002D01Rik | Cyb5r3 | Galnt12 | | | | Ptpn6 |
| Scgn | | | Prss30 | Dhrs1 | Mmp7 | | | | Ly6g6f |
| Neurod1 | | | Cubn | Ifi27l2b | Qsox1 | | | | Fyb |
| Nkx2-2 | | | Plec | Cyb5a | Fkbp11 | | | | Adh1 |
| Insm1 | | | Fgf15 | Cyp3a25 | Rep15 | | | | Tmem176b |
| Vim | | | Crip1 | Gda | Tmsb10 | | | | Hpgds |
| Rbp4 | | | Krt20 | Ckb | Pla2g10 | | | | Reep5 |
| Isl1 | | | Dhcr24 | Prap1 | Tsta3 | | | | Ptpn18 |
| Ddc | | | Myo15b | Cgref1 | Pdia6 | | | | Spib |
| Mtch1 | | | Amn | Dnase1 | Sdf2l1 | | | | Bpgm |
| Tph1 | | | Enpep | Aldh1a1 | S100a6 | | | | Galk1 |
| Cldn4 | | | Anpep | Khk | Manf | | | | Matk |
| Scg5 | | | Slc7a9 | Lpgat1 | Slc12a8 | | | | Tuba1a |
| Maged1 | | | Ocm | Treh | Creb3l1 | | | | 1810046K07Rik |
| Rprml | | | Anxa2 | Reg3a | Sh3bgrl3 | | | | Hmx2 |
| Cryba2 | | | Aoc1 | Acsl5 | Spdef | | | | Ccdc28b |
| Rph3al | | | Ceacam20 | Ace | Tpd52 | | | | Ethe1 |
| Celf3 | | | Arf6 | Aldob | Pdia5 | | | | Limd2 |
| Cacna1a | | | Abcb1a | H2-Q2 | Cmpk1 | | | | Sh2d7 |
| Trp53i11 | | | Xpnpep1 | Rdh7 | Serp1 | | | | Ccdc109b |
| Gpx3 | | | Vnn1 | Ckmt1 | Tmed3 | | | | Tspan6 |

TABLE 3-continued

Marker genes (3' droplet-based data) for intestinal epithelial cell-types

| Enteroendocrine | Enterocyte Immature Distal | Enterocyte Immature Proximal | Enterocyte Mature Distal | Enterocyte Mature Proximal | Goblet | Paneth | Stem | TA (G2) | Tuft |
|---|---|---|---|---|---|---|---|---|---|
| Pcsk1 | | | Cndp2 | Cyp3a13 | Selm | | | | Smpx |
| Fabp5 | | | Nostrin | P4hb | Creb3l4 | | | | Vav1 |
| Fxyd6 | | | Slc13a1 | Mdh1 | Smim6 | | | | Ly6g6d |
| Cplx2 | | | Aspa | Ppap2a | Krtcap2 | | | | Pik3r5 |
| Cdkn1c | | | Maf | Slc2a2 | Bace2 | | | | Nebl |
| Rundc3a | | | Myh14 | Cox7a1 | Stard3nl | | | | Plcg2 |
| Pycr2 | | | | Sec14l2 | Bcas1 | | | | Rbm38 |
| Myl7 | | | | Gsta4 | Nans | | | | Vdac3 |
| Ffar2 | | | | Mme | C1galt1c1 | | | | Krt18 |
| Prnp | | | | Retsat | Xbp1 | | | | Asah1 |
| Rimbp2 | | | | Mttp | Hpd | | | | Cd47 |
| Slc25a4 | | | | Creb3l3 | Slc50a1 | | | | Krt23 |
| Bambi | | | | Slc5a1 | Guk1 | | | | Bcl2l14 |
| Itm2c | | | | Sult1b1 | Tmed9 | | | | Lima1 |
| Cacna2d1 | | | | Hsd17b6 | Ssr4 | | | | Pygl |
| Fgd2 | | | | Scp2 | Hgfac | | | | Itpr2 |
| Gadd45a | | | | Cyb5b | Ostc | | | | Inpp5j |
| Cited2 | | | | Cyp2c65 | Creld2 | | | | Pea15a |
| Olfm1 | | | | Gpx4 | Sec61b | | | | Rac2 |
| Slc39a2 | | | | Xdh | Gale | | | | Pou2f3 |
| Ptov1 | | | | Cyp2d26 | Kdelr2 | | | | Atp2a3 |
| Rab3c | | | | Ugdh | Ssr2 | | | | Bmx |
| Tox3 | | | | Gstm6 | Ern2 | | | | Acot7 |
| Cdkn1a | | | | Ndufa1 | Ergic1 | | | | Gnai2 |
| Anxa6 | | | | Gpd1 | AW112010 | | | | Alox5 |
| Krt7 | | | | Cyp2c66 | Gcnt3 | | | | Ppp3ca |
| Btg2 | | | | | Guca2a | | | | Ptgs1 |
| Cnot6l | | | | | Klf4 | | | | Calm2 |
| Riiad1 | | | | | Sep15 | | | | Zfp428 |
| Marcksl1 | | | | | Galnt7 | | | | Tmem141 |
| Pax6 | | | | | Uap1 | | | | Myo1b |
| Wbp5 | | | | | Dnajc10 | | | | Siglecf |
| Scg3 | | | | | Ddost | | | | Pla2g4a |
| Nisch | | | | | Oit1 | | | | Inpp5b |
| Gstz1 | | | | | Foxa3 | | | | Fam221a |
| Bax | | | | | Tm9sf3 | | | | Bub3 |
| Gm43861 | | | | | Cracr2b | | | | Arpc5 |
| Slc18a1 | | | | | Vimp | | | | Pla2g16 |
| Gng4 | | | | | Capn9 | | | | 1110007C09Rik |
| | | | | | Scin | | | | Gimap1 |
| | | | | | Pdia3 | | | | Coprs |
| | | | | | Rnase1 | | | | Lect2 |
| | | | | | Calr | | | | Nrgn |
| | | | | | Wars | | | | Agt |
| | | | | | Snhg18 | | | | Ffar3 |
| | | | | | Dap | | | | Tmem45b |
| | | | | | Ttc39a | | | | Ccdc23 |
| | | | | | Dad1 | | | | Rgs2 |
| | | | | | Tnfaip8 | | | | Mlip |
| | | | | | Tram1 | | | | Csk |
| | | | | | Kdelr3 | | | | 2210016L21Rik |
| | | | | | Arf4 | | | | St6galnac2 |
| | | | | | Cmtm7 | | | | Ildr1 |
| | | | | | | | | | Gprc5c |
| | | | | | | | | | Mocs2 |
| | | | | | | | | | Nrep |
| | | | | | | | | | Pik3cg |
| | | | | | | | | | Malat1 |
| | | | | | | | | | Sec14l1 |
| | | | | | | | | | Ndufaf3 |
| | | | | | | | | | Inpp5d |
| | | | | | | | | | Pim3 |
| | | | | | | | | | Tmem9 |
| | | | | | | | | | Gga2 |
| | | | | | | | | | Nt5c3 |

Significance cut-offs: FDR (max): 0.05, Log2 fold-change: 0.5

TABLE 4

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| Gfra3 | Mep1b | Slc6a1 | Ccnb1 | Clca3 | Defa23 | Lgr5 | | Alox5ap |
| ChRb | Anpep | | Cdc20 | Zg16 | Gm15284 | Gkn3 | | Hck |
| Trp53i11 | Gsta1 | | Cenpa | Fcgbp | Defa17 | Ascl2 | | Lrmp |
| Neurod1 | Apoa1 | | Cdkn3 | Tff3 | Defa-rs7 | Olfm4 | | Avil |
| Vwa5b2 | Gm3776 | | Cdc25c | Agr2 | AY761184 | Rgmb | | Trpm5 |
| Cck | Igsf9 | | Ccnb2 | Scin | Defa-rs1 | Igfbp4 | | Spib |
| Rfx6 | Il18 | | Kif22 | Pdia5 | Gm7849 | 2210407C18Rik | | Rgs13 |
| Prnp | Ace2 | | Ube2c | Tpsg1 | Gm14851 | Jun | | Ltc4s |
| Pcsk1 | Creb3l3 | | Sapcd2 | Chst4 | Defa3 | Pdgfa | | Pygl |
| Syt13 | Krt20 | | Rbp7 | Bcas1 | Defa22 | Soat1 | | Sh2d7 |
| Rph3al | Slc9a3 | | Ccna2 | Bace2 | Gm21498 | Tnfrsf19 | | Dclk1 |
| Fabp5 | Dpep1 | | Aurka | Galnt12 | Defa26 | Cyp2e1 | | Alox5 |
| Pam | Slc25a45 | | Cdkn2d | Rep15 | Defa4 | Fstl1 | | Pik3r5 |
| Scgn | Rbp2 | | Kif23 | S100a6 | Defa20 | H2-Eb1 | | Fyb |
| Aplp1 | Ms4a8 | | Nek2 | Capn9 | Defa25 | Ifitm3 | | Vav1 |
| Fev | Reg3b | | Birc5 | Spdef | Gm14850 | Prelp | | Matk |
| Scg5 | Reg3a | | Plk1 | Atoh1 | Defa5 | Scn2b | | Tspan6 |
| Celf3 | Clec2h | | Tacc3 | Guca2a | Defa24 | A930009A15Rik | | Strip2 |
| Resp18 | Slc51b | | Melk | Pla2g10 | Gm15292 | H2-Ab1 | | Pou2f3 |
| Neurog3 | Cyp2d26 | | Cdca3 | Muc2 | Defa-ps1 | Slc1a2 | | 1810046K07Rik |
| Maged1 | Adh6a | | Hmmr | Mlph | Gm15315 | Cd74 | | Ptpn6 |
| Scg3 | Bco2 | | Spc25 | AW112010 | Mptx2 | Sp5 | | Bmx |
| Pax4 | Slc3a1 | | Tpx2 | Scnn1a | Gm15299 | Noxa1 | | Tuba1a |
| Olfm1 | Cyp3a13 | | Arhgef39 | Ern2 | Gm10104 | Rgcc | | Espn |
| Cplx2 | Slc16a5 | | Bub1b | Ttc39a | Lyz1 | Sorbs2 | | Plcb2 |
| Isl1 | Btnl1 | | 1190002F15Rik | Liph | Clps | Sectm1b | | Ffar3 |
| Gpx3 | 2010106E10Rik | | Kif4 | C1galt1c1 | Defa21 | H2-Aa | | Ccdc109b |
| Anxa6 | Maob | | Mad2l1 | Kcnk6 | Reg4 | Cdo1 | | Plcg2 |
| Gng4 | Sis | | Fbxl8 | Creb3l4 | Pnliprp2 | Slc14a1 | | Ly6g6f |
| Mreg | Acad11 | | Gpsm2 | Slc12a8 | Defa6 | Clca2 | | Hpgds |
| Map1b | Edn2 | | Ckap2l | Efcab4a | Pla2g2a | Tifa | | Pea15a |
| Bex2 | Spink3 | | Knstrn | Ptprr | Itln1 | Pls3 | | Ly6g6d |
| Baiap3 | H2-Q1 | | Id1 | Klk1 | Mmp7 | Hmgcs2 | | Pik3cg |
| Disp2 | Sult2b1 | | Cmc2 | Tnfaip8 | Gm21002 | Arid5b | | Inpp5d |
| 1700086L19Rik | Slc7a7 | | 1810065E05Rik | Lrrc26 | Gm7861 | Agr3 | | Ccdc28b |
| Lrp11 | 1700019G17Rik | | Cenpe | C1galt1 | Ang4 | Slc12a2 | | Snrnp25 |
| Rimbp2 | Dgat2 | | Pif1 | Galnt7 | Gm15308 | Rassf5 | | Kctd12 |
| Snap25 | Enpep | | Ckap5 | Fam174b | Habp2 | Rnf43 | | Siglec5 |
| Klhdc8b | Fmo5 | | Cnih4 | Sgsm3 | Pnliprp1 | Nrn1 | | Skap2 |
| Foxa2 | 2010001E11Rik | | Spc24 | Galnt3 | Gm6696 | Lamb3 | | Ccdc129 |
| Gck | Fam3b | | | Spats2l | Mptx1 | Cd44 | | Nebl |
| Pcsk1n | Slc26a6 | | | Ccl9 | Fam46c | Axin2 | | Gprc5c |
| Gdap1l1 | Mpp1 | | | Sytl2 | Samd5 | Slc27a2 | | Rgs22 |
| Map3k15 | Ces1f | | | Car8 | Lyz2 | Afap1l1 | | Gfi1b |
| Kcnh6 | Apoa4 | | | Uap1 | C4bp | Ccdc3 | | Hmx3 |
| Kcnb2 | Slc5a11 | | | Asph | 1810010D01Rik | Lrig1 | | Cbr3 |
| Prodh2 | 2010003K11Rik | | | Slc50a1 | Apoc2 | Noxo1 | | Pfkfb3 |
| Bex1 | Eci3 | | | Smim14 | AY761185 | Cdk6 | | Prss53 |
| Lhfpl2 | Cyp4f14 | | | Creb3l1 | Defb1 | Amica1 | | Itpr2 |
| Fam183b | Btnl6 | | | Hgfac | Pla2g2f | Tgif1 | | Limd2 |
| Nkx2-2 | Ace | | | Stard3nl | Copz2 | Tns3 | | Cd300lf |
| Pax6 | Hsd17b6 | | | Tspan13 | Scgb2b7 | Nr2e3 | | Chn2 |
| Adprm | Rdh7 | | | Gsn | Scgb2b19 | Efna4 | | Smpx |
| Dbpht2 | Alpi | | | Capn8 | Scgb2b20 | Rnf32 | | Ptgs1 |
| Myt1 | Gpd1 | | | Gcnt3 | Klf15 | Prss23 | | A4galt |
| Kcnk16 | Ptprh | | | Txndc5 | Sntb1 | 2010009K17Rik | | Rac2 |
| Tac1 | Papss2 | | | Atp2c2 | Ggh | Smoc2 | | Csk |
| Scarb1 | Ggt1 | | | Hpd | Cd244 | Mecom | | Slco4a1 |
| Acadsb | Aldh1a1 | | | Bhlhe40 | Gm15293 | Esrrg | | Ptpn18 |
| Vim | Naaladl1 | | | Tfcp2l1 | Gm7325 | Aqp1 | | Chat |
| Xpnpep2 | Agpat9 | | | Qsox1 | Fzd9 | Znrf3 | | Hebp1 |
| Acsl6 | H2-Q2 | | | St3gal6 | Fgfrl1 | Grb7 | | Ppp1r14c |
| Bcmo1 | Hsd17b2 | | | Rap1gap | Tesc | Phgdh | | Dgki |
| Parp6 | Exoc3l4 | | | Kctd14 | Slc1a4 | 2410004N09Rik | | Inpp5j |
| Plxnb1 | Hpgd | | | Kdelr3 | Lamb1 | Clca4 | | Tppp3 |
| Cnot6l | Gnpda1 | | | Galnt10 | Darc | Aqp4 | | Gng13 |
| Ncald | Gm1332 | | | Dnajc10 | Ddx26b | Lcp1 | | Ildr1 |
| Scg2 | Ms4a10 | | | Sytl4 | Slc30a2 | E030011O05Rik | | Cwh43 |
| Phldb2 | Gm7092 | | | Hid1 | Hspb8 | Snhg1 | | Il17rb |
| Peg3 | Ugt2a3 | | | Samhd1 | Sync | BC064078 | | Ncf2 |
| Mapre3 | Upp1 | | | Fkbp11 | Slc16a7 | Car12 | | Fut2 |
| Ids | Lrrc19 | | | Galnt5 | Hapln4 | Zbtb38 | | Coprs |
| Amigo2 | Fmo4 | | | Tmed3 | Insrr | Cdca7 | | Ddah1 |
| Dner | Hkdc1 | | | Ica1 | Acvrlc | Fam13a | | Tmem116 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| Syp | Nr1h3 | | | Pqlc3 | Syne4 | Shisa2 | | Sucnr1 |
| Tox3 | Themis3 | | | Tmem123 | Acox3 | Dtx4 | | Tmem176a |
| Insm1 | Agmo | | | Sdf2l1 | Dkk3 | Slc19a2 | | Ccrl1 |
| Adora3 | Slc6a20a | | | S100a14 | Ang2 | Fam115c | | 1110007C09Rik |
| Tmem106c | Soat2 | | | Ergic1 | Ang6 | Mir703 | | Adcy5 |
| Sstr1 | Ces2a | | | Efcab4b | Thbs1 | Cd14 | | Fnbp1 |
| Cbfa2t2 | Bcl2l15 | | | Foxa3 | Dll3 | Mettl20 | | Plk2 |
| Slc39a2 | Entpd5 | | | Stx17 | Ang5 | Myo9a | | Hmx2 |
| Rasd1 | Cndp2 | | | AI597468 | | App | | Tmem141 |
| Cacna2d1 | Tmem37 | | | Fxyd3 | | Clic6 | | Krt23 |
| Ngfrap1 | Gda | | | Cd97 | | Wee1 | | Gprc5a |
| Rab36 | Abcg5 | | | Csrp1 | | 2410006H16Rik | | Rgs2 |
| Akna | Ces2c | | | Pdia6 | | Lancl1 | | Camk2b |
| Ghrl | Mogat2 | | | Tinagl1 | | 1500012F01Rik | | Fes |
| Gpr116 | Abhd3 | | | Rcan3 | | Caspl2 | | Bpgm |
| 2610301B20Rik | St3gal4 | | | Fam114a1 | | Sh3rf1 | | Acacb |
| Rbfox2 | Gm8909 | | | Cmtm7 | | Lrp4 | | Il13ra1 |
| Pde1c | Slc5a1 | | | Ppapdc1b | | Arhgef26 | | Zfp428 |
| Mapk8ip2 | Tubal3 | | | Mon1a | | Etv6 | | Ppp1r3b |
| Scn3a | Gstm3 | | | Slc7a4 | | 1700024F13Rik | | Ccnj |
| Sstr5 | Sphk1 | | | Tnfrsf21 | | Cttnbp2 | | Bcl2l14 |
| Lypd1 | Slc26a3 | | | Tor3a | | Slc16a13 | | Tmem229a |
| Marcks | Tmem106a | | | Adrbk1 | | Htr4 | | Ethe1 |
| Riiad1 | Slc27a4 | | | P2rx4 | | Pdxk | | Runx1 |
| Trit1 | Sowaha | | | Myo5c | | Immp2l | | Gga2 |
| Ptpru | Slc6a4 | | | Nipal2 | | Rps15a-ps6 | | Apobec1 |
| Apbb1 | Mme | | | Tmem39a | | Rps15a-ps4 | | Serpini1 |
| Galr3 | Adamtsl5 | | | Sil1 | | Nap1l1 | | St6galnac6 |
| Rapgef4 | Aldh1l1 | | | Slc17a9 | | Sdc4 | | Fbxl21 |
| Sphkap | Gpt | | | Mcf21 | | Epn3 | | 9030624J02Rik |
| Golim4 | Igsf5 | | | Rasa4 | | Sipa1l1 | | Inpp5b |
| Nefm | Emp1 | | | Cgref1 | | Wfdc15b | | Samd14 |
| Cdk2ap1 | Cox7a1 | | | Galk2 | | Zfp341 | | Pgm2l1 |
| Tubb3 | Ugt2b5 | | | Wars | | Ngef | | Pla2g4a |
| Tmem182 | Apoc3 | | | Gm9994 | | Nrg4 | | Ptprc |
| Fam135a | Abcg8 | | | Edem1 | | Csad | | Aldh2 |
| Fam43a | Ugt2b36 | | | Mia3 | | Rpl34-ps1 | | Ifi27l1 |
| Golga7b | Pex11a | | | Slc35a1 | | Rin2 | | Pnpla3 |
| Slc26a4 | Osgin1 | | | Tm9sf3 | | Cd81 | | Jarid2 |
| Chd7 | Gsta4 | | | Fhl1 | | Irf2bp2 | | Rgs19 |
| Cerkl | Slc28a1 | | | Sec24d | | Sesn3 | | Reep5 |
| Cplx1 | Gm11437 | | | Sel1l3 | | Phlpp1 | | Tiparp |
| Galr1 | Nat8 | | | Tmed9 | | Yap1 | | Gnai2 |
| Gpr119 | Nr1i3 | | | Cd9 | | Mfge8 | | Fam49a |
| Fam160a2 | Slc51a | | | Rasd2 | | Zfp825 | | Cacna2d2 |
| Pcp4l1 | Fabp1 | | | Edem2 | | Itga1 | | Ypel2 |
| Efcab1 | Abcc2 | | | Golph3l | | Pcdh8 | | Cd24a |
| Maml3 | Apob | | | Arfip2 | | Vdr | | Acot7 |
| Ap3b2 | Mical2 | | | Tsta3 | | Kcnq1 | | Svil |
| Trf | Mgat4c | | | Tvp23b | | Slc28a2 | | Abhd16a |
| Rab31 | H2-Bl | | | Rnf39 | | Zfp36l1 | | Fam101a |
| Hnrnph3 | Hdhd1 | | | E130003G02Rik | | Urod | | Trim40 |
| Ffar1 | Sec23a | | | Aacs | | Rgs12 | | Trak1 |
| Emb | Slc7a9 | | | Chrm1 | | Nfib | | Sec14l1 |
| Th | Tmem86a | | | Fut4 | | Sdsl | | 4930539E08Rik |
| Ptprn | Npc1l1 | | | Vps37c | | Nfia | | Smtn |
| Prkar1b | Btnl2 | | | Creld2 | | | | Galk1 |
| Dock4 | Acot9 | | | Ikbip | | | | Tbc1d1 |
| Kirrel2 | Paqr7 | | | Nans | | | | Tmem176b |
| Sh2d5 | Cblc | | | Tpd52 | | | | Fcna |
| Tmem130 | Tmem253 | | | Tmem214 | | | | Abhd2 |
| Pde11a | Smlr1 | | | Anxa3 | | | | Hsbp1l1 |
| Nek5 | Abhd6 | | | Rassf6 | | | | Slc4a8 |
| Azi1 | Amn | | | Bcat2 | | | | Myo1b |
| 5430425J12Rik | Pbld2 | | | Tmem159 | | | | Tmem38b |
| Pnmal1 | Mttp | | | Stxbp6 | | | | Hk1 |
| Dnahc9 | Ap2a2 | | | Slc30a7 | | | | Neurl1a |
| Rnf122 | Ptk6 | | | Mansc1 | | | | Dmxl2 |
| Chst11 | Vwce | | | Gfpt1 | | | | Bub3 |
| Tekt2 | Cideb | | | Gmppb | | | | Ptprj |
| Mum1l1 | Sco2 | | | Sybu | | | | Trib2 |
| Trpm2 | Gramd3 | | | Srd5a1 | | | | Stard5 |
| Map9 | Apol10a | | | Tram1 | | | | Ubtd1 |
| Ctif | Dpyd | | | Slc39a7 | | | | Slc41a3 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| Btbd17 | Abat | | | Tmem248 | | | | Plekhg5 |
| Lrrc16b | Slc46a1 | | | Bet1l | | | | Rbm38 |
| Rufy2 | Adtrp | | | Sec23ip | | | | Fam57a |
| Ambp | Xdh | | | Cog6 | | | | Eef2k |
| Pkia | Tgfbi | | | Rab3d | | | | Cables2 |
| Pitpnc1 | Chp2 | | | D630039A03Rik | | | | Fbxo25 |
| Mapkbp1 | Gyk | | | Prrc1 | | | | Ap1s2 |
| Unc13a | Khk | | | Appl2 | | | | 1300002K09Rik |
| Gatm | Lct | | | 1810055G02Rik | | | | Ero1lb |
| Slc35d3 | Atp6v0a2 | | | Synj2 | | | | Clmn |
| Spred3 | Rhbg | | | 1700066B19Rik | | | | Fam49b |
| Zc3h12c | Tmem82 | | | Arfgap1 | | | | Cpvl |
| Mapk15 | Galm | | | Oit1 | | | | Prr15 |
| March4 | AA986860 | | | Ehd4 | | | | Lpcat4 |
| Pax6os1 | Shpk | | | Stx5a | | | | Tmem74b |
| Neurod2 | Slc15a1 | | | Plcb1 | | | | Mn1 |
| Cidea | Cyp4f40 | | | Ptger4 | | | | Eppk1 |
| Klhl32 | Sult1b1 | | | Slc39a11 | | | | Samd9l |
| Hrh3 | Slc13a1 | | | 5033406O09Rik | | | | Tmem245 |
| Slc8a1 | Cml1 | | | Pllp | | | | Glyctk |
| Klhl31 | Pm20d1 | | | Gpr20 | | | | Aldh3a2 |
| Gfra1 | Fahd1 | | | Spink4 | | | | Ppp3ca |
| Adgb | Trim31 | | | Nfkb2 | | | | Cpne3 |
| Lhx1 | H2-T3 | | | Tmco3 | | | | Slc4a7 |
| Plk5 | 0610005C13Rik | | | Mllt3 | | | | Nfatc1 |
| | Optn | | | Gmppa | | | | Kit |
| | Clec2e | | | D10Bwg1379e | | | | Fam117b |
| | Myo7a | | | Cdk5rap3 | | | | Nradd |
| | Slc37a4 | | | Smim6 | | | | Tmem121 |
| | Ppargc1a | | | Parm1 | | | | Cpm |
| | Stom | | | Fam69a | | | | Asah1 |
| | Reep6 | | | 1810007P106Rik | | | | Slc9a9 |
| | Cmbl | | | Kcnh3 | | | | Ubl7 |
| | Cdkn2b | | | Tspan1 | | | | Abca3 |
| | Pgm2 | | | B3gnt7 | | | | Pde6d |
| | Maf | | | Entpd4 | | | | Bmp2 |
| | Mia2 | | | Kdelr2 | | | | Kdm4a |
| | Slc11a2 | | | Sppl2a | | | | Camkk2 |
| | Spsb1 | | | Impad1 | | | | Arhgap8 |
| | Tmem236 | | | Mgat3 | | | | Agt |
| | Cd36 | | | Cpd | | | | Ptpra |
| | Treh | | | Asns | | | | Adh1 |
| | Gstk1 | | | Hyou1 | | | | Dusp14 |
| | Lipe | | | Uba7 | | | | Clic4 |
| | Tmem139 | | | Dnajc3 | | | | Gimap1 |
| | Cyp2c66 | | | Golt1b | | | | Cpne5 |
| | Gsdmd | | | Pygb | | | | Ceacam2 |
| | Ocm | | | Manf | | | | Zfp710 |
| | Srxn1 | | | Xbp1 | | | | Gcnt1 |
| | Lmbr1l | | | Galnt16 | | | | B4galt5 |
| | Lpgat1 | | | Hspa13 | | | | Suco |
| | Fez2 | | | Rab27b | | | | Pim3 |
| | Slc52a2 | | | Rasef | | | | Ogdhl |
| | Mocos | | | Itga2 | | | | Oas1g |
| | Nek3 | | | Gorasp1 | | | | Dcp1b |
| | Tm6sf2 | | | Pck1 | | | | Myzap |
| | Agpat2 | | | Pgm3 | | | | Cdkn1a |
| | Slc23a2 | | | Galnt6 | | | | Cd37 |
| | Xkr9 | | | Vimp | | | | Brms1 |
| | Tob1 | | | Golga5 | | | | Lrrc42 |
| | Clcn2 | | | Sec16a | | | | Pld2 |
| | Hectd3 | | | Eif2ak3 | | | | Tmem9 |
| | Tbc1d22a | | | Osbpl2 | | | | Cpeb4 |
| | Naip1 | | | Zfp467 | | | | Ssx2ip |
| | Ctss | | | Hdlbp | | | | Ddah2 |
| | Slc9a2 | | | Cbfa2t3 | | | | Tmem65 |
| | Cdc42ep2 | | | Zbp1 | | | | 5430417L22Rik |
| | 9030617O03Rik | | | B3gnt5 | | | | 2210016L21Rik |
| | Mall | | | Far1 | | | | Msi2 |
| | Pla2g12b | | | 0610007N19Rik | | | | B4galt4 |
| | Rhod | | | Zfp330 | | | | Rabgap1l |
| | Kbtbd11 | | | Gcc2 | | | | Pik3r3 |
| | Acox1 | | | Lman1 | | | | Nt5c3 |
| | Arhgap26 | | | Lamc2 | | | | Palld |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | Trim30d | | | Herpud1 | | | | AA467197 |
| | Tcn2 | | | Slc10a7 | | | | Pip5k1b |
| | Mylk | | | Serp1 | | | | Krt18 |
| | Thnsl2 | | | Scamp1 | | | | Map1a |
| | Fam213b | | | Gal3st2 | | | | Lmf1 |
| | Dhrs1 | | | Odf21 | | | | Arhgef28 |
| | Adh4 | | | Hilpda | | | | Nsfl1c |
| | Dgkq | | | Cog3 | | | | Txndc16 |
| | Ces2e | | | Alyref2 | | | | Pstpip2 |
| | Aldh1a7 | | | Galnt4 | | | | Ttll11 |
| | Myo5b | | | Prr24 | | | | Exph5 |
| | Dnm1 | | | Litaf | | | | 2700086A05Rik |
| | Frk | | | Fam98a | | | | Gadd45a |
| | Tsc22d3 | | | Pcsk9 | | | | Plekhs1 |
| | Slc35f5 | | | Zbtb8a | | | | Fam188a |
| | 2200002D01Rik | | | Tmem63a | | | | Jmy |
| | Cyp2c65 | | | Dap | | | | Atat1 |
| | S100g | | | Trim47 | | | | Arhgef2 |
| | Ugdh | | | Ssr3 | | | | Lmbr1 |
| | Cyp2c68 | | | Edem3 | | | | Rhoc |
| | Hagh | | | Tst | | | | Card10 |
| | Xpnpep1 | | | Ang | | | | Kcnj16 |
| | Cobl | | | Slc38a10 | | | | Arhgap4 |
| | Epb4.1l3 | | | Guk1 | | | | Acsl4 |
| | Mep1a | | | Pcsk7 | | | | Rhog |
| | Hnf4g | | | Trabd | | | | Fam221a |
| | Parp9 | | | Gfi1 | | | | Dynlt1b |
| | Cyp2j6 | | | Gnpnat1 | | | | C2 |
| | Sgpl1 | | | Pdxdc1 | | | | Zbtb41 |
| | Pccb | | | Hspa5 | | | | Socs1 |
| | Abcg2 | | | Slc35a2 | | | | Atp6ap1 |
| | Slc2a2 | | | Slc37a3 | | | | Fam171a1 |
| | Ephx2 | | | Arl1 | | | | Wnk2 |
| | Kcnk5 | | | Smim5 | | | | Kcnd3 |
| | Lrp1 | | | Ccnd3 | | | | Slc27a1 |
| | Tmem135 | | | Sar1a | | | | Atxn1 |
| | Dak | | | F2rl1 | | | | Rabgap1 |
| | Dusp12 | | | Stt3a | | | | Myrfl |
| | Gpr128 | | | Tdrd7 | | | | Crot |
| | Abcb1a | | | Spcs3 | | | | Tm4sf4 |
| | Tmem252 | | | Sidt1 | | | | Ube2j1 |
| | Slc7a8 | | | Pdia3 | | | | Sort1 |
| | 4931406C07Rik | | | Lss | | | | Lima1 |
| | Tm4sf5 | | | Cmpk1 | | | | Mov10 |
| | Akr1b7 | | | Naga | | | | Lca5 |
| | Tmem230 | | | Sh3bgrl3 | | | | Gimap9 |
| | Acbd4 | | | Slc41a2 | | | | Mlip |
| | Crat | | | Ostc | | | | 1110008P14Rik |
| | Pcsk5 | | | Fgfr3 | | | | Ckap4 |
| | Galt | | | Fut8 | | | | Tor4a |
| | Gm10768 | | | Ggcx | | | | Rmdn1 |
| | Cyp3a25 | | | Plac9a | | | | Oas2 |
| | Gstp2 | | | Sec61b | | | | Dsp |
| | Ilvbl | | | Bscl2 | | | | Sox9 |
| | Urgcp | | | Golm1 | | | | Osbpl3 |
| | Chchd7 | | | Klf4 | | | | Kif21b |
| | Car4 | | | Ssr4 | | | | Tbcb |
| | Slc13a2 | | | Srprb | | | | Arap2 |
| | Epha1 | | | Yipf6 | | | | Casp3 |
| | Dab1 | | | Clptm1l | | | | Enc1 |
| | Gstm6 | | | Id4 | | | | Il25 |
| | Sept9 | | | Arf4 | | | | Lman2l |
| | Adipor2 | | | Gale | | | | Zmiz1 |
| | Cast | | | Eif4ebp1 | | | | Nav2 |
| | Abp1 | | | Srpr | | | | Atp2a3 |
| | Casp6 | | | Tbc1d30 | | | | Gimap8 |
| | Itga3 | | | Akr1c14 | | | | Folr1 |
| | Rilp | | | Zc3h7a | | | | Fn1 |
| | Tmem41a | | | D17Wsu104e | | | | Hspa4l |
| | Nkiras2 | | | S100a16 | | | | Sufu |
| | March6 | | | Mknk2 | | | | Atp8a1 |
| | Gm9926 | | | Tmprss2 | | | | Vps53 |
| | Plin3 | | | Tc2n | | | | Rgs14 |
| | Rab11fip3 | | | Slc35c1 | | | | Gm17660 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | Retsat | | | Ufsp2 | | | | Pdcl |
| | Arg2 | | | Tmem165 | | | | Shkbp1 |
| | Slc39a5 | | | Tmsb10 | | | | Oas1a |
| | Pepd | | | Sec62 | | | | Pkp1 |
| | Idh1 | | | Bet1 | | | | Ccdc23 |
| | Ccdc134 | | | Cyp51 | | | | Il4ra |
| | Mgam | | | Fam3c | | | | 1700112E06Rik |
| | Ugt2b34 | | | Mfsd7a | | | | Dvl1 |
| | Ceacam20 | | | Slc37a1 | | | | Zfhx3 |
| | Slc2a9 | | | Cmtm8 | | | | Adam22 |
| | Frmd8 | | | Adam9 | | | | Gramd1c |
| | Smpdl3a | | | Art2a-ps | | | | Tmem45b |
| | Apol10b | | | Capns1 | | | | Unc5b |
| | Slc5a9 | | | Syt7 | | | | Mical3 |
| | Gna11 | | | Pdia4 | | | | Kctd13 |
| | Pls1 | | | Slc22a23 | | | | Ak7 |
| | Rab17 | | | Yipf5 | | | | Tcta |
| | Lgals3 | | | H2-T9 | | | | Nek7 |
| | Slc25a37 | | | Atf4 | | | | D730039F16Rik |
| | Ppap2a | | | Ick | | | | Plekho2 |
| | Gpr155 | | | Srm | | | | Myo6 |
| | Cml5 | | | Plaur | | | | Chdh |
| | Spns2 | | | Pyroxd1 | | | | Opn3 |
| | Acot11 | | | Fry | | | | Tle3 |
| | Vmp1 | | | Cyp2j9 | | | | Ttll10 |
| | Mertk | | | Sep15 | | | | Strada |
| | 2510049J12Rik | | | Sc4mol | | | | Ypel3 |
| | Zzef1 | | | Stk38l | | | | Cmip |
| | Bche | | | Bmp8a | | | | Cachd1 |
| | Abcd3 | | | Spryd3 | | | | Pigc |
| | Aqp11 | | | Gne | | | | Atp6v1d |
| | Gcnt2 | | | Aldh3b2 | | | | Rdx |
| | Acsl5 | | | Rell1 | | | | S100a11 |
| | Gng12 | | | Krtcap2 | | | | Spa17 |
| | Cda | | | Sec23b | | | | Gimap5 |
| | Fcgrt | | | St3gal1 | | | | Cystm1 |
| | Gm6034 | | | Tmem56 | | | | Zdhhc17 |
| | Sema4g | | | Tulp4 | | | | Lect2 |
| | Zfyve21 | | | Capn7 | | | | Vdac3 |
| | Pfkfb4 | | | Gpr180 | | | | Hspb11 |
| | D130043K22Rik | | | Txndc11 | | | | Gm4952 |
| | Cyp4v3 | | | Copb2 | | | | Slc16a2 |
| | C530008M17Rik | | | Calr | | | | Abhd5 |
| | Ptdss1 | | | Homer2 | | | | Rhbdf1 |
| | Gm766 | | | Ssr2 | | | | Cblb |
| | Tbc1d24 | | | Tbrg1 | | | | Nfe2l3 |
| | Cyb5b | | | Jtb | | | | Pla2g16 |
| | Maoa | | | Syvn1 | | | | Sept8 |
| | Vat1 | | | Morf4l2 | | | | Gpcpd1 |
| | Ehhadh | | | Rpn2 | | | | Psd3 |
| | Naprt1 | | | Ugp2 | | | | Anxa11 |
| | Slc3a2 | | | H13 | | | | Slc25a12 |
| | Dhrs11 | | | Slc16a6 | | | | Ehf |
| | Sh3tc1 | | | Slc39a1 | | | | Akr1b10 |
| | Irak2 | | | Gm1123 | | | | Dapp1 |
| | Btnl4 | | | Copg1 | | | | Vmn2r26 |
| | Stx12 | | | Ssr1 | | | | Esyt1 |
| | Dgat1 | | | Tmed2 | | | | Ppt1 |
| | Acaa1a | | | Ank3 | | | | Cd47 |
| | Cyp4f16 | | | Tmbim4 | | | | Chi3l1 |
| | Btnl5 | | | Rpn1 | | | | Mical1 |
| | Snx9 | | | Uggt1 | | | | Gna14 |
| | Ahnak | | | Utp11l | | | | Pacs2 |
| | Fam109a | | | Ppib | | | | Lyn |
| | Edn3 | | | Camsap3 | | | | Rmnd5a |
| | Ccl25 | | | Ddost | | | | Ankrd12 |
| | Zdhhc7 | | | Mesdc1 | | | | BC022687 |
| | Ppp1r14d | | | 4930404N11Rik | | | | Rit1 |
| | Slc43a2 | | | Sh3bgrl2 | | | | Camta2 |
| | Faah | | | Golgb1 | | | | Mocs2 |
| | Tymp | | | B3gnt3 | | | | Usp49 |
| | Acy1 | | | Dcbld2 | | | | Nrbp2 |
| | Cyb5r3 | | | Spcs2 | | | | Ifnar2 |
| | Rnf13 | | | Sec61a1 | | | | Epha4 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | Rxra | | | Cant1 | | | | Arl5a |
| | Dqx1 | | | Tpcn1 | | | | Rgl2 |
| | Snx13 | | | Gorasp2 | | | | St18 |
| | Acnat1 | | | Pmm2 | | | | BC016579 |
| | Ticam1 | | | Ano7 | | | | Tead1 |
| | Sidt2 | | | Rrbp1 | | | | Enpp4 |
| | Fam78a | | | Pacsin1 | | | | Tmem158 |
| | Aldh18a1 | | | Srp72 | | | | Tnfaip3 |
| | Rmdn3 | | | Tnk2 | | | | Gys1 |
| | Sat1 | | | Eif2ak4 | | | | Hivep2 |
| | Ckmt1 | | | Sec22b | | | | Cap1 |
| | Txlng | | | Tars | | | | Slc4a2 |
| | Slc31a1 | | | Slc1a5 | | | | Map4k4 |
| | Slc25a36 | | | Copb1 | | | | Desi1 |
| | Slc25a34 | | | Yif1b | | | | H2-D1 |
| | AU040320 | | | Etnk1 | | | | Man2a1 |
| | Marc2 | | | Ramp1 | | | | Cyp17a1 |
| | Aldob | | | Cltb | | | | Cyhr1 |
| | Gm7030 | | | Slc22a15 | | | | Morf4l1 |
| | Decr1 | | | Kif13a | | | | Mllt4 |
| | Sh3d21 | | | Yipf3 | | | | Phf17 |
| | Ugt1a1 | | | Ift20 | | | | Stox2 |
| | Ccs | | | Ufl1 | | | | Hist3h2a |
| | Kifc3 | | | Tm9sf2 | | | | Hdac6 |
| | Slc18b1 | | | Syngr2 | | | | Prox1 |
| | Aprt | | | Nucb1 | | | | Dtnb |
| | Slc22a1 | | | Gmds | | | | Lrch4 |
| | Acp6 | | | Sec61g | | | | Spire2 |
| | Ogdh | | | Rfc1 | | | | Klf6 |
| | Tfg | | | C2cd2l | | | | Rab5b |
| | Tstd1 | | | Smim3 | | | | Anxa4 |
| | Klc4 | | | Hsp90b1 | | | | Rab4b |
| | Itpk1 | | | Srp9 | | | | Iqsec1 |
| | Bmp3 | | | Ost4 | | | | Pdpk1 |
| | Pld1 | | | Tmem183a | | | | Stk40 |
| | Ezr | | | Dnajb11 | | | | Gde1 |
| | Coro2a | | | Tom1l1 | | | | Mtmr11 |
| | Ckb | | | Sh3pxd2a | | | | Cib2 |
| | Farp2 | | | Ier3ip1 | | | | March2 |
| | Pxdc1 | | | | | | | Capg |
| | Sar1b | | | | | | | Narf |
| | Scp2 | | | | | | | Mgst3 |
| | Ggact | | | | | | | Angel1 |
| | Cst6 | | | | | | | Bicd1 |
| | Sft2d2 | | | | | | | Ifitm1 |
| | Abr | | | | | | | Stx3 |
| | Glt28d2 | | | | | | | S100a1 |
| | Slc34a2 | | | | | | | Omd |
| | Fam160a1 | | | | | | | 0610040J01Rik |
| | Pcyt1a | | | | | | | Arpc5 |
| | Tep1 | | | | | | | Homer3 |
| | Hadha | | | | | | | Cdc42se1 |
| | Ccdc88c | | | | | | | Abcc3 |
| | Lpcat3 | | | | | | | Hsf2 |
| | Tbc1d14 | | | | | | | Pnpla6 |
| | Gucd1 | | | | | | | Ccdc68 |
| | Acadm | | | | | | | Fryl |
| | 2210404O07Rik | | | | | | | Lmtk2 |
| | Mvp | | | | | | | Tas1r3 |
| | Actn4 | | | | | | | 4931406H21Rik |
| | Tspan15 | | | | | | | Uspl1 |
| | Rufy3 | | | | | | | Ajuba |
| | Mcu | | | | | | | Kalrn |
| | Spint1 | | | | | | | Basp1 |
| | Sfxn1 | | | | | | | Pip5kl1 |
| | Alas1 | | | | | | | Slc26a2 |
| | Nipsnap3b | | | | | | | Atp2b2 |
| | Tor1aip2 | | | | | | | Smug1 |
| | Casp1 | | | | | | | Myadm |
| | Bpnt1 | | | | | | | D330041H03Rik |
| | Baiap2l1 | | | | | | | Wdfy2 |
| | Ifngr2 | | | | | | | Trim38 |
| | Pex19 | | | | | | | Arf3 |
| | Myl12b | | | | | | | Scand1 |

TABLE 4-continued

Marker genes (full-length plate-based data) for intestinal epithelial cell-types

| Enteroendocrine | Enterocyte | Enterocyte progenitor (early) | Enterocyte progenitor (late) | Goblet | Paneth | Stem | TA | Tuft |
|---|---|---|---|---|---|---|---|---|
| | 0610008F07Rik | | | | | | | Dpysl2 |
| | Atp1a1 | | | | | | | Ndufaf3 |
| | Itfg3 | | | | | | | Sik1 |
| | Dnpep | | | | | | | Wdr7 |
| | Akr7a5 | | | | | | | Sfxn3 |
| | Dlst | | | | | | | Kcnq4 |
| | Ugt1a7c | | | | | | | Mll1 |
| | Myo1d | | | | | | | Hsbp1 |
| | Tmem120a | | | | | | | Calml4 |
| | Cdh17 | | | | | | | Atf7ip |
| | Acaa2 | | | | | | | Gpr137b-ps |
| | Apol11b | | | | | | | Hap1 |
| | Hadh | | | | | | | Kctd15 |
| | Casp7 | | | | | | | Prcp |
| | Acp5 | | | | | | | 9430023L20Rik |
| | Rfk | | | | | | | Gmip |
| | Aldh9a1 | | | | | | | Cmtm3 |
| | Vipr1 | | | | | | | Madd |
| | Txndc17 | | | | | | | Krt222 |
| | Phgr1 | | | | | | | Nsf |
| | Eno1 | | | | | | | Klhl28 |
| | Hsd17b4 | | | | | | | Pparg |
| | Slc39a4 | | | | | | | Eml3 |
| | Nlrp6 | | | | | | | Phlda1 |
| | Pttg1ip | | | | | | | P2rx1 |
| | Il17rc | | | | | | | Pde9a |
| | Sqrdl | | | | | | | Otud7b |
| | Net1 | | | | | | | Tfpi2 |
| | Lad1 | | | | | | | Rilpl2 |
| | Gm5177 | | | | | | | Klf3 |
| | Mdh2 | | | | | | | Gyg |
| | 2210016F16Rik | | | | | | | 4930455F23Rik |
| | Erbb3 | | | | | | | Armcx1 |
| | Proz | | | | | | | Lzts2 |
| | Tax1bp3 | | | | | | | Plek |
| | Pgd | | | | | | | Vamp8 |
| | Sult1d1 | | | | | | | Stat2 |
| | Gpi1 | | | | | | | Znf512b |
| | Prap1 | | | | | | | Ptplad1 |
| | Lypla1 | | | | | | | 1110058L19Rik |
| | | | | | | | | Tmem160 |
| | | | | | | | | Tmem51 |
| | | | | | | | | Cdhr5 |
| | | | | | | | | Stk38 |
| | | | | | | | | Atp13a2 |
| | | | | | | | | Nptn |
| | | | | | | | | Sirt5 |
| | | | | | | | | Gabarapl2 |
| | | | | | | | | Nudt14 |
| | | | | | | | | 2010111I01Rik |
| | | | | | | | | Alkbh7 |
| | | | | | | | | Slc18a3 |
| | | | | | | | | 4930427A07Rik |
| | | | | | | | | Ttll7 |
| | | | | | | | | Acss2 |
| | | | | | | | | Siae |

Significance cut-offs: FDR (max): 0.05, Log2 fold-change: 0.5

TABLE 5

Consensus (full-length plate-based and 3' droplet-based) signatures for post-mitotic intestinal epithelial cells

| Goblet | Paneth | Tuft | Enteroendocrine | Enterocyte (Proximal) | Enterocyte (Distal) |
|---|---|---|---|---|---|
| Agr2 | Gm15284 | Alox5ap | Chgb | Gsta1 | Tmigd1 |
| Fcgbp | AY761184 | Lrmp | Gfra3 | Rbp2 | Fabp6 |
| Tff3 | Defa17 | Hck | Cck | Adh6a | Slc51b |
| Clca1 | Gm14851 | Avil | Vwa5b2 | Apoa4 | Slc51a |
| Zg16 | Defa22 | Rgs13 | Neurod1 | Reg3a | Mep1a |

TABLE 5-continued

Consensus (full-length plate-based and 3' droplet-based) signatures for post-mitotic intestinal epithelial cells

| Goblet | Paneth | Tuft | Enteroendocrine | Enterocyte (Proximal) | Enterocyte (Distal) |
|---|---|---|---|---|---|
| Tpsg1 | Defa-rs1 | Ltc4s | Fev | Creb3l3 | Fam151a |
| Muc2 | Defa3 | Trpm5 | Aplp1 | Cyp3a13 | Naaladl1 |
| Galnt12 | Defa24 | Dclk1 | Scgn | Cyp2d26 | Slc34a2 |
| Atoh1 | Defa26 | Spib | Neurog3 | Ms4a10 | Plb1 |
| Rep15 | Defa21 | Fyb | Resp18 | Ace | Nudt4 |
| S100a6 | Lyz1 | Ptpn6 | Trp53i11 | Aldh1a1 | Dpep1 |
| Pdia5 | Gm15292 | Matk | Bex2 | Rdh7 | Pmp22 |
| Klk1 | Mptx2 | Snrnp25 | Rph3al | H2-Q2 | Xpnpep2 |
| Pla2g10 | Ang4 | Sh2d7 | Scg5 | Hsd17b6 | Muc3 |
| Spdef | | Ly6g6f | Pcsk1 | Gstm3 | Neu1 |
| Lrrc26 | | Kctd12 | Isl1 | Gda | Clec2h |
| Ccl9 | | 1810046K07Rik | Maged1 | Apoc3 | Phgr1 |
| Bace2 | | Hpgds | Fabp5 | Gpd1 | 2200002D01Rik |
| Bcas1 | | Tuba1a | Celf3 | Fabp1 | Prss30 |
| Slc12a8 | | Pik3r5 | Pcsk1n | Slc5a1 | Cubn |
| Smim14 | | Vav1 | Fam183b | Mme | Plec |
| Tspan13 | | Tspan6 | Prnp | Cox7a1 | Fgf15 |
| Txndc5 | | Skap2 | Tac1 | Gsta4 | Crip1 |
| Creb3l4 | | Pygl | Gpx3 | Lct | Krt20 |
| C1galt1c1 | | Ccdc109b | Cplx2 | Khk | Dhcr24 |
| Creb3l1 | | Ccdc28b | Nkx2-2 | Mttp | Myo15b |
| Qsox1 | | Plcg2 | Olfm1 | Xdh | Amn |
| Guca2a | | Ly6g6d | Vim | Sult1b1 | Enpep |
| Scin | | Alox5 | Rimbp2 | Treh | Anpep |
| Ern2 | | Pou2f3 | Anxa6 | Lpgat1 | Slc7a9 |
| AW112010 | | Gng13 | Scg3 | Dhrs1 | Ocm |
| Fkbp11 | | Bmx | Ngfrap1 | Cyp2c66 | Anxa2 |
| Capn9 | | Ptpn18 | Insm1 | Ephx2 | Aoc1 |
| Stard3nl | | Nebl | Gng4 | Cyp2c65 | Ceacam20 |
| Slc50a1 | | Limd2 | Pax6 | Cyp3a25 | Arf6 |
| Sdf2l1 | | Pea15a | Cnot61 | Slc2a2 | Abcb1a |
| Hgfac | | Tmem176a | Cacna2d1 | Ugdh | Xpnpep1 |
| Galnt7 | | Smpx | Tox3 | Gstm6 | Vnn1 |
| Hpd | | Itpr2 | Slc39a2 | Retsat | Cndp2 |
| Ttc39a | | Il13ra1 | Riiad1 | Ppap2a | Nostrin |
| Tmed3 | | Siglecf | | Acsl5 | Slc13a1 |
| Pdia6 | | Ffar3 | | Cyb5r3 | Aspa |
| Uap1 | | Rac2 | | Cyb5b | Maf |
| Gcnt3 | | Hmx2 | | Ckmt1 | Myh14 |
| Tnfaip8 | | Bpgm | | Aldob | |
| Dnajc10 | | Inpp5j | | Ckb | |
| Ergic1 | | Ptgs1 | | Scp2 | |
| Tsta3 | | Aldh2 | | Prap1 | |
| Kdelr3 | | Pik3cg | | | |
| Foxa3 | | Cd24a | | | |
| Tpd52 | | Ethe1 | | | |
| Tmed9 | | Inpp5d | | | |
| Spink4 | | Krt23 | | | |
| Nans | | Gprc5c | | | |
| Cmtm7 | | Reep5 | | | |
| Creld2 | | Csk | | | |
| Tm9sf3 | | Bcl2l14 | | | |
| Wars | | Tmem141 | | | |
| Smim6 | | Coprs | | | |
| Manf | | Tmem176b | | | |
| Oit1 | | 1110007C09Rik | | | |
| Tram1 | | Ildr1 | | | |
| Kdelr2 | | Galk1 | | | |
| Xbp1 | | Zfp428 | | | |
| Serp1 | | Rgs2 | | | |
| Vimp | | Inpp5b | | | |
| Guk1 | | Gnai2 | | | |
| Sh3bgrl3 | | Pla2g4a | | | |
| Cmpk1 | | Acot7 | | | |
| Tmsb10 | | Rbm38 | | | |
| Dap | | Gga2 | | | |
| Ostc | | Myo1b | | | |
| Ssr4 | | Adh1 | | | |
| Sec61b | | Bub3 | | | |
| Pdia3 | | Sec14l1 | | | |
| Gale | | Asah1 | | | |
| Klf4 | | Ppp3ca | | | |
| Krtcap2 | | Agt | | | |
| Arf4 | | Gimap1 | | | |

TABLE 5-continued

Consensus (full-length plate-based and 3' droplet-based) signatures for post-mitotic intestinal epithelial cells

| Goblet | Paneth | Tuft | Enteroendocrine | Enterocyte (Proximal) | Enterocyte (Distal) |
|---|---|---|---|---|---|
| Sep15 | | Krt18 | | | |
| Ssr2 | | Pim3 | | | |
| Ramp1 | | 2210016L21Rik | | | |
| Calr | | Tmem9 | | | |
| Ddost | | Lima1 | | | |
| | | Fam221a | | | |
| | | Nt5c3 | | | |
| | | Atp2a3 | | | |
| | | Mlip | | | |
| | | Vdac3 | | | |
| | | Ccdc23 | | | |
| | | Tmem45b | | | |
| | | Cd47 | | | |
| | | Lect2 | | | |
| | | Pla2g16 | | | |
| | | Mocs2 | | | |
| | | Arpc5 | | | |
| | | Ndufaf3 | | | |

Significance cut-offs: FDR (max): 0.05, Log2 fold-change: 0.5 in both datasets

Figure 8H:
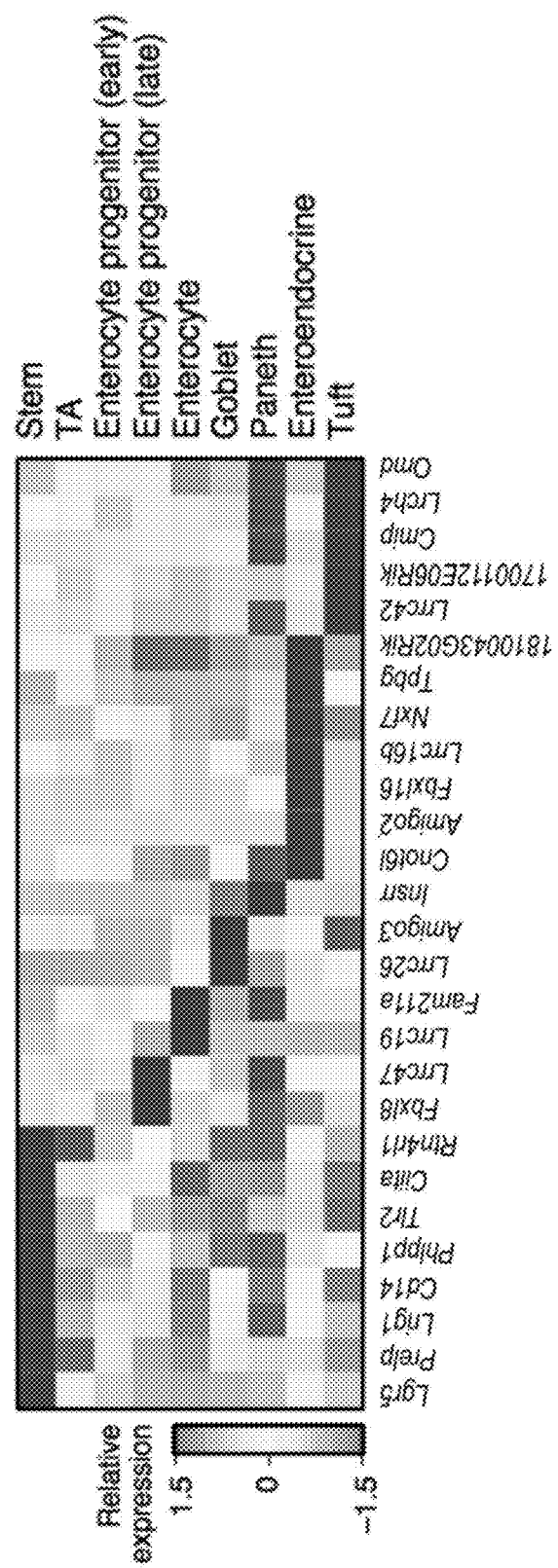

Next, leveraging the higher sensitivity of the plate-based, full-length scRNA-seq data, Applicants also identified enriched TFs, GPCRs and leucine-rich repeat (LRR) proteins (Methods) for each of the major cell types (FIGS. 1f, 1g, FIGS. 8e-8h and Table 6). Among TFs, these included several Krüppel-like family (KLF) TFs specific to secretory subtypes, such as Klf4, a known regulator of goblet cell development[15], and novel KLFs, including Klf5, expressed at significantly higher levels by Paneth cells, and Klf3 and Klf6 by tuft cells. Among cell-type enriched GPCRs (FIG. 1g, FIGS. 8e-8g and Table 6), the known sensory cell types (tuft and EECs) were most prominently represented, each with more than 10 enriched receptors. These included many nutrient-sensing receptors expressed on the EECs (e.g., Gpbar1-a, a bile acid receptor[36], and Gpr119, a sensor for food intake and glucose homeostasis[37]) and Drd3, a dopamine receptor (FIGS. 8e-8g) enriched in tuft cells. The family of pattern recognition receptors (PRR) containing LRR domains are variably deployed on surfaces of the normal intestinal epithelium. Interestingly, Tlr2 and its co-receptor Cd14 had a significantly higher expression (FDR<0.5, Methods) in the stem cell population (FIG. 8h). In sum, Applicants identified and characterized all major cell-types of the villous epithelium at single-cell resolution.

TABLE 6

| Stem | TA | Enterocyte progenitor (early) | Enterocyte progenitor (late) | Enterocyte | Goblet | Paneth | Entero-endocrine | Tuft |
|---|---|---|---|---|---|---|---|---|
| A. Transcription factors (TFs) (full-length plate-based data) | | | | | | | | |
| Ascl2 | Zfp808 | Zbtb44 | Id1 | Creb3l3 | Spdef | Klf15 | Neurod1 | Spib |
| Jun | Ctcf | Zfp72 | Pias4 | Nr1h3 | Atoh1 | Nr4a1 | Rfx6 | Pou2f3 |
| Sp5 | Zfp101 | Zfp709 | Foxm1 | Nr1i3 | Creb3l4 | Zfp667 | Fev | Gfi1b |
| Arid5b | Zfp652 | | Nfyc | Maf | Creb3l1 | | Neurog3 | Hmx3 |
| Tgif1 | | | Mycn | Tsc22d3 | Bhlhe40 | | Pax4 | Hmx2 |
| Nr2e3 | | | Hmgb2 | Hnf4g | Foxa3 | | Isl1 | Runx1 |
| Mecom | | | | Rxra | Nfkb2 | | Foxa2 | Jarid2 |
| Esrrg | | | | Batf2 | Xbp1 | | Nkx2-2 | Nfatc1 |
| Zbtb38 | | | | Zbtb7b | Zfp467 | | Pax6 | Zfp710 |
| Etv6 | | | | | Litaf | | Myt1 | Zbtb41 |
| Tgif2 | | | | | Zbtb8a | | Peg3 | Sox9 |
| Nr1d2 | | | | | Klf4 | | Tox3 | Zmiz1 |
| Zfp341 | | | | | Id4 | | Insm1 | Zfhx3 |
| Hes1 | | | | | Atf4 | | Etv5 | Nfe2l3 |
| Nfix | | | | | Dnajc1 | | Sox4 | Ehf |
| Repin1 | | | | | Tulp4 | | Zfp68 | Camta2 |
| Zfp825 | | | | | Foxp1 | | Lmx1a | St18 |
| Vdr | | | | | Nfxl1 | | Lcorl | Tead1 |
| Gtf2i | | | | | | | Zfp7 | Hivep2 |
| Nfib | | | | | | | Vezf1 | Prox1 |
| Nfia | | | | | | | Gm5595 | Klf6 |
| Relb | | | | | | | Pbx1 | Hsf2 |
| Hmga1-rs1 | | | | | | | Zfp787 | Pparg |
| Pms1 | | | | | | | Zfp62 | Klf3 |
| Gm6710 | | | | | | | Hhex | Stat2 |
| Atf7 | | | | | | | Etv1 | Znf512b |
| Zfp956 | | | | | | | Zfp92 | |
| Esr1 | | | | | | | Neurod2 | |

TABLE 6-continued

| Stem | TA | Enterocyte progenitor (early) | Enterocyte progenitor (late) | Enterocyte | Goblet | Paneth | Entero-endocrine | Tuft |
|---|---|---|---|---|---|---|---|---|
| Hmga2 | | | | | | | Zfp329 | |
| 0610010B08Rik | | | | | | | Zfp71-rs1 | |
| Hmga1 | | | | | | | Zfp30 | |
| Myc | | | | | | | Zkscan1 | |
| Zfp317 | | | | | | | Lhx1 | |
| Nfic | | | | | | | Rcor2 | |
| Zfp13 | | | | | | | Zfp266 | |
| Bcl6 | | | | | | | Sp4 | |
| Foxq1 | | | | | | | Atoh8 | |
| Zfp119b | | | | | | | Bach1 | |
| Hnf4a | | | | | | | Zfp236 | |
| Trp53 | | | | | | | Rfx2 | |
| Zfp369 | | | | | | | Zfp189 | |
| Zfp1 | | | | | | | Plag1 | |
| | | | | | | | Zfp821 | |
| | | | | | | | Zglp1 | |
| | | | | | | | Nanog | |
| B. G-coupled protein receptors (GPCRs) (full-length plate-based data) | | | | | | | | |
| Lgr5 | | | | Gpr128 | Cd97 | Fzd9 | Adora3 | Ffar3 |
| Htr4 | | | | Gpr160 | Chrm1 | Darc | Sstr1 | Gprc5c |
| Fzd7 | | | | Lpar1 | Ptger4 | Ccrl2 | Gpr116 | Sucnr1 |
| Gpr110 | | | | | Gpr20 | | Sstr5 | Ccrl1 |
| Lphn2 | | | | | F2rl1 | | Gpr22 | Gprc5a |
| | | | | | Ffar2 | | Galr3 | Opn3 |
| | | | | | Mtnr1a | | Galr1 | Vmn2r26 |
| | | | | | P2ry4 | | Gpr119 | Tas1r3 |
| | | | | | | | Ffar1 | |
| | | | | | | | Adora2a | |
| | | | | | | | Cxcr7 | |
| | | | | | | | Gpr6 | |
| | | | | | | | Hrh3 | |
| | | | | | | | Gpbar1 | |
| | | | | | | | Chrm4 | |
| | | | | | | | Glp1r | |
| | | | | | | | Htr1d | |
| C. Leucine-rich repeat (LRR) proteins (full-length plate-based data) | | | | | | | | |
| Lgr5 | | Fbxl8 | Lrrc19 | Lrrc26 | Insrr | | Cnot6l | Lrrc42 |
| Prelp | | Lrrc47 | Fam211a | Amigo3 | | | Amigo2 | 1700112E06Rik |
| Lrig1 | | | | | | | Fbxl16 | Cmip |
| Cd14 | | | | | | | Lrrc16b | Lrch4 |
| Phlpp1 | | | | | | | Nxf7 | Omd |
| Tlr2 | | | | | | | Tpbg | |
| Ciita | | | | | | | 1810043G02Rik | |
| Rtn4rl1 | | | | | | | | |

Significance cut-offs: FDR (max): 0.5

Figure 9A:
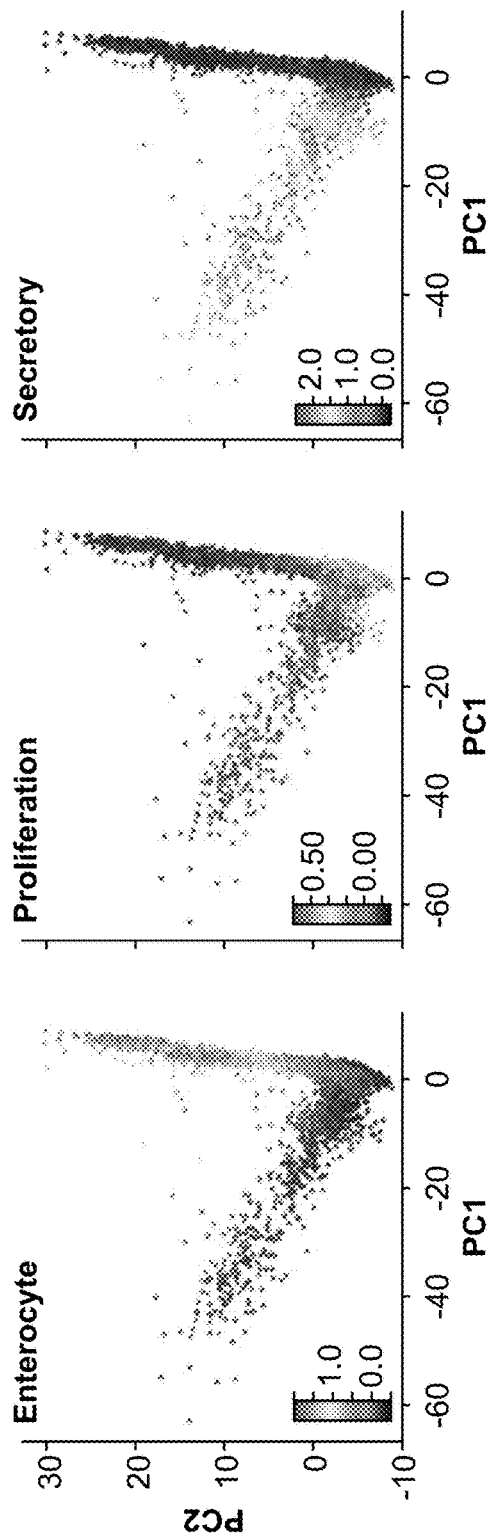
FIG. 9A-9E—Mapping of differentiation processes using low-dimensional embedding, related to FIG. 2 FIG. 9a. Principal components analysis (PCA) of IECs. Shown are the first two PCs (x and y axis) of a PCA of 7,216 IECs. Cells (points) are colored by the signature scores of enterocytes (left), cell-cycle (middle) and secretory cells (right). The secretory signature score is the sum of the Paneth, goblet, enteroendocrine and tuft signature scores (Methods).
Figure 9B:
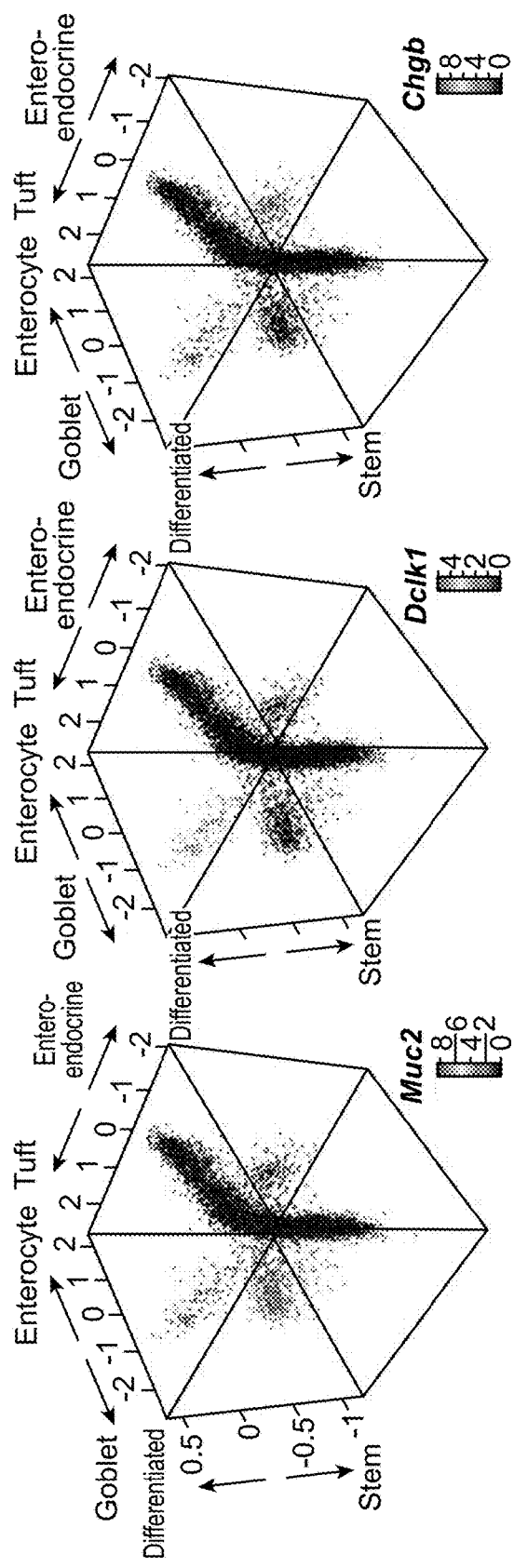
Figures 9C, 9D, 9E:
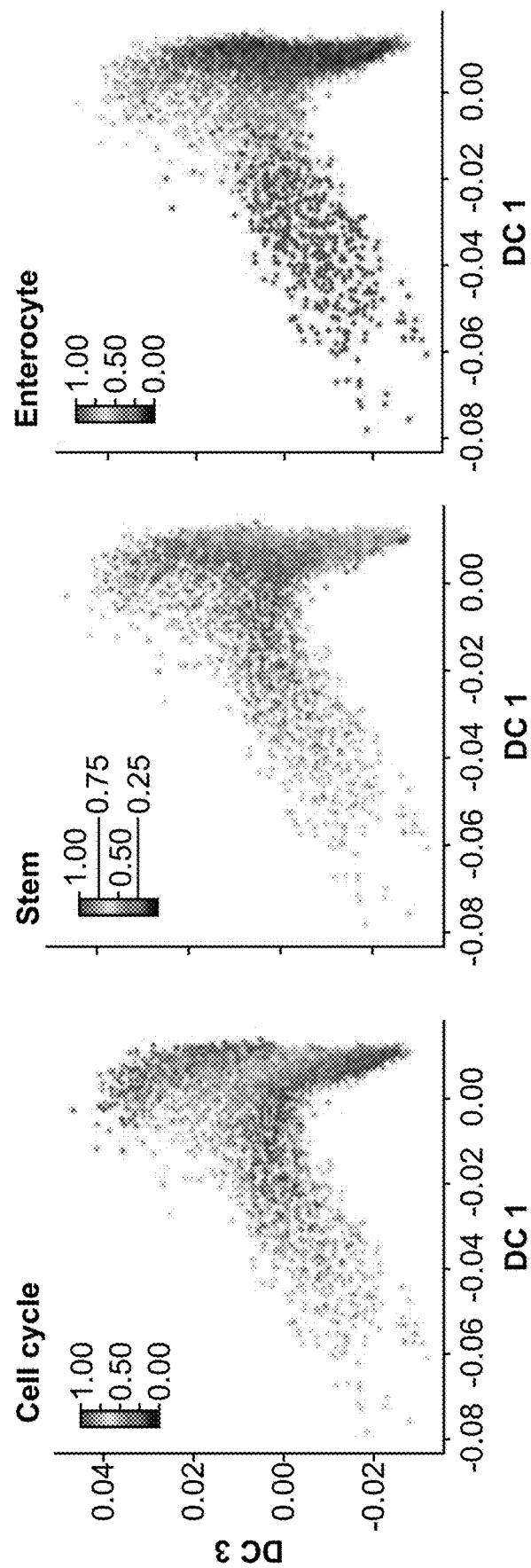

Example 3—Distinct Regulators are Associated with the Proliferation-Differentiation and Proximal-Distal Axes The largest components of variation (PC-i and PC-2) between single cells in the atlas reflect the processes of proliferation and differentiation in the small intestine (FIG. 9a). Applicants thus used the cell-type signatures (Table 4) to embed each cell in a three-dimensional space (FIG. 2a), such that its location corresponds to its lineage fate, and to its stage of differentiation towards that fate (Methods). Applicants confirmed that Lgr5-expressing cells were positioned at the base of the embedding (FIG. 2a, left). Scoring of a cell-cycle state signature[29] highlighted the presence of rapidly proliferating cells above the stem cells (FIG. 2a, center), with a somewhat lower expression of stemness related genes, but not yet expressing markers for differentiated cell types, corresponding to TA progenitor cells, as previously suggested[38]. The distinct "leaves" on top reflected Muc2-expressing goblet cells, Dclk1-expressing Tuft cells, and Chgb-expressing EECs (FIG. 9b), whereas the expression of the enterocyte marker Alpi gradually increased along a dense branch of cells moving towards the enterocyte lineage (FIG. 2a, right). Although the vast majority of these Alpi-expressing cells are well on their way to the enterocyte lineage, a small subset co-expresses Alpi and crypt-specific markers (Slc12a2, Ascl2, Axin2, and Lgr5) (data not shown), consistent with a recent report[39].

Focusing on the abundant population of enterocytes, Applicants used diffusion maps[40] to place them in a pseudo-temporal order (FIG. 2b-e). Several recent studies[41,42] have shown that cellular differentiation and fate determination can be modeled as a dynamic process on a high-dimensional manifold, which can be inspected by ordering cells—sampled simultaneously from an ongoing asynchronous process—in pseudo-time. In this case, considering the first and third diffusion components (DC-1 and 3) highlighted a trajectory from stem-like to progenitor to immature enterocytes (FIG. 2b, FIG. 9c-e and FIG. 10a-c).

Figure 10P:
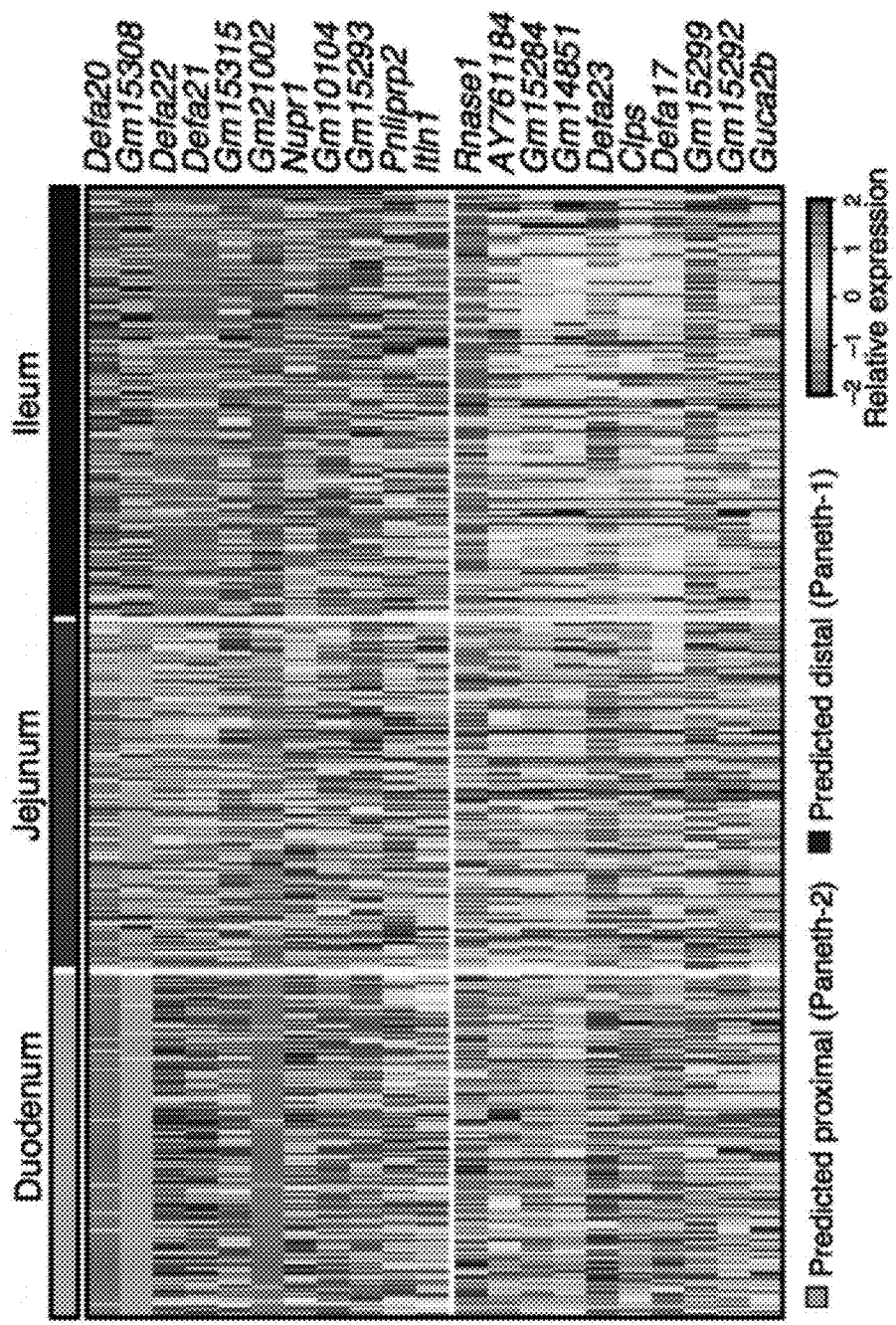
Figure 10Q:
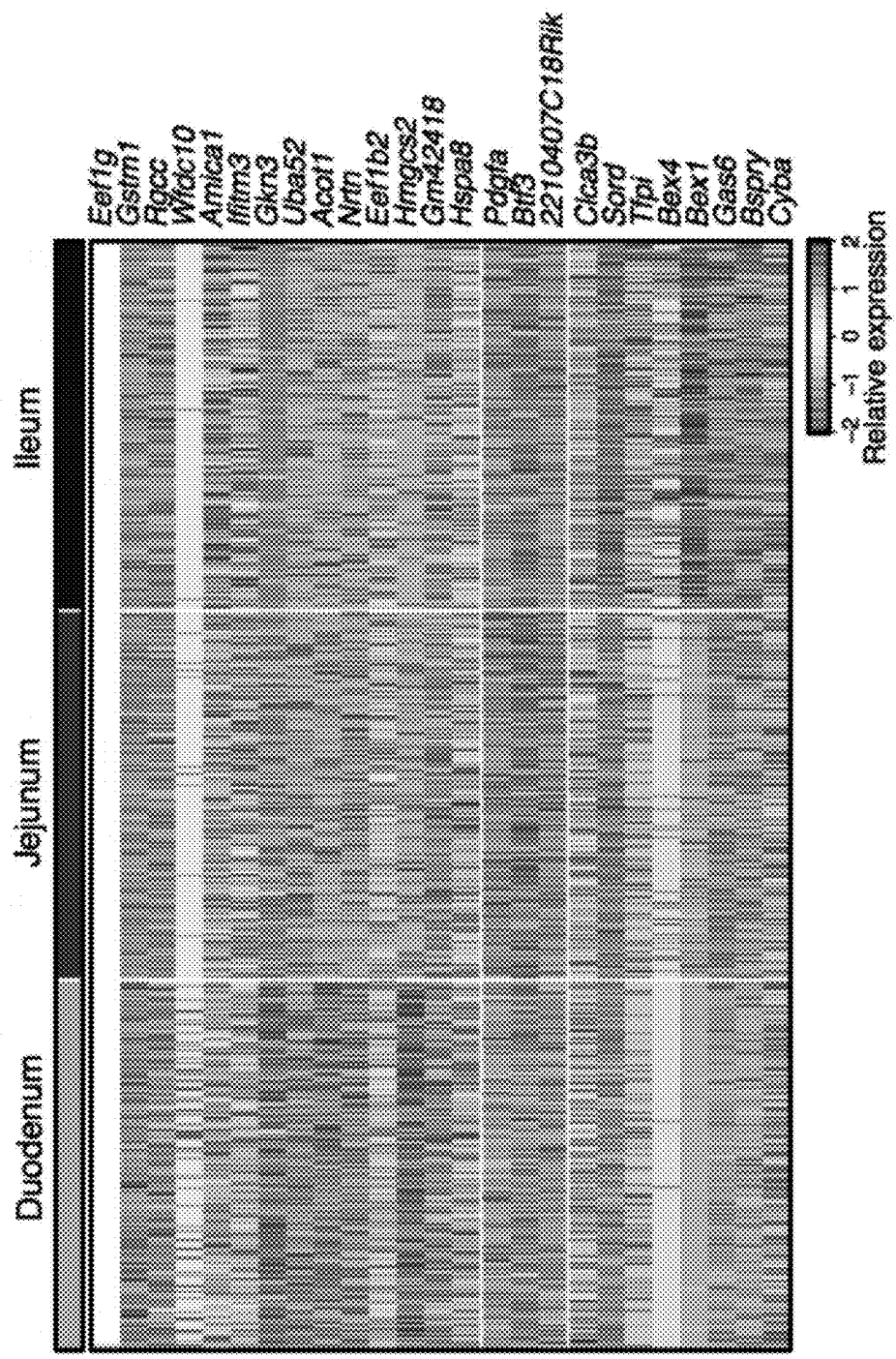

DC-2 captured a process of branching lineage commitment between enterocytes of the proximal (duodenum and jejunum) and distal (ileum) small intestine (FIG. 2c, FIG. 10d-f), emphasizing the adaptation of enterocytes to absorb different carbon sources, from easy to digest carbohydrates to more complex molecules such as fat. Applicants tested this prediction, by profiling another 11,665 single cells from the duodenum, jejunum and ileum separately (n=2 mice, FIG. 10h), and recovering genes differentially expressed in the 1,041 absorptive enterocytes from the different regions (Methods). Indeed, of the 64 and 44 genes identified as signature genes for mature proximal and distal enterocytes, respectively, (Methods, FIG. 1c and Table 3), 60 and 23, respectively, were also differentially expressed (FDR<0.05 Mann-Whitney U-test) between proximal (duodenum and jejunum) and distal (ileum) regions (FIGS. 10l and 10j). Furthermore, smFISH confirmed the regional distribution of enterocytes expressing Lct and Fabp6 markers[43] in the duodenum and ileum, respectively (FIG. 10k). Most marker genes of the two Paneth cell subsets (FIG. 10o) are enriched (FDR<0.05) in proximal or distal gut respectively, confirming that they reflect regional distinctions (FIG. 10p); the novel marker Mptx2 showed no regional specificity (Table 10). Finally, the stem cells in each region also express region-specific markers (FIG. 10q), which when examined in either the non-regional (FIG. 10r) or the regional (FIG. 10m) diffusion maps mark distinct ISC subsets, each likely foreshadowing the eventual distinct enterocytes from the corresponding region (FIG. 10n).

and function as metabolic signal transduction units[146]. Enteroendocrine cells (EECs) in the small intestine are a major site of hormone production, and were reported to comprise 8 distinct sub-classes, traditionally classified by the primary hormone they produce[11,47,48], such that cells expressing Sct, Cck, Gcg or GIP were traditionally termed S, I, L and K cells, respectively[12]. However, significant crossover between traditional subtypes has been observed[12,22], such that the same hormone may be expressed by more than one type. Thus, a classification based on a single "marker" hormone may not represent the true diversity and function of EECs (Gribble and Reimann, 2016), and may limit the ability in follow up studies based on these genes.

Applicants identified a cluster of EECs in both the whole SI (FIG. 1b, 310 cells) and regional datasets (FIG. 10h, 239 cells) based on expression of known markers, including Chromogranin A (Chga) and B (Chgb), which this study confirmed as the two best markers for this group identified by the unbiased analysis (FIG. 11e), along with GDNF

TABLE 10

DE results [droplet-data], ranked by Log2 fold-change Paneth-1 (distal) vs. Paneth-2 (proximal)

| Gene symbol | Mean expression (Log2 TPM + 1) Paneth-1 | Mean expression (Log2 TPM + 1 Paneth-2 | log2fe | p | p.adj |
|---|---|---|---|---|---|
| Defa20 | 8.43307629 | 4.191569275 | 4.241507015 | 4.59E−198 | 1.29E−193 |
| Gm15308 | 6.747161753 | 2.622293721 | 4.124868032 | 1.82E−194 | 2.55E−190 |
| Defa22 | 8.938663197 | 4.944112099 | 3.994551098 | 2.63E−177 | 2.45E−173 |
| Defa21 | 8.979216936 | 5.396694643 | 3.582522293 | 3.65E−165 | 2.56E−161 |
| Guca2a | 3.927258003 | 1.966457829 | 1.960800174 | 3.25E−158 | 1.82E−154 |
| Gm15315 | 2.93782559 | 1.484980923 | 1.452844667 | 1.03E−82 | 2.40E−79 |
| Gm21002 | 1.426481352 | 0.165194501 | 1.261286851 | 2.44E−108 | 9.77E−105 |
| Nupr1 | 2.47171844 | 1.419388432 | 1.052330007 | 2.80E−90 | 7.85E−87 |
| Gm10104 | 3.266743446 | 2.254967422 | 1.011776024 | 1.48E−90 | 4.61E−87 |
| Gm1123 | 1.646936159 | 0.685262667 | 0.961673491 | 4.34E−71 | 8.69E−68 |
| Agr2 | 2.958898977 | 2.108410455 | 0.850488522 | 9.78E−50 | 1.61E−46 |
| Muc2 | 2.572337443 | 1.749806632 | 0.822530811 | 6.74E−49 | 1.05E−45 |
| Gm15293 | 1.67374113 | 0.895914849 | 0.777826282 | 1.16E−44 | 1.55E−41 |
| Pnliprp2 | 2.801230998 | 2.134237786 | 0.666993213 | 1.69E−11 | 7.07E−09 |
| Tspan1 | 1.333205915 | 0.716544122 | 0.616661793 | 2.21E−46 | 3.09E−43 |
| Itln1 | 7.721067156 | 7.13664624 | 0.584420916 | 1.35E−15 | 8.40E−13 |
| Pglyrp1 | 2.681719453 | 2.143612461 | 0.538106992 | 5.20E−43 | 6.62E−40 |
| mt-Atp6 | 4.984661454 | 4.469107748 | 0.515553706 | 6.48E−12 | 2.79E−09 |
| Guca2b | 3.555007019 | 4.08419426 | −0.529187242 | 2.46E−42 | 3.00E−39 |
| Gm15292 | 4.123432202 | 4.663038688 | −0.539606487 | 1.24E−25 | 1.20E−22 |
| Gm15299 | 2.822490385 | 3.416108207 | −0.593617822 | 5.07E−36 | 5.91E−33 |
| Defa17 | 4.869214625 | 5.476804872 | −0.607590247 | 3.46E−58 | 6.45E−55 |
| Clps | 5.793805073 | 6.504310944 | −0.710505871 | 1.18E−50 | 2.07E−47 |
| Defa23 | 2.958117378 | 3.6903216 | −0.732204222 | 3.84E−21 | 3.36E−18 |
| Gm14851 | 8.518496669 | 9.343126247 | −0.824629578 | 3.56E−83 | 9.06E−80 |
| Gm15284 | 9.174886103 | 10.05353355 | −0.878647448 | 6.25E−73 | 1.35E−69 |
| AY761184 | 8.318749405 | 9.553086427 | −1.234337022 | 4.50E−104 | 1.57E−100 |
| Rnase1 | 1.026127868 | 2.459104539 | −1.432976671 | 3.18E−111 | 1.48E−107 |

Figures 2D, 2E:
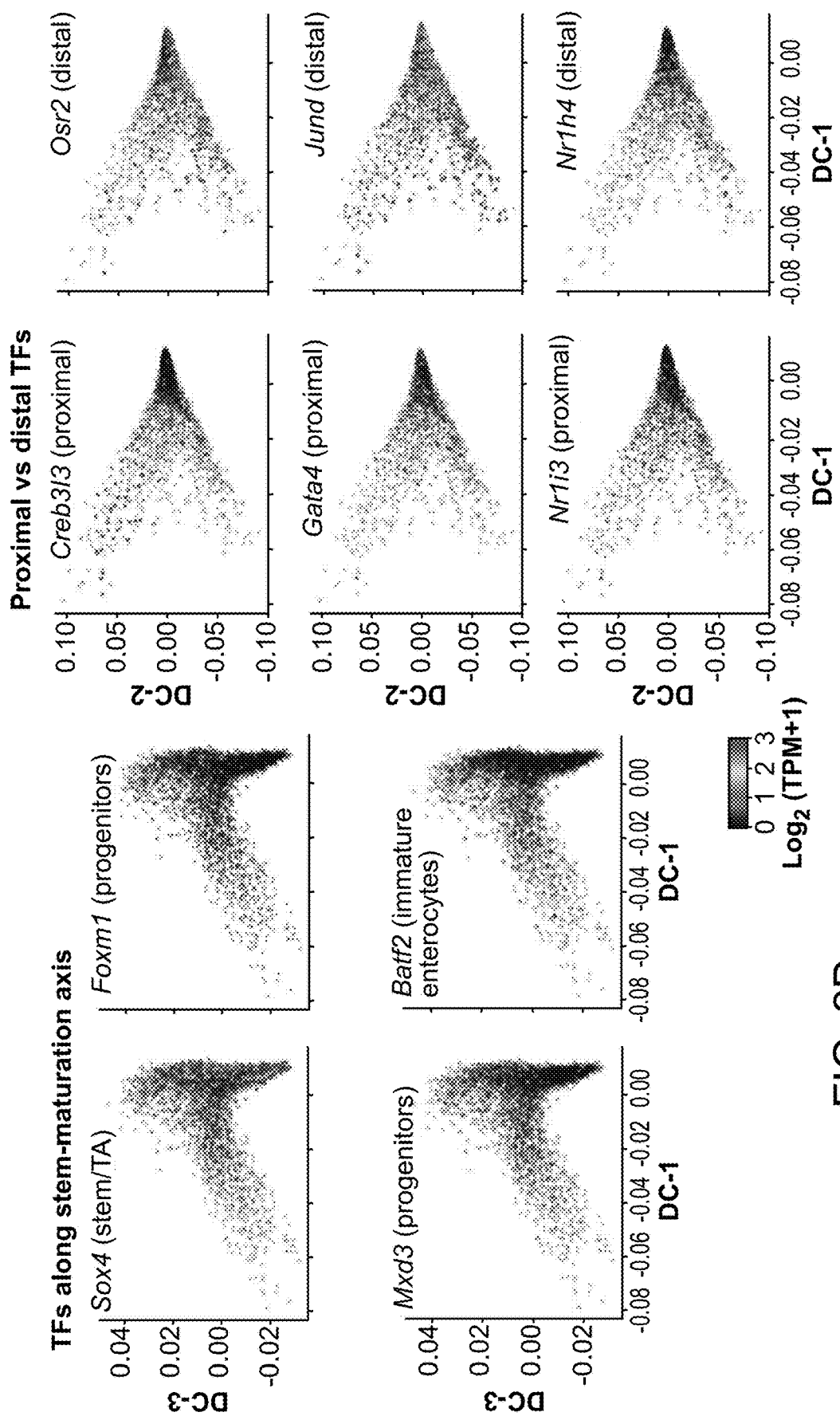

Finally, Applicants identified TFs with specific expression patterns in different regions of the diffusion map (Methods), associating regulators with early enterocyte lineage commitment (known: Sox4[44], and novel: Batf2, Mxd3 and Foxm1) (FIG. 2d and FIG. 10g), or with proximal and distal intestinal identity (known: Gata4, Nr1h4[41,46] and novel: Creb313, Jund, Osr2, Nr1i3) (FIG. 2e).

Figure 3A:
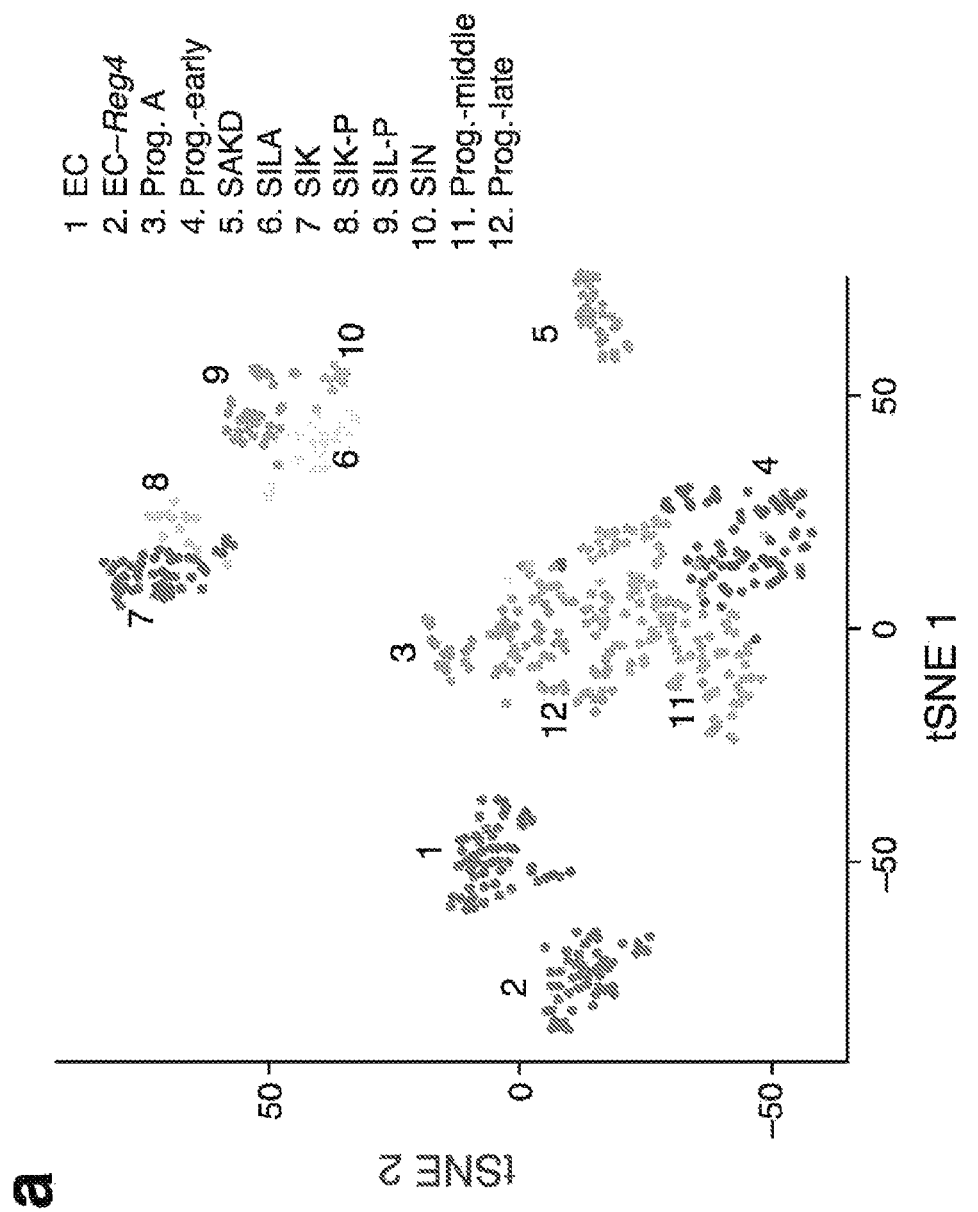
Figure 3B:
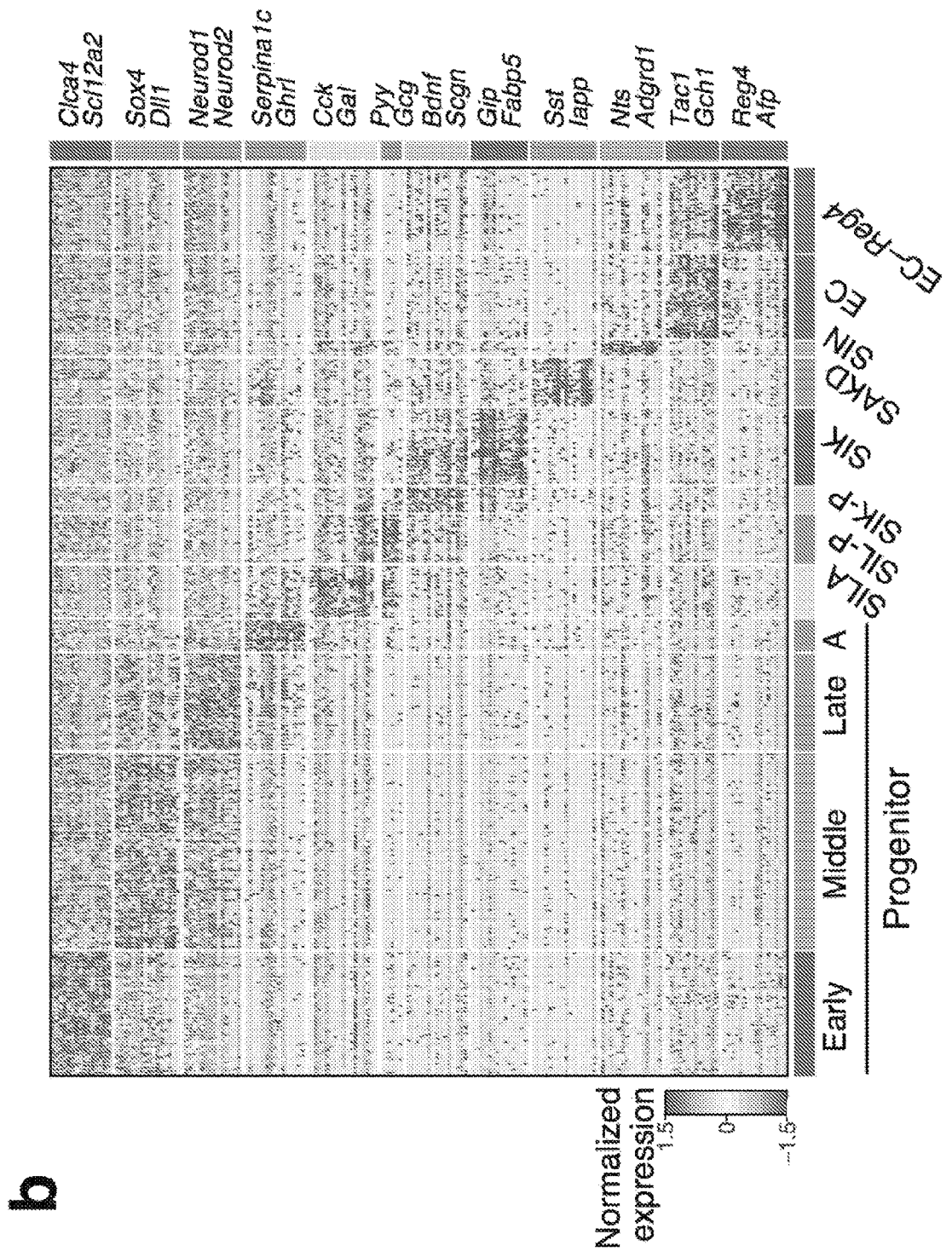

Example 4—Taxonomy of Enteroendocrine Cells is Defined by Hierarchical Hormone Expression Enteroendocrine cells (EECs) are key sensors of nutrients and microbial metabolites[11,12] that secrete diverse hormones family receptor alpha-3 (Gfra3) as a novel and specific marker (FIG. 11e), for a total of 533 EECs (Methods). To define putative EEC subtypes ab initio, Applicants separately clustered these 533 cells, and distinguished 12 clusters (FIG. 3a, FIG. 11a), each supported by a distinct gene signature (FIG. 3b, Table 7, Methods). Four of the EEC groups expressed markers of EEC precursors (Neurog3, Neurod1, Sox4), while the other eight represented mature EEC subsets. A recent study of scRNA-seq of organoid derived EECs showed EEC heterogeneity but with fewer EEC subsets[53].

TABLE 7

Summary of marker genes for enteroendocrine subsets

| Progenitor (early) | Progenitor (late) | Progenitor (mid) | Progenitor (A) | SAKD | SILA |
|---|---|---|---|---|---|
| Pycard | Tubb3 | Fcgbp | Maged2 | Sst | Cck |
| Oat | Neurod1 | Tff3 | Cdkn1a | Iapp | Parm1 |
| Clca3b | Neurod2 | Bcl2 | Serpina1c | Hhex | Scg2 |
| Cps1 | Gadd45a | Aldob | Acsl1 | Acot7 | Tspan13 |
| Dbi | Drap1 | Gadd45g | Ceacam10 | Rgs4 | Cpn1 |
| Prap1 | Btbd17 | Litaf | Zcchc12 | BC048546 | Crp |
| Ppp1r1b | Mrfap1 | Sox4 | Cxxc4 | Arg1 | Anpep |
| Hspe1 | Cyth2 | Slc39a2 | Il11ra1 | Asic5 | 0610011F06Rik |
| Mgst1 | Mapk15 | Tmsb10 | Cdkn1c | Kcnk2 | Gal |
| Gpx1 | Vasp | Fuca1 | Mboat4 | Fam151a | Fars2 |
| Pigr | Esd | Prom1 | 1500009L16Rik | Th | Hepacam2 |
| Tkt | Trp53i11 | Dll1 | Krt18 | Pdx1 | Gpr119 |
| Hspd1 | Clta | Mfge8 | Bambi | Fam46a | Gclm |
| C1qbp | Eif4a1 | Hmgb3 | Rgs17 | Serpina1a | Tm4sf4 |
| Cd74 | Btg2 | Top1 | Arx | Hgfac | Agr3 |
| Ccl25 | Tubb5 | Ddit4 | Plb1 | Tmem108 | Gnai1 |
| Mt1 | Dbn1 | Nek6 | Fxyd2 | Cd24a | Tm4sf5 |
| Csrp2 | Ypel3 | Gpx2 | Trp53i13 | Rbpms | Sult1d1 |
| Kcne3 | Psmd10 | Slc25a5 | Necab2 | | Krt20 |
| Cldn15 | Fhl2 | Pdha1 | Serpina1d | | Upp1 |
| Slc12a2 | Yipf4 | Txndc5 | Tuba1a | | Nr4a2 |
| Mrpl12 | Cct2 | Casp6 | Gng4 | | Itm2b |
| Amica1 | Rnase4 | Eif4g2 | Ghrl | | |
| Nop10 | Krt7 | Nme1 | Card19 | | |
| Tuba1b | Eif3l | Fubp1 | Arhgap22 | | |
| Mcm6 | Prmt1 | Llph | Fam183b | | |
| Pglyrp1 | Npc2 | Rps10 | Nefm | | |
| Banf1 | Gltscr2 | Bok | Isl1 | | |
| Aprt | Cdk2ap1 | Vgll4 | Akr1c19 | | |
| Reg3g | Tsg101 | Rnase1 | Cd177 | | |
| Idh3a | Eif3h | Rps4x | H1fx | | |
| 2810417H13Rik | Jund | Rpl26 | Capsl | | |
| Anp32b | Zfos1 | Eef1g | Nefl | | |
| Tomm5 | Mtch1 | Acadsb | Nkx2-2 | | |
| Phb2 | Cdk4 | Rps25 | Serpina1e | | |
| Fgfbp1 | Hpcal1 | Lypd1 | | | |
| Sdc4 | Hnrnpk | Hmgn1 | | | |
| Ncl | Fgd2 | Rps26 | | | |
| Lypd8 | Rph3al | Rps8 | | | |
| Ccnd2 | Prdx2 | Cd9 | | | |
| Ran | Crybb1 | Shfm1 | | | |
| Dmbt1 | Dact2 | Rps5 | | | |
| Reg3b | Csnk1a1 | Srsf2 | | | |
| Sdha | Calm2 | Sap30 | | | |
| Chchd10 | Eif3f | Hdac2 | | | |
| Aldh1b1 | Marcksl1 | Rplp0 | | | |
| Lgals9 | Hspa8 | Rps3 | | | |
| Atp5o | Tead2 | Cdc14b | | | |
| Snrpd2 | Srsf6 | Hnrnpab | | | |
| Ociad2 | Rcor2 | Qsox1 | | | |
| Hmgb2 | Adrm1 | Rpl8 | | | |
| Hspa9 | Eef2 | Sypl | | | |
| Prss32 | H3f3a | Tubb2b | | | |
| Tjp3 | Krt8 | Ywhaq | | | |
| Ndufb9 | Cd63 | | | | |
| Lsm2 | Psmc6 | | | | |
| Mcm2 | 2700060E02Rik | | | | |
| Dtymk | Neurog3 | | | | |
| Lsm4 | Ppib | | | | |
| Nucks1 | Tmem176b | | | | |
| Naa10 | Btf3 | | | | |
| Ranbp1 | Uqcrc2 | | | | |
| Nlrp6 | Pcbp1 | | | | |
| Cyc1 | Tpm4 | | | | |
| G3bp1 | Naca | | | | |
| Cox7b | Pcbp2 | | | | |
| Ube2c | Ooep | | | | |
| Cdca7 | Pfdn5 | | | | |
| Ndufv1 | Psma7 | | | | |
| Cenpa | Smarcd2 | | | | |
| Rnf186 | Sdcbp | | | | |
| Siva1 | Pdap1 | | | | |
| Cyba | Hn1 | | | | |
| 2700094K13Rik | Smim6 | | | | |
| Dctpp1 | Akr1c12 | | | | |

TABLE 7-continued

Summary of marker genes for enteroendocrine subsets

| | |
|---|---|
| Cdca8 | Cct4 |
| Snrpd1 | Cpt2 |
| Alyref | Ftl1 |
| Nhp2 | Igsf8 |
| Ldha | Commd3 |
| Tsfm | Hsp90ab1 |
| Mapk13 | Ppp1r14b |
| Aqp1 | Gadd45gip1 |
| H2-Ab1 | Rps21 |
| Mif | Akr1c13 |
| Mlec | Eif3k |
| Sri | Stard10 |
| Hes1 | Vwa5b2 |
| Pmf1 | Serbp1 |
| Lsm3 | |
| Rnaseh2c | |
| Marc2 | |
| Lyar | |
| Ppa1 | |
| Tomm40 | |
| B2m | |
| Plcb3 | |
| Uqcrc1 | |
| Cox5a | |
| Timm10 | |
| Exosc5 | |
| Cct3 | |
| Aars | |
| Mecr | |
| Spc24 | |
| Epcam | |
| Lmnb1 | |
| Prdx4 | |
| Gar1 | |
| Aadac | |
| Snrpb | |
| Kcnq1 | |
| Trim28 | |
| Cox6a1 | |
| Mettl1 | |
| Cox5b | |
| Ybx1 | |
| Ndufs7 | |
| Acat1 | |
| Ifrd2 | |
| Hsd17b10 | |
| Psme2 | |
| Ascl2 | |
| Atp5h | |
| Cebpb | |
| Cldn3 | |
| Cdca3 | |
| Agmat | |
| Snrpg | |
| Anapc13 | |
| Eif3b | |
| Pycrl | |
| Atp5j | |
| Cldn7 | |
| Fh1 | |
| Phb | |
| Sdhb | |
| Nxt1 | |
| Slc25a3 | |
| Myb | |
| Cox7a2 | |
| H2-DMa | |
| Vipr1 | |
| Fam195a | |
| H2-Eb1 | |
| Sdsl | |
| Mcm5 | |
| Cluh | |
| Eif5a | |
| Aimp2 | |
| Emg1 | |
| Rps27l | |
| Mcm3 | |

TABLE 7-continued

Summary of marker genes for enteroendocrine subsets

Srsf7
Uqcrq
Trap1
Tmem147
Atp5d
Rpl39
B4galnt1
Rcc2
Farsb
H2afx
Uqcr10
Ifngr1
Tyms
Hnrnpu
Ivns1abp
Atad3a
Tk1
Ifitm3
Klf5
Abhd11os
Gmnn
Kcnn4
Galk1
Ruvbl2
H2afv
Tfrc
H2afj
Atpif1
Prelid1
Slc39a5
Bdh1
Timm9
Noxo1
Bola3
Ndufa4
Pdss1
Txn2
Npm3
Rpl13
Ccnb2
Ccdc34
S100a10
Tmsb4x
Pa2g4
Rpsa
Cdk2ap2
Uqcr11
Birc5
Top2a
Anp32e
2200002D01Rik
Rpl12
Car9
Gjb1
Eef1d
Prdx6
Atp5j2
Ddx39
Rpl7
Txn1
Rps15
Rps16
Cox8a
Ndufa5
Aoc1
Mgam
Serinc3
Rfc3
Rrm1
Haus4
Stmn1
Rsl1d1
Rps19
Ccnd1
Gcat
Dhrs4
Atp5b
Fth1

TABLE 7-continued

Summary of marker genes for enteroendocrine subsets

Rplp1
Hnrnpa2b1
Pabpc1
Cox6c
Pebp1
Gm1123
Rpl37
Rpl18
Otc
Lig1
Vsig10
Atp5a1
Cks1b
Rpl34
Abhd11
Rplp2
Rps20
Shmt1
Gnb2l1
Dut
Nasp

| SIK | SIK-P | SIL-P | SIN | EC | EC Reg4 |
|---|---|---|---|---|---|
| Gip | Car8 | Pyy | Nts | Tac1 | Reg4 |
| Rbp2 | Cdhr5 | Gcg | Crip1 | Vim | Afp |
| Pkib | Bdnf | Rnf130 | Sct | Gch1 | S100a1 |
| Tpst1 | Hexb | Nostrin | Adgrd1 | Fev | Chga |
| Phlda1 | Gatm | Gpbar1 | Car4 | Scn3a | Ambp |
| Acadl | Rnf32 | Scin | Agr2 | Slc25a35 | Tpbg |
| Fabp5 | Entpd5 | | Id3 | Pdk3 | Apoc3 |
| Fam213a | Itm2c | | 4930539E08Rik | Slc38a11 | Gstt1 |
| Itpr1 | Fam105a | | Tppp3 | Tmem158 | Gstk1 |
| Tmprss7 | 1700086L19Rik | | Tnks1bp1 | Cox7a2l | Rgs2 |
| Fam167a | Il17re | | S100a11 | Igfbp3 | Mapk14 |
| Nrn1 | Tmem163 | | Ece1 | Mnx1 | Apoa1 |
| Gpx3 | Gm14964 | | Tmem38a | Serpinb1a | Rab3b |
| Rhou | Scgn | | Scg3 | Fam204a | Cyp2d26 |
| Bnip3 | Scarb1 | | Fxyd5 | Cyp4b1 | Gsdmd |
| Rogdi | Prps1 | | Espn | Hmgn3 | Serpinf2 |
| Scp2 | Pax6 | | Ffar1 | Glud1 | C1qa |
| Fabp1 | Resp18 | | Dnajc12 | Sepp1 | Me2 |
| Rbp4 | Slc6a19 | | Gchfr | Tph1 | Ucn3 |
| Tspan7 | 1110032F04Rik | | Uchl1 | Pfn1 | Ica1 |
| | Anxa6 | | Gcnt3 | Gspt1 | Ptprn |
| | Anxa5 | | Nrp1 | Gm43861 | Upb1 |
| | 1110017D15Rik | | Rprml | Bax | Itpr3 |
| | Cib2 | | Banf2 | Ddt | Psat1 |
| | Scg5 | | Qpct | Sec61b | Fxyd6 |
| | Abcc8 | | Myl7 | | Rpp25 |
| | Gmpr | | Sis | | Prodh2 |
| | Ffar4 | | Gucy2c | | Gde1 |
| | | | Disp2 | | C1qtnf4 |
| | | | Rab37 | | Ndufv3 |
| | | | Bcam | | Pcsk1 |
| | | | | | Tmem106a |
| | | | | | Bex2 |
| | | | | | Rhoc |
| | | | | | Trpa1 |
| | | | | | Slc18a1 |
| | | | | | Uqcc2 |
| | | | | | Ndufa2 |
| | | | | | Igfbp4 |
| | | | | | Ttr |
| | | | | | Acvrl1 |
| | | | | | Atp6v1b2 |
| | | | | | Atp5e |
| | | | | | Camk2n1 |
| | | | | | Lmx1a |
| | | | | | Qdpr |
| | | | | | Ssbp2 |
| | | | | | Rab3c |
| | | | | | S100a13 |
| | | | | | Edf1 |
| | | | | | Chgb |
| | | | | | Ddc |
| | | | | | Ngfrap1 |
| | | | | | Comt |

TABLE 7-continued

Summary of marker genes for enteroendocrine subsets

Minos1
Tmigd3
Tceb2
Atp5k
Pkdcc
Atp5g1
Gars
Rbp1

Significance cut-offs: FDR (Fisher's combined): 0.01, Log2 fold-change: 0.1, Fraction-expressing: 0.25

Figure 3C:
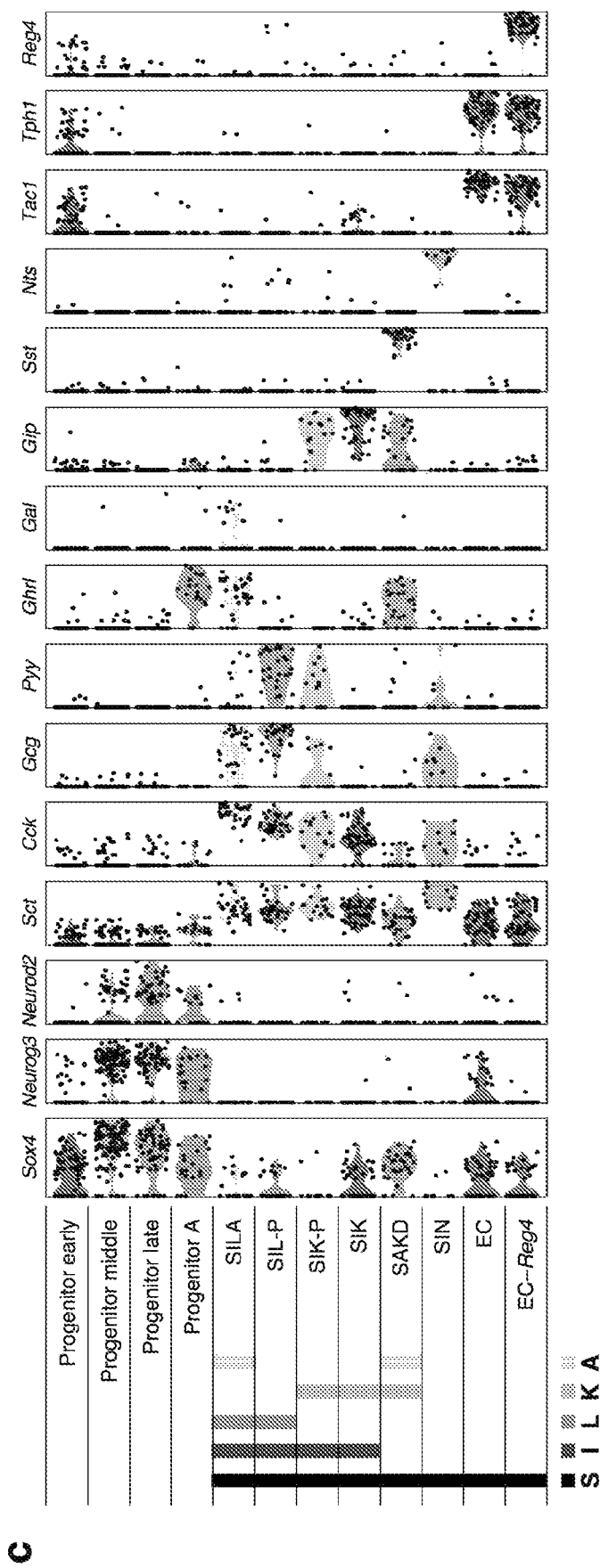
Figure 11C:
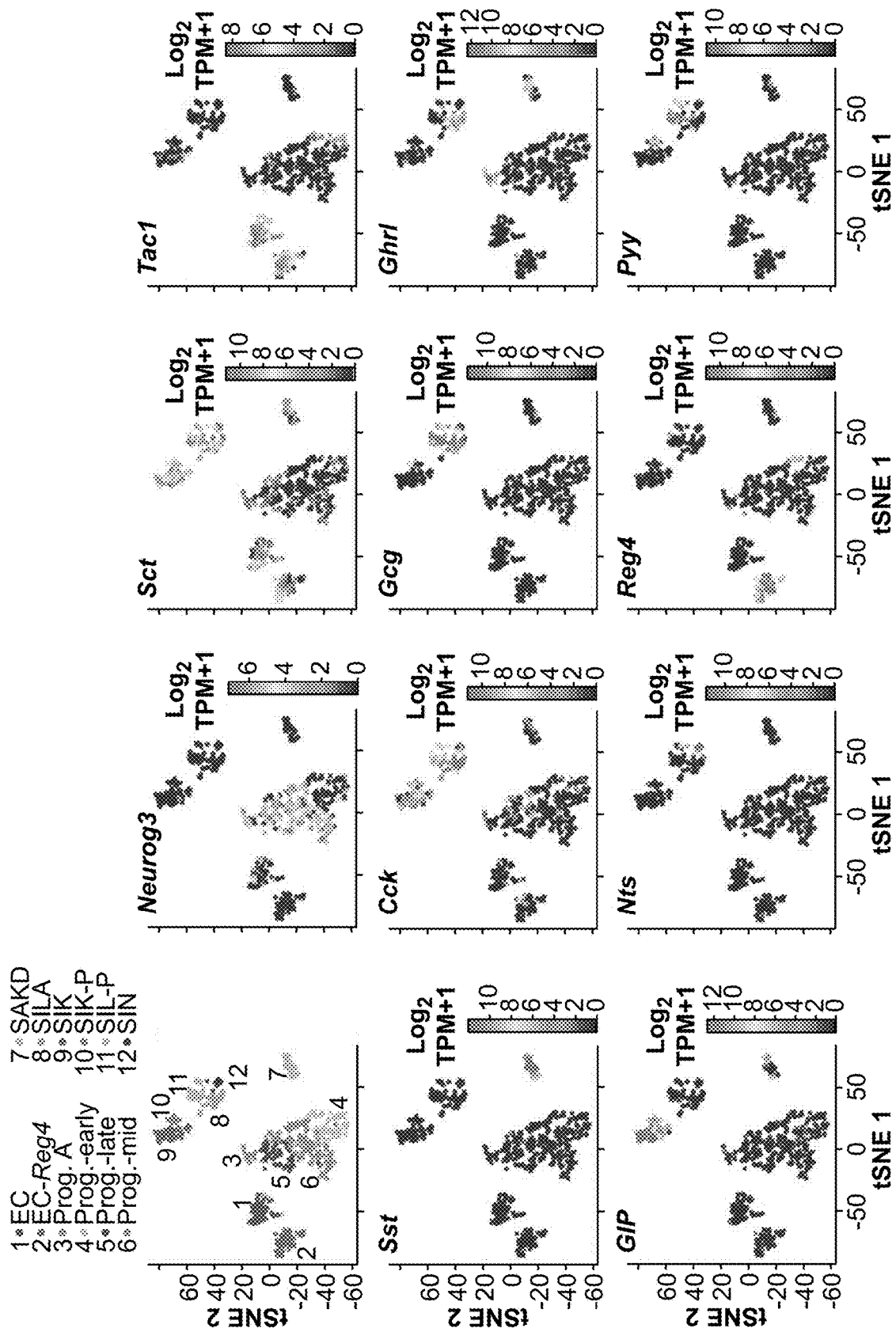

Applicants then compared this ab initio taxonomy to the canonical classification by the expression of the marker hormones in each cluster (FIG. 3c). Consistent with earlier reports[22,49] several key hormones were expressed across multiple clusters rather than in a single group of cells. For example, Secretin (Sct), previously reported to be produced solely by S-cells[11], was expressed by cells in all mature EEC clusters, albeit at varying levels (FIG. 3c). Similarly, Cholecystokinin (Cck), the canonical marker for I-cell s[49], was expressed in cells spanning five clusters. This surprisingly broad expression pattern of several hormones, particularly Sct and Cck, was reproducible and concordant in the high-coverage full-length scRNA-seq data, with excellent agreement in detection frequency across all GI hormones (FIG. 11b). In some cells, Cck was co-expressed with both glucagon (Gcg) and Ghrelin (Ghrl), the markers of L- and A-cells, respectively. Notably, Cck-expressing cells are a subset of those expressing Sct, and Gcg and Ghrl expression induces a further subdivision of the cells (FIG. 3c and FIG. 11c-d), which Applicants validated using smFISH (FIG. 3d).

Figure 11D:
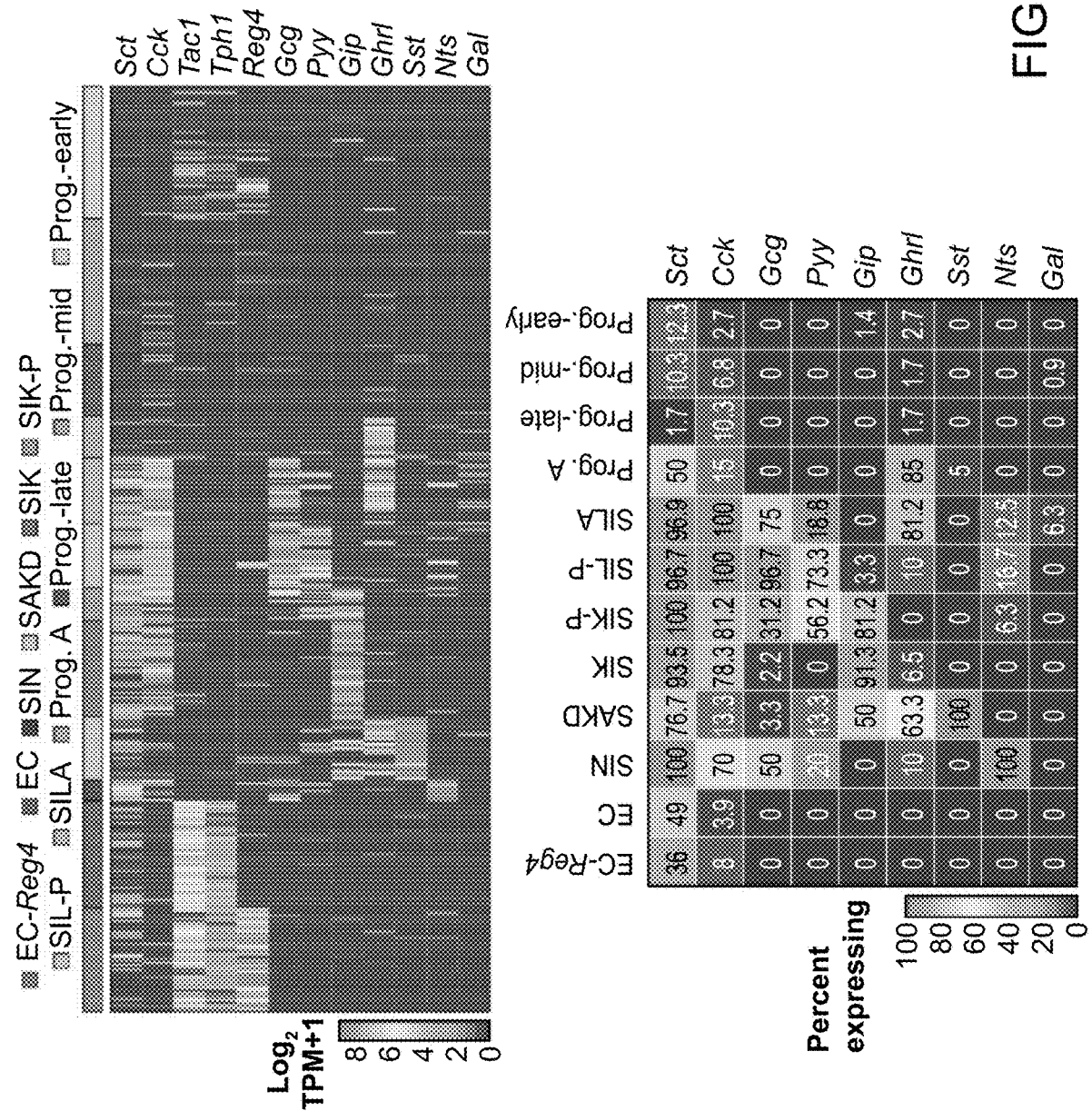
Figure 11E:
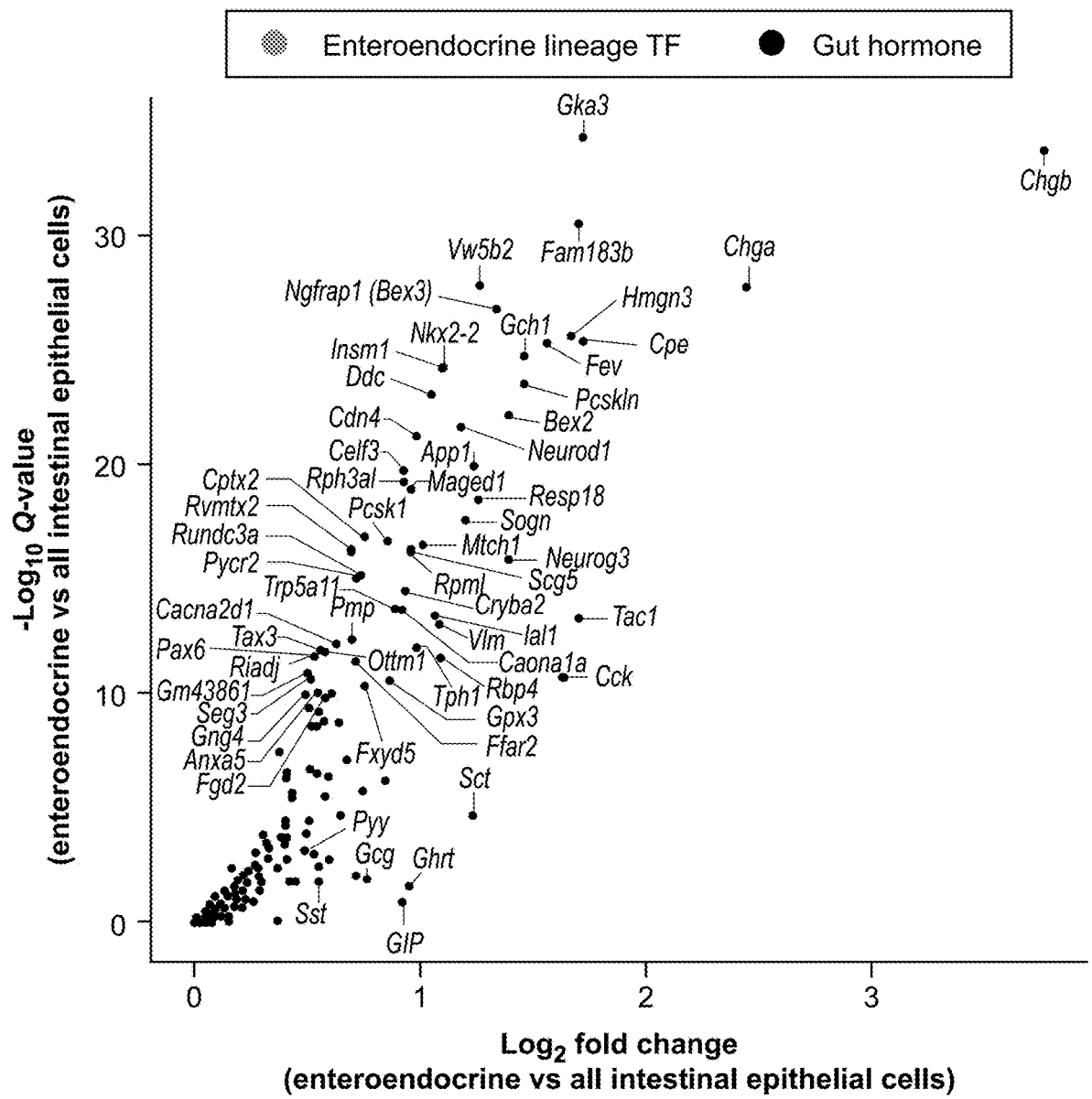

Applicants placed each cluster of mature EECs in the new taxonomy (FIG. 3c and FIG. 11d) and labeled it by the expression of canonical hormones if over 50% of the cells in the subset express a particular hormone, using bootstrap resampling-based hierarchical clustering (FIG. 12a) and cell-cell correlations (FIG. 12b) to assess the relationships between subsets. For example, in this taxonomy the Sct$^+$/Cck$^+$/Gcg$^+$/Ghrl$^+$ subset—the components of which were traditionally termed S, I, L and A cells respectively[12]—is annotated with the label S-I-L-A (FIG. 3c), which Applicants subsequently validated (FIG. 3d). Within each cluster, the marker hormones are co-expressed in individual cells, and therefore generally do not partition into further subsets (FIG. 11c-d). In addition to the more broadly expressed hormones, several hormones are subset-specific (FIG. 3c and FIG. 12c). In particular, Galanin (Gal) is specific to SILA, Neurotensin (Nts) to SIN, Nesfatin-1 (Nucb2) to SA, and Amylin (Iapp) and Somatostatin (Sst) to SAKD. This taxonomy represents a "snapshot" of the subsets of post-mitotic EECs: although Applicants did not see evidence for transitional states, Applicants cannot rule out the possibility of cells transitioning between hormonal profiles, especially in light of the current number of EECs in the cell atlas.

Some EEC subsets are preferentially localized to specific regions of the small intestine. Specifically, SILA, expressing Ghrelin (Ghrl), the hunger hormone[50], together with GCG, the incretin hormone 51, are enriched in the duodenum (FDR<0.25, $\chi^2$ test, Methods), while SIL-P and SIK-P, both expressing the hormone Peptide YY, which reduces appetite upon feeding[52], are found mainly in the ileum (FDR<0.1, $\chi^2$ test) (FIG. 3e and FIG. 11a), consistent with the roles of these hormones in the regulation of appetite[11].

Applicants note that a recent study[53] used scRNA-seq of 145 organoid-derived EECs to identify seven subsets. The present taxonomy of 12 subsets from 533 in vivo cells includes all those mature identified subsets[53], an additional three novel subsets (FIG. 12e, grey shading), including SIN, a particularly rare Nts-expressing subset, as well as a further sub-division of SIL and SIK cells that are enriched in the ileum, SIL-P and SIK-P.

Example 5—Two Sub-Types of Enterochromaffin Cells are Distinguished by Reg4 Expression Mature enterochromaffin cells (EC), EECs that secrete serotonin, regulate gut motility and secretory reflexes[54] and are implicated in diverse pathologies[55], partition into two clusters in the taxonomy. Both are readily identified by the expression of two canonical EC markers: Preprotachykinin-1 (Tac1), a precursor for neurokinin A and substance P, and Tryptophan hydroxylase 1 (Tph1), the rate-limiting enzyme in the biosynthesis of serotonin[56] (FIG. 3c and FIG. 11c-d). Comparing the gene signatures for the two clusters (FIG. 3b) highlighted Reg4 (regenerating islet-derived protein 4) and Afp as the top markers of one cluster ("EC-Reg4"), whereas Reg4 is barely detectable in the other cluster ("EC") (FIG. 3c). Although a recent single-cell study[23] suggested that Reg4 is a pan-enteroendocrine cell marker based on 238 cells from gut organoids, of the 7,216 cells Applicants profiled here, Reg4 is expressed in a subset of 35 out of 52 enterochromaffin cells (FIG. 3b-c and FIG. 11c-d), as well as in Paneth cells and in goblet cells (FIG. 12d). Applicants validated the partitioning of ECs by Reg4-specific expression in situ, validating the presence of two subsets of ECs (FIG. 3f).

As enteroendocrine cells play a central role in sensing luminal nutrients, Applicants examined the expression of genes encoding GPCRs in these cells, identifying those expressed significantly higher (FDR<0.25, Mann-Whitney U-test) in a given subset (FIG. 12f). Notably, the free fatty acid receptors 1 and 4 showed specific expression patterns. Ffar1 was highest in SIN cells, and also expressed by the Cck-expressing subsets previously collectively termed I-cells (SIL-P, STLA and SIK-P), while Ffar4 was highest in the GIP-expressing subsets (SIK and SIK-P). These receptors are known to induce the expression of GIP and Gcg to maintain energy homeostasis[51]. Ffar2 was expressed by some progenitors and by EC cells, but notably absent from GIP-expressing cells, while the oleoylethanolamide receptor Gpr119, important for food intake and glucose homeostasis[37], was expressed highest in SILA cells.

Example 6—Two Subgroups of Tuft Cells with Immune and Neuronal-Like Expression Programs Tuft cells are the chemosensory cells of the gut and are enriched for taste-sensing molecules[148]. Tuft cells, a relatively poorly characterized epithelial cell type, were recently shown to play a key role in the T helper 2 (Th2) response to parasitic worm infection, through secretion of the Interleukin-25 (Il25), a potent chemoattractant for type II innate lymphoid cells[14-16].

Figure 2F:
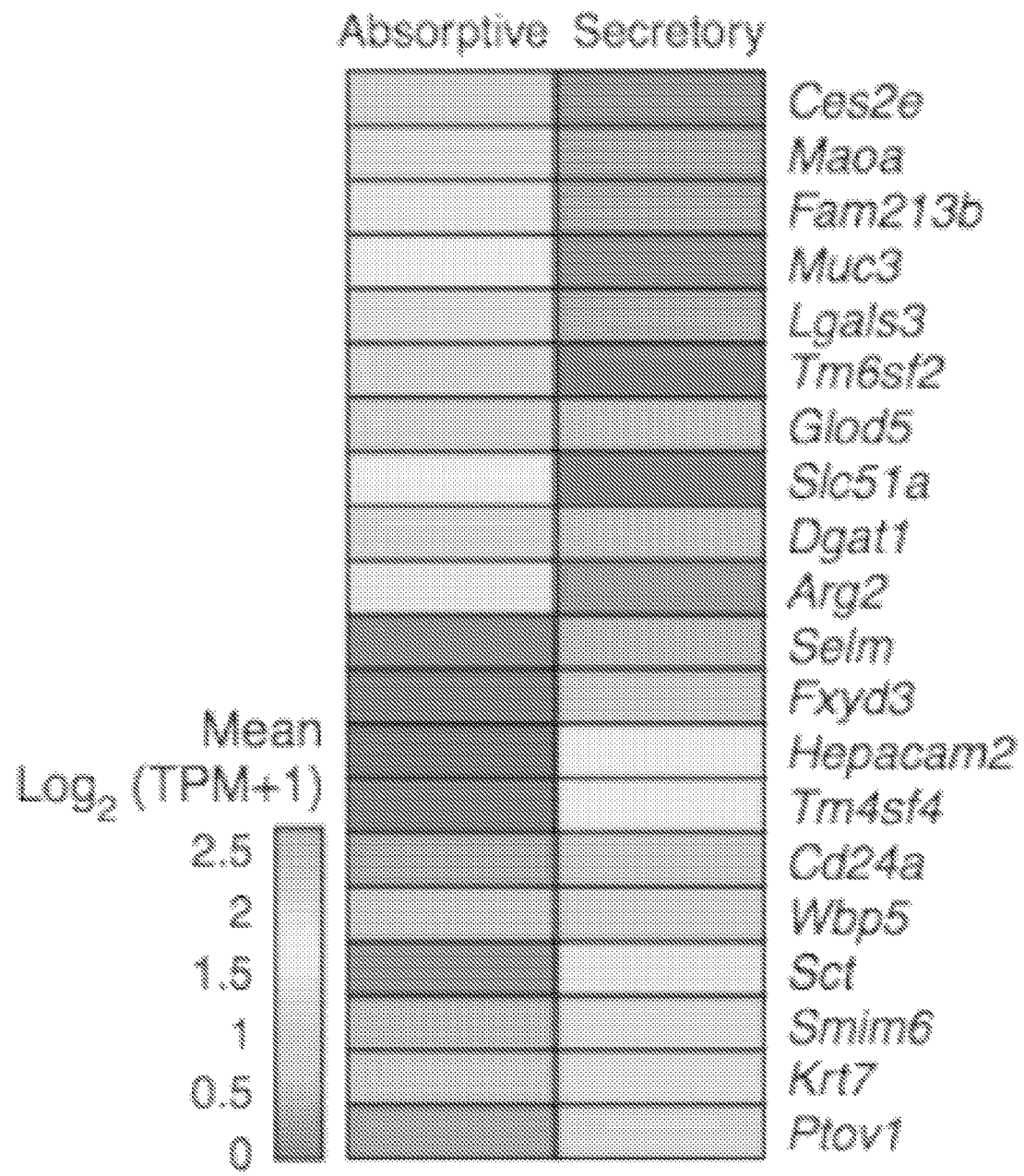
Figure 8I:
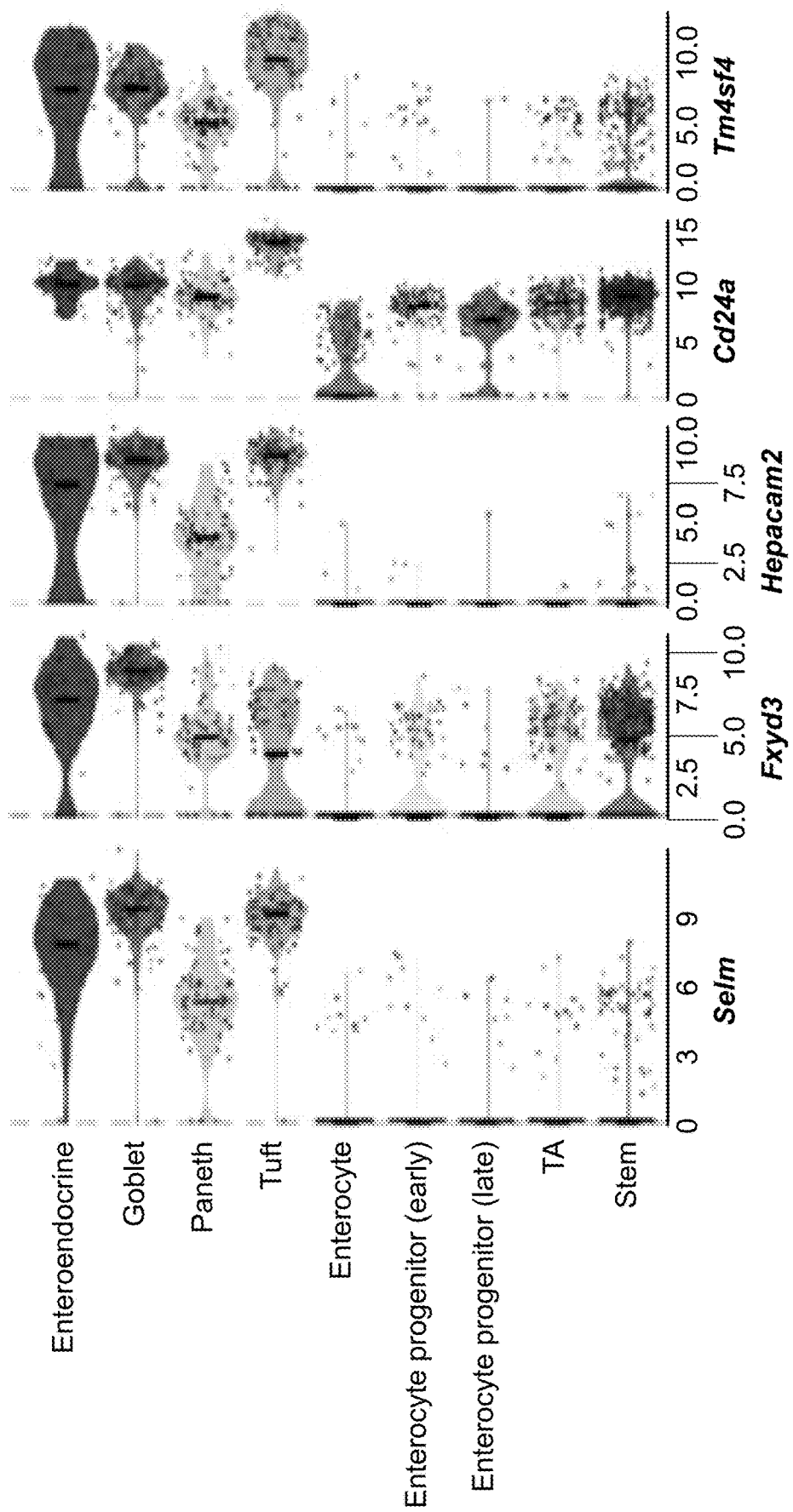

This study obtained sets of marker genes distinguishing the absorptive and secretory lineages and noticed that the known secretory lineage marker Cd24a (Sato et al., 2009) was indeed one of the specific markers for the secretory lineage (FIG. 2f). However, although Cd24a is broadly expressed by all secretory IECs, it was found to be expressed at a significantly higher level in tuft cells (FDR<0.05 Mann-Whitney U-test, FIG. 1C, FIG. 8I), which this study then confirmed at the protein level, observing a strong enrichment for tuft cells in a FACS sorted population of CD24+ high cells. This study therefore suggests that Hepacam2, a cell-surface marker, may be more useful to enrich for secretory cells without bias towards tuft cells (FIG. 8I).

A previous study[21] defined a tuft cell signature based on expression profiles of a bulk population of cells isolated using the cell surface marker Trpm5. The bulk signature had both neuronal and inflammation related gene modules; these could in principle be explained by either co-expression in the same cells or in distinct sub-types.

Figure 4A:
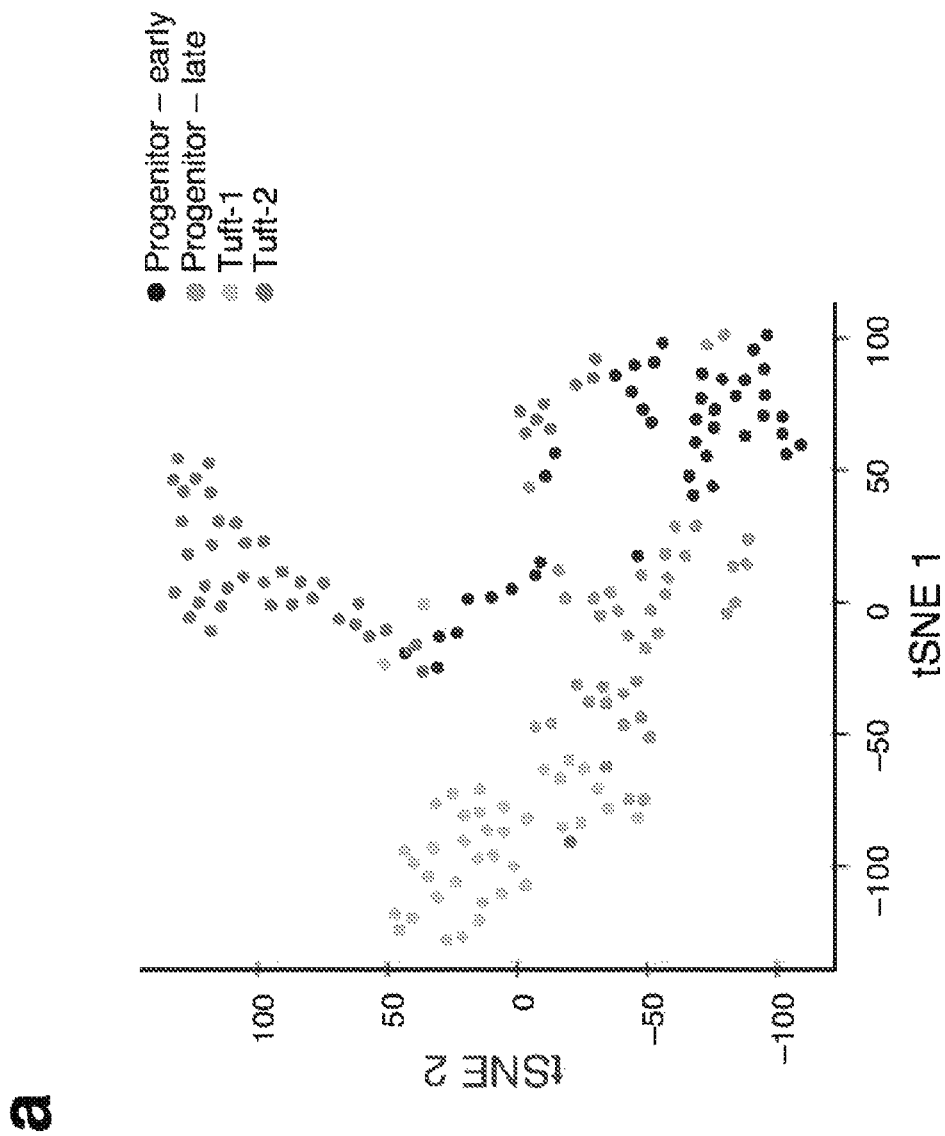
Figure 4B:
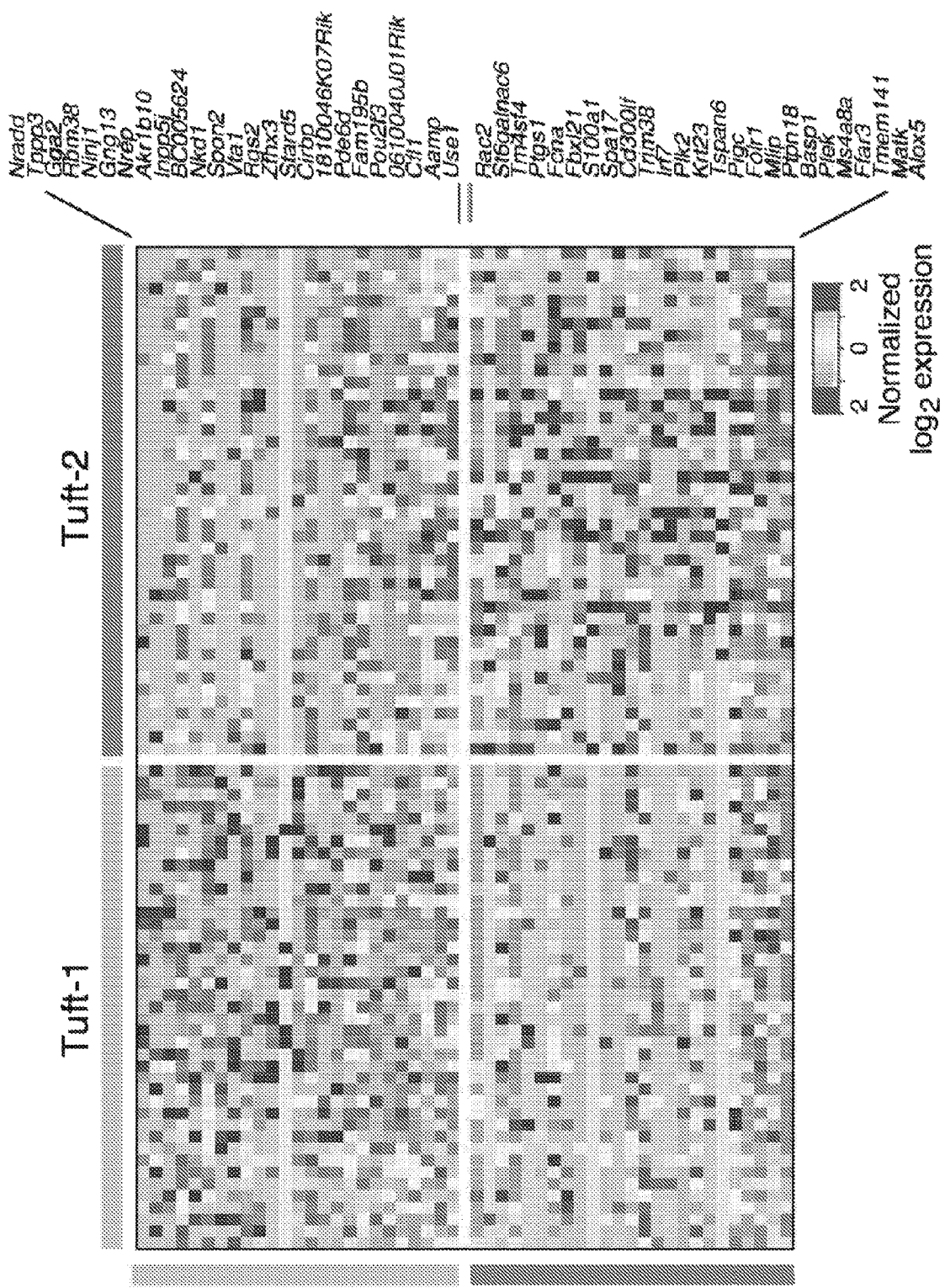
Figure 13A:
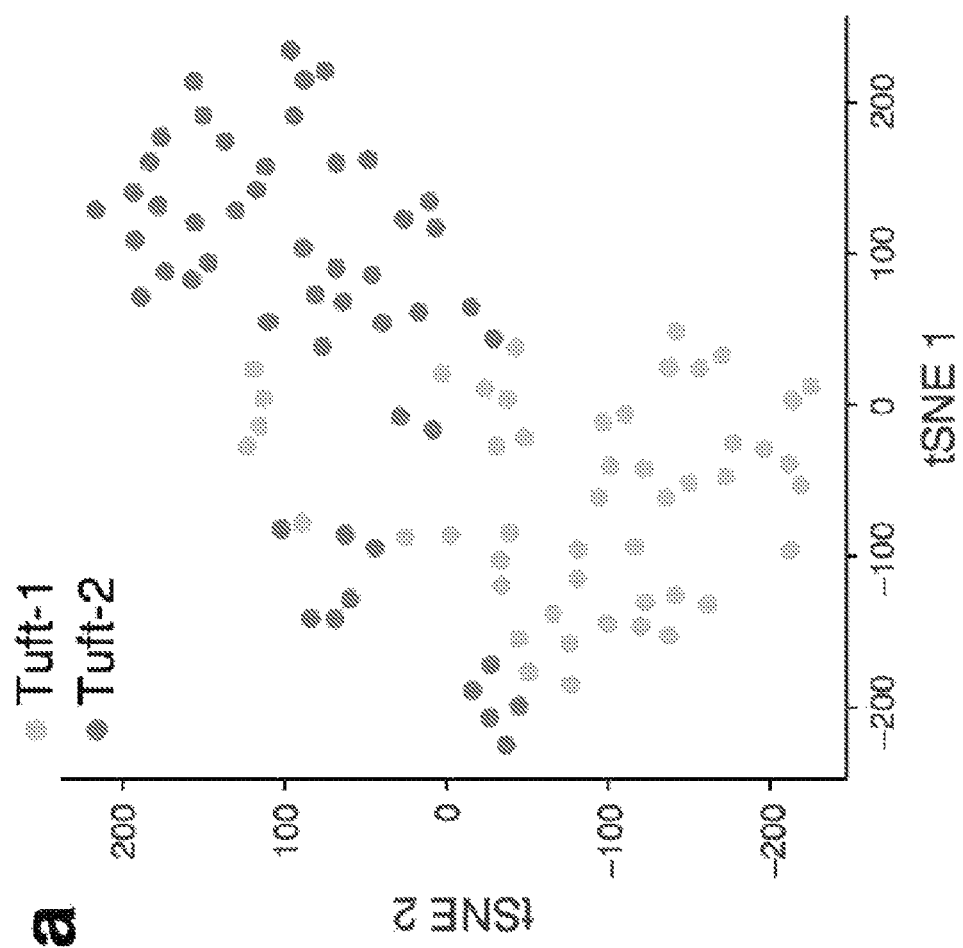
Figure 13B:

To distinguish these possibilities, Applicants re-clustered the 166 cells in the tuft cell cluster (FIG. 1b, FIGS. 7g and 7h), and found that the cells not only readily partitioned into progenitors (early and late) and mature tuft cells, but that the 84 mature tuft cells were further partitioned into two major sub-clusters (Methods), which Applicants termed Tuft-1 and Tuft-2 (FIG. 4a). Tuft-1 and Tuft-2 cells showed no significant distinction in spatial location along the SI (data not shown). Applicants confirmed the same sub-division by independent clustering of the 101 mature tuft cells (enriched by CD24a$^+$ sorting) in the deeper, full length scRNA-seq dataset (FIG. 13a). These two datasets enabled us to define a consensus signature, of 30 and 74 specific markers for the Tuft-1 and Tuft-2 clusters respectively, identified independently in both the 3' droplet and full-length datasets (FDR<0.01, Mann-Whitney U-test, Methods, FIG. 4b, FIG. 13b and Table 8).

TABLE 8

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| Nradd | Il13ra1 | Nradd | Siglec5 | Rac2 | Rac2 |
| Endod1 | Ywhaq | Tppp3 | Rac2 | Matk | St6galnac6 |
| Tppp3 | Tsc22d1 | Gga2 | Ptprc | Nrgn | Tm4sf4 |
| Gga2 | Rgs13 | Rbm38 | St6galnac6 | Siglecf | Ptgs1 |
| Rbm38 | Stx7 | Ninj1 | Tm4sf4 | Alox5 | Fcna |
| Ldhb | Ppp3ca | Gng13 | Smpx | Cd300lf | Fbxl21 |
| Slc44a2 | Nebl | Nrep | Ptgs1 | Ccdc28b | S100a1 |
| Stoml1 | Gng13 | Akr1b10 | C2 | Trpm5 | Spa17 |
| BC016579 | Skp1a | Inpp5j | Cpvl | Hck | Cd300lf |
| Rabl5 | Rbm38 | BC005624 | Fcna | Ptgs1 | Trim38 |
| Cbr3 | Nradd | Nkd1 | Fbxl21 | Tuba1a | Irf7 |
| Ninj1 | Calm2 | Spon2 | Ceacam2 | Ptpn18 | Plk2 |
| Cnp | Tppp3 | Vta1 | S100a1 | Tm4sf4 | Krt23 |
| Wdr6 | Rnf128 | Rgs2 | Spa17 | Ms4a8a | Tspan6 |
| Gadd45a | Sh3bgrl | Zfhx3 | Sucnr1 | Sh2d6 | Pigc |
| Gng13 | Rab10 | Stard5 | Gde1 | Krt23 | Folr1 |
| Usp11 | Ctsc | Cirbp | Kcnj16 | Folr1 | Mlip |
| Mblac2 | Nkd1 | 1810046K07Rik | AA467197 | S100a1 | Ptpn18 |
| Pik3r3 | Ppp1ca | Pde6d | Cd300lf | Ccnj | Basp1 |
| Nrep | Cirbp | Fam195b | Trim38 | Ptpn6 | Plek |
| Akr1b10 | Krcc1 | Pou2f3 | Vmn2r26 | Reep5 | Ms4a8a |
| Sphk2 | Use1 | 0610040J01Rik | Gcnt1 | Atp2a3 | Ffar3 |
| Ddah2 | Ckap4 | Cfl1 | Irf7 | Krt18 | Tmem141 |
| Haghl | Zfp428 | Aamp | Plk2 | Hebp1 | Matk |
| Suv420h2 | Nrep | Use1 | Glyctk | Agt | Alox5 |
| H2-L | Rsrp1 | H3f3b | Krt23 | Ffar3 | Ccnj |
| Ulk1 | Cetn2 | Cyb5r4 | Tmem116 | H2-D1 | S100a11 |
| Atp4a | Bri3 | Trappc3 | Fam188a | Romo1 | Gm4952 |
| Gltpd1 | Myo6 | Runx1 | Bmp2 | Yipf1 | Ncf2 |
| Ift43 | Vdac3 | Pla2g4a | Ctsc | Ift172 | Cfb |
| Usp11 | Chmp5 | | Tspan6 | Ly6g6f | Cpne3 |
| Mical1 | Hsbp1l1 | | Slc25a20 | 9030624J02Rik | Sdcbp2 |
| Homer3 | Dpcd | | Pigc | Basp1 | Col15a1 |
| Trafd1 | Eif1b | | Folr1 | Mien1 | Ly6g6f |
| Ldlrad4 | Ube2d3 | | Mlip | Mlip | Man2a1 |
| Pir | Pla2g4a | | B4galt4 | Tubb4b | Agt |
| Atp6v0c-ps2 | St3gal6 | | Txndc16 | Pnpla6 | Nrgn |
| Anapc2 | Bpgm | | Ptpn18 | Plk2 | Snrnp25 |
| Grpel2 | Lima1 | | Ccdc23 | Lman2l | Tmem245 |
| Tanc2 | Cby1 | | Capg | Tmem176a | Hck |
| Mta2 | Dazap2 | | Ly6g6d | H2afj | Gimap1 |
| Ankrd63 | Cdc42se1 | | Basp1 | Eloyl1 | Gprc5c |
| Exoc7 | Nsfl1c | | Abhd4 | Col15a1 | Coprs |
| Med27 | Aamp | | Plek | Tmem98 | Stk40 |
| Rmnd5a | Gdi2 | | Ms4a8a | Tspan6 | Tuba1a |
| Gpm6b | Mff | | Cwh43 | Fbp2 | Ttll10 |
| Plscr3 | Fkbp1a | | Tm7sf2 | Snrnp25 | Tmem176a |
| Dcxr | Hpgds | | Lect2 | Fes | Tubb4b |
| Stau1 | Scamp3 | | Ffar3 | Fdps | Romo1 |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| Inpp5j | Sub1 | | Adam22 | Irf7 | Fbp2 |
| Bin3 | Degs2 | | Oas1g | Ctsa | Dclk1 |
| Ssh1 | Wbp2 | | Slc2a1 | S100a11 | Tax1bp1 |
| Ap1s2 | Rnf5 | | Tmem141 | Lmf1 | Fes |
| Svil | Galk1 | | Gm17660 | Gprc5c | Hebp1 |
| Chd6 | Med10 | | Suco | Sh2d7 | Skap2 |
| Gimap8 | Tnfsf13os | | Matk | Fbxl21 | Clec4a1 |
| Bloc1s2a | Ola1 | | Ccdc109b | Tmem245 | Cox17 |
| Zfp191 | Rhoa | | Alox5 | Fcnaos | Mien1 |
| Nbeal2 | Psmd8 | | Acsl4 | Car7 | Car7 |
| Plekhg5 | Pla2g12a | | Trim40 | Aldh2 | Reep5 |
| Gtf2ird1 | Mpg | | Slc41a3 | D17Wsu92e | Tmem80 |
| Ogfr | Mftr11 | | Ccnj | Sdcbp2 | Ccdc28b |
| Hmg20b | Fam96a | | Rdx | Cox17 | Krt18 |
| Cdc42ep1 | Trappc1 | | Rmdn1 | Hypk | Ift172 |
| Gna14 | Srp14 | | Plekho2 | Tmem80 | Ptpn6 |
| Zfp810 | Cystm1 | | Cfi | Dyrk4 | Pnpla6 |
| Marveld2 | Tcta | | Car2 | Ubl7 | Isg15 |
| Thtpa | Pnrc1 | | Apobec1 | Fcna | Tmem57 |
| BC005624 | Ninj1 | | Mboat1 | Tmem141 | Abhd16a |
| Tcp11l2 | Ube2l3 | | Ccdc68 | Rtp4 | 1700112E06Rik |
| Shkbp1 | Cryzl1 | | Smg7 | Vav1 | Map1a |
| Pcyox1l | Lpcat4 | | Rgs13 | Man2a1 | Shf |
| Tmem131 | Rab3ip | | Oas2 | Trak1 | H2-D1 |
| Ssna1 | Fam103a1 | | Rhoc | Gimap1 | Lmf1 |
| Nkd1 | Zbtb20 | | Rnasel | Uba1 | |
| Ndufaf3 | Ociad2 | | Pparg | S100a13 | |
| Zfp872 | Cyb5r4 | | Gnai1 | Gucy2c | |
| Amz2 | Rab18 | | Bmx | Sec14l1 | |
| Cyb561d1 | H3f3a | | Atp2b2 | Atg101 | |
| Zfp444 | Leprot | | Dynlt1b | Ltc4s | |
| Src | Rab14 | | Sept8 | Lamtor4 | |
| Anxa11 | Fam195b | | Il17rb | Sfxn3 | |
| Pgm2l1 | Lrrc42 | | Kalrn | Fam98c | |
| Nsmce1 | Akr1b10 | | Opn3 | Map1a | |
| Snapc3 | Cyhr1 | | Dnase1l1 | Stk40 | |
| Abi2 | Cfl1 | | Ero1lb | Pigc | |
| Smug1 | Camk2d | | Asl | Isg15 | |
| Slco3a1 | Gm10384 | | Lrrc42 | Pradc1 | |
| Myo10 | Dcp1b | | Ifitm1 | Cpne3 | |
| Kcnn4 | Acss2 | | Atp6v0c | Dclk1 | |
| Ehmt2 | Prom1 | | Enpp4 | Fip1l1 | |
| Snap47 | Cutc | | Samd9l | Plek | |
| Snapin | Gng5 | | Abhd5 | Arhgap1 | |
| Tas1r3 | Dnaja2 | | S100a11 | Pqlc1 | |
| Ssh2 | Pold4 | | Fut2 | Tax1bp1 | |
| Fn1 | Dynlt3 | | Gm4952 | Abcc3 | |
| Tchp | Prdx2 | | Ccrl1 | 1700112E06Rik | |
| Nrbp2 | Rbm39 | | Tmem74b | Snf8 | |
| Atxn7l1 | Asah1 | | Enc1 | Sez6l2 | |
| Kif3b | Trappc6b | | Ncf2 | Gm4952 | |
| Ppp2r3d | Tm2d1 | | Scd2 | Zdhhc16 | |
| Atf7ip | 1810046K07Rik | | Il10rb | Rpp21 | |
| Adnp | Snx2 | | Kirrel3 | Adcy5 | |
| Dnahc8 | Cd24a | | Gpr64 | Slc4a2 | |
| Ctxn1 | Trappc3 | | Hist2h2aa1 | Tusc2 | |
| Tcf4 | Zfhx3 | | Rhbdf1 | Mrpl46 | |
| Cyth1 | Trappc6a | | Cfb | Clec4a1 | |
| Zscan21 | Capza2 | | Gm14288 | Csk | |
| Dync1i2 | Itfg1 | | A4galt | Cfb | |
| Nlrc4 | Dnaja1 | | Pmel | Kdm4a | |
| Ttc1 | Zfp410 | | Ifi27l1 | Trim38 | |
| Afap1l2 | Itpr2 | | Oas1a | Sdf4 | |
| Plod3 | Pop7 | | Cpne3 | Bst2 | |
| Utrn | Brk1 | | Rps6ka2 | Ap2s1 | |
| Kdm2a | Sept7 | | Tmem246 | Stat2 | |
| Etv4 | Anxa4 | | Sdcbp2 | 1810037I17Rik | |
| Maml1 | Mast4 | | Col15a1 | Coprs | |
| Spon2 | Tmx1 | | Ly6g6f | Pik3cg | |
| Gata5 | 1700123O20Rik | | Man2a1 | Plcg2 | |
| Tln1 | Gstm7 | | Chat | Cd37 | |
| Akap8l | Stxbp3 | | Rgs22 | Ttll10 | |
| F730043M19Rik | Dctn6 | | Pold4 | Skap2 | |
| Arl10 | Rassf6 | | Kctd13 | Dmxl2 | |
| Vta1 | Immp1l | | Cdhr2 | Mrpl41 | |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| Tbx3 | Pnrc2 | | Apip | Tmem57 | |
| Rbm5 | Sdcbp | | Gabarapl2 | St6galnac6 | |
| Gm6756 | Sdhaf4 | | Gpcpd1 | Cutal | |
| Epb4.1l1 | C2cd4b | | Pcdh20 | Shf | |
| Il4ra | Arl2 | | D730039F16Rik | Lpp | |
| Rgs2 | Slc44a3 | | Agt | Ncf2 | |
| Pcdh1 | Vapb | | Nrgn | Ap1s1 | |
| Arid3b | H3f3b | | Snrnp25 | Abhd16a | |
| Map1s | Pou2f3 | | Fam167a | Dalrd3 | |
| Ctnnal1 | Inpp5j | | Etohi1 | Spa17 | |
| Acap3 | Lpar6 | | Siae | Pde2a | |
| Mboat2 | Akirin2 | | Gstt1 | Cyp51 | |
| Unc45a | Map1lc3b | | Ndst1 | Scand1 | |
| Zfhx3 | Chmp3 | | Rhog | Trim31 | |
| Stard5 | Fnta | | Pot1a | Lrrc41 | |
| Hps5 | Phpt1 | | Tmem245 | | |
| Arrdc1 | Commd7 | | Hck | | |
| Taf8 | Syf2 | | Rab13 | | |
| Rac3 | Cdc42 | | Smyd1 | | |
| Gnb2 | Acot7 | | 2810468N07Rik | | |
| Ehmt1 | Mea1 | | Gimap1 | | |
| Inpp5b | Vapa | | Tmem219 | | |
| Pam16 | Ccdc109b | | Gprc5c | | |
| Cdc25b | Pip5k1b | | Slc6a8 | | |
| Gfod1 | Vta1 | | Coprs | | |
| B9d2 | Ube2r2 | | Fam49a | | |
| Wdr85 | Klf9 | | Uox | | |
| Atf6b | 0610040J01Rik | | Tmem121 | | |
| Gatad2a | Ndfip2 | | Tmem241 | | |
| Wdr13 | Actr10 | | Mgll | | |
| Zfhx2 | Manbal | | Hrsp12 | | |
| Ccdc92 | Morf4l2 | | Tcta | | |
| Nfe2l3 | Pigyl | | Tmc5 | | |
| Tead2 | Runx1 | | 1700011H14Rik | | |
| Rmnd5b | Rnf6 | | Mtmr11 | | |
| Dock7 | Ghitm | | Neurl1a | | |
| Wnk2 | Pim3 | | Stk40 | | |
| Snapc2 | Tank | | Klhl28 | | |
| Dixdc1 | Nubp2 | | Nek7 | | |
| Neu2 | Lsm1 | | Ak7 | | |
| Mcc | Zfand6 | | Tuba1a | | |
| Ythdf2 | Uros | | Slc16a3 | | |
| Stx4a | Snapc5 | | Prkce | | |
| Flii | Frg1 | | Neu1 | | |
| Mmp14 | Malat1 | | Irs2 | | |
| Hgs | Pla2g16 | | Tslp | | |
| Ptprf | 9130230L23Rik | | Ypel3 | | |
| Puf60 | Gga2 | | Ablim3 | | |
| Aldh7a1 | Tmem30b | | Crip1 | | |
| Prpf6 | Ube2k | | Gm14440 | | |
| Gdpd5 | Mocs2 | | Ppp1r3b | | |
| Gramd4 | Slmo2 | | Ppt1 | | |
| Mov10 | Atp6v1g1 | | Cdhr5 | | |
| Hipk3 | Dnajb1 | | Ttll10 | | |
| Mthfd1l | Stra6l | | Fbxo9 | | |
| Fam216a | Slc25a11 | | Gimap3 | | |
| Rab4b | Smim8 | | 1110032A03Rik | | |
| Sh3glb2 | Tpgs2 | | Rbpms | | |
| Cdc14b | Bub3 | | Cadps2 | | |
| Tmem63b | Rit1 | | Loh12cr1 | | |
| Leng1 | Hsbp1 | | Ccser2 | | |
| Nab2 | M6pr | | Tmem176a | | |
| AW554918 | Gemin7 | | Tubb4b | | |
| 4931428F04Rik | Cpq | | P2rx1 | | |
| Ddx42 | Jade1 | | Romo1 | | |
| Cttn | BC004004 | | Chac2 | | |
| Mtfmt | Sirt2 | | Ccbe1 | | |
| Stox2 | Tspan31 | | Lyn | | |
| Cirbp | Atg3 | | Bnip3 | | |
| Gm8096 | Bbs4 | | L1cam | | |
| Usf2 | Wbscr22 | | Fbp2 | | |
| Kcnh8 | Rgs2 | | Wdfy2 | | |
| Fam89b | Plaa | | Nsf | | |
| Fundc1 | Nudt14 | | Nfatc1 | | |
| Arhgef2 | Msi2 | | Rpl30 | | |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| Myo7b | Dnlz | | Necap1 | | |
| 1810046K07Rik | Akr1b3 | | Nlrx1 | | |
| Afap1 | Maf1 | | Ydjc | | |
| Gtdc1 | Pde6d | | Oasl2 | | |
| Chd4 | Stard5 | | Dpysl2 | | |
| Dclk3 | Phax | | Parp4 | | |
| C230052I12Rik | Slc23a3 | | Gm6644 | | |
| 2410018L13Rik | Prelid2 | | 1700047I17Rik2 | | |
| Arid2 | Strbp | | Fyb | | |
| Commd4 | Pea15a | | Gmpr | | |
| Pigv | Chn2 | | Enpp3 | | |
| St5 | Cmip | | Nptn | | |
| Pde6d | Diablo | | Serpini1 | | |
| Traf7 | Txndc9 | | Slc4a8 | | |
| Fam195b | Alox5ap | | Gprc5a | | |
| Ubn2 | 0610009L18Rik | | Fabp1 | | |
| Lzts2 | Taf12 | | Gm14295 | | |
| Mark2 | Acer3 | | Dclk1 | | |
| Pou2f3 | Mpv17l2 | | Terf2 | | |
| Csk | Nck1 | | Tax1bp1 | | |
| Plekhm2 | Tmbim1 | | Klf6 | | |
| Abhd8 | Metap2 | | Mn1 | | |
| Dopey2 | Hnrnpk | | Pygl | | |
| Ppil2 | Yif1b | | Sema7a | | |
| Hdac6 | Stat6 | | Chmp2a | | |
| Tmem158 | Dctn2 | | Sh3kbp1 | | |
| Vezt | Siah1a | | Bicd1 | | |
| Adora1 | Spon2 | | Atp6v1d | | |
| Fhad1 | Shisa5 | | Avpi1 | | |
| Gripap1 | Ppp1r35 | | Xaf1 | | |
| Sptbn1 | Arpc1b | | Atp6v0d1 | | |
| Tcea2 | Ppp6c | | Gm14436 | | |
| Sugp2 | BC005624 | | Sema5b | | |
| Efs | | | Chi3l1 | | |
| Sbf1 | | | Slc25a12 | | |
| Lrrc16a | | | Fes | | |
| Nsd1 | | | Fam177a | | |
| 0610040J01Rik | | | Hebp1 | | |
| Jup | | | Klf7 | | |
| Cacnb3 | | | Nudt8 | | |
| Stub1 | | | Tesk2 | | |
| Mob3a | | | Inpp5d | | |
| Zdhhc8 | | | Lrp12 | | |
| Hmx2 | | | Fam83d | | |
| Ywhab | | | Skap2 | | |
| AI846148 | | | Atg3 | | |
| Tet1 | | | Wdfy1 | | |
| Rab1b | | | Hipk1 | | |
| Hes6 | | | Efhd2 | | |
| Slc4a7 | | | Krt222 | | |
| 2410004818Rik | | | Trappc2 | | |
| Rest | | | Lipo1 | | |
| Abca7 | | | Syne2 | | |
| 1110004F10Rik | | | Clec4a1 | | |
| 9230110C19Rik | | | Ptpra | | |
| Kdm6b | | | Ttll7 | | |
| Gas8 | | | Lyrm2 | | |
| Cgn | | | Cox17 | | |
| Tnrc18 | | | Tm2d1 | | |
| Taok2 | | | Strip2 | | |
| Gpsm1 | | | Dock8 | | |
| Setx | | | Sdf2 | | |
| Patz1 | | | Hyi | | |
| Esyt1 | | | Gpr18 | | |
| Junb | | | Cables2 | | |
| Ntng2 | | | Sertad1 | | |
| Ncs1 | | | Mien1 | | |
| Ppm1m | | | Fam57a | | |
| Atxn2l | | | Ptpre | | |
| Arpc1a | | | 1810058I24Rik | | |
| Smarce1 | | | Car7 | | |
| Tmem231 | | | Lmtk2 | | |
| Cish | | | Tnnt1 | | |
| Agrn | | | Ypel5 | | |
| Abcc5 | | | Gtf2b | | |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| Plekhg2 | | | Zdhhc20 | | |
| Ssbp3 | | | Mapre2 | | |
| Sbk1 | | | Sik1 | | |
| 2700086A05Rik | | | Erp29 | | |
| Kdm5a | | | Tmem229a | | |
| Cfl1 | | | Gas7 | | |
| Ppp6r2 | | | Rnasek | | |
| Jmy | | | Tuba4a | | |
| Oas1h | | | Ppp1r14c | | |
| Fgf12 | | | Pacs2 | | |
| Mau2 | | | Pnpla3 | | |
| Irf2bp1 | | | Reep5 | | |
| Ogdhl | | | Rbm4b | | |
| Trerf1 | | | Tmem80 | | |
| Lamtor5 | | | Kctd15 | | |
| Lmnb2 | | | Capn1 | | |
| Dync1h1 | | | Ifnar2 | | |
| Dpp3 | | | Xrcc4 | | |
| Aldh4a1 | | | Tspan17 | | |
| Wwc1 | | | Hdac1 | | |
| Zfp459 | | | Ccdc28b | | |
| Pion | | | Tspan8 | | |
| Strn4 | | | Grina | | |
| Ppp2r5c | | | Fam46a | | |
| Stx8 | | | 4930539E08Rik | | |
| Wdr78 | | | Casp3 | | |
| Dsp | | | Adam1b | | |
| 9030624G23Rik | | | Mxd1 | | |
| Kifc2 | | | Fdft1 | | |
| Senp7 | | | Kcns3 | | |
| Aamp | | | Slc9a6 | | |
| 4931406H21Rik | | | Vamp4 | | |
| Gtf2f1 | | | Cd47 | | |
| Oas1c | | | Slc52a3 | | |
| Cachd1 | | | Gm3002 | | |
| Fis1 | | | Apba3 | | |
| Use1 | | | Syne3 | | |
| Kit | | | Krt18 | | |
| Zdhhc17 | | | Map1lc3a | | |
| Tmem9 | | | Rusc1 | | |
| H3f3b | | | Dctn3 | | |
| Narf | | | Gnat3 | | |
| Kcnh2 | | | Homer1 | | |
| Ddx17 | | | Gngt2 | | |
| Micall1 | | | Slc39a13 | | |
| Dnajb2 | | | Rgs19 | | |
| Ik | | | Emc2 | | |
| Flt3l | | | Tusc3 | | |
| Igfbp7 | | | Vps53 | | |
| Chdh | | | Gpr137b-ps | | |
| Pak1 | | | Kif2a | | |
| Hoxa5 | | | Ildr1 | | |
| Rnf114 | | | Limd2 | | |
| Mlec | | | Gm10406 | | |
| Rbm42 | | | Rab11a | | |
| Kdm4d | | | Ift172 | | |
| Fam50a | | | Tmem256 | | |
| Irgq | | | 6330407A03Rik | | |
| Irf5 | | | Fbxo36 | | |
| Cenpt | | | Ptpn6 | | |
| Iqsec1 | | | Exph5 | | |
| Dvl3 | | | Arl6 | | |
| Figf | | | Stx7 | | |
| Tmed1 | | | Dcaf15 | | |
| Znf512b | | | Lap3 | | |
| Podxl2 | | | Nav2 | | |
| Cyb5r4 | | | Lrrc57 | | |
| Plekha6 | | | Prox1 | | |
| Trappc3 | | | Pnpla6 | | |
| Snn | | | Syap1 | | |
| Zdhhc24 | | | Itih5 | | |
| Runx1 | | | Rock2 | | |
| Cd99l2 | | | Isg15 | | |
| Zc3h11a | | | Tprgl | | |
| Gse1 | | | Amdhd2 | | |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| Cdx1 | | | Unc13d | | |
| Camkk1 | | | AI462493 | | |
| Jag2 | | | Ampd3 | | |
| Arid4b | | | Gm14308 | | |
| 2310011J03Rik | | | Ell2 | | |
| Rnf111 | | | 0610031J06Rik | | |
| Eif4h | | | Zdhhc9 | | |
| Rraga | | | Zfp868 | | |
| Dyrk1b | | | Gys1 | | |
| Nfe2l1 | | | Tmem57 | | |
| Csrnp1 | | | Hspb11 | | |
| Cyld | | | Nebl | | |
| Tnip1 | | | Fbxo25 | | |
| Atp6v1e2 | | | Gbp3 | | |
| Tet3 | | | Cdkl2 | | |
| Pyrl1 | | | Zdhhc12 | | |
| Prpf38b | | | Gclm | | |
| Pla2g4a | | | Gm3317 | | |
| Pfkfb3 | | | Gm3494 | | |
| Ubr4 | | | 4833418N02Rik | | |
| Ppp2r1a | | | Ube2j1 | | |
| Polb | | | Htatsf1 | | |
| Igsf8 | | | Kif3a | | |
| Tmem223 | | | Lca5 | | |
| Tiam2 | | | Taf9b | | |
| Sptan1 | | | H2-Ke6 | | |
| Zmym3 | | | Bmyc | | |
| Shoc2 | | | Mtmr7 | | |
| Tnfrsf25 | | | Abhd16a | | |
| Celf1 | | | Itsn2 | | |
| Map4k4 | | | Atp6v0a1 | | |
| Hyal2 | | | Adra2a | | |
| Tjp3 | | | Dcp1b | | |
| Morf4l1 | | | Snx18 | | |
| Ccdc115 | | | Pxmp4 | | |
| Phip | | | Smap1 | | |
| Gclc | | | Cmip | | |
| Pcdhga5 | | | Atp6v0b | | |
| Polr3g | | | Dnahc6 | | |
| Pnn | | | 1700112E06Rik | | |
| Fam129b | | | Cpm | | |
| Trio | | | Arhgap4 | | |
| 4931440P22Rik | | | Ccdc129 | | |
| Lepre1 | | | Fnta | | |
| Agpat1 | | | Ccndbp1 | | |
| Kank1 | | | Itfg1 | | |
| Pard6g | | | Map1a | | |
| Mapk1ip1l | | | Efnb2 | | |
| Tmub2 | | | Shf | | |
| Fgd6 | | | H2-D1 | | |
| Safb2 | | | Tbcb | | |
| Band1 | | | Phf1 | | |
| Ajuba | | | Cry2 | | |
| Pou2f1 | | | Iqce | | |
| Pdlim5 | | | Cript | | |
| Dnmt3a | | | Sema3b | | |
| Fcho2 | | | Adh1 | | |
| Trib2 | | | Crot | | |
| Bptf | | | Eppk1 | | |
| Ctnna1 | | | B3gat3 | | |
| 2310035C23Rik | | | Arl8a | | |
| R3hdm4 | | | Gadd45g | | |
| | | | Alkbh7 | | |
| | | | Cib2 | | |
| | | | 2010012O05Rik | | |
| | | | Cic | | |
| | | | A630075F10Rik | | |
| | | | Gm14420 | | |
| | | | Rabgef1 | | |
| | | | Lgals8 | | |
| | | | Lmf1 | | |
| | | | Bad | | |
| | | | Cdipt | | |
| | | | Kank3 | | |
| | | | Mtpn | | |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| | | | Atp6v1e1 | | |
| | | | OTTMUSG00000016609 | | |
| | | | Myl6 | | |
| | | | Gfi1b | | |
| | | | Pigyl | | |
| | | | Ccdc126 | | |
| | | | Ocel1 | | |
| | | | Bloc1s1 | | |
| | | | Eml6 | | |
| | | | Kcnd3 | | |
| | | | Nfat5 | | |
| | | | Gm5617 | | |
| | | | Sos1 | | |
| | | | Man1a | | |
| | | | Acer3 | | |
| | | | Gm2382 | | |
| | | | Suox | | |
| | | | Chuk | | |
| | | | Coq10b | | |
| | | | Dhcr24 | | |
| | | | Srpx2 | | |
| | | | Epb4.1l4b | | |
| | | | Gemin7 | | |
| | | | Rab44 | | |
| | | | Elp5 | | |
| | | | Rasa2 | | |
| | | | Calml4 | | |
| | | | Slco4a1 | | |
| | | | Slc25a17 | | |
| | | | Arhgap5 | | |
| | | | Rbms3 | | |
| | | | Neat1 | | |
| | | | Nab1 | | |
| | | | Rdh14 | | |
| | | | 1700030A11Rik | | |
| | | | Tfpi2 | | |
| | | | Ccnc | | |
| | | | Zfp428 | | |
| | | | B3gnt6 | | |
| | | | Ddt | | |
| | | | Ostf1 | | |
| | | | Cdk11b | | |
| | | | Tmem79 | | |
| | | | Gm14306 | | |
| | | | Vps13a | | |
| | | | Fam3a | | |
| | | | Clca5 | | |
| | | | Dcaf12 | | |
| | | | Mbd6 | | |
| | | | Gramd1b | | |
| | | | Tbcc | | |
| | | | Wsb2 | | |
| | | | Tmem8 | | |
| | | | B4galt6 | | |
| | | | Psd3 | | |
| | | | Marveld3 | | |
| | | | Synrg | | |
| | | | Krcc1 | | |
| | | | Tshz1 | | |
| | | | Rogdi | | |
| | | | Rap2a | | |
| | | | Gm6249 | | |
| | | | Apc | | |
| | | | Enpp5 | | |
| | | | Otud7b | | |
| | | | Rilpl2 | | |
| | | | Stambpl1 | | |
| | | | Samd14 | | |
| | | | Ccdc104 | | |
| | | | Atp2b1 | | |
| | | | Phtf2 | | |

TABLE 8-continued

Summary of marker genes for tuft cell subsets

| Tuft-1 (plate) | Tuft-1 (droplet) | Tuft-1 (consensus) | Tuft-2 (plate) | Tuft-2 (droplet) | Tuft-2 (consensus) |
|---|---|---|---|---|---|
| | | | Ndrg1 | | |
| | | | Srp19 | | |
| | | | Tspyl1 | | |
| | | | B3galt5 | | |
| | | | Aldoc | | |

Significance cut-offs: FDR (Fisher's combined): 0.01, Log2 fold-change: 0.25

The Tuft-2 cell signature is enriched for immune-related genes (FDR<0.001, FIG. 13c-d), whereas genes related to neurogenesis and neuronal development (e.g., Nradd, Ninj1, Plekhg5 and Nrep) are among the most specific markers for the Tuft-1 cluster (FIG. 13d). Irf7 is the only Tuft-2 specific TF and may be a target used for modulating activity of Tuft-2 cells. This supports the hypothesis that the previously reported inflammation and neuronal signatures in bulk data[21] belonged to distinct tuft cell subsets. These two subsets may reflect dynamic states, transient stages of maturity, or two distinct bona-fide cell types.

Figure 4C:
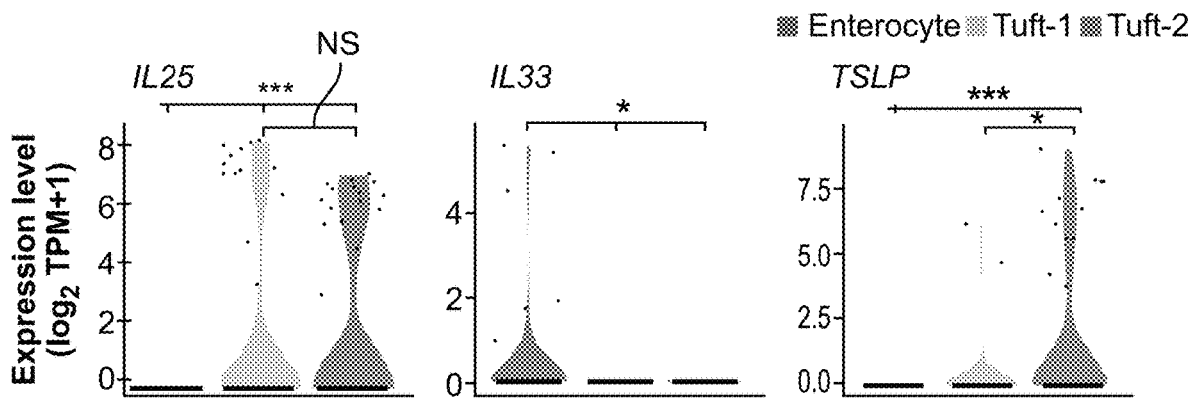
Figure 4D:
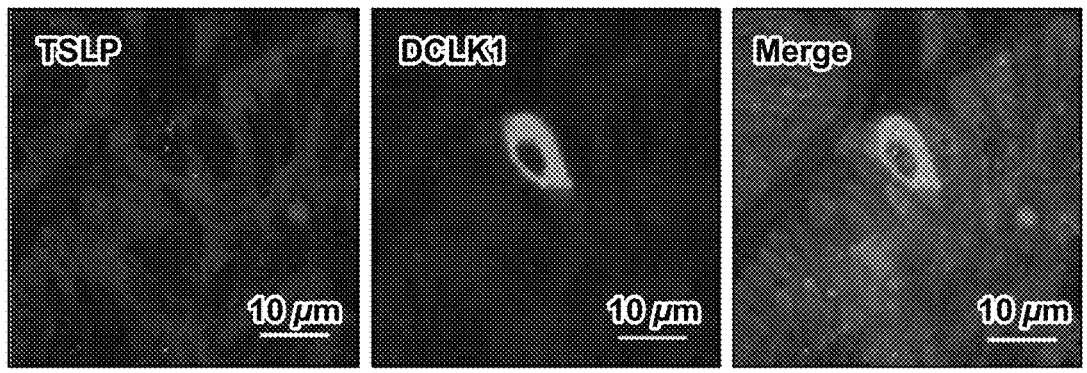
Figure 4E:
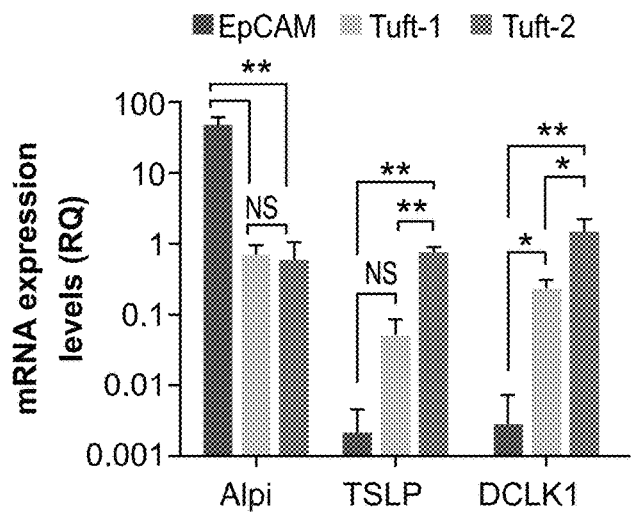

As tuft cells were recently shown to be important for communication with gut-resident immune cells[14-16], Applicants examined their expression of genes encoding epithelial cytokines. Both groups expressed Il25, consistent with recent findings[14], but neither expressed Il33 (in both datasets) (FIG. 4c), which may be due to the low level of this transcript. However, the expression of thymic stromal lymphopoietin (TSLP), an important Th2 promoting cytokine[3], was significantly higher in the Tuft-2 group (FDR<0.1, Mann-Whitney U-test) (FIG. 4c), a finding Applicants confirmed using smFISH and qPCR (FIG. 4d-e). TSLP expression by the Tuft-2 subset may, along with Il25, contribute to the induction of the Th2 response to intestinal parasites.

Finally, the Tuft-2 signature revealed that Ptprc, the gene encoding the pan-immune marker CD45, is expressed strongly and exclusively by Tuft-2 cells (FIG. 4f), a finding Applicants validated at the mRNA level in situ by co-FISH (FIG. 4g, top-left), at the protein level using FACS (FIG. 4g, top right) and by an immunofluorescence assay (IFA) (FIG. 4g lower panels and FIG. 13e). Finally, sorting for EpCAM*CD45+ cells (n=3 mice) followed by 3' droplet scRNA-seq of 332 cells, showed a strong enrichment for Tuft-2 cells (FIG. 4h and FIG. 13f). Applicants note that Applicants used a lenient sorting gate to ensure Applicants obtain sufficient numbers of these rare tuft cells, which led to a higher contamination rate of T cells, which Applicants removed using unsupervised clustering (T cell expression of Ptprc is ~25% higher than in sorted CD45+ Tuft-2 cells). To Applicants knowledge, this is the first finding of CD45+ cells from a non-hematopoietic lineage, and highlights the challenges associated even with even well-established molecular markers of cell types.

Taken together, the data suggests that tuft cells are a population of two distinct sub-types; Tuft-1 cells, with neuron-like features that may transmit taste-chemosensory signals to enteric neurons (Westphalen et al., 2014) and Tuft-2 cells with immune-like features that in addition to the taste-chemosensory ability, may communicate with immune cells, as suggested before (Gerbe et al., 2016; Howitt et al., 2016; von Moltke et al., 2016) to boost type-2 immunity upon signals from the lumen.

Example 7—Identification and Characterization of Microfold (M) Cells In Vivo

Surprisingly, the Tuft-2 subset expressed several of the genes previously reported to be specific to microfold (M) cells[17,58], including Rac2, Siglecf, and Gfi1b (Growth Factor Independent 1B Transcription Repressor), at a significantly higher mean level than Tuft-1 cells ($p<1\times10^{-5}$, Mann-Whitney U-test, FIG. 5a, FIG. 14a). M cells are derived from the common Lgr5+ stem cells of the intestinal epithelium[17], but reside exclusively above Peyer's patches (PP) within a distinct flat epithelial tissue known as the follicle associated epithelia (FAE). The FAE comprises a small fraction of the total intestinal epithelium (<1%)[18], and since M cells represent only a subset of the FAE, they were not detected in the initial atlas, as noted above (FIG. 1b). There are two alternative explanations for the observed overlap between Tuft-2 and M cell marker genes: (1) Tuft-2 cells are in fact rare M cells with an atypical location, that is, the previously proposed villous M cells[59], or (2) Tuft-2 cells are indeed a subset of tuft cells, which nevertheless express some M cell-related genes.

Figure 14E:
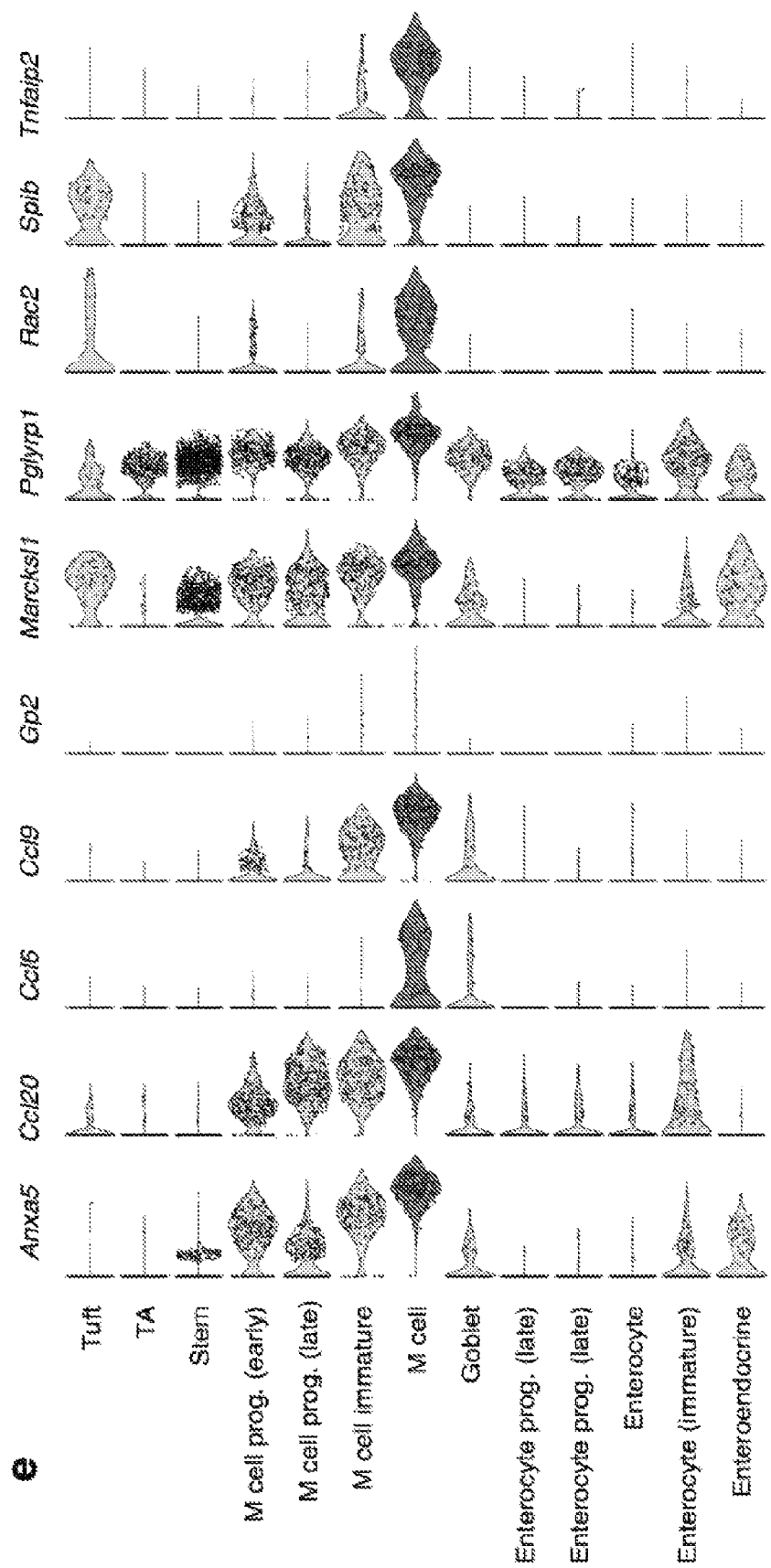
Figure 14F:
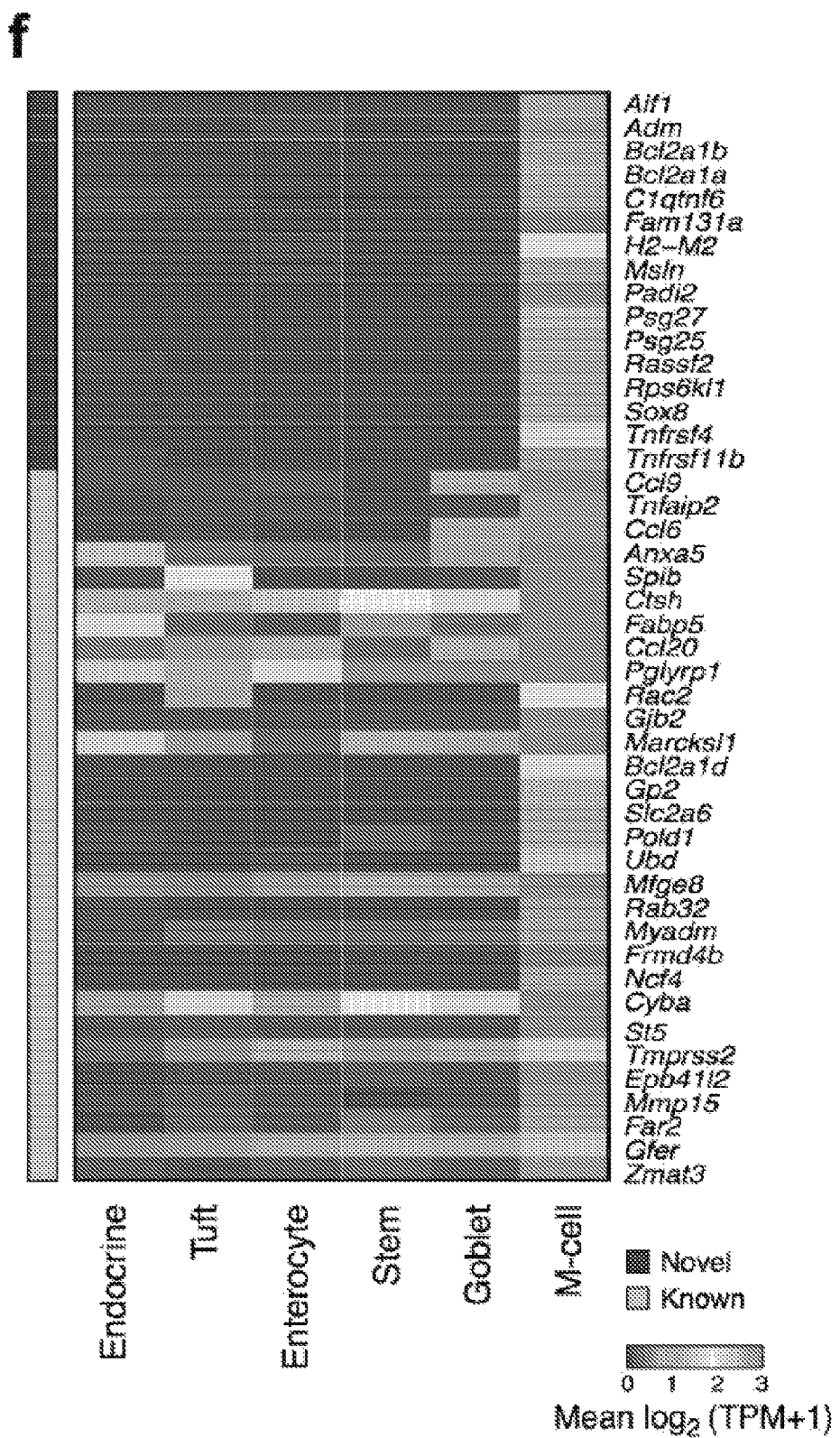
Figure 14I:
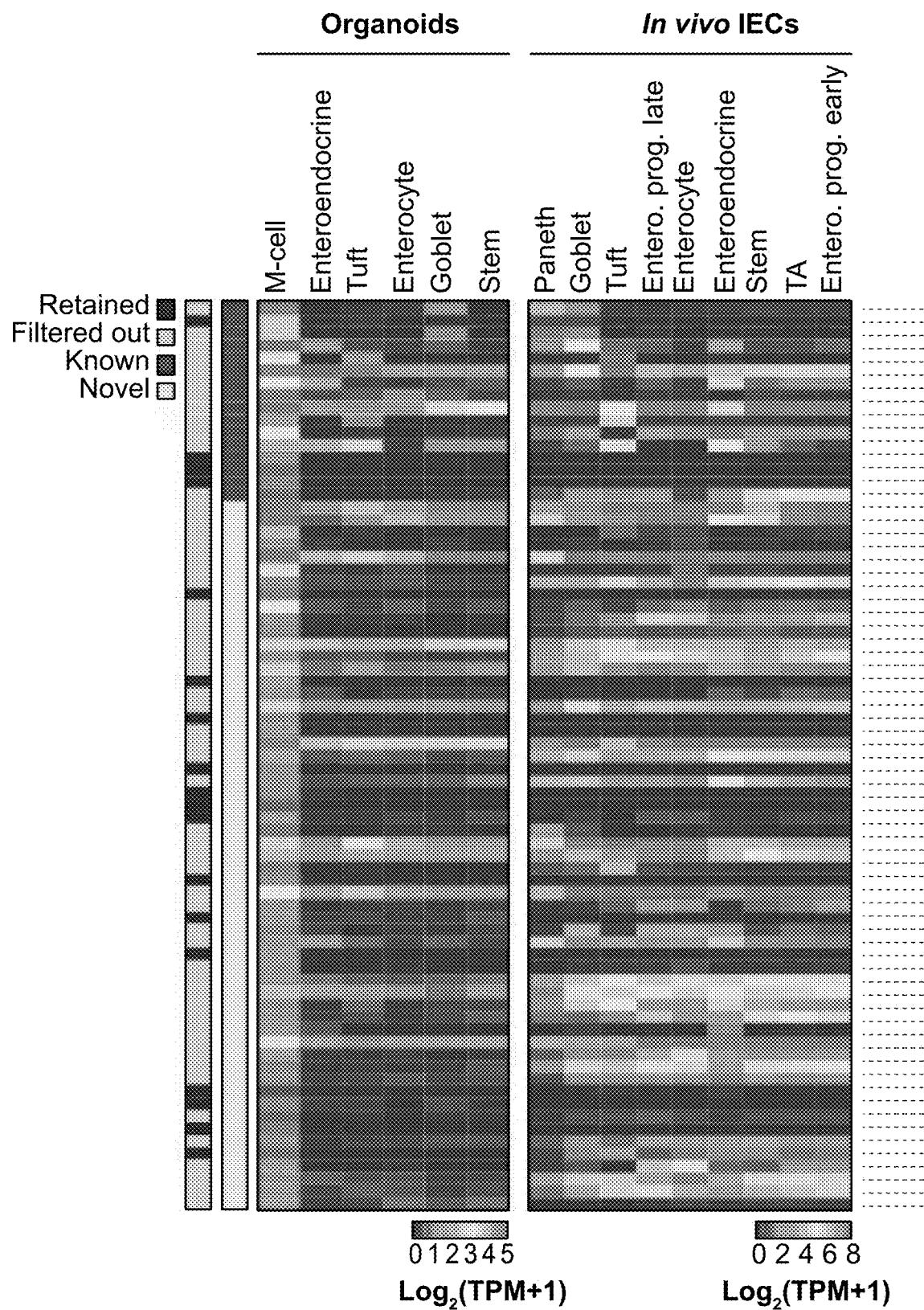

To distinguish between these possibilities, Applicants used both ex vivo and in vivo strategies, to determine an M cell signature at the single-cell level. First, Applicants used an ex vivo model of M cell differentiation, analyzing 5,434 cells from small intestinal organoids treated with RANKL[17] for 0, 3, and 6 days (FIG. 5b-c, FIG. 14b). One cluster of 378 cells (FIG. 5b) recovered by unsupervised clustering (Methods), was labeled as differentiated M cells by the expression of known M cell marker genes[58], not expressed by Tuft-2 cells, including Gp2 and Tnfaip2 (M-sec) (FIG. 14c-e). Based on this cluster, Applicants constructed signatures (FIG. 14i, Methods) of M cell specific genes and TFs in vitro (FIG. 14f-g, Table 9, Methods), highlighting several immune factors (e.g., Spib, Irf2, and Irf6).

TABLE 9

Summary of marker genes for Microfold (M) cells

| In vivo | In vitro |
|---|---|
| Ccl20 | Ccl9 |
| Clu | Serpinb1a |
| Mfge8 | Serpinb6a |
| Anxa5 | Tnfaip2 |
| Pglyrp1 | 1700011H14Rik |
| Ctsh | Ccl6 |
| Serpinb6a | Ly6a |
| H2-M2 | Anxa5 |
| Gp2 | Spib |
| Ubd | Ctsh |
| Lamp1 | Fabp5 |
| Cxcl16 | Ccl20 |
| Cyba | Pglyrp1 |

TABLE 9-continued

Summary of marker genes for Microfold (M) cells

| In vivo | In vitro |
|---|---|
| Scd1 | Tmsb4x |
| 1700011H14Rik | Rac2 |
| Aif1 | Dnase1 |
| Ctsd | Smpdl3a |
| Tnfaip2 | Far2os2 |
| Far2os2 | Rras2 |
| Slc2a6 | Nqo2 |
| Adgrd1 | Gjb2 |
| Ncf4 | 1110046J04Rik |
| Rnf128 | Npc2 |
| Il4i1 | Atp6v1c1 |
| Far2 | Marcksl1 |
| BC021614 | Psmb7 |
| D630011A20Rik | Psg27 |
| Vcam1 | AI118078 |
| Stx11 | Brk1 |
| Sdhaf1 | Msln |
| Ces1b | Tnfrsf4 |
| Itga3 | Cd63 |
| Msln | Rnf181 |
| Scarb2 | Sox8 |
| Tnfrsf4 | Pon2 |
| Fam98a | Bcl2a1d |
| Tmsb4x | Rassf2 |
| Nfkbia | Aif1 |
| Rnase1 | 1700025G04Rik |
| Vamp5 | C4bp |
| Gulo | Vamp8 |
|  | Prr13 |
|  | Bmp2 |
|  | Rps6kl1 |
|  | Degs2 |
|  | 9130008F23Rik |
|  | Il4i1 |
|  | Gm5549 |
|  | Npdc1 |
|  | Gp2 |
|  | H2-M2 |
|  | Vamp5 |
|  | Impa1 |
|  | Gpa33 |
|  | Cnp |
|  | Dapk2 |
|  | Rasd1 |
|  | Etfa |
|  | Mocs1 |
|  | Slc2a6 |
|  | Hars |
|  | Stk24 |
|  | Fam131a |
|  | Snhg18 |
|  | Pold1 |
|  | Agps |
|  | Bcl2a1b |
|  | Zfp36l1 |
|  | Btbd16 |
|  | Mylk |
|  | Cpt2 |
|  | Ahcyl2 |
|  | Ier5 |

Significance cut-offs:
in vivo: FDR (Fisher's combined): 0.001, Log2 fold-change: 0.5
in vivo: FDR (max): 0.05, Log2 fold-change: 0.5

Figure 5D:
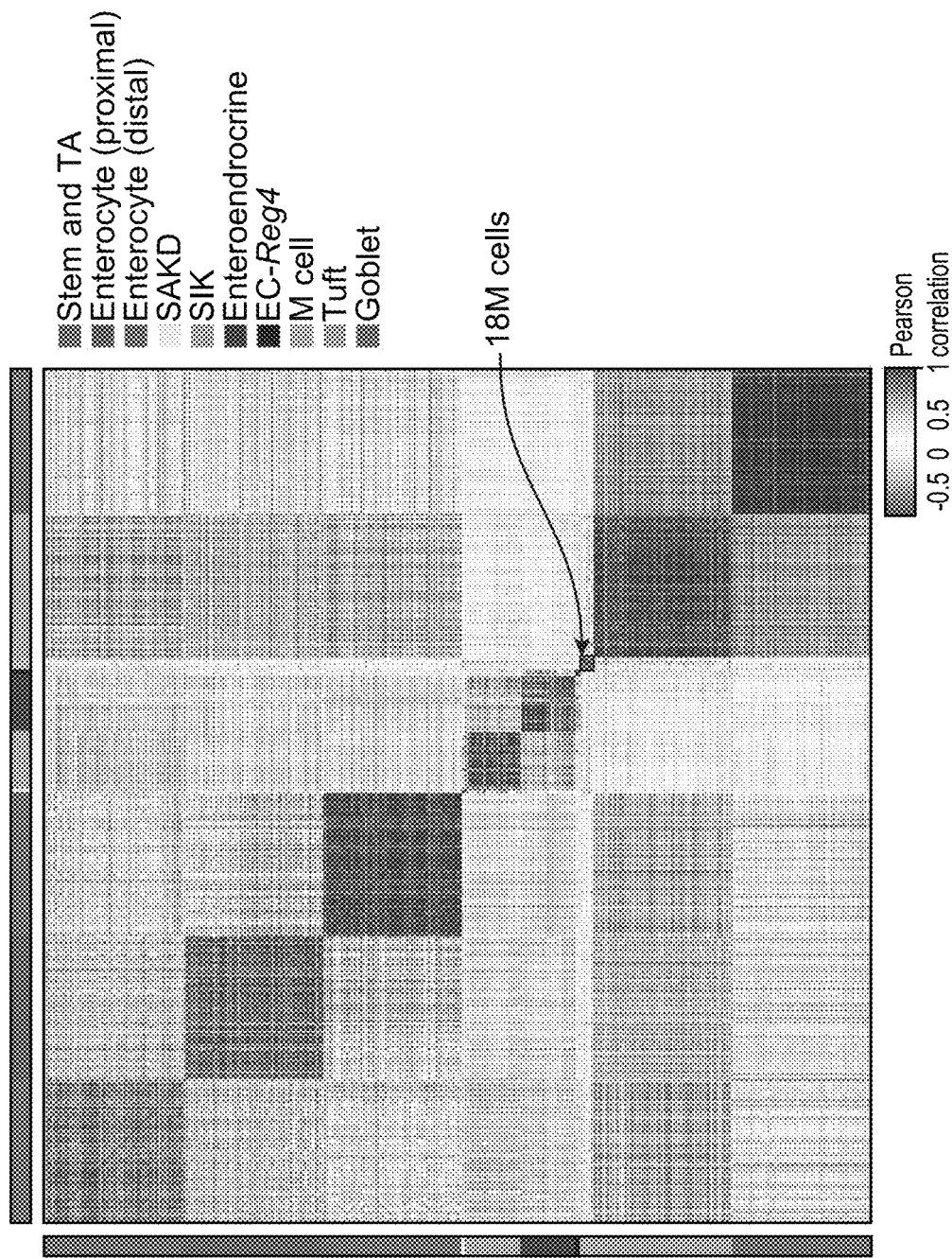

Next, to confirm the relevance of these signatures to M cells in vivo, Applicants profiled 4,700 EpCAM* cells from FAE of WT and Gfi1b-GFP labeled knock-in mice, a known marker for both tuft and M cells[17,60] (n=5 mice). A cluster of 18 cells (FIG. 5d, arrow; Methods), was enriched for known M cell markers (FDR<0.05, Mann-Whitney U-test), including Gp2, Ccl20, Tnfaip2, and Anxa5 (FIG. 5e). These cells also expressed high levels of the M cell signature genes derived from the in vitro data (p<10-4, Mann-Whitney U-test, FIG. 14h). Applicants then defined an in vivo signature of enriched markers and TFs (FIG. 5e-f, Methods). Notably, only one of the 7,216 cells in the sampling of the intestinal epithelium is positive for this M cell signature (data not shown), indicating that: (1) M cells are not readily obtained from scRNA-seq of epithelia without enrichment; (2) Peyer's patch M cells are extremely rare, and require specific FAE enrichment; the statistical model suggests that cells present at 0.07% or lower would be undetected with high (95%) probability (Methods); (3) Tuft-2 cells are not M cells, despite some genes expressed by both cell types; and (4) villous M cells are undetectable in the data. Applicants cannot rule out the possibility that Tuft-2 cells may have been previously erroneously termed "villous M cells", because of the partial similarity in some of their features.

Example 8—Pathogen-Specific Recalibration of Cell Proportions and Cell States in Response to Bacterial and Helminth Infections Immune and epithelial cell decisions to tolerate or elicit an immune response to specific gut pathogens play a key role in maintaining gut homeostasis[2]. Because the epithelial cells of the small intestine are generated in an ongoing, continuous and rapid process of differentiation from stem cells throughout life, it is likely that following infection with a pathogen, there are changes both in the relative composition of IEC sub-types and in the internal state of each type, as well as in global expression changes across multiple cell types. These three types of signals are challenging to distinguish in bulk analysis, whereas single-cell analysis can readily dissect each aspect.

Applicants therefore investigated the IEC responses to a common pathogenic bacterium, Salmonella enterica, which induces enteritis within hours[61,62], and to the helminth Heligmosomoidespolygyrus, a parasitic worm that damages the integrity of the small intestine and elicits a strong Th2 response[63]. Applicants profiled individual IECs using droplet-based 3' scRNA-seq two days after Salmonella (n=2 mice, 1,770 cells) or 3 days (n=2 mice, 2,121 cells) and 10 days (n=2 mice, 2,711 cells) after H. polygyrus infections, as well as 3,240 cells from control mice (n=4 mice). Applicants profiled an additional 389 cells with the deeper, full-length scRNA-seq, which Applicants used to obtain high-confidence 'consensus' differentially expressed genes for all comparisons that are independent of cell-type.

Figure 15A:
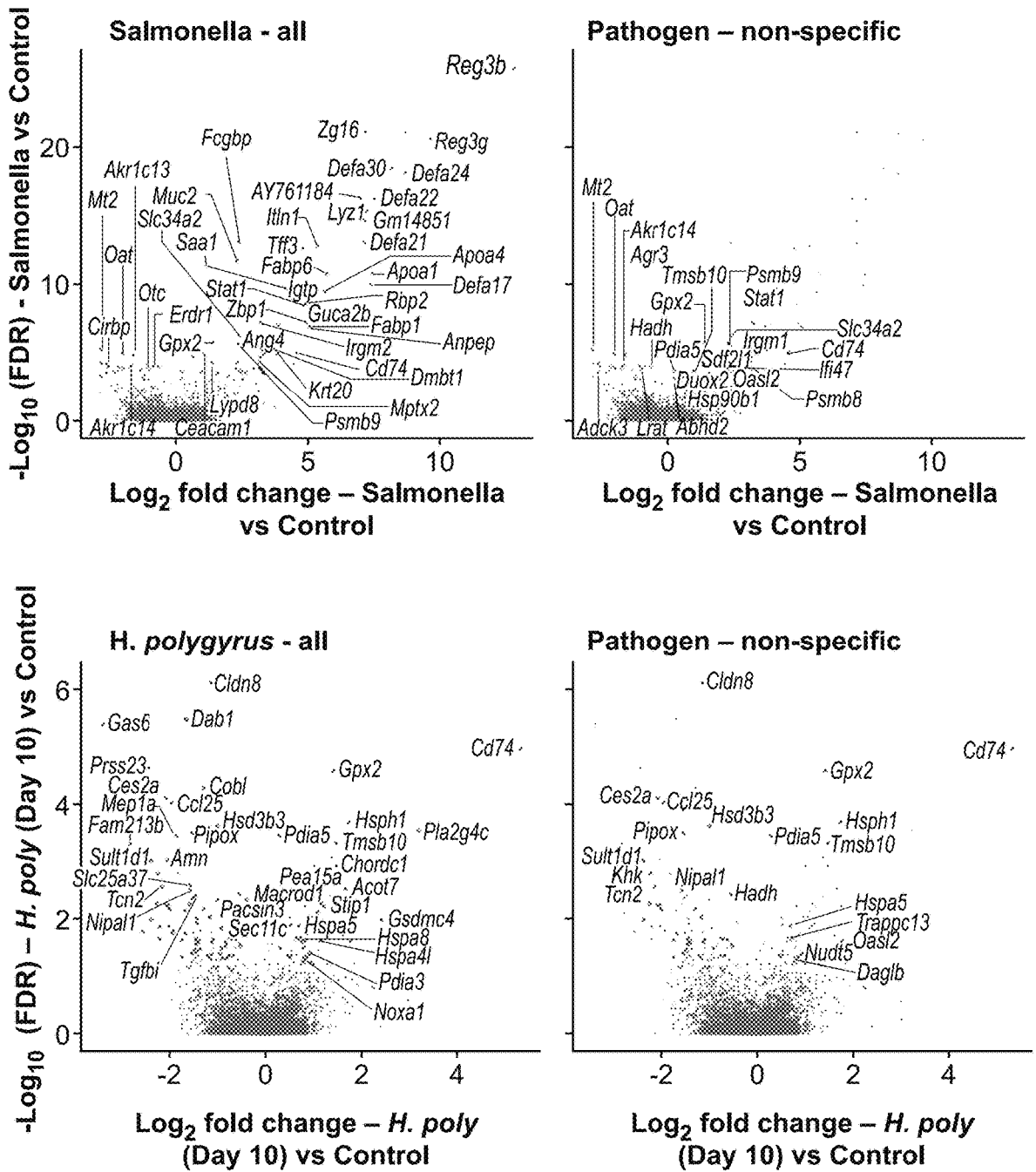
FIG. 15A-15F—Intestinal epithelial cell response to pathogenic stress, related to FIG. 6.
Figure 15B:
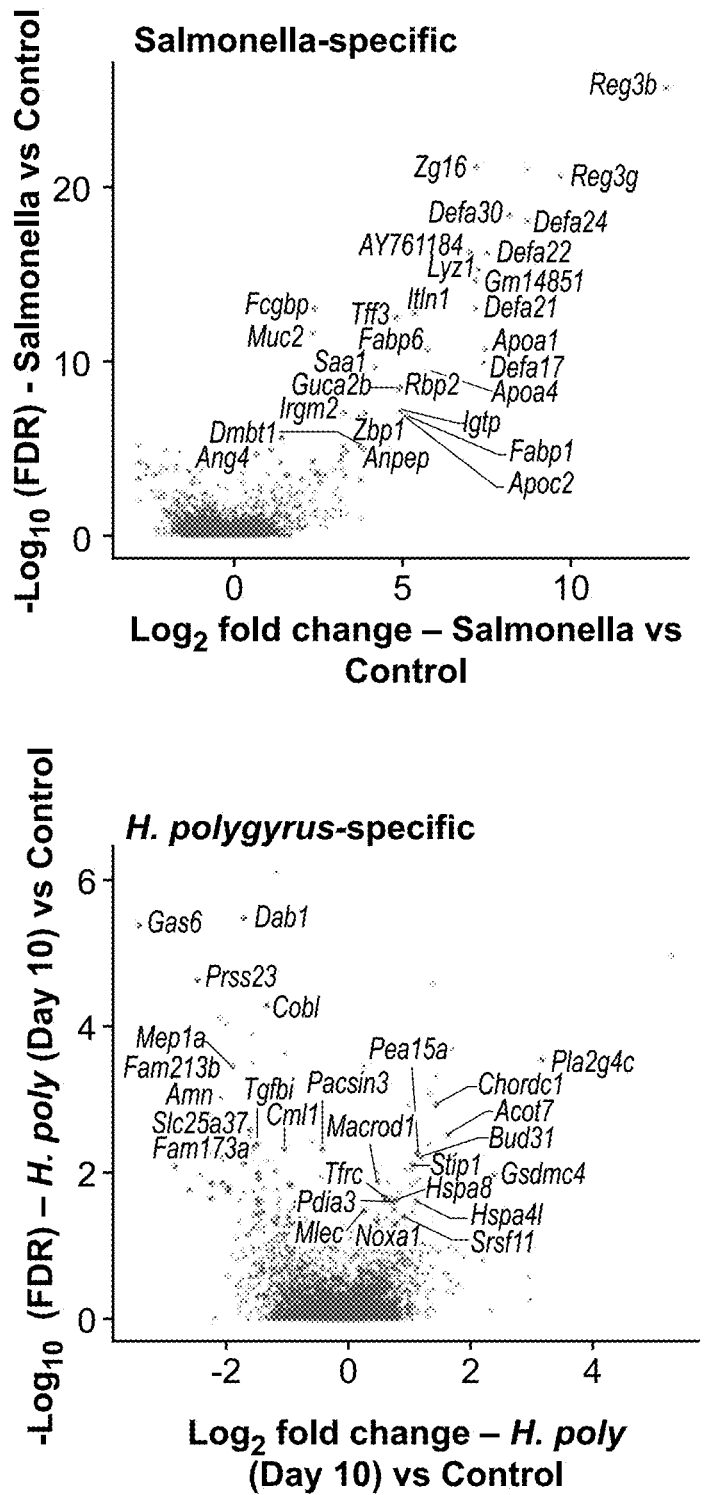
Figure 16A:
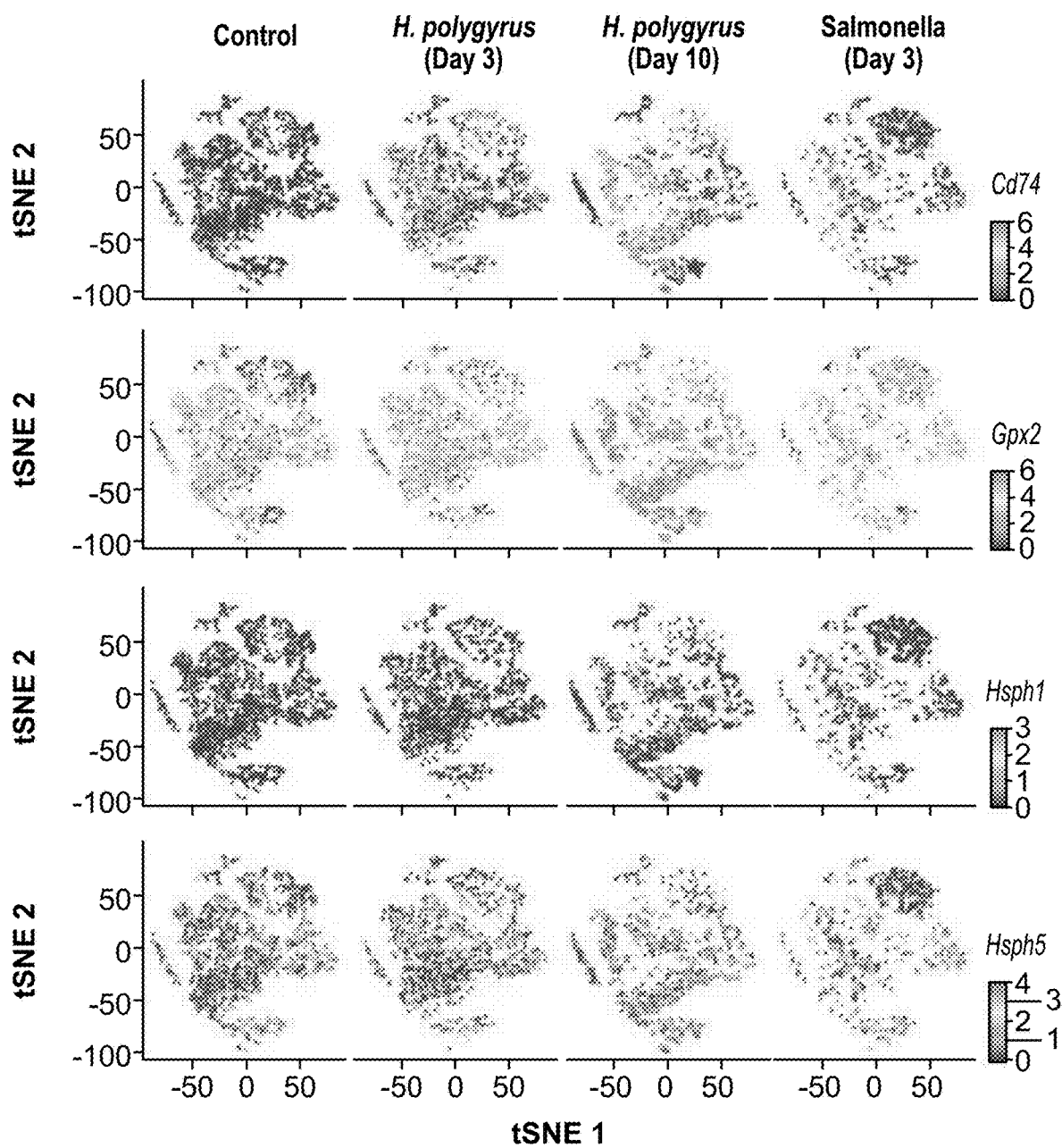
FIG. 16A-16D—Goblet and tuft cell responses to H. polygyrus show a unique defense mechanism, related to FIG. 6.

First, Applicants investigated the global effects of infection with Salmonella. In infected IECs, 571 genes were up-regulated vs. control cells (FDR<0.25, likelihood-ratio test, FIGS. 15a and 15b, top left) and these genes were enriched (FDR<0.001, hypergeometric test) for pathways involved in defense response to bacterium (FIG. 6a). Also up-regulated were genes involved in acute inflammatory programs such as the interferon-inducible GTPase (Igtp) and DNA-dependent activator of IFN-regulatory factors (Zbp1), or with a protective role in Salmonella infection, such as the anti-microbial lectins Reg3b and Reg3g[4,6,5] (FIG. 6b, top). In addition, Applicants identified a non-specific inflammatory response—a minority (112/571; 19%) of the genes up-regulated in response to Salmonella infection are also regulated in the same way in response to H. polygyrus (FDR<0.25, likelihood-ratio test), and are likely associated with a generalized acute stress response (FIGS. 15a and 15b, middle panels). Indeed, genes known to be involved in stress responses such as Gpx2, Hspa1 and Hsph5 were among those up-regulated in response to both pathogens (FIGS. 15a, 15b, and 10a). In particular, the invariant chain of MHC class II, Cd74, was also strongly induced (FDR<0.001, likelihood-ratio test) in both responses (FIG. 16a).

Figure 15C:
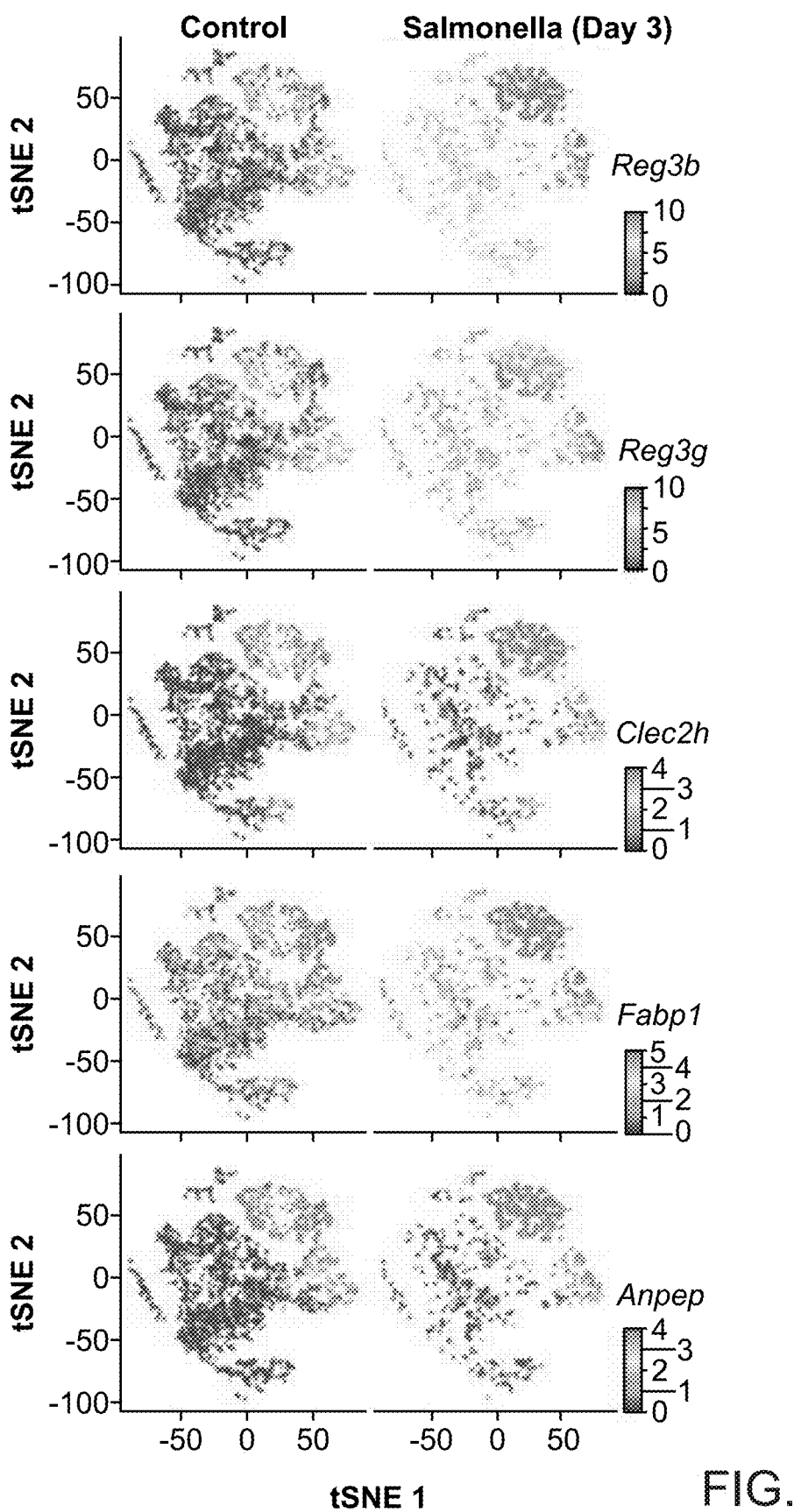
Figure 15D:
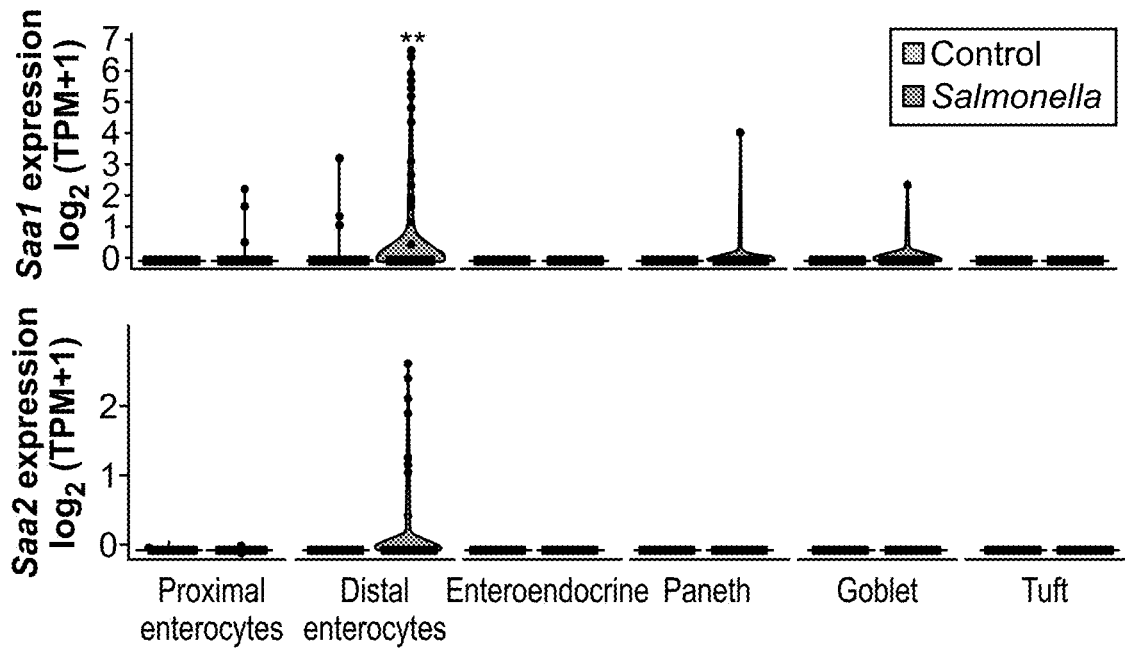
Figure 15E:
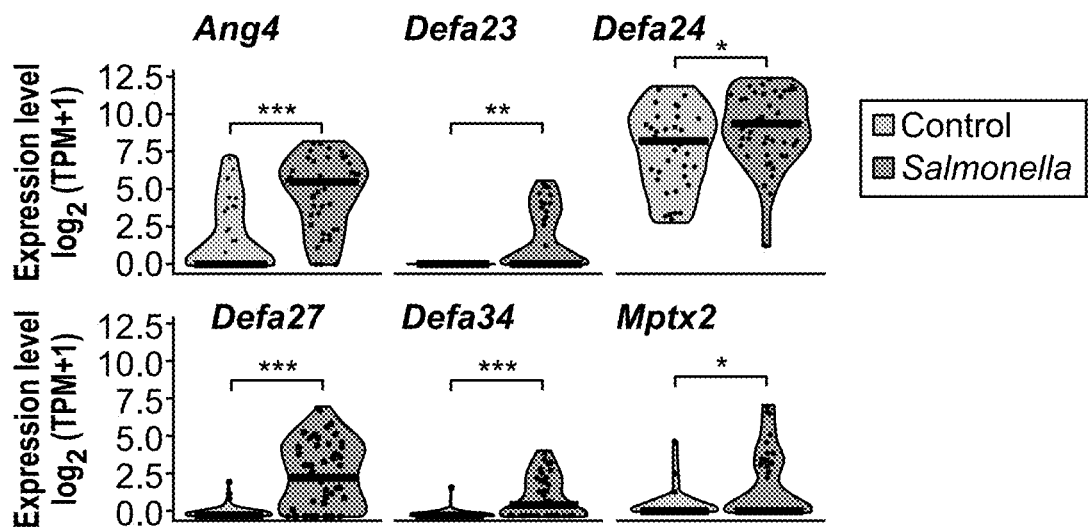

Second, Applicants identified cell-type-specific responses to *Salmonella* infection, most notably, an increase in the expression of both anti-microbial peptides and the mucosal pentraxin, Mptx2 (FIG. 1) in Paneth cells under infection (FIG. 15e). Comparing enterocytes in control and *Salmonella*-infected mice (424 vs. 705 cells) (FIG. 6e, top), Applicants found 40 enterocyte-specific genes significantly up-regulated (FDR<0.1, likelihood-ratio test), including the innate immune-related genes Tnfsf10 and Nlrp6. Among these cell-type-specific genes, 26 (65%) are induced in a *Salmonella*-specific manner (FIG. 6e, bottom, Methods), including several previously implicated in the response to *Salmonella* infection, such as Tgm2[66]. Comparing single enterocytes in control and *Salmonella*-infected mice (424 vs. 705 cells) (FIG. 6h), this study found significant up-regulation of innate immune-related molecules including Clec2d, Nlrp6 and Smad4 and (FIG. 6h, left). this study further refined the list to 52 *Salmonella*-specific genes (Methods) and found several genes previously implicated in the response to *Salmonella* infection such as Tgm2, Nlrp6 and Casp8 (FIG. 6h, right) (Man et al., 2013; Rodenburg et al., 2007; Wlodarska et al., 2014). Thus, the dramatic elevation in the number of enterocytes together with the retuning of their intrinsic cell states suggests an unappreciated crucial role of these absorptive cells in anti-microbial defense. In addition, the pro-inflammatory apolipoproteins[67] Serum Amyloid A1 and 2 (Saa1 and Saa2) were induced in the distal enterocytes, under *Salmonella* infection, with higher levels of Saa1 and Saa2 (FIGS. 15a, 15b, and 15c).

Notably, as a result of infection, some anti-microbial genes, that are enterocyte-specific in homeostatic conditions, are induced at two levels: (1) further induction in enterocytes; and (2) global induction in non-enterocyte cells, generating an overall elevated response of the tissue. Specifically, in control mice, expression of the Reg3 gene-family (Reg3a-g) was mainly restricted to absorptive enterocytes (Table 3-4). Upon *Salmonella* infection not only was their expression further elevated in absorptive enterocytes (FIG. 6b top, red dots), but Reg3b and Reg3g, largely undetectable in other cell types pre-infection, were up-regulated in all cell-types post-infection (FIG. 6b top, grey dots). Thus, the IEC response to *Salmonella* involves the induction in all cells of anti-microbial genes, including Clec2h, Anpep, and Enpep, that are only expressed in enterocytes in homeostasis (FIG. 6b top, FIG. 15c).

Figures 6D, 6E:
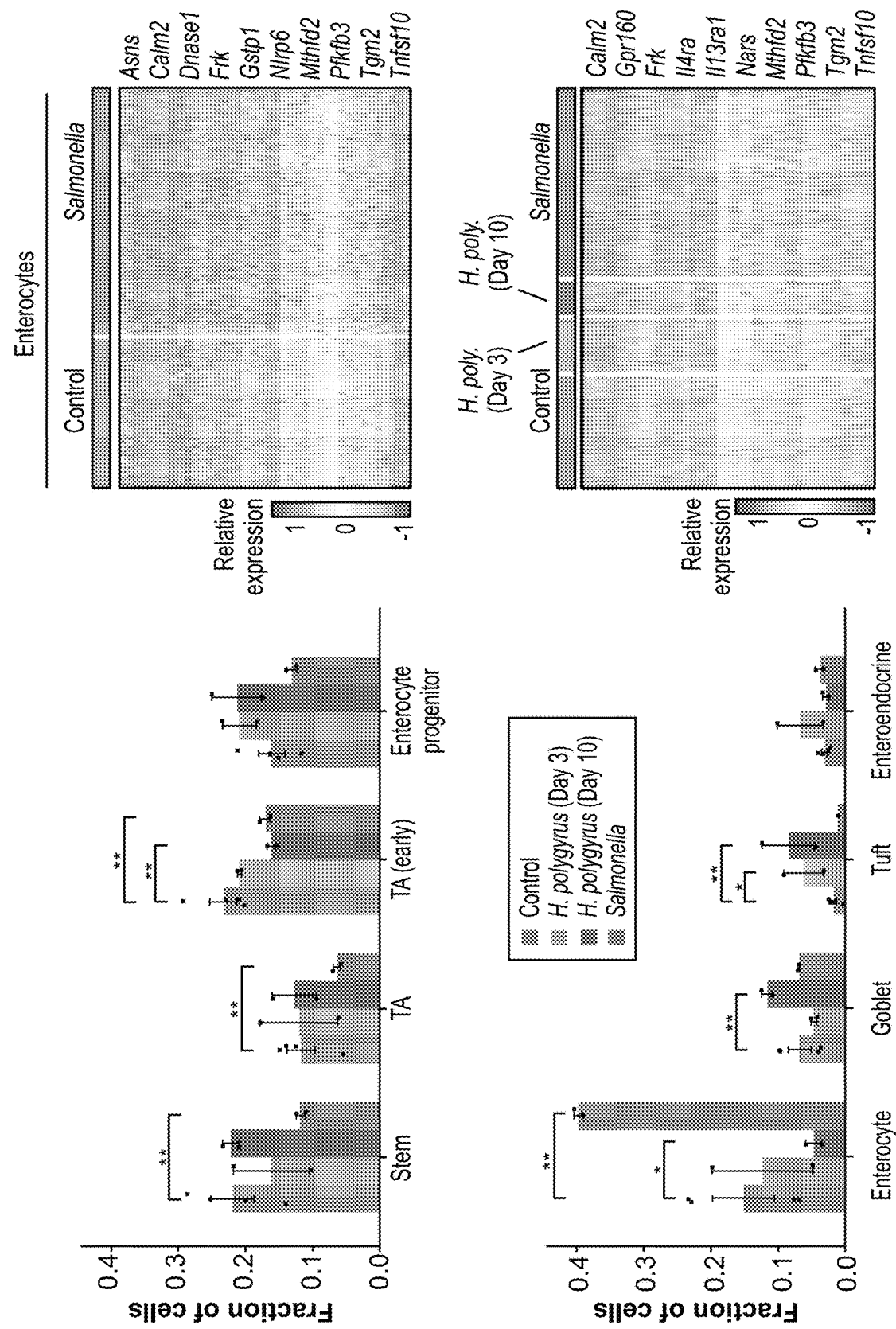
Figure 15F:
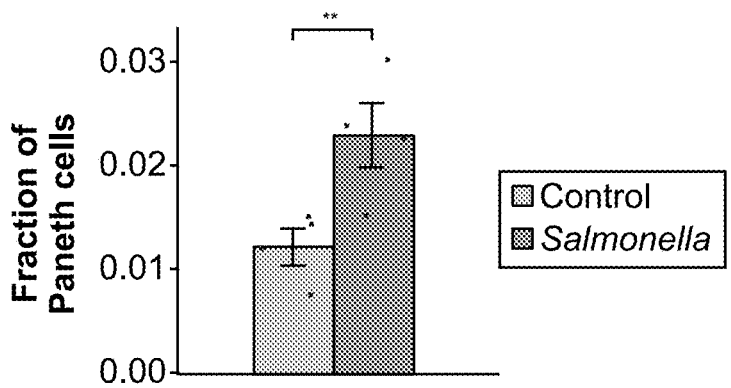

Third, Applicants systematically distinguished the contribution of changes in cell intrinsic expression programs vs. shifts in cell composition. Applicants used unsupervised clustering to determine the proportion of each of the different IEC populations (FIG. 6d), visualized by tSNE embeddings (FIG. 6c). Applicants observed a dramatic shift in cell proportions following *Salmonella* infection (FIG. 6d; Methods), with a substantial increase in the frequency of mature absorptive enterocytes (from 13.1% on average in control to 21.7% in infection; FIG. 6d) and a significant reduction in the proportion of TA (52.9% to 18.3%) and stem (20.7% to 6.4%) cells. Applicants initially recovered a low number of Paneth cells (Methods), and thus analyzed an additional 2,029 cells from an additional experiment (droplet-based scRNA-seq; n=4, *Salmonella*-treated mice), and found a substantial increase in mature Paneth cell proportions (from 1.1% to 2.3%, FDR<0.01), in agreement with a previous study that showed more positive staining of Paneth cells in *Salmonella* infection[68] (FIGS. 15e and 15f). These results suggest that the IEC response to *Salmonella* infection includes the induction of specific differentiation towards absorptive enterocytes and Paneth cells, most likely to increase production of anti-microbial peptides.

Figure 6F:
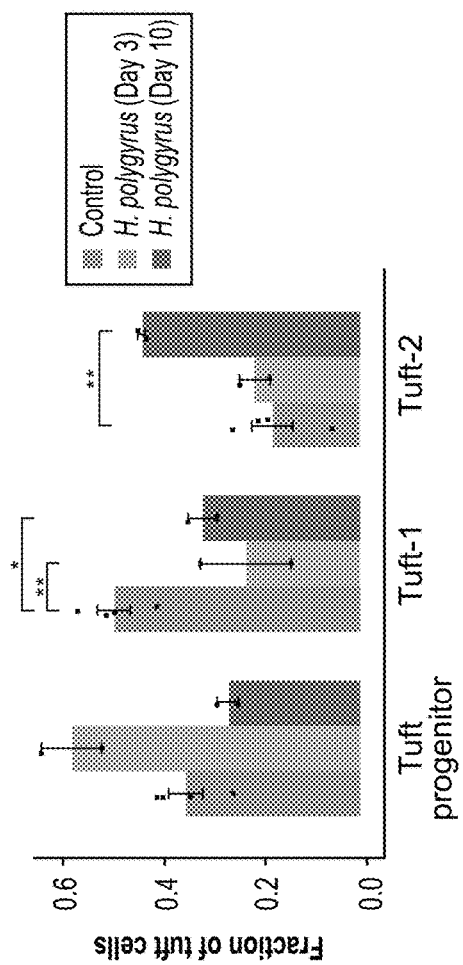
Figure 16B:
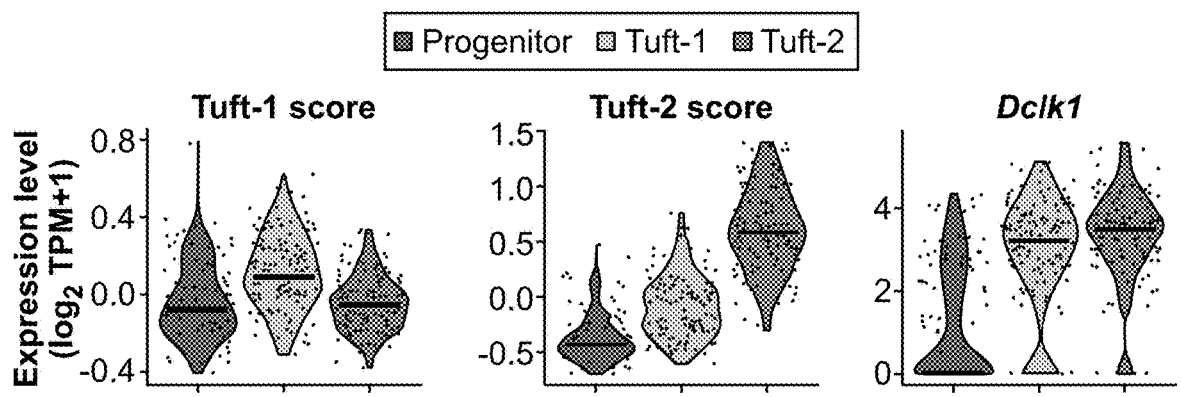
Figure 16C:
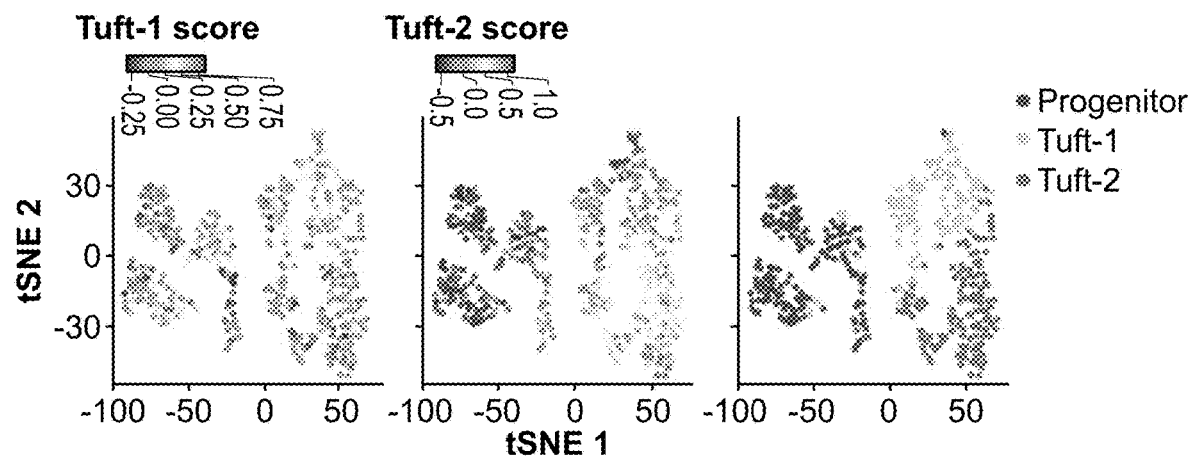

Next, analyzing IECs during infection with *H. polygyrus*, Applicants found a distinct recalibration of cell composition and cell states than in *Salmonella*. There are 299 genes up-regulated in *H. polygyrus* infected vs. control mice, 187 of which (62%) were specific to the *H. polygyrus* response (FDR<0.25, likelihood-ratio test, FIGS. 15a and 15b, bottom panels). These *H. polygyrus*-specific genes were enriched with inflammatory response molecules, including Dnaja1, Vcp, Noxa1 and Psmd6, the phospholipase Pla2g4c (FIGS. 15a and 15b, bottom right), and the tuft cell markers Acot7, Peal5a and Avil (FIGS. 15a and 15b bottom panels). This again suggested a change in cell composition, which Applicants then tested by unsupervised clustering. Indeed, at ten days post infection, there is a striking increase in goblet cells—known to be important for the epithelial response to the parasite 6 (on average, from 7.0% to 11.8%, FDR<1× $10^{-5}$, Wald test, Methods), and a reduction in enterocyte proportions (15.3% to 4.9%, FDR<1×$10^{-10}$, Wald test) (FIG. 6d). Tuft cell proportions were increased substantially at day three (1.9% to 6.3%, FDR<1×$10^{-5}$, Wald test), with a further increase by day ten (to 8.5%, FDR<1×$10^{-10}$, Wald test) (FIG. 6d). Within the tuft cell subset (409 cells overall, FIG. 16b-c) there was a significant elevation (17.2% to 43.0%, FDR<0.05, Wald test) in the proportion of immune-like Tuft-2 cells by day 10 (FIG. 6f), reflecting changes in tuft cell states along with the dynamic expansion in the overall tuft cell population in response to the parasite.

Figure 6G:
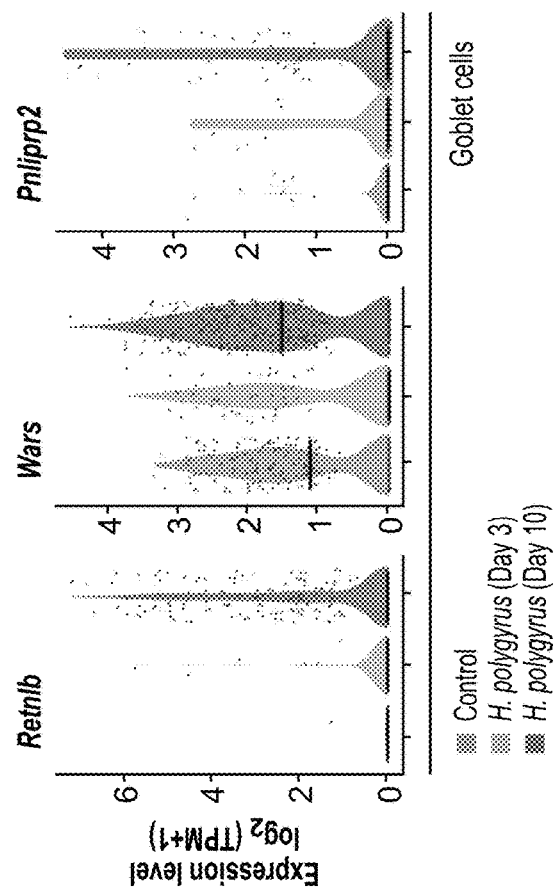
Figure 6H:
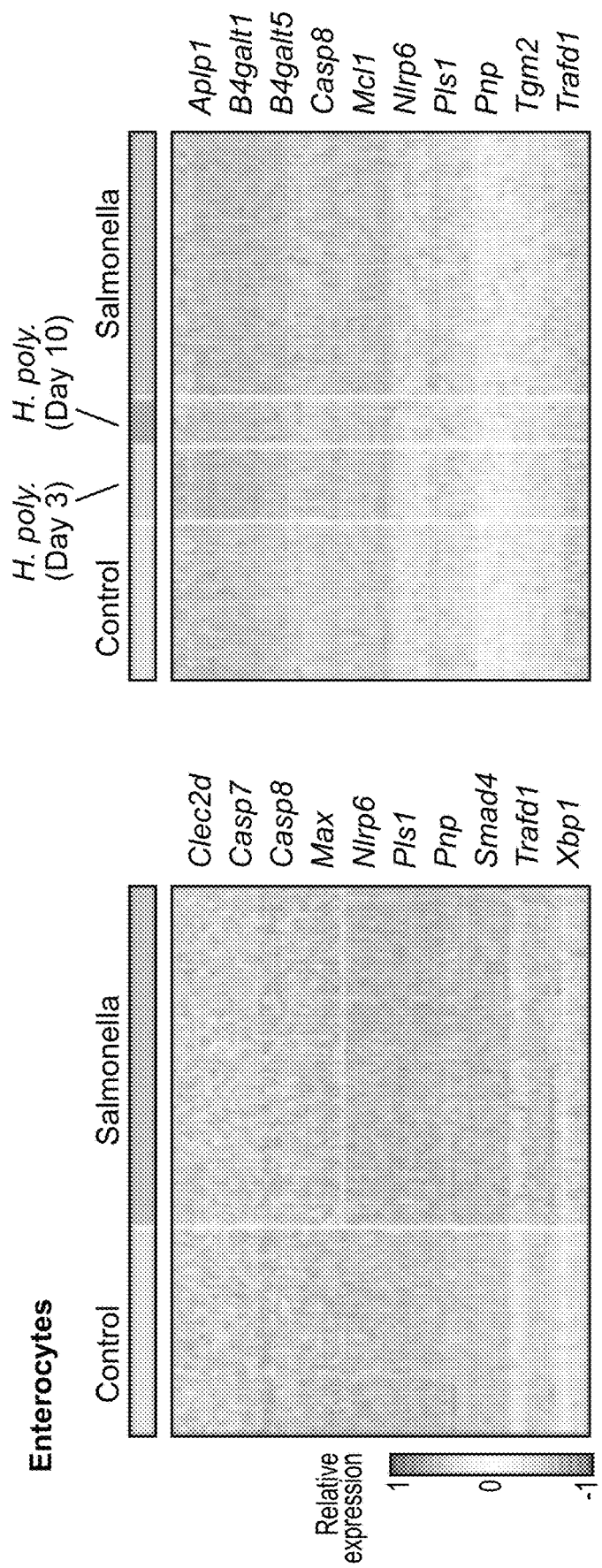
Figure 6I:
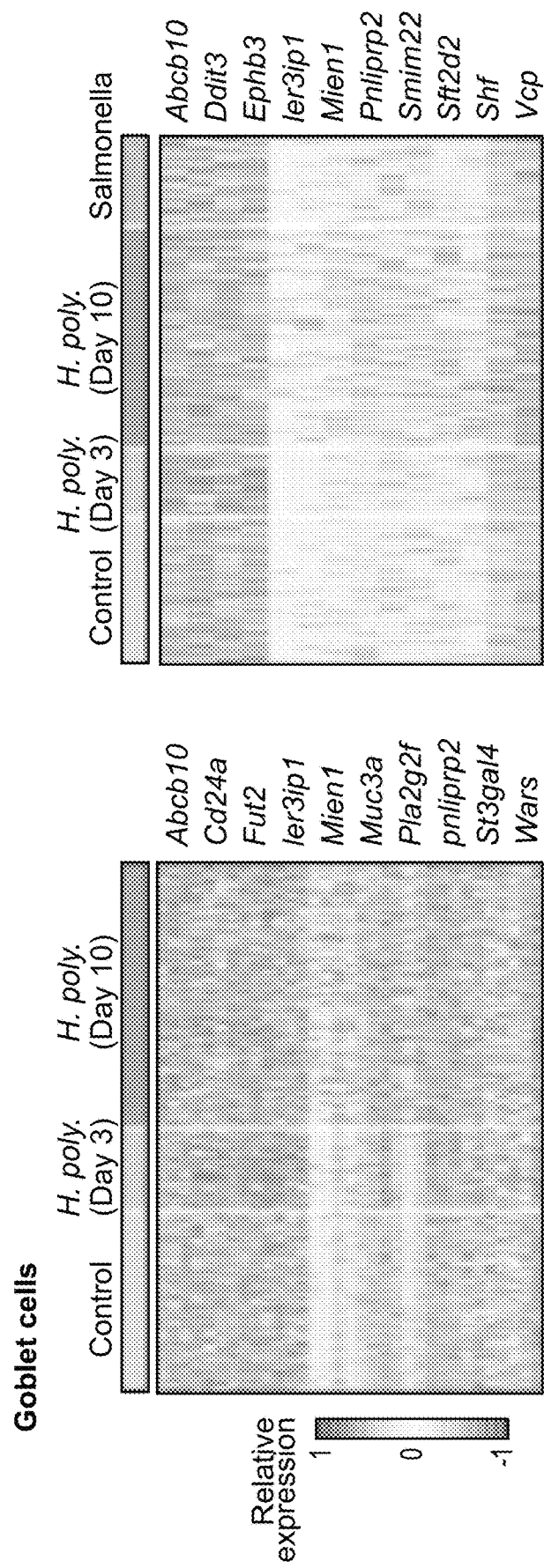
Figure 16D:
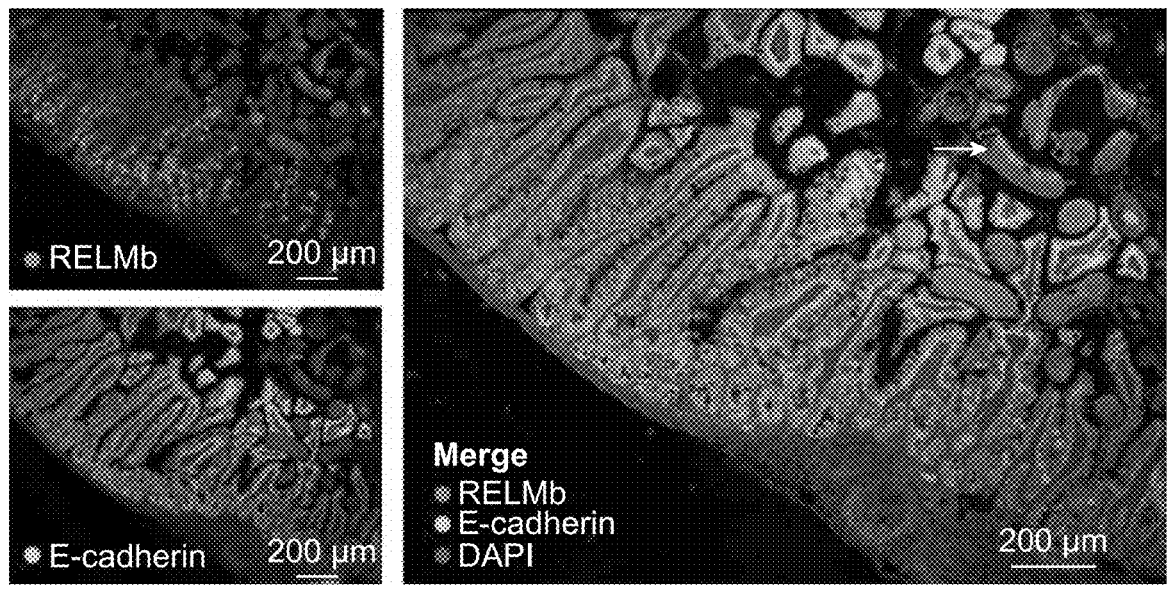

In addition to changes in cell proportions, within goblet cells there was a strong induction (FDR<1×$10^{-5}$, likelihood-ratio test; FIG. 6g) of several genes previously implicated in anti-parasitic immunity, including RELMp[69] (Retnlb, FIG. 16d), but also in genes (e.g., Wars and Pnlipr2; FIG. 6g), previously reported to be expressed in response to parasitic infection[70], but not known to be expressed by goblet cells. Further refining this gene set to those specific to the *H. polygyrus* pathogen revealed an up-regulation of genes related endoplasmic reticulum stress, specifically Ddit3, Ier3ip1 and Sft2d2, possibly involved in processing of secreted mucins to respond to the worm (FIG. 6i, right). Thus, *H. polygyrus* infection elicits shifts in both cell composition and cell state, with early expansion of tuft cells to initiate the Th2 response[14], and later expansion of goblet cell numbers to help prevent attachment of the helminth to the epithelial barrier via secreted mucins[71], along with an increase in the expression of key genes in the expanded goblet cells.

Table Legends

Table 2| Summary of single-cell RNAseq experiments. This table provides the number (after quality filtering, see Methods) of individual intestinal epithelial cells profiled in each of the in this study.

Table 3| Cell-type specific signature genes—droplet-based dataset. This table provides the lists of genes specific to each of the identified clusters of intestinal epithelial cells, identified using 3' droplet-based scRNA-seq data (FIG. 1b).

Table 4|Cell-type specific signature genes—plate-based dataset. This table provides the lists of genes specific to each of the identified clusters of intestinal epithelial cells, identified using full-length plate-based scRNA-seq data (Extended Data FIG. 2a).

Table 5|Consensus cell-type specific signature genes— both datasets. This table provides high-confidence lists of genes specific to each subtype of intestinal epithelial cells in both 3' droplet-based and full-length plate-based scRNA-seq datasets.

Table 6| Cell-type specific TFs and receptors. This table provides lists of genes annotated as either transcription factors (TFs), G protein-coupled receptors (GPCRs), or leucine-rich repeat (LRR) proteins, enriched in each subtype of intestinal epithelial cells in full-length plate-based scRNA-seq data.

Table 7| Enteroendocrine cell subset signature genes. This table provides the lists of genes specific to each of the identified clusters of enteroendocrine cells, identified using 3' droplet-based scRNA-seq data.

Table 8|Consensus tuft cell subset signature genes. This table provides the lists of genes specific to each of the identified subsets of tuft cells, identified using both 3' droplet-based and full-length plate-based scRNA-seq data.

Table 9| In vitro and in vivo M cell signature genes. This table provides the lists of genes specific to intestinal microfold (M) cells, using 3' droplet-based scRNA-seq data from in vitro cells derived from RANKL-treated organoids, and in vivo cells derived from the follicle associated epithelia (FAE) of wild-type mice.

Figure 10R:
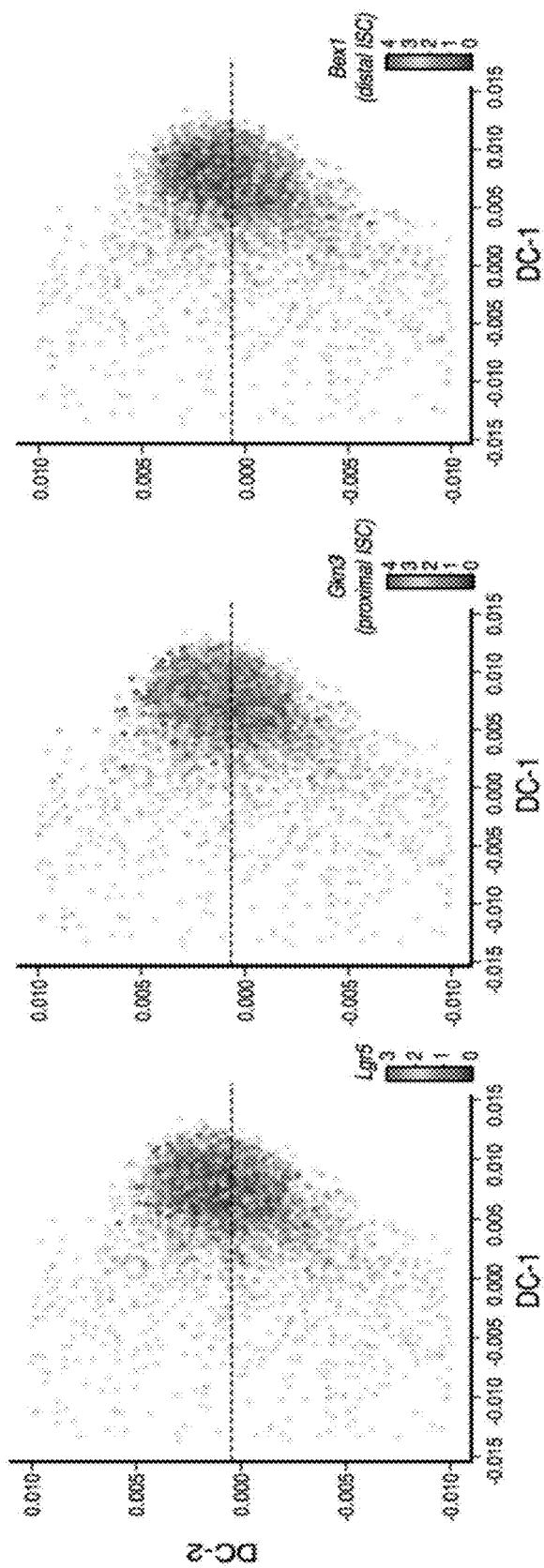

Table 10| Markers of proximal and distal Paneth cells. This table provides estimates of differential gene expression between two subsets of Paneth cells identified by clustering and interpreted (post-hoc) as derived from proximal and distal small intestine (FIG. 10A-10R).

Example 11—Discussion

The intestinal epithelium is the most diverse epithelial tissue in the body, composed of functionally and molecularly specialized subtypes. Here, Applicants dissected it into its different components using massively parallel scRNA-seq, analyzing a total of 53,193 IECs, to create a high-resolution single-cell atlas of the mouse intestinal epithelium, and reveal even further diversity than was previously appreciated. Using unsupervised analyses, Applicants identified and characterized the transcriptomes of the major differentiated epithelial cell-types: enterocyte, goblet, Paneth, enteroendocrine, tuft and microfold. Applicants also derived specific gene signatures for intestinal stem, transit-amplifying and various enterocyte precursor cells. For each major cell-type Applicants obtained specific markers, TFs and GPCRs and high-confidence consensus signatures from two complementary scRNA-seq methods (3' and full-length).

The single-cell profiling of tens of thousands of intestinal epithelial cells revealed coherent cell-specific transcriptional programs, some revising predicted marker expression, which Applicants validated in situ and in prospectively isolated cells. This emphasized the utility of unsupervised profiling of tissues to define new cell-type gene signatures, rather than solely relying on previously annotated individual marker genes, which may lead to biased isolation of subtypes. For example, Applicants discovered and validated that tuft cells are composed of two subsets, one of which expresses neuron-related genes which might mediate interaction with the enteric nervous system, while the other expresses genes related to inflammation and immunity, including the immune-cell marker gene Ptprc (CD45). This CD45+ tuft population expresses the epithelial cytokine TSLP, which may represent an additional mechanism by which epithelial cells communicate with gut-resident immune cells. Further studies would be required to determine whether the Tuft-1 and Tuft-2 cells represent two different developmental fates, or alternative cell states. In another example, Applicants found that several known tuft cell markers are also expressed by M cells, which may have confounded studies based on those markers. Using single-cell profiling Applicants resolve this ambiguity, providing novel specific markers and TFs to distinguish these rare cells, which may enable further insights into M cell biology.

The large number of cells profiled allowed Applicants to assess heterogeneity even within rare subpopulations such as enteroendocrine cells (EECs). From 533 EECs extracted from 18,881 epithelial cells (Table 2), Applicants identified and characterized the transcriptomes of 12 subsets, 8 of which are mature. Interestingly, EECs were more abundant than expected and partitioned into two main groups, enterochromaffin (2 subsets) and Secretinhigh (6 subsets) cells (FIG. 3). The Reg4 gene, a previously proposed marker for all EECs[23], was in fact expressed only in one of the groups of enterochromaffin cells. The in vivo sampling of EECs encompasses the subsets found in an organoid-derived EECs single-cell study[53], and highlights three additional mature EEC subsets (FIG. 12e). Two of these subsets (SIL-P and SIK-P) are enriched in the ileum, while SILA were found mainly in the duodenum, consistent with the regulatory roles of the hormones Ghrelin—an appetite stimulant—and GLP-1 and PYY, which together act as an 'ileal brake', a feedback loop which limits gastric emptying as nutrients arrive in the distal gut[11]. Further, Applicants found that most EEC subsets express more than one GI hormone and defined a novel taxonomy reflecting each subset's unique hormonal expression profile. An open challenge is to understand the specific role of each of these novels subsets in the orchestration of appetite, gut motility, nutrient absorption, or in the onset and treatment of diseases, such as Type 2 diabetes and obesity.

Molecular Underpinning for the Integration of Lumen Signals by the Gut Epithelium IECs play barrier roles, absorb nutrients, integrate and relay signals from the environment to the immune and enteric nervous systems[12]. The atlas resolves the cellular populations that are implicated in sensory pathways at unprecedented resolution. For example, Applicants found that two of the 10 most enterocyte-specific TFs were from the nuclear receptor (NR) family of proteins. These genes are crucial for sensing and metabolism of various substances. In particular, lipid homeostasis (Nr1h3), and sensing of endobiotic and xenobiotic substances, Nri3.

Similarly, Applicants provide an enhanced map of the GPCRs expressed by all cells, and particularly by EEC subsets. Most notably, the important cannabinoid receptor Gpr119[37] was enriched in the novel SILA subset (FDR<0.05, FIG. 12f), which co-expresses Ghrl and Gcg, genes encoding gut hormones that regulate appetite and satiety. Furthermore, several GPCRs enriched in EECs (FDR<0.05, FIGS. 8e-8g) may mediate communication with enteric neurons, including the metabotropic glutamate (Grm4) and acetylcholine (Chrm4) receptors. Additionally, the important neurotrophic cytokine brain-derived neurotrophic factor (Bdnf) was enriched in SIK-P cells (FDR<0.01, FIG. 3b), a possible additional EEC-neuron channel of communication. Tuft cells were also enriched for GPCR expression, supporting recent studies that they are specialized for chemosensory properties, especially taste sensing[72]. Indeed, the gene encoding taste receptor type 1 member 3 (Tas1r3) was expressed exclusively by tuft cells. Like EECs, tuft cells were enriched (FDR<0.05) for genes encoding GPCRs that sense nutrients, such as Ffar3 and Sucnr1 and for gamma-aminobutyric acid B (GABAB, Gabbr1) and dopamine (Drd3) receptors that may be involved in further crosstalk with enteric neurons.

The Adaptive Response of the Intestinal Epithelium to Pathogens Combines Cell Intrinsic and Cell Composition Changes Although many studies have shown an expansion of goblet cells and recently tuft cells in response to parasites[13-15], this analysis revealed that this dynamic restructuring of the epithelial barrier is specific to the identity of the individual pathogen and distinguished cell composition changes from changes in cell intrinsic programs. After infection with the parasitic worm *H. polygyrus*, there is, as reported, dramatic expansion of secretory cell types, initially an expansion of tuft cells, followed several days later by goblet cell metaplasia. While the overall Tuft cell population increased, the relative proportion of immune-like Tuft-2 subset was particularly expanded. In contrast, the pathogenic bacterium *Salmonella enterica* induced a strong expansion of absorptive enterocytes and Paneth cells. These dynamic shifts in epithelial composition constitute a generic response mechanism in which differentiation pathways are redirected to enhance the epithelial barrier under pathogenic insult.

These compositional changes are accompanied and enhanced by cell intrinsic changes to regulatory programs, both within specific cell types and across multiple cell types. During helminth infection, goblet cells induce the anti-parasitic molecules Retnlb, Wars and Pnliprp2. Upon *Salmonella* infection, Paneth cells not only increase in number, but also upregulate various genes encoding anti-microbial peptides (e.g., Lyz1, Defa5), and the mucosal pentraxin, Mptx2. Moreover, Applicants uncovered a novel epithelial cell response to *Salmonella*, where the expression of genes that are cell-type-specific in homeostatic conditions is broadened across multiple cell types during infection: the antimicrobial C-type lectins Reg3b and Reg3g, known to be crucial for preventing attachment of bacteria to the epithelium[73], are expressed only by enterocytes in normal conditions, but were globally up-regulated by all cells following *Salmonella* infection. This could only be distinguished by single-cell analysis.

In single-cell RNA sequencing there is a trade-off between sequencing fewer cells deeply and sequencing many cells at a lower coverage. This study pursued both directions simultaneously for maximal information capture, and showed that the very large cell numbers achievable with droplet-based methods enabled the discovery of extremely rare subtypes (Shekhar et al., 2016), while the high coverage (an average of more than 6,000 genes detected per cell) obtained by the plate-based data enabled the detection of less abundant mRNA molecules such as transcription factors, which frequently play important regulatory roles in gut function. Further, the high number of cells this study obtained from the rapidly differentiating intestinal epithelium constitutes a dense sampling of a dynamic process, and therefore provided a high level of 'pseudo-temporal' resolution. This enabled Applicants to profile gradual shifts in differentiation of the absorptive enterocytes, subsequently identifying both known and novel TFs such as Gata4 (Bosse et al., 2006) and Gata5 which are expressed coherently during differentiation toward proximal or distal mature enterocyte, respectively.

This study provides a detailed reference dataset and specific hypotheses for follow-up studies, including cell-type specific gene markers, TFs and GPCRs that may open the possibilities for novel clinical interventions in pathologies such as obesity, type-2 diabetes, and allergies. For example, the Tuft-2 cells, which secrete Th2-recruiting epithelial cytokines, may provide insight into mechanisms underlying food allergies. Furthermore, the characterization of epithelial differentiation dynamics in response to two enteric pathogens, may help find ways to manipulate epithelial cell differentiation to minimize gut pathologies, such as acute or chronic gut inflammation, identify cell-specific epithelial cell markers for restitution and inflammation resolution.

Understanding the development, differentiation and function of an organ, such as the intestine, requires the identification and characterization of all of its component cell types. In the small bowel, intestinal epithelial cells (IECs) sense and respond to microbial stimuli and noxious substances, provide crucial barrier function and participate in the coordination of immune responses. Here, this study profiled 24,423 individual IECs from mouse small intestine and intestinal organoid cultures. Taken together, the examples above demonstrate that using unsupervised clustering, Applicants defined specific gene signatures for major IEC lineages, including the identification of Mptx2, a mucosal pentraxin, as a novel Paneth cell marker responsive to *Salmonella* infection. In addition, this study identified unexpected diversity of rare hormone-secreting enteroendocrine populations, revealing co-expression programs of gut hormone genes, previously thought to represent different enteroendocrine subtypes, and constructed a novel hierarchical classification of these cells. this study also distinguished two subtypes of Dclk1-positive tuft cells, one of which (Tuft-2) expresses both the epithelial cytokine Tslp and the pan-immune cell marker Ptprc (CD45), which has not been previously associated with any non-hematopoietic cell type.

Finally, this study characterized how the intrinsic state and proportion of these cell types are reshaped in response to *Salmonella enterica* and *Heligmosomoides polygyrus* infections. *Salmonella* infection led to an increased number of Paneth cells and enterocytes, and a Paneth cell-specific up-regulation of both defensins and pentraxins, including Mptx1 and Mptx2. An absorptive enterocyte-specific anti-microbial program was broadly activated across all IEC types, demonstrating a previously uncharacterized cellular plasticity in response to pathogens. In contrast, *H. polygyrus* led to expansion of goblet and tuft cell populations. This increase in tuft cells was driven by an expansion of the Cd45+ Tuft-2 group. The comprehensive atlas highlights new markers and transcriptional programs, novel allocation of sensory molecules to cell types and organizational principles of gut homeostasis and physiology.

Example 12—T Helper Cells Modulate Intestinal Stem Cell Renewal and Differentiation Rapid generation of mature epithelial cell types in the small intestine occurs through continuous self-renewing, proliferation and differentiation of intestinal stem cells (ISCs)[2]. The niche that supports ISCs is composed of diverse cell types, including circulating immune cells[96]. However, little is known about interactions between immune cells and ISCs during homeostasis and disease, and it is unclear how niche dynamics affect eventual cell fate or the balance between self-renewal and differentiation.

Here, Applicants identify and characterize novel mechanisms for interaction between immune cells and ISCs. Using scRNA-seq, Applicants identified a putative molecular mechanism for CD4+ T cell interaction with specific subsets of Lgr5+ ISCs with enriched expression of MHC class II (MHCII) molecules and higher proliferation rates. Applicants characterized this putative interaction using scRNA-Seq and in situ analysis of canonical in vivo infection models, organoid assays, and T cell-depleted, $T_{reg}$-depleted, and inducible epithelial-specific MHCII-KO mouse models. Applicants found that CD4+T helper cells influence ISC renewal and epithelial differentiation via MHCII interaction. The study underscores the important anatomic positioning of CD4+ T cell-ISC interactions in the context of ISC renewal or contraction, gut inflammation, and tumorigenesis.

Applicants uncovered three distinct Lgr5+ crypt base columnar ISC[6] states distinguished by specific proliferation rates: low-cycling (ISC-I), primed (ISC-II) and high-cycling (ISC-III). Surprisingly, MHC class II (MHCII) molecules are enriched in the two proliferative states (ISC-II and ISC-III), suggesting a novel T cell-ISC interaction. Using co-culture of intestinal organoids[4] and T cells, cytokine stimulations, and in vivo mouse models, Applicants confirm that CD4+T helper (Th) cells modulate ISCs and their differentiation, in a manner specific to the Th subtypes and their signature cytokines and that depends on MHCII expression by ISCs. In particular, mice lacking Th cells show expansion of the ISC pool, specific $T_{reg}$ depletion in vivo results in substantial reduction of ISC numbers, whereas specific inducible knockout of MHCII in epithelial cells in vivo results in expansion of the ISC pool. The findings show that interactions between ISCs and Th cells mediated via MHCII expressed in epithelial tissue helps orchestrate tissue-wide responses to external signals.

Example 13—High Expression of MHCH Genes by ISC Subsets

Figure 21D:
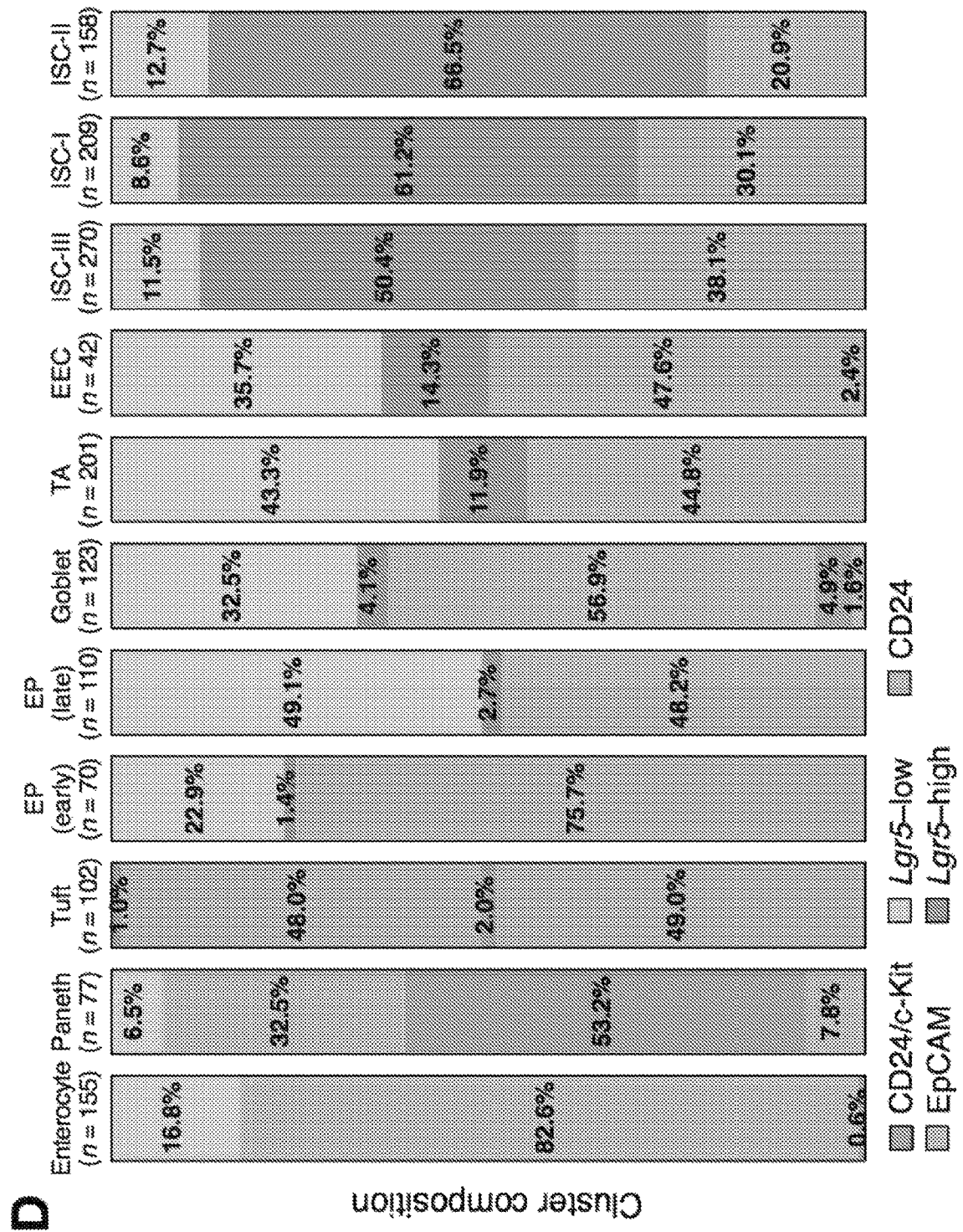
Figure 21G:
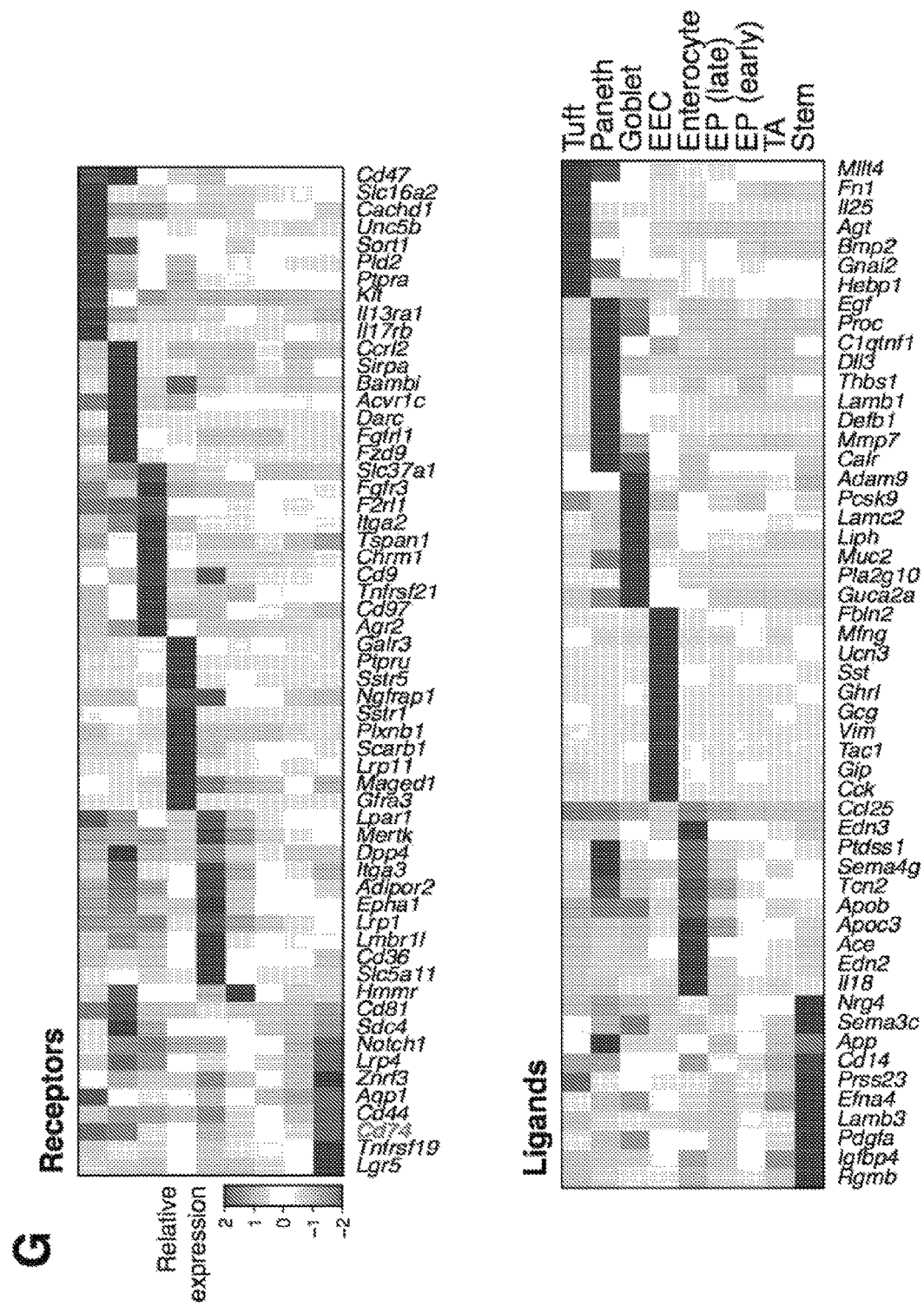

To identify potential mechanisms for ISC-immune cell interactions, Applicants searched for genes that are specifically expressed by ISCs compared to other gut epithelial cells and that encode cell surface or secreted proteins capable of interacting with cognate molecules on immune cells. Applicants collected full-length, high-coverage scRNA-seq (scRNA-seq) data of 1,522 EpCAM* intestinal epithelial cells (IECs) (see above examples) from crypt-enriched small intestine of WT and Lgr5-GFP mouse models[6] (Methods). Using unsupervised clustering (k-nearest neighbor (k-NN) graph-based clustering, Methods) of the 1,522 cells (table 11) Applicants identified 637 Lgr5-high (Lgr5$^{High}$) stem cells (FIG. 21A,B), as well as clusters corresponding to mature enterocytes, Paneth, goblet, tuft, and enteroendocrine cells (see above examples). Clustering of only the 637 ISCs (Methods) further partitioned the ISCs into three distinct subsets (ISC-I, -II and -III, FIG. 17A,B), all of which express known stem cell markers[103] including Lgr5 (FIG. 21C). This was consistent with recent scRNA-seq reports[30,145]. Applicants confirmed that all three subsets comprise Lgr5+ ISCs using the Lgr5-GFP mouse model[4]: the three stem cell populations were strongly enriched for GFP$^{high}$ cells (FIG. 21D), over 90% of the GFP$^{high}$ cells were allocated to one of the three stem cell subsets (FIG. 21E), and the three subsets are present in similar proportions in the duodenum, jejunum, and ileum (FIG. 21F and Methods). Lastly, Applicants identified differentially expressed genes between the three subsets, as well as between all ISCs and the other IECs that are annotated as receptors or ligands for cell-cell interactions[158] (FIG. 21G and table 12).

TABLE 11

| Dataset | Number of cells | Single-cell platform | Genes detected per cell (median) | Transcripts detected per cell (median) |
|---|---|---|---|---|
| T cell and cytokine-treated organoids | 23177 | Droplet-based | 2200 | 6401 |
| CD45+ immune cells | 5122 | Droplet-based | 1083 | 4086.5 |
| Nude mice | 2967 | Droplet-based | 1966 | 6275 |
| TCRb-KO mice | 9488 | Droplet-based | 1658 | 4162.5 |
| Foxp3-DTR mice | 3387 | Droplet-based | 2113 | 7644 |
| Epithelial-specific MHCII-KO mice | 3176 | Droplet-based | 2368 | 8968 |
| MHCII +/− stem cells | 503 | SMART-Seq2 | 5908 | No UMIs |
| Edu +/− stem cells | 117 | Div-Seq | 2529 | No UMIs |
| Total | 47937 | | | |

TABLE 12

| Stem | TA | EP (early) | EP (late) | Enterocyte | EEC | Goblet | Paneth | Tuft |
|---|---|---|---|---|---|---|---|---|
| A. Receptors enriched in IEC subsets ||||||||||
| Lgr5 | | Hmmr | | Slc5a11 | Gfra3 | Agr2 | Fzd9 | Alox5 |
| Tnfrsf19 | | | | Cd36 | Maged1 | Cd97 | Fgfrl1 | Il17rb |
| Cd74 | | | | Lmbr1l | Lrp11 | Tnfrsf21 | Darc | Il13ra1 |
| Cd44 | | | | Mylk | Scarb1 | Cd9 | Acvr1c | Kit |
| Aqp1 | | | | Slc2a2 | Plxnb1 | Chrm1 | Bambi | Ptpra |
| Znrf3 | | | | Lrp1 | Sstr1 | Tspan1 | Sirpa | Pld2 |
| Lrp4 | | | | Epha1 | Ngfrap1 | Itga2 | Ccrl2 | Sort1 |
| Notch1 | | | | Adipor2 | Pde1c | F2rl1 | | Unc5b |
| Htr4 | | | | Itga3 | Sstr5 | Fgfr3 | | Cachd1 |
| Sdc4 | | | | Dpp4 | Ptpru | Slc37a1 | | Slc16a2 |
| Cd81 | | | | Mertk | Galr3 | Plaur | | Cd47 |
| Itga1 | | | | Lpar1 | Bcam | Dcbld2 | | Ifr2 |
| Kcnq1 | | | | Fas | Galr1 | Mtnr1a | | Epha4 |
| Fzd7 | | | | Gpc4 | Acvrl1 | Ramp1 | | Ifitm1 |
| Tgfbr2 | | | | | Nrp1 | Ldlr | | Esam |
| Cftr | | | | | Ramp3 | | | |
| Ptprm | | | | | Hrh3 | | | |
| Ptch1 | | | | | Gfra1 | | | |
| Lphn2 | | | | | Htr1d | | | |
| Fgfr4 | | | | | Nt5e | | | |

TABLE 12-continued

| Stem | TA | EP (early) | EP (late) | Enterocyte | EEC | Goblet | Paneth | Tuft |
|---|---|---|---|---|---|---|---|---|
| B. Ligands enriched in IEC subsets | | | | | | | | |
| Rgmb | | | Il18 | Cck | Guca2a | Mmp7 | Alox5ap | |
| Igfbp4 | | | Edn2 | Gip | Pla2g10 | Defb1 | Hebp1 | |
| Pdgfa | | | Ace | Tac1 | Muc2 | Lamb1 | Gi2 | |
| Lamb3 | | | Apoc3 | Vim | Liph | Thbs1 | Bmp2 | |
| Ef4 | | | Apob | Gcg | Lamc2 | Dll3 | Agt | |
| Prss23 | | | Tcn2 | Ghrl | Pcsk9 | C1qtnf1 | Il25 | |
| Cd14 | | | Sema4g | Sst | Adam9 | Proc | Fn1 | |
| App | | | Ptdss1 | Tph1 | Calr | Egf | Mllt4 | |
| Sema3c | | | Edn3 | Ucn3 | Hsp90b1 | | | |
| Nrg4 | | | Ccl25 | Mfng | | | | |
| Mfge8 | | | Bmp3 | Fbln2 | | | | |
| Nrtn | | | Farp2 | Iapp | | | | |
| Gas6 | | | | Serping1 | | | | |
| Tnfsf10 | | | | Alb | | | | |
| Fbln1 | | | | Fgf14 | | | | |
| Rps19 | | | | Lama4 | | | | |
| Btc | | | | | | | | |
| Uba52 | | | | | | | | |

DE results, ranked by minimum Log2 fold-change
Significance cut-offs: FDR (max): 0.25, Log2 fold-change: 0.25 (Test: Mann-Whitney U-test)

Applicants found that CD74, the invariant chain of the MHCII complex, was highly expressed and specific to ISCs (FIG. 17C-E and FIG. 21G). Moreover, other MHCII genes were among the most strongly expressed by two out of three ISC subsets (ISC-II and -III) (FIG. 17C,D) compared to other IECs (FIG. 22A). These included many canonical components of the MHCII machinery, including H2-Ab1, H2-DMb1, H2-DMa, H2-Aa, Cd74, and the recently discovered co-stimulatory molecules Sectm1a and Sectm1b[109] (FIG. 17D), but not the canonical co-stimulatory molecules CD80 and CD86. Although MHCII expression has been previously reported in intestinal epithelial cells[105-108], it was not shown to be specific to ISCs. Applicants found that MHCII expression in the ISC$^{MHCII+}$ (ISC-II and -III) groups was the highest among all IECs at both the mRNA and protein levels (FIG. 22A,B). Applicants confirmed MHCII protein expression by ISCs using an immunofluorescence assay (IFA) and immunohistochemistry (IHC) with anti-MHCII antibodies in wild type mice, and its absence in a constitutive MHCII knockout (KO)[110] (FIG. 17E and FIG. 22C).

Example 14—MHCII-Expressing ISCs are More Proliferative

Figure 18A:
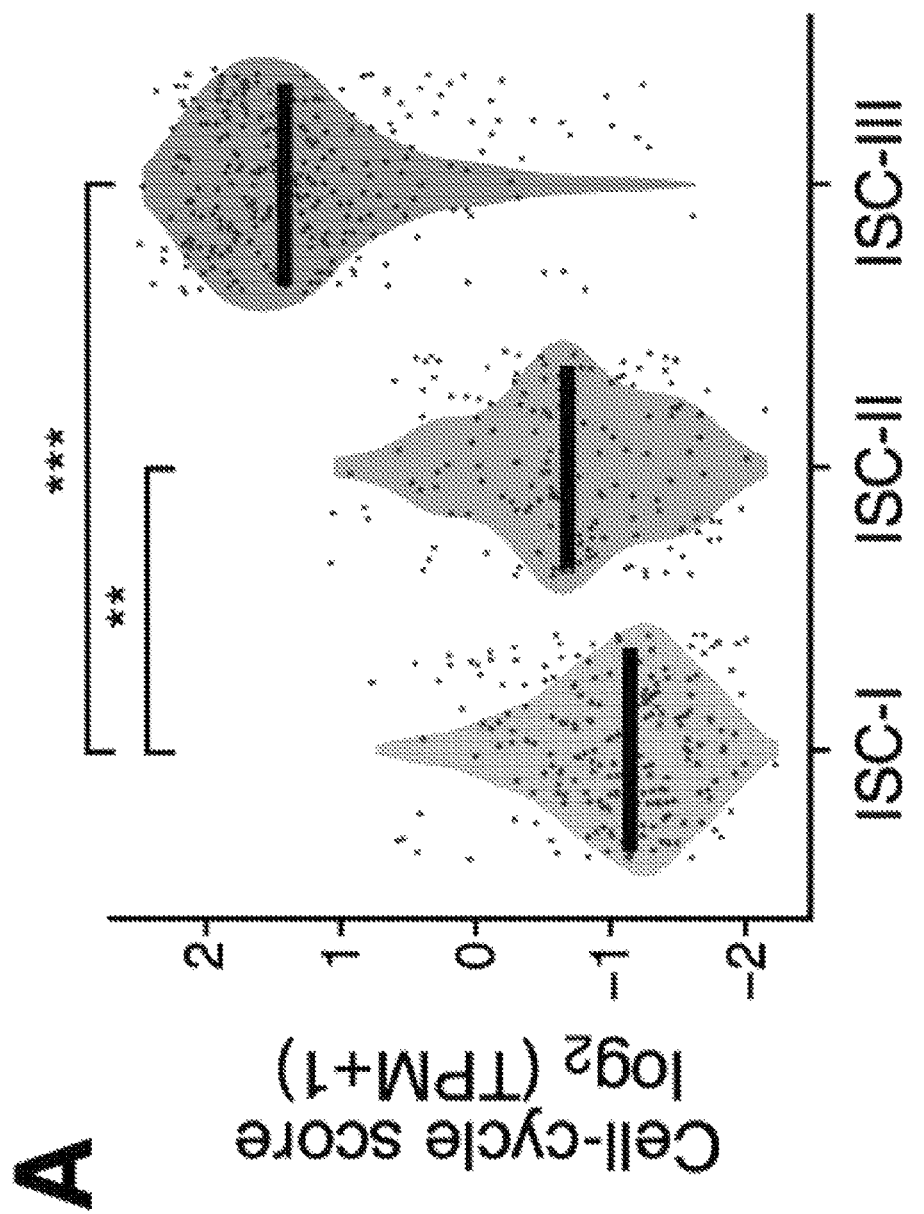
Figure 18B:
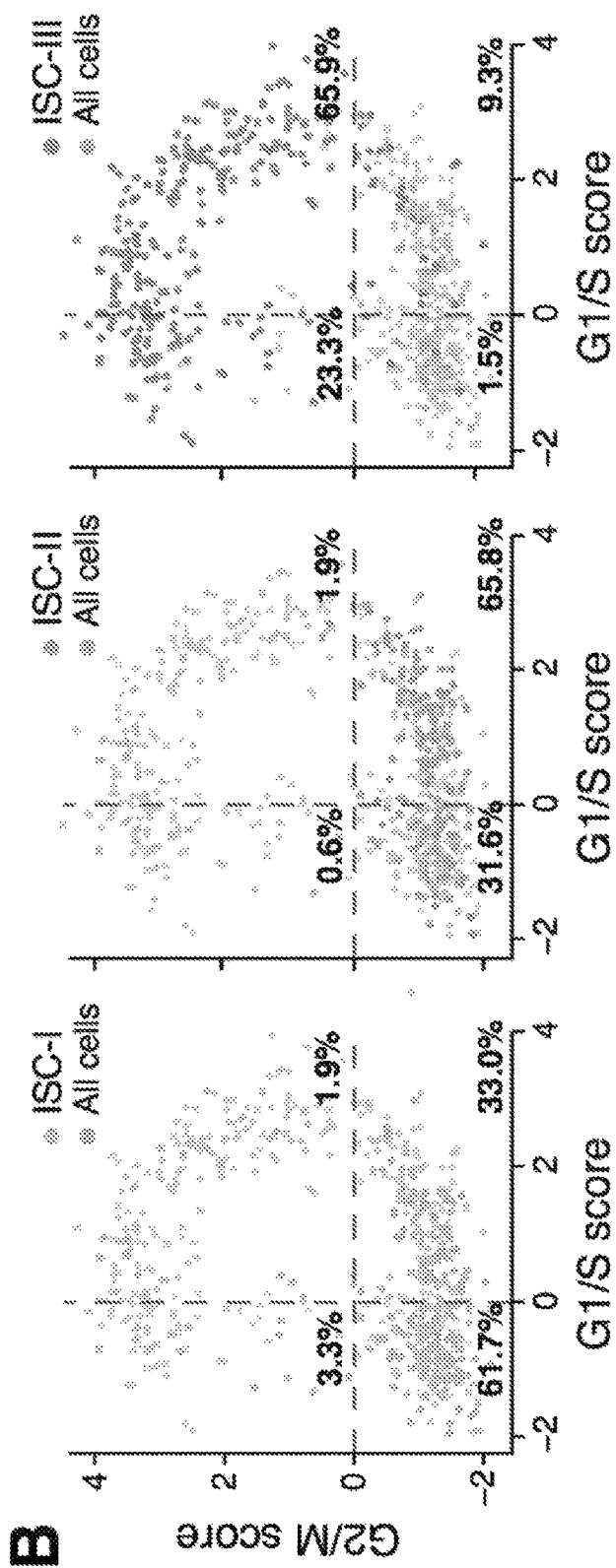
Figure 18C:
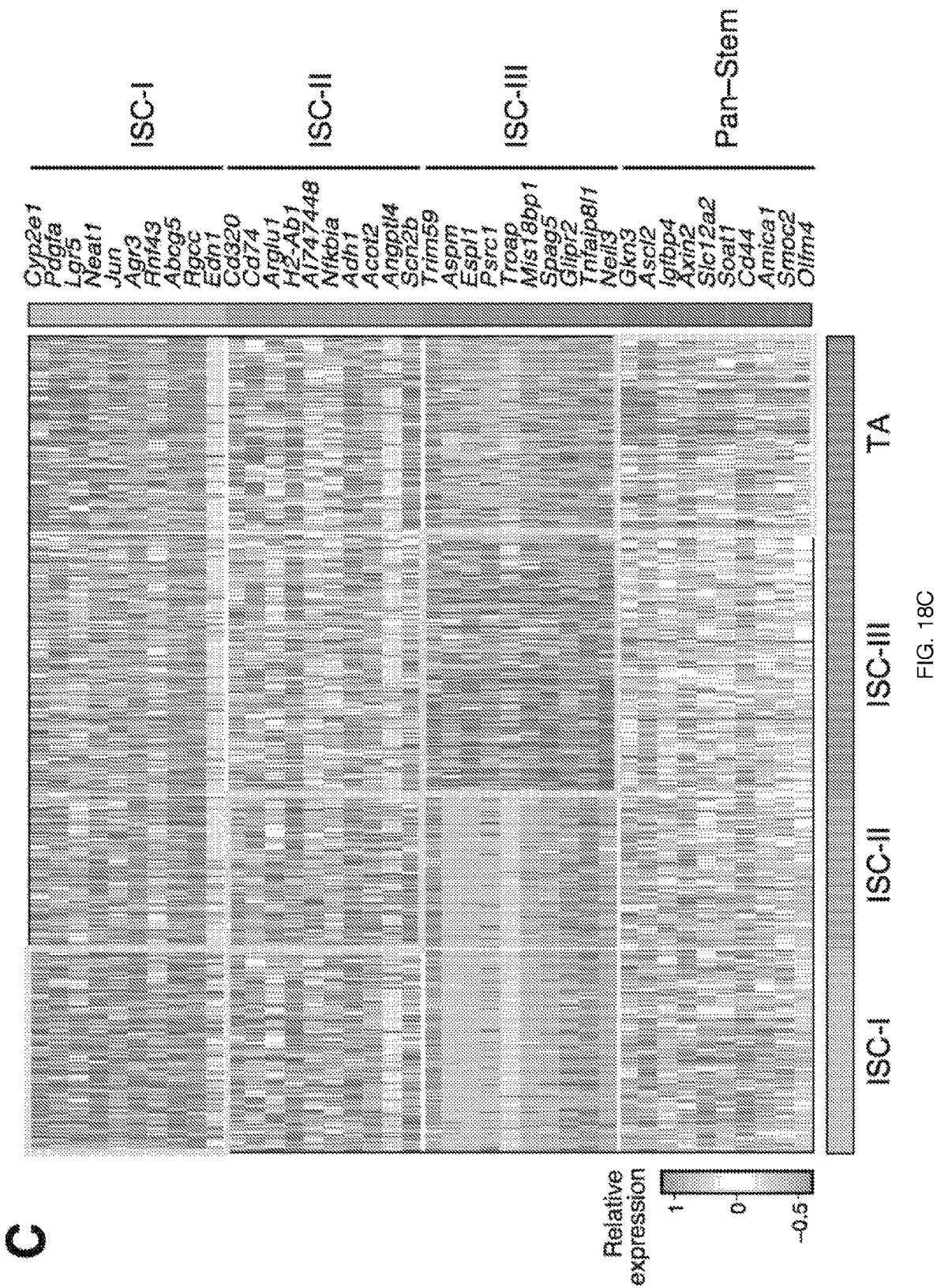
Figure 23A:
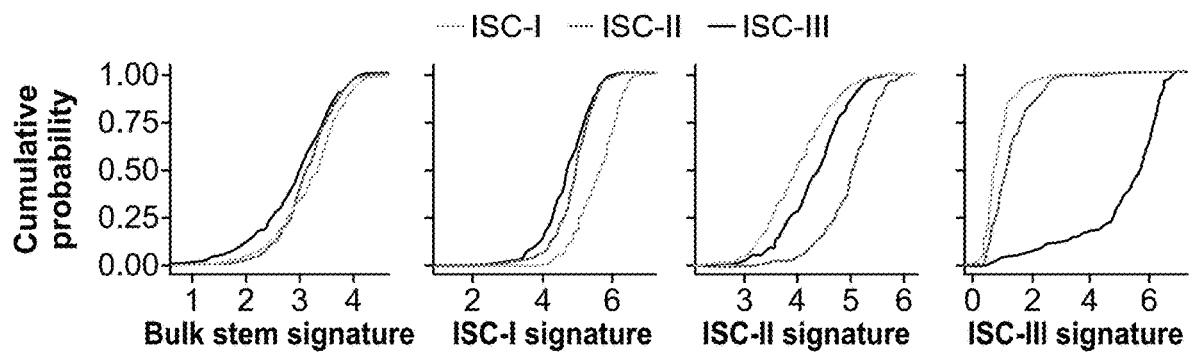
FIG. 23A-23C—ISC states are distinguishable beyond proliferation.
Figure 23B:
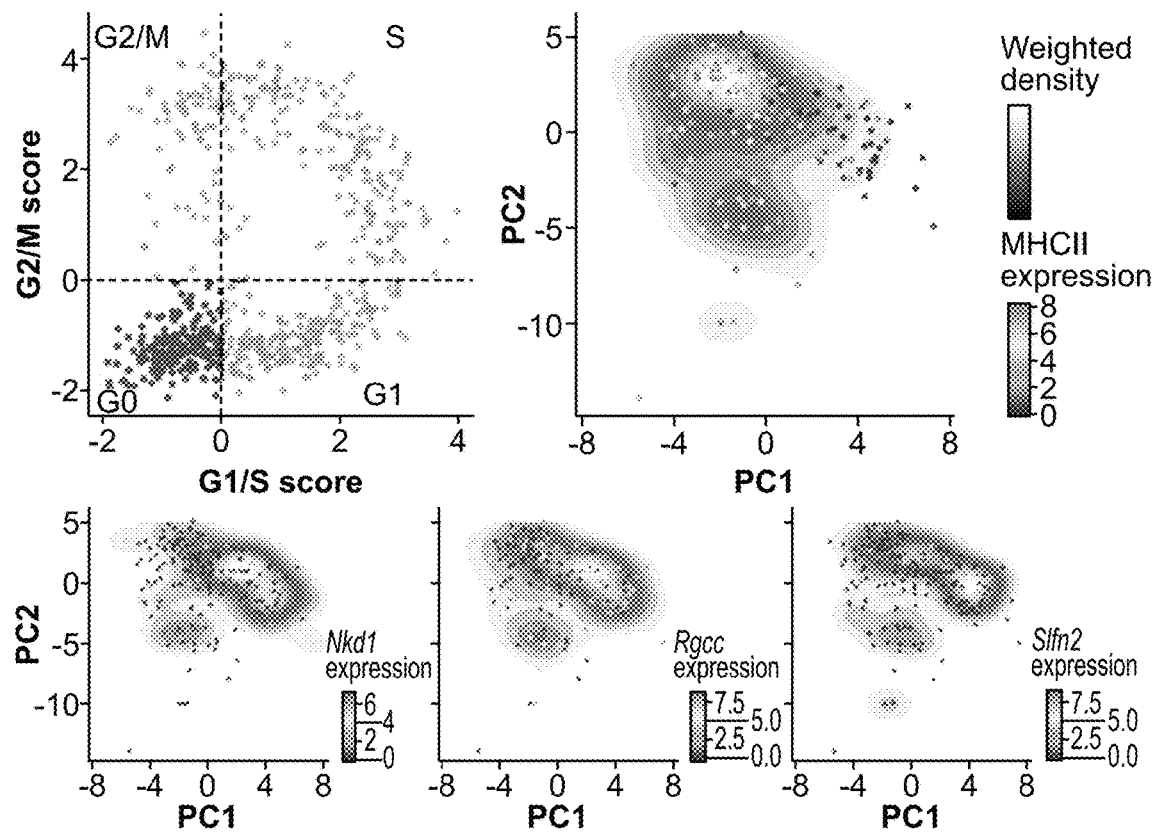

The three ISC subsets vary not only in their expression of the MHCII system, but also in their expression of signatures of the cell-cycle[29,98] (FIG. 18A,B). The subset with highest MHCII expression consisted primarily of cells in G1/S. The second subset, with lower but significant MHCII expression, had cells spanning several phases of the cell-cycle including G2/M. Applicants concluded that cells in both of these subsets are likely in highly proliferative states and termed these ISC-II and ISC-III, respectively. In contrast, the cells in the subset with low or no detectable expression of MHCII, termed ISC-J, also had low G1/S and G2/M scores (129 of 209 cells) and likely represented cells in G0. The low-cycling state of ISC-I was further supported by the higher expression of the histone demethylase Kdm5b, which is highly expressed in post-mitotic differentiated cells of the small intestine (FIG. 22D,E) and in low-cycling or quiescent cells in other system s[98-10]2* Such heterogeneity in the proliferative state of JISCs has been recently reported, including a quiescent ISC subset, which is enriched for Mex3a and correlates well with the low cycling ISC-I subset[30,145]. Importantly, while the cell-cycle status aligns with the partitioning of ISC-I, II and III subsets, the ISC subsets are discernable even when Applicants exclude canonical cell-cycle genes (FIG. 18C, FIG. 23A, table 13 and Methods) and even when analyzing only the 183 ISCs scoring at GO (FIG. 23B).

TABLE 13

Marker genes for intestinal stem cell (ISC subsets)

| ISC-III | ISC-II | ISC-II | ISC-I |
|---|---|---|---|
| Hist1h2ao | Cdk5rap2 | Rps27 | Pdgfa |
| Neil3 | Zranb3 | Rpl26 | Edn1 |
| Top2a | Xrcc2 | Angptl4 | Rgcc |
| Aurkb | Ipo9 | H2-Ab1 | Lgr5 |
| Pbk | Hmgb2 | Cd320 | Cyp2e1 |
| Ncaph | Brca2 | Ifitm3 | Jun |
| Hist2h3b | E2f7 | Scn2b | Agr3 |
| Cdca2 | Wdr62 | Rpl34-ps1 | Rnf43 |
| Ankle1 | Kifc1 | Arglu1 | Sorbs2 |
| Incenp | Spata24 | Al747448 | Fstl1 |
| Fbxo5 | Sephs1 | Gm6654 | Filip11 |
| Cdca5 | Nudt1 | Rn4.5s | Nrn1 |
| Cenph | Cep192 | Cd74 | Sord |
| Prc1 | Fen1 | Zyx | Nrld2 |
| Hist2h3c2 | Rfwd3 | Acot2 | Efna1 |
| Cks1b | Hist2h2ac | Nfkbia | Rnf32 |
| Cdca8 | Asrgl1 | H2-Eb1 | Fam13a |
| Bub1 | Tiam1 | Zcchc7 | Arhgef26 |
| Spag5 | Zfp367 | Rps15a-ps4 | Sypl |
| Hist1h4d | Nup62 | Dus2l | Tmem171 |
| Nusap1 | Clhc1 | Rangrf | Slc12a2 |
| Rhno1 | Troap | Gm11974 | Gm8979 |
| Cdk1 | Sin3a | Myc | Fgf1 |
| Ccnf | Ube2s | Rps28 | Ogt |
| Ndc80 | Eefsec | Snx16 | Fhdc1 |
| Ncapd2 | Rad9a | Per3 | Oat |
| Cenpm | Chchd6 | 4921508A21Rik | Arid5b |
| Esco2 | Cep55 | Car12 | Prss23 |
| Rad51ap1 | Mcph1 | Clec2d | Snx10 |
| Hist1h1e | 2310008H04Rik | Zfp106 | Chp1 |
| Psrc1 | Mybl2 | A230050P20Rik | Sh3rf1 |
| Haus5 | Mre11a | Clca2 | Lbh |
| Tubb5 | Rbbp8 | Sp140 | Myo9a |
| Poc1a | Xrcc1 | 2410006H16Rik | Soat1 |
| Cit | Hist1h3c | Ddo | Npc2 |
| Shcbp1 | Cdc7 | Rpl31-ps12 | Trim2 |

TABLE 13-continued

Marker genes for intestinal stem cell (ISC subsets)

| ISC-III | ISC-II | ISC-I |
|---|---|---|
| Mis18bp1 | Parpbp | Nfic |
| Asf1b | Pcnt | Arhgef4 |
| Cenpp | Nde1 | Zfp109 |
| Nrm | Gmnn | Pdrg1 |
| Nuf2 | Elof1 | Paics |
| Trim59 | Brca1 | Ndufa7 |
| Mis18a | Kif22 | Tomm7 |
| Smc4 | Mnd1 | 1600029O15Rik |
| 2810417H13Rik | Cenpf | Rps19-ps3 |
| Ska1 | Hnrnpul1 | C1ra |
| Kif20b | Itprip | Gstm1 |
| Kif20a | Pola2 | Snora43 |
| Rad51 | Med24 | Ankrd10 |
| Cenpn | Aspm | Relb |
| Mlf1ip | Ino80e | Slc15a2 |
| Haus8 | Pms2 | Clca4 |
| Chek2 | Lrrc45 | Rps17 |
| Rad54b | Krt15 | Gm15772 |
| Rad18 | Tcof1 | Rps25 |
| Plk4 | Odf2 | Rps18 |
| Kif18b | Lrr1 | Rpl37 |
| Ncapg | Mdc1 | Rps15a |
| Eme1 | Palb2 | Rps19 |
| Kif15 | Lage3 | Rpl32 |
| Cdca4 | 2810442I21Rik | Gm10548 |
| Ttk | Whsc1 | 6030458C11Rik |
| Ube2t | Ahctf1 | Rps13 |
| Kif11 | Gtpbp10 | Snhg8 |
| Hist1h2ab | Rasa3 | Klhdc5 |
| Mastl | Wdr8 | Ifitm2 |
| Spc25 | Naa40 | Rps29 |
| Tk1 | Ube2c | Rplp1 |
| Ctc1 | Xkr5 | Rps12 |
| Kif2c | Cenpo | Rpl36a |
| Hist1h1b | Nup214 | Rpl35 |
| Tnfaip8l1 | Nucks1 | Rpl38 |
| Rad54l | Parp2 | Dctd |
| Fbln1 | Stra13 | Rps15a-ps6 |
| BC030867 | Tex10 | Rpl37a |
| Tuba1b | Dclre1a | Rpl36 |
| Ttf2 | Pms1 | Urod |
| Rad51b | C230052I12Rik | Shmt1 |
| Sgol1 | 2810408I11Rik | Rps26 |
| Tinf2 | Rpap1 | 2210039O01Rik |
| Fancd2 | Topbp1 | Zbtb16 |
| Gtse1 | Dnmt1 | Noxa1 |
| Trip13 | Zfp41 | Rpl39 |
| H2afx | Fxn | Rps23 |
| H2-Q7 | Ubap2 | Pex26 |
| Ckap2l | Dnph1 | Cyba |
| Nup133 | Bard1 | Rps14 |
| Ccdc34 | E2f8 | Shfm1 |
| Cenpt | Fam84a | Gm12191 |
| Ncapg2 | Polq | Rpl11 |
| Espl1 | Pold1 | Mir703 |
| Cdc45 | Ckap5 | Rps21 |
| Aaas | Mettl14 | Rps10 |
| Stil | Hist1h2ai | Rpl35a |
| Rfc5 | Cox6b2 | Rps24 |
| Anln | Atad5 | Clec2g |
| Oip5 | 5830418K08Rik | Rpl31 |
| Ska3 | Ilf3 | Rpl23a |
| Haus1 | Hyls1 | Rps16 |
| Cyp39a1 | Nup107 | Rpl18a |
| Ect2 | Fgfr1op | |
| Smc2 | Tmco6 | |
| 2700094K13Rik | Hspa14 | |
| Zwilch | Spice1 | |
| Hist1h2ad | 2700029M09Rik | |
| Mns1 | Kbtbd4 | |
| Suy39h1 | Pom121 | |
| Bub1b | Phf6 | |
| Ddx11 | Med16 | |
| Hist1h2ae | Ephx1 | |
| Mxd3 | Flywch1 | |
| Ezh2 | 2810428I15Rik | |
| Cenpk | Dtymk | |
| Tyw1 | Nthl1 | |
| Fanci | Ccp110 | |
| Hist1h2ak | Fanca | |
| 6430706D22Rik | Topors | |
| Cmss1 | BC052040 | |
| Rsrc1 | Hist1h2bk | |
| Cks2 | Rnaseh2b | |
| Anapc15 | Dgcr8 | |
| Ncapd3 | Nup160 | |
| Sept10 | Wdr31 | |
| Eri2 | Smarca5 | |
| Rnf26 | G2e3 | |
| BC055324 | Nos2 | |
| Tmem194 | Hn1l | |
| Sgol2 | Sp1 | |
| Rrm2 | Nup205 | |
| Ercc6l | U2af2 | |
| Cep72 | Hist1h2ag | |
| A730008H23Rik | Ipo11 | |
| Znhit3 | Gas2l3 | |
| 5ass6 | Bcl2l12 | |
| Dsn1 | Kif24 | |
| Ticrr | Zfp1 | |
| Mcm10 | Rad1 | |
| Casc5 | Vars | |
| Cep57l1 | Skp2 | |
| Blm | Slc9a8 | |
| Dbf4 | Nudt21 | |
| AI450353 | Mum1 | |
| Fignl1 | Papd7 | |
| Prim2 | Lsm2 | |
| Kif18a | E4f1 | |
| Psmc3ip | Dek | |
| Mad1l1 | Bckdk | |
| Rbl1 | B3galtl | |
| Siah1b | Zfp101 | |
| Dnajc9 | 4932415G12Rik | |
| Melk | Hist1h1a | |
| Cep110 | Ncoa7 | |
| Racgap1 | Dars2 | |
| Trim37 | Hist1h3f | |
| Pck2 | Nt5dc2 | |
| Cenpc1 | Srrt | |
| Nsl1 | Zfp828 | |
| Ccdc77 | Hist1h3e | |
| Stmn1 | Hist1h2bb | |
| Brd8 | Slc20a2 | |
| Efcab11 | Hemgn | |
| Lmnb1 | Cse1l | |
| Exo1 | Zdhhc15 | |
| Haus6 | 1700063D05Rik | |
| Smc1a | Cdkn2c | |
| Med4 | Mtfr2 | |
| Rfc4 | Nudc | |
| Haus4 | Top3a | |
| Tacc3 | Pold2 | |
| Nnt | Rtel1 | |
| 4930579G24Rik | Rcc2 | |
| Hjurp | Fam76b | |
| Traip | Prdx4 | |
| Pkmyt1 | Nfix | |
| Vrk1 | Hist1h2bl | |
| D030056L22Rik | 4930503L19Rik | |
| Hirip3 | Ogg1 | |
| Cenpl | Kif14 | |
| Rbmx2 | Anapc11 | |
| Cenpq | Suz12 | |
| Cdo1 | Mtr | |
| Rfc3 | Notch2 | |
| Slc7a11 | Mbd4 | |
| 2700099C18Rik | Ccdc15 | |
| Mgme1 | Thada | |
| Mki67 | Hmgn2 | |
| Kifc5b | Pdik1l | |
| Tyms | Fam111a | |

TABLE 13-continued

Marker genes for intestinal stem cell (ISC subsets)

| ISC-III | ISC-II | ISC-I |
|---|---|---|
| Clspn | Mcm8 | |
| Nfyb | Lrrc49 | |
| Rangap1 | Fbxo48 | |
| Tube1 | Magoh | |
| Mis12 | Pds5b | |
| Pcbd2 | Kat7 | |
| Hist1h3b | Polr2f | |
| 1190002F15Rik | Gpr19 | |
| Cenpw | Rttn | |
| Atad2 | Lonp1 | |
| Hist1h2af | Hist1h2bn | |
| Cep128 | Cep250 | |
| 4930523C07Rik | Fbxl14 | |
| Pole | Hist1h3d | |
| Hist1h4i | Asb3 | |
| Cenpi | Tubgcp6 | |
| Haus3 | Cenpj | |
| Fancg | Ccdc14 | |
| Kntc1 | Tbrg3 | |
| Nelfe | Pced1a | |
| Cep57 | Prkd3 | |
| Cntrob | Tbc1d5 | |
| Spc24 | Eftud2 | |
| Repin1 | Cep135 | |
| Prim1 | Sae1 | |
| Pask | Snrpd1 | |
| Rbm15 | H2afv | |
| Ccdc18 | Ssrp1 | |
| Gmcl1 | Diap3 | |
| Nup37 | Senp8 | |
| Mms22l | Stag1 | |
| Rrm1 | 4930558J18Rik | |
| Arhgap11a | Depdc1b | |
| Tmpo | BC053749 | |
| Foxm1 | Brip1 | |
| Nmral1 | Fgr | |
| Cpsf4 | Rps6ka6 | |
| Bud13 | Hist2h4 | |
| Miip | Alpk1 | |
| Scltl | Ddx19a | |
| Exosc8 | Fam122b | |
| Iqgap3 | Ecm2 | |
| Sun2 | Hist1h3i | |
| Xrcc3 | Itga1 | |
| Nsmce4a | Gen1 | |
| Tmem107 | Zfp958 | |
| Hist1h2bj | Hist1h2bg | |
| Gins3 | Cep152 | |
| Gins4 | Dcp1a | |
| Ppie | Acsf2 | |
| Cbx5 | Hist1h3a | |
| Naa38 | | |
| 9430015G10Rik | | |
| Chaf1a | | |
| Depdc1a | | |
| Pmf1 | | |

DE results, ranked-by minimum Log2 fold-change
Significance cut-offs: FDR (max): 0.25, Log2 fold-change: 0.25 (Test: Mann-Whitney U-test)

Significance cut-offs: FDR (max):0.25, $Log_2$ fold-change: 0.25 (Test: Mann-Whitney U-test)

Figure 18D:
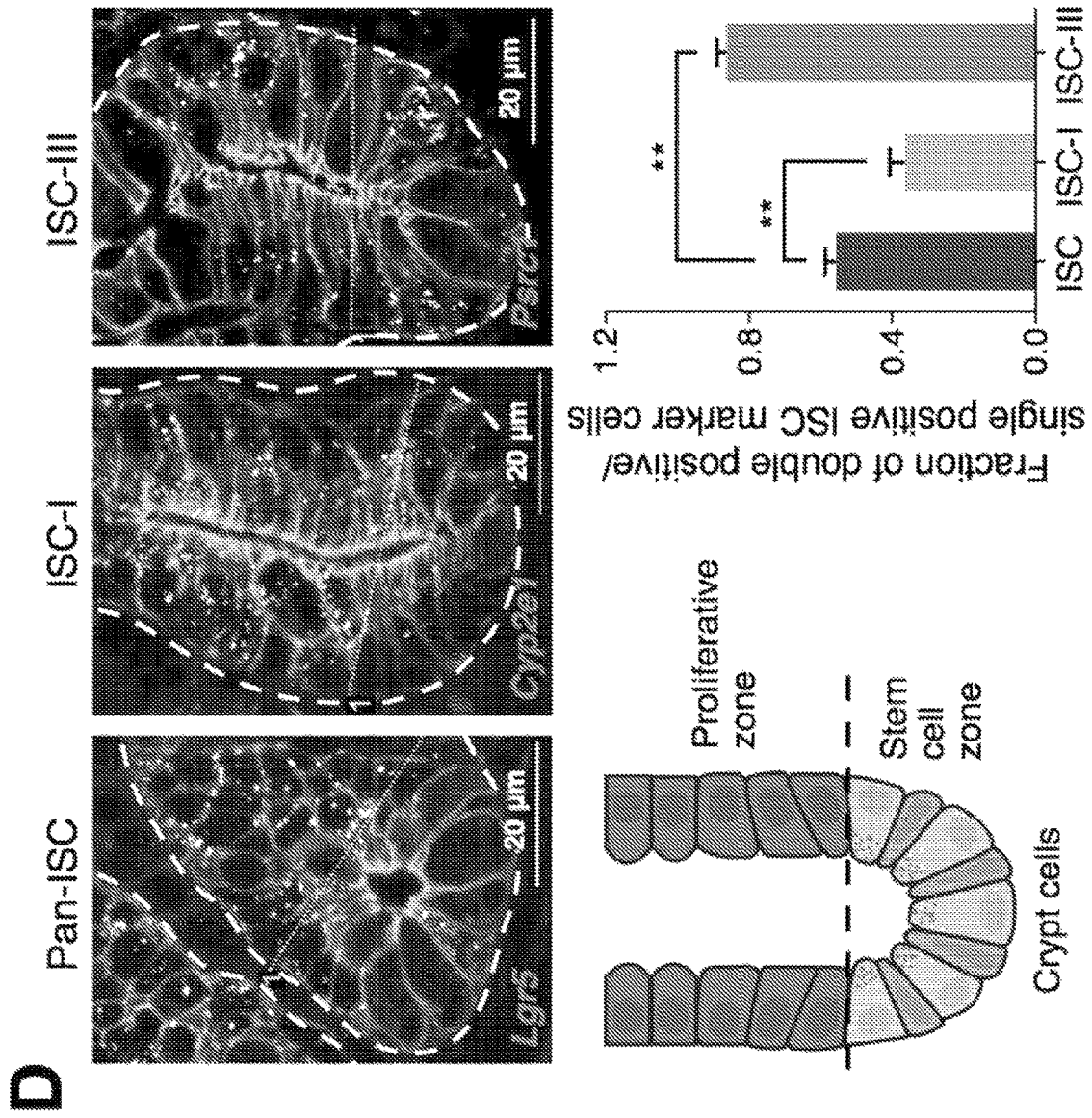
Figure 23C:
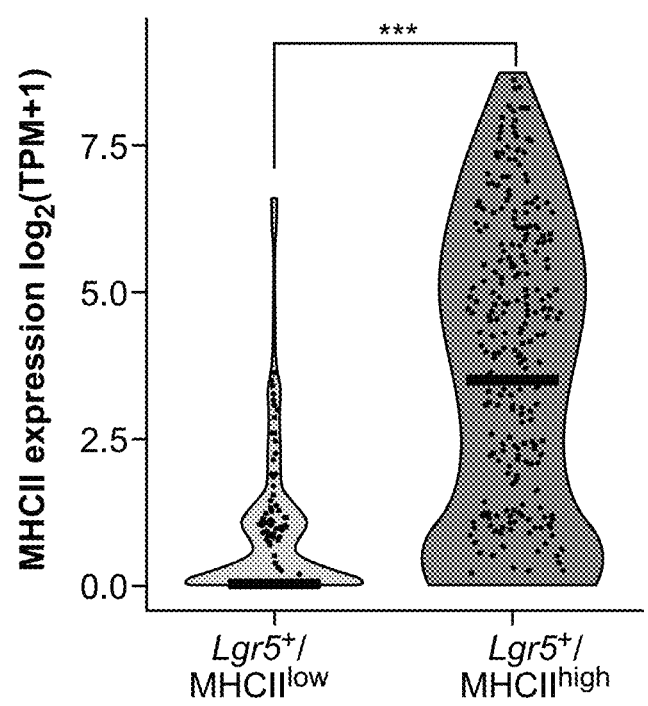

Applicants validated the association between the ISC subsets, MHC-II, and cell-cycle status by co-staining in situ (FIG. 18D), by in vivo EdU labeling followed by single-nucleus RNA-seq (Div-Seq)[104] (FIG. 18E), and by determining the proportion of EdU+ cells in subsets of $GFP^{high}$ cells with different levels of MHCII expression (FIG. 18F). Applicants also sorted single $MHCII^{high}$ and $MHCII^{low}$ ISCs from Lgr5-GFP mice and collected 503 full-length scRNA-seq profiles. $MHCII^{high}$ ISCs had a higher proportion of cells with high scores for ISC-II and -III state signatures, whereas $MHCII^{l}$ ISCs had a higher proportion of cells scoring highly for the ISC-I state, consistent with the in silico analysis (FIG. 18G and FIG. 23C). Taken together, these results support an association between MHCII expression and proliferative state within ISCs in vivo. Thus, the heterogeneity of Lgr5+ stem cells and MHC II expression is correlated with proliferation rates.

Example 15—T Helper Subsets and their Signature Cytokines Regulate ISC Renewal in Organoids Applicants hypothesized that ISCs may interact with CD4+ T helper (Th) cells via MHCII recognition and, as a consequence, CD4+Th cells may affect ISC fate via cytokine-receptor interaction. Importantly, IECs, including ISCs, express receptors for Th cytokines interferon gamma (IFNγ), interleukin-10 (IL-10), IL-13, IL-4 and IL-17A. Furthermore, intra-vital imaging showed that CD4+Th cells can be in very close proximity to stem cells in small intestinal crypts (FIG. 24A). Moreover, scRNA-seq of IECs following infection of mice with *Salmonella enterica* (*Salmonella*) or *Heligmosomoides polygyrus* (*H. polygyrus*) (see above examples), which induce Th1 (FIG. 24B-D and table 14) and Th2 responses, respectively, shows not only distinct shifts in the proportions of post-mitotic cells, such as tuft (in *H. polygyrus*) and Paneth (in *Salmonella*) cells (FIG. 24E-F), but also a reduction in ISC and stemness programs, and especially in ISC-I cells (FIG. 24G-J). The observed elevation in $ISC^{MHCII+}$ programs is consistent with the hypothesis presented herein, but in principle many other indirect cellular and molecular mechanisms in the complex cellular ecosystem of the crypt may also be involved.

TABLE 14

Differentially Expressed Genes from Salmonella/T cell Experiment

| Gene symbol | p-value | FDR | log2 fold-change (Salmonella vs control) |
|---|---|---|---|
| Calm1 | 1.18E−23 | 2.95E−21 | 1.128653532 |
| Junb | 2.22E−13 | 2.84E−11 | 0.922343664 |
| Rgs1 | 1.22E−09 | 9.70E−08 | 0.90722109 |
| AW112010 | 4.02E−11 | 4.08E−09 | 0.882531736 |
| Psme2 | 7.96E−19 | 1.67E−16 | 0.85264586 |
| Sub1 | 1.70E−09 | 1.33E−07 | 0.730407862 |
| Smim14 | 1.91E−48 | 1.39E−45 | 0.713186813 |

TABLE 14-continued

Differentially Expressed Genes from
Salmonella/T cell Experiment

| Gene symbol | p-value | FDR | log2 fold-change (Salmonella vs control) |
|---|---|---|---|
| Abracl | 5.26E−11 | 5.30E−09 | 0.705590876 |
| Arpc3 | 2.09E−08 | 1.43E−06 | 0.693757166 |
| Btg2 | 1.90E−12 | 2.18E−10 | 0.688618224 |
| Nkg7 | 1.98E−09 | 1.54E−07 | 0.650372119 |
| Id2 | 3.75E−07 | 2.12E−05 | 0.631388855 |
| B2m | 2.69E−37 | 1.24E−34 | 0.624813513 |
| Xist | 4.27E−10 | 3.74E−08 | 0.623695305 |
| Jchain | 2.43E−55 | 2.58E−52 | 0.619348354 |
| Cyba | 1.54E−06 | 7.90E−05 | 0.618514069 |
| Krtcap2 | 1.45E−07 | 8.76E−06 | 0.617106464 |
| Pla2g16 | 1.77E−07 | 1.05E−05 | 0.577104437 |
| Chchd2 | 7.96E−08 | 5.17E−06 | 0.549939574 |
| Rps5 | 1.13E−16 | 1.91E−14 | 0.515269867 |
| Psmb10 | 8.03E−06 | 0.000350304 | 0.509131756 |
| Sh3bgrl3 | 4.42E−07 | 2.45E−05 | 0.500991892 |
| Atp6v0e | 4.35E−05 | 0.001500809 | 0.500475437 |
| Ccnd2 | 0.000160872 | 0.004720606 | 0.493054715 |
| Nfltbia | 3.55E−06 | 0.000171052 | 0.492924891 |
| Tmsb4x | 3.38E−37 | 1.51E−34 | 0.490156017 |
| Ifi27 | 1.36E−07 | 8.27E−06 | 0.487025906 |
| Isg15 | 3.12E−09 | 2.36E−07 | 0.486670931 |
| S100a10 | 1.54E−05 | 0.000597678 | 0.483474613 |
| Psmb8 | 0.000263838 | 0.007387064 | 0.474360688 |
| Ly6a | 1.38E−13 | 1.85E−11 | 0.474228559 |
| Lsp1 | 0.000111676 | 0.003414759 | 0.471546502 |
| Hspe1 | 6.35E−13 | 7.84E−11 | 0.469026148 |
| Ddx5 | 1.31E−05 | 0.000522495 | 0.454772622 |
| Selk | 0.000148876 | 0.004415474 | 0.448543379 |
| Pomp | 0.001883281 | 0.038504182 | 0.448051882 |
| Rinl | 3.00E−10 | 2.74E−08 | 0.447734988 |
| Smdt1 | 0.000703146 | 0.016871834 | 0.446791846 |
| Ifi27l2a | 6.96E−05 | 0.002252116 | 0.445306177 |
| Hilpda | 2.18E−09 | 1.68E−07 | 0.443541779 |
| D8Ertd738e | 0.000425374 | 0.011050941 | 0.442635302 |
| Dusp1 | 7.55E−06 | 0.000335334 | 0.440551811 |
| Eef1b2 | 7.14E−05 | 0.00230645 | 0.434282154 |
| Cox5a | 0.001166387 | 0.025714511 | 0.434218726 |
| Cd3d | 0.000561225 | 0.013950873 | 0.430994366 |
| Zbp1 | 8.66E−09 | 6.11E−07 | 0.427088907 |
| Rgs2 | 1.80E−06 | 9.10E−05 | 0.42373264 |
| Ier2 | 0.000577873 | 0.014308444 | 0.409630962 |
| Cxcr6 | 2.54E−06 | 0.000125132 | 0.40702655 |
| Slc3a2 | 5.55E−07 | 3.01E−05 | 0.40634594 |
| Reg3b | 2.04E−45 | 1.35E−42 | 0.405331206 |
| Dnaja1 | 1.10E−09 | 8.80E−08 | 0.404993401 |
| Tspo | 1.86E−05 | 0.000708452 | 0.400191817 |
| Ptpn18 | 0.000280348 | 0.007718506 | 0.39934047 |
| Gng2 | 6.66E−06 | 0.000302824 | 0.392623524 |
| S100a13 | 9.43E−10 | 7.71E−08 | 0.392007234 |
| Psmb9 | 0.000442861 | 0.011440701 | 0.388451322 |
| Sft2d1 | 6.66E−26 | 1.92E−23 | 0.386440408 |
| Rtp4 | 4.00E−10 | 3.52E−08 | 0.385707221 |
| Gzmb | 0.001881431 | 0.038504182 | 0.384198212 |
| Rap1b | 0.000429056 | 0.011125674 | 0.383899103 |
| Tnfaip3 | 8.81E−11 | 8.63E−09 | 0.376865442 |
| Pfdn5 | 1.12E−07 | 7.01E−06 | 0.375618016 |
| Anapc11 | 4.26E−05 | 0.001478035 | 0.374627251 |
| Dusp5 | 1.82E−08 | 1.25E−06 | 0.372307003 |
| Cox4i1 | 0.000174131 | 0.00506666 | 0.372113042 |
| Vimp | 2.75E−10 | 2.55E−08 | 0.371638007 |
| Dynll1 | 1.82E−06 | 9.10E−05 | 0.371228125 |
| Ccl4 | 0.001138638 | 0.025300837 | 0.367968361 |
| Hsp90b1 | 0.000402674 | 0.010540449 | 0.366667958 |
| Nr4a1 | 7.82E−10 | 6.47E−08 | 0.366499363 |
| Mien1 | 0.001217125 | 0.026574848 | 0.361716432 |
| Vps37b | 2.55E−06 | 0.000125132 | 0.359046715 |
| Stat1 | 6.27E−05 | 0.002057285 | 0.358349786 |
| Srrm2 | 0.000267232 | 0.007446409 | 0.358285736 |
| Arf4 | 0.001538084 | 0.032355945 | 0.356176944 |
| Pim1 | 2.59E−08 | 1.76E−06 | 0.353890214 |
| Rpl8 | 0.000106482 | 0.003285009 | 0.351966724 |
| Bst2 | 1.49E−10 | 1.40E−08 | 0.338270772 |

TABLE 14-continued

Differentially Expressed Genes from
Salmonella/T cell Experiment

| Gene symbol | p-value | FDR | log2 fold-change (Salmonella vs control) |
|---|---|---|---|
| Lgals1 | 0.000230433 | 0.00652626 | 0.336473673 |
| Cdc37 | 0.000224918 | 0.006396289 | 0.335336424 |
| Rbx1 | 3.88E−06 | 0.000184946 | 0.331299382 |
| Pdia3 | 8.58E−06 | 0.000369516 | 0.32584681 |
| Actb | 4.83E−05 | 0.001640302 | 0.325247963 |
| Prdx6 | 9.00E−05 | 0.002834933 | 0.324311964 |
| Hspa1a | 0.00051395 | 0.013009714 | 0.319215945 |
| Reg3g | 7.21E−26 | 2.03E−23 | 0.311543438 |
| Gadd45b | 7.80E−05 | 0.00250092 | 0.310873502 |
| Psme1 | 5.76E−05 | 0.001909423 | 0.30933926 |
| Nmi | 0.000280922 | 0.007718928 | 0.304577401 |
| Dnajc3 | 3.32E−05 | 0.001183916 | 0.301515046 |
| Cd52 | 0.000285438 | 0.007811956 | 0.300835383 |
| Ltb | 5.12E−05 | 0.001729674 | 0.300665409 |
| Hsp90aa1 | 1.06E−08 | 7.35E−07 | 0.290538867 |
| Rps3 | 1.50E−05 | 0.000583814 | 0.288731652 |
| Fkbp2 | 1.92E−05 | 0.000726774 | 0.281893672 |
| Klf6 | 0.000531494 | 0.013380287 | 0.27648618 |
| Ms4a4b | 6.93E−07 | 3.73E−05 | 0.271739768 |
| Apoe | 1.97E−19 | 4.25E−17 | 0.266946569 |
| Jun | 8.64E−06 | 0.000370948 | 0.266254173 |
| Top1 | 0.000332921 | 0.008934559 | 0.263011938 |
| Malat1 | 9.14E−13 | 1.12E−10 | 0.254918868 |
| Rcbtb2 | 0.000643679 | 0.015634954 | 0.254782034 |
| IKtP | 0.000501421 | 0.012762689 | 0.254568857 |
| Crem | 2.80E−06 | 0.000135906 | 0.251739124 |
| Gadd45g | 0.001547992 | 0.032514888 | 0.25165128 |
| Ckb | 0.000578715 | 0.014308444 | 0.250782113 |
| Ifng | 3.01E−07 | 1.72E−05 | 0.246918508 |
| Klf13 | 0.000300654 | 0.008163732 | 0.245799788 |
| Tmem176b | 0.000419545 | 0.010920014 | 0.24295949 |
| Bhlhe40 | 2.13E−05 | 0.000795134 | 0.241029102 |
| Rpl29 | 0.000400532 | 0.010504274 | 0.228308488 |
| Phf5a | 4.25E−06 | 0.000200552 | 0.227437473 |
| Eef1d | 0.000141751 | 0.004240552 | 0.227174506 |
| Rpl13a | 1.83E−07 | 1.08E−05 | 0.226267252 |
| Gm20069 | 0.00049655 | 0.012702915 | 0.225396743 |
| Hcls1 | 9.87E−05 | 0.003085066 | 0.225098992 |
| Ubxn4 | 0.001783596 | 0.036847657 | 0.223796052 |
| Fos | 0.000292949 | 0.007970172 | 0.22186926 |
| Rps8 | 0.000686378 | 0.01653297 | 0.220429682 |
| Acyp1 | 0.000172943 | 0.005042699 | 0.220313546 |
| Rbm8a | 1.72E−05 | 0.000657608 | 0.2195112 |
| Tmem176a | 0.000144214 | 0.004286412 | 0.219466616 |
| Rpl22 | 0.0010439 | 0.023536275 | 0.21892921 |
| Mrps18c | 0.000503929 | 0.012779464 | 0.213717593 |
| Socs2 | 1.08E−05 | 0.000446185 | 0.21089867 |
| PISD | 1.37E−16 | 2.28E−14 | 0.208529307 |
| Dpcd | 0.001955817 | 0.039869238 | 0.200510473 |
| Gtf2a2 | 0.001455358 | 0.030897845 | 0.1948275 |
| DHRSX | 2.87E−14 | 4.05E−12 | 0.193790243 |
| Glipr1 | 0.000638339 | 0.01553253 | 0.191523994 |
| Myeov2 | 5.46E−11 | 5.47E−09 | 0.190880418 |
| Plcxd2 | 1.97E−05 | 0.000743392 | 0.190790235 |
| Supt4a | 0.000129691 | 0.003930827 | 0.19071591 |
| Vamp7 | 1.13E−13 | 1.53E−11 | 0.190682838 |
| Ankrd12 | 0.000150843 | 0.004464246 | 0.188913296 |
| Mrps16 | 0.001816879 | 0.037423371 | 0.186427879 |
| Hnrnpc | 0.000694357 | 0.016689935 | 0.182644473 |
| Ccr2 | 3.72E−06 | 0.000178021 | 0.174831982 |
| Abcb9 | 0.00107472 | 0.024152364 | 0.171035795 |
| Nabp1 | 0.002470198 | 0.048982214 | 0.169499105 |
| Emd | 7.74E−05 | 0.002486612 | 0.168790927 |
| Sdf2l1 | 3.34E−05 | 0.001190712 | 0.168108589 |
| Snw1 | 0.000741971 | 0.017741828 | 0.164269474 |
| Taf10 | 4.28E−05 | 0.001482087 | 0.163989001 |
| Ndufb3 | 0.001228413 | 0.026779016 | 0.163823435 |
| Tbx21 | 5.54E−05 | 0.001845568 | 0.162517072 |
| Rps14 | 7.72E−06 | 0.00034189 | 0.161411216 |
| Glrx3 | 8.72E−05 | 0.002751848 | 0.159115979 |
| Pim2 | 0.001170604 | 0.025762597 | 0.15276098 |
| Zbtb8os | 5.28E−05 | 0.001774762 | 0.152630286 |

TABLE 14-continued

Differentially Expressed Genes from
Salmonella/T cell Experiment

| Gene symbol | p-value | FDR | log2 fold-change (Salmonella vs control) |
|---|---|---|---|
| D16Ertd472e | 0.002070258 | 0.042023403 | 0.148981343 |
| Tln1 | 0.001393998 | 0.029916842 | 0.141187646 |
| Ndufv3 | 7.26E−06 | 0.000325043 | 0.14005431 |
| Ccr5 | 1.02E−05 | 0.000428319 | 0.13860814 |
| Dedd2 | 0.000497234 | 0.012702915 | 0.13830861 |
| Xaf1 | 0.000516541 | 0.013051404 | 0.136030525 |
| Rab7 | 0.000581739 | 0.014357532 | 0.135587641 |
| Ly6c2 | 0.000175104 | 0.005084269 | 0.135120244 |
| Pim3 | 0.001856607 | 0.038100695 | 0.134987109 |
| Med21 | 0.001488094 | 0.031496099 | 0.134968786 |
| Plk3 | 0.000142686 | 0.004257751 | 0.129547897 |
| Prr7 | 0.000854496 | 0.019983055 | 0.129084504 |
| BC005624 | 0.001127705 | 0.025128764 | 0.128308379 |
| Nfkbid | 0.000459516 | 0.011826749 | 0.127706803 |
| Tuba1b | 4.56E−05 | 0.001560521 | 0.126670612 |
| Hsph1 | 0.001387589 | 0.029825608 | 0.125987552 |
| Lilr4b | 0.000658783 | 0.015917899 | 0.125446798 |
| Ctla2a | 0.002288141 | 0.045705699 | 0.12424592 |
| Kdm6b | 0.000327638 | 0.0088099 | 0.122748701 |
| Ndufa2 | 5.16E−05 | 0.001738653 | 0.121692914 |
| Prkca | 0.000349469 | 0.009306368 | 0.121562129 |
| Stk10 | 0.000236908 | 0.006682244 | 0.121189747 |
| Ccdc59 | 0.000845532 | 0.01980694 | 0.120335461 |
| Ifngr1 | 2.59E−06 | 0.000126627 | 0.120124601 |
| Xbp1 | 0.001429512 | 0.030395815 | 0.119072023 |
| Ankrd39 | 2.11E−09 | 1.63E−07 | 0.11833683 |
| Eif3c | 0.00036251 | 0.009598185 | 0.117575325 |
| Hcst | 7.79E−06 | 0.000342967 | 0.117027687 |
| Spn | 0.001660668 | 0.034618536 | 0.116613194 |
| Ifit1 | 0.000627752 | 0.015328897 | 0.116222819 |
| Maff | 0.001858033 | 0.038100695 | 0.116142761 |
| Ran | 1.39E−06 | 7.19E−05 | 0.114082542 |
| Mospd3 | 0.000503872 | 0.012779464 | 0.109317184 |
| Sec62 | 2.33E−05 | 0.000852499 | 0.105713043 |
| Anp32a | 2.39E−15 | 3.62E−13 | 0.102997468 |
| Lin54 | 0.000153332 | 0.004528213 | 0.09867853 |
| Gna15 | 0.002288427 | 0.045705699 | 0.098420282 |
| Bcl2a1d | 4.30E−09 | 3.21E−07 | 0.098055225 |
| Snrpe | 0.001408694 | 0.030092066 | 0.097796541 |
| Wbp4 | 0.00102029 | 0.023155061 | 0.09730782 |
| Rab5c | 2.03E−05 | 0.000761069 | 0.094992526 |
| Il4 | 0.001402097 | 0.030003629 | 0.091926089 |
| 15-Sep | 0.000140081 | 0.00419971 | 0.09050334 |
| Ltb4r1 | 0.001704444 | 0.035371043 | 0.089383368 |
| Atf3 | 0.000519273 | 0.013096484 | 0.088091359 |
| Lamtor5 | 2.02E−05 | 0.000761069 | 0.086917525 |
| Naa20 | 0.001270069 | 0.027470466 | 0.0864599 |
| Il2rg | 8.62E−07 | 4.51E−05 | 0.086410203 |
| Atp5j2 | 5.08E−09 | 3.73E−07 | 0.084607163 |
| Plac8 | 2.03E−05 | 0.000761069 | 0.084184959 |
| Naca | 2.17E−12 | 2.48E−10 | 0.082107769 |
| Chd3 | 0.000536577 | 0.013475028 | 0.077391312 |
| Il18r1 | 0.002248927 | 0.045177944 | 0.076594245 |
| Ucp2 | 1.03E−05 | 0.000428319 | 0.076248598 |
| Cebpb | 1.02E−05 | 0.00042689 | 0.075317658 |
| Gm10250 | 8.18E−07 | 4.31E−05 | 0.072711965 |
| Cox7a2 | 0.001461865 | 0.030988402 | 0.072365739 |
| Pnkd | 0.00054747 | 0.013682794 | 0.071264978 |
| Psmb7 | 0.000686631 | 0.01653297 | 0.070601573 |
| Uqcrb | 1.88E−05 | 0.000715493 | 0.070517427 |
| Atp6v1f | 0.000336281 | 0.009007236 | 0.069670105 |
| Ly6g5b | 0.000821149 | 0.019268412 | 0.069265168 |
| Alyref | 0.000274635 | 0.007591455 | 0.067409343 |
| Psme2b | 1.33E−10 | 1.28E−08 | 0.064130804 |
| Defa21 | 0.00103194 | 0.023342797 | 0.063948829 |
| Set | 5.13E−06 | 0.000240256 | 0.063941739 |
| Bin2 | 5.53E−06 | 0.000256262 | 0.061959051 |
| Ndufa4 | 0.000156862 | 0.004612751 | 0.061117505 |
| Calca | 0.000655063 | 0.015855725 | 0.060004539 |
| Ubald2 | 3.77E−07 | 2.12E−05 | 0.059722105 |
| Hmgn1 | 0.000747058 | 0.017801867 | 0.057163607 |
| Btg3 | 6.32E−06 | 0.000290007 | 0.056793066 |

TABLE 14-continued

Differentially Expressed Genes from
Salmonella/T cell Experiment

| Gene symbol | p-value | FDR | log2 fold-change (Salmonella vs control) |
|---|---|---|---|
| C1qc | 0.000343428 | 0.009163166 | 0.054120122 |
| Srp9 | 0.000362311 | 0.009598185 | 0.053237042 |
| C1qb | 0.001157251 | 0.025590992 | 0.052977089 |
| Tomm20 | 1.36E−05 | 0.000536923 | 0.052652913 |
| Gm12166 | 0.000101436 | 0.00315045 | 0.052652708 |
| C1qa | 0.002029111 | 0.041302428 | 0.051369964 |
| Btf3 | 8.49E−31 | 3.01E−28 | 0.048657304 |
| Marveld1 | 0.000292074 | 0.00796205 | 0.044649267 |
| Cdc26 | 7.27E−06 | 0.000325043 | 0.042668786 |
| Ost4 | 1.59E−17 | 2.81E−15 | 0.041785155 |
| Emc8 | 0.001615131 | 0.033822306 | 0.040914098 |
| Rpp40 | 0.001681739 | 0.035004989 | 0.039190514 |
| Mapk6 | 0.000750206 | 0.017846132 | 0.038854196 |
| Oas3 | 0.001231589 | 0.026805966 | 0.037621216 |
| Eif4b | 0.000763155 | 0.018091868 | 0.037071348 |
| Cit | 0.001282402 | 0.027693868 | 0.036571859 |
| Adrm1 | 0.000129128 | 0.003922383 | 0.036547855 |
| Sh3tc1 | 0.001402385 | 0.030003669 | 0.036348937 |
| Nudc | 1.68E−05 | 0.000643762 | 0.035193904 |
| Ywhaq | 1.68E−05 | 0.000643762 | 0.034843215 |
| Rwdd1 | 0.000375848 | 0.009913354 | 0.032910616 |
| Il1b | 0.00028368 | 0.007779254 | 0.032548613 |
| Rapgef2 | 0.002474646 | 0.049000115 | 0.032354773 |
| Mark4 | 0.001645146 | 0.034398733 | 0.031744372 |
| Nudt21 | 5.85E−06 | 0.000270593 | 0.030964531 |
| Ccdc12 | 5.67E−08 | 3.73E−06 | 0.029923296 |
| Ndufs6 | 0.000204583 | 0.005842031 | 0.029619252 |
| Ppdpf | 1.09E−07 | 6.90E−06 | 0.022913421 |
| Arpp19 | 0.00011577 | 0.003532148 | 0.02242489 |
| Rps10 | 2.33E−07 | 1.36E−05 | 0.020798392 |
| Atox1 | 7.58E−10 | 6.31E−08 | 0.020316819 |
| Cox6b1 | 0.000603725 | 0.014847116 | 0.020178401 |
| Tomm5 | 0.000614677 | 0.015062858 | 0.019194104 |
| Rhoa | 1.03E−06 | 5.35E−05 | 0.018671698 |
| Ubl5 | 1.28E−11 | 1.37E−09 | 0.017987761 |
| Ociad1 | 0.001534514 | 0.032330068 | 0.016351438 |
| Rps2 | 9.68E−05 | 0.003034258 | 0.014967452 |
| Gm8797 | 4.55E−05 | 0.001559963 | 0.014708703 |
| Ndufb8 | 0.000431831 | 0.011176659 | 0.014130734 |
| Uxt | 0.001687494 | 0.035071963 | 0.013411744 |
| Ahsa1 | 6.34E−05 | 0.00207198 | 0.01273965 |
| Eef1g | 5.13E−09 | 3.75E−07 | 0.011258205 |
| Eif3m | 0.000273842 | 0.007584705 | 0.011035919 |
| Bcl2a1b | 4.61E−05 | 0.001574122 | 0.00966195 |
| Aip | 7.49E−06 | 0.000333935 | 0.008054643 |
| Laptm5 | 8.04E−05 | 0.002561934 | 0.007527761 |
| Hdac1 | 2.23E−05 | 0.000829303 | 0.004111386 |
| Gpi1 | 1.25E−08 | 8.66E−07 | 0.003638036 |
| Plekhj1 | 0.000617317 | 0.015100775 | −0.000607892 |
| Spag7 | 1.97E−07 | 1.16E−05 | −0.001985676 |
| Ap2s1 | 8.01E−05 | 0.002555277 | −0.002392336 |
| Psmc5 | 0.00212389 | 0.042774416 | −0.004331097 |
| Gmfg | 0.000756303 | 0.017960253 | −0.004902303 |
| Rps3a1 | 6.48E−06 | 0.000295372 | −0.005444651 |
| Tubb4b | 1.59E−05 | 0.000618735 | −0.005454596 |
| Ndufs5 | 0.000286207 | 0.007817536 | −0.00636948 |
| Psmb5 | 1.16E−11 | 1.26E−09 | −0.007926068 |
| Iscu | 2.26E−05 | 0.000834458 | −0.008287323 |
| Psmd11 | 0.00010811 | 0.003320311 | −0.008999655 |
| Tspan12 | 0.000981354 | 0.022418672 | −0.013146056 |
| Tmbim6 | 0.000322207 | 0.008697692 | −0.013269842 |
| Sept1 | 4.52E−13 | 5.63E−11 | −0.013643756 |
| Arl1 | 0.000538182 | 0.013475028 | −0.014402086 |
| Dynlt1f | 0.00184541 | 0.037954491 | −0.014501539 |
| Ndufc1 | 7.09E−07 | 3.78E−05 | −0.018912464 |
| Mrpl52 | 1.38E−07 | 8.39E−06 | −0.019112568 |
| Gjb3 | 0.000608871 | 0.01494707 | −0.019192032 |
| Cd74 | 1.08E−17 | 1.96E−15 | −0.019435495 |
| Mlph | 0.001327075 | 0.028569315 | −0.021362356 |
| Wdr83os | 1.31E−09 | 1.04E−07 | −0.022245122 |
| Dbnl | 0.002504286 | 0.049304461 | −0.02252523 |
| Zfand6 | 1.32E−05 | 0.000525023 | −0.022643199 |

TABLE 14-continued

Differentially Expressed Genes from
Salmonella/T cell Experiment

| Gene symbol | p-value | FDR | log2 fold-change (Salmonella vs control) |
|---|---|---|---|
| Frg1 | 0.001129076 | 0.025128764 | −0.023666352 |
| Fcer1g | 6.10E−09 | 4.37E−07 | −0.024711871 |
| Vdac3 | 0.000171007 | 0.004996811 | −0.026032626 |
| Fkbp8 | 0.001011147 | 0.02301131 | −0.02621955 |
| Ndufb2 | 4.11E−05 | 0.001435339 | −0.026554454 |
| Psmb3 | 3.15E−05 | 0.001129936 | −0.026953799 |
| Tinag | 0.000894054 | 0.020707408 | −0.027048045 |
| Gata4 | 4.71E−05 | 0.001604133 | −0.02751504 |
| Mrps5 | 0.001711384 | 0.035461824 | −0.028271578 |
| Gkn3 | 0.000555072 | 0.013822784 | −0.028435034 |
| Eif3j1 | 0.000167762 | 0.00491237 | −0.029029837 |
| Nfib | 0.002374943 | 0.047296955 | −0.029063759 |
| Mef2c | 0.000392737 | 0.010319437 | −0.029200832 |
| Mrpl51 | 7.47E−05 | 0.002405338 | −0.030248663 |
| Rpl6 | 2.10E−11 | 2.18E−09 | −0.03034436 |
| Rnase1 | 0.001807365 | 0.037282965 | −0.032108999 |
| Gpd1 | 0.000409187 | 0.010690683 | −0.032414892 |
| Pitx2 | 0.000265248 | 0.007406059 | −0.032898164 |
| Morf4l1 | 0.000155165 | 0.004572566 | −0.033763952 |
| Slc22a18 | 0.002115069 | 0.042737384 | −0.033910875 |
| Rnf32 | 0.000184887 | 0.005334692 | −0.035118478 |
| Lrrc58 | 0.000137165 | 0.004121202 | −0.036026804 |
| Cap1 | 0.002122365 | 0.042774416 | −0.036706341 |
| Rap1a | 2.26E−05 | 0.000834458 | −0.036822225 |
| Cox8a | 1.24E−05 | 0.000503707 | −0.038285402 |
| Smoc2 | 0.002126187 | 0.042774416 | −0.038458372 |
| Cdo1 | 0.001517349 | 0.032017225 | −0.038827932 |
| Pgk1 | 0.001262302 | 0.027345261 | −0.039562545 |
| Chmp4b | 4.24E−06 | 0.000200483 | −0.039687678 |
| Bri3 | 2.24E−06 | 0.000110402 | −0.040207358 |
| Cxadr | 0.000808476 | 0.019003302 | −0.040609528 |
| Rgn | 6.42E−05 | 0.002093104 | −0.04139476 |
| Sarnp | 7.00E−06 | 0.000315231 | −0.043268875 |
| Irf6 | 0.000583864 | 0.014384278 | −0.043377557 |
| Med29 | 0.000537521 | 0.013475028 | −0.043755269 |
| Ddost | 8.17E−07 | 4.31E−05 | −0.043918052 |
| Rreb1 | 0.001557821 | 0.032671684 | −0.044917115 |
| Snx7 | 0.002523513 | 0.049612332 | −0.045072003 |
| Heph | 5.39E−05 | 0.001804066 | −0.045605047 |
| Ddx18 | 0.000278034 | 0.007670072 | −0.045896158 |
| Pcyt2 | 9.97E−05 | 0.003110162 | −0.046115356 |
| Lrig1 | 0.001413285 | 0.030143547 | −0.046854975 |
| Emc4 | 2.49E−05 | 0.000906305 | −0.047059246 |
| Dnajb6 | 3.23E−10 | 2.94E−08 | −0.04764962 |
| Nxf1 | 0.000956643 | 0.021926638 | −0.0480384 |
| Map1lc3b | 0.000239904 | 0.006752967 | −0.048704723 |
| Sostdc1 | 0.001509092 | 0.031891674 | −0.048823005 |
| Khdrbs1 | 1.25E−05 | 0.000505157 | −0.049068883 |
| Slc44a2 | 0.000100316 | 0.00312266 | −0.049736036 |
| Pyrl3 | 0.000130864 | 0.003957719 | −0.049870039 |
| Erdr1 | 1.25E−07 | 7.63E−06 | −0.05040306 |
| Scamp1 | 0.000264034 | 0.007387064 | −0.05045353 |
| Efna1 | 8.10E−05 | 0.002572295 | −0.050831899 |
| Tspan1 | 0.000369301 | 0.009759295 | −0.050936005 |
| Npm3 | 6.98E−07 | 3.74E−05 | −0.051140625 |
| Slc22a1 | 0.001144048 | 0.025380247 | −0.05181036 |
| Nrn1 | 0.000232188 | 0.006562511 | −0.051887717 |
| Gm17430 | 0.000765341 | 0.018112636 | −0.052174495 |
| S100g | 0.000305934 | 0.008290819 | −0.052458718 |
| Tmc4 | 0.001938351 | 0.039571573 | −0.052588444 |
| Slc12a2 | 0.001093644 | 0.024458331 | −0.053040505 |
| Prkar1a | 0.002256308 | 0.045260435 | −0.054327179 |
| Cth | 0.001425251 | 0.030351915 | −0.054721249 |
| Anapc13 | 4.75E−06 | 0.000223473 | −0.055747452 |
| Gucy2c | 8.54E−05 | 0.002707651 | −0.055760058 |
| Pyrl2 | 0.000775843 | 0.018329794 | −0.056351045 |
| Psap | 0.000924087 | 0.021357534 | −0.056864819 |
| Snrpd2 | 1.93E−11 | 2.02E−09 | −0.057756599 |
| Plekha6 | 0.000202765 | 0.005802113 | −0.059101636 |
| Tmem98 | 0.002464366 | 0.048936776 | −0.059516442 |
| Rbp7 | 0.000103224 | 0.00319879 | −0.059800587 |
| U2af2 | 0.000414803 | 0.010816961 | −0.060183305 |

TABLE 14-continued

Differentially Expressed Genes from
Salmonella/T cell Experiment

| Gene symbol | p-value | FDR | log2 fold-change (Salmonella vs control) |
|---|---|---|---|
| F11r | 0.000123558 | 0.00376144 | −0.060190526 |
| Ndufa1 | 1.19E−07 | 7.37E−06 | −0.06141001 |
| Aadac | 0.000494276 | 0.012674188 | −0.062952231 |
| Them6 | 0.00176893 | 0.03659938 | −0.063971964 |
| Llph | 8.32E−06 | 0.00036034 | −0.063980616 |
| Fgthp1 | 0.0002615 | 0.007345913 | −0.064587036 |
| Mir142hg | 0.001047169 | 0.02357154 | −0.06459351 |
| Rnf186 | 0.001240056 | 0.026905508 | −0.065030745 |
| Dbndd2 | 0.000552157 | 0.01377501 | −0.065179907 |
| Reg4 | 0.002492713 | 0.049146635 | −0.065613984 |
| Cycs | 4.40E−05 | 0.001512653 | −0.066410785 |
| Golga7 | 7.76E−06 | 0.000342533 | −0.067164391 |
| Lamtor4 | 0.001304945 | 0.028136724 | −0.067603146 |
| Ddx3y | 6.26E−06 | 0.000288518 | −0.068385312 |
| Tkfc | 0.001089459 | 0.02440423 | −0.069811702 |
| Cftr | 3.60E−06 | 0.000172881 | −0.070425381 |
| Rpl26 | 9.52E−10 | 7.74E−08 | −0.070972322 |
| S100a11 | 1.79E−05 | 0.000684348 | −0.07153835 |
| Uqcrq | 2.55E−05 | 0.000923378 | −0.072069226 |
| Ap2m1 | 2.96E−11 | 3.05E−09 | −0.074287984 |
| Sema4g | 0.001012291 | 0.02301131 | −0.074586783 |
| Vdr | 0.000341775 | 0.009136695 | −0.074701199 |
| Tpm3 | 4.39E−08 | 2.92E−06 | −0.077034339 |
| Cdx1 | 5.31E−05 | 0.001782052 | −0.077115309 |
| Nsa2 | 0.002086711 | 0.042288028 | −0.077996265 |
| Rpl7 | 1.55E−39 | 7.63E−37 | −0.07809032 |
| Mrps27 | 0.000956598 | 0.021926638 | −0.079123719 |
| Prss32 | 0.000325404 | 0.008766889 | −0.079505502 |
| Gm8444 | 0.001188949 | 0.026071714 | −0.07960046 |
| Pafah1b1 | 0.002092323 | 0.042339663 | −0.080687581 |
| Lfng | 0.000866914 | 0.020239221 | −0.082033908 |
| Cdh17 | 0.002263227 | 0.045333424 | −0.082677121 |
| Chgb | 0.000268239 | 0.007459411 | −0.082679409 |
| Car9 | 6.85E−05 | 0.002228778 | −0.082849397 |
| Arf1 | 0.000214499 | 0.006112553 | −0.083101456 |
| Eif4e | 0.000352892 | 0.009379462 | −0.08324988 |
| Gipc2 | 0.000894459 | 0.020707408 | −0.083784124 |
| Atp5e | 3.85E−10 | 3.43E−08 | −0.083932547 |
| Smim22 | 0.00249146 | 0.049146635 | −0.084908939 |
| Jup | 6.92E−06 | 0.000312753 | −0.085525179 |
| Elf3 | 0.001175499 | 0.025829217 | −0.08779431 |
| Ppp1cc | 1.14E−05 | 0.00046807 | −0.087991226 |
| Rpl23 | 3.90E−07 | 2.18E−05 | −0.08836392 |
| Pdcd5 | 8.11E−08 | 5.24E−06 | −0.088685541 |
| Ndufa5 | 4.29E−05 | 0.001482087 | −0.088888151 |
| Mid1ip1 | 0.001190308 | 0.026071714 | −0.089050551 |
| Tfrc | 3.93E−05 | 0.00137459 | −0.089322612 |
| Nhp2l1 | 3.00E−09 | 2.29E−07 | −0.089383901 |
| Lsm5 | 8.73E−09 | 6.13E−07 | −0.09027659 |
| Nono | 0.000227567 | 0.006458319 | −0.090653867 |
| Calml4 | 0.000948524 | 0.02184926 | −0.091570173 |
| Rpl38 | 2.90E−05 | 0.001045629 | −0.092199763 |
| Nop56 | 0.001106669 | 0.024709642 | −0.092892274 |
| Akr1b3 | 5.15E−07 | 2.81E−05 | −0.093252803 |
| Tmed10 | 0.000180569 | 0.005231959 | −0.093361704 |
| Rab25 | 1.12E−05 | 0.000460269 | −0.093627145 |
| Gstp1 | 2.04E−17 | 3.53E−15 | −0.093634152 |
| Ndufa7 | 0.000876011 | 0.020382747 | −0.093917389 |
| Adck5 | 0.001087614 | 0.024402455 | −0.094035687 |
| Ndufs3 | 3.93E−14 | 5.49E−12 | −0.095049898 |
| Bcdin3d | 0.001042109 | 0.023534301 | −0.095786834 |
| Cd200 | 0.002070613 | 0.042023403 | −0.096979962 |
| Eif4ebp2 | 0.000382608 | 0.010072441 | −0.098156424 |
| Btg1 | 1.10E−17 | 1.97E−15 | −0.098476056 |
| Eif2s3y | 1.05E−07 | 6.67E−06 | −0.099335072 |
| Arg2 | 0.000107992 | 0.003320411 | −0.102320674 |
| Gm17541 | 8.10E−11 | 8.00E−09 | −0.10235054 |
| Anp32b | 4.51E−07 | 2.48E−05 | −0.102494704 |
| Cda | 6.17E−05 | 0.00203088 | −0.102855817 |
| Mt2 | 9.77E−06 | 0.000412747 | −0.104938007 |
| Crb3 | 0.000500601 | 0.012762689 | −0.105970034 |
| Serinc3 | 5.49E−06 | 0.00025543 | −0.106977827 |

TABLE 14-continued

Differentially Expressed Genes from
Salmonella/T cell Experiment

| Gene symbol | p-value | FDR | log2 fold-change (Salmonella vs control) |
|---|---|---|---|
| Serf2 | 0.002387328 | 0.047475189 | −0.107394319 |
| Higd1a | 3.10E−07 | 1.76E−05 | −0.107398778 |
| Hnrnpl | 0.001029569 | 0.02332733 | −0.108234712 |
| H3f3b | 2.31E−05 | 0.000850104 | −0.108900214 |
| Romo1 | 1.20E−15 | 1.84E−13 | −0.110435858 |
| Rab4b | 0.000974971 | 0.022309724 | −0.111453594 |
| Mrps21 | 1.20E−22 | 2.80E−20 | −0.112407421 |
| Sult1d1 | 9.21E−06 | 0.000393962 | −0.113023284 |
| Csrp2 | 1.09E−05 | 0.000450204 | −0.113272748 |
| Arfgap2 | 0.00078473 | 0.018508107 | −0.113554847 |
| Cotl1 | 6.93E−05 | 0.002247035 | −0.114465919 |
| Timm10b | 7.83E−06 | 0.000343731 | −0.115736988 |
| Acap1 | 0.000137036 | 0.004121202 | −0.115884447 |
| Cps1 | 1.76E−07 | 1.05E−05 | −0.116429397 |
| Hnrnpu | 1.27E−05 | 0.000512104 | −0.116567904 |
| Trp53 | 7.92E−05 | 0.002533125 | −0.116834656 |
| Rbbp7 | 0.000635927 | 0.015501151 | −0.117776095 |
| Aldob | 5.98E−05 | 0.001977564 | −0.118012625 |
| Ucicr10 | 1.42E−11 | 1.51E−09 | −0.118718549 |
| Rpl19 | 1.18E−05 | 0.000481676 | −0.119269491 |
| Apoc3 | 0.002490863 | 0.049146635 | −0.119290943 |
| Pkm | 2.89E−06 | 0.000139683 | −0.119434328 |
| Neat1 | 0.001010126 | 0.02301131 | −0.119679174 |
| Gm10076 | 1.27E−05 | 0.000510429 | −0.119835213 |
| Rpl22l1 | 3.28E−10 | 2.96E−08 | −0.120286253 |
| Prmt1 | 0.000456346 | 0.011767088 | −0.120364176 |
| Fbp2 | 1.16E−05 | 0.000473251 | −0.120421256 |
| Tpi1 | 0.00018787 | 0.005409482 | −0.120536318 |
| Clca3b | 4.41E−07 | 2.45E−05 | −0.121134785 |
| Otc | 1.13E−07 | 7.09E−06 | −0.12147471 |
| Arpc4 | 5.58E−11 | 5.55E−09 | −0.121509241 |
| Hmgb2 | 2.69E−14 | 3.84E−12 | −0.123153195 |
| Got2 | 3.23E−05 | 0.001155665 | −0.123455698 |
| Usp50 | 6.14E−08 | 4.00E−06 | −0.12426682 |
| Gm1123 | 5.44E−05 | 0.001815245 | −0.124750581 |
| Ankrd23 | 1.33E−06 | 6.91E−05 | −0.125867995 |
| Tmem258 | 1.78E−07 | 1.05E−05 | −0.126070377 |
| Lsr | 9.49E−06 | 0.000402498 | −0.127021555 |
| Prdx1 | 3.02E−05 | 0.001085935 | −0.127299244 |
| Il21r | 2.78E−06 | 0.000135515 | −0.128525173 |
| Tm4sf5 | 2.86E−05 | 0.001035727 | −0.129849721 |
| Psma5 | 1.64E−05 | 0.000633218 | −0.130617578 |
| Tceb2 | 2.46E−10 | 2.30E−08 | −0.131036639 |
| Ppp1r1b | 8.22E−07 | 4.32E−05 | −0.132623344 |
| Srsf2 | 9.38E−06 | 0.000399059 | −0.133754037 |
| Max | 0.000486666 | 0.012502259 | −0.13578747 |
| Zg16 | 1.65E−11 | 1.74E−09 | −0.135955998 |
| Ctdsp1 | 0.000955008 | 0.021926638 | −0.136074913 |
| Ckmt1 | 1.43E−05 | 0.000561718 | −0.137278599 |
| Sumo1 | 9.81E−10 | 7.93E−08 | −0.138312102 |
| Guca2a | 0.000110785 | 0.003395031 | −0.138663687 |
| Acat2 | 0.001166558 | 0.025714511 | −0.139051666 |
| Rpl31 | 0.000269046 | 0.007466831 | −0.139231296 |
| Arhgap9 | 3.56E−05 | 0.001254208 | −0.140503281 |
| Rps19 | 0.00064945 | 0.01574745 | −0.140677081 |
| Phb2 | 5.76E−05 | 0.001909423 | −0.141626589 |
| Cd3e | 5.89E−12 | 6.62E−10 | −0.141928473 |
| Eif3e | 0.000869575 | 0.020267098 | −0.141971695 |
| Bnip3l | 2.87E−10 | 2.64E−08 | −0.142521317 |
| Reg1 | 1.46E−10 | 1.38E−08 | −0.144419477 |
| Ndufab1 | 3.02E−07 | 1.72E−05 | −0.14501124 |
| Clptm1 | 0.001216008 | 0.026574848 | −0.145675639 |
| Aldoa | 2.11E−08 | 1.44E−06 | −0.14575859 |
| Anxa4 | 0.00165685 | 0.034591114 | −0.146517483 |
| Thumpd3 | 0.000944827 | 0.021800423 | −0.146965109 |
| Actr3 | 1.21E−10 | 1.17E−08 | −0.147334014 |
| Ghrl | 1.37E−05 | 0.000541033 | −0.149503207 |
| Ldha | 0.00236922 | 0.047251065 | −0.149739699 |
| Apoa1 | 8.57E−08 | 5.51E−06 | −0.150985939 |
| H2afj | 6.29E−07 | 3.39E−05 | −0.152033766 |
| Stap1 | 0.001235938 | 0.026858339 | −0.154142042 |
| Tpt1 | 1.15E−07 | 7.17E−06 | −0.155163258 |

TABLE 14-continued

Differentially Expressed Genes from
Salmonella/T cell Experiment

| Gene symbol | p-value | FDR | log2 fold-change (Salmonella vs control) |
|---|---|---|---|
| Pet100 | 5.28E−10 | 4.59E−08 | −0.155632034 |
| Vcp | 2.49E−05 | 0.000906305 | −0.155714714 |
| Ubc | 1.23E−05 | 0.00049841 | −0.156333907 |
| Ctsd | 0.000746746 | 0.017801867 | −0.156864343 |
| Cmtm7 | 7.71E−12 | 8.45E−10 | −0.157618838 |
| Rbm3 | 7.93E−06 | 0.000346759 | −0.157706418 |
| Plscr1 | 1.30E−05 | 0.000521728 | −0.15809926 |
| Atp6v1g1 | 1.40E−13 | 1.86E−11 | −0.159358817 |
| Sf3b4 | 1.03E−08 | 7.18E−07 | −0.160503814 |
| Eif2s2 | 1.21E−12 | 1.47E−10 | −0.161798642 |
| Itgae | 0.000884992 | 0.020557111 | −0.162914853 |
| Tomm6 | 2.79E−07 | 1.61E−05 | −0.164944166 |
| Fam103a1 | 3.44E−05 | 0.001220358 | −0.166408387 |
| R3hdm4 | 5.04E−07 | 2.76E−05 | −0.167872943 |
| Mapk13 | 1.70E−07 | 1.02E−05 | −0.168974023 |
| Cd63 | 1.79E−06 | 9.10E−05 | −0.169221111 |
| Mrfap1 | 3.66E−16 | 5.81E−14 | −0.170886321 |
| Smim4 | 1.37E−05 | 0.000539498 | −0.17255981 |
| Naa38 | 1.09E−05 | 0.000449154 | −0.175083285 |
| Chst12 | 0.000142942 | 0.004257751 | −0.175489203 |
| Mlf2 | 6.46E−06 | 0.000295372 | −0.1756574 |
| Gabarapl2 | 1.52E−09 | 1.20E−07 | −0.176202783 |
| Il2 | 1.60E−06 | 8.17E−05 | −0.177920057 |
| Snrpc | 6.74E−10 | 5.72E−08 | −0.179498699 |
| Eif5a | 2.36E−07 | 1.37E−05 | −0.179638975 |
| Gimap1 | 5.25E−07 | 2.86E−05 | −0.182961218 |
| Adh1 | 6.02E−05 | 0.001986286 | −0.183744991 |
| Rpl27a | 1.45E−05 | 0.000567368 | −0.184148833 |
| Pfn1 | 2.31E−05 | 0.000850104 | −0.184523757 |
| Gip | 1.81E−06 | 9.10E−05 | −0.184676985 |
| Hmha1 | 3.47E−05 | 0.001226422 | −0.185557417 |
| U2af1 | 6.74E−10 | 5.72E−08 | −0.185980232 |
| Gpx4 | 2.26E−25 | 6.02E−23 | −0.187577605 |
| Cox17 | 1.29E−12 | 1.53E−10 | −0.1876349 |
| Sepw1 | 0.000563639 | 0.013985737 | −0.189872911 |
| Cfl1 | 3.96E−06 | 0.000187922 | −0.190080986 |
| Gltscr2 | 3.70E−05 | 0.00130153 | −0.190660783 |
| Tmem256 | 9.17E−10 | 7.55E−08 | −0.190687493 |
| Hypk | 1.13E−11 | 1.23E−09 | −0.191129014 |
| Ogt | 0.000799907 | 0.018833915 | −0.194764759 |
| Sap30bp | 0.000137159 | 0.004121202 | −0.199360474 |
| Fabp1 | 4.67E−18 | 8.96E−16 | −0.202459845 |
| Dpm3 | 9.68E−11 | 9.42E−09 | −0.20330322 |
| Tspan8 | 7.70E−09 | 5.49E−07 | −0.20400037 |
| Mgst1 | 4.10E−08 | 2.74E−06 | −0.204314729 |
| Ccl25 | 2.05E−06 | 0.00010145 | −0.205801582 |
| Gng5 | 1.22E−28 | 3.84E−26 | −0.2059489 |
| Cd9 | 8.71E−05 | 0.002751848 | −0.208341043 |
| Rps26 | 2.88E−16 | 4.63E−14 | −0.210539521 |
| Adipor1 | 0.00018915 | 0.005435022 | −0.21143777 |
| U2af1l4 | 3.71E−07 | 2.10E−05 | −0.212026954 |
| Krt18 | 3.10E−08 | 2.09E−06 | −0.212277253 |
| Agr2 | 1.19E−07 | 7.37E−06 | −0.212628934 |
| Eif4a2 | 6.45E−14 | 8.91E−12 | −0.213255921 |
| Ddx39 | 0.000200421 | 0.005746914 | −0.214185426 |
| Gsto1 | 3.75E−05 | 0.001316946 | −0.21460018 |
| Snrnp70 | 5.37E−06 | 0.000250823 | −0.214798748 |
| Mif | 1.85E−17 | 3.24E−15 | −0.218626358 |
| Arl6ip5 | 8.19E−06 | 0.000356137 | −0.219060653 |
| H3f3a | 4.68E−16 | 7.36E−14 | −0.220638419 |
| Gm26917 | 6.87E−10 | 5.79E−08 | −0.222170656 |
| Id3 | 3.38E−05 | 0.001200478 | −0.225168136 |
| Aldh1b1 | 7.92E−09 | 5.62E−07 | −0.225890742 |
| Olfm4 | 4.22E−15 | 6.28E−13 | −0.226917485 |
| Fbxo9 | 4.97E−05 | 0.001683917 | −0.227644937 |
| Arhgef1 | 2.05E−06 | 0.00010145 | −0.227868504 |
| Fus | 9.50E−08 | 6.05E−06 | −0.228198886 |
| Tomm7 | 1.90E−13 | 2.45E−11 | −0.228474446 |
| Prap1 | 9.16E−05 | 0.002877938 | −0.230061987 |
| Rpl11 | 5.80E−09 | 4.19E−07 | −0.230491391 |
| Gm9843 | 9.54E−37 | 4.12E−34 | −0.232703739 |
| Jund | 2.84E−18 | 5.60E−16 | −0.234327283 |

TABLE 14-continued

Differentially Expressed Genes from Salmonella/T cell Experiment

| Gene symbol | p-value | FDR | log2 fold-change (Salmonella vs control) |
|---|---|---|---|
| Cldn3 | 3.37E−10 | 3.02E−08 | −0.235607026 |
| Gpx2 | 1.38E−10 | 1.31E−08 | −0.238094143 |
| Gpr34 | 0.000182405 | 0.005274111 | −0.238138374 |
| Rab11a | 0.00114605 | 0.025383906 | −0.239313165 |
| Prelid1 | 7.51E−10 | 6.29E−08 | −0.241082516 |
| Kcnn4 | 8.52E−06 | 0.000368007 | −0.241655469 |
| Eno1 | 5.10E−18 | 9.66E−16 | −0.242969595 |
| Lypd8 | 4.44E−08 | 2.94E−06 | −0.245609774 |
| Tecr | 1.07E−05 | 0.000444517 | −0.24790683 |
| Usmg5 | 7.70E−12 | 8.45E−10 | −0.247997316 |
| Izumo1r | 6.30E−05 | 0.002062994 | −0.248540975 |
| Atp5b | 2.89E−07 | 1.66E−05 | −0.248608921 |
| Apol9b | 1.35E−05 | 0.000536923 | −0.250507281 |
| Bola2 | 2.59E−12 | 2.93E−10 | −0.252908982 |
| Rpl39 | 4.28E−19 | 9.10E−17 | −0.253289426 |
| Rps4x | 2.32E−14 | 3.35E−12 | −0.25420105 |
| Mt1 | 5.97E−09 | 4.30E−07 | −0.254472217 |
| Rab11b | 3.59E−09 | 2.69E−07 | −0.255656133 |
| Mei1 | 4.36E−09 | 3.24E−07 | −0.256882343 |
| Myl6 | 2.11E−42 | 1.27E−39 | −0.261264827 |
| Pltp | 1.37E−06 | 7.10E−05 | −0.261686733 |
| Lat2 | 8.66E−08 | 5.54E−06 | −0.264000265 |
| Fam204a | 9.28E−06 | 0.000395675 | −0.268699484 |
| Lamp1 | 2.33E−05 | 0.000852468 | −0.268736821 |
| Pigr | 1.48E−12 | 1.72E−10 | −0.271394304 |
| Snrpf | 1.74E−13 | 2.27E−11 | −0.273975768 |
| Cox6c | 3.01E−09 | 2.29E−07 | −0.274892469 |
| Ywhah | 3.35E−13 | 4.21E−11 | −0.28737841 |
| Ube2d2a | 1.82E−06 | 9.10E−05 | −0.288562356 |
| Rpl30 | 3.97E−33 | 1.48E−30 | −0.292919812 |
| Dazap2 | 0.000736174 | 0.017633736 | −0.299370918 |
| Rplp1 | 4.53E−09 | 3.34E−07 | −0.299513649 |
| Cox7a2l | 7.31E−23 | 1.77E−20 | −0.299837214 |
| Cldn7 | 5.80E−10 | 4.98E−08 | −0.300973484 |
| Fdps | 3.21E−15 | 4.82E−13 | −0.304320227 |
| Uqcrc1 | 1.60E−05 | 0.000618735 | −0.306304084 |
| Bloc1s1 | 5.05E−16 | 7.85E−14 | −0.306633853 |
| Ubac2 | 2.06E−05 | 0.000768392 | −0.31536904 |
| Myl12b | 4.15E−05 | 0.001444391 | −0.315668379 |
| Cox5b | 7.79E−30 | 2.69E−27 | −0.320495645 |
| Atp5a1 | 6.91E−06 | 0.000312753 | −0.320843607 |
| Rsrp1 | 0.00031908 | 0.008630154 | −0.321111854 |
| Coro1b | 7.42E−07 | 3.94E−05 | −0.321479217 |
| Trmt112 | 6.82E−15 | 1.00E−12 | −0.322307369 |
| Cd96 | 0.00010489 | 0.003243149 | −0.326342505 |
| Rpl18a | 1.31E−58 | 1.65E−55 | −0.329972136 |
| Rplp2 | 3.25E−13 | 4.13E−11 | −0.343177914 |
| Defa24 | 3.87E−08 | 2.59E−06 | −0.344513641 |
| Tmem50a | 4.00E−07 | 2.23E−05 | −0.345319749 |
| Srsf5 | 1.99E−06 | 9.92E−05 | −0.346984087 |
| Son | 7.60E−23 | 1.81E−20 | −0.348768488 |
| Rpl36al | 1.98E−40 | 1.05E−37 | −0.352894615 |
| Fabp2 | 5.53E−09 | 4.02E−07 | −0.361669577 |
| Eef2 | 5.75E−08 | 3.76E−06 | −0.36452842 |
| Atpif1 | 1.61E−06 | 8.23E−05 | −0.364597234 |
| Mgst3 | 1.00E−13 | 1.37E−11 | −0.369358767 |
| Uqcr11 | 2.35E−16 | 3.82E−14 | −0.370979839 |
| Epcam | 1.23E−07 | 7.58E−06 | −0.37536499 |
| Hnrnpf | 3.91E−10 | 3.47E−08 | −0.375773994 |
| Eif4a1 | 5.43E−18 | 1.01E−15 | −0.377946033 |
| Smim24 | 5.73E−10 | 4.95E−08 | −0.378117929 |
| Gpx1 | 1.01E−05 | 0.00042447 | −0.378748233 |
| Gm11808 | 1.31E−12 | 1.54E−10 | −0.379634593 |
| Rpl3 | 1.07E−21 | 2.46E−19 | −0.382043961 |
| Rps15 | 4.07E−18 | 7.91E−16 | −0.396778066 |
| Atp5g1 | 1.83E−32 | 6.64E−30 | −0.397705218 |
| Eef1a1 | 2.33E−14 | 3.35E−12 | −0.401632875 |
| Rnaset2b | 4.07E−23 | 1.00E−20 | −0.404534803 |
| Gdi2 | 1.07E−09 | 8.58E−08 | −0.406713053 |
| Tmsb10 | 1.26E−12 | 1.50E−10 | −0.410582889 |
| H2afz | 1.66E−18 | 3.36E−16 | −0.412958982 |
| Pebp1 | 2.59E−18 | 5.19E−16 | −0.412964547 |

TABLE 14-continued

Differentially Expressed Genes from Salmonella/T cell Experiment

| Gene symbol | p-value | FDR | log2 fold-change (Salmonella vs control) |
|---|---|---|---|
| Krt8 | 1.94E−16 | 3.19E−14 | −0.41446198 |
| Rpl18 | 2.43E−45 | 1.53E−42 | −0.416112016 |
| Tmed2 | 1.65E−13 | 2.18E−11 | −0.421077644 |
| Hnrnpk | 3.05E−11 | 3.13E−09 | −0.445839105 |
| Tff3 | 1.31E−18 | 2.70E−16 | −0.455488415 |
| Pabpc1 | 8.94E−21 | 1.99E−18 | −0.468184428 |
| Spint2 | 7.04E−12 | 7.85E−10 | −0.474889556 |
| Ndufb4 | 4.66E−17 | 7.96E−15 | −0.486497174 |
| Rps20 | 8.15E−20 | 1.79E−17 | −0.487321252 |
| Hspa8 | 1.89E−26 | 5.68E−24 | −0.4950503 |
| Tma7 | 6.24E−26 | 1.83E−23 | −0.505701124 |
| Ndufa3 | 2.47E−33 | 9.49E−31 | −0.509768398 |
| Spink4 | 2.14E−21 | 4.85E−19 | −0.54536397 |
| Atp5k | 3.09E−25 | 8.07E−23 | −0.549752833 |
| Rnaset2a | 3.36E−34 | 1.37E−31 | −0.576446866 |
| Phgr1 | 1.53E−25 | 4.14E−23 | −0.578892514 |
| Cd3g | 8.16E−18 | 1.50E−15 | −0.590708529 |
| Oat | 1.26E−25 | 3.48E−23 | −0.606412607 |
| Snrpg | 4.67E−39 | 2.22E−36 | −0.616788797 |
| Grcc10 | 3.34E−35 | 1.40E−32 | −0.632983931 |
| Fabp6 | 5.15E−29 | 1.69E−26 | −0.638768681 |
| Krt19 | 7.16E−28 | 2.20E−25 | −0.643695979 |
| Rps16 | 4.52E−63 | 7.81E−60 | −0.653062852 |
| Rpl35a | 1.46E−48 | 1.12E−45 | −0.655362777 |
| Rps25 | 4.84E−47 | 3.35E−44 | −0.659384847 |
| Rpl34 | 7.60E−40 | 3.89E−37 | −0.738476086 |
| Cirbp | 1.22E−12 | 1.47E−10 | −0.739976945 |
| Wdr89 | 3.77E−52 | 3.72E−49 | −0.740352801 |
| Crip1 | 6.28E−24 | 1.61E−21 | −0.752519528 |
| Rpl35 | 9.76E−61 | 1.50E−57 | −0.755798009 |
| Lgals4 | 1.05E−28 | 3.36E−26 | −0.76804491 |
| Uba52 | 1.50E−33 | 5.91E−31 | −0.776797758 |
| Rpsa | 4.04E−41 | 2.32E−38 | −0.787041205 |
| Rps21 | 4.12E−50 | 3.56E−47 | −0.803152132 |
| Cd7 | 2.61E−07 | 1.51E−05 | −0.81072919 |
| Ubb | 9.95E−56 | 1.15E−52 | −0.83426418 |
| Oaz1 | 8.30E−52 | 7.65E−49 | −0.838563122 |
| Ptma | 7.12E−49 | 5.79E−46 | −0.90555849 |
| Lgals2 | 1.77E−40 | 9.81E−38 | −0.994549436 |
| Rpl37a | 3.25E−84 | 2.24E−80 | −1.065484227 |
| Gm42418 | 4.18E−29 | 1.41E−26 | −1.097083007 |
| Rpl37 | 3.58E−74 | 8.24E−71 | −1.163940545 |
| Rps15a | 1.85E−78 | 8.53E−75 | −1.21769999 |
| Rps27rt | 9.82E−78 | 3.39E−74 | −1.335144476 |
| Comt | 1.65E−60 | 2.28E−57 | −1.362366005 |
| Rps28 | 1.54E−69 | 3.05E−66 | −1.416466439 |
| Rpl13 | 5.42E−76 | 1.50E−72 | −1.447928292 |
| Rpl41 | 5.36E−143 | 7.40E−139 | −1.506115902 |

All genes shown are significantly DE (FDR <0.05, likelihood-ratio test)

Figures 25A, 25B:
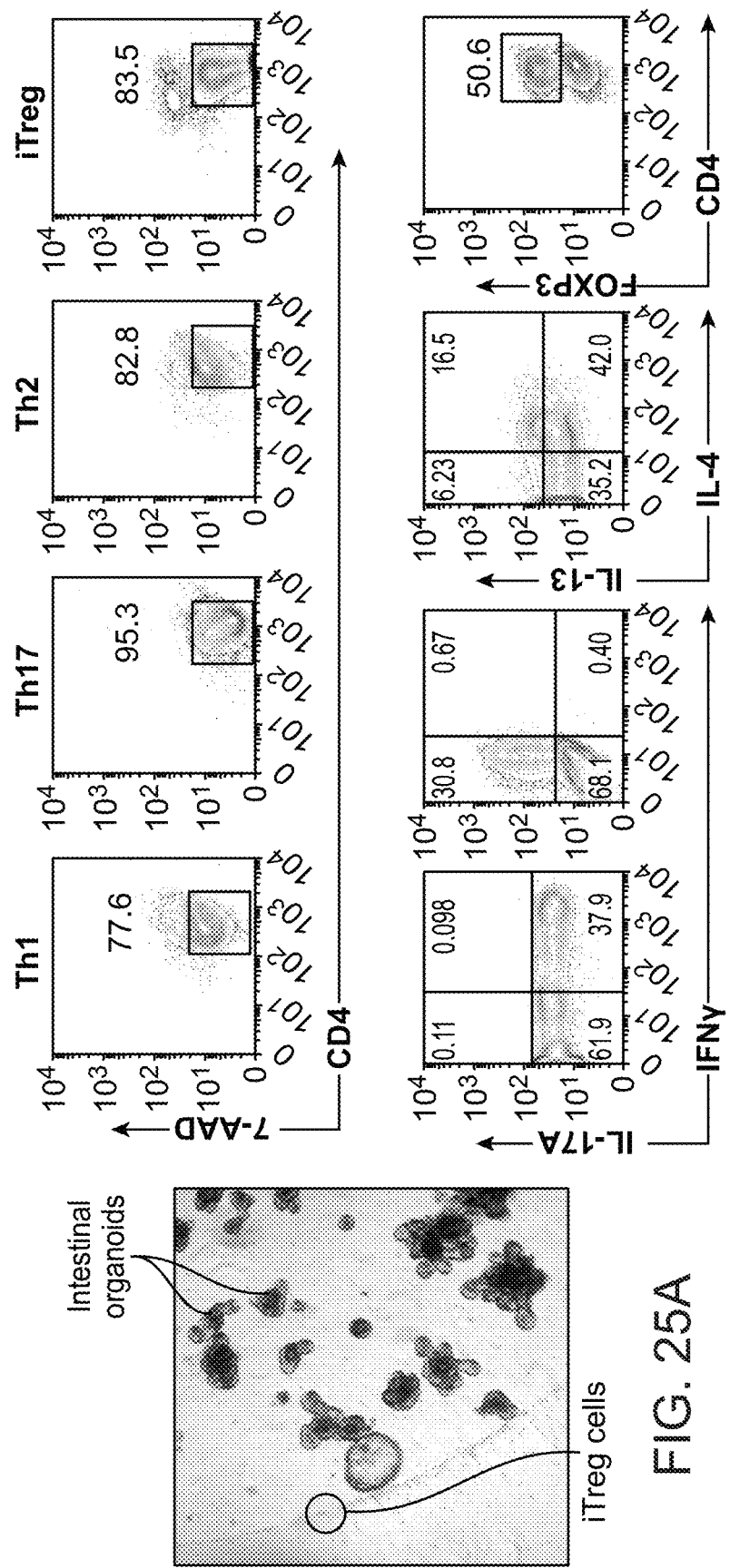
FIG. 25A-25G—Characterization of intestinal organoids co-cultured with T helper (Th) cells or treated with their key cytokines.
Figure 25C:
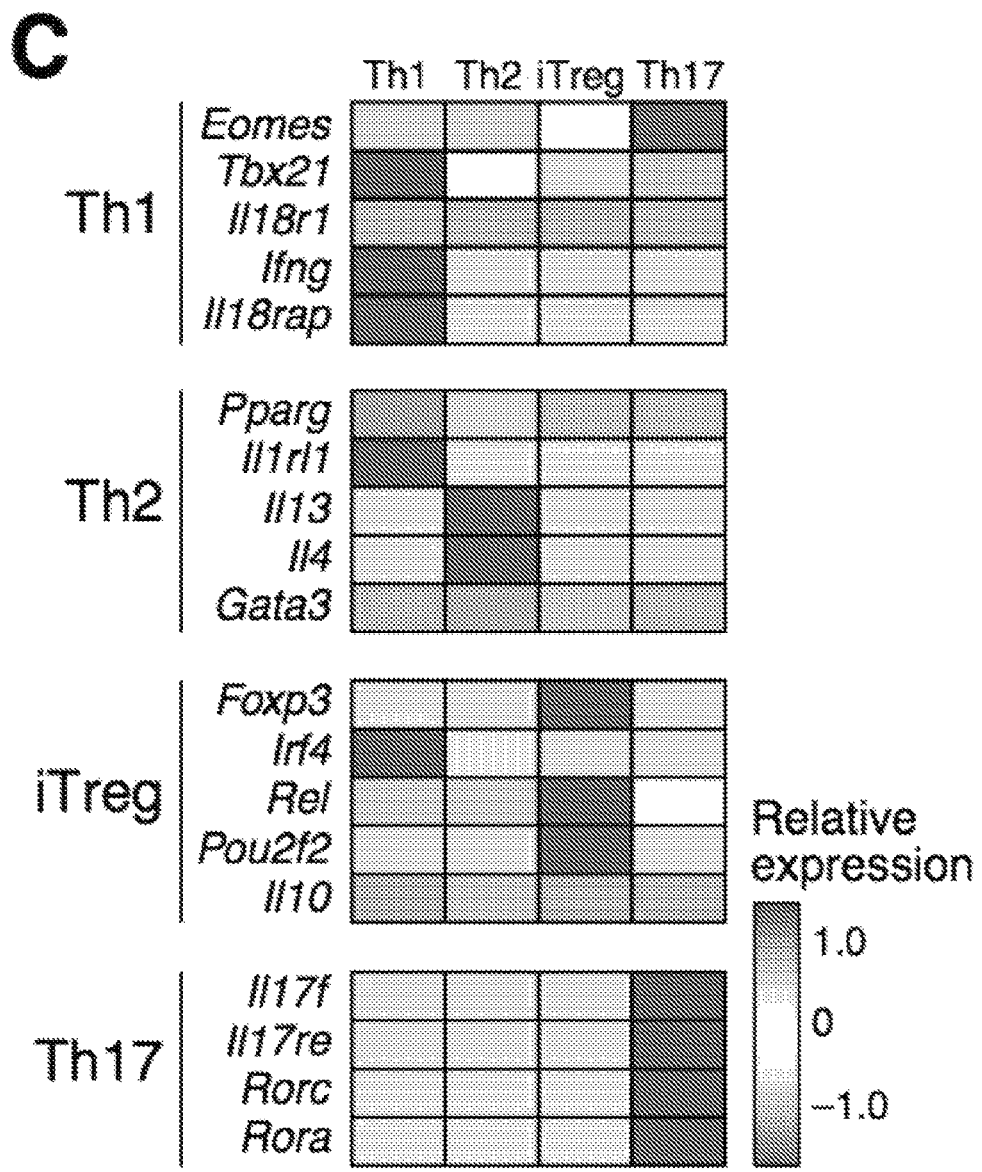
Figure 25D:
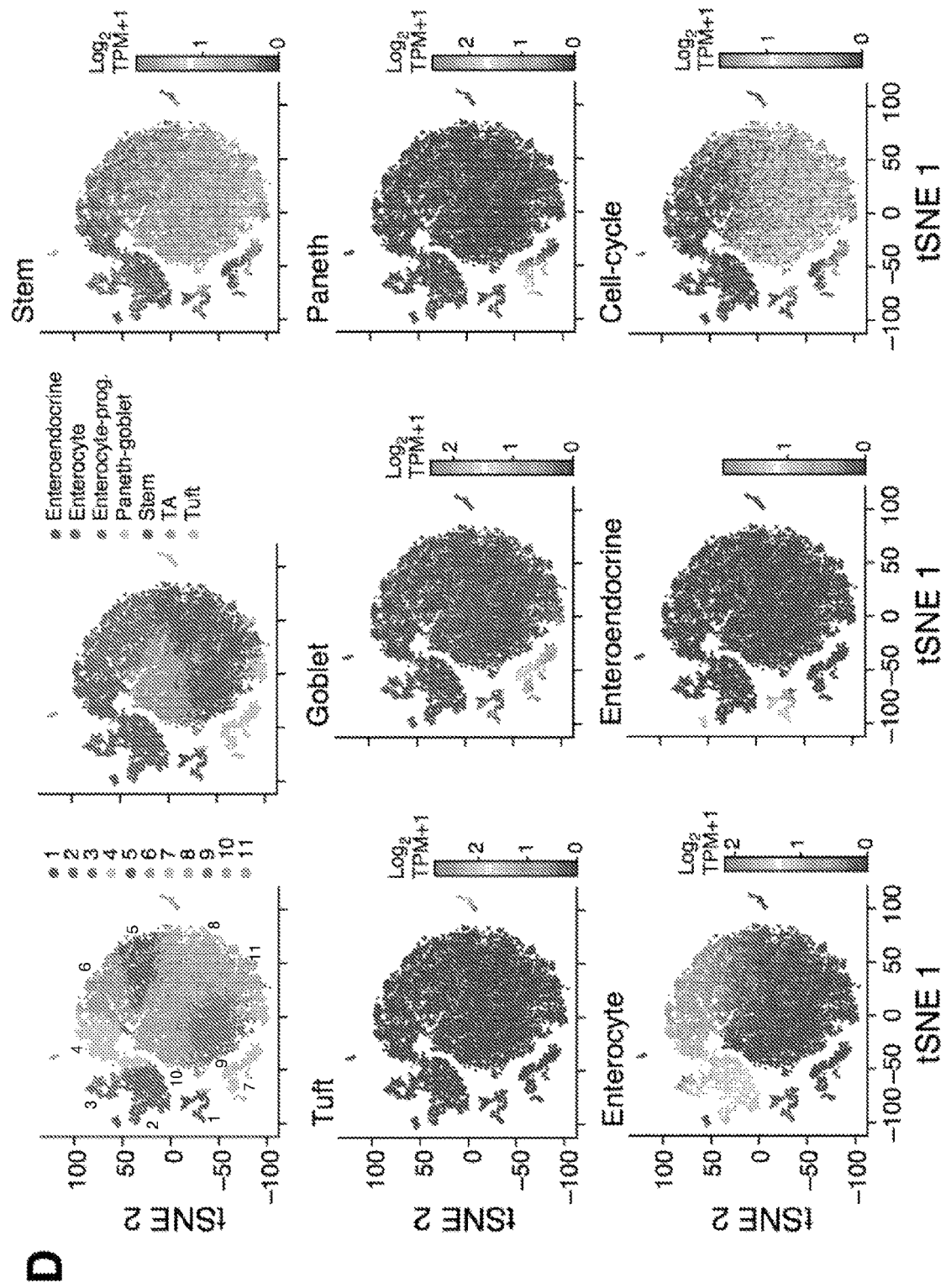
Figure 25E:
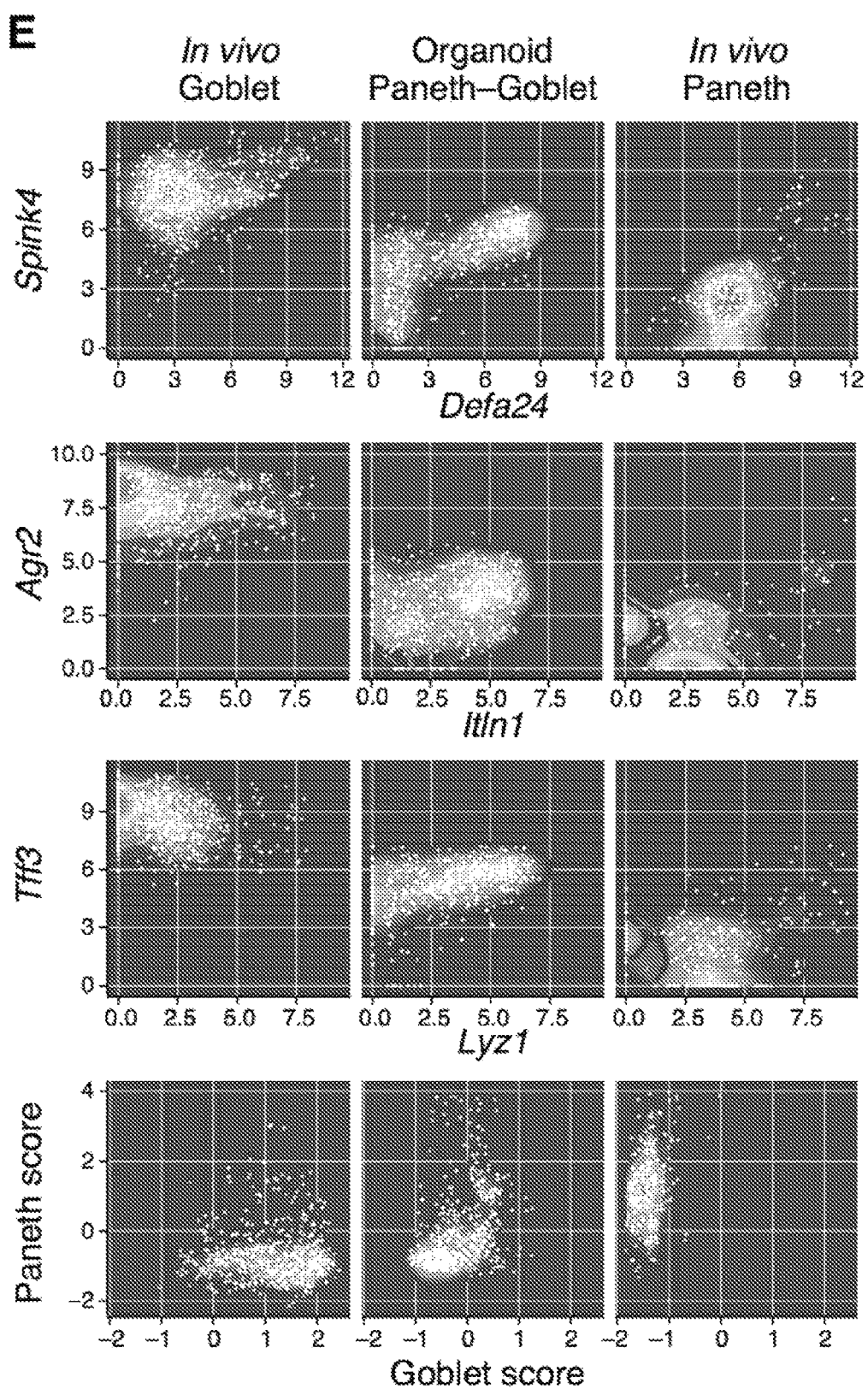
Figure 25F:
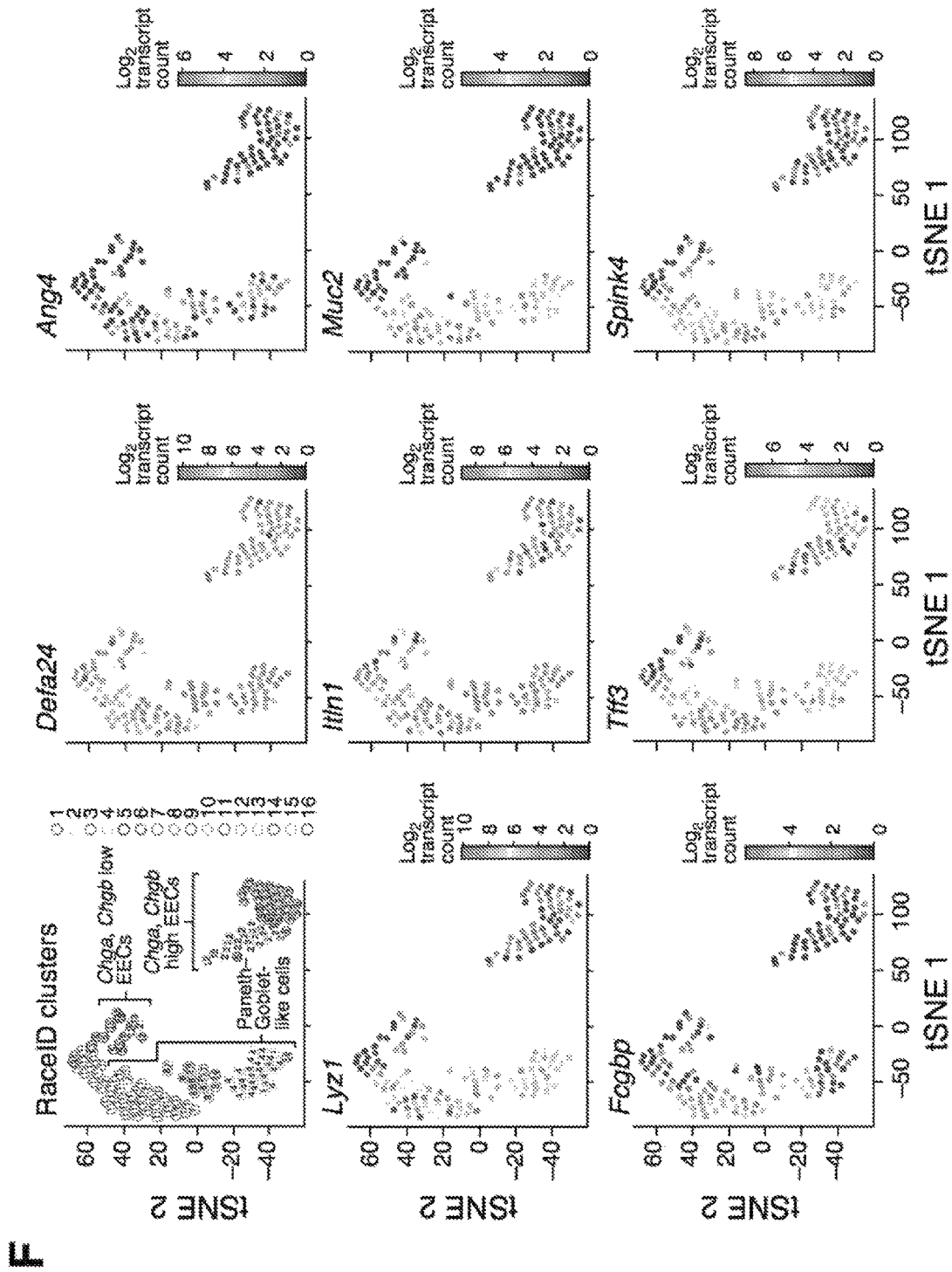
Figure 25G:
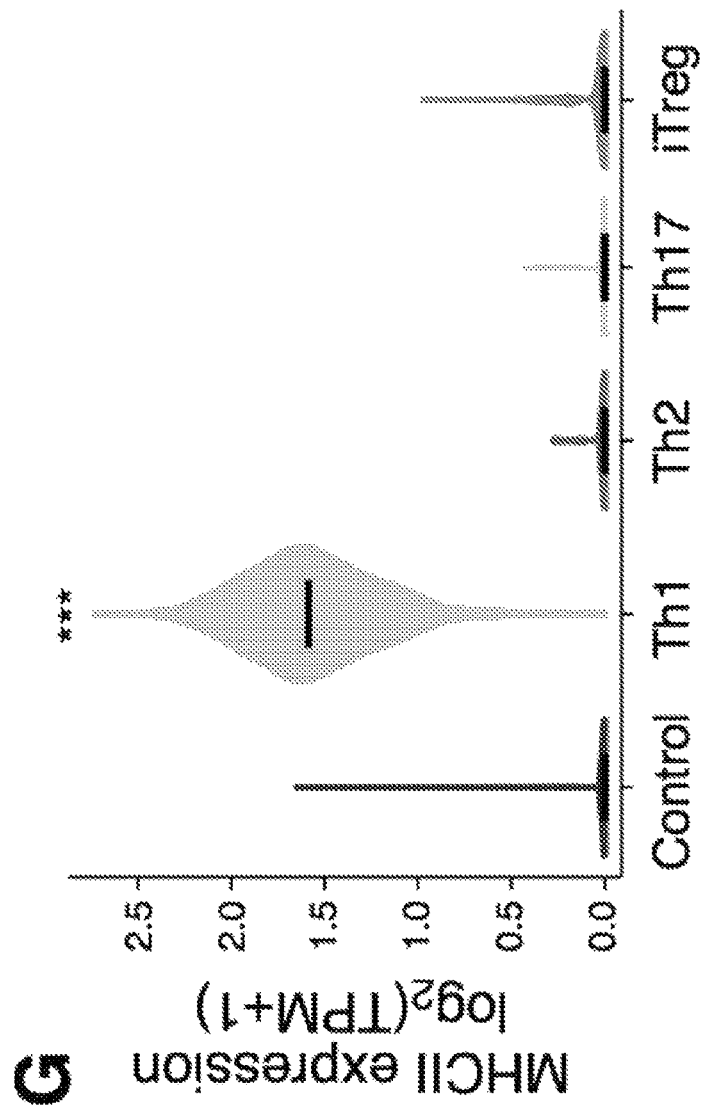

To dissect the potential interactions between T helper cells and ISCs independently of other contributions to the niche, Applicants therefore next used the intestinal organoid system[4] in which immune cells are natively absent but can be added in a controlled manner[123]. Applicants introduced either specific CD4+ T helper subsets (FIG. 25A) or their corresponding signature cytokines to organoid cultures, and used scRNA-seq to identify changes in the proportions or expression programs of ISCs. In one set of experiments, Applicants co-cultured organoids with CD4+ T cells that were polarized ex vivo towards Th1, Th2, Th17, and iT$_{reg}$ cells[124] (FIG. 25B). In a parallel set, Applicants stimulated organoids derived from C57BL/6J WT mice with key cytokines produced by each of the four T helper subsets: IFNγ (Th1), IL-13 (Th2), IL-17a (Th17), and IL-10 (inducible T$_{reg}$, iT$_{reg}$). In each experiment, Applicants collected droplet-based scRNA-seq profiles (Methods). For co-cultures, Applicants computationally distinguished (post-hoc) T cells from epithelial cells by their profiles (Methods) and confirmed the Th cell state by mRNA expression of signature cytokines and transcription factors (FIG. 25C). Although ex vivo polarized T helper cells share many hallmarks with their in vivo counterparts, they do not perfectly recapitulate them. In particular, Th2 differentiation yielded only 16.5% ITL-4 and IL-13 expressing cells, while other T helper subsets had higher differentiation rates (FIG. 25B). There are also several differences between organoids and in vivo IECs (FIG. 25D-G): Organoids are enriched for stem cells[4,125] (FIG. 25D), the goblet and Paneth lineages do not fully diverge (FIG. 25E), also in independently-generated organoids[23] (FIG. 25F), and MHCII expression was not detected in the organoid culture (FIG. 25G); thus, any impact of Th cell co-cultures is likely mediated through cytokine secretion from the polarized Th cells.

Figure 26A:
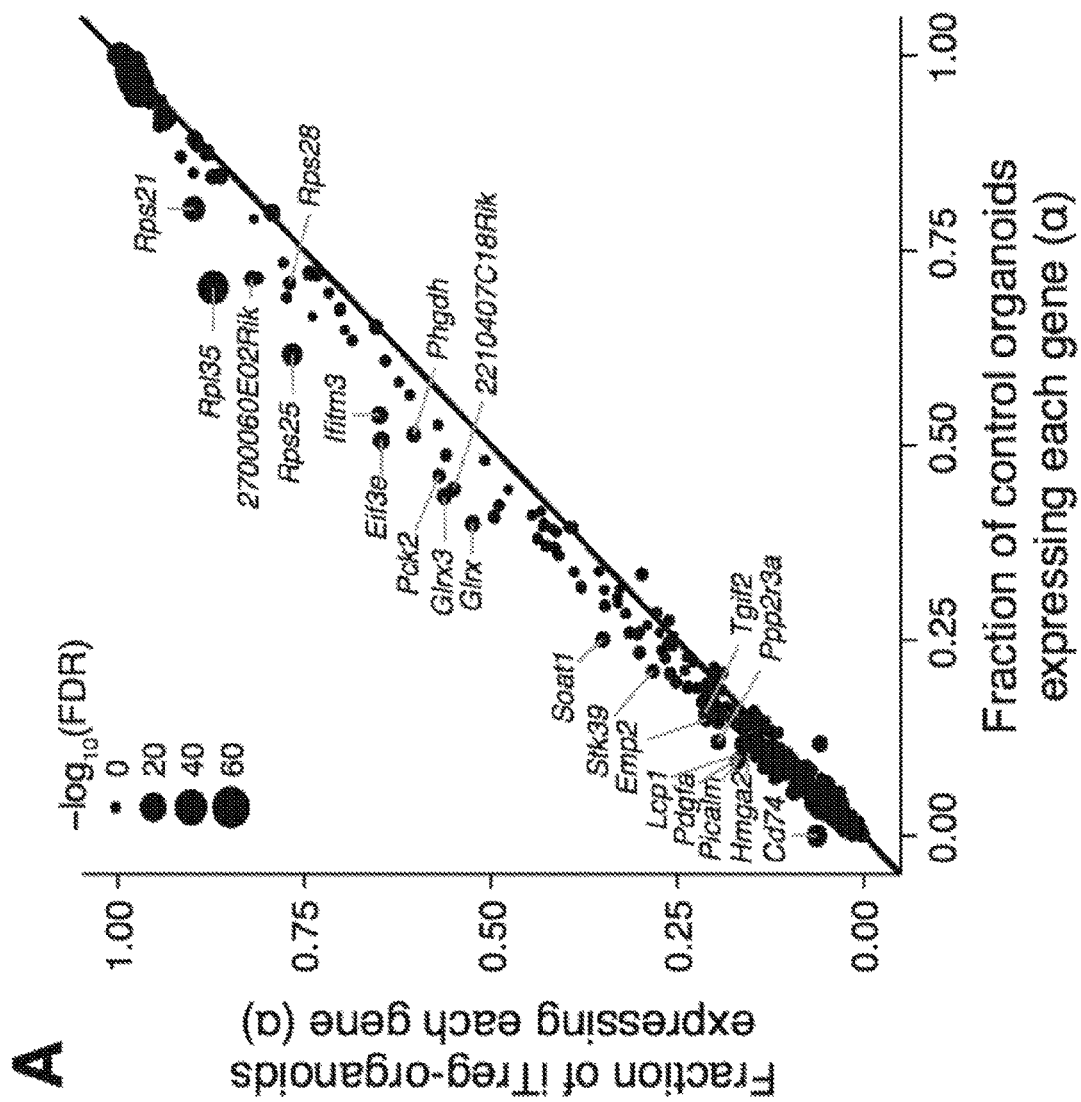
Figure 26B:
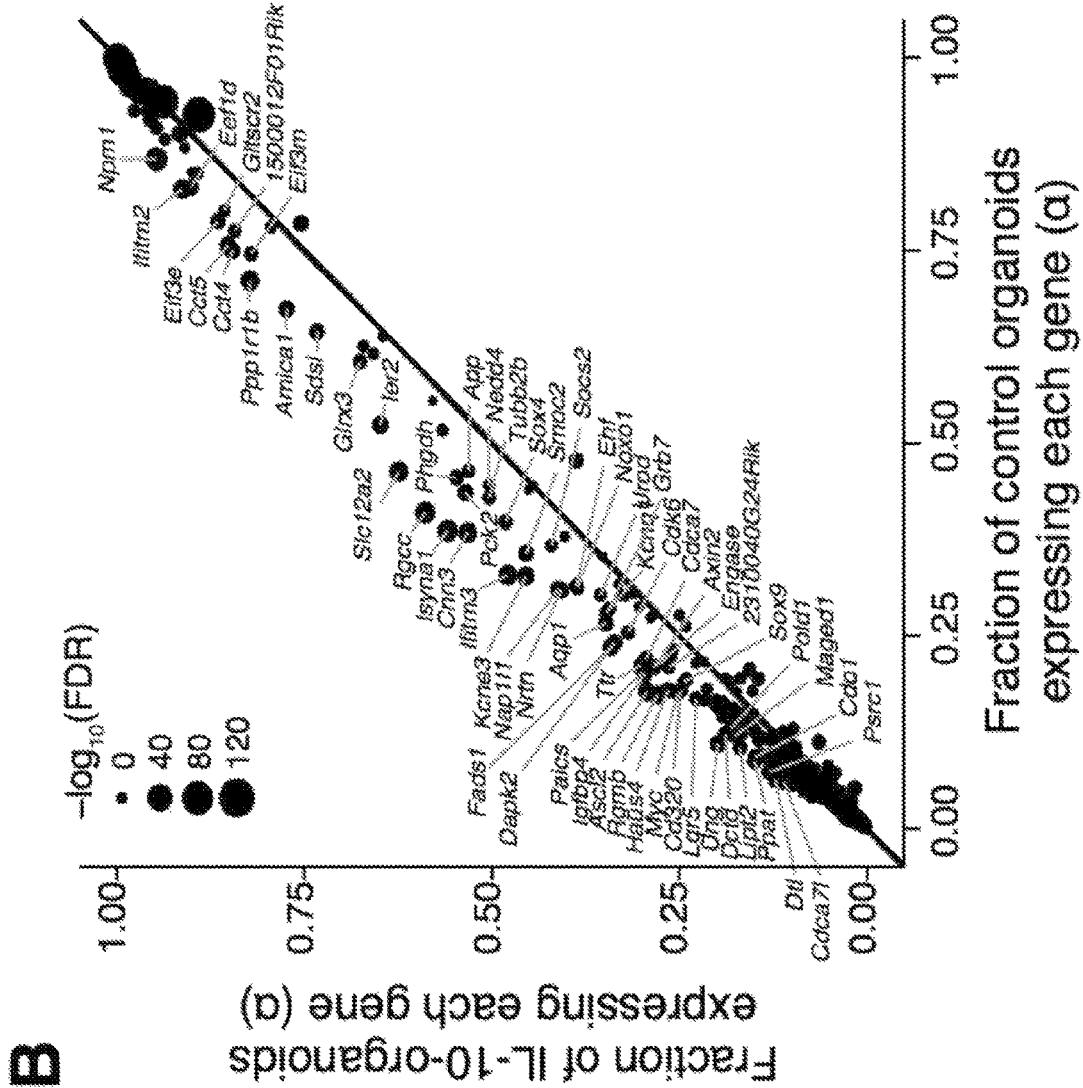
Figure 26C:
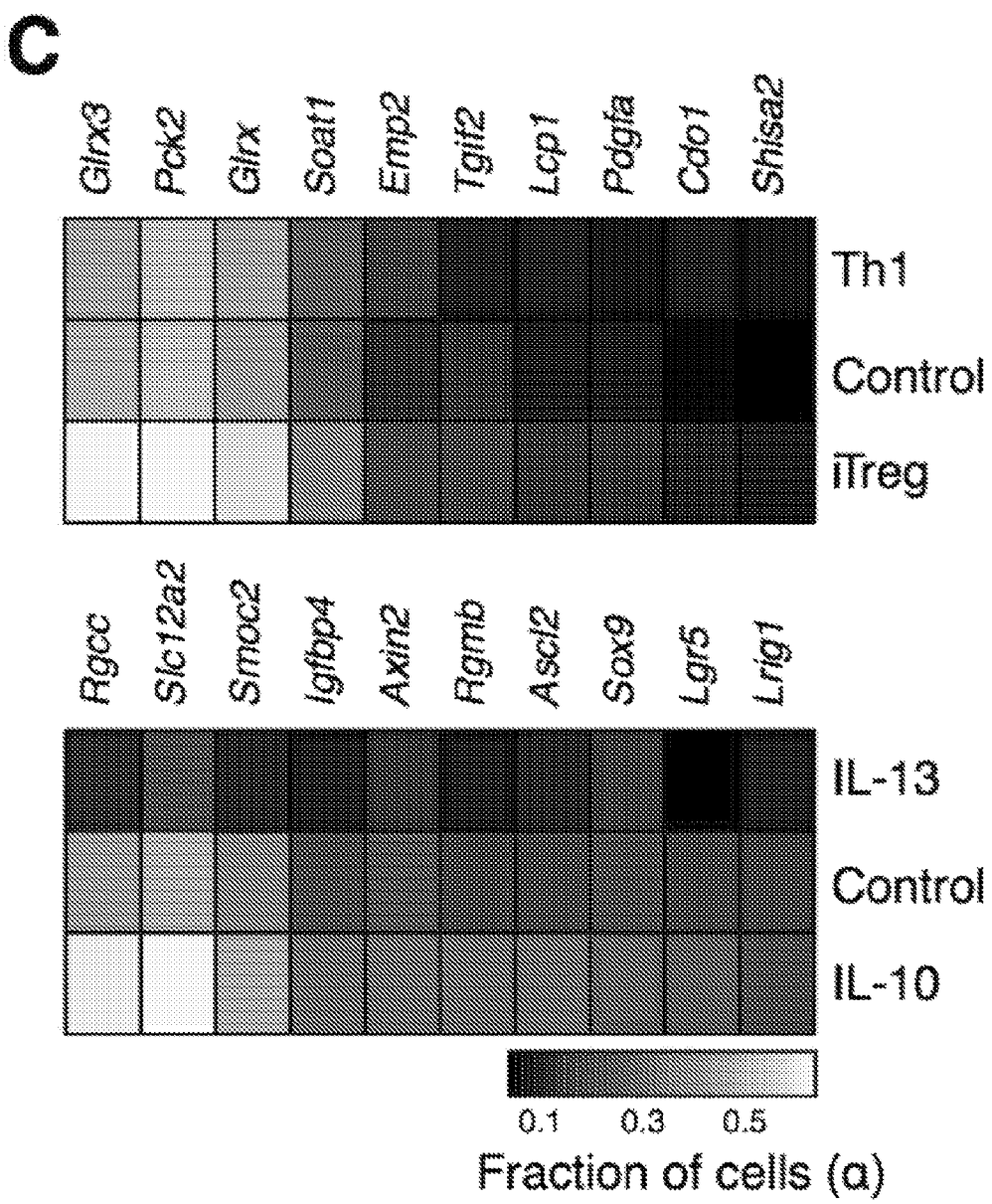

Each of the Th co-cultures or corresponding cytokine treatments resulted in a distinct modulation of the organoid ISC compartment (FIG. 19A,B and FIG. 26A-C). Strikingly, co-cultures with iT$_{regs}$ and treatment of organoids with their associated cytokine IL-10 led to organoid ISC expansion (FIG. 19A,B, FIG. 26A-C, Methods), while co-cultures with Th1, Th2 and Th17 cells or treatment with IL-13 or IL-17 all reduced the size of the ISC pool of the organoids. Consistent with their depleted stem cell pool, organoids co-cultured with Th1, Th2, or Th17 cells or treated with IL-17a all showed elevated numbers of TA cells ($p<10^{-4}$, hypergeometric test, FIG. 19A,B). Note, for IFNγ, Applicants used a low concentration (0.5u/ml) to avoid organoid apoptosis[126], which did not elicit any effect (FIG. 19A, top). In addition, the treatments impacted cell differentiation: IL-13 treatment decreased the proportion of secretory 'Paneth-goblet' cells, and increased tuft cells (FIG. 19A,C)[14,16]; Th1 co-culture up-regulated Paneth cell-specific genes (FIG. 26D-F), consistent with in vivo observations (FIG. 24F); and Th2 cell co-cultures had the opposite effect (FIG. 26D,E).

The effects of Th cell subsets and cytokines on ISC numbers suggest that they affect ISC renewal potential, which in turn should affect the ability of ISCs to form organoid cultures. To test this hypothesis, Applicants assessed whether key cytokines affect ISC clonogenicity[159]. Applicants reseeded equal numbers of cytokine-treated organoids in new cultures and quantified the number of organoids after three days (n=6 replicates per each group, Methods). Consistent with the hypothesis, there was a significant reduction in the clonogenicity of organoids treated with the ISC-reducing cytokine IL-13, whereas the ISC-expanding cytokine IL-10 induced higher clonogenicity (FIG. 19D), confirming the ability of this T$_{reg}$-generated cytokine to rejuvenate the stem cell pool.

Example 16—Elevation in ISC Pool Under Epithelial MHCII Ablation In Vivo

Since the MHCII system is not expressed in organoids, Applicants next assessed its role in IECs in vivo by its conditional KO. Applicants crossed H2-Ab1$^{fl/fl}$ [132] to Villin-Cre-ER$^{T2}$ 133 mice, generating a mouse model of specific and inducible MHCII knockout in IECs (MHCII$^{Δgut}$). Applicants profiled 1,559 IECs from the MHCII$^{Δgut}$ mice (n=5) 10 days after Tamoxifen induction and 1,617 IECs from floxed control (MHCII$^{fl/fl}$) littermates (n=5 mice). Applicants validated that MHCII is successfully knocked-out in EpCAM* IECs (FIG. 20A and FIG. 27A), but not in CD11b$^+$ dendritic cells in the mesenteric lymph node (FIG. 27B).

Figure 28A:
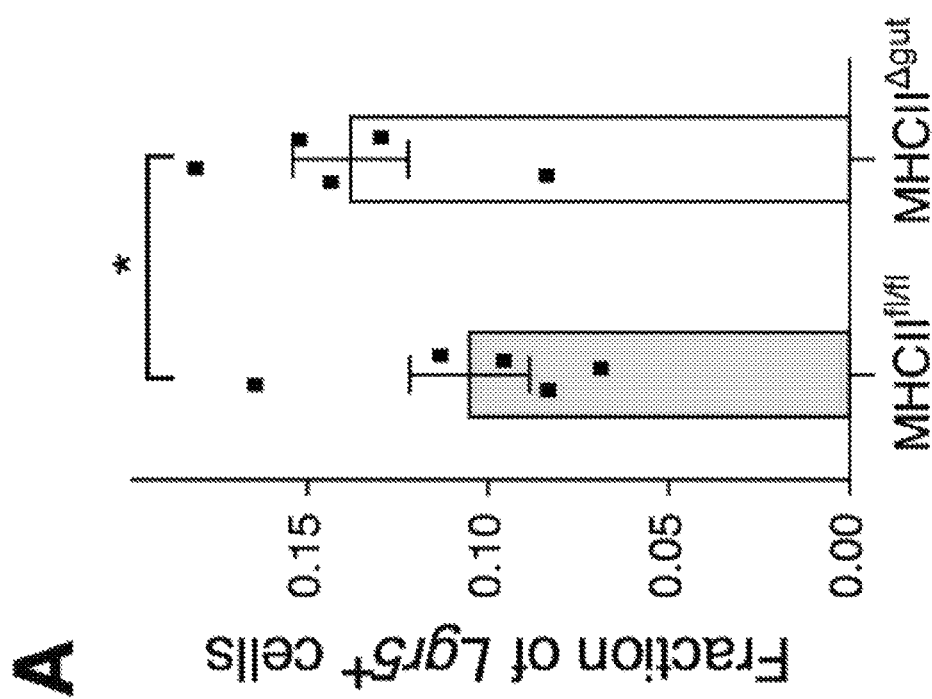
FIG. 28A-28E—Impact of MHCII knockout in gut epithelial cells on the ISC pool.
Figure 28B:
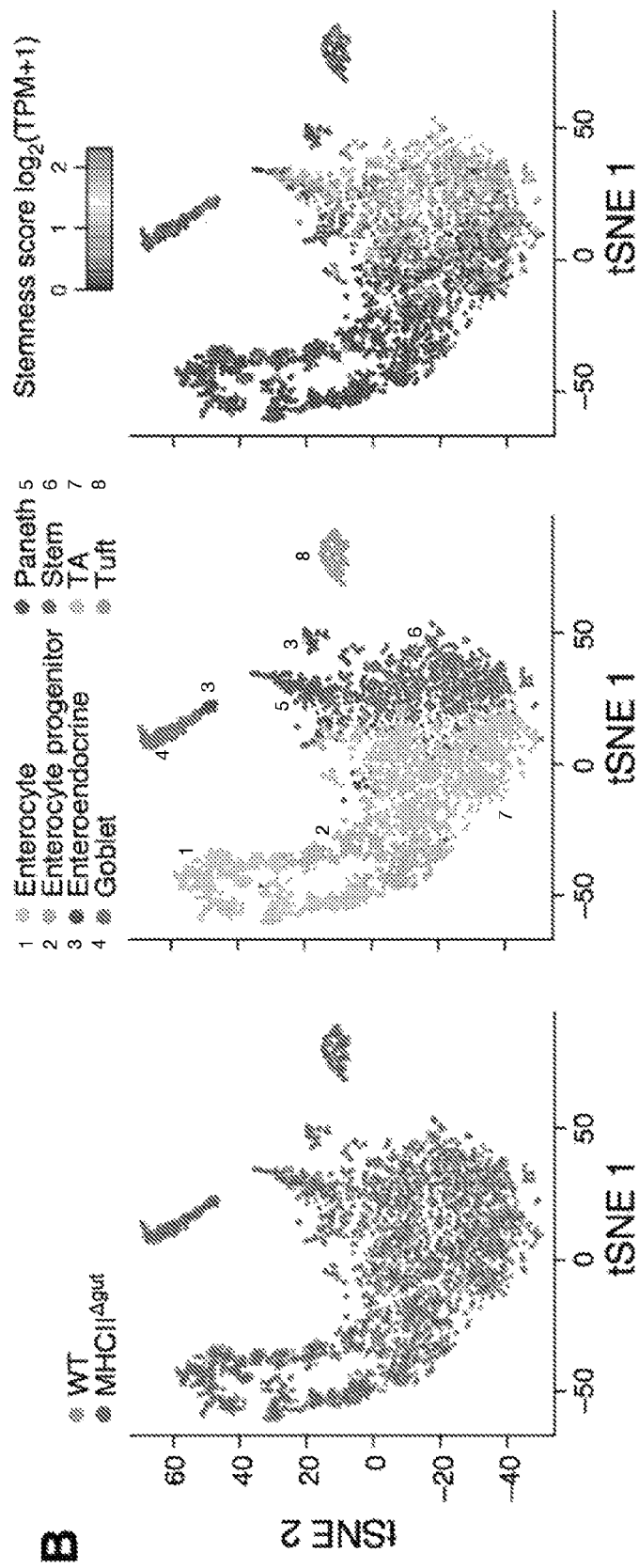
Figure 28C:
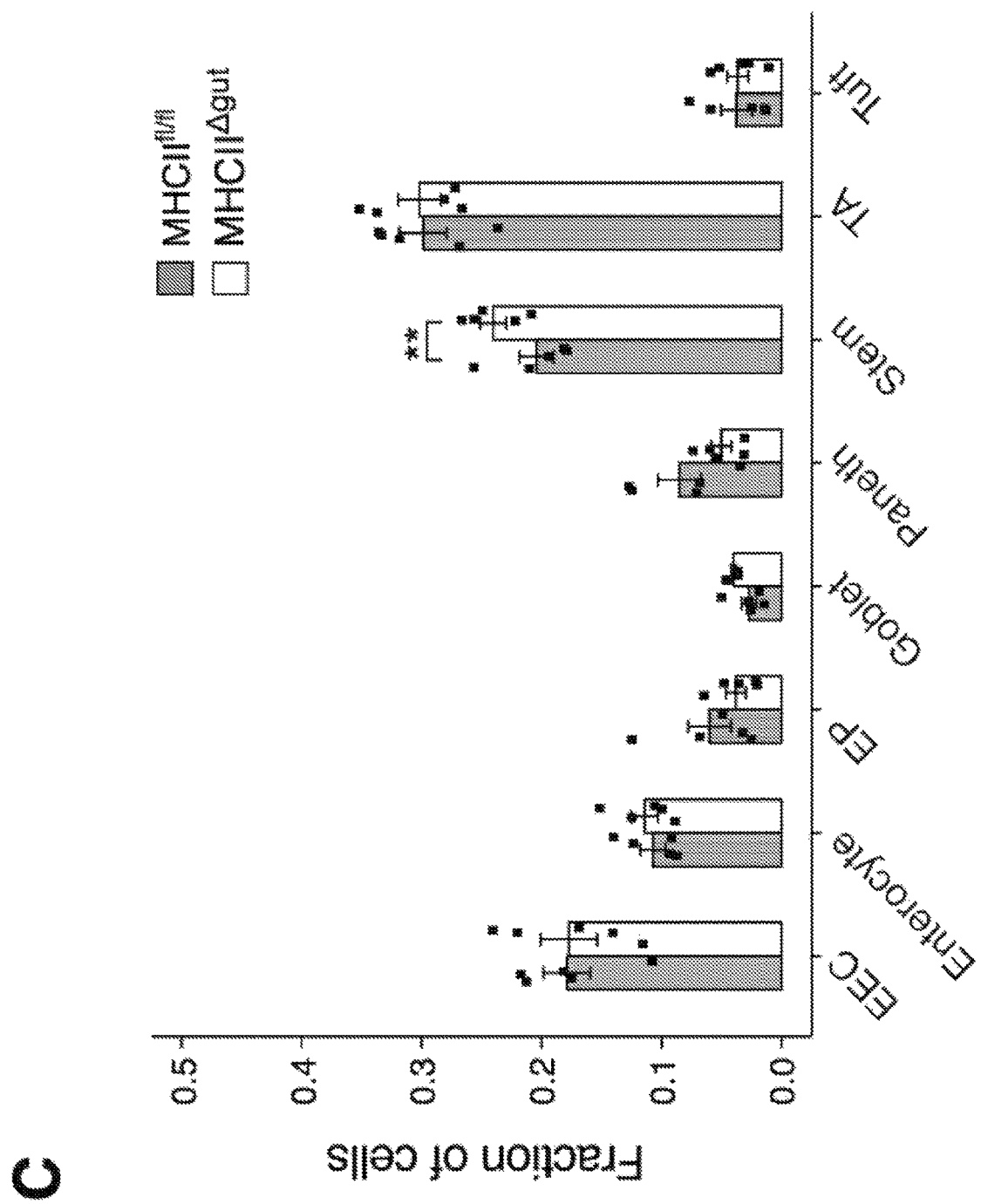
Figure 28D:
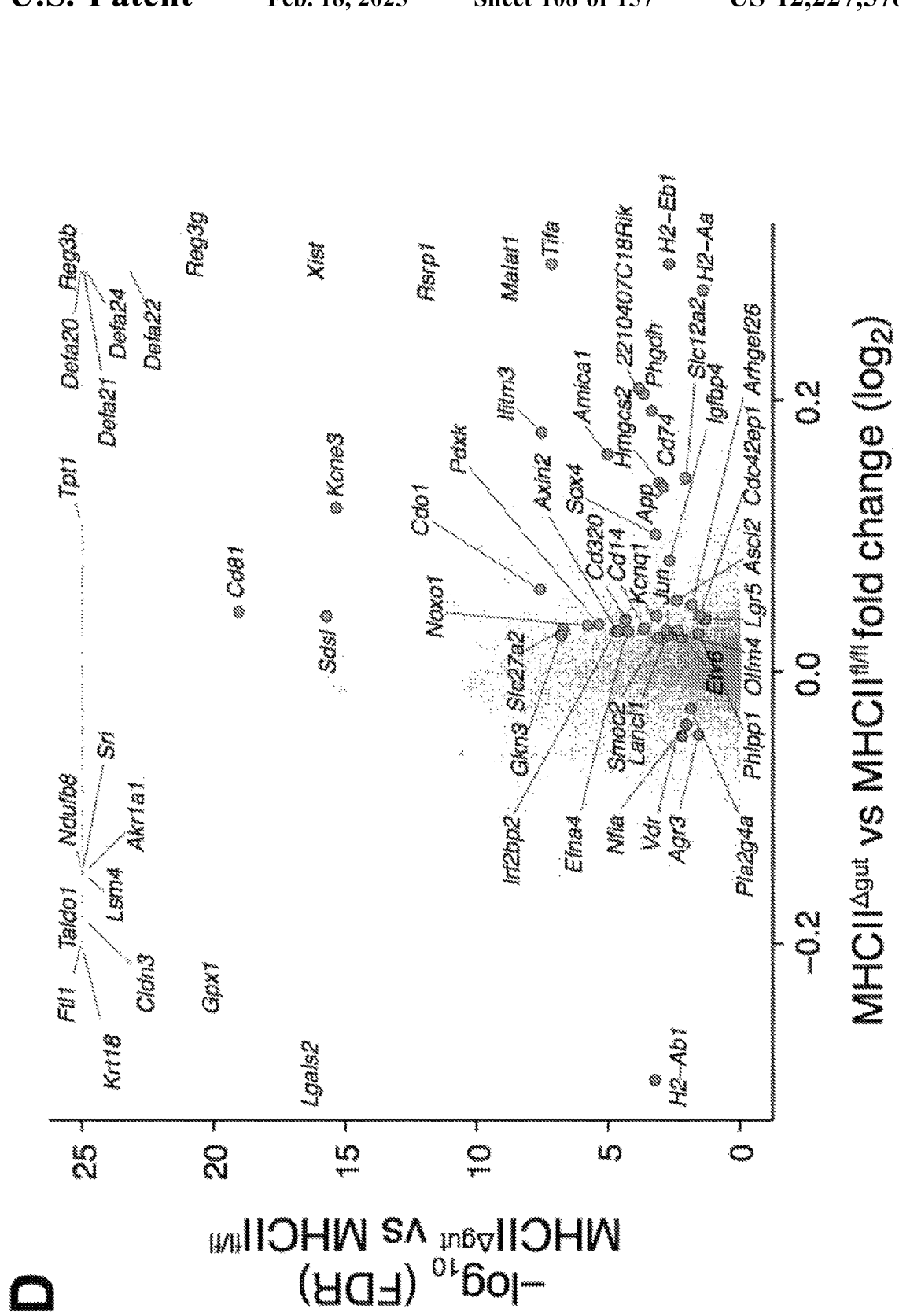
Figure 28E:
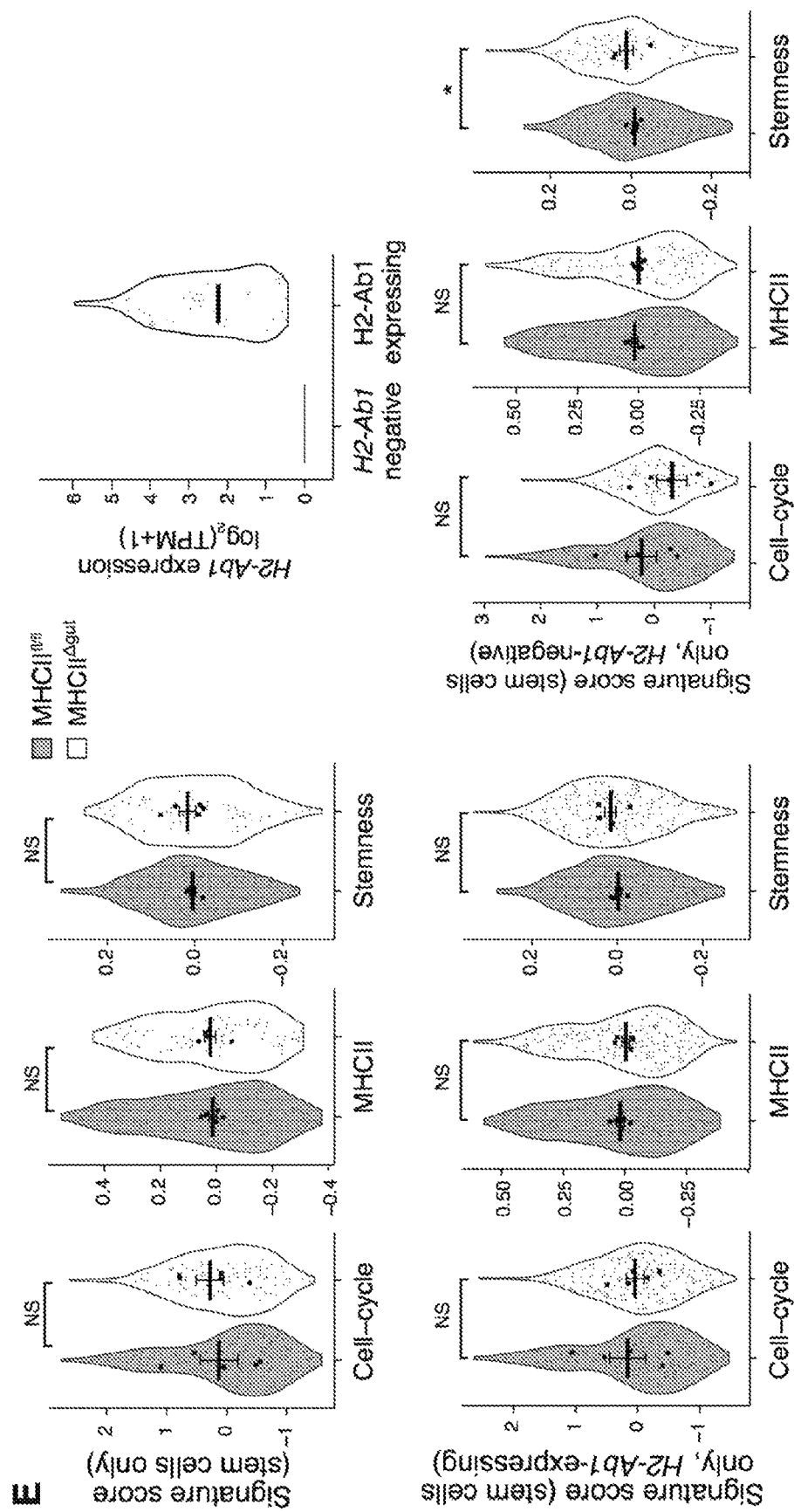

Strikingly, the fraction of Lgr5$^+$ cells was 31.3% higher in MHCII$^{Δgut}$ mice ($p<0.05$, likelihood-ratio test, FIG. 28A), which Applicants confirmed by Lgr5-smFISH (FIG. 20B), and the proportion of ISCs as defined by unsupervised clustering (FIG. 28B,C) which was 17.6% higher (FDR<0.05, likelihood-ratio test, FIG. 20C). Consistently, stem cell markers are overrepresented ($p<10^{-6}$, hypergeometric test, FIG. 28D) among the genes up-regulated in the MHCII$^{Δgut}$ (FDR<0.05, likelihood-ratio test), including canonical ISC markers (e.g., Lgr5, Olf4, Smoc2, and Igfbp4, FIG. 28D). Furthermore, Applicants separately analyzed only MHCII$^{Δgut}$ ISCs in which H2-Ab1 is confirmed to be silenced (defined as no detectable mRNA) or only MHCII$^{Δgut}$ ISCs in which H2-Ab1 mRNA is still expressed (FIG. 28E, bottom left vs. right). Applicants find that in MHCII$^{Δgut}$ ISCs in which H2-Ab1 is confirmed to be silenced, expression of stem cell markers[103] was significantly higher than in stem cells still expressing H2-Ab1 ($p<0.05$, likelihood-ratio test). Finally, the ISC-III signature score was significantly lower in stem cells from MHCII$^{Δgut}$ mice (FIG. 20D), suggesting that the ISCs in the expanded pool are shifted toward the ISC$^{MHCII-}$ state. Taken together, these data suggest that MHCII$^{Δgut}$ increased ISC numbers and the expression of stem cell markers.

Example 17—T Cells Modulate ISC Renewal and Differentiation In Vivo

Figure 29A:
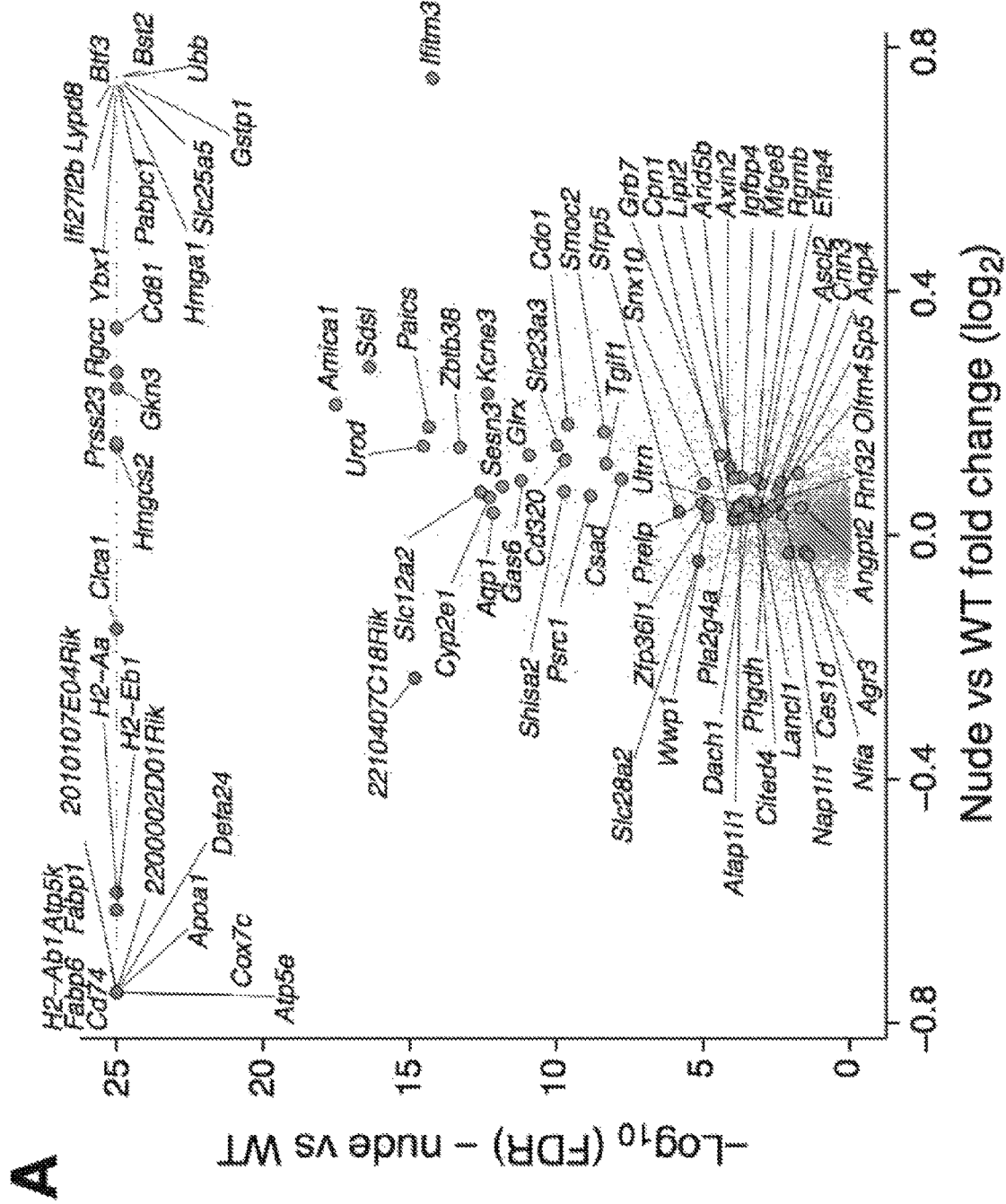
FIG. 29A-29F—An expanded ISC pool in T cell-depleted mouse models. Volcano plots (FIG. 29A, FIG. 29C) show mean log 2 fold-change (x-axis) and significance ($-\log_{10}$(FDR), Methods) of differential expression between 7,216 cells from WT mice (n=6), 2,967 cells from nude mice (A, n=2 mice) or 9,488 cells from TCRβ-KO mice (C, n=2 mice). Green dots: up-regulated ISC genes, red dots: down-regulated ISC genes (FDR<0.05, likelihood-ratio test), grey dots: non-DE genes. Bar plots (FIG. 29B, FIG. 29D) show frequency (y-axis) of each major IEC-type (x-axis), as determined by unsupervised clustering (Methods), in cells from WT (grey) vs. nude (white, B) or TCRβ-KO mice (white, FIG. 29D). Dots correspond to individual mice. Error bars are SEM. (* FDR<0.05, ** FDR<0.005, * ** FDR<10-5, likelihood-ratio test).
Figure 29B:
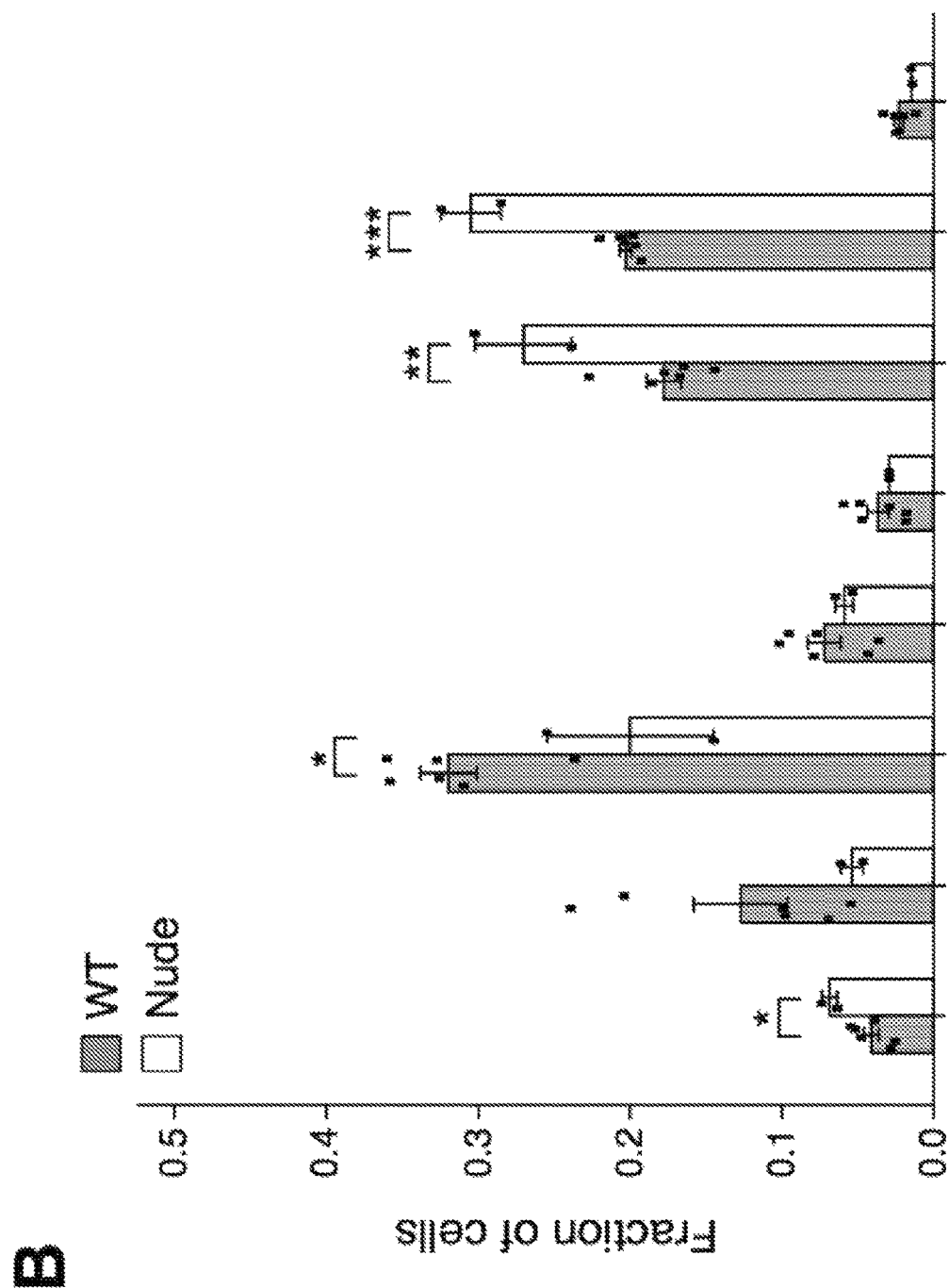
Figure 29C:
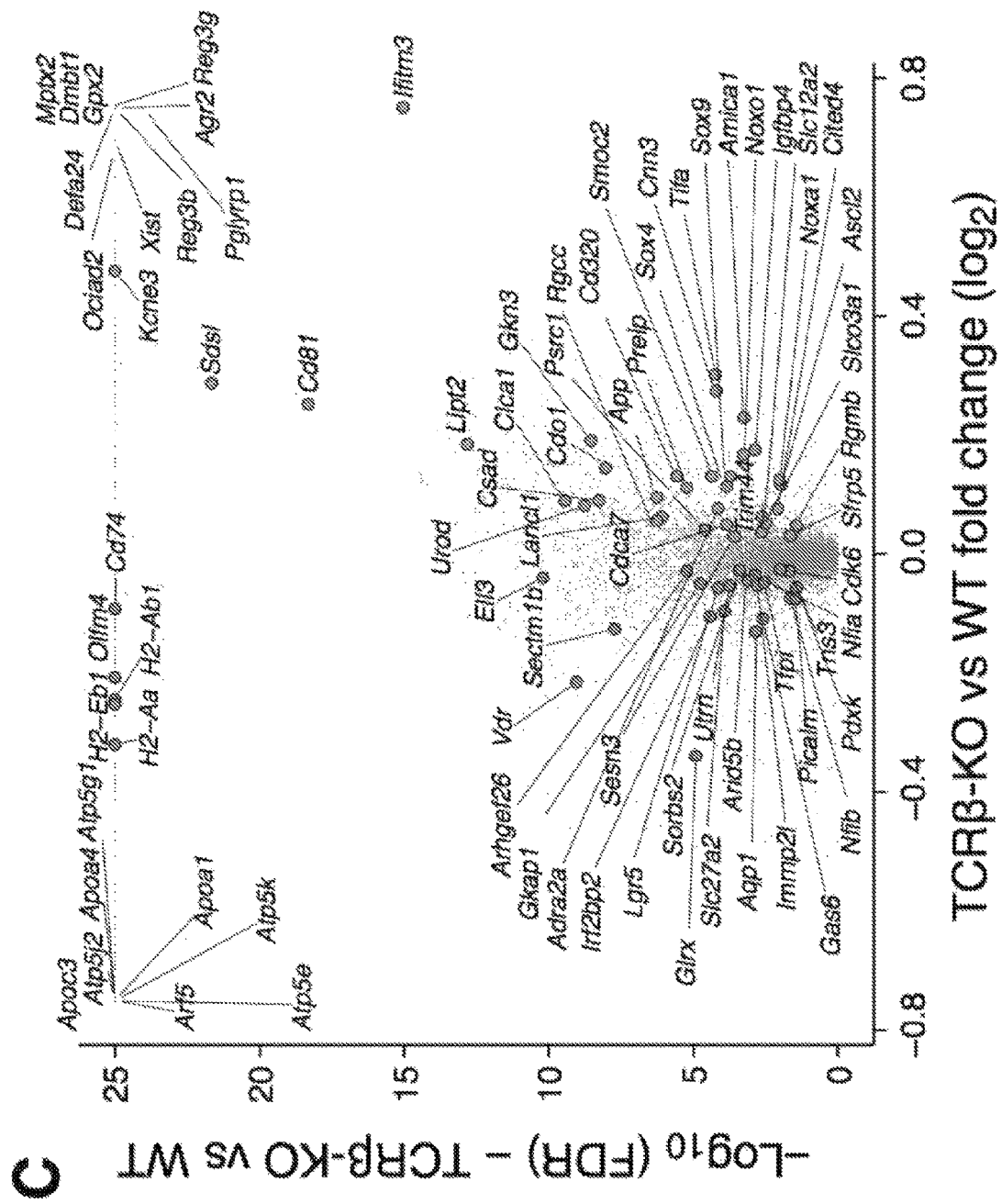
Figure 29D:
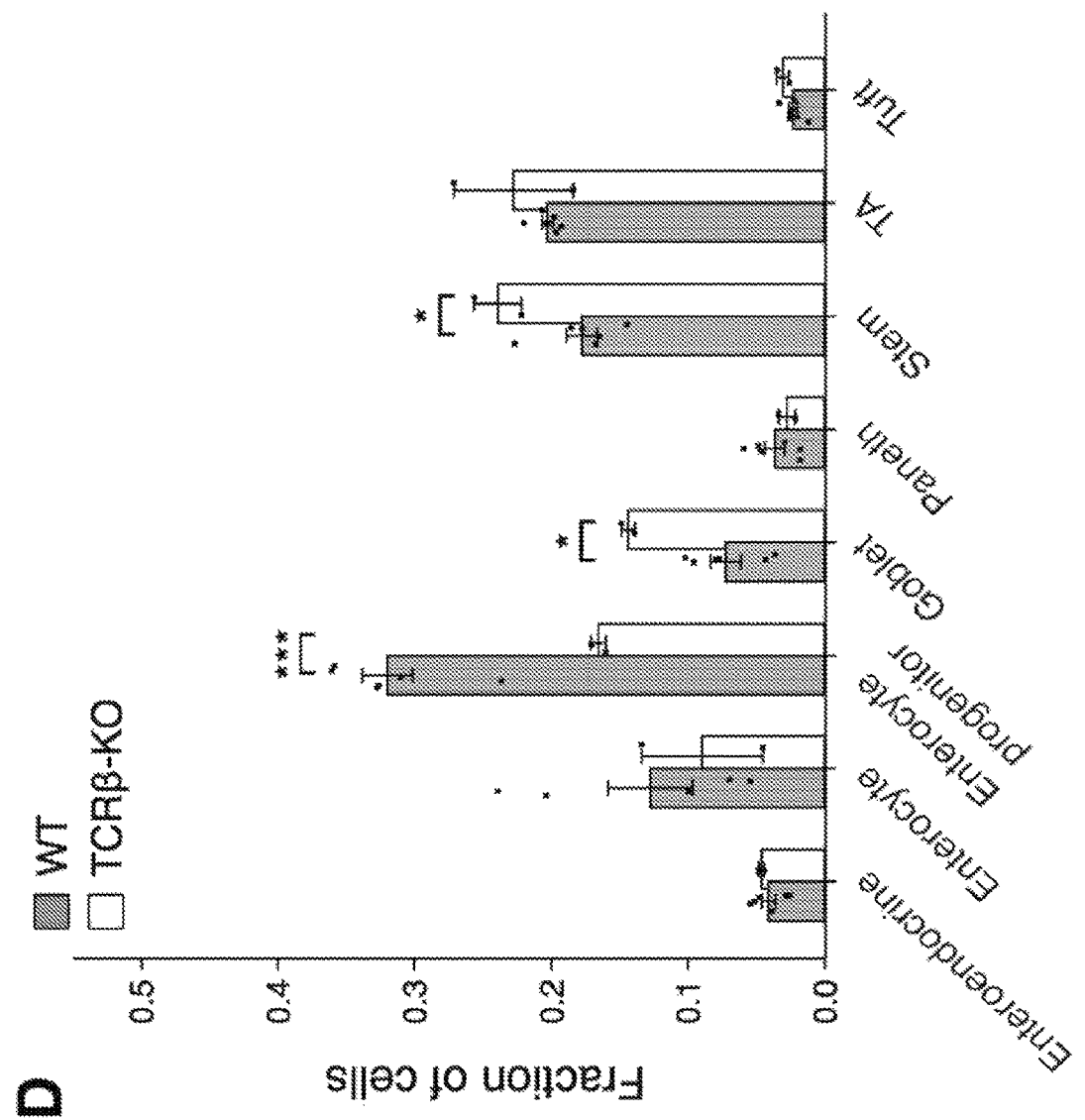
Figure 29E:
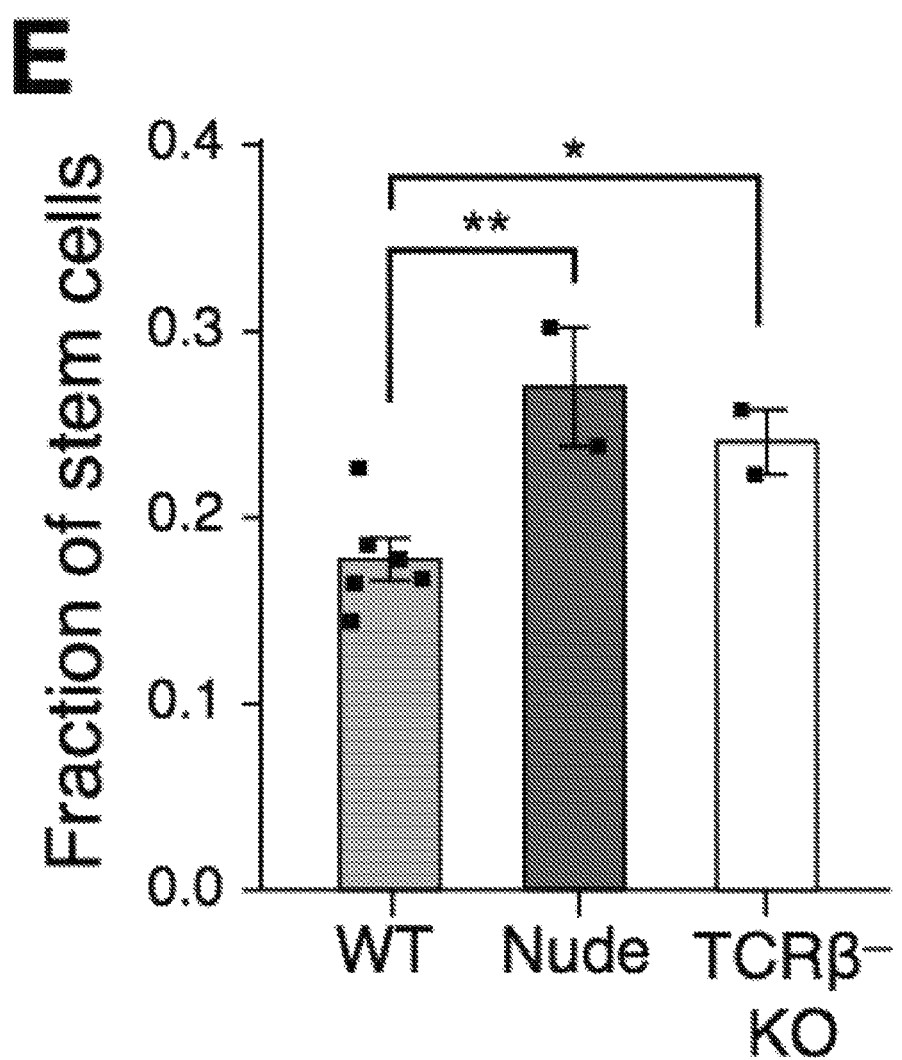
Figure 29F:
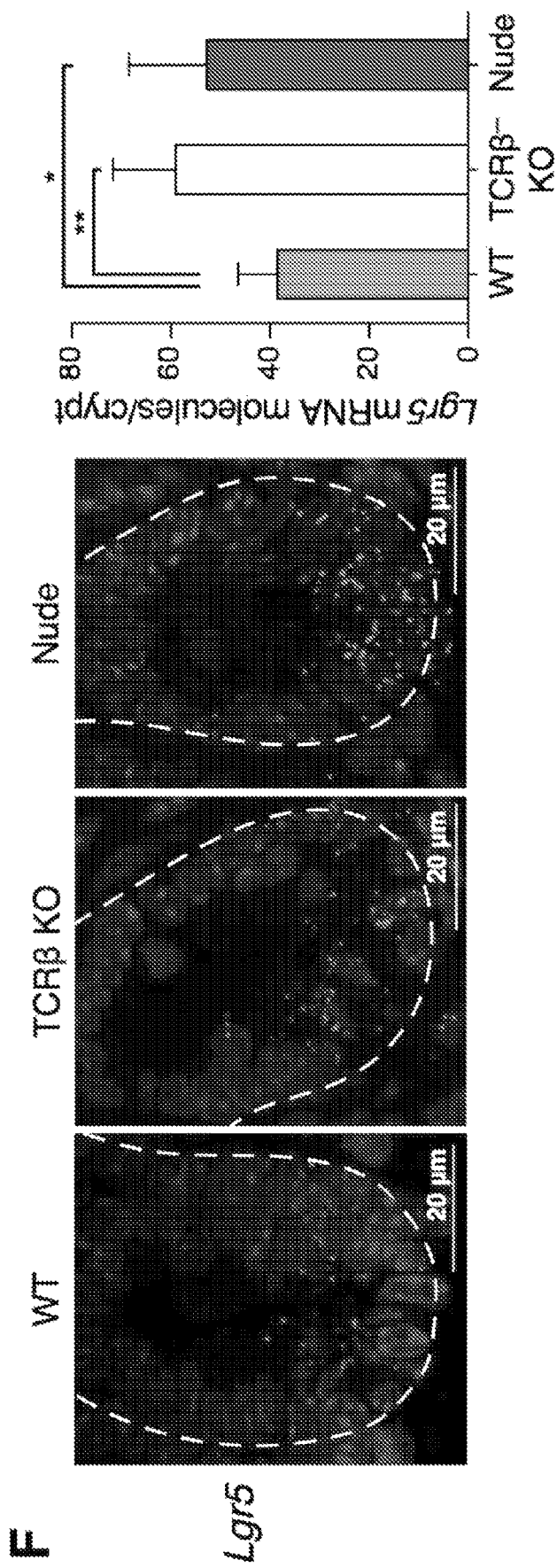

Our organoid assays predicted that Th cell subsets have distinct effects on intestinal epithelial cell differentiation. To demonstrate the relevance of the T cell-ISC interaction in vivo, Applicants first assessed two T cell-deficient mouse models. First, Applicants profiled 2,967 individual IECs isolated from athymic B6 nude mice[127] (n=2), characterized by T cell depletion. Unsupervised clustering revealed a markedly higher fraction of stem cells (52.5% increase, FDR<10$^{-3}$, likelihood-ratio test, Methods) compared to control mice (n=6, FIG. 29A,B,E). Consistently, stem cell markers were enriched (56 of 1,804 genes, $p<10^{-6}$, hypergeometric test, FIG. 29A) among genes overall up-regulated in cells of nude vs. controls (FDR<0.05, likelihood-ratio test). Similar analysis of 9,488 individual IECs profiled from TCRβ-KO mice (n=2)[128], characterized by a lack of a/P T cells, also showed a significant expansion of the ISC pool (35.0% increase, FDR<0.05, likelihood-ratio test; FIG. 29C-E). Applicants confirmed the increased ISC numbers in situ in both T cell depleted models using Lgr5 single-molecule FISH (smFISH, FIG. 29F).

Example 18—T$_{reg}$ Cells are Essential to Maintain the ISC Niche In Vivo

Figure 30A:
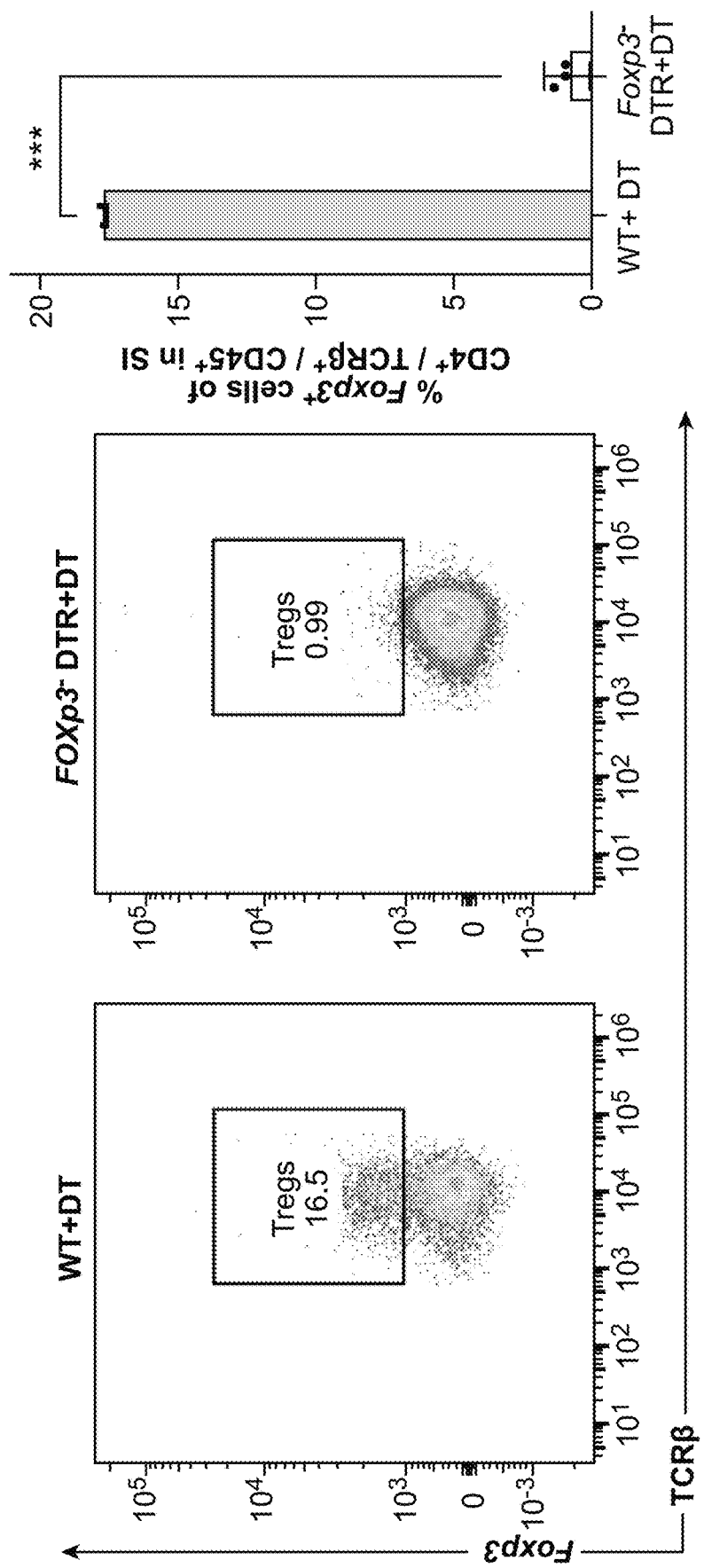
Figure 30B:
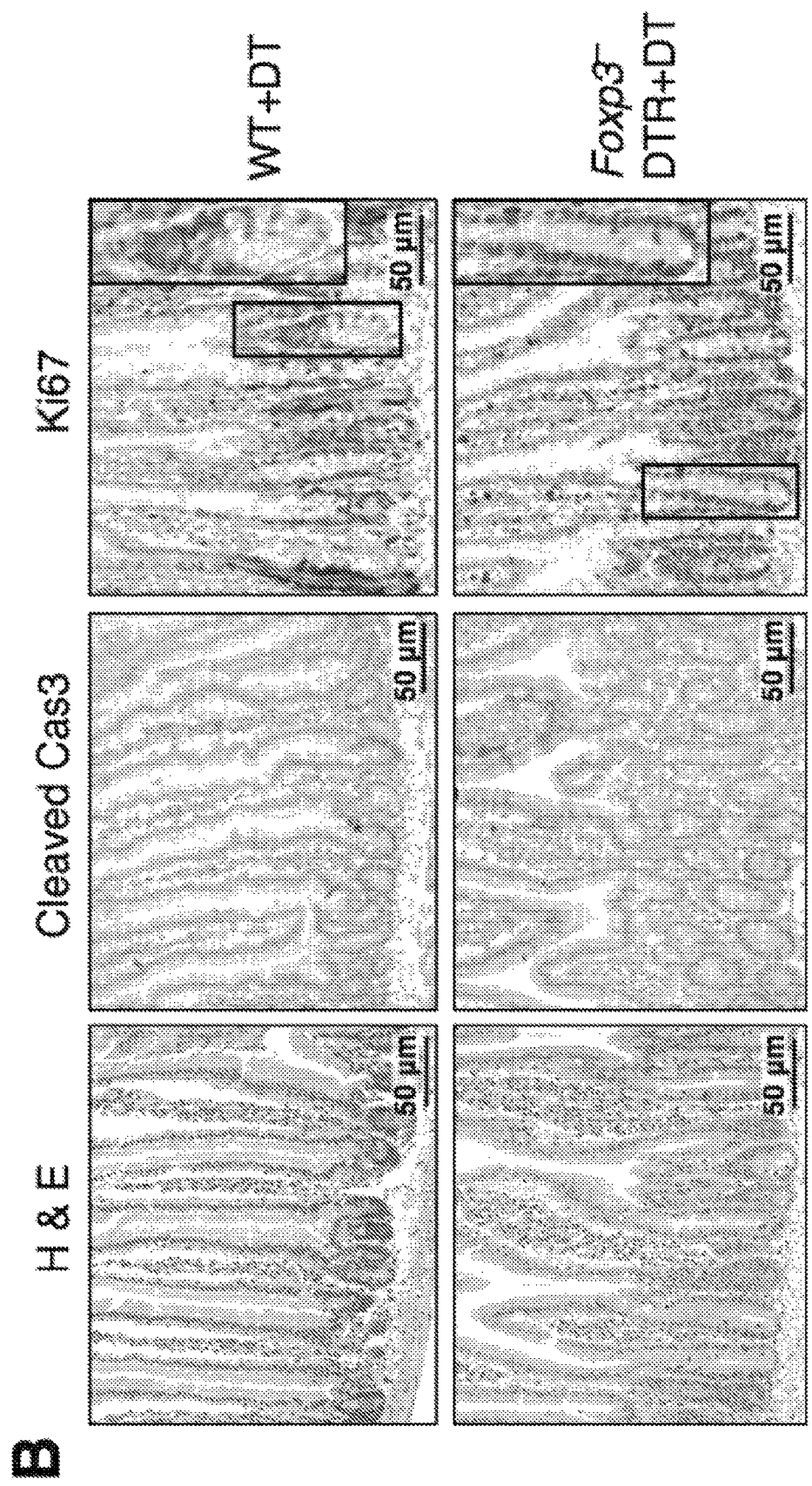
Figure 30E:
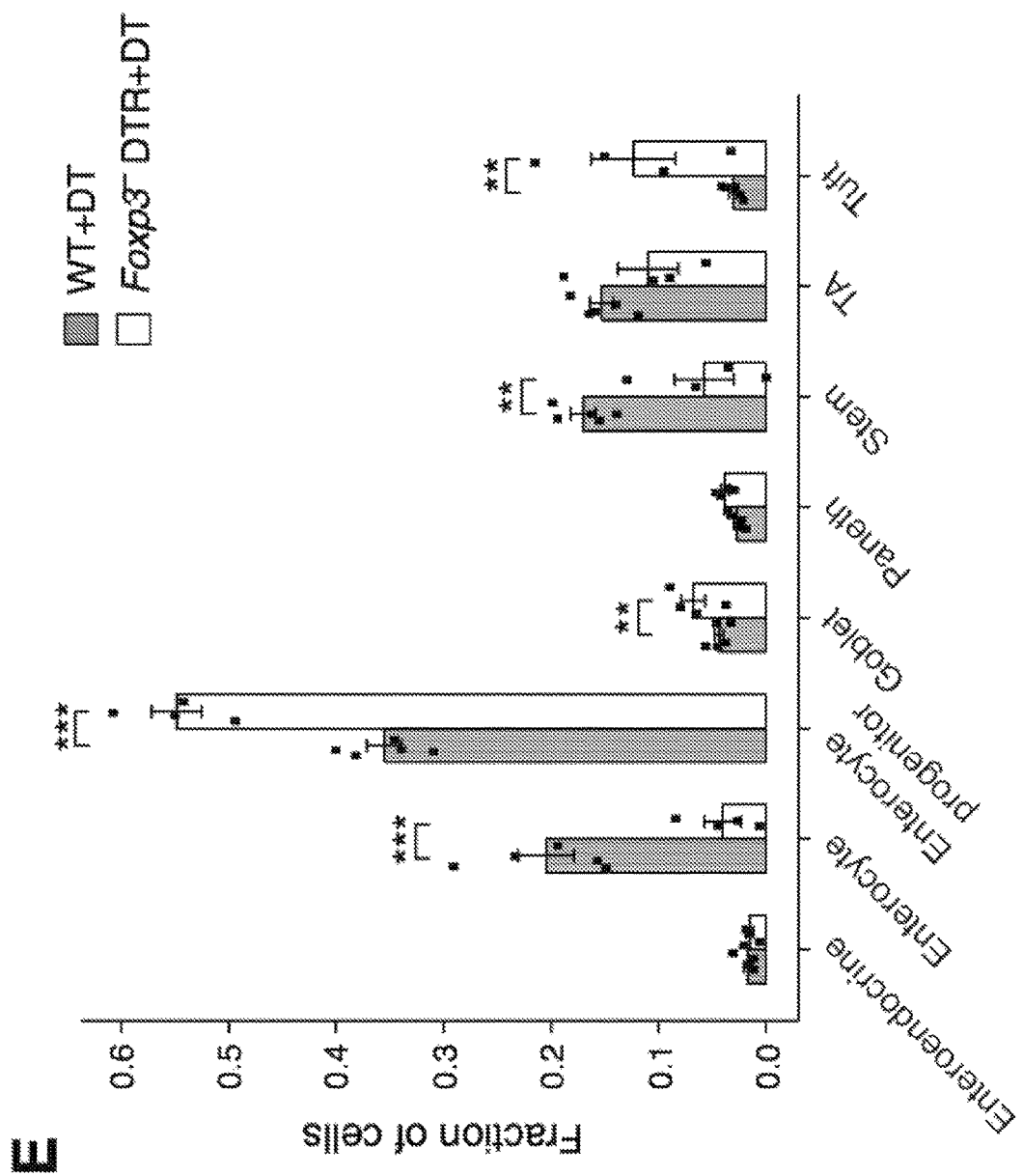

Our organoid assays also predicted that T$_{reg}$ cells promote renewal of the ISC pool. To test for this effect in vivo, Applicants used the Foxp3-DTR mouse[129], in which T$_{reg}$ cells are specifically depleted upon application of diphtheria toxin (DT). Applicants profiled 3,387 IECs from both Foxp3-DTR (n=4) and matched control mice (n=5) treated with DT for 7 days and confirmed T$_{reg}$ ablation in the lamina propria (FIG. 30A). At this time point, there was little cell death or tissue inflammation in IECs of Foxp3-DTR vs. control mice (FIG. 30B), suggesting that the longer term effects of T$_{reg}$ depletion are not yet apparent[129]. However, consistent with our hypothesis, there was a substantial reduction (66.3% decrease, FDR<0.005, likelihood-ratio test) in ISC numbers in the epithelia of the Foxp3-DTR mice, as assessed by unsupervised clustering (FIG. 20E), the fraction of cells in which Lgr5 mRNA was detected ($p<0.005$, likelihood-ratio test, FIG. 30C), and smFISH (FIG. 20F). Consistently, stem cell marker genes were overrepresented among those down-regulated across all cells in T$_{reg}$-depleted mice ($p<0.005$, hypergeometric test, FIG. 30D). There was also a substantial depletion of mature enterocytes (0.8-fold decrease, FDR<10$^{-5}$), and expansion of tuft cells (4.1-fold increase, FDR<0.005) (FIG. 30E), which Applicants confirmed by IFA staining (FIG. 30F). Applicants did not observe significant changes in the expression of Notch signaling pathway components ($p=1$), or Notch targets[130] ($p=0.31$, hypergeometric test), which a recent study implicated in regulation of hair follicle stem cells by T$_{regs}$[154].

All cell types in the Foxp3-DTR mice, including ISCs, showed strongly elevated expression of MHCII genes ($p<5\times10^{-4}$, likelihood-ratio test, FIG. 4G). Amongst stem cells, there was an increase in proliferation, as indicated by both the distribution of cell-cycle signature scores and mKi67 staining (p<0.005, likelihood-ratio test, FIG. 4F and FIG. 10B). Furthermore, and also consistent with our predictions, ISCs from $T_{reg}$-ablated Foxp3-DTR mice had an increased proportion of MHCII positive, proliferative ISCs and a decrease in $ISC^{MHCII-}$ (ISC-I, FIG. 4D).

Example 19—Discussion

Previous studies of stem cell dynamics and differentiation processes[136,137], focused on the role of the epithelial-intrinsic or stromal niche signals using lineage tracing. Here, Applicants investigated the possibility of interactions between adaptive immune cells and ISCs. Combining scRNA-seq with homeostatic or perturbed conditions that manipulate either T helper cells, their cytokines, or MHCII expression by epithelial cells allowed Applicants to assay comprehensive "snapshots" of ISC abundance and the fate of their progeny, followed by in silico inference of cell states and differentiation. In unperturbed mice, the expression of MHCII is high yet variable across ISCs, such that both ISC-II and III ($ISC^{MHCII+}$) express high levels of the MHCII molecules, whereas ISC-I ($ISC^{MHCII-}$) do not. Using controlled manipulation experiments in organoids and mice followed by scRNA-seq, Applicants established a crosstalk between Th cells and ISCs.

In particular, the in vitro and in vivo results support a model in which Th cells interact with ISCs via MHCII molecules, impacting the ISC pool and resultant differentiation pathways through their key cytokines (FIG. 20I). In this model, $T_{reg}$ cells, which are enriched in the small intestine, maintain the ISC niche. They may be elevated after a strong inflammatory response[135] to serve as a feedback effectors in order to replenish and maintain stem cell numbers. Conversely, Th1 and Th2 cells or their signature cytokines both reduce ISC numbers, and bias IEC differentiation toward specific epithelial cell-types, perhaps in order to respond to either bacterial (Th1 cells, Paneth cell increase) or parasitic (Th2 cells, tuft cell increase) insults. Th17 cells, which are highly enriched in the small intestine[134], reduce the number of ISCs, which may reflect a shift in the balance between stem cell renewal and differentiation. In this way, epithelial and immune response could be integrated to titrate responses to dense luminal flora, avoiding continuous inflammation, while reacting to pathogens: first, the intestinal stem cells utilize the equilibrium of pro-inflammatory and anti-inflammatory signals to balance between renewal and differentiation; second, distinct Th cell subsets can boost the desired immune response by affecting renewal and differentiation processes of the gut epithelia concordantly with signals arriving from the gut lumen. If this novel role for MHCII in T cell communication with stem cells also exists in other mucosal or non-mucosal compartments, it may open the possibility of a general mechanism in which adaptive immune cells regulate parenchymal stem cells in order to maintain tissue homeostasis under normal and pathological conditions.

Example 20—Supporting Experiments

Figure 31A:
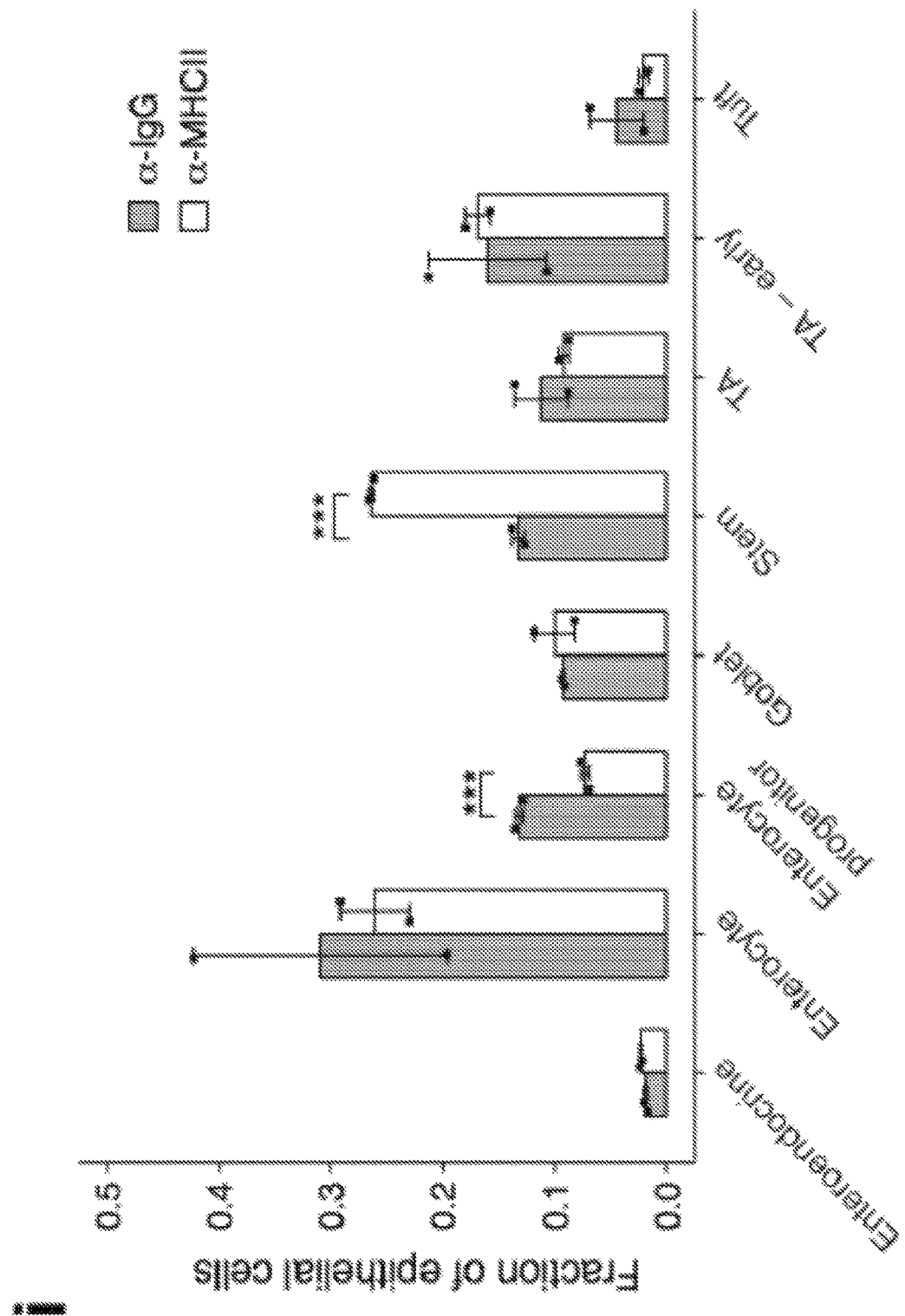
FIG. 31A-31D—FIG. 31a. MHC II blocking antibody increases ISC numbers and abolishes tuft cell hyperplasia during *H. polygyrus* infection. Frequencies (y-axis) of cells of each subtype in mice infected with *H. polygyrus* and treated with MHC II blocking antibody, relative to their proportions after treatment with a non-specific Immunoglobulin G (IgG) control (dashed line). IEC cell-types were identified by unsupervised clustering of 7,785 single cells obtained from droplet-based 3' scRNA-seq data (Methods). *$p<1\times10^{-5}$, **$p<1\times10^{-20}$ (hypergeometric test).

Applicants assessed the potential role of MHCII in the changes in ISC state and subsequent differentiation, by again infecting mice with *H. polygyrus* for 3 days, but this time concurrently treating them with either MHCII-blocking or control anti-IgG antibodies, followed by scRNA-seq and cell-type identification using clustering (FIG. 31a). Stem cells increased with MHCII-blocking antibodies.

Figure 31B:
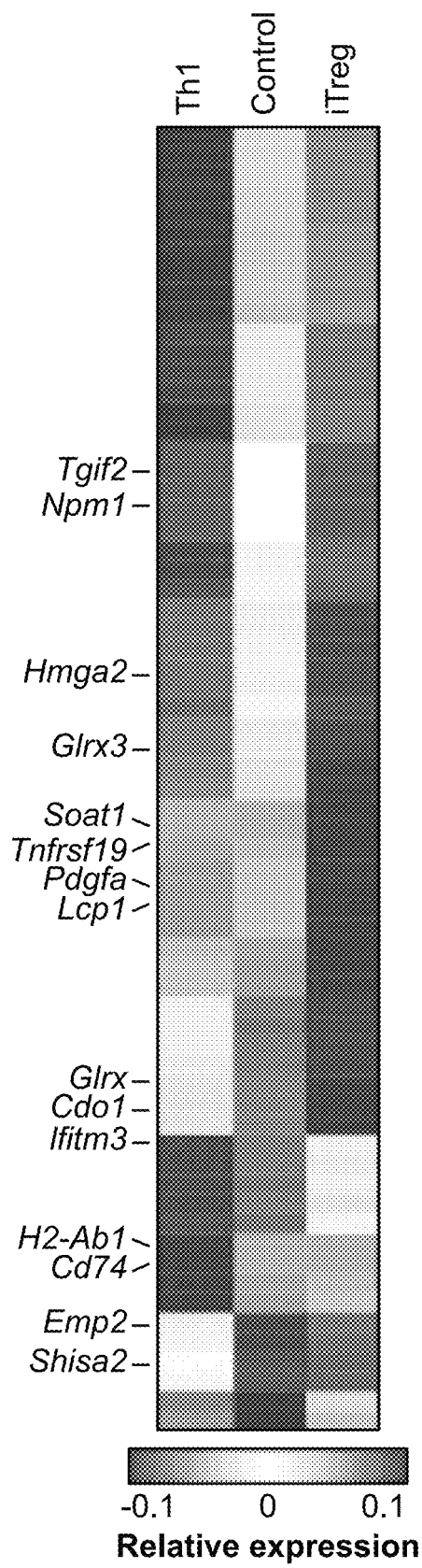

Consistently, there was an increase in the fraction of cells expressing known stem cell marker genes (FDR<0.05) in iTreg-co-cultured organoids compared to control organoids. These included Soatl, Pdgfa and Glrx (FIG. 31b), which are members of the stem cell signature. This study did not observe changes in the stemness score (Methods) of ISCs in organoids co-cultured with Th17 cells or iTregs, suggesting that the expansion in the number of cells is not accompanied by a change in their cell intrinsic programs in these cases.

Figure 31C:
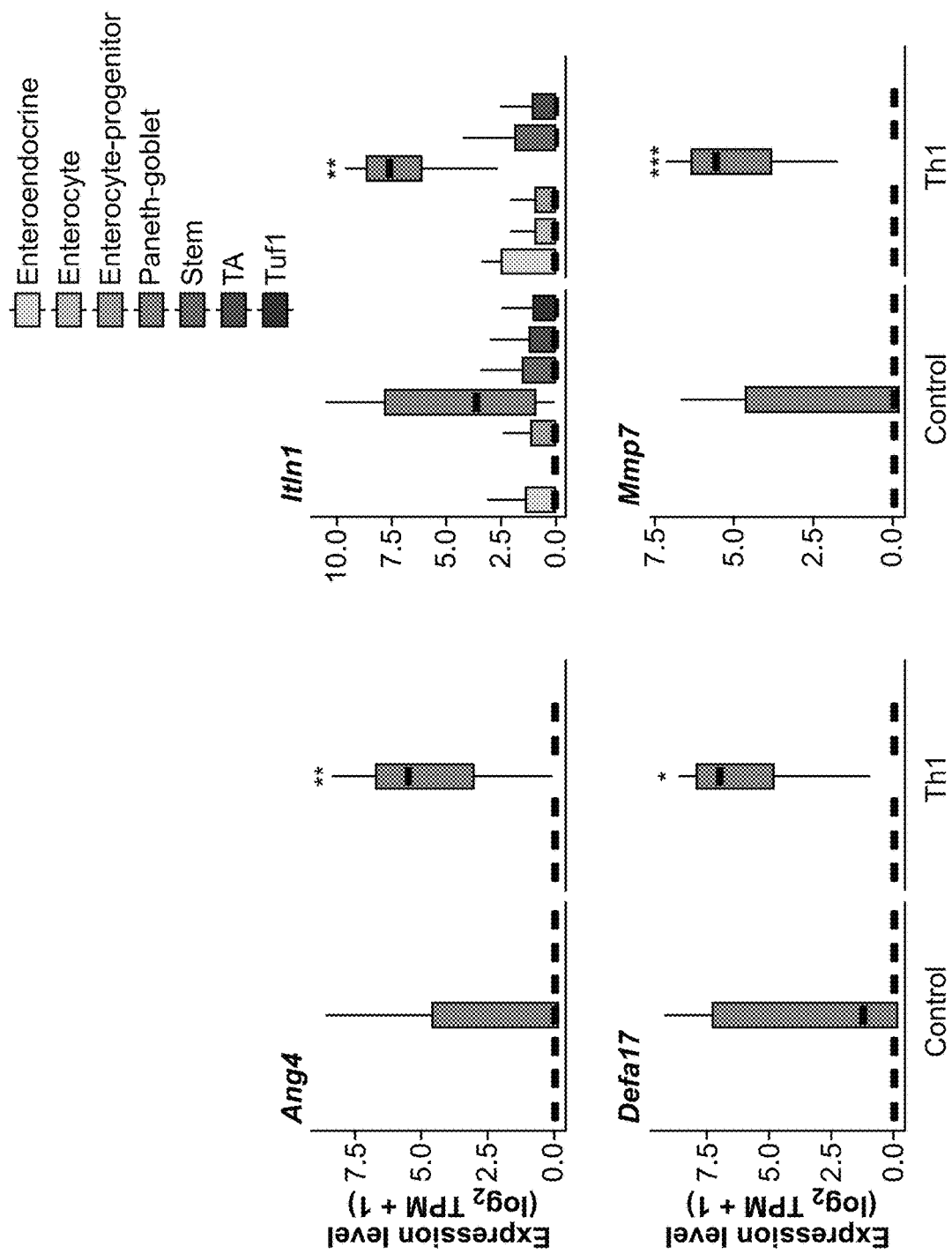
Figure 31D:
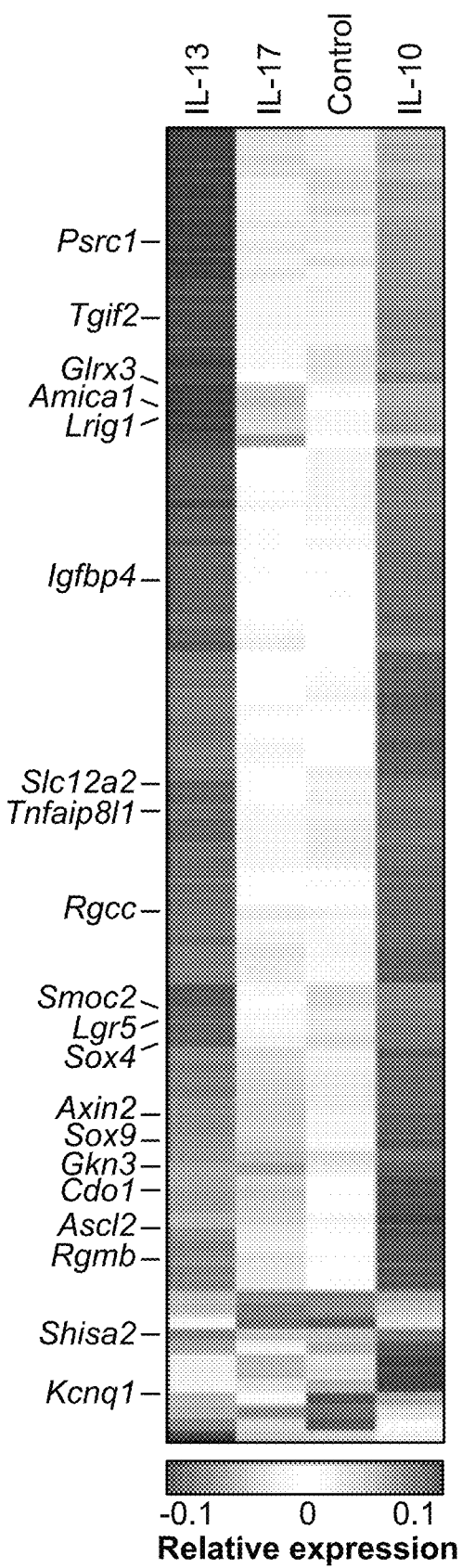
Figure 32A:
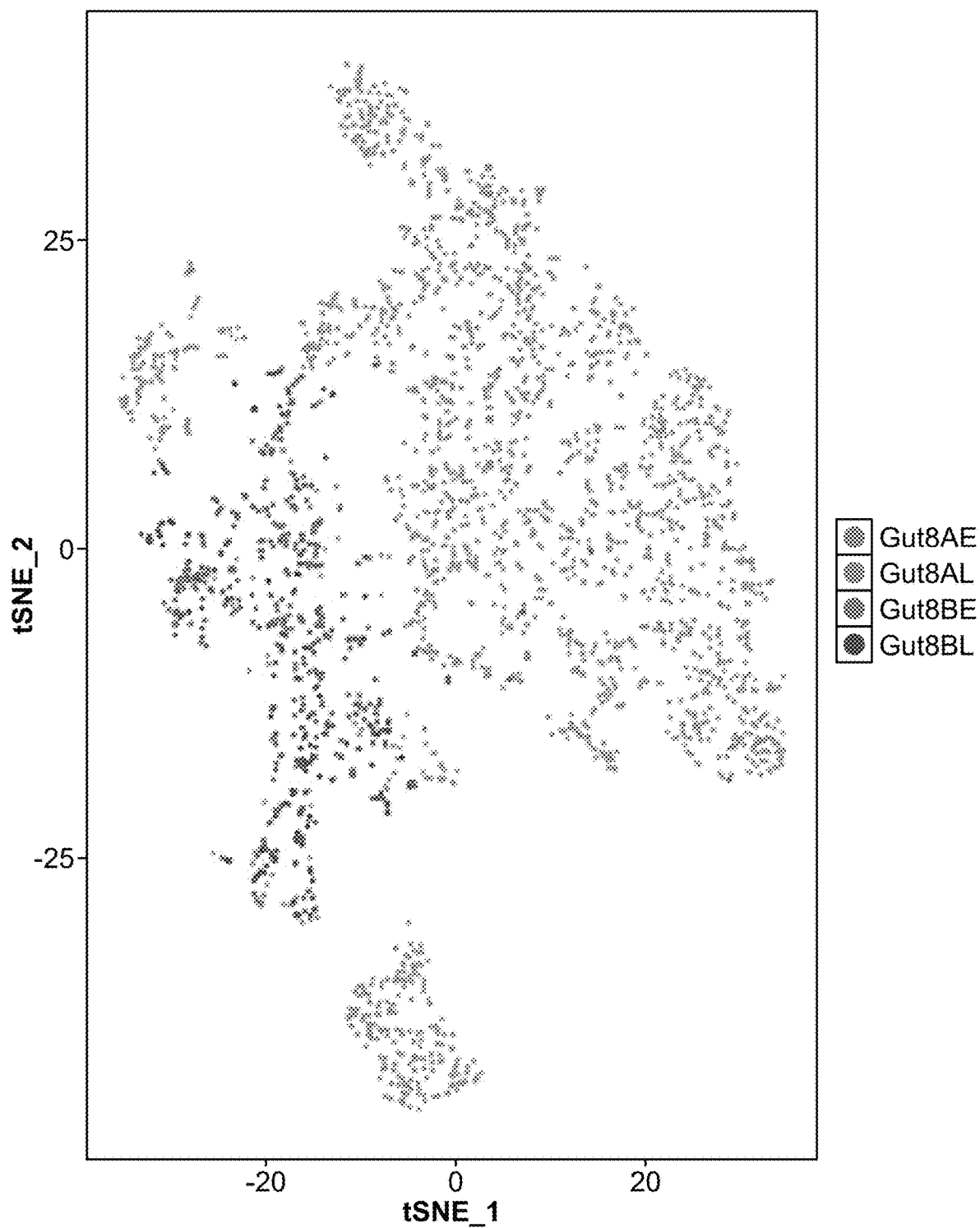
FIG. 32A-32D—Gut atlas of ulcerative colitis biopsy.
Figure 32B:
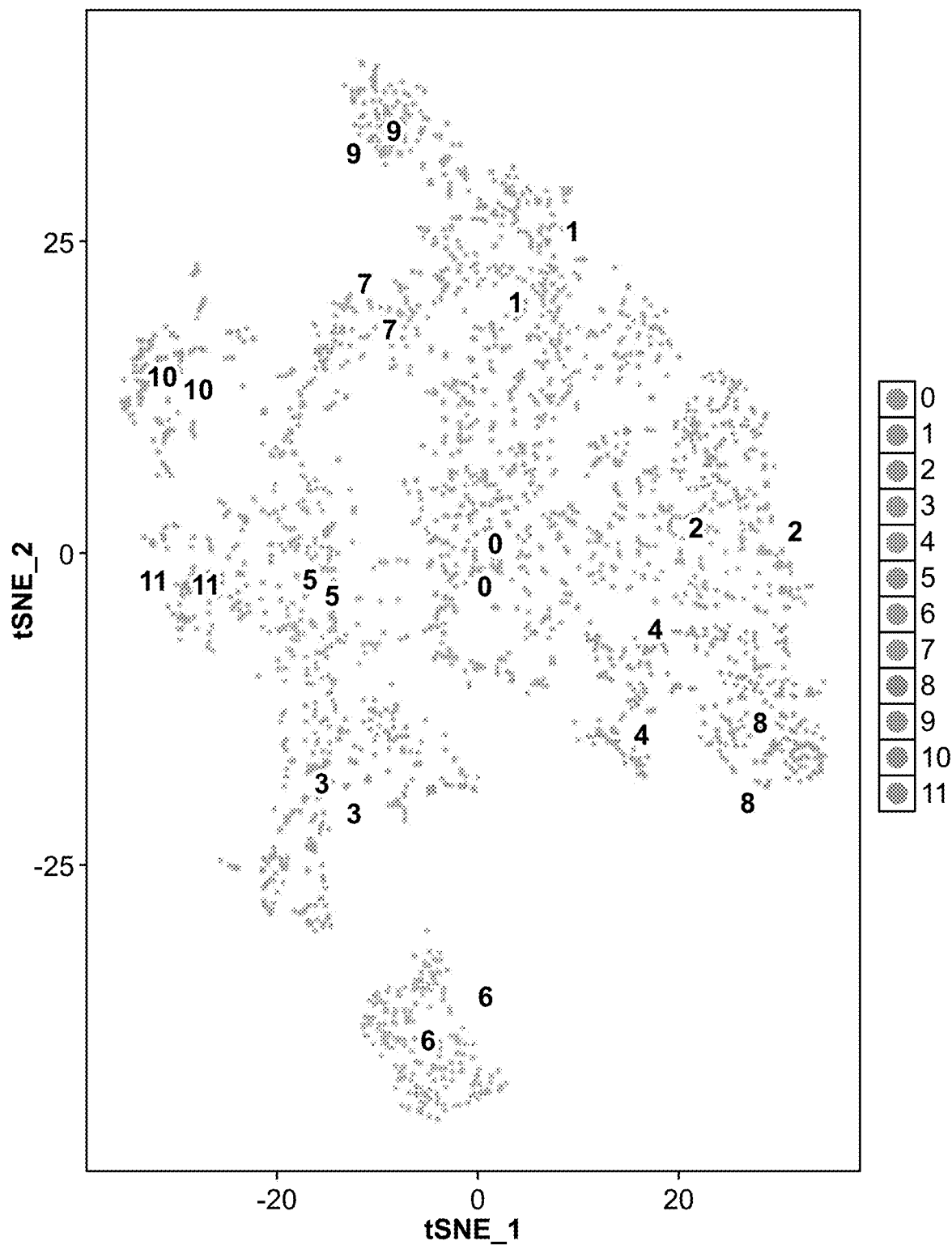
Figure 32C:
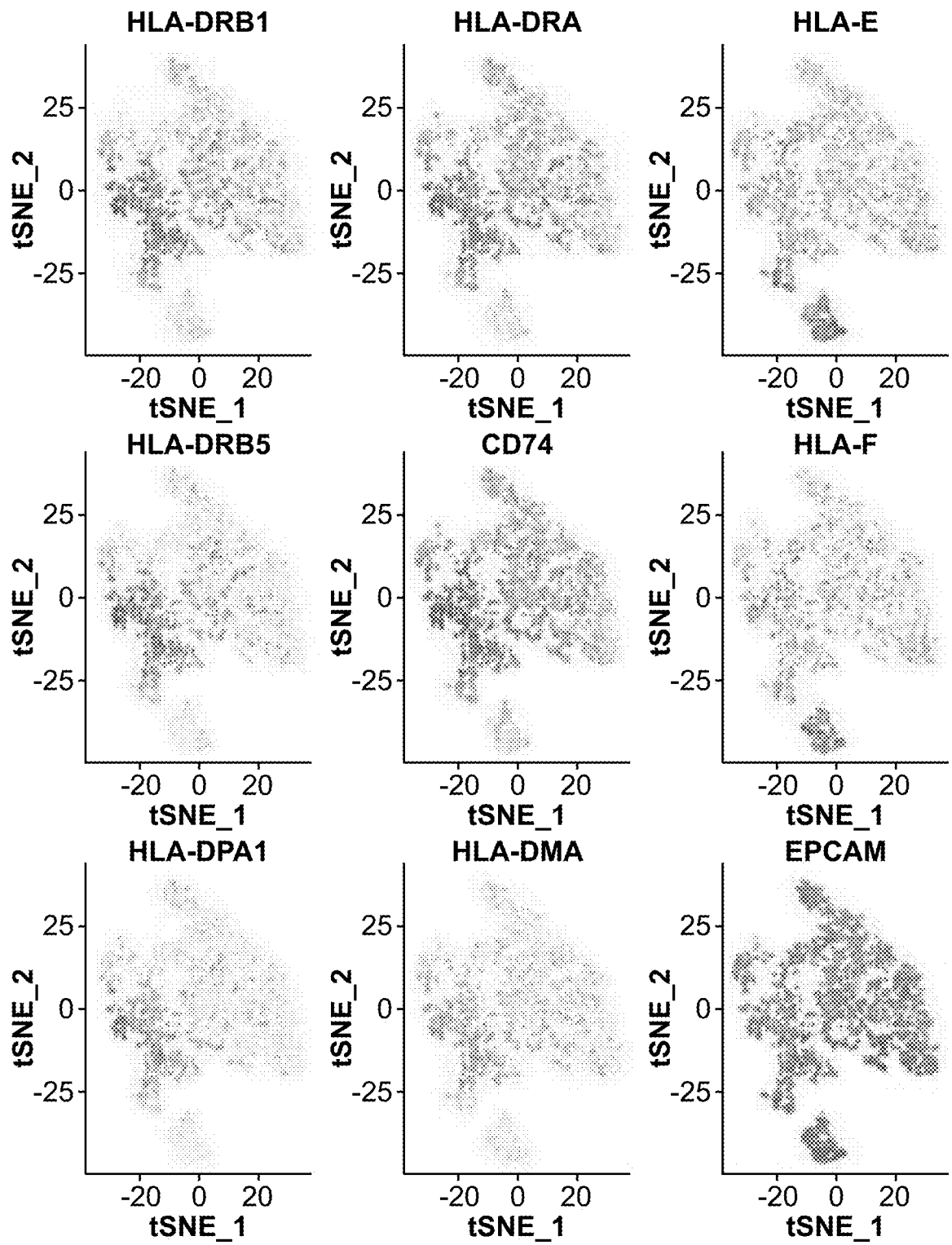
Figure 32D:
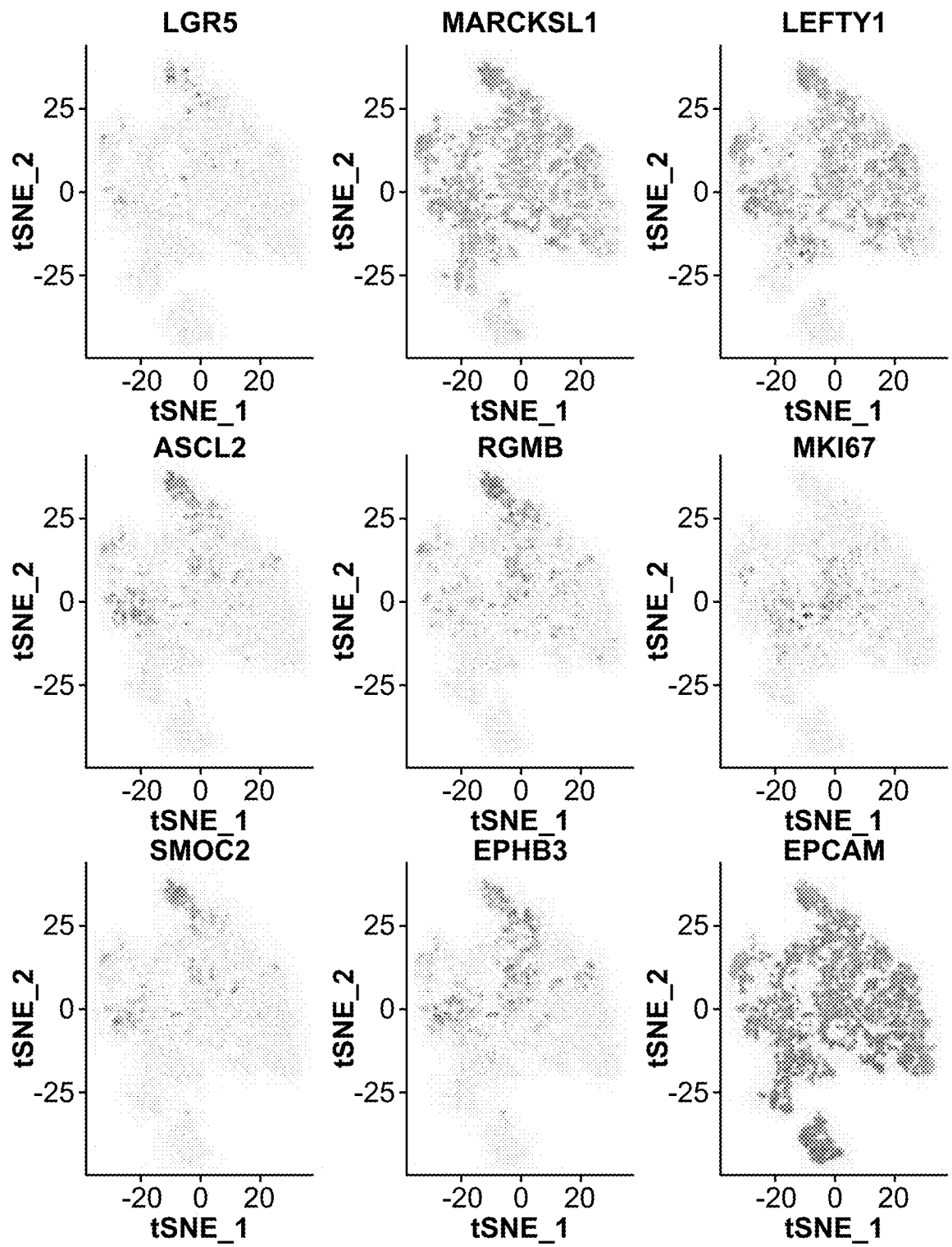
Figure 33A:
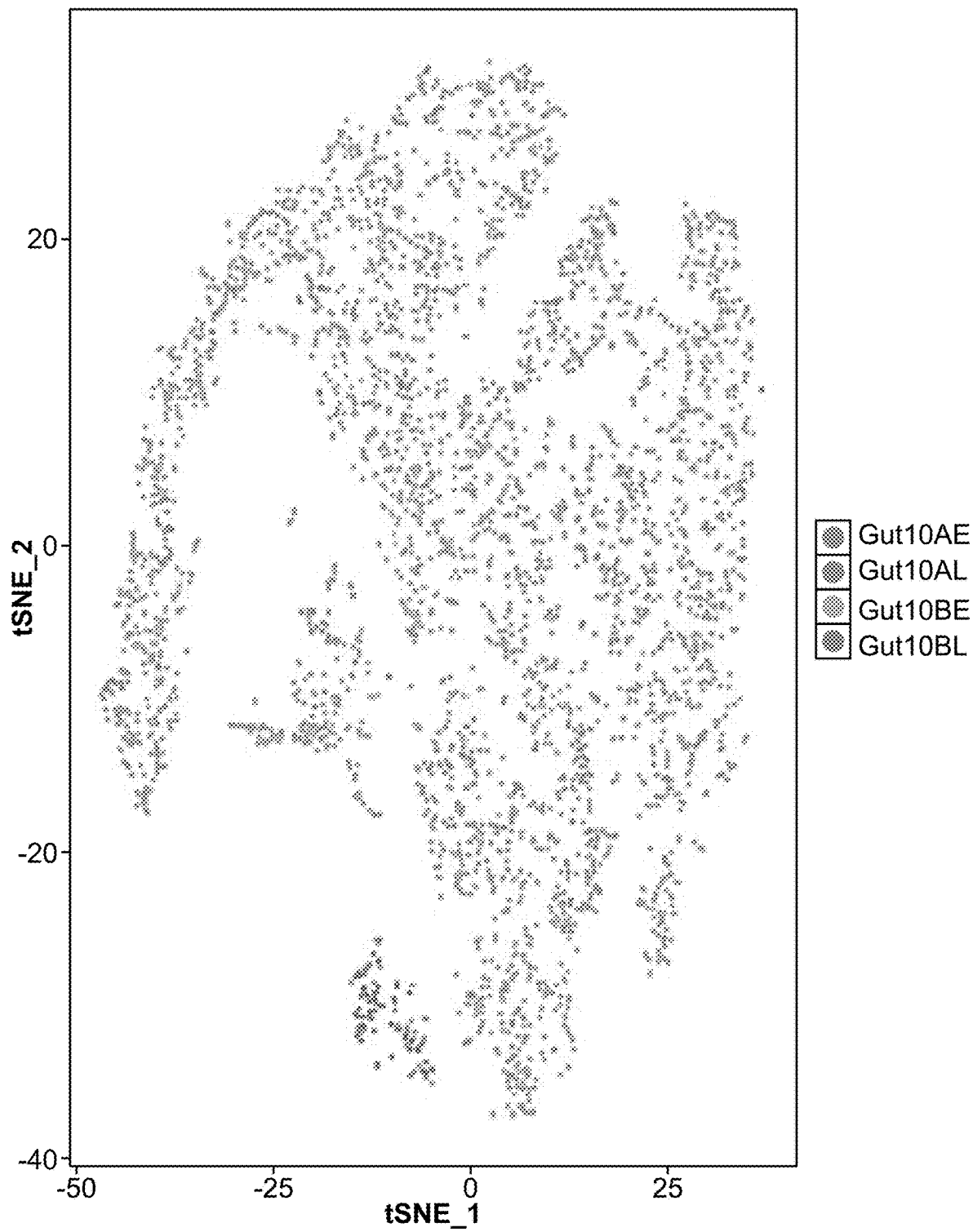
FIGS. 33A-33D—Gut atlas of normal biopsy.
Figure 33B:
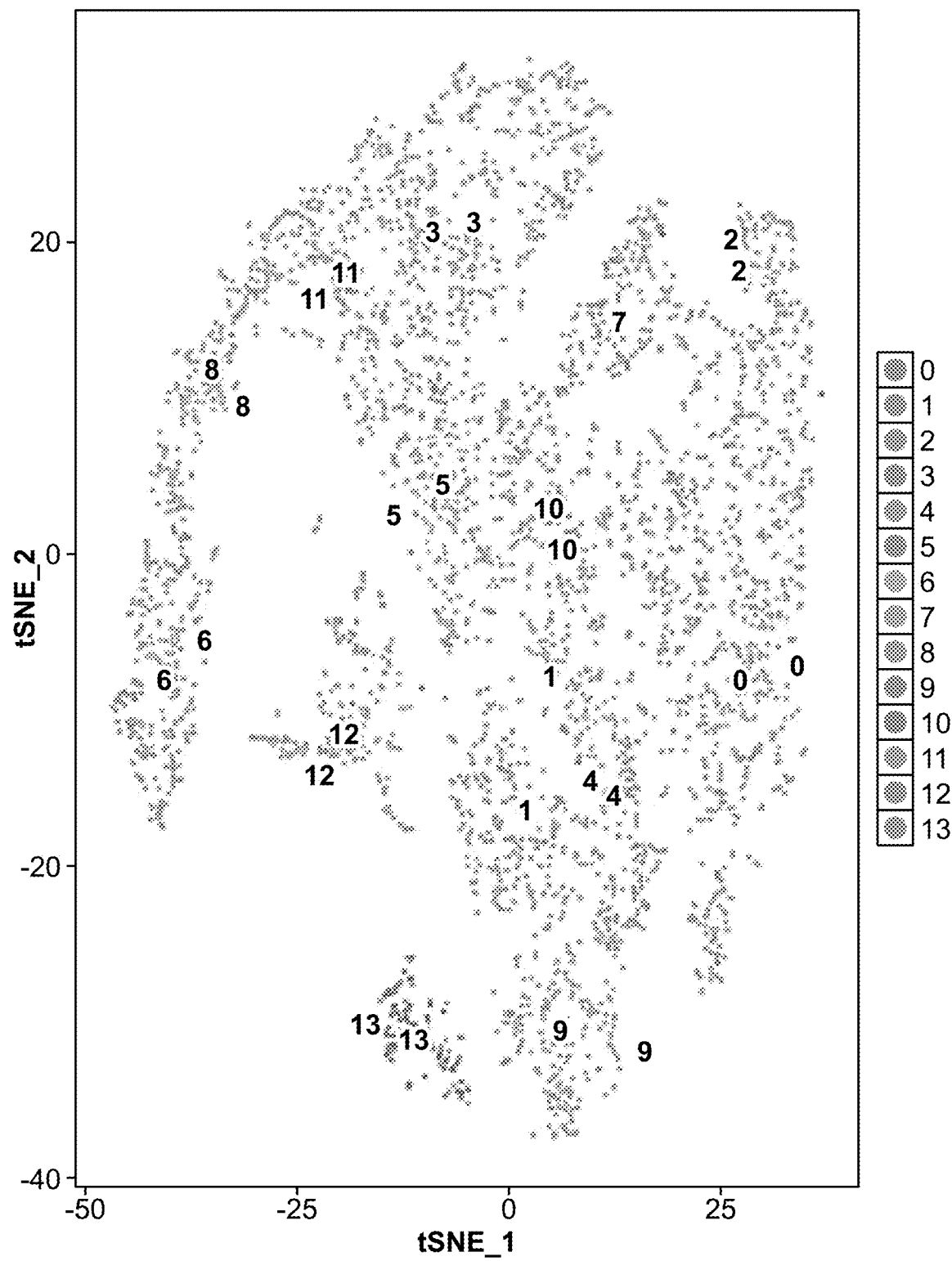
Figure 33C:
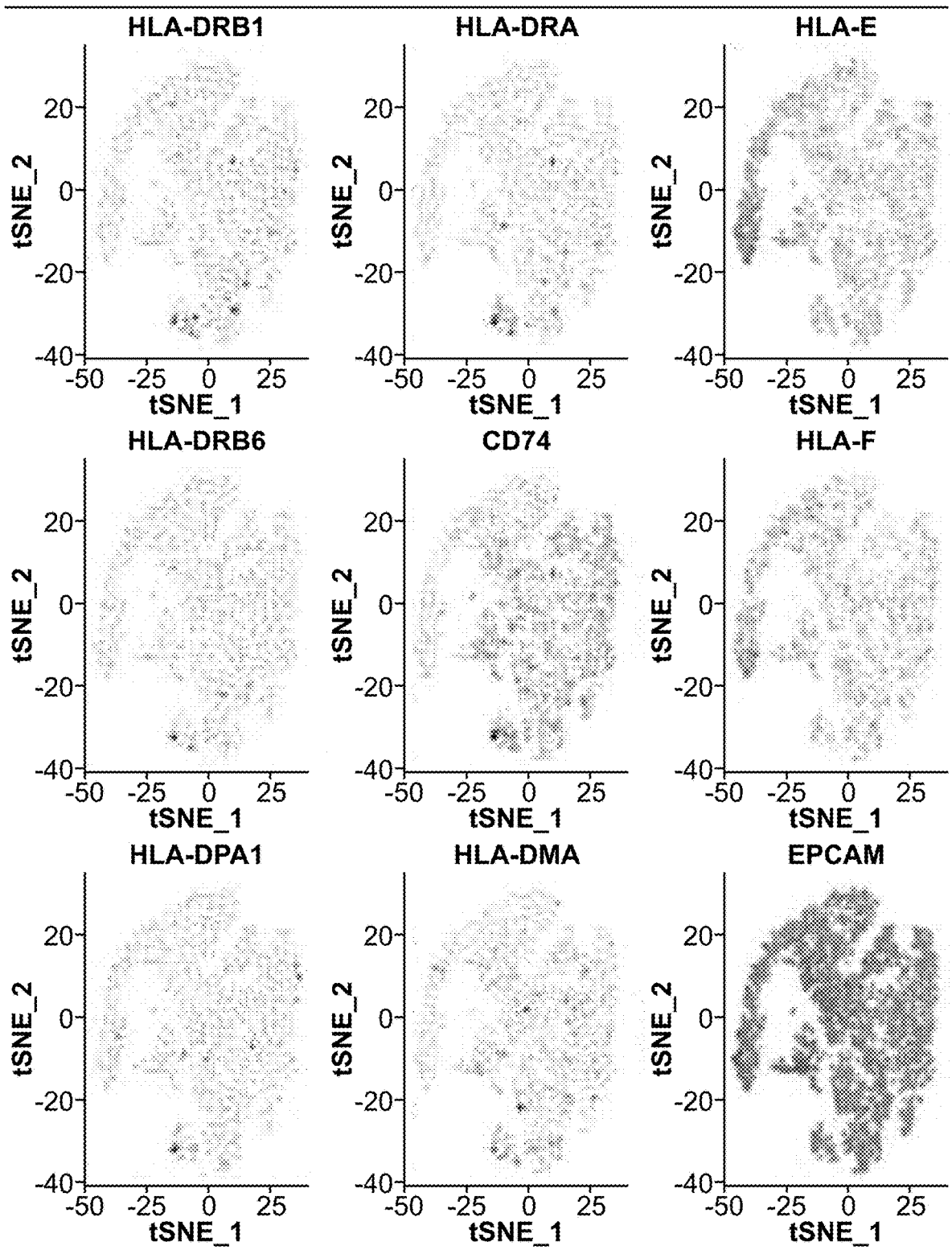
Figure 33D:
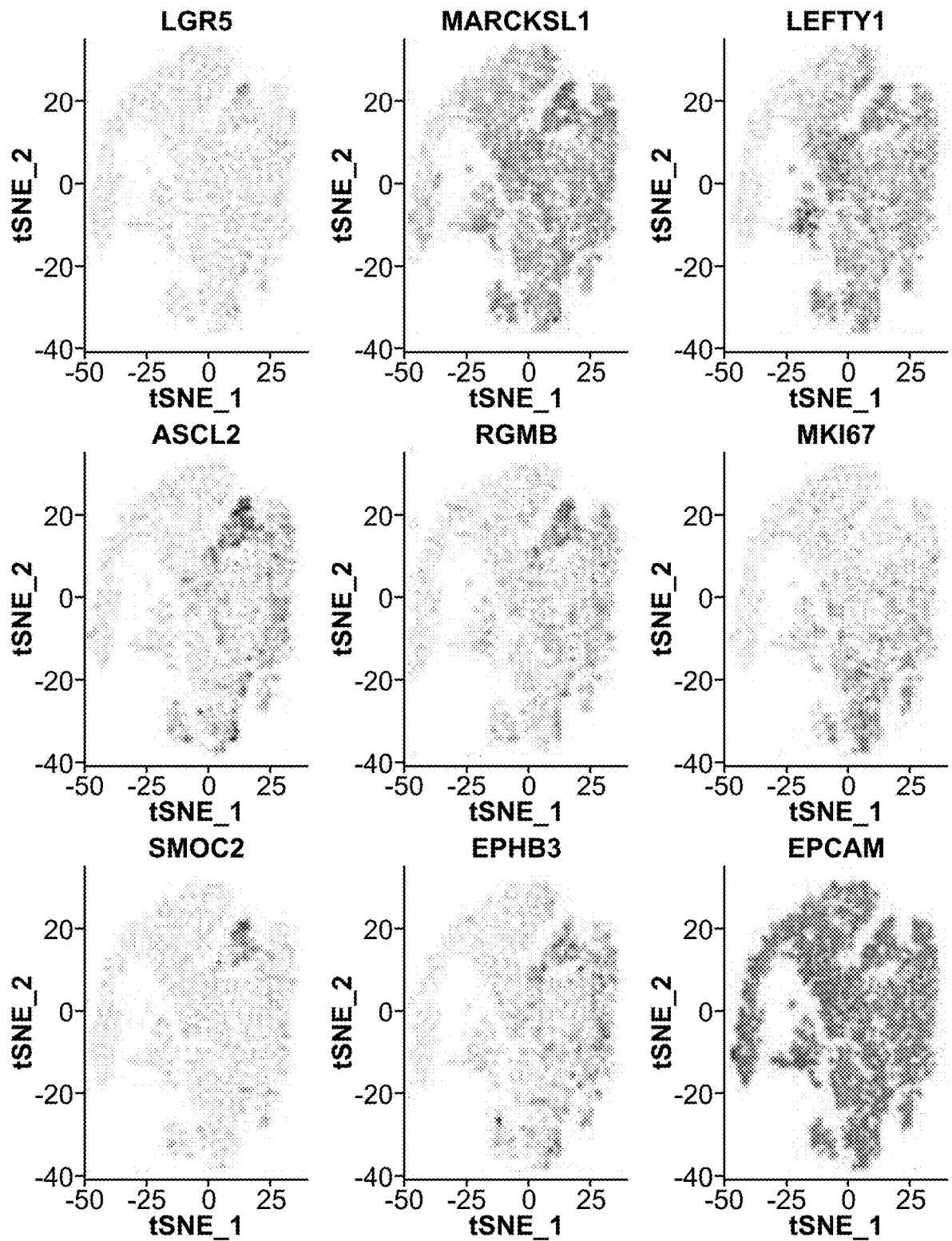
Figure 34A:
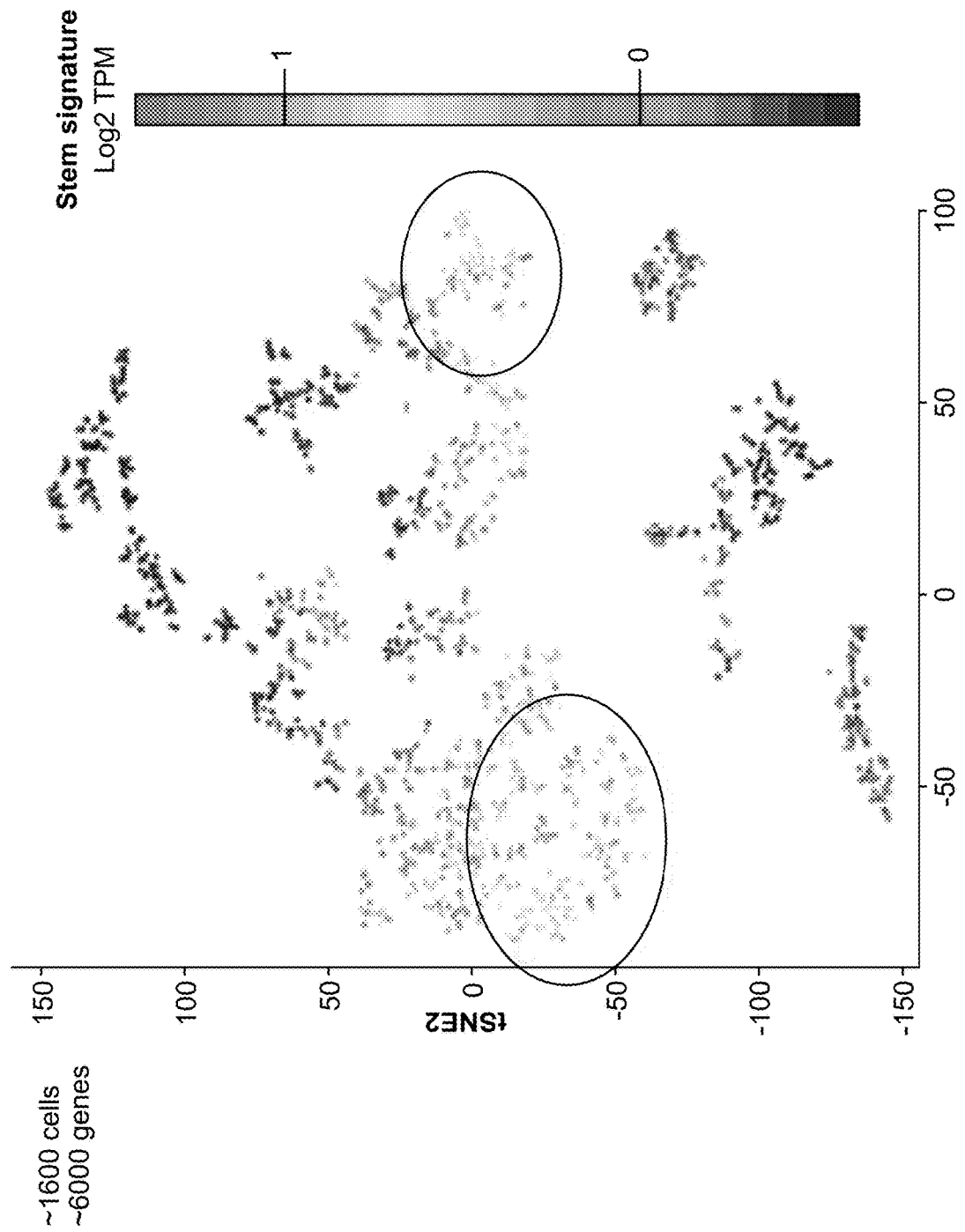
FIG. 34A-34D—Single cell sequencing of small intestinal epithelium.
Figure 34B:
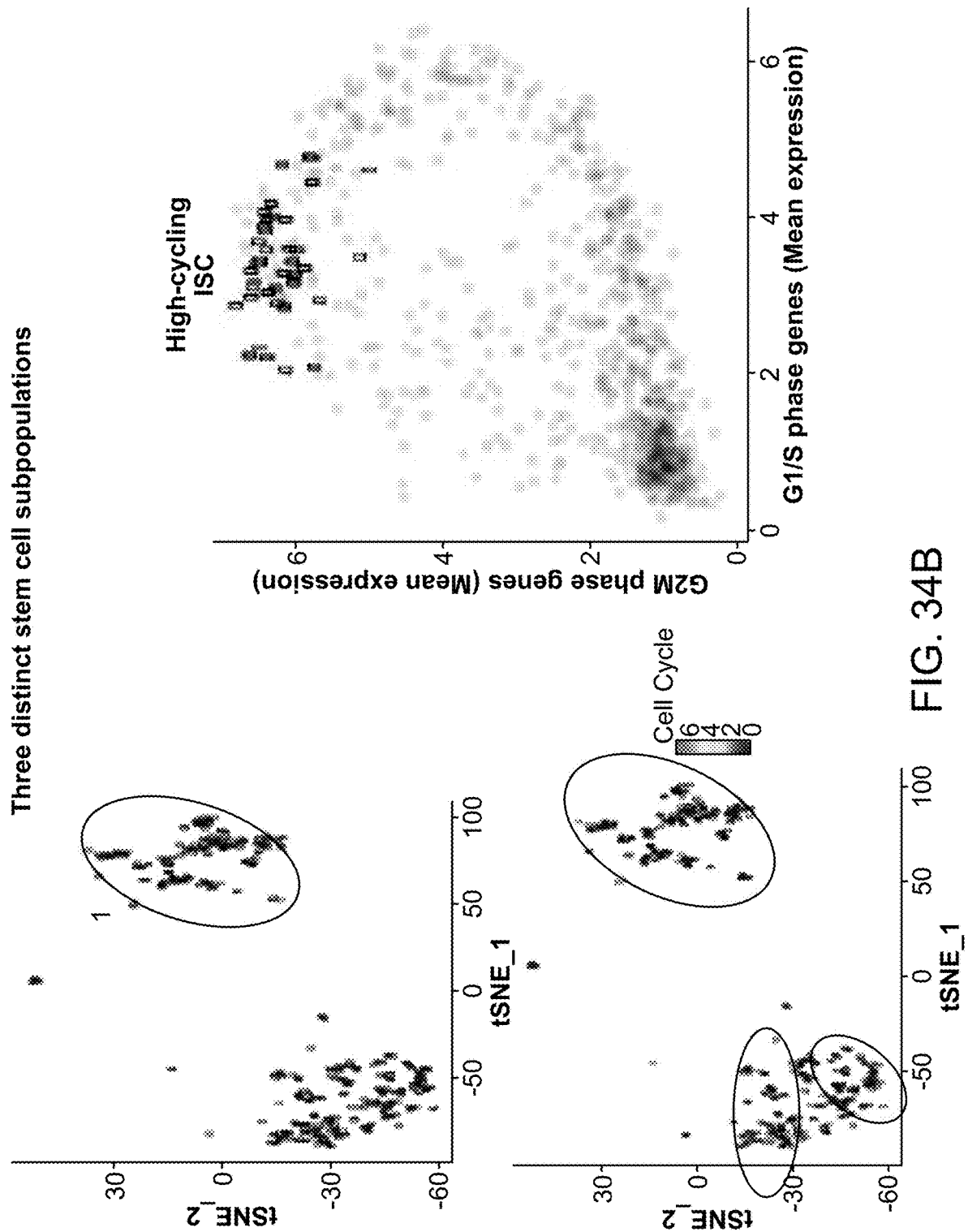
Figure 34C:
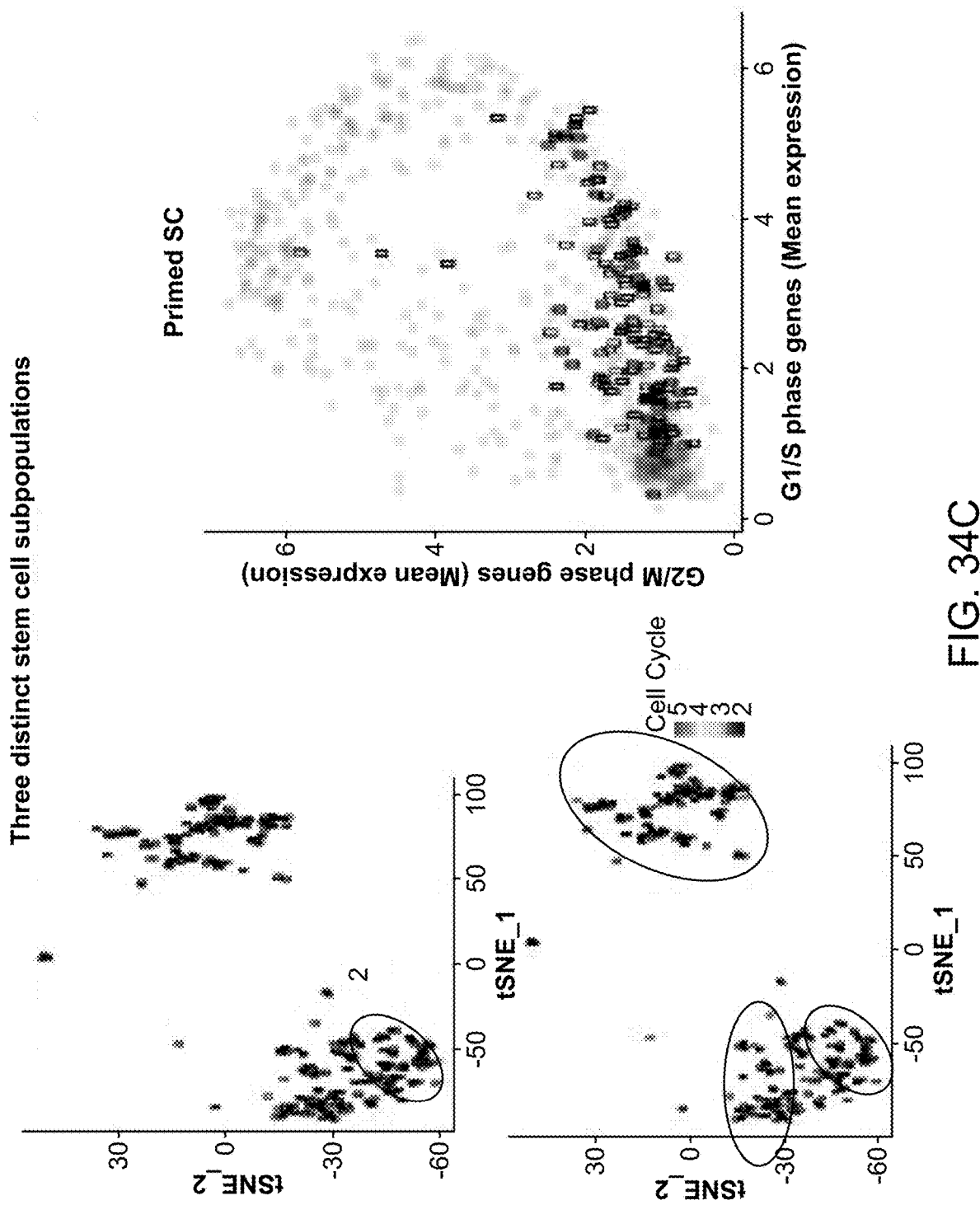
Figure 34D:
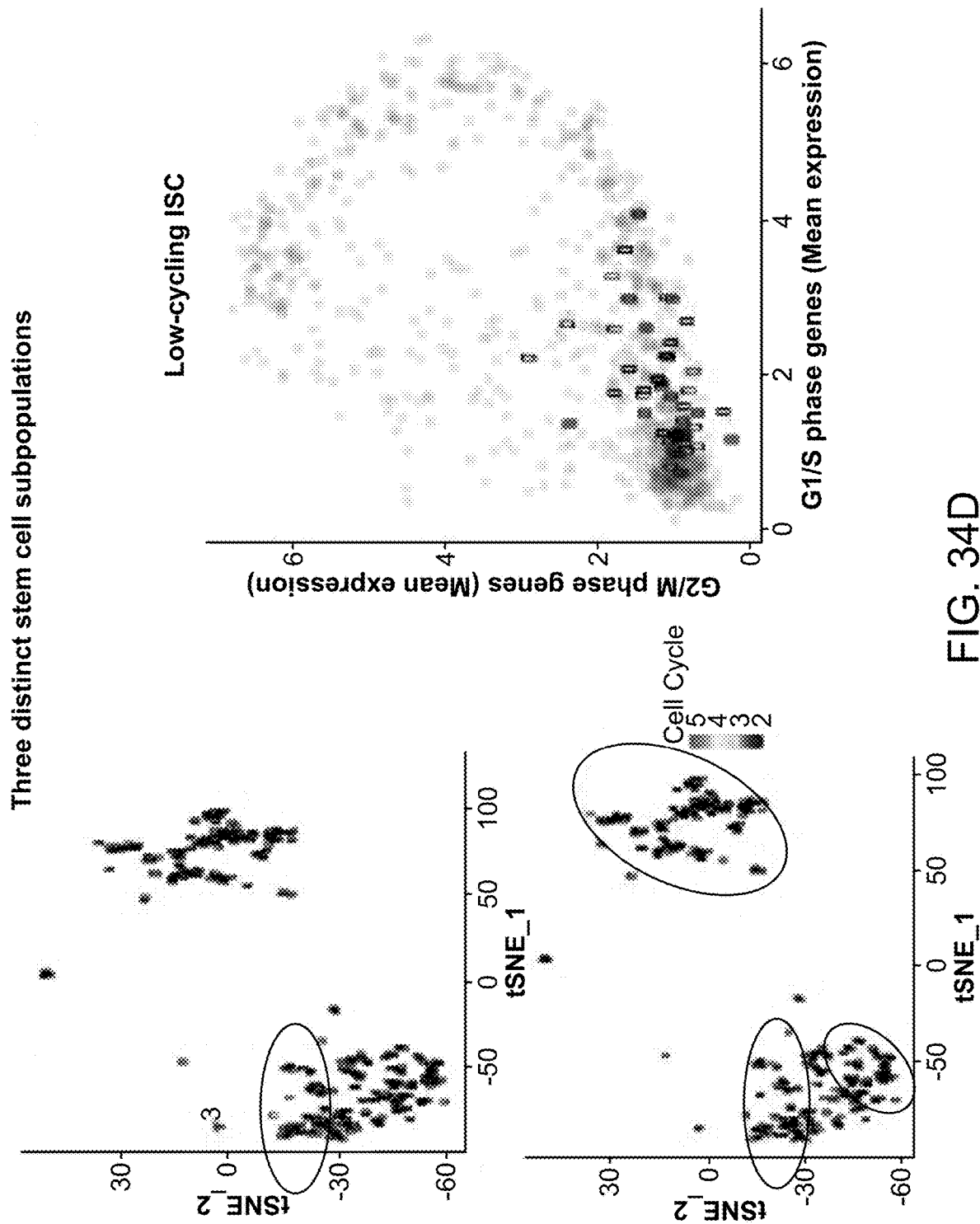
Figure 35:
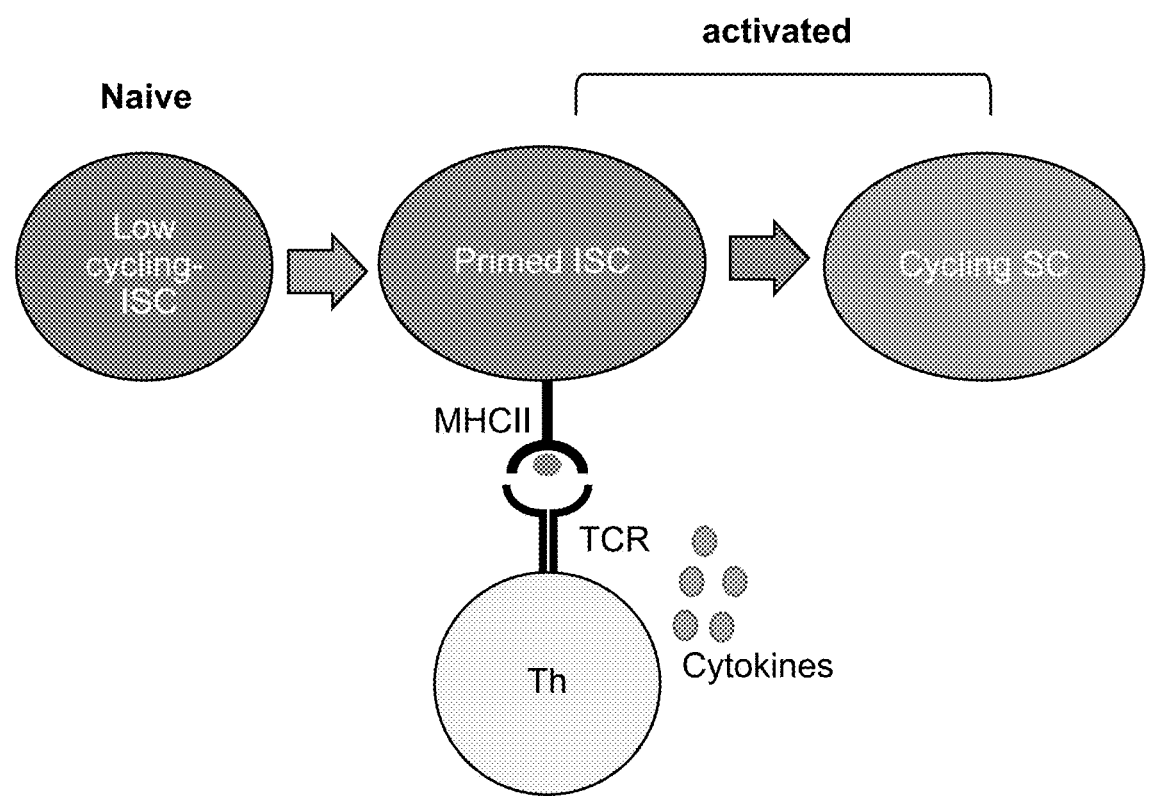
FIG. 35—Intestinal stem cell differentiation.
Figure 36A:
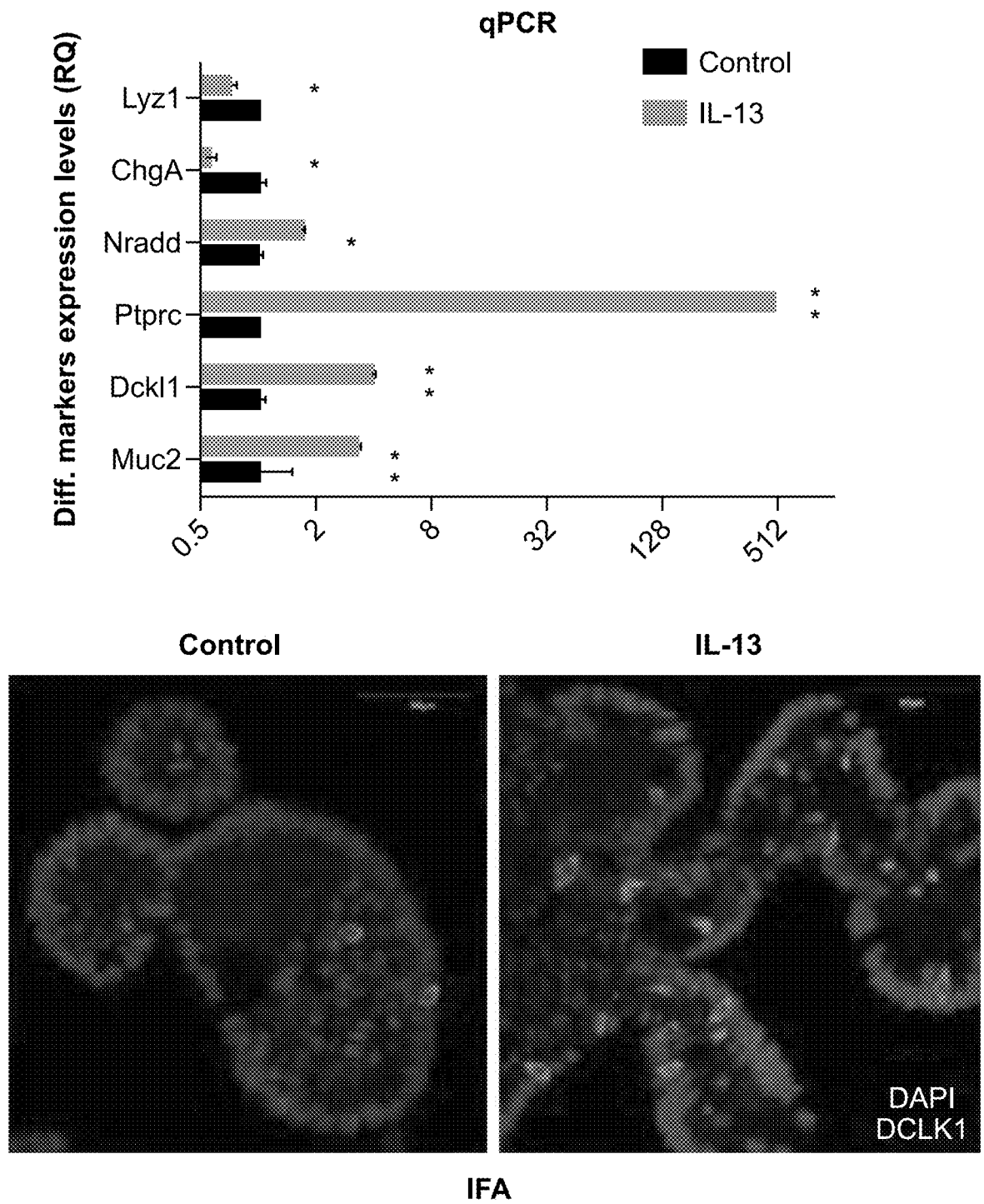
FIG. 36A-36D—Goblet and Tuft/microfold cell differentiation.
Figure 36B:
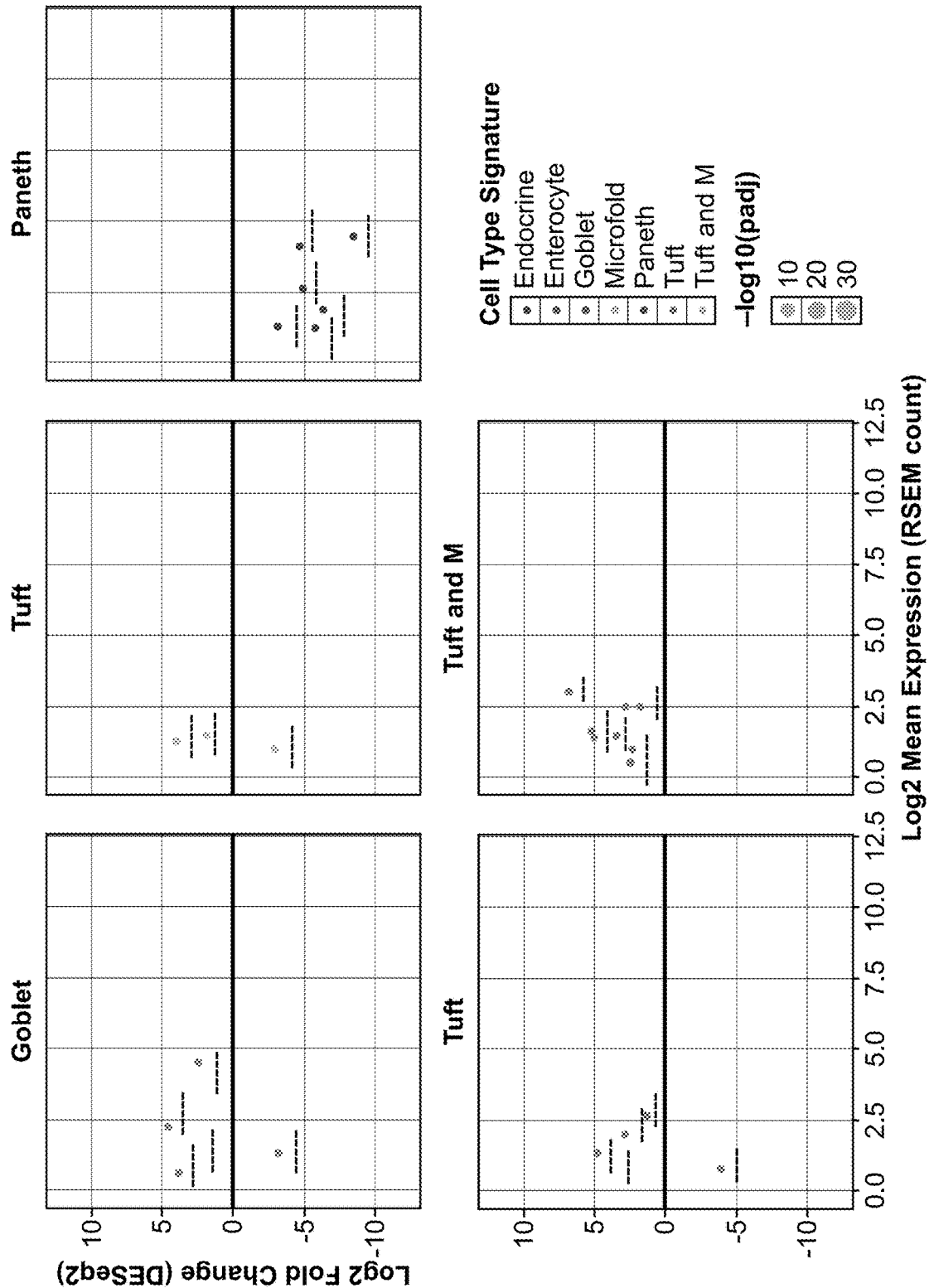
Figure 36C:
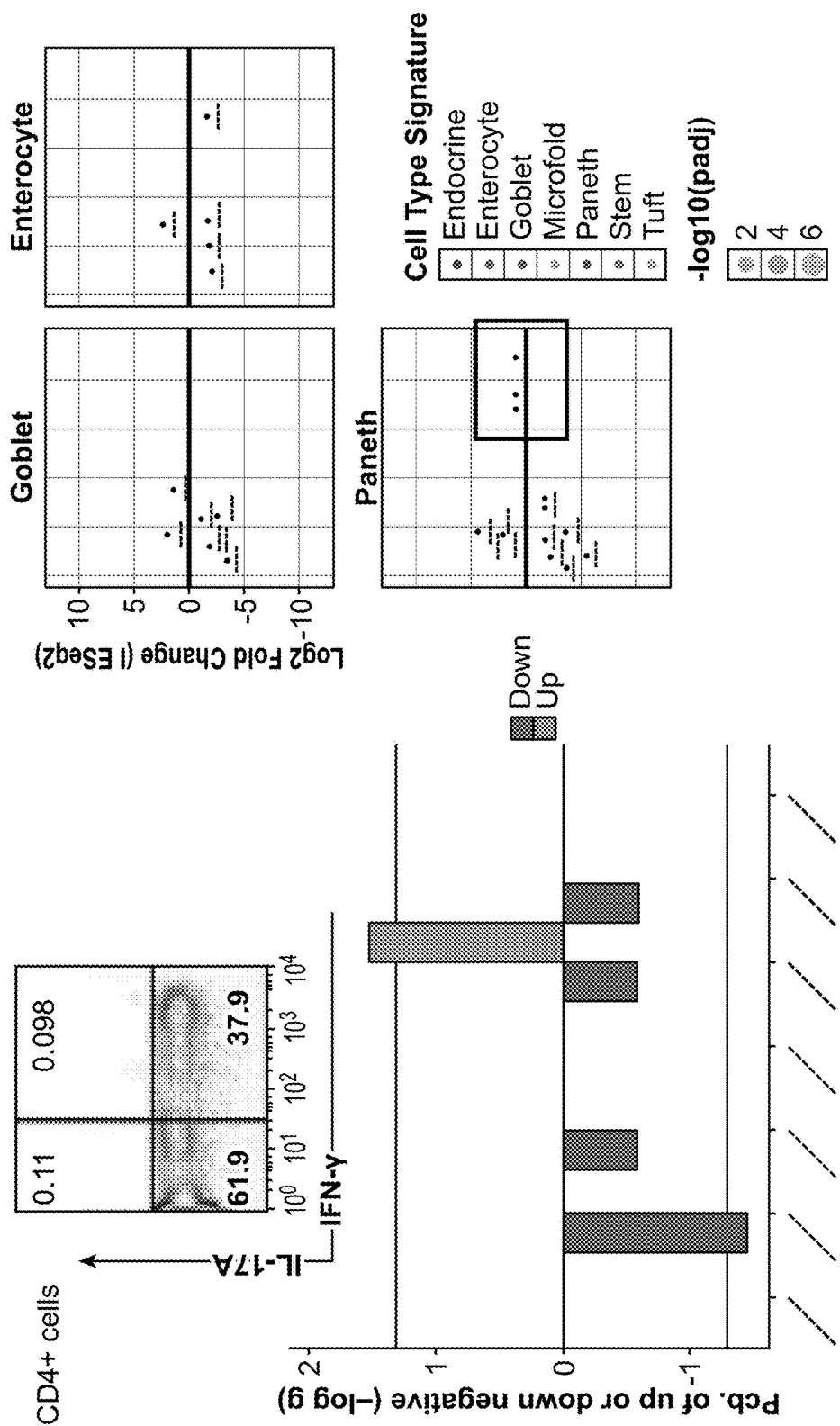
Figure 36D:
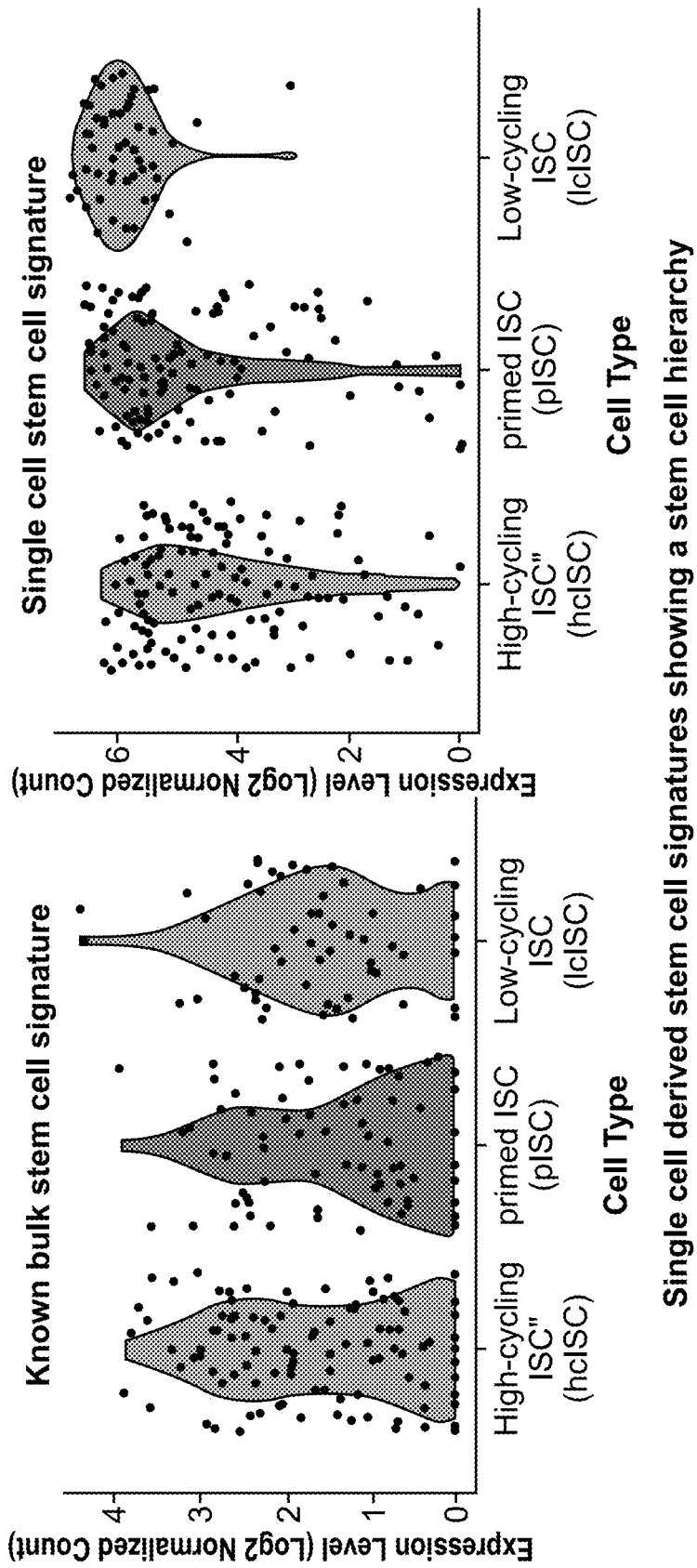
Figure 37:
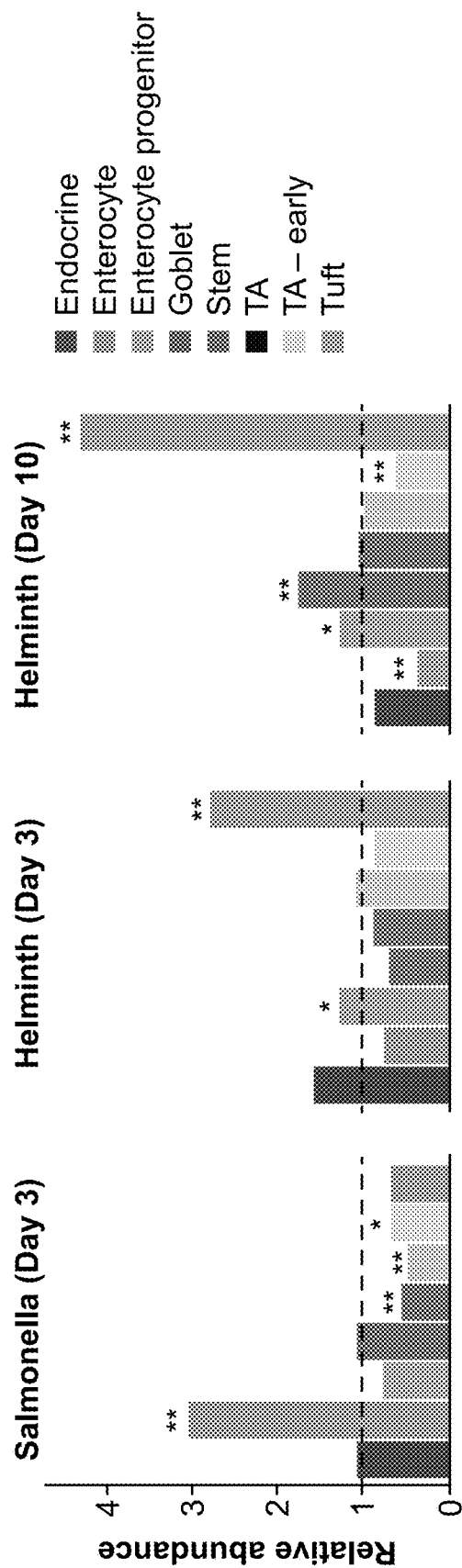
FIG. 37—Shift in intestinal stem cell differentiation.

In organoids co-cultured with Th1 cells, there was a strong upregulation of Paneth cell-specific genes, especially anti-microbial peptides (AMPs) capable of enhancing type I immunity, namely Defa17, Defa24, Lyz1, Itln1, Mmp7, and Ang4 (FDR<10-4; FIG. 31c). Co-cultures with Th1, Th2 and Th17 cells or treatment with IL-13 or IL-17 all reduced the size of the ISC pool, whereas only iTregs and their associated cytokine IL-10 led to ISC expansion. This was accompanied by a strong down-regulation of stem cell markers in ISCs (FDR<1×10$^5$) including Lgr5, Ascl2 and Smoc2 (FIG. 31d).

Example 21—Gut Atlas Analysis of Human Biopsies Distinguishes Inflammatory Conditions from Normal Based on the aformentioned observations in murine models, studies were conducted with human tissue. A biopsy was obtained from a human patient with ulcerative colitis. A separate biopsy was obtained from a patient control, i.e. without inflammatory disease. The biopsies were processed as before, on the basis of expression patterns, to identify cell types. FIG. 32 shows epithelial clusters in ulcerative colitis. (Blue: Uninflamed, Red: Inflamed), while FIG. 33 shows the corresponding clusters from normal tissue (Blue Uninflamed, Green: Uninflamed). One of the most striking changes separating inflamed and uninflamed epithelium in the UC patient is expression of HLA-DR/DP genes and associated machinery such as HLA-DM and CD74. The same differences were observed in another patient (data not shown). The UC data also shows a cluster of cells with scattered Lgr5 but overall high sternness programs, proliferative intermediate cells, and also a unique population of "healthy" cells, which overlaps with markers in the healthy patient. The data shows differentiation trajectories being affected by the inflammatory disease. It clear is that much of the diversity of epithelial cells is lost in the UC patient, in involved tissue, and even in uninvolved tissue. The data also demonstrates how gut atlas analysis can be performed to identify disease, and the nature and extent of the pathology. Such analysis is useful to direct treatment and monitor treatment and disease progression.

Example 22—Gut Atlas Analysis in Human Colon from Healthy Subjects

Applicants have generated a foundational resource in the healthy gut for: (1) Cell composition (i.e., changes in proportions of different cell types/states), (2) Cell intrinsic states (i.e., changes in gene expression within a cell type), (3) Cell-cell interactions (i.e., changes in cell-cell interaction mechanisms), and (4) the relevant cell types for each gene (e.g., GWAS genes).

Applicants used droplet-based scRNA-seq of colonoscopy samples from healthy individuals to generate the cell atlas. The samples were obtained from 10 healthy individuals (37,435 non-inflamed cells). The samples were small biopsies containing about <80,000 cells. The biopsies were fresh and dislocation and processing were performed by applicants.

Figure 38:
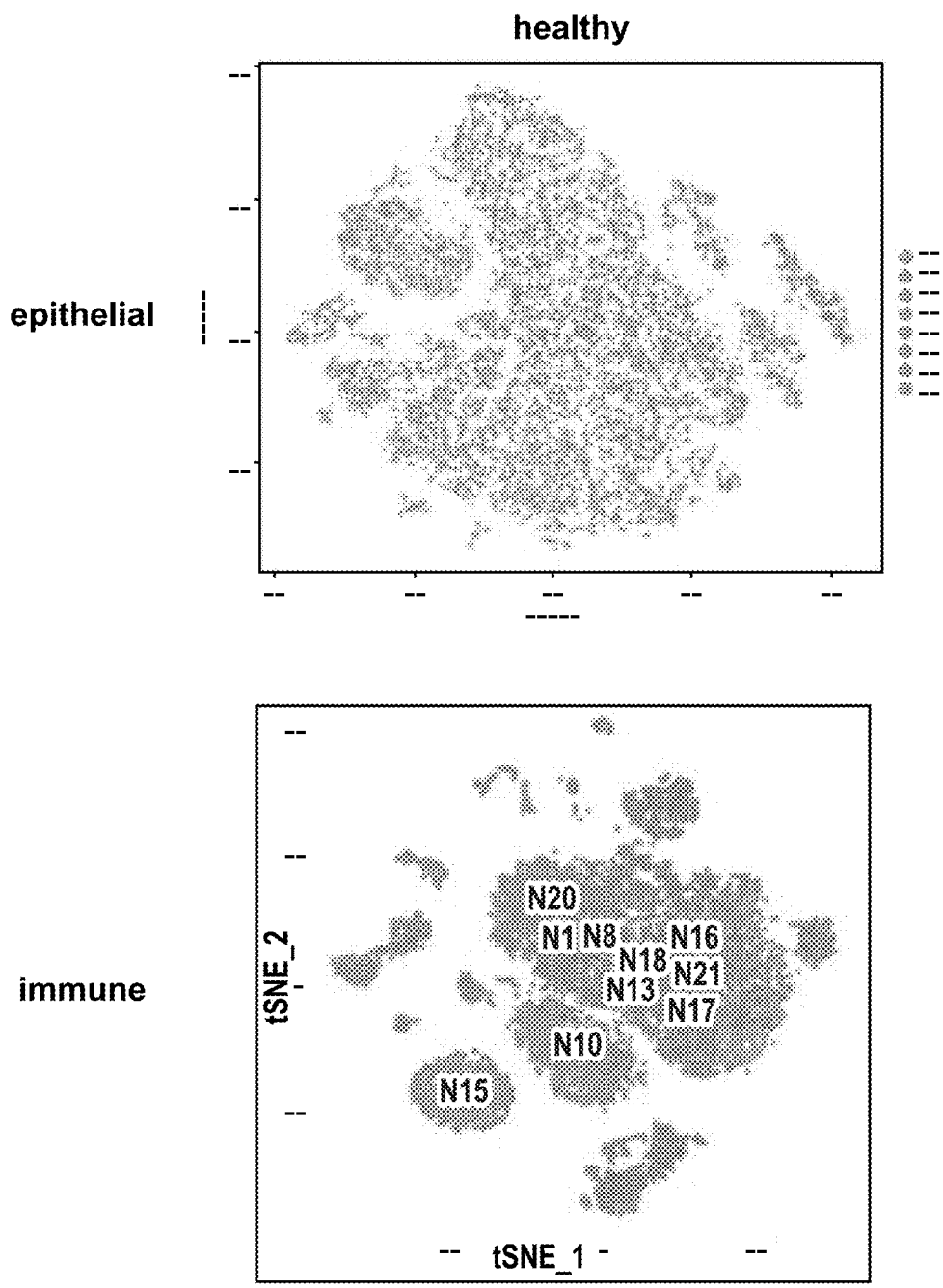
FIG. 38 illustrates that epithelial cells in healthy cells partition by cell type in tSNE plots.
Figure 40:
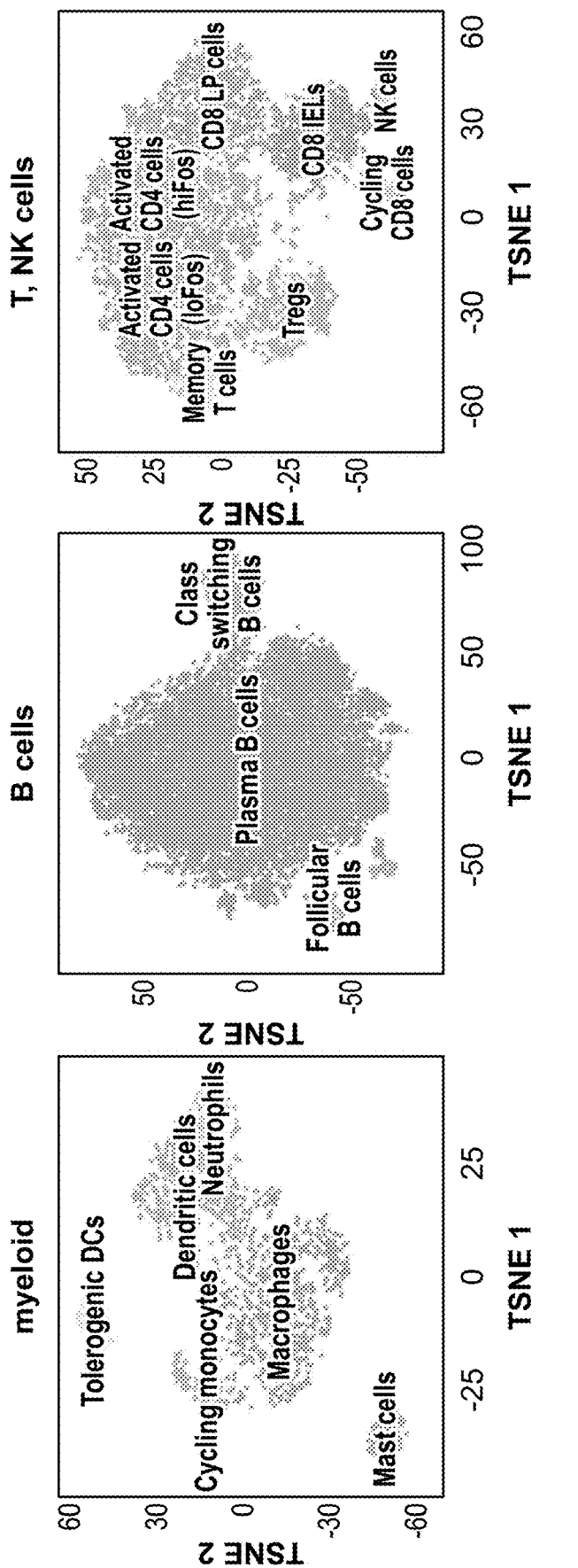
FIG. 40 illustrates that the atlas uncovers almost all cell types and subtypes in the colon.
Figure 41:
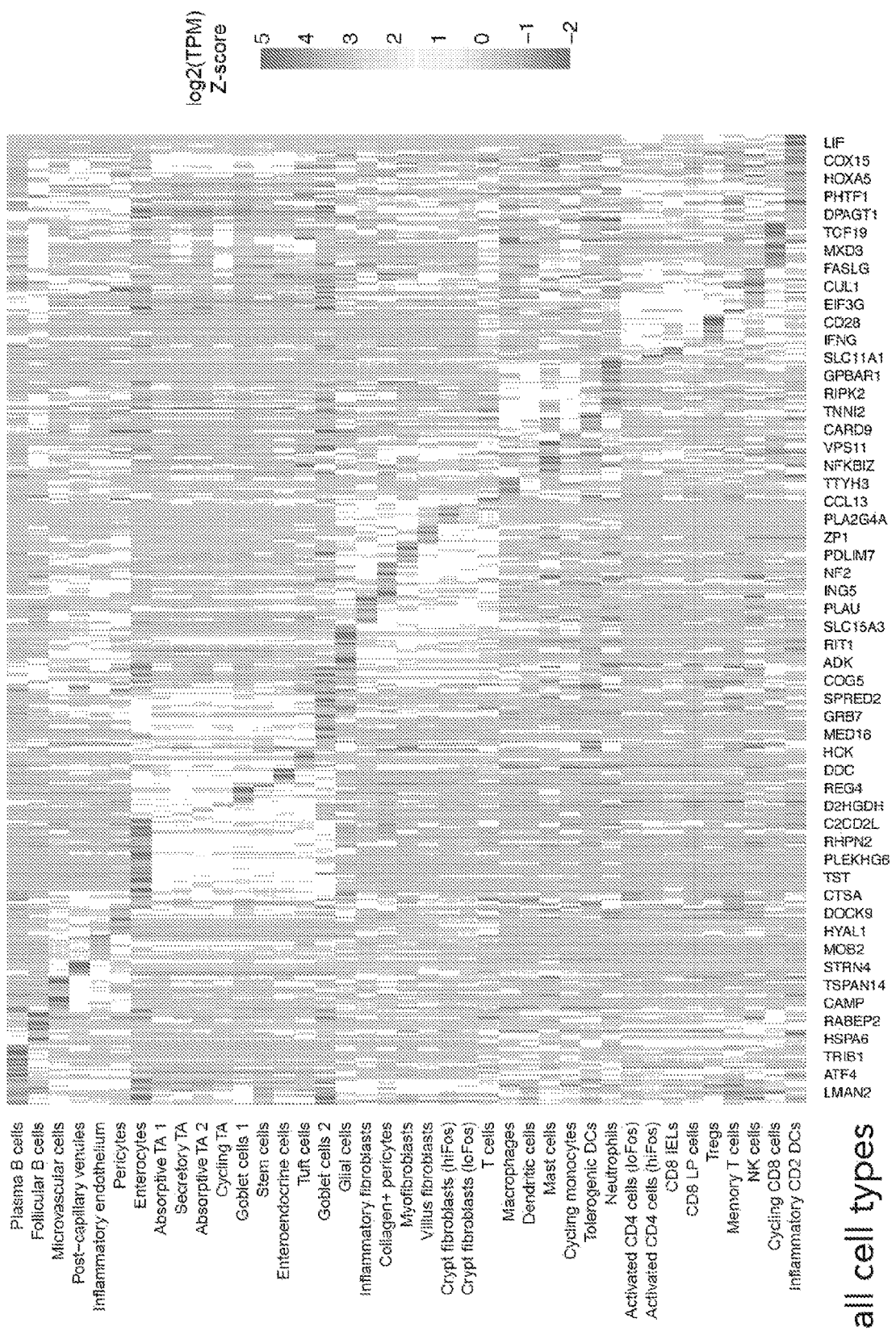
FIG. 41 illustrates the cell-of-origin for key IBD GWAS genes.
Figure 42A:
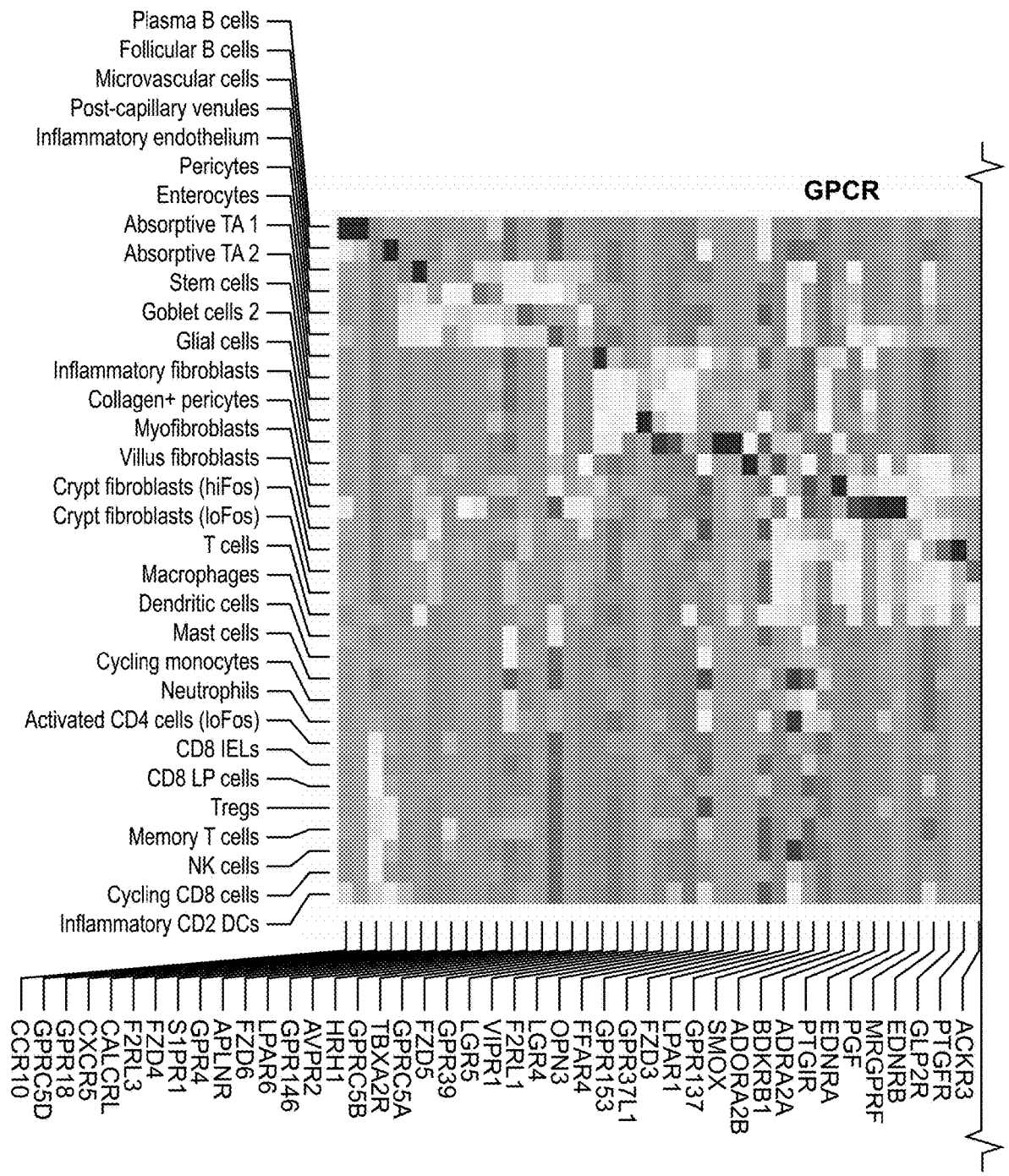
FIGS. 42A-42B illustrates the cell-of-origin for key IBD GWAS G-protein coupled receptor (GPCR) genes.
Figure 42B:
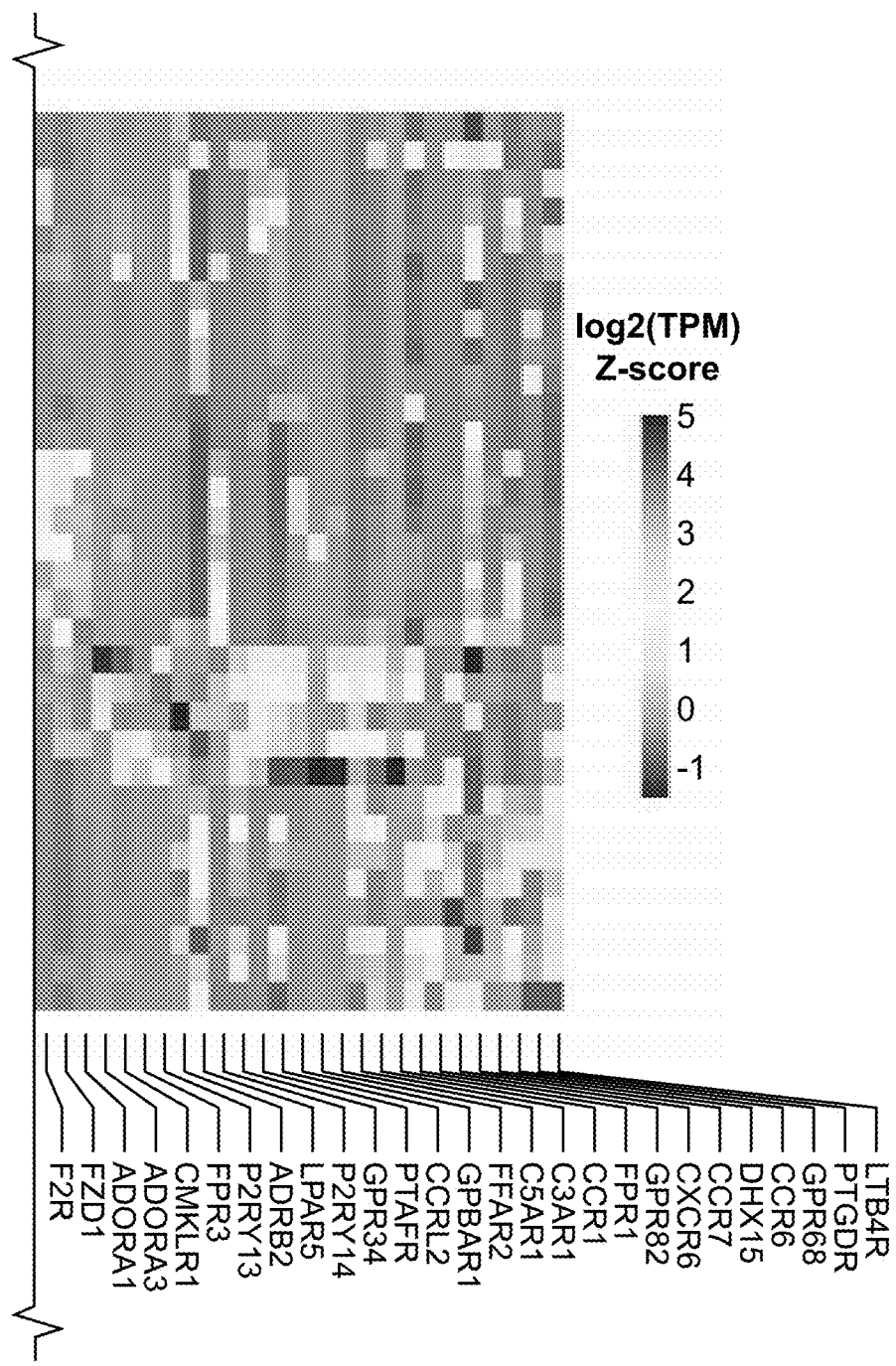
Figure 43A:
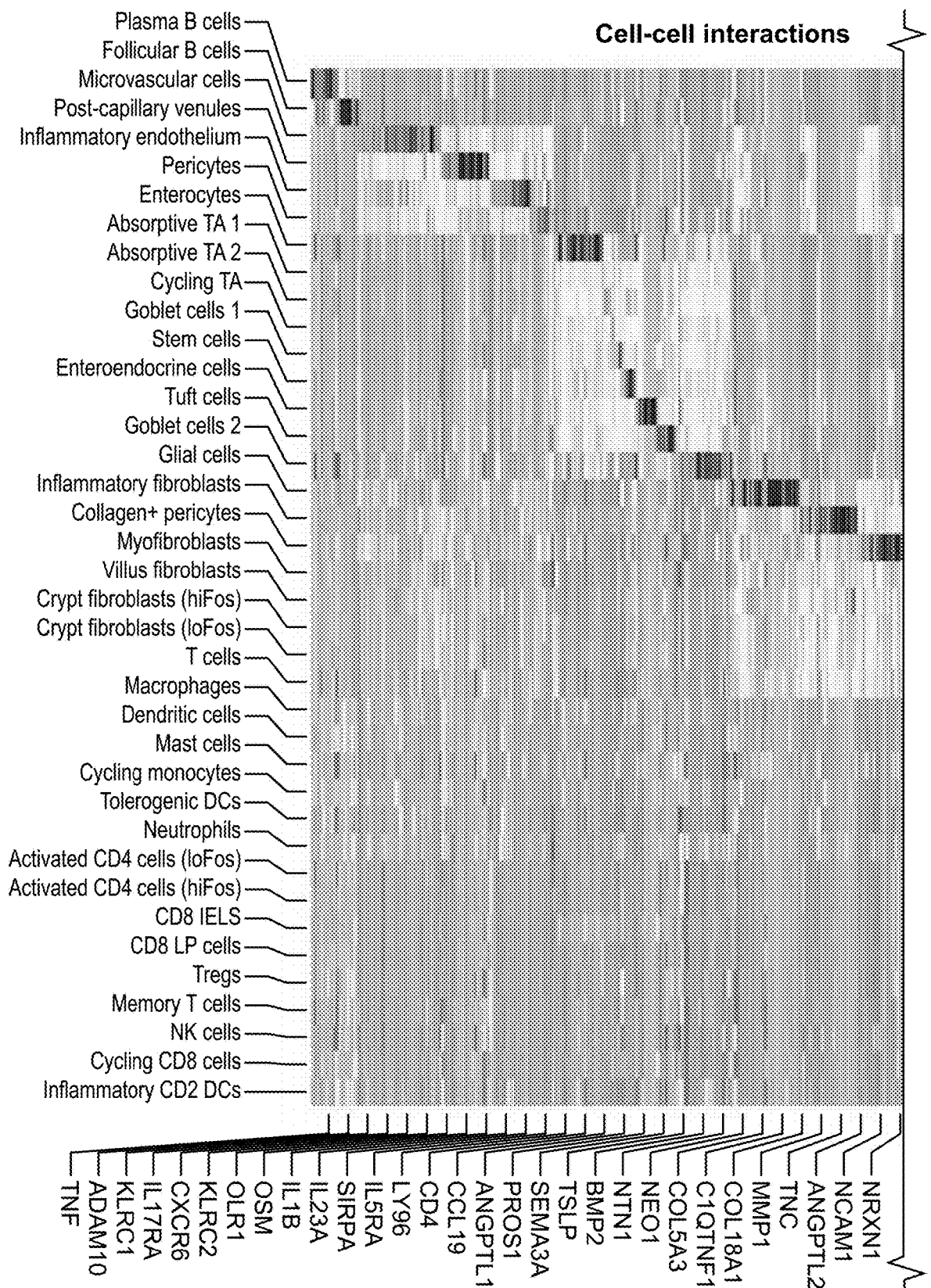
FIGS. 43A-43B illustrates the cell-of-origin for key IBD GWAS cell-cell interaction genes.
Figure 43B:
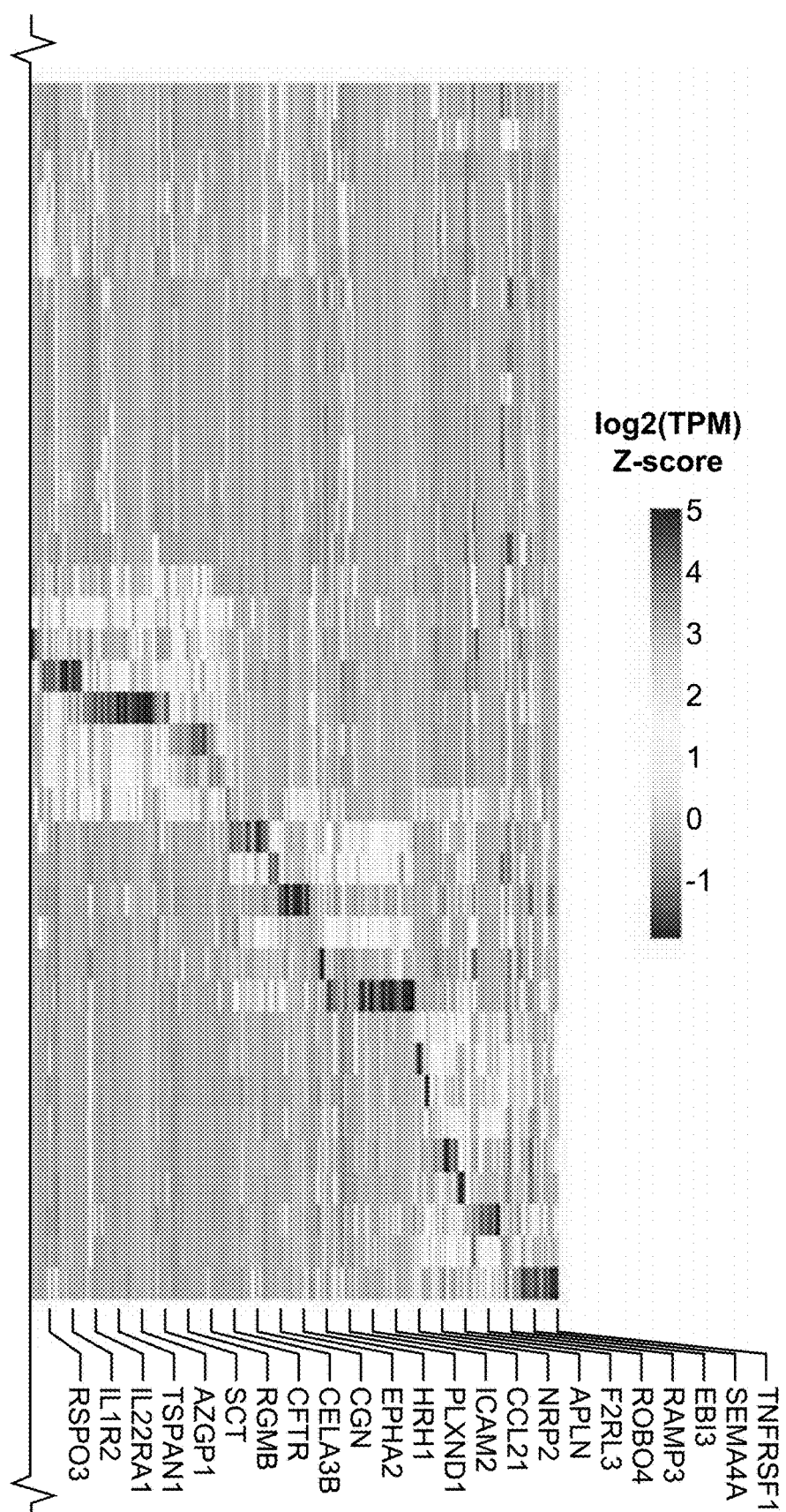
Figure 44A:
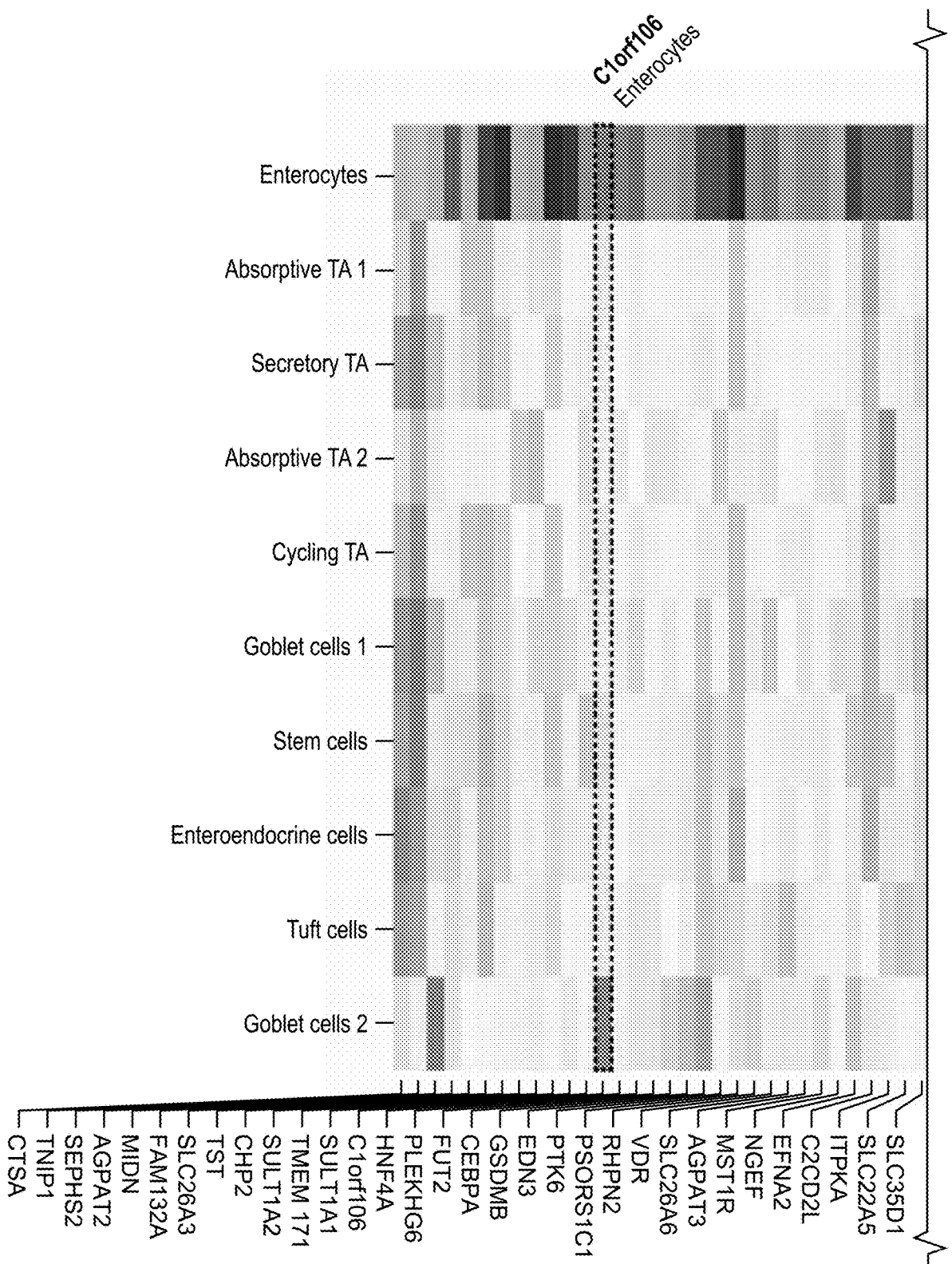
FIGS. 44A-44C illustrates the cell-of-origin for key IBD GWAS genes expressed in epithelial cells.
Figure 44B:
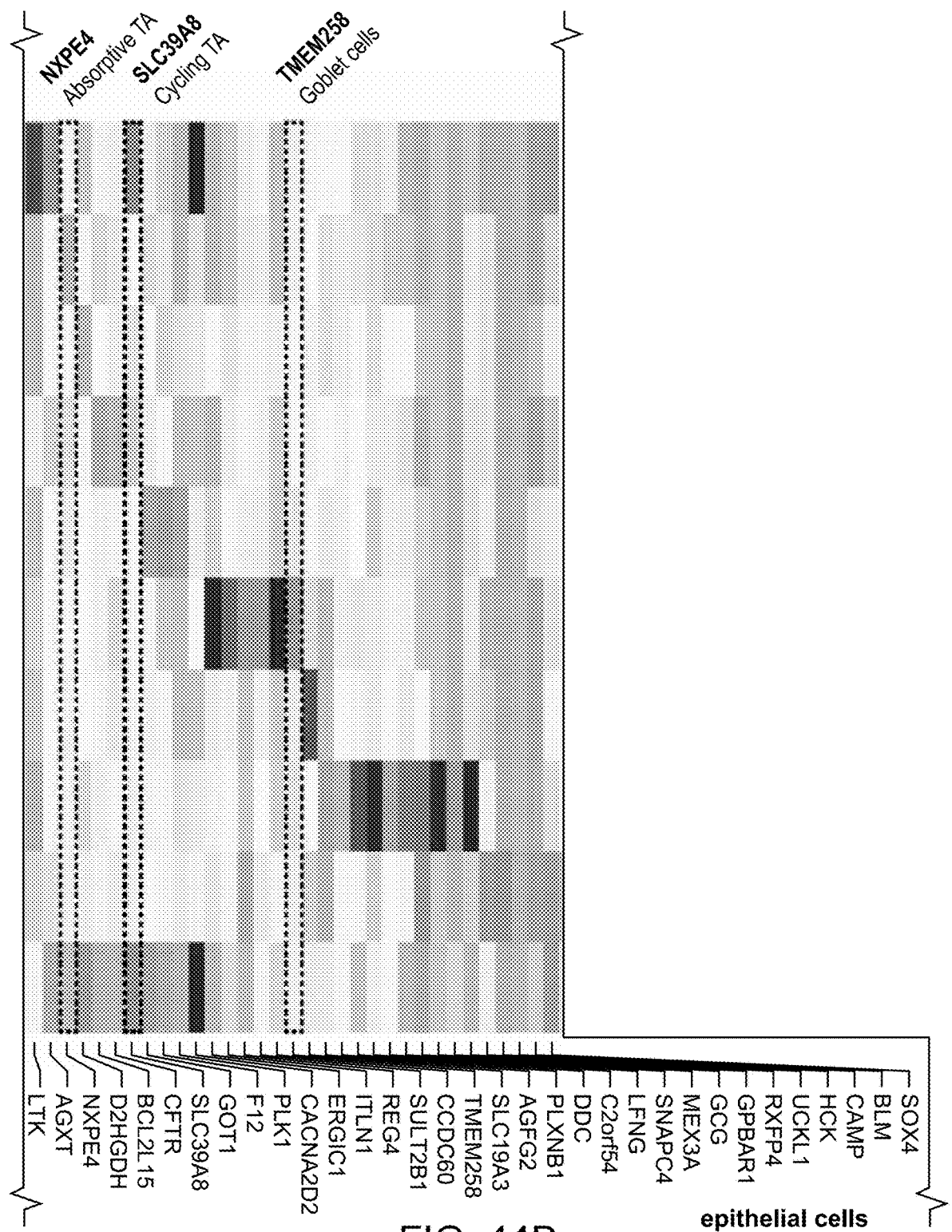
Figure 44C:
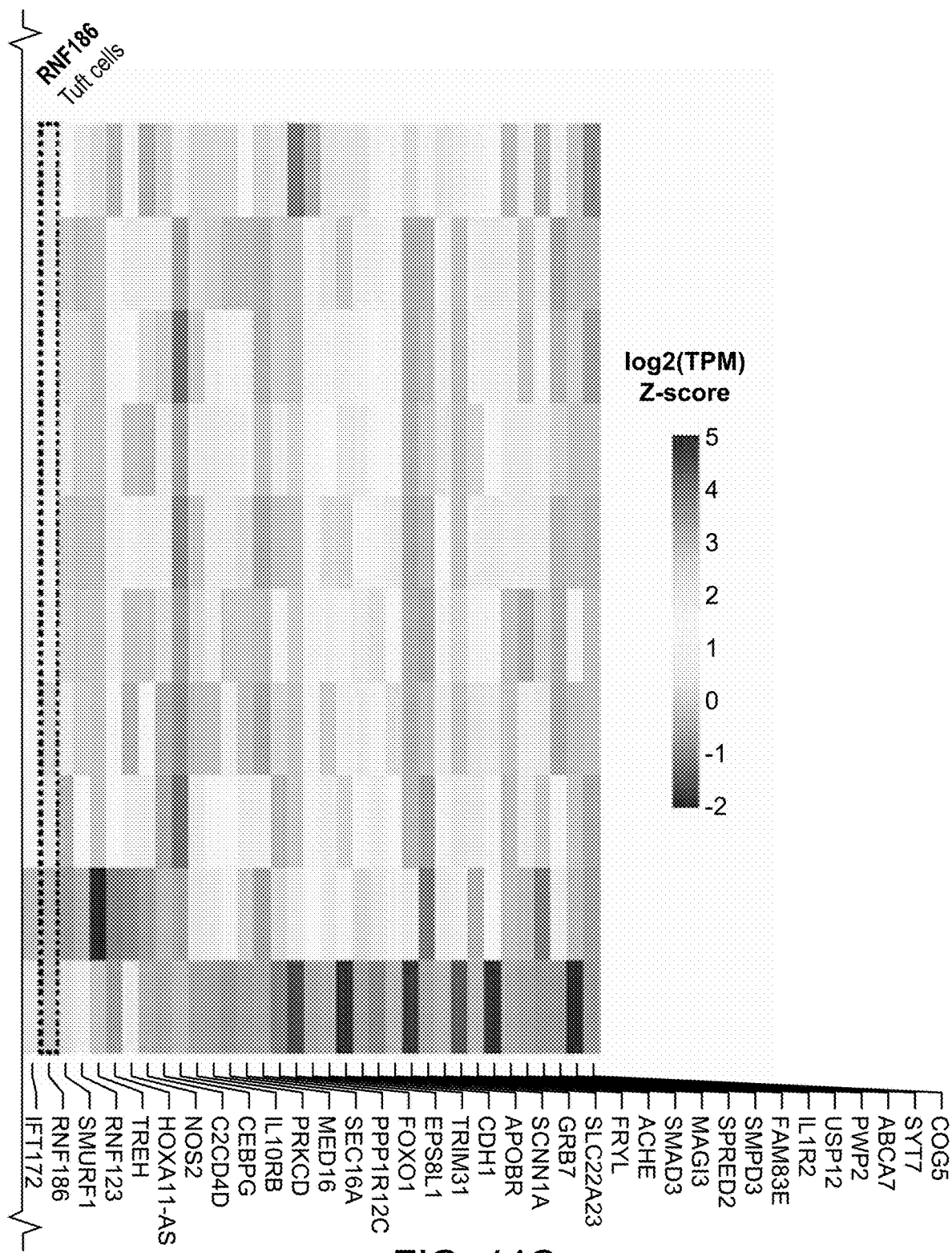

FIG. 38 shows that clustering analysis partitioned cells by cell type in the healthy samples. FIGS. 39 and 40 show that the atlas uncovers almost all cell types and subtypes in the colon. Applicants identified the following cell types and subtypes in the colon: Plasma B cells, Class switching B cells, Follicular B cells, T cells, Macrophages, Dendritic cells, Mast cells, Cycling monocytes, Tolerogenic DCs, Neutrophils, Activated CD4 cells loFos, Activated CD4 cells hiFos, CD8 IELs, CD8 LP cells, Tregs, Memory T cells, NK cells, Cycling CD8 cells, Microvascular cells, Post-capillary venules, Vitamin metabolizing, Endothelial pericytes, Enterocytes, Tuft cells, Goblet 2, Absorptive TA 1, Secretory TA, Absorptive TA 2, Cycling TA, Goblet 1, Stem cells, Enteroendocrine, Glial cells, Inflammatory fibroblasts, Fibroblast pericytes, Myofibroblasts, Villus fibroblasts, Crypt fibroblasts (hiFos) and Crypt fibroblasts (loFos). Applicants identified markers specific for each cell type. Table 15 A-D shows the top 250 genes expressed in each cell type.

TABLE 15

| Plasma_B_cells | Class_switching_B_cells | Follicular_B_cells | Microvascular_cells | Post-capillary_venules | Vitamin_metabolizing | Endothelial_pericytes | Enterocytes | Tuft_cells | Goblet_2 |
|---|---|---|---|---|---|---|---|---|---|
| HERPUD1 | IGLL5 | CD79A | PRSS23 | DARC | CD320 | RGS5 | RPL15 | AZGP1 | MUC2 |
| IGJ | IGJ | MS4A1 | RGCC | NPC2 | RAMP2 | HIGD1B | RPS2 | LRMP | TFF1 |
| SSR4 | TMSB10 | CD79B | PLVAP | CLDN5 | CLDN5 | CD320 | RPL13 | SH2D6 | RPL13 |
| SEC11C | CFL1 | VPREB3 | VWA1 | CPE | PLVAP | PLVAP | RPS6 | MARCKSL1 | ZG16 |
| XBP1 | TMSB4X | TCL1A | PASK | MADCAM1 | SLC9A3R2 | CLDN5 | GUCA2A | AVIL | RPL10 |
| MZB1 | PFN1 | FCRLA | GNG11 | CLU | GNG11 | CRIP2 | RPL10 | BIK | RPL15 |
| FKBP11 | MYL6 | CD37 | CA4 | DUSP23 | IGFBP4 | RAMP2 | AQP8 | SH2D7 | RPS4X |
| DERL3 | FTH1 | CD19 | CD36 | JAM2 | TXNIP | CAV1 | RPL32 | HCK | RPS2 |
| SPCS2 | GAPDH | SMIM14 | CD320 | PLVAP | ENPP2 | ESAM | RPS4X | ANXA4 | RPS18 |
| TNFRSF17 | ACTB | CST3 | VWF | LY6E | CLEC14A | GNG11 | RPS19 | PTGS1 | RPS19 |
| CD79A | IGLL1 | CD63 | ENG | ECSCR | TMEM88 | CD36 | SLC26A3 | ALOX5 | RPL32 |
| SSR3 | TNFRSF17 | LTB | RAMP2 | SDCBP | ESAM | COX4I2 | RPLP1 | ANXA13 | FCGBP |
| UBE2J1 | CD79A | LIMD2 | SLC9A3R2 | TSPAN7 | CRIP2 | NDUFA4L2 | RPS18 | KRT18 | RPL19 |
| SPCS1 | DERL3 | CD22 | ESAM | EGFL7 | SPARCL1 | IGFBP4 | PLAC8 | IL17RB | S100P |
| DNAJB9 | MT-CO1 | BLK | CRIP2 | VWF | HLA-E | MGP | CEACAM7 | TPM1 | CEACAM5 |
| EAF2 | MZB1 | LGALS3 | GSN | GNG11 | RAMP3 | EGFL7 | FXYD3 | TRPM5 | TSPAN1 |
| FKBP2 | SERF2 | PTPRCAP | SPARCL1 | RAMP2 | CD59 | TMEM88 | KRT20 | EIF1B | RPL11 |
| MANF | AL928768.3 | AL928768.3 | FKBP1A | APLNR | CAV1 | SPARCL1 | FABP1 | BMX | RPS9 |
| PRDX4 | ACTG1 | HLA-DQA1 | TMEM204 | RAMP3 | VAMP5 | RBP7 | PRAP1 | HPGDS | RPS14 |
| SDF2L1 | RPL28 | CD53 | ITM2B | ITM2B | IFI27 | IGFBP7 | TSPAN1 | POU2F3 | FXYD3 |
| SERP1 | RPS24 | BANK1 | RBP5 | CTNNAL1 | JAM2 | MYL9 | CEACAM5 | GNG13 | RPL10A |
| AL928768.3 | MT-CO3 | RHOH | TM4SF18 | IGFBP4 | ECSCR | SLC9A3R2 | SDCBP2 | HTR3E | RPL35 |
| SPCS3 | ATP5E | S100A6 | RAMP3 | NNMT | SEPW1 | TINAGL1 | SRI | PSTPIP2 | LYPD8 |
| CYBA | COX4I1 | GPR18 | EGFL7 | HLA-E | EGFL7 | NOTCH3 | MS4A12 | SPIB | RPL12 |
| WT1-AS | HLA-A | CORO1A | HSPG2 | GIMAP7 | BCAM | CLEC14A | PHGR1 | PLCG2 | RPS5 |
| CRELD2 | PPAPDC1B | BCAS4 | CCDC85B | GPR126 | GIMAP7 | TXNIP | C19orf33 | ELF3 | MUC1 |
| VIMP | GNG7 | CXCR5 | ECSCR | ICAM1 | CD36 | ENPP2 | RPS8 | MATK | ENTPD8 |
| SEC61B | UBA52 | CD74 | TMEM88 | HHEX | NPDC1 | JAM2 | RPS9 | KRT8 | RPLP1 |
| PDIA6 | ICAM3 | SERPINA9 | SDPR | GIMAP4 | RBP7 | SDPR | RPL10A | C11orf53 | RPS8 |
| HSP90B1 | UQCR11 | LRMP | VAMP5 | TNFSF10 | GSN | GIMAP7 | CTD-2228K2.5 | TFF3 | RPL35A |
| GNG7 | RPS12 | FCGRT | BCAM | LINC01013 | CYYR1 | RAMP3 | RPL35 | EPCAM | RPL26 |
| PPAPDC1B | SSR4 | EAF2 | CAV1 | AC011526.1 | SDPR | TM4SF1 | MISP | RASSF6 | CLDN4 |
| CD27 | S100A6 | RGS13 | MGP | CLEC14A | EFNA1 | ECSCR | GUCA2B | RGS13 | RPS13 |
| FAM46C | PPDPF | CXCR4 | EMCN | IGFBP7 | ICAM2 | HLA-E | RPS5 | FYB | TFF3 |
| PDIA4 | RPL31 | POU2AF1 | ELTD1 | NPDC1 | TM4SF1 | CYYR1 | TMEM54 | CRYM | REP15 |
| ISG20 | CHCHD2 | SMARCB1 | PLAT | NCOA7 | EMCN | IFITM3 | RPS7 | PRSS3 | FAM3D |
| PABPC4 | BTF3 | CD52 | KDR | CAV1 | IFITM3 | SPARC | SLC51B | IGJ | RPS27A |
| TRAM1 | SRP14 | SPIB | CLEC14A | LMO2 | MGP | A2M | RPL19 | TREH | RPS3 |
| ANKRD37 | CD27 | MGST3 | HLA-E | SNCG | TSPAN7 | GSN | RPL11 | SPINT2 | GNB2L1 |
| RPL36AL | TOMM7 | BLNK | IGFBP7 | CTGF | FKBP1A | CALD1 | CDHR5 | IL13RA1 | RPS7 |
| C19orf10 | PFDN5 | HLA-DRA | FLT1 | TM4SF1 | IL3RA | HSPA1A | RPL5 | NMU | RPS16 |
| CCR10 | MYL12B | CD72 | PODXL | FAM213A | IFITM1 | CAV2 | RPL35A | SOX4 | CLDN7 |
| IGLL5 | YBX1 | POU2F2 | SEPW1 | SPARCL1 | PODXL | CCDC85B | RPS13 | DPYSL3 | RPL6 |
| HSPA5 | EAF2 | ACTR3 | IGFBP4 | CRIP2 | IFITM2 | VWF | CLDN7 | ASCL2 | RPLP2 |

TABLE 15-continued

| | | | | | | | | |
|---|---|---|---|---|---|---|---|---|
| ACTB | UBE2I | FCRL2 | HTRA1 | ITM2A | TGFBR2 | VAMP5 | RPL12 | LGALS4 | RPS15 |
| LMAN2 | SRGN | HMGN1 | SPARC | FAM167B | STOM | ZFP36 | RPS23 | HEPACAM2 | RPS15A |
| MEI1 | RPL30 | CD40 | CAV2 | FKBP1A | PPA1 | HLA-C | CEACAM1 | LGALS1 | MUC13 |
| DUSP5 | EIF3K | ARPC2 | SLC14A1 | ESAM | ENG | HSPB1 | CA2 | HOTAIRM1 | RPLP0 |
| SELK | NDUFA11 | GGA2 | AC011526.1 | IFITM3 | HES1 | HLA-DRA | ANPEP | PLEKHB1 | SDCBP2 |
| UBC | CYTIP | EZR | SH3BP5 | TMEM100 | CD34 | EGR1 | LYPD8 | CLDN4 | RPL8 |
| FCRL5 | RPL23 | HERPUD1 | FAM167B | CCL14 | VWF | TM4SF18 | KRT8 | PPAP2C | ELF3 |
| CST3 | TRAM1 | NCF1 | FAM213A | BCAM | HLA-C | IFI27 | LINC01133 | PPDPF | GDPD3 |
| TXNDC11 | ATPSG2 | IRF8 | SNCG | GIMAP1 | RBP5 | CSRP2 | RPS3 | PTPN18 | NACA |
| UAP1 | FAM46C | HLA-DPA1 | GIMAP7 | CD34 | CAV2 | JUNB | RPS12 | OGDHL | RPS12 |
| PIM2 | TCEB2 | HLA-DQB1 | CDC37 | IFI27 | SLC14A1 | NOSTRIN | RPLP0 | MDK | RPL23A |
| CFL1 | PTMA | HLA-DPB1 | IFITM3 | TGFBR2 | PRSS23 | FOS | RPL26 | FXYD3 | RPL5 |
| SPAG4 | ERLEC1 | LAPTM5 | RP11-536O18.2 | CYBA | PLAT | CDH5 | GNB2L1 | OCIAD2 | CLDN3 |
| YPEL5 | SH3BGRL3 | UBE2J1 | PPAP2A | RBP5 | CDC37 | RNASE1 | SFN | RP11-93B14.5 | PHGR1 |
| PFN1 | EDF1 | HLA-DOB | TSC22D1 | CYYR1 | A2M | GADD45B | RPS15A | CLDN3 | RPS23 |
| S100A6 | HM13 | FCER2 | IFITM2 | ZNF385D | CCDC85B | IFITM2 | RPL14 | ESPL1 | C19orf33 |
| TPD52 | RPS7 | C12orf75 | ICAM2 | NRN1 | TNFSF10 | FRZB | RPS14 | FABP1 | GUCA2B |
| CHPF | KDELR1 | SWAP70 | PTRF | HLA-DRA | EPAS1 | IER2 | PRSS3 | ALOX5AP | PLAC8 |
| RP11-29O5.1 | ARHGDIB | HMCES | EHD4 | ADIRF | RNASE1 | ENG | LGALS3 | ANXA3 | RPL4 |
| HSPA1B | FKBP11 | BTG1 | NQO1 | CD320 | OAZ2 | CTGF | RPL6 | CD74 | BCAS1 |
| POU2AF1 | PABPC4 | P2RX5 | CLDN5 | CD59 | SRP14 | JUN | RPL4 | FURIN | RPS6 |
| JUN | SPCS3 | LY86 | CD59 | SRPX | CTGF | ICAM2 | RPS16 | PPP1R1B | RPL13A |
| BTG2 | RPL38 | CYTIP | COL4A1 | ENG | HLA-DRB1 | BGN | RPS15 | MT-CO3 | TBX10 |
| TXNDC15 | COX6B1 | METAP2 | PPAP2B | CFI | GIMAP4 | TPPP3 | RPL23A | ANKS4B | TUBB2A |
| TSC22D3 | ALDOA | CD180 | HLA-C | HLA-A | HLA-DRA | FOSB | PTMA | HSPB1 | TM4SF5 |
| TMEM258 | RPS11 | AICDA | CXorf36 | HSPB1 | ELTD1 | RBP5 | PKIB | NCMAP | SMIM6 |
| TMED10 | CLIC1 | CD9 | NPDC1 | HLA-DPB1 | ITM2B | HLA-DPB1 | RPS27A | DEFB1 | VSIG2 |
| MCL1 | TPI1 | LY9 | ARHGAP29 | PIM3 | FAM107A | HES1 | AMN | ZFP36 | SERPINA1 |
| TMSB10 | TXNDC15 | HLA-DRB1 | ANGPT2 | HLA-DRB5 | AC011526.1 | HLA-DRB1 | RPL27A | CC2D1A | IFI27 |
| TPST2 | RPL10A | ANXA2 | SEPW1 | SEPW1 | APP | HLA-DRB5 | GPA33 | COX5A | LGALS9B |
| ACTG1 | CHST12 | ISG20 | SDPR | SDPR | MPZL2 | MGLL | GCNT3 | MT-CO1 | KRT20 |
| NR4A1 | NDUFA13 | SEPW1 | TM4SF1 | ENPP2 | IGFBP7 | SLC14A1 | PRDX6 | EHF | ZG16B |
| S100A10 | TRMT112 | ARHGDIB | APP | NOSTRIN | TMEM204 | SEPW1 | AGPAT2 | CALM2 | MT-CO1 |
| TNFRSF18 | DPP7 | HMGA1 | BAALC | DNAJA1 | GPR146 | EPAS1 | AOC1 | SOX9 | PTMA |
| ERLEC1 | IFNAR2 | TCEA1 | C16orf80 | PTRF | CD74 | FKBP1A | SULT1A2 | IFT172 | SERINC2 |
| NUCB2 | RPL11 | AICDA | EFNA1 | KCTD12 | FLT1 | ITM2B | MEP1A | 7SK | RPL14 |
| TMSB4X | MYL12A | POLD4 | ACVRL1 | IFITM2 | C16orf80 | SNCG | RPL8 | ITM2C | TRIM31 |
| RPN2 | RPSA | CD83 | LXN | HLA-DRB1 | ACVRL1 | C8orf4 | RPL31 | CASP6 | RPL24 |
| SUB1 | RPL26 | BASP1 | IGFBP3 | MYCT1 | FAM167B | SOCS3 | SMIM22 | EMP3 | AMN |
| PNOC | ISG20 | STAG3 | CYYR1 | GIMAP5 | MMRN2 | LDB2 | TMIGD1 | COX6C | TPSG1 |
| SELM | ATP6V1G1 | S100A11 | MYL12A | CCDC85B | MGLL | ELTD1 | KRT19 | ATP1A1 | FFAR4 |
| SLAMF7 | RPL27 | SNX29P2 | MGLL | CNN3 | HLA-DPB1 | PLAT | CA4 | PHGR1 | KLK1 |
| | | TPD52 | | | | | | | |

TABLE 15-continued

| | | | | | | | | |
|---|---|---|---|---|---|---|---|---|
| IFNAR2 | POU2AF1 | IFI27 | HLA-A | LMCD1 | NOSTRIN | EMCN | CCDC115 | TMEM54 |
| DDOST | ALG5 | ARPC3 | HLA-DRA | KANK3 | GIMAP1 | ID3 | GFI1B | RPL27A |
| MYL12B | PSMA7 | HTR3A | STOM | CD74 | BST2 | GIMAP4 | HSPA1A | RPS20 |
| TNFRSF13B | RPL24 | GCSAM | EGLN3 | HLA-DPA1 | HYAL2 | PRSS23 | S100A11 | CDHR5 |
| FGF23 | SLC25A3 | PNOC | ROBO4 | HLA-C | TIMP3 | BST2 | KIAA1324 | CLTB |
| LMAN1 | SEC62 | E2F5 | SPTBN1 | CDH5 | TM4SF18 | CD59 | EPS8L3 | RPL29 |
| ANKRD28 | CNPY2 | CD27 | ABI3 | ADM5 | HHEX | FAM167B | NREP | CREB3L1 |
| CD38 | BST2 | RAC2 | HLX | NFKBIA | GIMAP5 | TSC22D1 | HLA-DPB1 | RPL3 |
| ICAM3 | TMEM230 | AC023590.1 | STX7 | SPARC | RASIP1 | HSPA1B | HLA-DRA | EPCAM |
| GAPDH | RPL37 | | HLA-B | PALMD | SLCO2A1 | RGS16 | HLA-DRB1 | FOXA3 |
| DNAJB11 | CD63 | LYL1 | TGFBR2 | CHCHD10 | SNCG | PDGFRB | MYO1B | RPL31 |
| ARF4 | SLAMF7 | TMSB10 | S100A13 | LPCAT4 | FAM213A | ADIRF | B2M | CAPN8 |
| AC104699.1 | LGALS1 | UCP2 | MMRN2 | ERG | HLA-DPA1 | GJA4 | GADD45B | GPA33 |
| CDK2AP2 | GYPC | IL32 | IVNS1ABP | SH3BP5 | HEY1 | TGFBR2 | KLK11 | CFDP1 |
| TMEM59 | RPS9 | HLA-DMA | CTGF | STXBP6 | SOX17 | KLF2 | CLRN3 | TMSB10 |
| ALG5 | NDUFA4 | SELT | F2RL3 | BST2 | PTRF | MFGE8 | ATP2A3 | RPS25 |
| C16orf74 | COX5B | LAT2 | ENPP2 | CAV2 | EMP2 | APP | NDUFB4 | RPS24 |
| SRPRB | DUSP5 | IFITM3 | WWTR1 | SMAD1 | RPL12 | PODXL | COX7A2 | AQP8 |
| CIRBP | RPS13 | BFSP2 | EXOC3L2 | CLIC2 | NKX2-3 | TIMP3 | S100A14 | KRT18 |
| FTH1 | HNRNPDL | GDI2 | B2M | IFIT1 | SYNPO | HLA-A | EIF5 | RPL30 |
| TMED2 | LRPAP1 | HLA-DMB | NOTCH4 | TPD52L1 | SOCS3 | BCAM | PRDX2 | FAM177B |
| RGS2 | PARK7 | HHEX | GABARAPL2 | SOCS3 | NRN1 | SLC2A3 | CYB5A | RPL18 |
| IGFBP7 | MEI1 | LGALS4 | IFI27 | GALNT15 | RPLP0 | DNAJA1 | C15orf48 | LGALS4 |
| RABAC1 | RPL19 | EPCAM | S100A16 | HLA-DQA1 | IFIT3 | MCAM | CLDN7 | RPL7A |
| CD74 | RHEB | MZB1 | HES1 | CYP1B1 | CDH5 | SERPING1 | CHPT1 | SPATS2L |
| SSR2 | VIM | SIT1 | GMFG | ICAM2 | HLA-A | CD74 | CKB | KRT8 |
| ARHGDIB | RPL32 | PLEKHF2 | IL3RA | HSPA1A | IER2 | SYNPO | COX7C | PRR15L |
| DNAJB1 | COX7C | TNFRSF13B | GAS6 | IRF1 | TSC22D1 | ISYNA1 | SLC25A6 | PRSS3 |
| CYTIP | COX6A1 | RHOC | IDO1 | FBLN2 | RND1 | COX7A1 | MAP7 | DHRS9 |
| ZBP1 | PTPRCAP | OAZ1 | COL4A2 | HYAL2 | KANK3 | LHFP | VSNL1 | PIGR |
| HM13 | SMARCB1 | KRT18 | MSN | EIF1 | THBD | SRGN | MT-ND4 | NEAT1 |
| AMPD1 | COMMD3 | LCP1 | FSCN1 | SELP | NQO1 | THBD | BUB3 | PLA2G10 |
| MYL12A | LSP1 | HVCN1 | HHEX | LIFR | C8orf4 | EFNA1 | KRT19 | EEF1D |
| RHOC | PSENEN | C15orf48 | MYCT1 | S100A16 | LDB2 | MMRN2 | CCDC28B | RPL27 |
| GSN | RPS25 | KRT8 | ACE | TCF4 | ARHGAP29 | HLA-DPA1 | SRI | SCNN1A |
| IFI27 | ARL6IP4 | ITM2B | TSPAN7 | MPZL2 | C10orf10 | FAM107A | SMIM22 | FABP1 |
| REEP5 | EMC4 | MBD4 | EPAS1 | YBX3 | EHD4 | IRF1 | FBP1 | RPL28 |
| TMEM208 | ARPC3 | BIK | FAM110D | EGR1 | HSPB1 | CLIC2 | H1F0 | SMIM22 |
| SDC1 | ATP5O | TXN | C9orf3 | ARL2 | HLA-DRB5 | PTRF | ALDH2 | FAM101A |
| GLA | MT-ND4 | CCND3 | CALCRL | MTUS1 | GABARAPL2 | CYGB | PAFAH1B3 | FTL |
| TUBA1A | GMFG | DEF8 | HLA-DRB1 | B2M | NOTCH4 | RPLP0 | MAOB | FAU |
| EEF1D | SRPRB | RASGRP2 | SOX18 | SNHG7 | GPR116 | PPA1 | HLA-DRB5 | HIST1H1C |
| KDELR2 | ATP5B | MARCKSL1 | FABP5 | FAM110D | HEG1 | MYCT1 | HLA-DMA | PARM1 |

TABLE 15-continued

| | | | | | | | |
|---|---|---|---|---|---|---|---|
| B4GALT3 | NDUFA1 | NEIL1 | GALNT18 | CALCRL | CLIC2 | H3F3B | RPS24 | ACTG1 | CEACAM6 |
| PDE4B | RPL37A | SUGCT | ITM2A | ELTD1 | SRGN | B2M | C15orf48 | MIEN1 | CEACAM7 |
| RGCC | RAC1 | RP11-164H13.1 | A2M | PIR | FABP5 | SPINT2 | NACA | MT-CYB | GSN |
| LGALS1 | EIF3F | RFTN1 | IFITM1 | JUNB | NFIB | GPX3 | HSD17B2 | HOXB6 | ARL14 |
| RGS1 | DNAJB11 | ITM2C | IGFBP6 | IL3RA | AIF1L | TSPAN7 | SLC17A4 | TIMP1 | MISP |
| LGALS3 | ATP5J | MT2A | NOSTRIN | RNASE1 | ADAM15 | COL18A1 | TMSB10 | GPX2 | CA2 |
| PDK1 | MT-ATP6 | TNFAIP8 | JAM2 | IL33 | NOV | FLT1 | RPL36 | ZFHX3 | GUCA2A |
| TMEM176B | RPS20 | ZCCHC7 | RNASE1 | VGLL4 | C9orf3 | SOD3 | EEF1D | CD9 | MLPH |
| SH3BGRL3 | MGAT1 | LINC00926 | MYL12B | IFIT3 | S100A16 | EIF1 | SLC44A4 | MALAT1 | CEACAM1 |
| IFITM3 | CRELD2 | AIM2 | SLCO2A1 | EFEMP1 | SH3BP5 | COL1A2 | CDKN2B-AS1 | RPL37A | SPINT2 |
| KIAA0125 | UBL5 | STK17A | CALM1 | HLA-B | PPAP2B | | LGALS4 | NCK2 | YBX1 |
| MYL6 | MT-CYB | CISD3 | NES | KLF4 | B2M | | IFI27 | TAS1R3 | RPL36 |
| SRGN | SELM | CYB561A3 | KANK3 | TESC | PIK3R3 | | PPDPF | PIK3CG | SCGB2A1 |
| RP11-492E3.2 | VAMP2 | SLBP | ARHGAP18 | EPCAM | PLLP | | BTNL3 | RBM38 | C15orf48 |
| TRIB1 | OSTC | TMEM156 | | STOM | C10orf54 | | NPM1 | LDHA | NAAA |
| CITED2 | ICAM2 | BACH2 | | CD55 | SPARC | | BTNL8 | COX5B | MT-ND2 |
| ID2 | EMP3 | LMNA | CLIC2 | RND1 | | APOLD1 | ELF3 | ESPN | RPSA |
| EV12B | NACA | ATP1A1 | LDB2 | CDC42EP3 | | NRN1 | HN1 | ESYT2 | CLDN8 |
| KRTCAP2 | CALM2 | GYPC | MPZL2 | TIMP1 | | HES4 | POLD4 | PSMD9 | ASS1 |
| BEX5 | RPS3 | RMI2 | PEA15 | HES1 | | SOX17 | ST14 | ANXA2 | S100A6 |
| CISD2 | NDUFS8 | PPP1CC | MCAM | TSPAN4 | | LGALS1 | SLC6A8 | MT-ND1 | POLD4 |
| SEPW1 | COX7A2 | UBE2N | DLL4 | PLK2 | | ZFP36L1 | CLTB | TXN | MXD1 |
| ANXA1 | PLP2 | AGR2 | MFNG | ATP5G3 | | REM1 | LAMB3 | STMN1 | PFDN5 |
| RPN1 | CCR10 | PARP1 | C8orf4 | TXNIP | | ID1 | SLC51A | DEGS1 | SLC25A6 |
| EIF1 | TPD52 | MME | HLA-DPB1 | HLA-DMA | | NPDC1 | CLDN23 | PMM1 | MYO15B |
| FOSB | SELT | HCLS1 | BST2 | BAG3 | RPS2 | AC011526.1 | CDHR1 | HOXA11-AS | MLLT3 |
| HAX1 | ZNF706 | PABPC1 | PTPRB | PDLIM4 | GIMAP6 | CFI | TMEM45B | IP6K2 | TP53INP2 |
| IL32 | PIM2 | IGLL5 | TSPAN4 | MGP | ID1 | CYB5R3 | TMEM37 | TMEM176B | RPL18A |
| IFITM2 | HINT1 | RGS16 | ACTN4 | ID3 | TAGLN2 | EFHD1 | CHP2 | ZNHIT3 | UBA52 |
| TMED4 | UAP1 | CD1C | IPO11 | PHGR1 | ZFP36 | OAZ2 | GPRC5A | ATP5B | MT-CO2 |
| SEMA4A | SNRPD2 | RGS19 | DUSP6 | TIE1 | S100A13 | CD34 | HPGD | IFITM2 | ST3GAL4 |
| RAB30 | S100A10 | PAX5 | TEK | AGR2 | CYBA | NES | CKB | RPL36 | ITM2C |
| SLC17A9 | SLC35B1 | ETHE1 | GUK1 | SEMA6A | TACC1 | SRP14 | FCGBP | HMX2 | ATP5G2 |
| SLC38A5 | REEP5 | HLA-DQA2 | ID3 | HLA-B | LAP3 | HHEX | AK1 | TSC22D3 | LMO7 |
| CAPZB | TMEM66 | DCK | CDH5 | TAGLN2 | CFLAR | TMEM204 | ASS1 | ACADSB | RPL34 |
| PTPRCAP | ATRAID | ITSN2 | IMP3 | KRT222 | HSPA1A | C1QTNF1 | PRR15 | S100A4 | AGR2 |
| H3F3B | SOD1 | SH2B2 | TBCD | TMEM176A | LMCD1 | GABARAPL2 | ITM2C | RHEB | AC009133.21 |
| COPE | RPS23 | SUSD3 | CABP1 | SORBS2 | TINAGL1 | COL3A1 | TMPRSS2 | SPINT1 | SYTL2 |
| WNT10A | GUK1 | SRSF3 | GIMAP1 | ST8SIA4 | DLL4 | MYH9 | YBX1 | IMP4 | RAB27A |
| TMED9 | TMED4 | LYN | JUP | IFI6 | TNFRSF4 | DNAJB1 | S100A11 | LSMD1 | RPL37 |
| CUTA | RPS21 | SYPL1 | TNFRSF4 | LGALS4 | PTP4A3 | PHGR1 | PRR13 | ATPIF1 | CKB |
| E2F5 | DNAJC1 | ARPC1B | ARHGDIB | GIMAP8 | KDR | LGALS4 | KRT18 | ADH5 | VILL |
| HSPA1A | NDUFB2 | CTSD | PRX | KRT8 | SPTBN1 | ITGA7 | DHRS11 | H2AFJ | CA4 |
| SELT | MT-ND5 | IL16 | GRB10 | BAALC | HLX | HEY1 | HNRNPA1 | IGFBP2 | LINC01133 |

TABLE 15-continued

| | | | | | | | | |
|---|---|---|---|---|---|---|---|---|
| HES1 | NUCB2 | ZFAND6 | PCDH12 | FAM107A | ROBO4 | FAM222B | GNA11 | RAB4A | RP11-294O2.2 |
| EZR | PABPC1 | PRPSAP2 | NRP1 | JUN | PTPRB | HSPG2 | NDRG1 | SPATS2L | S100A14 |
| DUSP1 | RPL12 | MAP3K7CL | SRGN | S100A13 | IFI6 | GPR116 | CCL15 | AFAP1L2 | MEP1A |
| RNU12 | ATF4 | S100A10 | ERG | ZFP36 | FAM110D | TACC1 | RPL27 | WFDC2 | CYBA |
| PAIP2B | DNAJB9 | PXK | NKX2-3 | A2M | ATOH8 | BBX | SPINT1 | DNAJB1 | MT-CO3 |
| SPINK2 | B4GALT3 | RP11-960L18.1 | CLIC4 | DTL | APLNR | SH3BP5 | DEFB1 | SKAP2 | PKIB |
| SLC35B1 | HNRNPA1 | CCR7 | TUBA1B | EID1 | LPAR6 | C10orf10 | CFDP1 | HLA-DQB1 | KCNK1 |
| SMARCB1 | NEDD8 | LSM10 | SLC25A6 | PKP4 | PRMT1 | DHRS9 | ANXA5 | MAST2 |
| SEPP1 | CISD2 | LYPLA1 | LAYN | CCL21 | PALMD | TNS1 | RPL31 | EIF4A1 |
| DNAJC1 | KRTCAP2 | DCAF12 | TMEM255B | HLA-DQB1 | COL15A1 | FAM213A | PTPRH | PBXIP1 | CLDN23 |
| SEL1L | ERGIC2 | CTSH | GIMAP4 | LIMCH1 | SEMA3G | LCN6 | FLNB | COL27A1 | HPGD |
| HSP90AA1 | UQCRQ | TMEM243 | LIMCH1 | GADD45B | NDUFA12 | PPP1R14A | ACAA2 | MT-ND5 | SMIM5 |
| AC093818.1 | CNBP | TFEB | THBD | CD9 | RGS3 | FAM110D | PRSS8 | RAB25 | MALAT1 |
| HLA-A | LAMTOR4 | AC079767.4 | CD74 | CXorf36 | TMEM255B | RPLP1 | RPS11 | FRAT2 | SPINT1 |
| ICAM2 | COX6C | UBE2G1 | HLA-DPA1 | HAPLN3 | CHCHD10 | SDCBP | RPL37 | AOC1 | MT-ATP6 |
| TPI1 | CD44 | WIPF1 | TSPAN12 | VIM | COX4I1 | SOX7 | C10orf99 | GSTP1 | PRSS8 |
| EMB | LMAN1 | KIAA0125 | CDC42EP1 | ADCY4 | CD151 | GEM | RHOC | MT-CO2 | CLCA4 |
| QPCT | TMBIM4 | HNRNPC | COX7A1 | WARS | ARL2 | EMP2 | RPL34 | RTN4 | MT-ND4 |
| SPATS2 | CST3 | FXYD3 | SCARF1 | PLAT | SLC25A6 | LMO2 | EIF4A1 | TUBA1A | RPS3A |
| RHOH | C4orf3 | ID2 | TXNIP | ACVRL1 | ID3 | NEAT1 | CDA | RPS27L | EEF2 |
| APOE | EIF4A2 | CBX3 | SEMA3F | MEOX1 | SCARF1 | TIE1 | BLOC1S1 | CCDC14 | ST14 |
| MANEA | FXYD5 | SNAP23 | RHOA | CYB5A | GALNT18 | IGFBP6 | HHLA2 | FUT3 | MUC12 |
| IRF4 | NDUFB8 | MOB1A | LDHB | INPP1 | LIFR | COL4A1 | AHCYL2 | TP53I3 | HIST1H2AC |
| ANXA2 | AUP1 | DBNL | SORBS2 | LDB2 | SWAP70 | APLNR | LDHB | MCL1 | RHOC |
| IFITM1 | DDOST | DOK3 | TACC1 | IL1R1 | RPL29 | SEPP1 | GDPD3 | TSPO | RP11-665N17.4 |
| JSRP1 | GSTK1 | PLCG2 | ITGA6 | TMEM176B | SEC14L1 | PLK2 | HRCT1 | ZFP36L1 | RPL37A |
| COMMD3 | C19orf43 | KRT19 | KIFC3 | ARL4A | RPS19 | HYAL2 | MT-CO2 | CMTM8 | MT-ND1 |
| SRM | PRDX2 | IGJ | LGALS4 | CTHRC1 | RPL10A | RPS29 | FAM3D | PRDX5 | TSPAN3 |
| CXCL14 | SKP1 | SQRDL | TIE1 | PRCP | HLA-DMA | RNASET2 | ATP5G2 | HES6 | IGJ |
| SMDT1 | A1BG | FCRL3 | HLA-DRB5 | IFIT2 | RRAS | TAGLN2 | FAM132A | PTMA | RPS11 |
| MT-CO3 | SAP18 | RRAS2 | PRDX1 | TMEM173 | LCN6 | SLCO2A1 | SLC9A3R1 | NDUFB11 | EIF1 |
| RPS5 | TMA7 | CERS4 | PELO | FAM198B | WARS | PKIG | PKP3 | CHN2 | KRT19 |
| IL2RG | UBE2D3 | OSER1 | TP53I11 | FABP1 | EPHX1 | KRT8 | STAP2 | TMEM63A | HSP90AB1 |
| SRPR | DHRS7 | LMO2 | SERPINI1 | GPR146 | DUSP6 | RPS2 | SLC22A18 | RASSF7 | BEST2 |
| ERGIC2 | RPS15 | TAGAP | PPA1 | MLEC | JUNB | CXorf36 | ESPN | VIL1 | RASEF |
| PTMS | LGALS3 | FTL | FAM101B | MMP28 | PRKCDBP | LRRC32 | MT-CO3 | MT-ATP6 | AOC1 |
| PLP2 | PSMB6 | BTK | S100A6 | SQSTM1 | RPL18 | RHOA | VIM | CERS6 | SPDEF |
| OSTC | SDF2L1 | ATP5I | PPFIBP1 | KRT18 | RALB | GIMAP1 | TIP3 | ID3 | LGALS9C |
| CNPY2 | CHID1 | ANP32B | RPL12 | SERTAD1 | SORBS2 | LIFR | PCK1 | CDH17 | NPM1 |
| S100A4 | ATPSG3 | PTPRC | TMEM173 | IFITM1 | EIF1 | HDAC7 | CTSA | TMSB10 | PCK1 |

TABLE 15-continued

| Absorptive_TA_1 | Secretory_TA | Absorptive_TA_2 | Cycling_TA | Goblet_1 | Stem_cells | Enteroendocrine | Glial_cells | Inflammatory_fibroblasts | Fibroblast_pericytes |
|---|---|---|---|---|---|---|---|---|---|
| SRP14 | RBM39 | RCSD1 | ANKRD65 | LPAR6 | | ALPL | TSPAN4 | BSG | ARPC1B | PABPC1 |
| PPIB | LAMP2 | TUBB4B | PLXNA2 | RASIP1 | | FOS | C10orf54 | ARL14 | IFI6 | NLN |
| SIL1 | ATP6V0E1 | RPS4Y1 | APLN | ALDH1A1 | | RPS5 | CYBA | TSPAN8 | FAM200B | SEPP1 |
| GLRX | ITM2B | MLEC | CD93 | MX1 | | TMEM173 | IFIT3 | ENTPD8 | CDX2 | VIPR1 |
| CD69 | EVI2B | GSTP1 | ITGA1 | PTPRB | | CALM1 | HEG1 | CDH17 | HOXB9 | HNRNPA1 |
| RPL28 | EIF3H | CCNI | C10orf54 | NKX2-3 | | KLF2 | GIMAP5 | MT-ND5 | COX6A1 | GPRIN2 |
| SLC25A4 | SEC11C | HLA-A | VAT1 | PPP1R15A | | VWA1 | NQO1 | CDKN2B | AP1M2 | BTNL3 |
| TMBIM6 | UFM1 | RP11-138I18.2 | KLHDC8B | NEAT1 | | ADCY4 | IL3RA | PEX26 | RNF186 | QSOX1 |
| S100A11 | OS9 | NPM1 | PHGR1 | IGJ | | NES | PTPRB | SLC25A6 | RPS21 | SMIM14 |
| TNFRSF4 | C11orf31 | SGPP1 | TINAGL1 | MEIS2 | | ETS2 | KANK3 | SLC25A5 | SHC1 | BTNL8 |
| LGALS4 | ANXA7 | HSH2D | CYBA | GIMAP6 | | MGAT1 | IFITM1 | GGT6 | CD14 | ITLN1 |
| JTB | CALM1 | BLVRB | ME3 | SRGN | | SERPING1 | NKX2-3 | LSR | DPP7 | NEDD4L |
| RPL8 | PSMB3 | ORAI2 | TNFSF10 | CLDN7 | | SNX3 | TMEM176B | NLN | LYZ | GPR153 |
| THAP2 | TPT1 | TNFRSF17 | SERPINE1 | LAPTM4A | | COX7A1 | GPRC5B | RPL18A | SEPP1 | TDP2 |
| COTL1 | TAPBP | ALOX5 | RHOC | PLA1A | | ACTN4 | TCF21 | APOBEC3B | PERP | CYSTM1 |
| TIFA | CHPF | PTPN6 | EPHX1 | EPAS1 | | CARHSP1 | NDUFA12 | PABPC1 | RNF24 | SH3BGRL3 |
| TXNIP | ERGIC3 | ACTG1 | NDUFA12 | SLC41A3 | | ERG | ARID5B | EIF1 | TBC1D2B | CDHR2 |
| FCRLA | DERL2 | GPSM3 | PTMA | LAYN | | RPS4X | RAC1 | IL32 | MACROD1 | PTPRF |
| ENO1 | HIGD2A | MTMR14 | CCND1 | ASRGL1 | | RAC1 | TNFSF10 | SULT1A1 | MYO10 | ISG20 |
| CD151 | 15-Sep | FAM65B | GIMAP5 | FOS | | CYB5R3 | EPHX1 | LMO7 | RPS11 | LSR |
| BRSK1 | ARPC2 | TFF3 | RPLP1 | IFI6 | | LRRC32 | PRKCDBP | CGN | IFITM3 | FBXO32 |
| ARPC1B | NDUFB4 | KLHL5 | GPX1 | CSF2RB | | IMP3 | ITGA1 | RPL37A | EPHB3 | OASL |
| A2M | RPLP2 | GRB2 | RBP7 | CSRP2 | | RNASET2 | PLAU | S100A14 | ASMTL | RPL23 |
| AC104024.1 | ST13 | GNG7 | KRT8 | C10orf128 | | BTNL9 | FAM162B | LLGL2 | YPEL5 | CYP3A5 |
| LMTK3 | JTB | CCDC69 | SEC14L1 | DDX5 | | RPL13 | DUSP1 | IFITM3 | H2AFY2 | SLC26A3 |
| SSR1 | ATP5D | CR2 | CHCHD10 | GBP2 | | YBX3 | ACTN4 | MVP | STK38 | PRAP1 |
| RNASET2 | NUDT22 | TMEM141 | PKIG | IFI44L | | HPCAL1 | APOL3 | CLCN2 | JUNB | MT-ND5 |
| COX5B | GNL3 | DDX39A | PSMB5 | TIMP3 | | RPS18 | COL6A2 | TPRN | PPAP2A | SLC44A4 |
| SEC61A | NDUFB11 | SRGN | ARHGEF15 | EIF4A2 | | ELK3 | ROBO4 | ACOX1 | LACTB2 | KCNK5 |
| HSH2D | NHP2L1 | MEF2C | SCARB1 | EVA1C | | KLF4 | UBC | AKR1B10 | TAGLN2 | RASSF7 |
| ATP5E | ARF1 | HLA-DRB5 | PRKCH | IDH2 | | PVRL2 | IGJ | CA12 | SMARCC1 | H2AFJ |
| DCN | SEC61A1 | LAMTOR4 | MCF2L | RAB13 | | RHOC | WNT6 | MT-ATP6 | GAPDH | CA1 |
| CHID1 | CHMP2A | REL | GPR116 | NEDD9 | | SNHG7 | TMEM255B | MPST | AC005355.2 | STARD10 |
| MT-CO1 | RPL14 | KIAA0226L | DYNLL1 | DNAJB4 | | CTNNBIP1 | COL15A1 | TSPAN3 | TMPRSS2 | CDH1 |
| RP11-16E12.2 | NPM1 | PRDX5 | HEG1 | NR2F2 | | RPL28 | ADAMTS1 | FAU | C7orf55 | STAP2 |
| ERGIC3 | ARMCX3 | CCDC109B | OSBPL1A | CAPG | | RASIP1 | RPL10 | PARK7 | AC005355.2 | STX19 |
| TXNDC5 | SRPR | PPDPF | ARL2 | IPO11 | | HYAL1 | PTMA | C1orf106 | TSPAN13 | PLAUR |
|  |  |  |  |  |  |  |  |  | SNX3 |  |

| Absorptive_TA_1 | Secretory_TA | Absorptive_TA_2 | Cycling_TA | Goblet_1 | Stem_cells | Enteroendocrine | Glial_cells | Inflammatory_fibroblasts | Fibroblast_pericytes |
|---|---|---|---|---|---|---|---|---|---|
| TXN | MT-ND1 | FABP1 | EPCAM | TFF3 | B2M | PCSK1N | CRYAB | VCAM1 | RGS5 |
| GPX2 | B2M | SELENBP1 | LGALS4 | KLK1 | LEFTY1 | CRYBA2 | ALDH1A1 | NNMT | BGN |
| MGST1 | TFF3 | CA2 | MGST1 | ITLN1 | TMSB4X | SCGN | GPM6B | LUM | CSRP2 |
| EPCAM | MT-ATP6 | LGALS4 | AGR2 | FCGBP | ASCL2 | CHGA | PLP1 | SOD2 | NDUFA4L2 |

TABLE 15-continued

| | | | | | | | | | |
|---|---|---|---|---|---|---|---|---|---|
| AGR2 | PRDX5 | C15orf48 | C15orf48 | AGR2 | MT-ND4 | PYY | SPP1 | CCL2 | MYL9 |
| C15orf48 | MUC2 | S100A14 | GPX2 | CLCA1 | LGALS4 | SCG5 | S100B | TDO2 | MFGE8 |
| PPP1R1B | FCGBP | PHGR1 | KRT8 | LRRC26 | SMOC2 | GCG | FXYD1 | COL3A1 | TINAGL1 |
| LGALS4 | KLK1 | KRT19 | CLDN7 | RETNLB | PRDX5 | FEV | PRNP | C1S | TSC22D1 |
| HMGCS2 | RPL36 | ETHE1 | CLDN3 | MUC2 | RGMB | MS4A8 | PMP22 | MFAP4 | COX4I2 |
| TSPAN8 | AGR2 | FXYD3 | PIGR | WFDC2 | MT-CYB | TTR | CLU | C1R | FRZB |
| C10orf99 | PIGR | LGALS3 | HLA-DPA1 | SPINK1 | FXYD3 | CACNA1A | TUBA1A | MMP2 | ADIRF |
| UGT2B17 | ITLN1 | UQCRQ | PHGR1 | SPINK4 | GPX2 | PRDX5 | CD9 | CTSK | TPPP3 |
| ATP5B | GPX2 | PIGR | FXYD3 | KRT18 | CDCA7 | HLA-C | MPZ | PDPN | HIGD1B |
| CLDN7 | ATP5G1 | COX5B | TXN | REP15 | MT-CO3 | HOXB9 | SPARC | FBLN1 | COL18A1 |
| S100A14 | MT-ND1 | MT-ND1 | ARHGDIB | ZG16 | TSPAN8 | FXYD3 | NRXN1 | DCN | GPX3 |
| PHGR1 | EPCAM | MT-CO2 | VIM | SERPINA1 | PHGR1 | STARD10 | DKK1 | CTSC | SOD3 |
| ELF3 | LGALS4 | COX4I1 | ELF3 | TPSG1 | MT-ND2 | RAB26 | CYR61 | RARRES2 | IGFBP7 |
| PIGR | ZG16 | C10orf99 | HLA-DPB1 | LGALS4 | MT-ND1 | B2M | LG14 | GPX3 | NET1 |
| CDX1 | MT1G | MT-CO3 | BST2 | ST6GALNAC1 | EPCAM | LGALS4 | MATN2 | APOE | CALD1 |
| MT1G | CLDN3 | MT-ND4 | TUBB4B | FAM3D | ELF3 | PHGR1 | TUBB2B | SELM | 4-Sep |
| CLDN3 | FABP1 | MT-ATP6 | CD74 | KRT8 | PIGR | RAB3B | ANXA2 | CALD1 | TPM2 |
| FABP1 | PHGR1 | MT1G | KRT18 | EPCAM | HLA-C | KRT18 | PMEPA1 | IFITM3 | SERPINI1 |
| FXYD3 | KRT8 | TST | S100A14 | STARD10 | MT-ATP6 | MARCKSL1 | PCSK2 | TMEM176A | NOTCH3 |
| KRT8 | CLCA1 | ATP5G3 | MT1G | PHGR1 | MT-ND3 | MDK | PEBP1 | CYGB | PGF |
| COX5A | COX4I1 | KRT8 | ARPC1B | SMIM22 | KRT8 | SLC29A4 | GFRA3 | DYNLT1 | HES4 |
| ATP5G3 | CLDN7 | CA1 | ATP5G1 | FXYD3 | MT-CO1 | KRT8 | CAPS | COL1A2 | ACTA2 |
| KRT18 | TMEM54 | TMEM54 | HMGCS2 | GMDS | PPP1R1B | EPCAM | CALM2 | ADAMDEC1 | MGP |
| PRDX5 | FXYD3 | CHCHD10 | KRTCAP3 | HEPACAM2 | EPHB3 | ELF3 | MYOT | WARS | ISYNA1 |
| CYC1 | MT-ND2 | ATP5G1 | CD9 | RNASE1 | SMIM22 | SST | L1CAM | TMEM176B | PDGFRB |
| RPLP0 | RPS14 | SLC26A2 | HLA-DRB1 | KRT19 | KRT18 | HLA-B | S100A1 | COL6A2 | SPARC |
| ATP5G1 | MALAT1 | TXN | PPP1R1B | MT-ND1 | HSPB1 | TMSB4X | COMT | CFD | FAM162B |
| MT1E | IGJ | B2M | CLDN4 | CLDN3 | CLDN7 | ARX | CD59 | GGT5 | HSPB1 |
| SLC25A5 | KRT18 | CLDN7 | TSPAN8 | VSIG2 | CLDN4 | VIM | PLEKHB1 | NDN | H2AFJ |
| TIMP1 | CLDN4 | CES2 | HLA-DRA | C15orf48 | RPS18 | CLDN3 | TIMP3 | FOXF1 | BCAM |
| LEFTY1 | RPL37A | COX7A2 | SUCLG1 | PIGR | C15orf48 | HLA-DPA1 | CDH19 | NINJ1 | PLXDC1 |
| FAM3D | RPS29 | UQCR10 | CDX1 | CLDN7 | HMGCS2 | C15orf48 | SMIM5 | PLAU | CD36 |
| UQCRH | MT-CO2 | COX6C | NUPR1 | ANXA13 | HLA-B | FABP1 | TSPAN11 | LAP3 | CAV1 |
| KLF5 | RPS18 | COX6B1 | FAM3D | SPDEF | RPS24 | RPL37A | NTM | EMILIN1 | DSTN |
| CHCHD10 | C15orf48 | HMGCS2 | CYC1 | MT-CO3 | RPS21 | MLXIPL | C8orf4 | IGFBP7 | PRSS23 |
| CLDN4 | MT-CO3 | AKR1C3 | FABP1 | TMEM141 | CLDN3 | COX6C | CNN3 | STMN2 | REM1 |
| LGALS3 | TSPAN8 | CKB | PRDX5 | ANG | RPL36 | C19orf77 | MAL | CXCL14 | LHFP |
| SUCLG2 | EIF1 | EPCAM | SMIM22 | COX6C | SPINK1 | HLA-DRA | FIBIN | EPSTI1 | COL4A2 |
| CD9 | SPINK1 | HSD11B2 | LGALS1 | ELF3 | RPL37 | NEUROD1 | FBLN2 | HAPLN3 | RGS16 |

TABLE 15-continued

| | | | | | | | | | | |
|---|---|---|---|---|---|---|---|---|---|---|
| TSPO | RPL35 | SMIM22 | AGR2 | TMEM141 | S100A14 | MT-CO2 | CPE | CCL2 | CD63 | LURAP1L |
| KRT19 | SMIM22 | SMIM22 | TMEM54 | TMEM54 | HMGCS2 | RPS6 | SMIM22 | CBR1 | GBP1 | TPM1 |
| SMIM22 | SPINK4 | MT-ND5 | CKB | CKB | BEST2 | SLC12A2 | TSPAN1 | FGFBP2 | SPARC | TAGLN |
| C19orf33 | STARD10 | AMN | CST3 | CST3 | MB | RPL37A | HLA-DRB1 | ARHGAP15 | COL1A1 | EGR1 |
| NXPE4 | FAM3D | MGST1 | NDUFAB1 | NDUFAB1 | FABP1 | S100A14 | TFF3 | LGALS1 | PKIG | IFITM3 |
| B2M | MT-CYB | MT-CYB | C10orf99 | C10orf99 | CREB3L1 | RPL31 | IGJ | JUN | LGALS1 | HLA-C |
| SUCLG1 | MT-ND3 | COX8A | ITM2C | ITM2C | RPL36 | RPL12 | HLA-DPB1 | PRKCDBP | SERPING1 | EHD2 |
| ATP5A1 | RPS21 | C19orf33 | TMSB4X | TMSB4X | GPX2 | MT1G | CLDN4 | SNCA | CFH | MEST |
| ATP5F1 | CD74 | TMEM141 | ARPC2 | ARPC2 | CLDN4 | BST2 | ITM2B | RPS6 | DMKN | PKIG |
| GAPDH | HLA-DPA1 | COX6A1 | HLA-DRB5 | HLA-DRB5 | S100A6 | ACTB | SEPP1 | IGFBP7 | SERPINF1 | LGALS1 |
| COX4I1 | HLA-C | AKR7A3 | SPINK1 | SPINK1 | RP11-234B24.2 | MARCKSL1 | IFITM3 | NDRG2 | PAQR5 | STOM |
| COX5B | WFDC2 | MT1E | PLP2 | PLP2 | URAD | PDZK1IP1 | RTN1 | COL9A3 | THY1 | A2M |
| RP11-519G16.5 | ATP5I | GOLM1 | SPINT2 | SPINT2 | TCEA3 | MGST1 | SPINK1 | ST6GALNAC2 | SOD3 | STEAP4 |
| TMEM54 | TMEM141 | AKR1B10 | HLA-DMA | HLA-DMA | TSPAN8 | RNF186 | LDHA | TTR | | PTGIR |
| ETHE1 | ELF3 | PRSS3 | HLA-DMB | HLA-DMB | MT1G | GNB2L1 | VWA5B2 | TMEM176B | CNOT4 | RPLP2 |
| UQCRC2 | RETNLB | CLDN3 | MT1E | MT1E | TSPAN1 | RPS3 | CD74 | RPS2 | LINC01082 | PTK2 |
| CA2 | TIMP1 | CISD3 | COX5A | COX5A | TMEM61 | RPLP0 | RPL36 | FOS | TNFRSF1A | RBPMS |
| TMEM141 | HMGCS2 | ATP5D | ATP5B | ATP5B | RAP1GAP | ETS2 | SOX4 | APIS2 | PMP22 | EPS8 |
| HLA-E | RPS3 | MT-CO1 | ECH1 | ECH1 | C10orf99 | HLA-A | SCT | WISP2 | GSTT1 | PPP1R14A |
| CDX | PPP1R1B | MT-ND2 | TUBA1A | TUBA1A | REG4 | CD63 | BEX2 | HES1 | SGCE | SRGN |
| COX6C | RPS15 | CHP2 | IGJ | IGJ | PRDX5 | CST3 | ISL1 | VIM | TPM2 | COL3A1 |
| C1QBP | TMEM54 | H3F3B | FXYD5 | FXYD5 | MT-ND4 | ARHGDIB | ANXA5 | RGS16 | A2M | GEM |
| RPSA | KRT19 | KRT18 | SELENBP1 | SELENBP1 | CCL15 | FAM3D | GSN | FEZ1 | TFPI | CRIP2 |
| KRTCAP3 | MT1E | NDUFA1 | ETFB | ETFB | UQCRH | MT-ND5 | RPS29 | SORBS2 | CLEC11A | ZFP36L1 |
| OLFM4 | ZFP36 | VSIG2 | HLA-DQB1 | HLA-DQB1 | H3F3B | CKB | S100A14 | FCGR2B | FTH1 | ARID5A |
| UQCRFS1 | RPL12 | TIMP1 | SRI | SRI | NANS | RPS4X | HOXB8 | IFITM3 | MFGE8 | ARVCF |
| S100A10 | KRTCAP3 | COX7C | KRT19 | KRT19 | NPDC1 | GSN | CHGB | RP4-792G4.2 | SPON2 | EPHX1 |
| ATP5C1 | COX5B | FAM3D | KLF5 | KLF5 | MT-ATP6 | C10orf99 | GUCY2C | RHOB | GBP4 | HLA-A |
| H3F3B | IGLL5 | PDE4C | IGLL5 | IGLL5 | MT-CYB | FABP1 | FXYD5 | TMEM176A | C2 | ADAMTS1 |
| GSN | RPS9 | EIF1 | LGALS3 | LGALS3 | MT-CO2 | ALDH1B1 | CLDN7 | ART3 | SFTA1P | PRKCDBP |
| MRPL12 | MGST1 | COX5A | HADH | HADH | IGJ | MT1E | HLA-DMA | EGR1 | LAPTM4A | MAP3K7CL |
| CD74 | C10orf99 | LGALS1 | CDX2 | CDX2 | MT-ND2 | TRABD2A | HLA-DRB5 | RPL8 | TIMP1 | NDUFAF4 |
| CKMT1B | RPL8 | CD74 | UQCRC1 | UQCRC1 | IGFBP2 | KLK1 | KRT19 | TUBB2A | CDH11 | C1R |
| SLC25A6 | ITM2B | TSPAN1 | SMAGP | SMAGP | SPINT2 | SELENBP1 | PRDX2 | PDLIM4 | LY6E | CALM2 |
| ARHGDIB | RPLP2 | CLDN4 | TIMP1 | TIMP1 | EIF1 | STARD10 | SPINT2 | IL11RA | PLAT | C8orf4 |
| RPS2 | CHCHD10 | TSPAN8 | ACTB | ACTB | C2orf82 | AGR2 | EIF1 | RPS19 | CEBPB | SDC2 |
| MPC2 | UBC | SLC22A18AS | LY6E | LY6E | COX5A | RPL26 | ETV1 | ANXA5 | APOL1 | TCF21 |
| SELENBP1 | HLA-DRB1 | CYC1 | COA3 | COA3 | IFI27 | SPINT2 | HLA-E | SOCS3 | PROCR | ESAM |

TABLE 15-continued

| | | | | | | | |
|---|---|---|---|---|---|---|---|
| RPS24 | COX6B1 | MT-ND3 | COTL1 | HES6 | ARPC1B | QPCT | RPS18 | TMEM205 | HEYL |
| RPS18 | ATP5D | ATPIF1 | IGFBP2 | COX5B | KRT19 | KIF12 | PHLDA3 | GADD45G | KNOP1 |
| MAOA | NDUFB11 | UQCR11 | ACADS | TIMP1 | RPS5 | DDC | NRN1 | EVA1A | EFHD1 |
| RPL8 | C19orf33 | ELF3 | PLA2G2A | CDC42EP5 | RPS2 | LITAF | TSPAN15 | ICAM1 | SERPING1 |
| CKB | S100A14 | SDCBP2 | STARD10 | FOXA3 | RPL13 | TMEM144 | MIA | FHL2 | RCAN2 |
| MPST | HLA-DRA | ATP5I | CES2 | S100A4 | TFF3 | TMEM61 | COL18A1 | KLF6 | C1QTNF1 |
| IGJ | RPS5 | IGJ | TST | PPDPF | S100A11 | MT-ND3 | RPLP1 | LGALS3BP | RBPMS2 |
| TRABD2A | COX5A | LEFTY1 | CKMT1B | ZG16B | MYL6 | COX5A | SPARCL1 | RCN1 | SERPINH1 |
| ATP5O | RPS12 | TSPO | ATP5G3 | MT-CO1 | AQP1 | IGLL5 | TPT1 | BST2 | NDRG2 |
| RPS6 | RPL13 | SRI | CISD3 | IL1R2 | FERMT1 | LY6E | C1orf198 | CCL8 | FXYD6 |
| HINT1 | ARHGDIB | UQCRC1 | | TMEM176B | MT-ND4L | MPC2 | SCCPDH | GALNT11 | COL6A1 |
| SPINK1 | C2orf82 | MGST3 | ISG15 | HSD11B2 | RABAC1 | IFITM2 | IGFBP3 | S100A10 | GPRC5C |
| HLA-DPA1 | RPS8 | S100A6 | RARRES2 | CD9 | HLA-DPA1 | UCP2 | ECM1 | S100A4 | MAP1LC3A |
| ECH1 | RPS2 | MRPL41 | MPC2 | BTG1 | RPL29 | NDUFB11 | CYR61 | RPL11 | RERG |
| PHB | TCEA3 | TCEA3 | HLA-E | UQCR10 | LY6E | COX6B1 | F3 | RASSF4 | GUCY1B3 |
| CES2 | HLA-DPB1 | NDUFB9 | ECHS1 | IFIT172 | HLA-E | HEPACAM2 | HSD11B1 | TNFAIP6 | ASPN |
| AKR1C3 | LEFTY1 | COX7B | CKMT1A | COX6B1 | SLC25A6 | HLA-A | CEBPD | SGCE | EPAS1 |
| CKMT1A | ACTB | ZFP36 | UQCRQ | TPM1 | TIMP1 | COX4I1 | IGFBP6 | COL1A2 | CTSF |
| PLA2G2A | LRRC26 | ATP5J | GGH | ZFP36 | RPL8 | CXXC4 | EFEMP2 | NNMT | UBA2 |
| RPL5 | MUC5B | ATP5B | TSPO | SERF2 | CD74 | KIAA1324 | SEPP1 | CADM4 | GUCY1A3 |
| UQCR10 | NUPR1 | SLC39A5 | MPST | TSTA3 | RPL35A | TPH1 | PRR24 | TAX1BP3 | RPS14 |
| IGFBP2 | MT-ND5 | KRTCAP3 | ATP5F1 | MGST1 | RPL10A | VAMP5 | COL18A1 | RPL19 | LRRC32 |
| COX7C | CKB | NXPE4 | COX4I1 | TSPAN13 | KRTCAP3 | ATP5G1 | NAB2 | RPS3 | MSC |
| COX6B1 | UQCR10 | GPT | ATPIF1 | C19orf33 | UBB | RPS9 | SCARA5 | TFAP2A | NR2F2 |
| LCN2 | SELENBP1 | MS4A12 | CYCS | MT-ND3 | RPS12 | MT-ND4 | TNFAIP6 | RCAN1 | LGALS3BP |
| RPL7A | RPL27A | ANXA5 | UQCRH | ATP5G3 | KLF5 | SLC25A6 | TNIP2 | IER2 | ANGPT2 |
| ZFP36 | MT-CO1 | ACADS | ZFP36 | FAM195A | NOS2 | MT-ND1 | TCF21 | MYL9 | CD151 |
| RPS8 | UQCRQ | SLPI | MACROD1 | ITM2B | RPL5 | ERI3 | PRR16 | RPS14 | SORBS3 |
| CMBL | STRA13 | PXMP2 | COX5B | RAB25 | OLFM4 | ZFP36 | IFI35 | GPNMB | MCAM |
| FAM84A | RPL7A | NDUFB2 | STAP2 | FTL | SOX4 | S100A11 | PTGIR | TUBA1B | COL1A2 |
| PEBP1 | RPL32 | FAM162A | RPLP0 | CDX1 | RPL32 | RPS14 | BRCC3 | GPX3 | GNG11 |
| S100A4 | RPS19 | DBI | RP11-519G16.5 | STAP2 | RPS23 | NPC2 | EID1 | FAM210B | PTMS |
| STARD10 | CISD3 | ARHGDIB | COX6C | DNAJA1 | SEPP1 | PCBD1 | ID3 | POSTN | MYH11 |
| HLA-C | TPSG1 | PPP1R14D | RGS10 | TMEM54 | GUK1 | RPS21 | CADM2 | PSMA2 | RNASET2 |
| IGFBP7 | AMN | GPX2 | SLC44A4 | FABP2 | COX5A | CKB | GATM | APOC1 | RPLP1 |
| PPP1R14D | URAD | UQCRH | NANS | ATP5I | RPS8 | ATP5G2 | HSPB2 | CXCL1 | THY1 |
| HLA-DPB1 | MT2A | TMEM45B | NDUFV1 | CHCHD10 | MLXIP | GPBAR1 | RHOC | S100A13 | TGFBI |
| PDE4C | RPLP1 | CYSTM1 | RPS18 | ARPC1B | CEACAM5 | SELENBP1 | RPLP2 | CD302 | COL6A2 |
| RPS3A | TSPO | MYO1A | B2M | TSTD1 | RPS19 | NDUFA3 | RPL18 | RBP1 | ASAH1 |
| PCK1 | COX6C | CDHR5 | NBL1 | UBC | QTRT1 | SMIM6 | NGFR | EMP3 | PLOD2 |
| GSTA1 | RPL18 | SLC44A4 | ALDH2 | PPP1R1B | IFITM3 | RPS11 | HSPA2 | BSG | RARRES2 |
| RPL26 | DUSP1 | DHRS11 | GNAI2 | DDX5 | STXBP6 | KLK1 | ASPA | SPG20 | EFEMP1 |
| STAP2 | HERPUD1 | ADIRF | C1QBP | ACTB | RPL14 | BAIAP3 | FST | TNFRSF11B | SOCS3 |
| RPS3 | RPS6 | PPP1R1B | S100A4 | MLPH | CDX1 | RPS2 | MARCKS | UBE2L6 | RPS18 |
| RPL10A | TMSB10 | CKMT1B | MLEC | ETHE1 | RPL30 | RPL18 | KCNMB4 | IL7 | RPS19 |
| SEPP1 | RPSA | MT1M | SUCLG2 | SH3BGRL3 | RPS9 | RPL12 | SBSPON | PSME2 | LBH |
| ATP5I | ARPC1B | HLA-C | MINOS1 | KIAA1324 | | MYL12A | PSAP | SCT | SELM |

TABLE 15-continued

| | | | | | | | | |
|---|---|---|---|---|---|---|---|---|
| FAM162A | DDX5 | ITM2B | S100A10 | KRT20 | RPL7A | TM4SF5 | OLFML2A | IL11 | NEXN |
| UQCRC1 | ATP5G3 | PKIB | OAZ1 | HSPA1A | CDX2 | CADPS | RPL10 | SRGN | CDS2 |
| TCEA3 | UQCRH | USMG5 | PSAP | STRA13 | HLA-DRB1 | C21orf58 | SEPP1 | IGJ | GADD45B |
| CHP2 | NDUFA1 | FAM195A | ATP5I | IFITM2 | IFI27 | DNAJC12 | C1S | ARID5B | COX7A1 |
| RPL31 | ANXA5 | FCGBP | TIMM13 | CKB | RPS14 | CTSC | RPL13A | EDEM2 | FKBP7 |
| ATP5D | TIMM13 | IFITM3 | SEPP1 | AC011523.2 | IFITM2 | PPT1 | CXXC5 | PSMA4 | HLA-B |
| RPL37A | HLA-B | MPC2 | HSPD1 | HLA-C | TXN | RARRES1 | S100A6 | TAP2 | CD248 |
| SRI | COX8A | S100A10 | RPL36 | UGT2B17 | RPL34 | RPS3 | EMP2 | IFI6 | PTRF |
| HLA-DRB1 | CDX1 | MISP | UQCRFS1 | ENTPD8 | ISG15 | DNAJA1 | RPL13 | FBLIM1 | F2R |
| SELK | HLA-E | STAP2 | ATP5A1 | COX4I1 | HLA-DPB1 | SNX3 | MXRA8 | COL5A2 | MRVI1 |
| TSPAN1 | SEPP1 | MGAT4B | ANXA5 | CST3 | IGJ | NGFRAP1 | SERPING1 | FOSB | NFASC |
| RPS23 | CDC42EP5 | SULT1A1 | HLA-C | RGCC | PFN1 | ISG15 | RPS4X | ATP5E | PPIL4 |
| SOCS3 | SNX3 | PYCARD | S100A6 | B2M | AP003774.1 | CDX1 | RPL31 | PCOLCE | STK16 |
| RAB25 | CYC1 | ATP1A1 | SFN | RAB15 | GPR160 | RPL38 | RPL28 | COL14A1 | SMDT1 |
| MT1X | HLA-DRB5 | DNAJA1 | ATP5O | CD74 | H3F3B | C12orf75 | SRGN | ETHE1 | NF2 |
| COX6A1 | MRPL12 | ZG16 | AP1M2 | NDUFA1 | TAX1BP3 | PPP1R1B | FGL2 | CDK2AP2 | ATF3 |
| NACA | HLA-DMA | ASL | MT2A | MT1E | RPS8 | | TBCB | IFITM2 | APOE |
| RPS29 | IFITM2 | NPM1 | RAC2 | ERI3 | HLA-DRB5 | ENTPD2 | ANXA5 | | FLNA |
| GMDS | RPL28 | MPST | RGCC | TST | HLA-DMA | LYZ | SELM | TRIM47 | TUBA1A |
| COA3 | RPL38 | MUC4 | GSN | ERN2 | S100A4 | HMGCS2 | PHLDA1 | TSPAN4 | RRAD |
| UBC | RPS11 | UBC | STRA13 | TNNC2 | NUPR1 | PAM | EID1 | PDGFRA | TRIB2 |
| RPL36 | DNAJA1 | SLC26A3 | ATP5I2 | NEURL1 | RPL18 | PLA2G12A | NGFRAP1 | ISG15 | OAZ2 |
| SPINT2 | HLA-A | SLC51B | CA2 | GSN | RPL27A | ACTB | ANGPTL7 | CD276 | RPL19 |
| ITM2C | RPL37 | URAD | PEBP1 | LGALS3 | RPS15 | SPINK4 | RPS8 | ADM | HRC |
| IFITM3 | COX7C | HLA-B | TYMP | CAMK2N1 | HLA-DRA | IFITM1 | RPL26 | APH1A | HCFC1R1 |
| ETHE1 | S100A4 | | PRDX2 | SMAGP | RPS15A | COX8A | JUNB | IL34 | HEY2 |
| DNPH1 | HLA-DQB1 | HLA-E | H3F3B | IFITM3 | ANXA5 | IGFBP2 | SLITRK6 | FILIP1L | C11orf96 |
| ISG15 | MZT2B | CDH17 | SQRDL | TSPO | RPL38 | TSTD1 | RPS12 | MAD2L2 | LAPTM4A |
| SLC25A3 | LITAF | CKMT1A | GJB1 | CAPN9 | TMEM54 | LYPD8 | RPL15 | ADD3 | RPL27A |
| UGT2A3 | ISG15 | ANPEP | PBK | MALAT1 | FXYD5 | RPSA | RPL12 | TAGLN2 | RPL11 |
| SLC39A5 | TRABD2A | SLC25A5 | RPL37A | CDX2 | RPL24 | C4orf48 | SLC22A17 | PHGR1 | ARHGEF17 |
| RPL12 | MZT2A | ABCC3 | UCP2 | TMEM176A | RPS29 | HLA-DQB1 | RERG | SQSTM1 | CACNA1H |
| RPL29 | TSC22D3 | UQCRFS1 | TPM4 | IGLL5 | PSMB9 | GPX2 | PCBP4 | PLAC9 | TGFB1I1 |
| FAM195A | TSTD1 | IGLL5 | CHCHD10 | SLC44A4 | ARSE | MLXIP | CADM1 | MESDC2 | COTL1 |
| URAD | ARPC2 | DUSP1 | TMEM98 | TTC39A | RPSA | LAP3 | RPS23 | NR2F1 | PLEKHA4 |
| NDUFA10 | ECI1 | TRMT112 | ADIRF | COX7B | RPL11 | ATP5E | ATF3 | SERPINH1 | RPS13 |
| SQRDL | ETFB | IFITM2 | DDT | OAZ1 | CTSC | HSPA1A | RPS27A | NUBP2 | GULP1 |
| HSPD1 | MPC2 | SHD | AKR1B10 | COX8A | EEF1B2 | AGR2 | ITPR1 | LAMA4 | PARM1 |
| DDT | IGFBP2 | JUNB | S100A16 | JUNB | ARPC2 | TNNC1 | LGALS3BP | CYB5R1 | OLFM2 |
| IFITM2 | PLA2G2A | TSC22D3 | PLEKHJ1 | UQCRQ | CAPZB | TPPP3 | FSTL3 | TSPAN9 | RPS5 |
| NUPR1 | TST | ATP5E | LGALS3BP | MARCKSL1 | ZKSCAN1 | SOCS3 | RPS5 | SEC63 | RASL12 |
| TPI1 | GSTP1 | TMSB10 | ARPC3 | SCNN1A | TYMP | MT-ATP6 | FAU | DKK3 | S100A10 |

TABLE 15-continued

| | | | | | | | | |
|---|---|---|---|---|---|---|---|---|
| NOX1 | HIST1H4C | TXNDC17 | NOX1 | LYPD8 | KIAA1324 | QTRT1 | F10 | RPS6 |
| ACADS | SDCBP | HLA-DRA | EEF1B2 | COX7A2 | LRIG1 | HERPUD1 | AGT | ITGA7 |
| ATPIF1 | DNPH1 | SQRDL | FAM162A | CTD-2547H18.1 | IMPDH2 | EIF1B | COX5B | DOCK7 |
| TSC22D3 | RPL31 | CIRBP | RPS14 | RASD1 | GLTSCR2 | MRPL41 | BBIP1 | ANGPT1 |
| TMSB10 | SOCS3 | SERINC2 | GGCT | CIRBP | RNF43 | CD55 | TNIP1 | CD74 |
| RPS27A | S100A4 | DDT | RPS8 | KRTCAP3 | RPS27A | PEMT | COTL1 | CLMN |
| ANXA5 | PRDX2 | LDHB | TCEA3 | H1F0 | ATP1A1 | PRSS3 | IFIT1 | ENTPD3 |
| PRSS3 | RP11-357H14.17 | NDUFB7 | GMDS | NXPE4 | PSME2 | C10orf54 | IFITM1 | RPL36 |
| TFF3 | COX7B | CMBL | RPS6 | RPS24 | RPL23 | CKMT1A | PTGDS | MAB21L2 |
| GOLM1 | HSPA1A | IF127 | ETHE1 | RPL37A | RPS7 | TCEA3 | CD40 | ILK |
| RPS15A | RARRES2 | AOC1 | LAMTOR4 | PCBD1 | DYNLL1 | TYMP | ALDH1A3 | COASY |
| HLA-B | CLUH | RAB25 | MT-ND1 | YPEL5 | RPLP2 | S100A4 | ACP5 | RPL28 |
| MACROD1 | RPLP0 | KLF5 | RPL8 | HLA-E | LGR5 | PSMB9 | NUPR1 | MSRB3 |
| PXMP2 | MPST | PCK1 | SH3BGRL3 | MUC1 | OAZ1 | RPL18 | GSN | CYGB |
| TST | SPINT2 | SPINT2 | HLA-B | ITM2C | SOCS3 | RPS15 | OS9 | PDE1A |
| COX7A2 | TXN | TCEB2 | IMPDH2 | ATP5G1 | EIF3D | MT1G | MRFAP1 | FHL2 |
| AP1M2 | GSN | NDUFA2 | TUFM | KCNMA1 | SUCLG1 | RPL32 | CLEC2B | CCL2 |
| TUBB | UQCRC1 | C2orf82 | PXMP2 | PRR15L | HSPA1A | PIGR | ARHGDIB | ZNF580 |
| IGLL5 | CES2 | HERPUD1 | NDUFA10 | RPL26 | URAD | MT-CO3 | GNG11 | CASC3 |
| GJB1 | RPL29 | S100A16 | LYZ | HLA-DRB1 | PTGDR | CUTA | NUMA1 | SH3BGRL3 |
| EIF1 | ATPIF1 | GSN | PHB | CYC1 | CHDH | KIAA1456 | PPAP2B | HLA-F |
| ARPC1B | ST6GALNAC1 | HNRNPA1 | VIL1 | AGR3 | KCNN4 | CTSD | LGALS4 | TMEM98 |
| CISD3 | MGAT4B | BCL2L15 | NDUFA1 | FFAR4 | PSMA7 | RAC1 | SYPL1 | RRAGA |
| PKIB | MLEC | LAPTM4A | ACTR3 | AMN | TAGLN2 | QDPR | FBN1 | LINC00152 |
| GPR160 | REP15 | UGT2B17 | HINT1 | RPS29 | C19orf33 | C19orf45 | FABP1 | LGI4 |
| MRPS33 | IFI27 | STARD10 | RAB25 | SCGB2A1 | EPHB2 | RPL13 | TMEM119 | MXRA8 |
| DCTPP1 | FBL | EID1 | IRF8 | KLF5 | ETHE1 | WFDC2 | MMP3 | GPI |
| AKR1B1 | DNAJB1 | NDUFB3 | CHP2 | DUSP1 | PABPC1 | HSPB1 | ATPIF1 | 10-Sep |
| CDH17 | UQCR11 | MRPL12 | AKR1B1 | DNAJC12 | SELM | RPL31 | S100A3 | MYLK |
| AKR7A3 | RNASE1 | ESRRA | FCGRT | MUC4 | ITM2B | CD59 | C1RL | CDC146 |
| HSPA1A | NDUFS5 | MT2A | RPS3 | ATP5J2 | IGLL5 | OCIAD2 | AKR1B1 | PTP4A3 |
| RPS14 | IMPA2 | PNRC1 | RPL26 | RAB27A | MPST | KIAA1377 | HTRA3 | NNT-AS1 |
| PLP2 | DDT | NDUFV1 | RPL10A | COX7C | UQCRH | CENPV | NBL1 | ARHGAP29 |
| RGS10 | MYL12A | GJB1 | HOXB7 | IL32 | UBC | EMC10 | SLC9A3R2 | FILIP1 |
| MT-CYB | RHOA | MYO1D | MAOA | PSAP | TDGF1 | PLAUR | TYMP | SCN4B |
| TKT | RPL11 | NAP1L1 | AMN | RP11-357H14.17 | PPAP2C | DNAJB9 | PUS3 | FOS |
| MDH2 | RPL10A | VIL1 | TSPAN1 | HLA-DRA | NQO1 | RPL37 | EZR | RPS15 |
| ITM2B | NDUFB7 | DDX5 | MT1M | HSPA8 | RARRES2 | EPHB3 | PRKCDBP | MOCS1 |
| HLA-DRA | RAB25 | TMC4 | MRPL12 | MUC5B | S100A6 | GADD45B | ANG | PPP1R15A |
| EEF1B2 | SUCLG1 | NDUFS7 | ITM2B | PLA2G10 | HLA-DQB1 | HIST1H4C | OLFML3 | EPC1 |
| DUSP1 | FAM195A | SOCS3 | NPC2 | MPC2 | TSC22D3 | SERINC2 | GRAMD3 | FXYD5 |
| PSMB9 | MUC4 | MAOA | NXPE4 | DUSP2 | CDKN1A | CTSS | AHNAK | VIM |
| AMN | SFN | KRT20 | UQCRC2 | TRABD2A | TGIF1 | URAD | CDC42EP1 | SERTAD3 |
| AKR1B10 | MT1X | PLCD3 | SDC1 | DYRK4 | AP000344.3 | RGS2 | IFIT3 | RPL8 |
| FBL | GCHFR | SFN | ACAT1 | KLK15 | C10orf54 | NDUFA11 | RPL27A | ID3 |

TABLE 15-continued

| | | | | | | | | | |
|---|---|---|---|---|---|---|---|---|---|
| NDUFAB1 | MUC1 | ROMO1 | IFITM2 | LXN | SH3BGRL3 | ATP6AP2 | RPL5 | PGRMC1 | HN1 |
| DBI | FKBP1A | SSR2 | RPS21 | NDUFB4 | WNK2 | NUDT16L1 | C1R | PSMB9 | EFEMP2 |
| CBLC | DCTPP1 | CFTR | CENPW | BCAS1 | PSAP | RPL27A | ST3GAL6 | MDK | LSP1 |
| GNB2L1 | RPS16 | LDHD | H2AFZ | CREB3L4 | AXIN2 | NFASC | ANK3 | PUSL1 | C1QTNF2 |
| NDUFV1 | SLC44A4 | HLA-A | DNPH1 | MRPL27 | MYC | RGS10 | RBMS1 | MYL9 | HOXB-AS1 |
| CST3 | PSAP | NDUFB10 | LAD1 | TYMP | RGCC | RPS12 | RPS13 | EPCAM | TMC4 |
| YBX1 | TSPAN1 | CD9 | GADD45B | HSPA1B | LGALS3 | NPDC1 | PLSCR4 | PTGES | PLEKHH2 |
| MARCKSL1 | CD9 | SUCLG1 | IGFBP7 | CTSC | IFITM1 | RP11-279F6.1 | MAPRE2 | CAPG | C1S |
| RPS7 | NME1 | C19orf70 | TUBA1C | CLRN3 | CYBA | GCHFR | CADM3 | AGTRAP | C1orf54 |
| TIMM13 | NDUFS8 | MINOS1 | PRSS8 | TXN | EPB41L4A-AS1 | RPS4X | IER3 | VAMP5 | IFIT1 |
| CYCS | C14orf2 | MT1H | RPSA | PDZK1IP1 | MYL12B | SYT7 | DST | CD320 | IRF1 |
| NDUFA9 | ATP6V0E1 | LAMTOR4 | RPS12 | CYBA | ZNF703 | GRN | RPL4 | RAB13 | HSPA2 |
| RPS5 | CENPM | RNF186 | RP11-357H14.17 | HPCAL1 | MYB | RASD1 | PFN1 | TLCD1 | DDX5 |
| TUFM | UBE2D3 | EIF4A1 | CNN2 | CMAS | ZFP36 | CCDC24 | RTN4 | MEG3 | CDK19 |
| ATP5G2 | CA2 | PLAC8 | MRPS25 | LINC00261 | S100A16 | RPLP2 | TIMP4 | TMEM100 | LIG1 |
| RARRES3 | JUNB | PLA2G10 | SLIRP | NDUFA4 | TMEM141 | UQCR11 | TALDO1 | RFK | CTDSP1 |
| RPL32 | LAPTM4A | SLC22A18 | UGT2B17 | GUCA2A | CA2 | COX5B | SH3BGR | SAMD11 | TYROBP |
| PPIA | S100A11 | SELK | NDUFS8 | SLC25A5 | TMEM176B | RHOA | FADS3 | CTC-276P9.1 | SDHD |
| CYSTM1 | RPL26 | PAPSS2 | PPT1 | KREMEN1 | SMAGP | ANG | PHLDB1 | HOXA10 | RPS3 |
| JUNB | PXMP2 | HINT1 | HSPA1A | PNRC1 | ATP5G2 | RPL28 | ZFYVE21 | UGCG | PDLIM2 |
| SLC44A4 | CTSC | ATP5J2 | MDH2 | NEDD4L | PERP | MT-CO2 | IL32 | CTSL | CYP4X1 |
| DNAJB9 | RPL19 | SEPP1 | PRDX4 | DNAJB1 | CFD | ARPC1B | ST3GAL4 | LEPROT | NUP85 |
| RNF186 | VSIG2 | MVP | ATP5D | AOC1 | HSPA5 | ISYNA1 | H3F3B | C12orf44 | TPD52L2 |
| PSAP | NBL1 | GIPC1 | RPS29 | ISG15 | RPS11 | TMEM54 | TMEM59L | WFDC1 | CARKD |
| RPL18 | CENPV | HRCT1 | COX6B1 | FAM162A | S100A13 | COX7C | UBR4 | ARHGAP24 | CBWD1 |
| CASP6 | ADIRF | MT1X | UQCR10 | CKMT1A | RPS13 | TPM4 | UBA52 | CLDN3 | SPRED1 |
| S100A13 | CDHR1 | HLA-DRB1 | RPL7A | C9orf152 | PTPRO | GNG4 | LHPP | TRPA1 | MRPS6 |
| IMPDH2 | ITM2C | NDRG1 | SERINC2 | ATP2C2 | PDZK1IP1 | NACA | CTNNA1 | HAPLN1 | ISCA1 |
| EEF2 | TMSB4X | ID1 | NDUFB7 | S100A10 | NDUFB4 | RPL15 | ZNF428 | TRAFD1 | SLC25A4 |
| RPL13 | STAP2 | PTMA | MRPL16 | KLK3 | WNK2 | RAB25 | ARMCX1 | INTS12 | FRMD3 |
| MTCH2 | RAB7A | EEF1D | HERPUD1 | C12orf57 | SAT1 | RPS20 | CMTM5 | TPST1 | EBF1 |
| RPL14 | GMDS | ITM2C | RPL13 | SLC12A2 | ANXA2 | RHOA | TNFRSF12A | PAPPA | TIMP1 |
| RPL3 | TMEM176B | PADI2 | TPM1 | DCTPP1 | TIMM13 | MYL12A | RPL29 | FAM105A | LPL |
| RPL11 | FOS | NDUFB1 | SH3YL1 | TMSB10 | COPE | UQCR10 | RPS29 | COPA | GNAI1 |
| RPS9 | TRPM4 | DPP7 | HSD17B11 | GADD45B | VAMP8 | PRR15L | ARHGAP12 | EHD2 | RSBN1L |

| Myofibroblasts | Villus_fibroblasts | Crypt_fibroblasts_(hiFos) | Crypt_fibroblasts_(loFos) | T_cells | Macrophages | Dendritic_cells | Mast_cells | Cycling_monocytes | Tolerogenic_DCs |
|---|---|---|---|---|---|---|---|---|---|
| ACTA2 | NSG1 | ADAMDEC1 | CFD | DCN | FTL | CST3 | TPSAB1 | FTL | SNX3 |
| TAGLN | F3 | CFD | DCN | LUM | C1QB | CLEC10A | VWA5A | PSAP | CPVL |
| MYL9 | FRZB | DCN | ADAMDEC1 | CFD | C1QC | HLA-DPB1 | LTC4S | MS4A6A | IDO1 |
| TPM2 | CXCL14 | C1S | FBLN1 | ADAMDEC1 | PSAP | HLA-DPA1 | C1orf186 | GPX1 | CST3 |
| PDLIM3 | DMKN | LUM | LUM | C1R | C1QA | HLA-DQB1 | CPA3 | AIF1 | CLEC9A |
| ACTG2 | VSTM2A | FBLN1 | MFAP4 | C1S | CTSB | FCER1A | SLC18A2 | C1QA | LGALS2 |
| HHIP | POSTN | HAPLN1 | C1R | FBLN1 | CD68 | HLA-DQA1 | HPGDS | C1QC | C1orf54 |

TABLE 15-continued

| | | | | | | | | |
|---|---|---|---|---|---|---|---|---|
| SOSTDC1 | BMP4 | CCL8 | APOE | TCF21 | CTSD | HLA-DRA | MAOB | C1QB | HLA-DPB1 |
| MYLK | ENHO | C1R | C1S | APOE | TYROBP | HLA-DRB1 | HDC | CST3 | DNASE1L3 |
| FHL1 | PLAT | MFAP4 | SOD3 | COL3A1 | SAT1 | CD74 | CLU | TYROBP | IRF8 |
| HSD17B6 | MMP2 | APOE | TCF21 | CXCL12 | LGMN | AIF1 | NFKBIZ | IGSF6 | HLA-DPA1 |
| MYL6 | EDNRB | CTSC | COL1A2 | MFAP4 | FCER1G | LST1 | RP11-354E11.2 | CD68 | CD74 |
| TPM1 | HSD17B2 | CCL2 | ABCA8 | GPX3 | MS4A7 | IL1B | SAMSN1 | CTSB | HLA-DQB1 |
| MYH11 | COL6A1 | COL3A1 | COL3A1 | HAPLN1 | MS4A6A | LYZ | GATA2 | DNASE1L3 | LSP1 |
| DSTN | COL6A2 | TCF21 | CTSC | CFH | AIF1 | CPVL | ANXA1 | FCER1G | COTL1 |
| CNN1 | SDC2 | COL3A1 | CYGB | SERPINF1 | ACP5 | AMICA1 | GLUL | MS4A7 | HLA-DQA1 |
| NDUFA4 | AGT | | | COL1A2 | MS4A4A | | FCER1A | MS4A4A | HLA-DRA |
| TGFB1I1 | TMEM176B | ABCA8 | CXCL12 | CCL2 | DNASE1L3 | HLA-DMA | KRT1 | NPC2 | AIF1 |
| NPNT | IGFBP3 | SOD3 | CTSK | PPAP2B | GPX1 | TYROBP | CAPG | LYZ | HLA-DQB2 |
| | | | | | | FCER1G | | | |
| DCN | NBL1 | STMN2 | TMEM176B | PLAC9 | IGSF6 | SPI1 | CTSG | IL1B | HLA-DRB1 |
| PDLIM7 | CYGB | CXCL14 | GPX3 | PTN | FUCA1 | MS4A6A | PPP1R15A | VSIG4 | SPI1 |
| PRKCDBP | FENDRR | PROCR | RBP1 | PTGDS | FCGRT | HLA-DQB2 | SLC45A3 | LST1 | LYZ |
| | | | | | | HLA-DMB | | | |
| WFDC1 | RARRES2 | GPX3 | PROCR | IGFBP7 | SEPP1 | CFP | HPGD | SDS | HLA-DOB |
| CXCL14 | FOXF1 | CXCL12 | COL6A2 | PROCR | HLA-DMB | | HS3ST1 | CTSD | HLA-DRB5 |
| | | | | | NPC2 | | | | |
| COL3A1 | MFGE8 | A2M | PLAC9 | COL6A2 | HLA-DRB5 | HLA-DRB5 | GMPR | GRN | HLA-DQA2 |
| | | | | | IGSF6 | | | | |
| COL1A2 | CAV1 | RBP1 | CCL8 | CTSC | HLA-DPA1 | HLA-DPA1 | KIT | CPVL | ACTB |
| SMTN | ECM1 | COL1A1 | CXCL14 | CXCL14 | STAB1 | LGALS2 | RGS13 | FGL2 | LST1 |
| FLNA | TPM2 | SERPINF1 | SOD3 | | HLA-DQA1 | PLAUR | CD9 | SPI1 | RGS10 |
| HHIP-AS1 | MFAP4 | PTN | LINC01082 | CYGB | HLA-DPB1 | CD83 | FCER1G | HLA-DPB1 | BATF3 |
| C1S | PDGFRA | CCL13 | CALD1 | CCL13 | RNASET2 | IFI30 | NFKBIA | SAT1 | CADM1 |
| SELM | COL3A1 | TMEM176B | A2M | CCL8 | LST1 | PLD4 | BTK | CD74 | MPEG1 |
| PPIC | COL1A2 | CTSK | TMEM176A | IFITM3 | LYZ | CD1C | HSP90AB1 | HLA-DRB1 | ASB2 |
| LUM | GPX3 | LINC01082 | COL1A1 | PMP22 | HLA-DRA | MNDA | CD44 | HLA-DQA1 | C1orf162 |
| PPP1R14A | C1S | SERPINF1 | SERPINF1 | CCL11 | CD14 | COTL1 | MITF | HLA-DPA1 | PPT1 |
| ADAMDEC1 | LGALS1 | IFITM3 | | RARRES2 | HLA-DMA | GPX1 | SERPINB1 | RNASE6 | FGL2 |
| COL1A1 | CALD1 | CFH | CFH | GSN | GPNMB | HLA-DQA2 | LMNA | FAM26F | S100A6 |
| | | | | | | ITGB2 | | | |
| TM4SF1 | TMEM119 | IGFBP7 | ADH1B | CD2 | HLA-DRB1 | ADRB2 | PLAUR | HLA-DMB | |
| COL6A2 | FAM150B | CCL11 | SERPING1 | COL14A1 | PLA2G7 | SGK1 | VIM | CTSZ | BASP1 |
| NBL1 | WFDC1 | CLEC11A | CCL2 | ADH1B | APOC1 | GPR183 | TYROBP | HLA-DRA | CD83 |
| NEXN | APLP2 | ADH1B | CLEC11A | SCARA5 | CD74 | FGL2 | SRGN | HLA-DRB5 | KIAA0226L |

TABLE 15-continued

| LGALS1 | COL1A1 | GGT5 | HAPLN1 | A2M | SDS | C1orf162 | IL1RL1 | RNASET2 | HLA-DMA |
|---|---|---|---|---|---|---|---|---|---|
| C1R | BMP5 | PLAC9 | GGT5 | COL1A1 | CTSS | SRGN | SDPR | PLA2G7 | SGK1 |
| ILK | PDLIM1 | SCARA5 | RARRES2 | FXYD1 | LAPTM5 | FAM26F | FAM46A | SEPP1 | TMSB4X |
| KCNMB1 | TMSB4X | VCAM1 | SCARA5 | DKK3 | CD163L1 | RNASE6 | BTG2 | CD14 | RGCC |
| SPARC | SCPEP1 | DKK3 | CCL13 | CALD1 | RNASE6 | LY86 | ALOX5 | HLA-DQB1 | PLEK |
| CSRP1 | PDGFD | COL6A2 | LGALS3BP | CD3D | VSIG4 | RGS2 | NSMCE1 | STAB1 | S100B |
| MFAP4 | MMP11 | PMP22 | GSN | PPAP2A | HLA-DQB1 | DNASE1L3 | CTNNBL1 | HLA-DMA | SERPINF2 |
| CALD1 | MMP1 | TMEM176A | MMP2 | ADAM28 | GRN | CTSH | MIR24-2 | LAPTM5 | ARPC2 |
| IGFBP7 | SPARC | SEPP1 | DKK3 | TMEM176B | ADORA3 | CD1E | LEO1 | CLEC10A | SMCO4 |
| LINC01082 | TMEM176A | MATN2 | CCL11 | CLEC11A | CTSZ | FCGR2B | SDCBP | ACP5 | ITGB2 |
| HSPB1 | IGFBP7 | PPAP2A | PMP22 | CTSK | S100A11 | MS4A7 | PTGS1 | HLA-DMB | HCK |
| APOE | PROCR | CYR61 | PPAP2B | EFEMP1 | SPI1 | LAPTM5 | LAT2 | AP2S1 | CST7 |
| POSTN | LGALS3BP | CALD1 | HAAO | PCOLCE | PLD3 | SAT1 | ALOX5AP | NCF4 | UCP2 |
| APOC1 | PPP1R14A | ADAM28 | ADAM28 | HAAO | TREM2 | CD1D | FTH1 | S100A11 | WDFY4 |
| FBLN1 | PKIG | RARRES2 | CD63 | CD69 | FOLR2 | C1QA | DDX5 | IGF1 | CPNE3 |
| TMEM176B | IGFBP6 | MMP2 | PCOLCE | EMILIN1 | CYBA | CXCL16 | AC020571.3 | A2M | TNNI2 |
| SPARCL1 | TRPA1 | BMP4 | BMP4 | STMN2 | CST3 | ACTB | DNAJA1 | CCL3 | GLIPR1 |
| CAV1 | SERPING1 | SERPING1 | COL6A1 | MMP2 | RNASE1 | RNASET2 | BACE2 | ITGB2 | DUSP2 |
| LMOD1 | TIMP1 | VIM | SEPP1 | GGT5 | ATP6V1F | HCK | CD69 | SLC7A7 | PTPRE |
| AOC3 | MYL9 | SGCE | SPON2 | HAAO | CCL3 | CACNA2D3 | DUSP6 | CD300A | RNASET2 |
| CFD | MRPS6 | EFEMP1 | SPARC | NDN | SLC40A1 | CORO1A | MLPH | LGMN | ARPC1B |
| RBPMS | PCOLCE | PCOLCE | PPP1R14A | SPON2 | LIPA | MPEG1 | JUN | SLC40A1 | LY86 |
| TCEAL4 | SLITRK6 | IFITM3 | PPAP2A | RBP1 | GLUL | ARPC1B | IL1RAPL1 | TYMP | SLAMF8 |
| IFITM3 | C1R | ECM1 | FHL2 | CD52 | CSTB | VSIG4 | SIGLEC8 | C1orf162 | SLAMF7 |
| TUBB6 | IFITM3 | LTBP4 | LGALS1 | THY1 | CPVL | BID | RAB27B | GLUL | C20orf27 |
| MMP2 | TCF21 | PTGDS | PTGDS | BMP4 | ASAH1 | STX11 | LAT | RGS10 | LIMD2 |
| MXRA8 | SERPINF1 | LAPTM4A | MFGE8 | VCAN | VAMP8 | CTSS | UBB | VAMP8 | FLT3 |
| CD151 | TGFBI | SPARC | EMILIN1 | GNG11 | SCT | FTL | ACOT7 | SRGN | FAM49B |
| TCF21 | REEP2 | CD63 | VIM | PPP1R14A | ATP6V0D2 | SAMHD1 | STMN1 | P2RY6 | PARVG |
| ACTN1 | SOX6 | COL6A1 | PRKCDBP | ABCA8 | RENBP | GLIPR1 | FXYD5 | C1orf54 | CORO1A |
| PDIA5 | TSLP | PPP1R14A | THY1 | LAPTM4A | CREG1 | CSF2RA | EGR2 | MNDA | BID |
| PMP22 | CLEC11A | SPON2 | SELM | TMEM176A | CLEC10A | CD68 | ALDH1A1 | AMICA1 | GCSAM |
| EFEMP2 | INSC | HAAO | GNG11 | LGALS1 | FCGR2A | LSP1 | NCOA4 | IFI30 | RAB32 |
| LGALS3BP | CTC-276P9.1 | FOS | LAPTM4A | LTB | FAM26F | INSIG1 | GCSAML | CTSH | FAM26F |
| CD9 | SRGN | SNAI2 | LTBP4 | LINC01082 | RGS10 | IL8 | CD33 | FCGRT | CD9 |
| EMILIN1 | RBP4 | NNMT | TIMP1 | PAMR1 | TMSB4X | NR4A3 | STX3 | CSF1R | LCP1 |
| TUBA1A | LTBP4 | FHL2 | STMN2 | PLTP | CTSL | ARPC3 | SVOPL | FCGR2A | ARHGDIB |
| GSN | PITX1 | GNG11 | EFEMP2 | IGFBP6 | NCF4 | DUSP2 | ATP6V0A2 | TGFBI | CKS2 |
| MRGPRF | LAPTM4A | MEG3 | SNAI2 | NDUFA4L2 | AP2S1 | FAM110A | LAPTM4A | LGALS1 | SUSD3 |
| MFGE8 | EMILIN1 | TM4SF1 | ECM1 | VIM | LY86 | CD33 | HSP90AA1 | MPEG1 | PABPC1 |
| COL6A1 | MAGED2 | FABP4 | SGCE | SELM | IGF1 | TMSB4X | CD63 | GPR183 | FKBP1B |
| | GLP2R | | | | HLA-DRB5 | | | | |
| UBE2E3 | LAMA4 | EMILIN1 | VCAM1 | CIRBP | FGL2 | C1QC | ANKRD28 | SERPINF1 | GSTP1 |
| C9orf3 | A2M | LGALS3BP | IL34 | FABP4 | AKR1B1 | CD86 | LAPTM5 | TBXAS1 | PPDPF |
| PTMS | PROM1 | EFEMP2 | IGFBP6 | S100A4 | MALAT1 | RGS10 | EGR1 | IL8 | P2RY6 |
| SERPINF1 | RGS10 | CXCL1 | SPARCL1 | QSOX1 | AMICA1 | PHACTR1 | ARL5B | CTSS | FCER1G |
| JUNB | LHFP | LGALS1 | NOVA1 | RGCC | APOE | PPDPF | CATSPER1 | APOC1 | NAP1L1 |
| RCN1 | BAMBI | PLAT | FBLN5 | FBLN5 | IFI30 | AOAH | HSPH1 | RNF130 | CD48 |
| FXYD1 | RBPMS | IGFBP6 | NGFRAP1 | PLAT | CD163 | PYCARD | KLRG1 | HCK | TYMP |
| CES1 | ANXA5 | SOCS3 | PLTP | MEG3 | ITGB2 | PTPRE | CLIC1 | ALOX5AP | LAPTM5 |

TABLE 15-continued

| | | | | | | | | |
|---|---|---|---|---|---|---|---|---|
| NUPR1 | AKR1B1 | TPM2 | MATN2 | SRGN | ARHGDIB | TSC22D1 | CD36 | MT-ND2 |
| RARRES2 | BSG | SMPDL3A | FXYD1 | TIMP1 | RNF130 | S100A4 | ADORA3 | ID2 |
| SRGN | PRR16 | NDN | EDIL3 | GSTT1 | PLEK | ATP6V1F | SIRPA | AMICA1 |
| FN1 | MAP1B | SELM | TPM2 | EMID1 | TYMP | CTD-3203P2.2 | CYBA | AIM2 |
| SDC2 | GADD45G | FXYD1 | SFTA1P | SERPING1 | HLA-DQB2 | SGK1 | PLD3 | CLNK |
| FOXF1 | TSPAN4 | C2 | TSPAN4 | CD3E | S100A9 | RENBP | PDLIM1 | LGALS3 |
| PCOLCE | S100A13 | PLTP | MEG3 | ANXA1 | CD300A | PLIN2 | RGS1 | IFI27 |
| SERPING1 | GLT8D2 | VCAN | EPHX1 | LTBP4 | UCP2 | PTPN6 | GPNMB | CSF2RA |
| SCPEP1 | HSPB1 | NGFRAP1 | QSOX1 | CCL5 | GRN | ANXA2 | CD4 | VMO1 |
| AC131025.8 | C11orf96 | QSOX1 | MYL9 | NPL | NCF4 | FAM212A | RGS2 | DUSP4 |
| SGCE | EFEMP2 | SDC2 | SRGN | HCK | TBXAS1 | FOSB | TIMP1 | ID3 |
| MIR145 | FGF9 | EPHX1 | TM4SF1 | LILRB4 | C1QB | ASAH1 | APOE | SAT1 |
| CRYAB | EID1 | GSTM3 | EFEMP1 | C1orf54 | ARRB2 | HSPA8 | OAZ1 | TLR10 |
| LTBP1 | PTMS | SPARCL1 | PLAT | C5AR1 | IFI27 | ASRGL1 | VIM | TYROBP |
| CRIP2 | COL5A1 | TIMP1 | OLFML3 | LGALS1 | ARL5B | LYL1 | ATP6V0B | MIR142 |
| DUSP1 | MXRA8 | GSTM3 | MYL9 | RNF130 | DUSP1 | EIF4G2 | CORO1A | GPR183 |
| CERCAM | FKBP10 | FHL1 | GSTM3 | PHGR1 | CD48 | STXBP6 | HLA-DQA2 | TSPO |
| TPPP3 | PTGDR2 | SRGN | CCDC80 | CD209 | RHOG | TNFSF10 | CREG1 | MNDA |
| SH3BGRL | CPE | COLEC11 | DPT | TTYH3 | RGS1 | GRAP2 | HLA-DQB2 | PFN1 |
| VIM | SGCE | EDIL3 | RAB13 | PRDX1 | NR4A2 | NFKBID | S100A9 | LGALS1 |
| CKB | TNC | IL34 | ITIH5 | RAB42 | NCF2 | CSF2RB | PPT1 | GPX1 |
| NGFRAP1 | TAGLN | PRKCDBP | NNMT | IL1B | HCLS1 | RAC2 | LY86 | HSPA1A |
| PTCH1 | DCN | C11orf96 | SDC2 | FABP3 | ARPC2 | NR4A1 | TXN | ACTG1 |
| SOD3 | TXNL1 | ARHGDIB | FSTL1 | MPEG1 | PILRA | HSPA1B | EPCAM | CCND1 |
| COL4A2 | EMID1 | FBLN5 | LOXL1 | CD36 | CD53 | H3F3B | LILRB4 | CNN2 |
| LRRC17 | CRISPLD2 | SFTA1P | FABP4 | SLC7A7 | P2RY13 | SMYD3 | FUCA1 | LTB |
| GNG11 | SRPX2 | EID1 | S100A13 | NNRI | CLEC4A | MPP1 | FXYD5 | SAMHD1 |
| CYBA | C1orf21 | FXYD6 | COL14A1 | C3AR1 | PPT1 | FAR2 | GNAI2 | NAAA |
| RBP1 | NDN | MYL9 | NDN | CHMP1B | CHMP1B | LM04 | ADAP2 | ITM2C |
| IER2 | ISCU | THY1 | MXRA8 | CAPG | GPSM3 | SRSF5 | CSF2RA | HCLS1 |
| CPQ | CD9 | LINC01116 | UBE2E3 | ADAP2 | ZNF385A | ARHGDIB | LGALS4 | TACSTD2 |
| MAP1LC3A | ACP1 | TPI1 | FHL1 | OTOA | ATF3 | EIF3D | NINJ1 | PSMB9 |
| BMP5 | PALLD | LOXL1 | TAC3 | CFD | LITAF | EGR3 | ATP5G1 | XCR1 |
| OSR1 | F2R | MXRA8 | IFITM2 | HSD17B14 | ZNF331 | CD82 | FCGR1A | PLCD1 |
| AKR7A2 | BST2 | IRF1 | C6orf48 | LAMB1 | PARVG | MYADM | EMP3 | SERPINB9 |
| NDN | CPM | PITX1 | EID1 | MATN2 | MIR142 | TESPA1 | KRT18 | TMEM176B |
| PKIG | SELM | MFGE8 | PITX1 | CD83 | NAMPT | RASSF5 | CAMK1 | GMFG |
| S100A13 | PTN | UBE2E3 | C2 | SPARC | P2RY6 | CALB2 | PHGR1 | COX7A2 |
| HMG20B | WNT5B | FGF7 | LRP1 | CNBP | FAM49B | BIRC3 | CD163L1 | CD99 |
| RP11-332H18.4 | SERPING1 | SERPINH1 | NUPR1 | NANS | FTH1 | HINT1 | KRT8 | PPM1J |
| | | OLFML3 | VKORC1 | FSTL1 | GAPT | | | |
| | | | APOC1 | EEF1D | NPC2 | | | |
| | | | | AEBP1 | ITGB2-AS1 | | | |
| CFH | RBP1 | ARID5B | FKBP10 | SERPINH1 | HLA-DOA | CD22 | C3AR1 | H2AFY |
| GAS6 | FBLN1 | PPIC | FXYD6 | NNMT | RGS1 | IL18 | IFI27 | PYCARD |
| FOSB | NDUFA4L2 | RAB13 | LAMA4 | WNT2B | CYBA | HSPD1 | S100A4 | RGS1 |
| LPP | PCDH18 | CFL1 | PPIC | C11orf96 | OAZ1 | STXBP2 | RAB31 | TMEM59 |
| PALLD | APOD | JUNB | DMKN | PDPN | PID1 | MBOAT7 | DAB2 | SRGN |
| TTLL7 | KREMEN1 | KCNS3 | EMID1 | GZMK | CCL3 | RGCC | ANXA1 | ZYX |
| IGFBP5 | TUBA1A | S100A13 | NDUFA4L2 | ELANE | CD4 | IER2 | ATP6V1F | CLEC7A |
| LAPTM4A | ID1 | CEBPD | PLAU | TRIM22 | A2M | MSRA | TUBB4B | NABP1 |
| WLS | ADM | TSPAN4 | FOXF1 | CLEC14A | IL8 | JUNB | CD209 | ZFP36L2 |
| | | | | | C1orf162 | | | |
| | | | | | NAGK | | | |
| | | | | | CSF1R | | | |
| | | | | | CXCR4 | | | |
| | | | | | ARL4C | | | |

TABLE 15-continued

| | | | | | | | | |
|---|---|---|---|---|---|---|---|---|
| EDNRB | PRKCDBP | APOC1 | FN1 | PITX1 | ATP6V0B | PDLIM1 | BHLHE40 | TFF3 | ABB |
| FAM127A | IFITM1 | LAMA4 | GLT8D2 | SLC25A5 | HLA-DQA2 | IGJ | ARHGEF6 | LSP1 | MT-ND1 |
| ARHGDIB | CXCL12 | C6orf48 | COL5A1 | CXCL1 | FTH1 | NCF1 | CST3 | ARHGDIB | CD37 |
| CSRP2 | TSHZ2 | ZFP36L1 | CTC-276P9.1 | COL6A3 | CAMK1 | G0S2 | DUSP10 | UCP2 | FNBP1 |
| TIMP2 | LRRN4CL | GLT8D2 | COLEC11 | IDH2 | GPR34 | HSPA1A | SCYL1 | CXCL16 | EVI2A |
| MAMDC2 | PTCH1 | NDUFA4L2 | CFL1 | COLEC11 | SLAMF8 | VAMP8 | RGS10 | HBEGF | HAVCR2 |
| P2RY14 | LAMB1 | EMID1 | EHD2 | COX5A | S100A6 | TNFSF13B | PRDX6 | ZNF331 | ARPC3 |
| S100A4 | HHIP | CCL7 | RBPMS | MXRA5 | IL18BP | H2AFY | ACTG1 | FCGR2B | CD63 |
| TRIP6 | VIM | SRPX | COL18A1 | EDIL3 | CTSH | OLR1 | CHST2 | CTSC | HES1 |
| SH3BGRL3 | NNMT | TIMP3 | SCPEP1 | EFEMP2 | ARHGDIB | MT-CYB | CD37 | RB1 | KIAA1598 |
| CBR1 | CIRBP | ANGPTL4 | SMPDL3A | PPIC | PLTP | TMEM59 | DDX3X | SRI | VAC14 |
| MMP14 | CAPZB | SCPEP1 | WFDC1 | TDO2 | COTL1 | CXorf21 | ESYT1 | YWHAH | IGFBP7 |
| SEPW1 | CD63 | DPT | DUSP1 | C4orf3 | ARL4C | CNPY3 | CRBN | RENBP | TAP1 |
| MFAP5 | TGFB1I1 | ADM | COX5A | VPS25 | FPR3 | SYTL2 | SGK1 | LDLRAD4 |
| FENDRR | IL32 | GADD45B | FOSB | FNDC1 | SRGN | EIF4A1 | CTSD | CD163 | ELOVL5 |
| CALU | PLK2 | NUPR1 | C6orf48 | CYP7B1 | HMOX1 | THEMIS2 | HNRNPM | C5AR1 | IL16 |
| TMEM176A | TBX2 | LRP1 | SERPINE2 | SPRY1 | TNFSF13B | C20orf27 | P2RY14 | LILRB2 | RGS19 |
| CTSK | ANGPTL4 | CYBA | FAM127A | PCDH7 | CYBB | CD300A | CD83 | COTL1 | DUSP10 |
| C1QTNF2 | PCSK6 | RAB34 | TMEM119 | ZFP36L2 | LAIR1 | S100A11 | SLC2A6 | CLEC4A | PDLIM7 |
| SNAI2 | TSPAN2 | PRNP | GSTM5 | DMKN | GLIPR1 | YBX1 | CKS2 | TMSB4X | TWF2 |
| COL4A1 | WLS | EGR1 | CPQ | ALDOA | ITM2B | LGALS1 | ARHGAP18 | LAIR1 | CTSZ |
| CD63 | AEBP1 | ZFP36 | RAB34 | COL6A1 | YWHAH | IGFBP7 | TIMP3 | ASAH1 | IFITM3 |
| COX7A1 | SCUBE2 | PROS1 | AKR1B1 | HTRA3 | TGFBI | ANXA1 | TMEM154 | EEF2 | CXCR4 |
| LOXL2 | LANCL2 | ITIH5 | CD81 | PRKCDBP | HLA-DOA | PTPRC | CMA1 | PLD4 | COX5B |
| CYB5R3 | LOXL2 | CD81 | SLC9A3R2 | CXCR4 | CCL4 | AGPAT9 | MALAT1 | MAFB | VIM |
| FOS | FIP1L1 | CIRBP | TNFAIP6 | KRT8 | DAB2 | FCGR2A | RGS1 | RPL24 | SELPLG |
| IL32 | RTN4 | FOXF1 | FILIP1L | KLRB1 | EBI3 | CTSZ | DNAJB1 | FCER1A | CFL1 |
| RPL28 | ADH5 | CCDC80 | VCAN | PHLDA1 | GATM | PPIF | FCGRT | PLTP | ATG3 |
| CFL2 | TM4SF1 | NEGR1 | TGFB1I1 | FGF7 | ATOX1 | DOK2 | PFN1 | TUBA1B | C12orf5 |
| LTBP4 | C7orf50 | COX5A | COL15A1 | LAMA4 | FCGR3A | MT-ND2 | EXD3 | RPS27A | PNMA1 |
| VCL | SEMA4D | NOVA1 | ATRAID | TAC3 | ARPC3 | GNA15 | LIF | GMFG | APOL3 |
| P2RX1 | PXDN | FN1 | TFPI | COL18A1 | TNFAIP8L2 | KRT18 | GBE1 | AXL | RAB31 |
| WNT2B | HAAO | CPQ | WNT2B | SPINT2 | ABB | HERPUD1 | CHORDC1 | CLEC7A | MT-CYB |
| PARVA | NPY | ID3 | SERPINH1 | THNSL2 | RHOG | HBEGF | GAPT | PRDX5 | MYCL |
| S100A6 | RGCC | FKBP10 | PRNP | NEXN | RGS2 | SCIMP | HSPE1 | CD83 | IFNGR1 |
| ECM1 | SGCB | BST2 | CTSF | RNASE1 | CCL18 | LCP1 | ITM2B | HCST | GYPC |
| TCEAL1 | FHL1 | WFDC1 | MDK | FXYD6 | HN1 | PTGS2 | UBXN10 | GNPDA1 | GPSM3 |
| LAMA4 | TPBG | TDO2 | ACTA2 | LOXL1 | RAC1 | LIMD2 | CNIH1 | IGJ | PLEKHO1 |
| VKORC1 | NUPR1 | DMKN | CST3 | CD81 | TMEM176B | PMAIP1 | SLC16A3 | TUBB | LSM6 |
| NME4 | TBX3 | COL5A2 | KLF6 | TMEM66 | KRT8 | PABPC1 | GNPTAB | RPL31 | MSL3 |
| TMEM98 | RGS1 | COL14A1 | TGFBI | CRIP2 | PYCARD | KDM6B | TSPO | DUSP1 | UQCR10 |
| | | PGRMC1 | TIMP3 | TIMP3 | PILRA | IL32 | RPL28 | RPL35A | LGALS4 |
| | | PHGR1 | ABCA6 | H3F3B | LGALS4 | FPR3 | MAML1 | P2RY13 | CXCR3 |
| | | SH3BGRL3 | FGF7 | IRF1 | SLCO2B1 | PFN1 | TUBA1B | CD9 | CIITA |
| | | ANXA5 | CYBRD1 | ECM1 | SMS | BSG | UBE3A | BLVRA | BCL2A1 |
| | | EHD2 | MMP23B | IFI27 | CORO1A | GMFG | NFE2L2 | GLIPR1 | ROGDI |
| | | TAC3 | EVA1A | DDR2 | ZNF331 | SLC31A2 | SH3BGRL3 | TNFSF13B | TGFBI |
| | | VASN | PTMS | SLC9A3R2 | ARRB2 | SNX10 | ELF1 | GATM | MIR4435-1HG |
| RPLP2 | LEPROT | SLC25A5 | TNFRSF1A | SGCA | IFI27 | SEPW1 | PRKAR1A | OSM | CKLF |
| TIMP1 | GNAI1 | AEBP1 | C7 | CD74 | SIGLEC7 | ZFP36 | ENPP3 | CLDN7 | IGJ |

TABLE 15-continued

| | | | | | | | |
|---|---|---|---|---|---|---|---|
| CD74 | MSC | RBPMS | RP11-14N7.2 | COL15A1 | GPR183 | GALNT6 | NCF1 | BST2 |
| PPP1CC | PTX3 | CCNI | RGCC | SFTA1P | DOK2 | CCL2 | CTSL | DGAT2 |
| A2M | ACTA2 | CNBP | CDH11 | CDK2AP2 | CLEC4A | ACTR3 | GM2A | NDUFB9 |
| CTSS | CD74 | SPRY1 | FGFR4 | PTGER2 | CECR1 | TMEM66 | LRRC25 | COX6C |
| PTS | LRP1 | SEC11C | BST2 | FABP1 | TMEM37 | NCF4 | C15orf48 | MT-ND5 |
| PPAP2A | TMEM98 | PLAU | IGFBP5 | TNFAIP3 | RHOC | BEX4 | AKR1B1 | KLF6 |
| TTC3 | PLBD1 | IFITM2 | CXCL1 | FGFR2 | ANXA1 | BLVRA | RAB42 | KRT18 |
| ADH5 | CPQ | 4-Sep | CP | FHL1 | PHGR1 | SERP2 | GSN | 1-Mar |
| MCL1 | VASN | GSTM5 | C16orf89 | KRT18 | AP1B1 | TM65F1 | TREM2 | EVI2B |
| FAM105A | AMPD3 | ABCA6 | LINC01116 | RND3 | NCF1 | ITM2A | RPL34 | CPPED1 |
| MAGED2 | IGFBP5 | FILIP1L | CIRBP | SCPEP1 | GRB2 | DHRS7 | SLCO2B1 | FERMT3 |
| NKX2-3 | MXRA5 | MT-ND2 | SAMD11 | MAPK10 | GAL3ST4 | IFI27 | ADAMDEC1 | ST8SIA4 |
| RAB34 | PHGR1 | LEPROT | SAT1 | LY6E | ID1 | 2-Sep | TSPO | PTPRC |
| SGCA | STMN2 | FSTL1 | SH3BGRL3 | CLEC2B | RAB32 | HSPA9 | TRPM2 | GNAI2 |
| CCDC107 | GULP1 | MT-CO2 | MIR497HG | FTH1 | CSF3R | FECH | RPL18 | ATP5J |
| SERPINH1 | CCDC68 | TUBA1A | PHGR1 | NUPR1 | GSN | PRDX5 | RPL5 | GPR137B |
| FILIP1L | SPON2 | HES1 | HTRA3 | CD5 | RAB31 | IFITM10 | H2AFZ | HSPA1B |
| MINOS1 | CH25H | CSF1 | AEBP1 | IL34 | ID3 | HSPA1A | SDSL | RNASE6 |
| AEBP1 | PLAU | CDK2AP2 | TMEM9 | EMP3 | TNFAIP8L2 | DLC1 | MT1E | AKIRIN2 |
| NEO1 | MRVI1 | CDH1 | S100A4 | NUDT16L1 | SOD2 | HIF1A | FABP1 | LITAF |
| EID1 | CD151 | PFN1 | SCT | CDC80 | SLAMF8 | LYN | ENG | TOMM34 |
| PDGFC | CNTFR | HTRA3 | MXRA5 | IL1R1 | CCL3L1 | DDX3Y | TNFAIP8L2 | PTPRCAP |
| DCTN2 | COL6A3 | RND3 | CNBP | EVL | GPSM3 | ZEB2 | LIPA | AP1S2 |
| CBR3 | PDLIM4 | HSPA1A | IFITM1 | RP11-14N7.2 | TFPT | MKNK1 | NCF2 | BSG |
| RCAN2 | CYTL1 | JUN | PDLIM3 | CSF1 | ANXA5 | RHOG | ARL4C | MT-ND4 |
| RERG | COL4A5 | MT-ND4 | KCNS3 | GNAO1 | RABAC1 | RBMX | MGST1 | MCL1 |
| CLEC11A | HMGB1 | CST3 | ISLR | LRP1 | S100A6 | CDK5 | GPSM3 | ACTR3 |
| FSTL1 | ST5 | HINT1 | HSPA8 | ITIH5 | FCGRT | DDX39A | RAC1 | CD40 |
| C2 | GADD45B | TNFAIP6 | PFN1 | MFGE8 | COX6C | TMSB10 | CECR1 | MT-ATP6 |
| FHL3 | ID3 | CHL1 | BDH2 | DUSP2 | CD52 | EIF1 | ARPC1B | PPA1 |
| TGM2 | CYR61 | ADAMTS1 | ELANE | FHL2 | RB1 | NEK6 | PARVB | KCNMB1 |
| MORF4L2 | CTSK | ACTA2 | HINT1 | TRAT1 | MPP1 | CSF2 | CYBB | MAP4K1 |
| TMEM47 | CTSK | SERPINE2 | WARS | FARP1 | SLC7A8 | CSF1 | VMO1 | EPCAM |
| ISG20 | ENPP6 | C16orf89 | COX7A1 | MRPL23 | TNFAIP2 | CXCL14 | SLC16A3 | MYADM |
| ACTB | LUM | MYL12A | PAMR1 | TM4SF1 | SCIMP | PIK3R6 | DOK2 | CAP1 |
| CD99 | HOXA10 | RCN1 | LY6E | LAMA2 | TFF3 | GPR65 | TNFAIP2 | SIGLEC10 |
| EFEMP1 | SERPINH1 | IGJ | CRYAB | GZMA | NCKAP1L | RPS4Y1 | ARRB2 | CECR1 |
| ZYX | FILIP1L | TMEM98 | MYL12A | PAM | FXYD3 | VAV1 | ATPIF1 | ACTN1 |
| SAMD11 | SEC62 | ELANE | SPRY1 | RNASET2 | ARPC1B | IL4R | COX5B | RAB7L1 |
| SSPN | GPC1 | MAMDC2 | IL6ST | GPC6 | SIGLEC1 | SELM | ITGB7 | FAM110A |
| RBBP7 | ARPC1B | CTC-276P9.1 | ANGPTL1 | IL7R | TUBA1B | EVL | NAGK | LINC00152 |
| CPED1 | PDPN | CD302 | GAS6 | IFITM2 | BSG | HNRNPA2B1 | ATF3 | INPP5D |
| RGS10 | TUSC3 | PCDH18 | NENF | FBN1 | EEF2 | BCL2A1 | IL1RN | PHGR1 |
| CREB3 | RP11-332H18.4 | FAM92A1 | RUNX1T1 | ACTA2 | BST2 | RALB | SUCLG1 | GRN |
| DDAH2 | C12orf57 | GRK5 | CYBA | RARRES3 | LGALS3 | CORO1A | HSD17B14 | AC093673.5 |
| SEPP1 | NOVA1 | WNT2B | ANXA1 | ADM | MNDA | RAB32 | CD86 | C12orf57 |
| MIR143HG | WFS1 | MDK | NEGR1 | FKBP10 | RAB20 | WDR45B | KRT19 | PHACTR1 |
| NENF | NGFRAP1 | POSTN | CYCS | COL5A1 | FCGR1A | LINC00863 | TTYH3 | CD86 |
| PITX1 | CDH11 | ISLR | COL6A3 | CCDC127 | PTAFR | ABCB8 | ANXA5 | S100A4 |
| COL6A3 | OLFML3 | EPHA7 | SLC25A5 | GAPDH | CD53 | EIF2AK1 | SOD2 | DAPP1 |
| KANK2 | ZFP36L1 | ANGPTL1 | PAM | MGST1 | HCLS1 | SAR1B | BST2 | RHOG |

TABLE 15-continued

| | | | | | | | | | |
|---|---|---|---|---|---|---|---|---|---|
| NUDT4 | PDE1A | PHLDA1 | IL32 | VKORC1 | LSP1 | SOCS3 | RHBDD2 | CAPG | CYB5R3 |
| ARHGEF25 | ECHDC2 | HSD11B1 | CRIP2 | HSD11B1 | AGR2 | IFNGR1 | DHRS9 | FOLR2 | C10orf128 |
| MMP23B | BRK1 | FTH1 | TDO2 | DUSP23 | C12orf57 | JUNB | SEMA7A | PRDX2 | RHOF |
| THYN1 | HLA-A | RGCC | COL4A2 | CHCHD10 | AOAH | GHRL | CDC28A | STX11 | KRT8 |
| RGS1 | TCF4 | IL6ST | RGS1 | SSBP3 | STMN1 | MT-ND5 | TRAPPC2P1 | SNCA | ANXA6 |
| ARPC1B | SEC11C | SMIM10 | PCDH18 | NGFRAP1 | GMFG | NAGK | IGFBP7 | PTGS2 | ITM2B |
| RCN3 | COL4A6 | TMEM150C | P4HA2 | ARHGAP24 | IRF8 | CIITA | GPR35 | CMKLR1 | SCNM1 |
| SQRDL | RCAN2 | CTSF | CYB5R3 | EID1 | AXL | CPPED1 | PAK1 | ATP5B | PRDX5 |
| APCDD1 | SCARB2 | ATP6AP2 | TSTD1 | ID4 | MMP14 | LGALS3BP | PARVB | RPL37A | CAT |
| RP11-532F6.3 | MMP14 | AKR1B1 | EEF1D | C11orf58 | C15orf48 | KLF4 | RARRES1 | RASSF4 | PTRHD1 |
| NDUFB9 | SH3BGRL3 | SVEP1 | MT-CO2 | TRPM2 | CREG1 | WAS | IL5RA | S100A6 | CD72 |

| Neutrophils | Activated_CD4_cells_loFos | Activated_CD4_cells_hiFos | CD8_IELs | CD8_LP_cells | Tregs | Memory_T_cells | NK_cells | Cycling_CD8_cells | Inflammatory_CD2_DCs |
|---|---|---|---|---|---|---|---|---|---|
| S100A9 | RPLP1 | IL32 | CCL5 | CCL5 | IL32 | LDHB | NKG7 | CD3D | LST1 |
| SOD2 | RPS3 | ANXA1 | CD7 | IL32 | CORO1B | RPL11 | TYROBP | CD3E | IL4I1 |
| IL1B | IL32 | KLF6 | GZMA | NKG7 | BATF | CCR7 | FCER1G | NKG7 | KRT86 |
| PLAUR | RPL10 | S100A4 | NKG7 | CCL4 | TIGIT | RPS12 | XCL2 | CD2 | LTB |
| LST1 | RPS25 | CD69 | HOPX | GZMA | PFN1 | RPL32 | CTSW | CCL5 | FXYD5 |
| AIF1 | RPSA | DNAJA1 | IL32 | DUSP2 | BTG1 | RPS3 | XCL1 | CD7 | ALDOC |
| SPI1 | RPL32 | HSPA8 | CKLF | CD8A | CD3D | RPL19 | CLIC3 | IL32 | KRT81 |
| G0S2 | ANXA1 | CD3D | KLRC2 | SH3BGRL3 | ARHGDIB | RPLP2 | IL2RB | GZMA | ID2 |
| LYZ | RPL2 | RPLP1 | CD160 | CST7 | CREM | RPL13 | GZMA | CST3 | LTA4H |
| SAT1 | RPL19 | LTB | GZMB | CD8B | ICA1 | RPS15A | CCL4 | ITM2A | NFKBIA |
| FPR1 | RPS19 | CCL5 | PTPRCAP | CD52 | C9orf16 | RPS14 | GSTP1 | TUB4B | ZFP36L1 |
| TYROBP | TPT1 | CD52 | TMIGD2 | ZFP36L2 | DNPH1 | RPL23A | KLRC1 | CTSW | CASP3 |
| FCER1G | RPS15A | ID2 | HCST | HCST | TNFRSF4 | RPL31 | MATK | PTPRCAP | TNFRSF25 |
| SERPINA1 | RPLP0 | SH3BGRL3 | EVL | HOPX | CARD16 | RPSA | APOBEC3G | GZMB | HSPA8 |
| FTH1 | RPL13 | BTG1 | CD52 | PFN1 | RAP1A | RPS4X | CST7 | VIM | MIR24-2 |
| FCGR1A | RPL11 | TNFAIP3 | CD3D | LTB | ARPC1B | RPL18 | GZMA | CD8A | LIF |
| S100A8 | RPL28 | TNFRSF25 | GNLY | TMSB4X | CTLA4 | RPS6 | GNLY | CD8B | TYROBP |
| IGSF6 | RPS12 | CALM1 | CD3E | BTG1 | NDUFV2 | RPS13 | GZMK | B2M | DUSP1 |
| IL1RN | RPL13A | TSC22D3 | SH3BGRL3 | GZMB | FOXP3 | RPL28 | CD7 | CD96 | NXT1 |
| HLA-DRA | RPL30 | EIF1 | RAC2 | CD3D | PMVK | RPL27A | KLRD1 | AC092580.4 | HNRNPA0 |
| CTSS | RPS27A | TMEM66 | CTSW | CD3E | | RPS2 | HCST | SH3BGRL3 | MPG |
| TYMP | RPL4 | CD2 | PHGR1 | GZMH | PBXIP1 | RPS25 | EIF3G | HCST | HMGN3 |
| FAM26F | RPS14 | ZFP36L2 | IGJ | CKLF | LCK | LTB | PFN1 | PLA2G16 | CXCR4 |
| HLA-DQB1 | RPS6 | RPS3 | TMSB4X | MYL12A | CD63 | RPS18 | PRF1 | TMIGD2 | NR4A1 |
| FGL2 | RPL23A | RPSA | GAPDH | CXCR4 | BIRC3 | RPL30 | FGR | IFNG | CSF2 |
| CPVL | RPS2 | CD3E | CORO1A | CFL1 | PTPRCAP | RPL4 | KRT81 | HCST | PRMT10 |
| STX11 | CD52 | TMSB4X | ABI3 | NR4A2 | ITM2C | RPS9 | HOPX | PLA2G16 | CD83 |
| HLA-DRB1 | RPS18 | RPS19 | PRF1 | B2M | UCP2 | RPL35A | CAPG | TMIGD2 | DNAJA1 |
| CD14 | RPL6 | SRSF7 | ACTB | ARHGDIB | IL2RG | RPS27A | CCL3 | IFNG | H2AFY |
| FTL | LTB | HSP90AA1 | CD3G | LYAR | AC017002.1 | RPS8 | KLRF1 | RAC2 | SRSF2 |
| HLA-DPB1 | RPL27A | DUSP1 | ARHGDIB | ANXA1 | SRGN | RPL10A | MAP3K8 | GYPC | TMIGD2 |
| HLA-DQA1 | S100A4 | MYL12A | SIRPG | RPL28 | LGALS1 | GNB2L1 | SRGN | SPINT2 | OTUD5 |
| | RPL10A | ARHGDIB | LCK | CTSW | CD44 | CD63 | IFITM2 | LGALS4 | CD300LF |

TABLE 15-continued

| | | | | | | | | |
|---|---|---|---|---|---|---|---|---|
| COTL1 | RPL3 | ACTB | ACTG1 | TMEM66 | CALM3 | RPS23 | CD3D | HLA-DRA | SPINK2 |
| NCF2 | RPS16 | RPL28 | RARRES3 | C9orf142 | DUSP4 | RPS20 | STK17A | CD69 | TPT1 |
| HLA-DRB5 | RPS5 | CORO1A | PFN1 | PSMB9 | RGS1 | RPL14 | FAM117A1 | LY6E | TLE1 |
| LILRB2 | IL7R | RPLP2 | | CD247 | TNFRSF1B | RPL36 | PTP4A1 | LDHA | DLL1 |
| APOBEC3A | RPL31 | PFN1 | | STK17A | MIR4435-1HG | RPL37 | ITGB2 | ARHGDIB | PTGDR |
| EREG | RPL14 | ABRACL | CAPG | PTPRCAP | LAIR2 | RPL13A | CCL5 | GIMAP7 | NCOA7 |
| C1orf162 | UBA52 | IL7R | TBC1D10C | LAG3 | ICOS | IL32 | BTG1 | SRGN | CD52 |
| S100A11 | RPS15 | LEPROTL1 | XCL2 | CORO1A | TNFRSF18 | RPL27 | NR4A2 | TBC1D10C | AMICA1 |
| CDC42EP2 | RPL18 | RAC2 | FABP1 | HLA-B | HLA-A | PABPC1 | APMAP | CD52 | MAFF |
| PLEK | SH3BGRL3 | B2M | ARPC2 | GZMM | ACTB | RPL26 | DUSP2 | RPL8 | BIRC3 |
| MS4A7 | RPS20 | CD47 | CD96 | IFNG | SPOCK2 | RPL8 | PTGDR | EPCAM | JUNB |
| LY86 | RPS13 | IFITM3 | C9orf142 | TUBA4A | ANKRD12 | SELL | GZMH | RARRES3 | TOX2 |
| HLA-DPA1 | RPL27 | APRT | LGALS4 | ID2 | EIF3H | RPS21 | CORO1A | CD9 | DRAP1 |
| IFI30 | RPS8 | HLA-DRA | FTH1 | S100A4 | GSTP1 | RPL5 | KRT86 | H2AFZ | CD69 |
| HLA-DMB | EEF1B2 | RPLP0 | XCL1 | RPS19 | B2M | RPS15 | CD160 | ATPIF1 | IL23R |
| LGALS2 | RPS23 | IL2RG | CD8A | CORO1A | CORO1A | RPL10 | LAT2 | MSN | ARL4A |
| ITGB2 | RPS4X | TPT1 | 1-Sep | CD7 | CD27 | LGALS1 | ID2 | APOBEC3G | TCIRG1 |
| C5AR1 | RPL12 | RPL10 | CST3 | ACTB | CCL5 | RPS16 | MIB2 | GZMM | UBB |
| SRGN | ARHGDIB | CD53 | AC092580.4 | HLA-A | LAT | RPL34 | ALOX5AP | SLC9A3R1 | IER2 |
| CYBA | RPS3A | DNAJB1 | CFL1 | CD2 | PKM | RPL29 | BCO2 | CDKN2A | CAT |
| TIMP1 | RPL35A | PTGER4 | CST7 | PSME1 | PPP1R18 | RPL12 | NCR3 | COX5B | EIF1 |
| CD74 | RPL5 | ID3 | CLIC1 | ALOX5AP | ANXA1 | TMEM66 | ARPC5L | C15orf48 | AREG |
| CST3 | RPL15 | PPP2R5C | PPP1CA | RPL27A | EEF1D | FXYD5 | MYL12A | ICAM3 | FOSB |
| CD36 | RPL37 | CD40LG | IL2RB | HSPA8 | HINT1 | ARHGDIB | FTL | TXN | ZFP36 |
| TNFSF13B | RPL8 | HLA-DPB1 | ALOX5AP | LEPROTL1 | IL10 | RPS5 | CD97 | SKAP1 | TCP1 |
| MS4A6A | TMEM66 | CKLF | TIGIT | SRGN | RAC2 | RPLP1 | PPP1R2 | PIM1 | CD164 |
| BID | RPL34 | RPS12 | RPS19 | HSPB1 | ASB2 | RPS7 | CD247 | SLA2 | DDX3X |
| GBP1 | CD3D | RPS27A | IGLL5 | SRRT | LAG3 | EEF1B2 | GUPR2 | TRAT1 | METTL9 |
| GLRX | RPL29 | PHLDA1 | PLEKHF1 | RPS27A | FOS | RPS19 | CLIC1 | CXCR3 | ZNF75A |
| NFKBIA | IGFBP7 | RPL19 | ACAP1 | RPL30 | ATP5L | CD52 | SLC35E1 | TCEA2 | C16orf91 |
| MNDA | PTGER4 | FTL | PTPN6 | CXCR3 | TBC1D4 | FAU | 7-Sep | PRKCH | NR4A2 |
| CXCL10 | RPL35 | DRAP1 | P2RY11 | CALM1 | FYB | RPL7A | CHST12 | ATP5B | TNFRSF18 |
| ACTB | CD3E | CD63 | ID2 | KLF6 | TNFRSF9 | RPL28 | CDC42SE1 | EMP3 | MAP3K8 |
| FCN1 | RPS7 | DEDD2 | MYL12A | RPL13A | PTTG1 | GLTSCR2 | C20orf24 | MARCKSL1 | TEX30 |
| IL8 | TOMM7 | GPSM3 | FASLG | CREM | RHOH | NOSIP | LSP1 | HLA-DRB1 | BZW1 |
| ARPC1B | CXCR4 | DDX5 | CYTIP | BIN1 | RHOG | NPM1 | SAMD3 | | H3F3B |
| HLA-DQA2 | MYL12A | | KLRD1 | RPL23A | GMFG | LEF1 | PTPRCAP | HLA-B | DDX18 |
| PILRA | RPL18A | UBE2D3 | DRAP1 | APRT | CST3 | RPL6 | HSPB1 | PEBP1 | MRPL18 |
| LILRB1 | BTG1 | CFL1 | CD8B | RPS20 | CD52 | ZFP36L2 | ABHD17A | TRAF3IP3 | PRPF6 |
| FGR | RPL9 | GRN | CLIC3 | HLA-C | PPP1R2 | RPL15 | RGCC | ATP5G1 | PRAM1 |
| NINJ1 | RPL7A | PSMB9 | IFITM3 | CYBA | UBE2D2 | EIF3E | CD44 | RPL37A | SLC43A2 |
| CD86 | TMSB4X | TPM3 | CXCR3 | ABRACL | FYB | TCF7 | MAPK1 | HLA-DPB1 | RAN |
| LINC00877 | CD63 | CD48 | PPP1R18 | TC2N | TNFRSF9 | HINT1 | LDLRAD4 | PRF1 | FCER1G |
| OAZ1 | CORO1A | RPL14 | RPS4Y1 | 1-Sep | PTTG1 | RPS29 | ACTB | HOPX | MGAT4A |
| TREM1 | FAU | PDCL3 | ACTR3 | CD99 | CD2 | RPLP0 | EVL | GSTP1 | SLC25A39 |
| ASGR1 | CD2 | SAMSN1 | GRN | EVL | TRAF3IP3 | UBA52 | TMIGD2 | PDLIM7 | NFKBIZ |

TABLE 15-continued

| | | | | | | | | | |
|---|---|---|---|---|---|---|---|---|---|
| HLA-DMA | TNFAIP3 | PSME2 | RGL4 | ICAM3 | NTMT1 | LEPROTL1 | MRPL3 | CST7 | BLVRA |
| TNFAIP2 | RPL36 | RPS6 | TPI1 | IFITM3 | RPS15A | RPL22 | GZMM | GRN | FOS |
| ARPC3 | CCL5 | SRGN | COTL1 | LCK | ADTRP | RPL38 | ZFP36L2 | HLA-DPA1 | RNASET2 |
| CAMK1 | EEF1D | RPL32 | TRAPPC1 | C12orf75 | CACYBP | ITM2C | NUDT14 | IFITM2 | IL2RG |
| S100A4 | GPSM3 | ALOX5AP | KLRC1 | ARPC2 | S100A4 | HSPA1A | TESC | LCK | EIF4A1 |
| CPPED1 | LDHB | RPS20 | HSPA1A | FYN | GPR183 | RPL3 | SH2D1B | EVL | LINC00299 |
| RAB20 | RPS9 | ARHGDIA | CIB1 | XCL1 | JUN | TRAT1 | CHD2 | GZMK | EMP3 |
| RIPK2 | LEPROTL1 | SOCS1 | PSMB10 | PRF1 | ENO1 | EEF1D | FAM49B | SIRPG | DNAJB1 |
| CXCL9 | PFN1 | DDIT4 | ITGA1 | PSAP | UBC | EEF2 | VDAC1 | LGALS3 | IL7R |
| LAP3 | KLF6 | MIR24-2 | LAT2 | ATP5E | TNIP2 | BTF3 | BIN2 | NANS | BST2 |
| ATP6V0B | CALM1 | HLA-B | CD244 | YPEL5 | 1-Sep | LGALS3 | ARHGDIA | CD74 | CREM |
| HCK | CD69 | HLA-DRB1 | ITGAE | DRAP1 | EVL | SMDT1 | CDHR1 | CYC1 | SLC16A3 |
| GCA | APRT | PGK1 | ENO1 | MCL1 | CXCR6 | PFDN5 | SIGIRR | AGR2 | KIAA1324 |
| RP11-290F20.3 | GLTSCR2 | LAPTM4A | BCAS4 | CRTAM | HSPA8 | TOMM7 | VPS37B | HLA-C | UNC93B1 |
| LILRB4 | GPR183 | FDX1 | CDK2AP2 | PPP1CA | TAPSAR1 | HNRNPA1 | TNFRSF18 | SH2D1A | ENO1 |
| CD37 | RPL26 | RPL27A | NFKBIA | RPLP1 | GNB2L1 | EIF3F | GRK6 | LAPTM5 | SKIL |
| PRELID1 | RPL36AL | RPS4X | PTMA | RPS15A | XRCC6 | CCDC109B | DUSP1 | SLC25A5 | RNF139 |
| RNASET2 | GIMAP7 | CITED2 | GIMAP7 | GSTK1 | CYTIP | PTPRCAP | ZFP36 | CORO1A | HSP90AA1 |
| GCH1 | HSPB1 | PSME1 | RPLP2 | TIMP1 | CD37 | CD3D | SELM | HLA-A | BEX2 |
| CYBB | ABRACL | RAN | NPC2 | CLIC1 | RPL13A | EEF2 | IDS | HSPD1 | TMEM243 |
| NCF4 | PSAP | MALAT1 | ARPC1B | ID3 | NSA2 | RPL23 | PRDX1 | RPL36 | DDIT4 |
| IL23A | HLA-DPB1 | H3F3B | VASP | TMA7 | CD3E | RPS3A | RHOF | IL2RB | RBM39 |
| RP11-701P16.5 | RPL24 | RPS15A | LSP1 | PTPRC | HMGN1 | PSAP | LGALS3 | LSP1 | SIK1 |
| SERPINB9 | HLA-DRB1 | FOSB | HERPUD1 | PPP2R5C | TRAPPC4 | GIMAP7 | CFL1 | TSPAN5 | PSMD13 |
| MPEG1 | PTPRCAP | CXCR4 | RGCC | RGCC | TRAPPC1 | RPL24 | CMC1 | GCHFR | RASD1 |
| CCL3 | KLRB1 | BCAS2 | PTPN22 | RNF167 | SH2D1A | LIMD2 | RNF113A | ATP5G3 | AQP3 |
| CFD | IFITM3 | ALG13 | CISH | MYL12B | TIMP1 | RPL37A | IL2RG | HIST1H4C | MED30 |
| UBE2D1 | HLA-DPA1 | LCK | MATK | PSME2 | ARID5B | RPL9 | TIMM8B | GPX2 | HHEX |
| THEMIS2 | FTL | RPL11 | HSPA1B | HMOX2 | SKAP1 | RPS11 | FASLG | RPL38 | ZNF331 |
| STXBP2 | EVL | CDC42SE2 | SOCS3 | RPL13 | DOK2 | TRAF3IP3 | TMSB4X | SAMSN1 | BTG2 |
| ARRB2 | APOE | RPL13 | RPS3 | CD59 | SNRPB | RPS24 | SRSF5 | COX5A | RPL22L1 |
| GPX1 | FXYD5 | CACYBP | RPL13A | SAMSN1 | ISG20 | PASK | LAMTOR5 | HN1 | NCR3 |
| TIFAB | CD74 | IDS | PSME1 | RARRES3 | TNFRSF14 | TPT1 | AKNA | HLA-DQA1 | MYADM |
| CORO1A | HLA-DRA | GALM | PTPN7 | TRAPPC1 | FXYD5 | NACA | USF2 | ATP5O | LPXN |
| DUSP2 | DDX5 | CD6 | CD2 | TAPBP | CDKN2A | CORO1A | RAC2 | UQCR10 | RBPJ |
| TESC | RPS4Y1 | CCL20 | ASB2 | SH3KBP1 | RPL36AL | COX7C | NDUFB8 | UBE2C | UBE2S |
| CD68 | RGCC | RPS2 | OSTF1 | APOBEC3G | PCBP1 | IFITM3 | SDHC | GMFG | DPAGT1 |
| SPHK1 | TC2N | RPL31 | DOK2 | GLIPR2 | LAPTM5 | EIF3H | RANGRF | GNG2 | NHP2 |
| KYNU | HSPA1A | UBE2D2 | ITGB7 | PSMB10 | PTPN2 | CXCR4 | KLRB1 | FYN | CYCS |
| BCL2A1 | CMPK1 | IL4I1 | MT-CO1 | DHRS7 | UXS1 | ANAPC5 | PSMB2 | HES1 | PRR5 |
| GLUL | CD6 | SLAMF1 | CD59 | RPL19 | PMAIP1 | RPL18A | SLC16A3 | GNLY | CCT4 |
| BLVRA | IL2RG | FOS | TNFRSF18 | TSC22D3 | UGP2 | CD7 | RIN3 | ID2 | HMGN1 |
| KDM6B | SRGN | MGAT4A | RPLP1 | MALAT1 | 9-Sep | DENND2D | RBM38 | UQCRQ | BCAS2 |
| NAMPT | NPM1 | TRMT112 | FCER1G | STK17A | ARF6 | MZT2A | ID1 | XCL1 | BTG1 |
| SLC31A2 | TSC22D3 | FAM96B | LAG3 | DENND2D | CMC2 | FAIM3 | UBXN2B | HLA-DMA | MAP2K1 |
| NUP214 | PDCL3 | IL12RB1 | HSPB1 | RPL31 | LIMD2 | RPL35 | LINC00667 | RPS29 | CXXC5 |
| ABI3 | ZFP36L2 | SVIP | ARL6IP5 | ITM2A | PSME1 | OCLAD2 | CST3 | ANXA1 | ATG4B |

TABLE 15-continued

| | | | | | | | | |
|---|---|---|---|---|---|---|---|---|
| SELK | CD59 | CCR6 | WAS | CDK2AP2 | LEPROTL1 | GPSM3 | PPP5C | RGCC | SFPQ |
| PSAP | CFL1 | RPL36AL | BUB3 | MZT2A | TMSB4X | C6orf48 | ID3 | CCNB1 | SRGN |
| SAMSN1 | SOCS1 | PLP2 | RGS1 | RGS1 | IGBP1 | UBB | DRAP1 | BST2 | NPC2 |
| PPIF | NACA | CYCS | CD69 | SOCS1 | PYHIN1 | RNF138 | NFKBIA | ATP5A1 | TUBA4A |
| ATF5 | RPL38 | TTC39C | SLC16A3 | GUK1 | BCAS2 | CYTH1 | CCNL1 | CLEC2D | CALM1 |
| AMICA1 | CKLF | HLA-DPA1 | HLA-DRA | GRAP2 | PHLDA1 | SERPINB6 | NXT1 | ECHS1 | TXK |
| IGJ | CD37 | NOP58 | RPS3A | C19orf60 | PRR13 | CCL5 | ARID5A | CCNB2 | SPTLC2 |
| ITM2C | SH2D2A | ENO1 | PTTG1 | TNFAIP3 | ZNHIT1 | FAM177A1 | AGTRAP | ATP5J2 | ANP32A |
| YBX1 | GNB2L1 | MYADM | LDLRAD4 | IL2RG | SOD1 | DCXR | ARHGDIB | TNFRSF18 | CCR6 |
| ACSL1 | IGJ | RPS25 | CD53 | DDX5 | MAPK1IP1L | NUCB1 | CBX3 | CKS2 | PROSC |
| RNASE6 | BTF3 | HNRNPA0 | PSAP | EEF1D | OSER1 | DAP3 | TCEB2 | NCAPH | TXNL1 |
| ZFAND5 | NPC2 | JUN | PTGER2 | RPS12 | CASP4 | P4HB | RPS3 | RPL5 | TRAF4 |
| GRN | CXCL14 | YPEL5 | SH3BP1 | ARPC1B | RGCC | FYB | ZNF814 | RAC1 | HSP90AB1 |
| WAS | CCDC109B | PPP1R15A | CHMP4A | PTGER4 | NAMPT | HLA-DPA1 | LINC00996 | ARPC1B | SRSF5 |
| TNFAIP8 | LGALS1 | SERP1 | IDH2 | ZNF331 | 6-Sep | FOSB | PSMA7 | ABI3 | SLA |
| JUN | HSPA8 | RPS14 | RPS27A | BUB3 | ID1 | 6-Sep | CD69 | GPX1 | RNF19B |
| ASGR2 | CRIP1 | LSM2 | EVL | RBM8A | GBP2 | CHI5L2 | YPEL3 | MT1G | COL9A2 |
| CXCL2 | HSPA1B | PSAP | EEF1A1 | CAP1 | SSU72 | ID3 | APRT | CYTIP | NFKB1 |
| FCGR1B | CCR6 | FAU | HCLS1 | RPS18 | COPE | CST3 | HMGN1 | SURF4 | PPP2CA |
| LIMD2 | RPS29 | RPL13A | MYL12B | 7-Sep | YWHAZ | ARPC1B | CPNE1 | CTSH | NAP1L1 |
| DOK2 | PFDN5 | CRIP1 | CRIP1 | C19orf24 | COMMD3 | JUNB | IGFBP7 | FXYD5 | SRP9 |
| PFN1 | TTC39C | PTPRCAP | PABPC1 | HLA-DRB1 | GLRX | RARRES3 | PPP1CA | PFKP | BEX4 |
| LILRA2 | RPS21 | DHRS7 | LYAR | FAM177A1 | RBBP4 | BEX2 | YWHAZ | CRIP1 | TMEM123 |
| PYCARD | C9orf142 | H2AFZ | FYN | CRIP1 | PTPRC | ICOS | EBP | ZAP70 | TUB4B |
| ISG15 | RPL37A | AMD1 | BIN1 | ABT1 | HIGD2A | HLA-DRB1 | MIR24-2 | ICOS | LGALS3BP |
| KMO | RPL17 | CD74 | RGS19 | CXCL14 | SMS | IFITM1 | ZNF331 | MT1E | TNF |
| IL10 | PABPC1 | ODF2L | DEF6 | RPS25 | CCL20 | PFN1 | GCHFR | RPL12 | HSPD1 |
| CTSH | EIF1 | SND1 | RPL18A | SNRPB | ANP32A | CD3E | TRAPPC1 | RORA | SAMD10 |
| CD48 | GSTK1 | OSTF1 | IFI27 | RPS2 | NPM1 | TBC1D10C | DDIT4 | IL2RG | CSTB |
| RTN1 | ARL4A | ERP29 | LCP1 | EIF1 | NAPA | RNASET2 | GRB2 | IFI16 | CRIP1 |
| IKZF1 | YPEL5 | PNP | HENMT1 | CTSB | APOE | EIF2S3 | OCIAD2 | ETFB | CD47 |
| SH3BGRL3 | CD7 | ARL4A | CXCR6 | BAX | RPL15 | CASP8 | MPG | UPP1 | EMC10 |
| C19orf38 | HCST | RPL30 | RPL9 | MFSD10 | HSPB11 | FXN | RALA | ATP5J | SACM1L |
| RIN3 | LAPTM5 | MRPL11 | FCGRT | RPL36AL | ACTR3 | CYLD | C19orf25 | S100A4 | ANXA5 |
| PSME2 | ITM2C | AATF | RPS10 | RORA | CDC42SE2 | SC5D | SNRPA1 | PSMB9 | IFI44L |
| HCLS1 | ID2 | RPL4 | CCL4 | SRSF7 | TMEM66 | LMNA | BUB3 | STK17A | CAPG |
| CD83 | FYB | MCL1 | RPS27 | HNRNPUL1 | SNX5 | MAL | PLAC8 | RPS14 | FAM213B |
| AP1S2 | TUBA4A | JUNB | APOBEC3G | COPE | CHCHD10 | AIM1 | PDCD4 | KRT19 | EIF3D |
| LCP1 | 1-Sep | BAZ1A | CD99 | FTL | ICAM3 | TMSB4X | SLC25A39 | TIMM13 | EIF4G2 |
| ITGAX | RPL22 | EIF4A3 | TPM3 | C9orf78 | JUNB | MRPL16 | RPL7L1 | CD247 | ERBB2IP |
| PKM | RORA | CREM | RPL17 | PDCL3 | LIMS1 | COTL1 | NSMCE1 | RPS4Y1 | ARF1 |
| CFL1 | LAPTM4A | SRSF2 | GYPC | TAGAP | EPSTI1 | CRLF3 | BUD31 | RPL7A | PARL |
| VAMP8 | PLD3 | RPS5 | GSTK1 | UBE2D3 | C19orf43 | H2AFV | PAPOLA | TMSB4X | HSPA5 |
| IFNGR2 | SNRPD2 | MRPL34 | IL2RG | C14orf1 | PIM2 | AAK1 | CALM1 | RPS18 | ZFAS1 |
| NPC2 | METTL9 | SNHG8 | ATP5E | PLP2 | LINC00152 | SLC2A3 | MRPS11 | GZMH | GSN |
| RILPL2 | B2M | C9orf142 | GYG1 | GPSM3 | GTF3C6 | CTSD | C1orf162 | SRI | WDR45B |
| CSF1R | CACYBP | MTFP1 | FOSB | UBE2L3 | SOCS1 | AC013264.2 | PSME2 | PIGR | TPM3 |
| GPBAR1 | SAMSN1 | RPS8 | SASH3 | GPR65 | RPL11 | TMSB10 | LDHB | KRT18 | SERTAD2 |
| OSM | HIGD2A | PRR5 | C19orf53 | ATP6V0E1 | UFC1 | 1-Sep | CD59 | COX4I1 | CA13 |

TABLE 15-continued

| | | | | | | | | |
|---|---|---|---|---|---|---|---|---|
| CCRL2 | ARPC1B | ACTG1 | RAC2 | TSC22D1 | IGBP1 | RBCK1 | CCL4 | AKAP17A |
| CLEC10A | 9-Sep | CHCHD7 | KLRD1 | ARPC4 | RPS4Y1 | GRN | CENPW | CUTA |
| IL4I1 | GPR171 | RPS13 | HLA-DRA | NUDT1 | ZFP36 | BCAP31 | STOM | CDC42SE1 |
| CD52 | AES | PTGER2 | EBP | ANAPC16 | COMMD6 | AIM1 | CREM | PRKAR1A |
| SYK | LAT | HSPE1 | CYBA | TPRKB | DNMT1 | TGFB1 | PTTG1 | EPS8L2 |
| CHMP1B | ACTB | TC2N | PSME2 | PHGR1 | GIMAP4 | TIPARP | RPL35A | H2AFX |
| NLRP3 | NKG7 | SAP18 | TMUB1 | WDR1 | CXCL14 | MYO1F | FKBP11 | CXCL2 |
| HBEGF | DYNLT3 | RORA | EGR1 | RNF149 | YPEL5 | SF3B2 | PHB | ALG13 |
| | | | CD74 | HLA-DQA1 | | | | |
| CCL3L1 | TRAT1 | CCDC109B | GZMM | GAPDH | WHSC1L1 | NDUFS8 | PTGER2 | SNRPB |
| IFI27 | EIF3E | CDK2AP2 | CAPN12 | STUB1 | ZNF331 | RTN3 | SUCLG1 | B3GALT5 |
| IL27 | RARRES3 | UBE2S | SPINT2 | SNRPD2 | CD27 | NDUFA3 | ACAP1 | NRBP1 |
| ATP6V1F | OXNAD1 | LAT | C9orf78 | CSNK1D | GSTK1 | PPP1R14B | AIP | AUP1 |
| ARHGDIB | SERPINB6 | CD97 | POLR3GL | SMCO4 | SSU72 | PTMA | PLEKHF1 | GPATCH3 |
| TMSB10 | SPINT2 | GSTK1 | PDLIM1 | HSPA1A | HLA-DPB1 | SH2D1A | UQCR11 | TRIAP1 |
|  |  |  | RPL14 | EEF2 |  |  |  |  |
|  |  |  |  | LDHB |  |  |  |  |
| VSIG4 | COMMD6 | PSENEN | RALY | CUTA | SPOCK2 | PIGX | HSPE1 | SF1 |
| ANXA2 | HNRNPA1 | LDHA | RPL22L1 | TNIP1 | TIMP1 | PTPN4 | TPM1 | GPR65 |
| VASP | ACP5 | EIF4A1 | FAM96B | SKP1 | SLC25A6 | JAK1 | HINT1 | VEZT |
| PPDPF | RAP1A | FUS | TOMM7 | ITM2A | C1orf228 | IRF8 | DBI | PCBP1 |
| ARL5B | RPSAP58 | HNRNPUL1 | SNRPB2 | HCLS1 | LCK | TADA3 | CCND3 | NR1H2 |
| MT-CYB | EEF1A1 | C14orf166 | METTL5 | HLA-G | NAA38 | HSPE1 | ITK | FKBP3 |
| GBP5 | CREM | SPINT2 | RPL32 | GYPC | DCK | GGA1 | RPS6 | TNFRSF4 |
| PSTPIP2 | RCAN3 | SURF4 | PNN | RPS3 | GPR18 | RTCA | CLDN7 | CD3E |
| GPR183 | CD48 | MZT2A | MBP | SH3BGRL3 | CTSC | TLN1 | CD53 | GPR68 |
| HCAR2 | SPOCK2 | CXXC1 | CLDND1 | RPS27L | HERPUD1 | TRMT2A | EEF2 | TNFSF4 |
|  |  |  | MT-CYB |  |  |  |  |  |
| SAMHD1 | TNFSF13B | PCBP1 | GTF3A | GPX1 | TPI1 | PSTPIP1 | SH2D2A | H2AFZ |
| HAPLN3 | EIF3H | RPS18 | ATF6B | SNRPB2 | RGCC | GGNBP2 | COX6B1 | PSME1 |
| CAPG | SAT2 | ANXA5 | TSC22D4 | AKIRIN2 | LINC00861 | NHP2 | HMGA1 | JMY |
| EPSTI1 | LYAR | HMGN1 | CDC42SE2 | PSMD8 | CD59 | PSD4 | RNF187 | NUP54 |
| RNF130 | PLP2 | HCST | LAPTM4A | COX17 | EVL | RTFDC1 | NDUFA11 | XCL1 |
| ID3 | MZT2A | PSMA7 | ALG13 | UBE2I | CORO1B | PSMD6 | HMGN1 | GNA15 |
| CREM | MGAT4A | LAPTM5 | SCML4 | SELT | CYCS | DCXR | STMN1 | LTC4S |
| LITAF | SMDT1 | TIMP1 | PTPN4 | IL2RA | ZNHIT3 | TSPAN32 | UQCRC2 | TXNDC17 |
|  |  |  | COMMD6 |  |  |  |  |  |
|  |  |  | CD9 |  |  |  |  |  |
|  |  |  | CD74 |  |  |  |  |  |
|  |  |  | HLA-DRB5 |  |  |  |  |  |
|  |  |  | RP11-47L3.1 |  |  |  |  |  |
| CXCL3 | ANXA5 | EML4 | PHGR1 | FAIM3 | TOMM20 | CUTC | LAT | GATA3 |
| PLA2G7 | ENO1 | AMICA1 | EPSTI1 | GK | TUBA4A | ATP6V1G1 | HLA-DQB1 | N4BP2L2 |
| UBE2E2 | TMEM14B | ICAM3 | CASP4 | NAA38 | 9-Sep | IFITM1 | AK2 | CTSH |
| H2AFY | PSME1 | IL17A | CTSB | PSMA2 | DGUOK | C19orf66 | WDR54 | SLC39A4 |
| UBXN11 | CYCS | EIF1AX | ARPC3 | SNRPD2 | LYRM4 | PPP1R18 | RPS24 | PER1 |
| RGS2 | ATP5L | DYNLT3 | APRT | RPL24 | FTL | TMEM14C | TSC22D3 | AC022182.3 |
| RHOG | RBM3 | IFITM2 | RPL7 | CSRNP1 | JUN | ALKBH2 | MTPN | HCST |
| CASP1 | ICAM3 | PRKCQ-AS1 | VAMP8 | PIK3IP1 | LAT | POLR2L | MYO1G | PCDH9 |
| CD274 | ALOX5AP | RBL2 | RPL4 | BLVRB | ID3 | METRNL | KLRG1 | TPI1 |
| HCAR3 | C19orf24 | HSP90B1 | RPL27 | SLAMF1 | PIK3IP1 | SERBP1 | NRM | RP11-425D10.10 |
|  |  |  | HLA-DQB1 | RPL18 | OAZ2 |  |  | SERTAD1 |
|  |  |  | RPL3 |  |  |  |  |  |
| LINC00936 | GMFG | SNRPB | OXNAD1 | UBXN1 | FOS | C9orf16 | FOSL2 | KIT |
| TUBA1B | NEAT1 | FERMT3 | NEDD8 | FTL | HSPB1 | BHLHE40 | 1-Sep | ERGIC3 |
| IL18BP | EGR1 | GHITM | C11orf31 | H2AFV | AES | TSC22D4 | PRDX5 | |

TABLE 15-continued

| | | | | | | | |
|---|---|---|---|---|---|---|---|
| C12orf57 | PTPRC | SELT | SAMSN1 | HSPA9 | COX4I1 | S100A6 | SSBP4 | ZNF814 |
| EMG1 | CD97 | NFKBIA | PSMB9 | TPM3 | LINC00649 | RBM39 | RPS13 | FOSL2 |
| PTGS2 | UBE2D2 | RPS16 | CD37 | CHMP4A | LRRFIP1 | RNF125 | GIMAP1 | LYPLA2 |
| MYO1F | TXNIP | RPL22L1 | ANAPC16 | PSENEN | RAB1A | MAFF | MPC2 | SIVA1 |
| NADK | GTF3A | ISG20 | RPL21 | HSD17B10 | MALAT1 | SLC9A3R1 | COX7C | JTB |
| RABAC1 | RPS11 | SNRPD2 | RPSA | MLX | HLA-DRA | STXBP2 | GMNN | ANP32E |
| A2M | PPP2R5C | IFI35 | RPL34 | RPL34 | HLA-DRA | CLDND1 | GNB2L1 | RNFT1 |
| GDI2 | SNRPG | CASP1 | HMOX2 | CIB1 | GTF3A | AP2M1 | PABPC1 | EIF5 |
| GLIPR1 | TMA7 | NPC2 | LSM10 | OCIAD2 | ABHD14B | PSMD8 | HLA-DRB5 | BAD |
| | | | PSMD13 | SLC38A1 | ACP5 | | | |
| HSPB1 | RPL22L1 | SLC1A5 | PGK1 | TADA3 | CHCHD7 | VAPA | FAM162A | PNP |
| DSTN | IFITM2 | TRAPPC1 | TYROBP | IDH2 | RAN | SOCS1 | OASL | HNRNPK |
| NMI | DUSP2 | TUBA4A | HLA-DRB1 | GHITM | CD74 | HNRNPA2B1 | OSTF1 | MGMT |
| CD9 | RPL23 | MAX | C11orf48 | NHP2L1 | VAMP2 | DHRS7 | DOK2 | TCTN3 |
| DUSP1 | SCML4 | UXT | RPL28 | ATP5D | APRT | AKIRIN2 | C1QBP | C6orf57 |
| MCL1 | C19orf53 | HSPB1 | GGA1 | ACADVL | C19orf43 | COA5 | LIMD2 | PCNP |
| BSG | GGA1 | RBM3 | EEF1D | ATP8A1 | RNF213 | COMMD6 | CD160 | TP53I13 |
| MT-ND3 | MZB1 | RAB8A | LAPTM5 | GATA3 | ZC2HC1A | ATG12 | TUBB | C3orf17 |
| RNF19B | ARHGEF1 | TAPBP | GPR34 | NAA50 | ALDOA | ARPC2 | RPL24 | MRPS15 |
| GLIPR2 | HERPUD1 | RPL23A | TSTA3 | AKR1A1 | G3BP2 | KLHDC4 | DDT | GPX7 |
| PSMB9 | JUN | EMP3 | BANF1 | CD97 | HCST | LRRFIP1 | GTPBP1 | CASP6 |
| GAPT | PHLDA1 | UBA52 | CDIP1 | MZB1 | CIB1 | APOBR | ATP2B4 | HLA-B |
| NAGK | PRKCQ-AS1 | CRIP1 | C11orf31 | MEA1 | PDCL3 | ETF1 | NDUFC1 | CRTC2 |
| C10orf54 | ZFAS1 | NR4A2 | STXBP2 | PSMB8 | SSBP1 | CASP4 | RAB27A | MBOAT7 |
| CTSB | EEF2 | TAP1 | RPL22 | MYEOV2 | CCT7 | CASP3 | PRDX3 | TNFAIP3 |
| CD53 | COTL1 | SS18L2 | CALM1 | UBE2I | HPRT1 | CD53 | CXCR6 | DCAF11 |
| CSF3R | TRAPPC6A | FLT3LG | RPL36A | ZFP36 | PTGES3 | U2AF1 | RPL23 | SRSF7 |
| SCIMP | CTSD | GPR183 | NUDT14 | FIBP | MRPS35 | TSEN15 | CDC20 | PPP1R11 |
| MT-ND4 | NDUFS5 | IRF1 | IRF2 | C14orf166 | SRP19 | AOAH | NASP | ZNF207 |
| PSMA4 | CLIC1 | CXCR3 | MRPL46 | SIGIRR | HSP90B1 | HLA-DPA1 | RHOF | FURIN |
| | | | | | BUB3 | | | |
| HCST | RPS24 | PPP6C | YPEL5 | RPL10 | BTG3 | PHGR1 | OBFC1 | CDKN3 | WDR83OS |

Figure 45A:
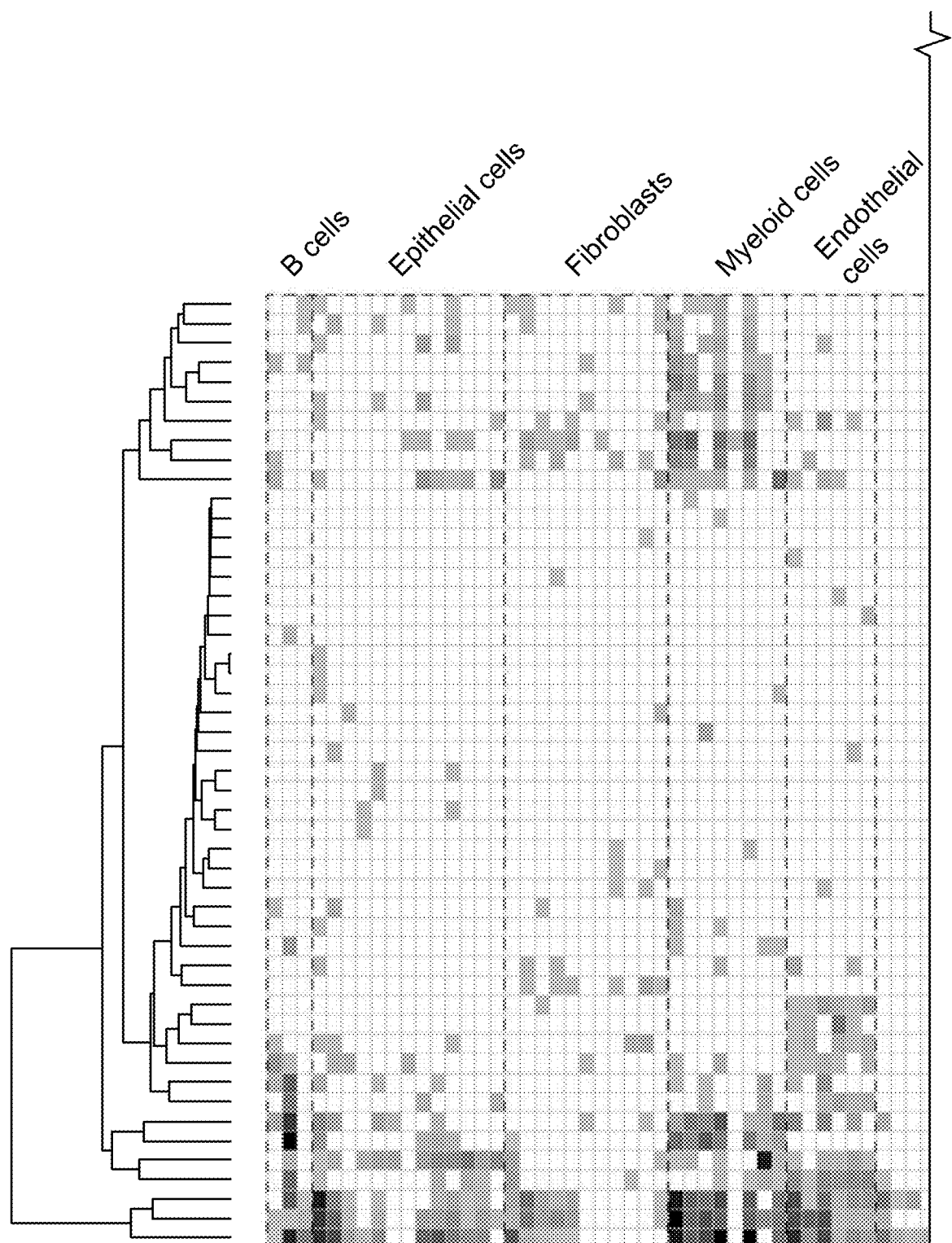
FIGS. 45A-45B illustrates that the atlas can be used to determine the cell-of-origin for GWAS genes for other indications.
Figure 45B:
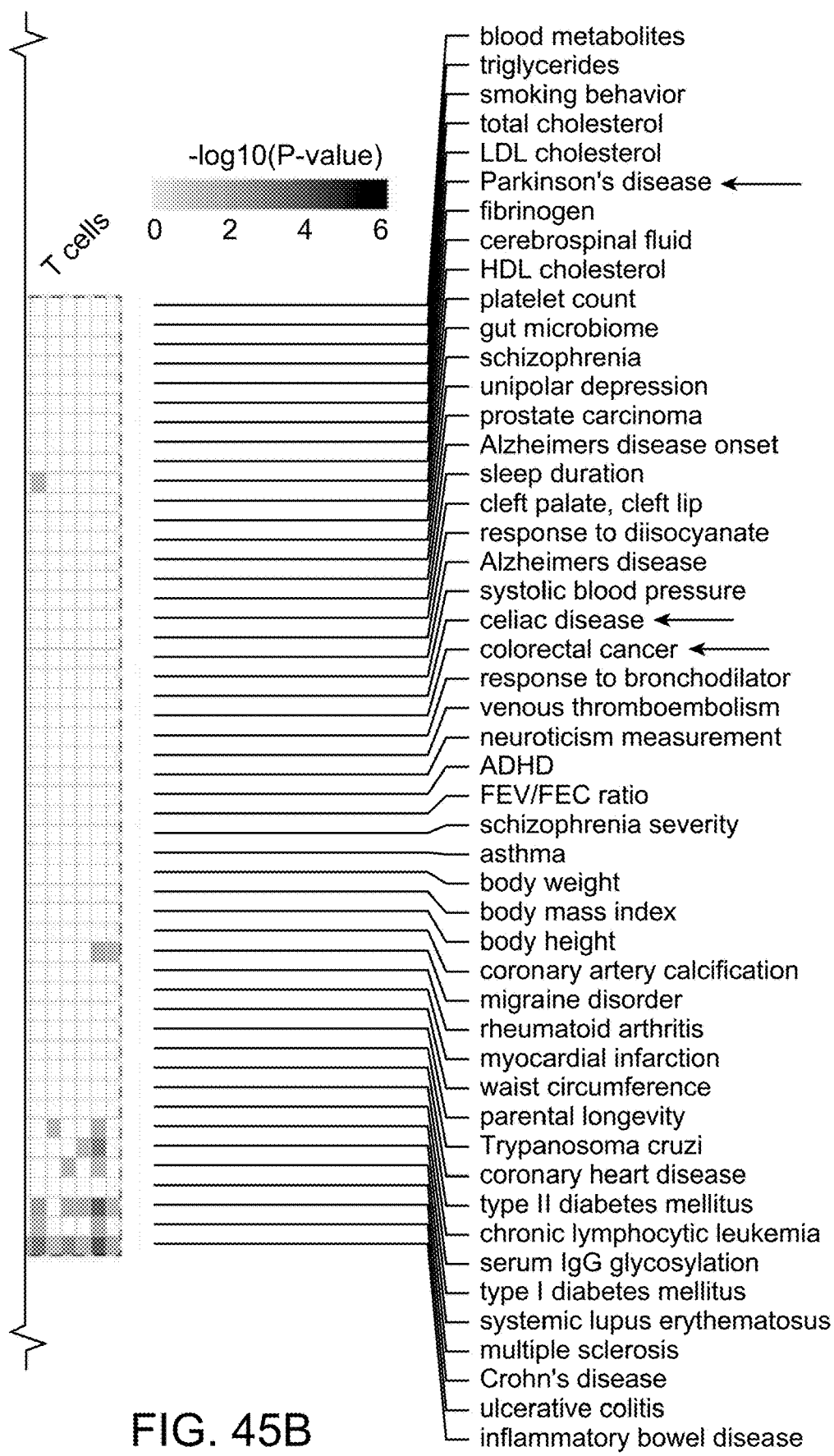

Applicants were able to determine the cell of origin for genes associated with disease by genome wide association (GWAS) (e.g., IBD). Applicants show heatmaps for GWAS genes expressed in each cell type (FIGS. 41-45). Applicants show a heatmap for G-protein coupled receptors (GPCR), genes involved in cell-cell interactions, and in epithelial cells in the gut cell types. (FIGS. 42A, 42B, 43A, 43B, 44A, 44B and 44C). Key genes are highlighted in FIGS. 44A-44C. FIGS. 45A and 45B shows that genes associated with other disease indications can be localized to specific cell types in the atlas.

Figure 46:
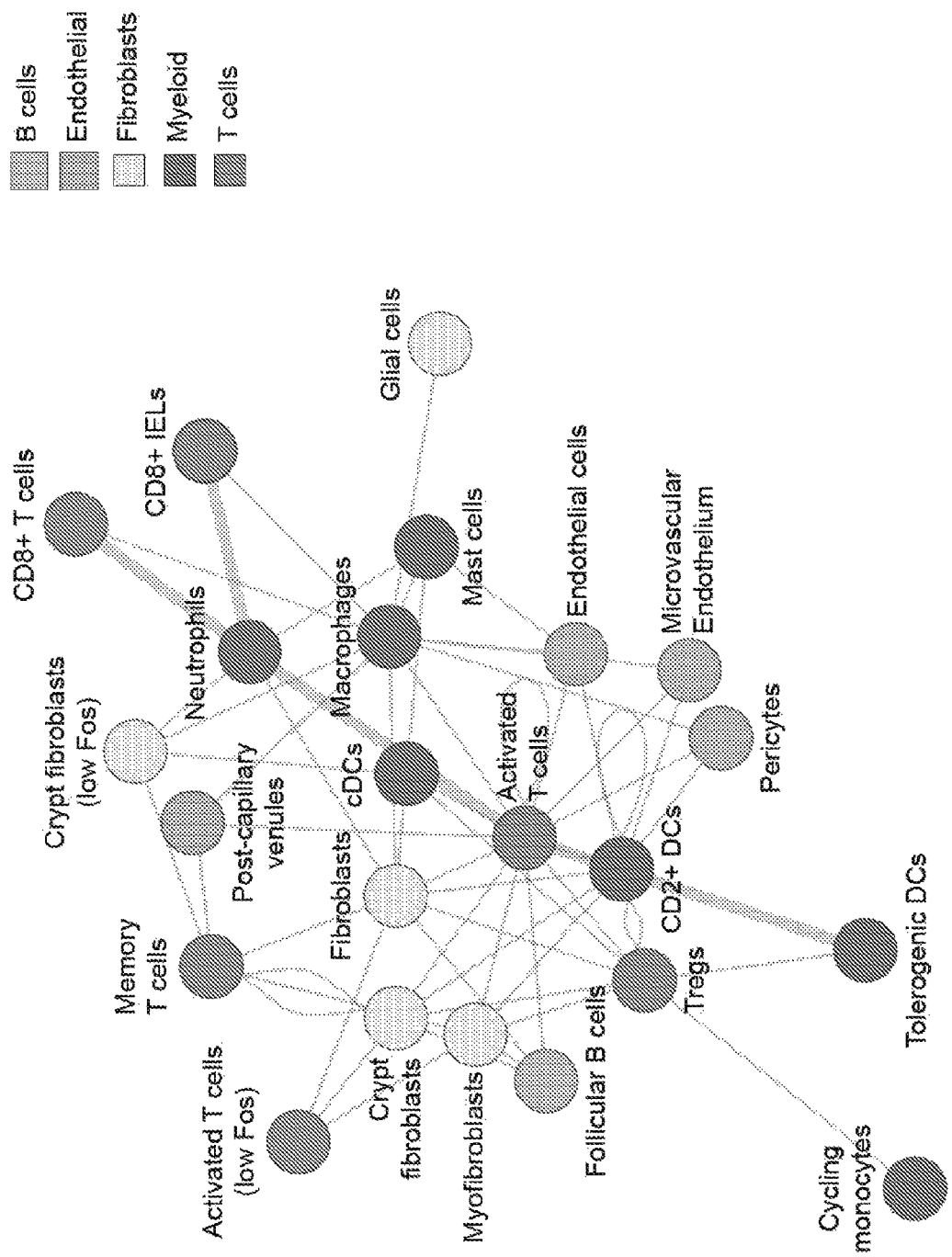
FIG. 46 illustrates that the atlas can be used to determine cell-cell interaction mechanisms.
Figure 47:
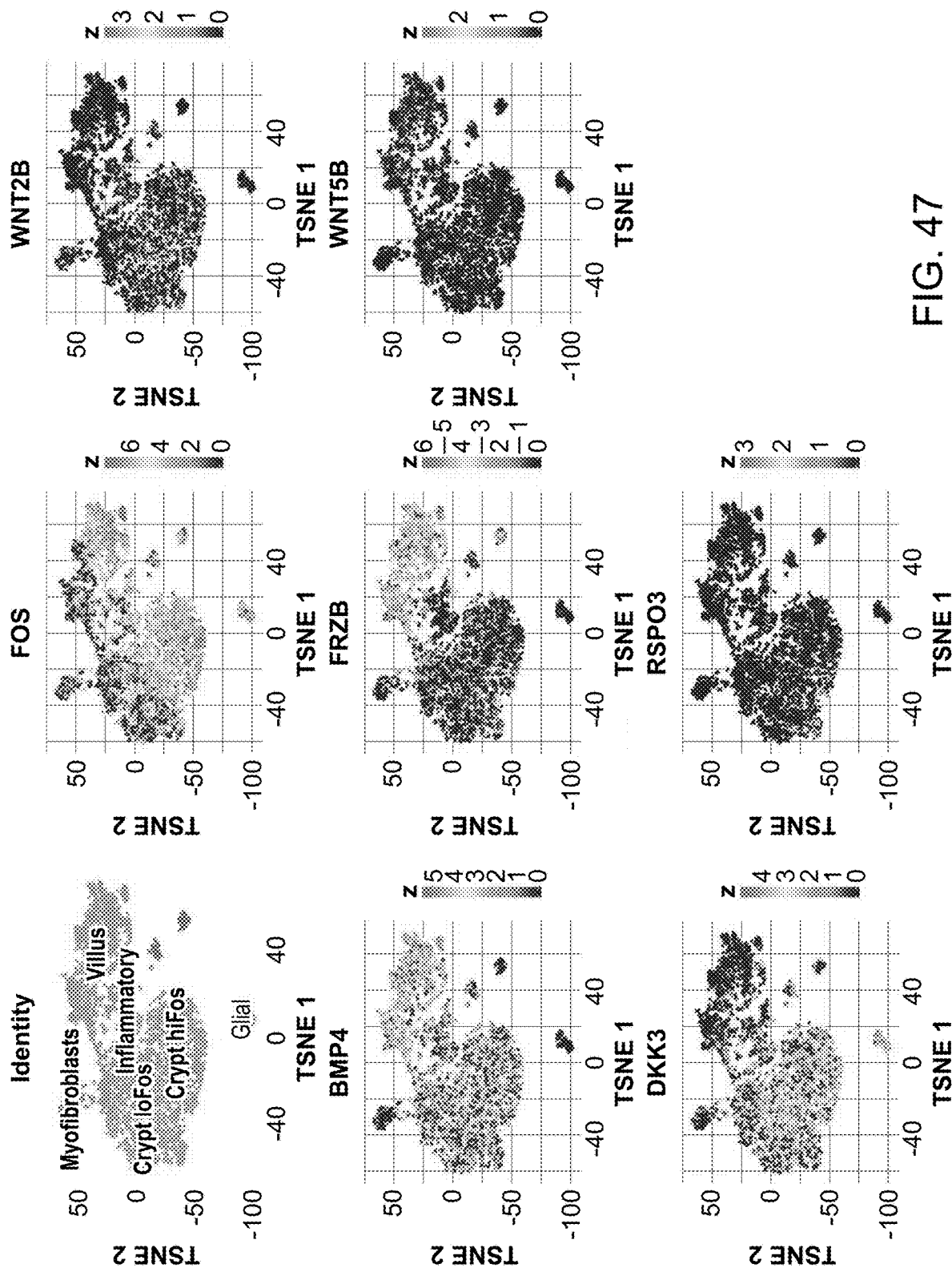
FIG. 47 illustrates that the atlas can be used to determine fibroblasts that support the stem cell niche.

Applicants also show that the atlas may be used to determine cell-cell interaction mechanisms within the gut (FIG. 46). Finally, Applicants show that fibroblasts that support the stem cell niche can be identified using the atlas (FIG. 47).

Example 23—Materials and Methods

Mice

All mouse work was performed in accordance with the Institutional Animal Care and Use Committees (IACUC) and relevant guidelines at the Broad Institute and MIT, with protocols 0055-05-15 and 0612-058-15. Seven to ten weeks old female or male C57BL/6J wild-type, Lgr5-EGFP-IRES-CreER$^{T2}$ (Lgr5-GFP), MHCII-KO, Foxp3—DTR, B6 Nude and TCRβ-KO mice, obtained from the Jackson Laboratory (Bar Harbor, ME) or Gfi1b$^{eGFP}$/+(Gfi1b-GFP) were housed under specific-pathogen-free (SPF) conditions at the Broad Institute, MIT or at the Harvard T. H. Chan School of Public Health animal facilities. MHCII-EGFP was obtained from Hidde Ploegh's lab and Lgr5-tdTomato-MHCII-EGFP and H2-Ab1$^{fl/fl}$-Villin-CreER$^{T2}$ (MHCIIDgut) mice were crossed for this study. All mice were housed under specific-pathogen-free (SPF) conditions at either the Broad Institute or MIT animal facilities; infection experiments were conducted at the laboratory of Dr. HN Shi, maintained under specific pathogen-free conditions at Massachusetts General Hospital (Charlestown, MA), with protocol 2003N000158. BrdU and EDU incorporation: EdU was injected intraperitoneally (IP) into Lgr5-GFP mice at 100 mg kg$^{-1}$ for 2 or 4 hours before tissue collection.

*Salmonella enterica* and *H. polygyrus* infection. C57BL/6J mice (Jackson Laboratory) were infected with 200 third-stage larvae of *H. polygyrus* or 10' *Salmonella enterica* at the laboratory of Dr. HN Shi, maintained under specific pathogen-free conditions at Massachusetts General Hospital (Charlestown, MA), with protocol 2003N000158. *H. polygyrus* was propagated as previously described[76]. Mice were sacrificed 3 and 10 days after *H. polygyrus* infection. For the MHCII blocking experiment, mice infected with *H. polygyrus* were injected with 500 g of blocking anti-mouse MHCII antibody (BioXCell) or Rat IgG2b isotype control (BioXCell) one-day prior to and for 2 consecutive days after *H. polygyrus* infection. For *Salmonella enterica*, mice were infected with a naturally streptomycin-resistant SL1344 strain of S. *Typhimurium* (10' cells) as described[76] and were sacrificed 48 hours after infection.

Foxp3-DTR. Foxp3 and wild-type C57BL/6J mice were injected intraperitoneally with diphtheria toxin (DT) at 22.5 ng/g body weight every other day for one week and then sacrificed.

MHCII deletion in intestinal epithelial cells. Cre activity was induced in 7-10 weeks old mice by intraperitoneal injection (IP) of Tamoxifen (SIGMA), diluted in corn oil, 4 mg per injection, 3 times, every other day. Mice were sacrificed 10 days after the first injection.

Cell Dissociation and Crypt Isolation

Crypt isolation. The small intestine of C57BL/6J wild-type, Lgr5-GFP or Gfi1b-GFP mice was isolated and rinsed in cold PBS. For all mice, crypts were isolated from the whole small intestine or the duodenum, jejunum and ileum compartment to account for regional distribution of Lgr5$^+$ stem cells. The small intestine was extracted and rinsed in cold PBS. The tissue was opened longitudinally and sliced into small fragments roughly 0.2 cm long. The tissue was incubated in 20 mM EDTA-PBS on ice for 90 min, while shaking every 30 min. The tissue was then shaken vigorously and the supernatant was collected as fraction 1 in a new conical tube. The tissue was incubated in fresh EDTA-PBS and a new fraction was collected every 30 min. Fractions were collected until the supernatant consistent almost entirely of crypts. The final fraction (enriched for crypts) was washed twice in PBS, centrifuged at 300g for 3 min, and dissociated with TrypLE express (Invitrogen) for 1 min at 37° C. The single cell suspension was then passed through a 40 μm filter and stained for FACS sorting for either scRNA-seq method (below) or used for organoid culture.

FAE isolation. Epithelial cells from the follicle associated epithelium were isolated by extracting small sections (0.5 cm) containing Peyer's patches from the small intestine of C57Bl/6J or Gfi1b$^{eGFP/+}$ mice.

Immune cell isolation. Immune cells from the Lamina Propria were isolated enzymatically by incubating the small intestine with Liberase™ (100 ug/mL, Sigma) and DNaseI (100 ug/mL, Sigma) for 30 min at 37° C. Immune cells were also isolated from the mesenteric lymph nodes (mLN). Cells were then incubated with CD3, CD4, CD45, or CD11b FACS-labeled antibodies and sorted for scRNA-seq.

Cell Sorting

For plate-based scRNA-seq experiments, a fluorescence-activated cell sorting (FACS) machine (Astrios) was used to sort a single cell into each well of a 96-well PCR plate containing 5 μl of TCL buffer with 1% 2-mercaptoethanol. For EpCAM$^+$ isolation, cells were stained for 7AAD- (Life Technologies), CD45$^-$(eBioscience), CD31–(eBioscience), Ter119- (eBioscience), EpCAM$^+$ (eBioscience), and for specific epithelial cells Applicants also stained for CD24+/- (eBioscience) and c-Kit$^{+/-}$ (eBioscience). To enrich for specific IEC populations, cells were isolated from Lgr5-GFP mice, stained with the antibodies mentioned above and gated on GFP-high (stem cells), GFP-low (TAs), GFP-/CD24+/c-Kit$^{+/-}$ (secretory lineages) or GFP-/CD24-/EpCAM$^+$ (epithelial cells). For Tuft-2 isolation, epithelial cells from 3 different mice were stained as above only this time Applicants used EpCAM$^+$/CD45+ and sorted 2000 single cells. A population control of 200 cells was sorted into one well and a no-cell control was sorted into another well. After sorting, the plate was sealed tightly with a Microseal F and centrifuged at 800g for 1 min. The plate was immediately frozen on dry ice and kept at −80° C. until ready for the lysate cleanup. Bulk population cells were sorted into an Eppendorf tube containing 100 μl solution of TCL with 1% 2-mercaptoethanol and stored at −80° C.

For droplet-based scRNA-seq, cells were sorted with the same parameters as described for plate-based scRNA-seq, but were sorted into an Eppendorf tube containing 50p of 0.4% BSA-PBS and stored on ice until proceeding to the GemCode Single Cell Platform or the Chromium Single Cell 3' Library.

Plate-Based scRNA-Seq

Single cells:. Libraries were prepared using a modified SMART-Seq2 protocol as previously reported[32]. Briefly, RNA lysate cleanup was preformed using RNAClean XP beads (Agencourt) followed by reverse transcription with Maxima Reverse Transcriptase (Life Technologies) and whole transcription amplification (WTA) with KAPA HotStart HIFI 2×ReadyMix (Kapa Biosystems) for 21 cycles. WTA products were purified with Ampure XP beads (Beckman Coulter), quantified with Qubit dsDNA HS Assay Kit (ThermoFisher), and assessed with a high sensitivity DNA chip (Agilent). RNA-seq libraries were constructed from purified WTA products using Nextera XT DNA Library Preparation Kit (Illumina). On each plate, the population and no-cell controls were processed using the same method as the single cells. The libraries were sequenced on an Illumina NextSeq 500.

Bulk samples: Bulk population samples were processed by extracting RNA with RNeasy Plus Micro Kit (Qiagen) per the manufacturer's recommendations, and then proceeding with the modified SMART-Seq2 protocol following lysate cleanup, as described above.

Droplet-Based scRNA-Seq

Single cells were processed through the GemCode Single Cell Platform using the GemCode Gel Bead, Chip and Library Kits (10× Genomics, Pleasanton, CA), or the Chromium Single Cell 3' Library, Gel Bead and Chip Kits (10× Genomics, Pleasanton, CA), following the manufacturer's protocol. Briefly, single cells were sorted into 0.4% BSA-PBS. An input of 6,000 cells was added to each channel of a chip with a recovery rate of 1,500 cells. The cells were then partitioned into Gel Beads in Emulsion (GEMs) in the GemCode instrument, where cell lysis and barcoded reverse transcription of RNA occurred, followed by amplification, shearing and 5' adaptor and sample index attachment. Libraries were sequenced on an Illumina NextSeq 500.

Div-Seq

Lgr5-GFP mice were intraperitoneally (IP) injected with 100 mg kg EdU (Click-iT Plus EdU Pacific Blue Flow Cytometry Assay Kit, Thermo Fisher Scientific) for 2 hours and then sacrificed. Crypts were isolated as described above and Lrg5hi cells were FACS sorted into PBS, spun down to remove the supernatant, flash frozen and stored in −80° C. Nuclei were then isolated using EZ Prep NUC-101 (Sigma) per manufacturer's recommendation, and then incubated in the Click-iT Cocktail per manufacturer's recommendations for 30 min, washed in 1% BSA-PBS and counterstained with Vybrant DyeCycle Ruby stain (Thermo Fisher Scientific) for 15 min. Nuclei were then individually sorted into the wells of 96 well plates with TCL+1% 2-mercaptoethanol as described before[14] using FACS, based on positive Ruby and either $EdU^{high}$ or $EdU^{low}$. Plate-based single nucleus RNA-seq (snRNA-Seq) was then performed as described above for scRNA-seq.

Immunofluorescence and Single-Molecule Fluorescence In Situ Hybridization (smFISH)

Immunofluorescence (IFA) and immunohistochemistry (IHC): Staining of small intestinal tissues was conducted as described[13]. Briefly, tissues were fixed for 14 hours in formalin, embedded in paraffin and cut into 5 μm thick sections. Sections were deparaffinized with standard techniques, incubated with primary antibodies overnight at 4° C. and then with secondary antibodies at RT for 30 min. Slides were mounted with Slowfade Mountant+ DAPI (Life Technologies, S36964) and sealed.

Single-molecule fluorescence in situ hybridization (smFISH): RNAScope Multiplex Fluorescent Kit (Advanced Cell Diagnostics) was used per manufacturer's recommendations with the following alterations. Target Retrieval boiling time was adjusted to 12 minutes and incubation with Protease IV at 40° C. was adjusted to 8 minutes. Slides were mounted with Slowfade Mountant+ DAPI (Life Technologies, S36964) and sealed.

CombinedIFA and smFISH was implemented by first performing smFISH as described above, with the following changes. After Amp 4, tissue sections were washed in washing buffer, incubated with primary antibodies overnight at 4° C., washed in 1×TBST 3 times and then incubated with secondary antibodies for 30 min at room temperature. Slides were mounted with Slowfade Mountant+ DAPI (Life Technologies, S36964) and sealed.

Image Analysis

Images of tissue sections were taken with a confocal microscope Fluorview FV1200 using Kalman and sequential laser emission to reduce noise and signal overlap. Scale bars were added to each image using the confocal software FV10-ASW 3.1 Viewer. Images were overlaid and visualized using Image J software[77]. Quantification of proliferating stem cells. Combined IFA and smFISH images of wildtype C57BL/6J small intestinal tissues were assessed by staining for E-Cadherin to mark cell borders, the canonical proliferation marker mKi67, and either the common ISC marker Lgr5, the predicted 1cISC markers (Cyp2e1 or Fgfr4) or the predicted hcISC markers (Psrc1 or Cenpf). A line was drawn to establish the bottom of the crypt, termed "stem cell zone", and quantification was only assessed within that zone. For each ISC subset marker, more than 10 randomly chosen intact crypts were analyzed. Cells were examined by double blind quantification and were determined double positive if they coexpressed mKi67 and one of the ISC subset markers. Proliferating cells in each ISC subset was measured by calculating the fraction of double positive cells out of all cells positive for the specific ISC subset marker. Automated quantification of Lgr5 mRNA molecules in smFISH images of intestinal crypts within different mouse models (FIGS. 20 and 29) was performed using a custom Python script written using OpenCV.

Antibodies and Probes

Antibodies usedfor IFA: rabbit anti-DCLK1 (1:200, Abcam ab31704), rat anti-CD45 (1:100, Biolegend 30-F11), goat anti-ChgA (1:100, Santa Cruz Sc-1488), mouse anti-E-cadherin (1:100, BD Biosciences 610181), rabbit anti-RELMO (1:200, Peprotech 500-β215), rat anti-Lysozyme (1:200, Dako A0099) and anti-mouse I-A/I-E (1:100, Biolegend 107601). Alexa Fluor 488-, 594-, and 647-conjugated secondary antibodies were used and obtained from Life Technologies.

Probes used for single-molecule RNAscope (Advanced Cell Diagnostics): Cck (C1), Ghrl(C2), GCG (C3), Tphl (C1), Reg4 (C2), TSLP (C1), Ptprc (C1) andMptx2 (C1). Probes used for single-molecule RNAscope (Advanced Cell Diagnostics): Lgr5 (C1,C3), Cyp2e1 (C2), Psrc1 (C1), Fgfr4 (C2), Cenpf (C3), mKi67 (C1,C3).

Th Cell Polarization In Vitro

CD4+naïve ($CD44^{lo}CD62L^+$ $CD25^-$) T cells were isolated from spleen and lymph nodes of 7-10 weeks old C57BL/6J mice using flow cytometry cell sorting. The purity of isolated T cell populations routinely exceeded 98%. Naïve T cells were stimulated with plate-bound anti-CD3 (145-2C11, 1 mg/ml) and anti-CD28 (PV-1, 1 mg/ml) and polarizing cytokines (Th1: 4 ng/ml IL-12; Th2: 4 ng/ml IL-4; Th17: 10 ng/ml IL-6, 2 ng/ml TGF-β1; iTreg: 5 ng/ml TGF-β1; all cytokines from R&D).

Intestinal Organoid Cultures

Organoid cultures. Following crypt isolation from the whole small intestine[142], the single cell suspension was resuspended in Matrigel (BD Bioscience) with 1 μM Jagged-1 peptide (Ana-Spec). Roughly 300 crypts embedded in 25 μl of Matrigel were seeded onto each well of a 24-well plate. Once solidified, the Matrigel was incubated in 600β1 culture medium (Advanced DMEM/F12, Invitrogen) with streptomycin/penicillin and glutamax and supplemented with EGF (100 ng/mL, Peprotech), R-Spondin-1 (600 ng/mL, R&D), Noggin (100 ng/mL, Prepotech), Y-276432 dihydrochloride monohydrate (10 μM, Tochris), N-acetyl-1-cysteine (1 μM, Sigma-Aldrich), N2 (1X, Life Technologies), B27 (1X, Life Technologies) and Wnt3A (25 ng/mL, R&D Systems). Fresh media was replaced on day 3, and organoids were passaged by dissociation with TrypLE and resuspended in new Matrigel on day 6 with a 1:3 split ratio. For selected experiments, organoids were additionally treated with RANKL (100 ng/mL, Biolegends). For T helper cell co-culture experiments, organoids were cultured with Th1, Th2, Th17 or iTregs. Roughly 10,000 T helper cells were added to each well of 500 organoids and were supplemented either to the medium or suspended in the Matrigel. Treated organoids were dissociated and subjected to scRNA-seq using both methods.

Cytokine treated organoids. Organoids were additionally treated with 0.5U/ml IFNγ, 20 ng/ml IL-13, 20 ng/ml IL-17A or 10 ng/ml IL-10 in the culture medium for 3 days. Re-seeding after cytokine treatment. 500 organoids/well were treated with cytokines, as in the cytokine treated organoids above, collected after 3 days and then re-seeded at 500 organoids/well in media without cytokines. Each day, images were taken at 2× magnification and quantification of organoids number was performed with the ImageJ software. Two-Photon Intra-Vital Microscopy (2P-IVM) of T Cells and ISCs To generate gut-homing T cells visualized by 2P-IVM, a combination of modified protocols[143,144] was used. CD4+ T cells were isolated from spleen, pLN and mLN from β-actin-RFP mice using a MACS CD4 T cell positive-selection kit (Miltenyi clone L3T4) following the manufacturer's instructions. Plates were pre-treated with Sug/mL anti-CD3 (clone 145-2C11) and 1 ug/mL anti-CD28 (clone 37.51) and 1A-10$^6$ CD4+ T cells were added to each well for a final volume of 2.5 mL in complete RPMI1640 media supplemented with all-trans Retinoic Acid (100 nM, Sigma R2625). The T cells were cultured for 96 hours before replacing half of the volume with fresh media containing 20U/mL of rIL-2 and then cultured for another 48 hours. Before adoptive transfer into Lgr5-GFP hosts, the gut-homing phenotype was validated with flow cytometry for a407 and CCR9 expression. 1A~10$^7$ cells were then transferred into recipient mice for two hours, and treated with 20 ug of anti-CD3 (clone 2C11). 2P-IVM was performed 72 hours following transfer. The small intestine was surgically exposed through a laparotomy incision. Anesthetized mice were placed on a custom-built stage with a loop of the intact small intestine fixed to a temperature-controlled metallic support to facilitate exposure of the serosal aspect to a water-immersion 20× objective (0.95 numerical aperture) of an upright microscope (Prairie Technologies). A Mai Tai Ti:sapphire laser (Spectra-Physics) was tuned between 870 nm and 900 nm for multiphoton excitation and second-harmonic generation. For dynamic analysis of cell interaction in four dimensions, several X/Y sections (512×512) with Z spacing ranging from 2 m to 4 μm were acquired every 15-20 seconds with an electronic zoom varying from 1× to 3X. Emitted light and secondharmonic signals were directed through 450/80-nm, 525/50-nm and 630/120-nm bandpass filters and detected with non-descanned detectors. Post-acquisition image analysis, volume-rendering and four-dimensional time-lapse videos were performed using Imaris software (Bitplane scientific software).

Analysis

Pre-processing of droplet (10X) scRNA-seq data. Demultiplexing, alignment to the mm10 transcriptome and UMI-collapsing were performed using the Cellranger toolkit (version 1.0.1) provided by 10× Genomics. For each cell, Applicants quantified the number of genes for which at least one read was mapped, and then excluded all cells with either fewer than 800 detected genes. Expression values Ei,j for gene i in cell j were calculated by dividing UMI count values for gene i by the sum of the UMI counts in cell j, to normalize for differences in coverage, and then multiplying by 10,000 to create TPM-like values, and finally calculating $\log_2(TPM+1)$ values. Batch correction was performed using ComBat[78] as implemented in the R package sva[79], using the default parametric adjustment mode. The output was a corrected expression matrix, which was used as input to further analysis.

Selection of variable genes was performed by fitting a generalized linear model to the relationship between the squared co-efficient of variation (CV) and the mean expression level in log/log space, and selecting genes that significantly deviated (P<0.05) from the fitted curve, as previously described[80].

Pre-processing of SMART-Seq2 scRNA-seq data. BAM files were converted to merged, demultiplexed FASTQs using the Illumina provided Bcl2Fastq software package v2.17.1.14. Paired-end reads were mapped to the UCSC hg19 human transcriptome using Bowtie[81] with parameters "-q --phred33-quals -n 1 -e 99999999-1 25 -I1 -X 2000 -a -m 15 -S -p 6", which allows alignment of sequences with one mismatch. Expression levels of genes were quantified as using transcript-per-million (TPM) values calculated by RSEM$^2$ v1.2.3 in paired-end mode. For each cell, Applicants quantified the number of genes for which at least one read was mapped, and then excluded all cells with either fewer than 3,000 detected genes or a transcriptome-mapping of less than 40%.

Selection of variable genes was performed by fitting a generalized linear model to the relationship between the squared coefficient of variation (CV) and the mean expression level in log/log space, and selecting genes that significantly deviated (p<0.05) from the fitted curve, as previously described[80].

For re-analysis of published data[23] (FIG. 25F) normalized transcript counts were downloaded directly from the published data tables. Cell-quality filtering, transcript count normalization, tSNE, and clustering using the RaceID algorithm[23], were all performed using R scripts published online by the authors, using all default settings.

Dimensionality reduction using PCA and tSNE. Applicants restricted the expression matrix to the subsets of variable genes and high quality cells noted above, and values were centered and scaled before input to PCA, which was implemented using the R function 'prcomp' from the 'stats' package for the SMART-seq2 dataset. For the droplet dataset, Applicants used a randomized approximation to PCA, implemented using the 'rpca' function from the 'rsvd' R package, with the parameter k set to 100. This low-rank approximation was used as it is several orders of magnitude faster to compute for very wide matrices. Given that many principal components (PCs) explain very little of the variance, the signal to noise ratio can be substantially improved by selecting a subset of n 'significant' PCs. After PCA, significant PCs were identified using the permutation test described in 83, implemented using the 'permutationPA' function from the 'jackstraw' R package. This test identified 13 and 15 significant PCs in the 10× and SMART-Seq2 datasets of FIG. 1, respectively. Only scores from these significant PCs were used as the input to further analysis.

For visualization, the dimensionality of the datasets was further reduced using the 'Barnes-hut' approximate version of the t-distributed stochastic neighbor embedding (tSNE) [84],[85]. This was implemented using the 'Rtsne' function from the 'Rtsne' R package using 20,000 iterations and a perplexity setting that ranged from 10 to 30 depending on the size of the dataset. Scores from the first n PCs were used as the input to tSNE, where n was determined for each dataset using the permutation test described above.

Identifying cell differentiation trajectories using diffusion maps. Prior to running diffusion-map dimensionality reduction Applicants selected highly variable genes in the data as follows. Applicants first fit a null model for baseline cell-cell gene expression variability in the data based on a power-law relationship between coefficient of variation (CV) and the mean of the UMI-counts of all the expressed genes, similar to [86]. Next, Applicants calculated for each gene the difference between the value of its observed CV and that expected by the null model ($CV_{diff}$). The histogram of $CV_{diff}$ exhibited a "fat tail". Applicants calculated the mean and standard deviation σ of this distribution, and selected all genes with $CV_{diff} > \mu + 1.67\sigma$, yielding 761 genes that were used for further analysis.

Applicants performed dimensionality reduction using the diffusion map approach[40]. Briefly, a cell-cell transition matrix was computed using the Gaussian kernel where the kernel width was adjusted to the local neighborhood of each cell, following[87]. This matrix was converted to a Markovian matrix after normalization. The right eigenvectors $v_i$(i=0, 1, 2, 3, . . . ) of this matrix were computed and sorted in the order of decreasing eigenvalues 1i(i=0, 1, 2, 3, . . . ) after excluding the top eigenvector $v_0$, corresponding to 1=1 (which reflects the normalization constraint of the Markovian matrix). The remaining eigenvectors $v_i$(i=1, 2 . . . ) define the diffusion map embedding and are referred to as diffusion components ($DC_k$(k=1, 2, . . . )). Applicants noticed a spectral gap between the $\lambda_4$ and the $\lambda_5$, and hence retained $DC_1$- $DC_4$.

Removing contaminating immune cells and doublets. Although cells were sorted prior to sequencing using EpCAM, a small number of contaminating immune cells were observed in the 10× dataset. These 264 cells were removed by an initial round of unsupervised clustering (density-based clustering of the tSNE map using 'dbscan' [88] from the R package 'fpc') as they formed an extremely distinct cluster. In the case of the SMART-Seq2 dataset, several cells were outliers in terms of library complexity, which could possibly correspond to more than one individual cell per sequencing library or 'doublets'. These cells were then removed by calculating the top quantile 1% of the distribution of genes detected per cell and removing any cells in this quantile.

Cluster analysis (e.g., k-NN graph based clustering). To cluster single cells by their expression, Applicants used an unsupervised clustering approach, based on the Infomap graph-clustering algorithm[25], following approaches recently described for single-cell CyTOF data[89] and scRNA-seq[26]. Briefly, Applicants constructed a k-nearest-neighbor (k-NN) graph on the data using, for each pair of cells, the Euclidean distance between the scores of significant PCs to identify k nearest neighbors. The parameter k was chosen to be consistent with the size of the dataset.

Specifically, k was set to 200 and 80 for the droplet dataset of 7,216 cells (FIG. 1a), the SMART-Seq2 dataset of 1,522 cells (FIGS. 8a and 8b). RANKL-treated organoids contained 5434 cells and k was set to 200, while the *Salmonella* and *H. polygyrus* dataset contained 9842 cells and k was set to 500. For cluster analyses within celltypes, specifically the EEC and tuft cell subsets, Applicants used the Pearson correlation distance instead of Euclidean, and set k=15, k=30 and k=40 for the enteroendocrine subtypes (533 cells), and 166 and 102 tuft cells in the 10× and SMART-Seq2 datasets respectively.

Specifically, k was set to 600, 200 and 50 for the droplet dataset of 23,177, 4,332 and 1,090 cells from combined T cell and cytokines (FIG. 25d), IL-13-treated and Th1 cocultured organoids, respectively. For in vivo mouse models (FIG. 28b), k was set to 100, 300, 175, and 100 for nude mice, TCRβKO, Foxp3-DTR and MHCII gut respectively. For sub-clustering of stem cell subsets, Applicants used k=150 and k=40 for the 637 and 123 Lgr5+ stem cells from the plate-based and the previously published[12] datasets, respectively. The *Salmonella* and *H. polygyrus* dataset (FIG. 24b-d) contained 5,122 immune cells and k was set to 200, while for the blocking antibody experiment (7,785 cells), k was set to 200.

The nearest neighbor graph was computed using the function 'nng' from the R package 'cccd'. The k-NN graph was then used as the input to Infomap[25], implemented using the 'infomap.community' function from the 'igraph' R package.

Detected clusters were mapped to cell-types or intermediate states using known markers for intestinal epithelial cell subtypes. (FIG. 7e and 7 FIGS. 8a and 8b). In the case of the enteroendocrine cell (EEC) sub-analysis (FIG. 3), any group of EEC progenitor clusters with average pairwise correlations between significant PC scores r>0.85 was merged, resulting in 4 clusters, which were annotated as Prog. (a) based on high levels of Ghrl and Prog. (early), (mid) and (late) - based on decreasing levels of stem (Slc12a2, Ascl2, Axin2) and cell-cycle genes and increasing levels of known EEC regulatory factors (Neurod1, Neurod2 and Neurog3) from early to late (FIG. 11c). For the SMART-Seq2 dataset, two clusters expressing high levels of stem cell marker genes (FIGS. 8a and 8b) were merged to form a 'Stem' cluster and two other clusters were merged to form a 'TA' cluster.

For the cluster analysis of the follicle-associated epithelium (FAE) dataset of 4700 cells, the M cells were exceedingly rare (0.38%), and therefore the 'ClusterDP' method[90] was used to identify them, as it empirically performed better than the kNN-graph algorithm on this dataset containing such a rare subgroup. As with the kNN methods, ClusterDP was run using significant (p<0.05) PC scores (19 in this case) as input, and was implemented using the 'findClusters' and 'densityClust' functions from the 'densityClust' R package using parameters rho=1.1 and delta=0.25.

Detected clusters were annotated by cell types or states using known markers for IEC subtypes. Specifically, for each known epithelial type Applicants selected five canonical marker genes (e.g., Lgr5, Ascl2, Slc12a2, Axin2 and Olfm4 for stem cells, or Lyz1, Defa17, Defa22, Defa24 and Ang4 for Paneth cells), and scored all clusters for their expression (see below for signature scoring procedure). In all cases, one cluster unambiguously expressed each cell-type signature, with two exceptions: in the plate-based dataset, two clusters both expressed high levels of ISC markers (FIG. 21a) and accordingly were merged to form a 'Stem' cluster and two other clusters were merged to form a 'TA' cluster based on high expression of cell-cycle genes and low-to-moderate expression of ISC genes.

Extracting rare cell-types for further analysis. The initial clustering of the whole-gut dataset (7,216 cells, FIG. 1b) showed a cluster of 310 EECs and 166 tuft cells. The tuft cells were taken 'as is' for the sub-analysis (FIG. 4a-b), while the EECs were combined with a second cluster of 239 EECs identified in the regional dataset (FIG. 10h) for a total of 533 EECs. A group of 16 cells co-expressed EEC markers Chga, Chgb with markers of Paneth cells including Lyz1, Defa5 and Defa22, and were therefore interpreted as doublets, and removed from the analysis, leaving 533 EECs, which were the basis for the analysis in FIG. 3. To compare expression profiles of enterocytes from proximal and distal small intestine (FIGS. 10l and 10j), the 1,041 enterocytes identified from 11,665 cells in the regional dataset (FIG. 10h) were used.

Defining cell-type signatures. To identify maximally specific genes for cell-types, Applicants ran differential expression tests between each pair of clusters for all possible pairwise comparisons. Then, for a given cluster, putative signature genes were filtered using the maximum FDR Q-value and ranked by the minimum $\log_2$ fold-change. The minimum fold-change and maximum Q-value represent the weakest effect-size across all pairwise comparisons, therefore this a stringent criterion. Cell-type signature genes shown in (FIG. 1c, FIG. 14h, and Tables 3-5 and 9) were obtained using a maximum FDR of 0.05 and a minimum $\log_2$ fold-change of 0.5.

In the case of signature genes for subtypes within cell-types (FIG. 3b, FIG. 4b and FIG. 13b), an aggregate p-value (across the pairwise tests) for enrichment was computed using Fisher's method - a more lenient criterion than simply taking the maximum-value - and a maximum FDR Q-value of 0.01 was used, along with a cutoff of minimum $\log_2$ fold-change of 0.25 for tuft cell subsets (FIG. 4b., FIG. 13b and Table 8) and 0.1 for enteroendocrine subsets (FIG. 3b., Table 7). Due to low cell numbers (n=18), this Fisher p-value was also used for the in vivo M cell signature, with an FDR cutoff of 0.001 (FIG. 5d), Table 9). Marker genes were ranked by minimum $\log_2$ fold-change. Differential expression tests were carried out using the Mann-Whitney U-test (also known as the Wilcoxon rank-sum test) implemented using the R function 'wilcox.test'. For the infection experiments (FIG. 6), Applicants used a two part 'hurdle'-model to control for both technical quality and mouse-to-mouse variation. This was implemented using the R package MAST[91], and p-values for differential expression were computed using the likelihood-ratio test. Multiple hypothesis testing correction was performed by controlling the false discovery rate[92] using the R function p.adjust.

Assigning the three ISC states to region of origin using supervised classification. To study the anatomical distribution of ISCs in different parts of the small intestine, Applicants used a classification approach. First, Applicants sequenced a total of 11,665 cells drawn from each of the duodenum, jejunum and ileum, and identified 2,965 of them as ISCs using unsupervised clustering as described above. Next, Applicants developed a classifier for the anatomical origin of ISCs, by compiling a discriminative feature set using the expression levels of all genes differentially expressed (FDR<0.1, Mann-Whitney U-test, $\log_2$ fold-change>0.25) between stem cells from the three regions, and also the scores along the first 25 PCs. A 'random forest' classifier was trained on these features, and subsequently distinguished between ISCs from the three regions with an average out-of-bag accuracy of 92.9%. Finally, Applicants used the trained classifier to classify the 637 ISCs (FIG. 17) and infer the fraction of cells drawn from each intestinal region found in each ISC state (FIG. 21f).

Cell-cell similarity matrix. To visualize heterogeneity of ISCs within the 'Stem' cluster (637 cells), cell-cell similarities were computed. Principal component (PC) scores for each cell were computed across the 637 cells using the R function 'prcomp' as described above. The distance between cell i and j was calculated as the Pearson correlation between the scores of these two cells along the first 10 PCs. This distance matrix was then hierarchically clustered using Ward's method, implemented using the R function 'hclust' (with the 'method' argument set to 'ward. D2'), and visualized as a heatmap using the R function 'aheatmap' (FIG. 17b).

Cell-cycle andISC subset signatures. To identify maximally specific genes associated with the three ISC subsets, Applicants performed differential expression tests between each possible pairwise comparison between clusters. To ensure specificity of the detected marker genes to stem cells, the set of clusters included both the three ISC subsets (3 clusters), and all other detected IEC clusters (8 clusters; FIG. 21a, top right panel) for a total of 11 clusters.

Then, for a given cluster, putative signature genes were filtered using the maximum FDR Q-value and ranked by the minimum log 2(fold-change). The minimum fold-change and maximum Q-value represent the weakest effect-size across all pairwise comparisons, therefore this is a stringent criterion. ISC subset signatures (Table 3) were obtained using a maximum FDR of 0.25 and a minimum log 2(fold-change) of 0.25. To exclude the explicit effect of known cell-cycle genes on the gene signature of the ISC subsets Applicants filtered out any gene annotated as directly participating in cell-cycle regulation. Annotated cell-cycle genes were downloaded from the gene ontology (GO): amigo.geneontology.org/amigo/term/GO:0007049, and any gene appearing on this list was removed from the signature gene sets.

Gene sets associated with G1/S and G2/M phases of the cell-cycle were downloaded from www.cell.com/cms/attachment/2051395126/2059328514/mmc2.xlsx [Macosko 2015]. A set of cell-cycle genes to assess overall proliferation (see below for scoring procedure) was defined as the union of the G1/S and G2/M sets.

Scoring cells using signature gene sets. To obtain a score for a specific set of n genes in a given cell, a 'background' gene set was defined to control for differences in sequencing coverage and library complexity between cells in a manner similar to[29]. The background gene set was selected to be similar to the genes of interest in terms of expression level. Specifically, the 10n nearest neighbors in the 2-D space defined by mean expression and detection frequency across all cells were selected. The signature score for that cell was then defined as the mean expression of the n signature genes in that cell, minus the mean expression of the 10n background genes in that cell.

Estimates of cell type sampling frequencies. For each cell-type the probability of observing at least n cells in a sample of size kis modeled using the cumulative distribution function of a negative binomial NBcdf(k, n, p), where p is the relative abundance of this cell type. For m cell types with the same parameterp the overall probability of seeing each type at least n times is NBcdf(k; n, p)^m. Such analysis can now be performed with user specified parameters at satijalab.org/howmanycells.

EEC dendrogram. Average expression vectors were calculated for all 12 EEC subset clusters, using $log_2(TPM+1)$ values, and restricted to the subset of 1,361 genes identified as significantly variable between EEC susbsets (p<0.05), as described above. The average expression vectors including these genes were hierarchically clustered using the R package pvclust (Spearman distance, ward. D2 clustering method), which provides bootstrap confidence estimates on every dendrogram node, as an empirical p-value over 100,000 trials (FIG. 12a).

Cell-type specific TFs, GPCRs and LRRs. A list of all genes identified as acting as transcription factors in mice was obtained from AnimalTFDB 9s, downloaded from: www.bioguo.org/AnimalTFDB/BrowseAllTF.php?spe=Mus_musculus. The set of G-protein coupled receptors (GPCRs) was obtained from the UniProt database, downloaded from: www.uniprot.org/uniprot/?query=family %3A %22g+protein+coupled+receptor%22+AND+organ ism %3A %22Mouse+%5B10090%5D%22+AND+reviewed %3Ayes&sort=score. Functional annotations for each protein (FIGS. 8e-8g) were obtained from the British Pharmacological Society (BPS) and the International Union of Basic and Clinical Pharmacology (IUPHAR) data, downloaded from: www.guidetopharmacology.org/GRAC/GPCRListForward?class=A. The list of leucine-rich repeat proteins (LRRs) was taken from 94. To map from human to mouse gene names, human and mouse orthologs were downloaded from Ensembl (latest release 86, www.ensembl.org/biomart/martview), and human and mouse gene synonyms from NCBI (ftp.ncbi.nlm.nih.gov/gene/DATA/GENE_INFO/Mammalia/). For each human LRR gene, all human synonyms were mapped to the orthologous gene in mouse using the ortholog list, and mouse gene names were mapped to those in the single-cell data using the synonym list.

Cell-type enriched TFs, GPCRs and LRRs were then identified by intersecting the list of genes enriched in to each cell type with the lists of TFs, GPCRs and LRRs defined above. Cell-type enriched genes were defined using the SMART-Seq2 dataset, as those with a minimum log 2 fold-change of 0 and a maximum FDR of 0.5, retaining a maximum of 10 genes per cell type in FIG. 1f, FIG. 1g. and 8 FIG. 8h, while complete lists are provided in Table 6. In addition, a more extensive panel of cell-type specific GPCRs was identified (8 FIGS. 8e-8g) by selecting a more lenient threshold. This was achieved by comparing each cell-type to all other cells, instead of the pairwise comparisons described in the previous section, and selecting all GPCR genes differentially expressed (FDR<0.001).

Testing for changes in cell type proportions. Applicants model the detected number of each cell-type in each analyzed mouse as a random count variable using a Poisson process. The rate of detection is then modeled by providing the total number of cells profiled in a given mouse as an offset variable, while the condition of each mouse (treatment or control) was provided as a covariate. The model was fit using the R command 'glm' from the 'stats' package. The p-value for the significance of the effect produced by the treatment was then assessed using a Wald test on the regression coefficient.

In the case of the assessment of the significance of spatial distributions of enteroendocrine (EEC) subsets (FIG. 3e), the comparison involved more than two groups. In particular, the null hypothesis was that the proportion of each EEC subset detected in the three intestinal regions (duodenum, jejunum, and ileum) was equal. To test this hypothesis Applicants used analysis of variance (ANOVA) with a $\chi^2$-test on the Poisson model fit described above, implemented using the 'anova' function from the 'stats' package.

Testing for shifts in cell proportions in intestinal organoids. Under several conditions, Applicants observed dramatic changes in the frequency of epithelial cell subtypes (FIG. 19). The statistical significance of these shifts was assessed by calculating, for each condition comparison and cell type, the exact hypergeometric probability (without replacement) of the observed change in cell numbers.

Specifically, given that m and n total cells (of all cell types) are sequenced in a treatment and control condition respectively, Applicants test, for a given cell type, whether the number of k and q of observed cells of type C in total and treatment condition respectively, significantly deviates from a null model given by the hypergeometric distribution. The probability of observing these values was calculated using the R function 'phyper' from the stats' package, using the command:

$$P=\text{phyper}(q,k,m,n)$$

and was reported as a hypergeometric p-value.

Testing for shifts in cell proportions in vivo. In the case of in vivo perturbation experiments (FIG. 20), Applicants used a regression model to control for any mouse-to-mouse variability amongst the biological replicates. For each cell-type, Applicants model the number of cells detected in each analyzed mouse as a random count variable using a negative binomial distribution. The rate of detection is then modeled by providing the natural log total number of cells profiled in a given mouse as an offset variable. The condition of each mouse (i.e., treatment/KO or control) was provided as a covariate. The model was fit using the R command 'glm' from the 'stats' package. The p-value for the significance of the effect produced by the treatment/KO was then assessed using a Wald test on the regression coefficient.

Gene set enrichment and GO analysis. GO analysis was performed using the 'goseq' R package[95], using significantly differentially expressed genes (FDR<0.05) as target genes, and all genes expressed with log $2(TPM+1)>3$ in at least 10 cells as background.

REFERENCES

1 Clevers, H. Wnt/beta-catenin signaling in development and disease. *Cell* 127, 469-480, doi:10.1016/j.cell.2006.10.018 (2006).
2 Peterson, L. W. & Artis, D. Intestinal epithelial cells: regulators of barrier function and immune homeostasis. *Nature reviews. Immunology* 14, 141-153, doi:10.1038/nri3608 (2014).
3 Ferraris, R. P., Villenas, S. A. & Diamond, J. Regulation of brush-border enzyme activities and enterocyte migration rates in mouse small intestine. *The American journal of physiology* 262, G1047-1059 (1992).
4 Sato, T. et al. Single Lgr5 stem cells build crypt-villus structures in vitro without a mesenchymal niche. *Nature* 459, 262-265, doi:10.1038/nature07935 (2009).
5 Gerbe, F., Legraverend, C. & Jay, P. The intestinal epithelium tuft cells: specification and function. *Cellular and molecular life sciences: CMLS* 69, 2907-2917, doi:10.1007/s00018-012-0984-7 (2012).
6 Barker, N. et al. Identification of stem cells in small intestine and colon by marker gene Lgr5. *Nature* 449, 1003-1007, doi:10.1038/nature06196 (2007).

7 Barker, N., van Oudenaarden, A. & Clevers, H. Identifying the stem cell of the intestinal crypt: strategies and pitfalls. *Cell stem cell* 11, 452-460, doi:10.1016/j.stem.2012.09.009 (2012).

8 Clevers, H. The intestinal crypt, a prototype stem cell compartment. *Cell* 154, 274-284, doi:10.1016/j.cell.2013.07.004 (2013).

9 Salzman, N. H., Ghosh, D., Huttner, K. M., Paterson, Y. & Bevins, C. L. Protection against enteric *salmonellosis* in transgenic mice expressing a human intestinal defensin. *Nature* 422, 522-526, doi:10.1038/nature01520 (2003).

10 Pelaseyed, T. et al. The mucus and mucins of the goblet cells and enterocytes provide the first defense line of the gastrointestinal tract and interact with the immune system. *Immunological reviews* 260, 8-20, doi:10.1111/imr.12182 (2014).

11 Gribble, F. M. & Reimann, F. Enteroendocrine Cells: Chemosensors in the Intestinal Epithelium. *Annual review of physiology* 78, 277-299, doi:10.1 146/annurev-physiol-021115-105439 (2016).

12 Furness, J. B., Rivera, L. R., Cho, H. J., Bravo, D. M. & Callaghan, B. The gut as a sensory organ. *Nature reviews. Gastroenterology & hepatology* 10, 729-740, doi: 10.1038/nrgastro.2013.180 (2013).

13 Biton, M. et al. Epithelial microRNAs regulate gut mucosal immunity via epithelium-T cell crosstalk. *NatImmunol* 12, 239-246, doi:10.1038/ni.1994 (2011).

14 Howitt, M. R. et al. Tuft cells, taste-chemosensory cells, orchestrate parasite type 2 immunity in the gut. *Science* 351, 1329-1333, doi:10.1126/science.aaf1648 (2016).

15 von Moltke, J., Ji, M., Liang, H. E. & Locksley, R. M. Tuft-cell-derived IL-25 regulates an intestinal ILC2-epithelial response circuit. *Nature* 529, 221-225, doi: 10.1038/nature16161 (2016).

16 Gerbe, F. et al. Intestinal epithelial tuft cells initiate type 2 mucosal immunity to helminth parasites. *Nature* 529, 226-230, doi:10.1038/nature16527 (2016).

17 de Lau, W. et al. Peyer's patch M cells derived from Lgr5(+) stem cells require SpiB and are induced by RankL in cultured "miniguts". *Molecular and cellular biology* 32, 3639-3647, doi:10.1128/MCB.00434-12 (2012).

18 Mabbott, N. A., Donaldson, D. S., Ohno, H., Williams, I. R. & Mahajan, A. Microfold (M) cells: important immunosurveillance posts in the intestinal epithelium. *Mucosal immunology* 6, 666-677, doi:10.1038/mi.2013.30 (2013).

19 Heinz, S., Romanoski, C. E., Benner, C. & Glass, C. K. The selection and function of cell type-specific enhancers. *Nature reviews. Molecular cell biology* 16, 144-154, doi:10.1038/nrm3949 (2015).

20 Wagner, A., Regev, A. & Yosef, N. Revealing the vectors of cellular identity with single-cell genomics. *Nat Biotechnol* 34, 1145-1160, doi:10.1038/nbt.3711 (2016).

21 Bezencon, C. et al. Murine intestinal cells expressing Trpm5 are mostly brush cells and express markers of neuronal and inflammatory cells. *The Journal of comparative neurology* 509, 514-525, doi:10.1002/cne.21768 (2008).

22 Habib, A. M., Richards, P., Rogers, G. J., Reimann, F. & Gribble, F. M. Co-localisation and secretion of glucagon-like peptide 1 and peptide YY from primary cultured human L cells. *Diabetologia* 56, 1413-1416, doi:10.1007/s00125-013-2887-z (2013).

23 Grun, D. et al. Single-cell messenger RNA sequencing reveals rare intestinal cell types. *Nature* 525, 251-255, doi:10.1038/nature14966 (2015).

24 Zheng, G. X. et al. Haplotyping germline and cancer genomes with high-throughput linked-read sequencing. *Nat Biotechnol* 34, 303-311, doi:10.1038/nbt.3432 (2016).

25 Rosvall, M. & Bergstrom, C. T. Maps of random walks on complex networks reveal community structure. *Proceedings of the National Academy of Sciences* 105, 1118-1123, doi:10.1073/pnas.0706851105 (2008).

26 Shekhar, K. et al. Comprehensive Classification of Retinal Bipolar Neurons by Single-Cell Transcriptomics. *Cell* 166, 1308-1323.e1330, doi:10.1016/j.cell.2016.07.054 (2016).

27 Amir el, A. D. et al. viSNE enables visualization of high dimensional single-cell data and reveals phenotypic heterogeneity of leukemia. *Nat Biotechnol* 31, 545-552, doi:10.1038/nbt.2594 (2013).

28 van der Maaten, L. & Hinton, G. Visualizing Data using t-SNE. *J Mach Learn Res* 9, 2579-2605 (2008).

29 Kowalczyk, M. S. et al. Single-cell RNA-seq reveals changes in cell cycle and differentiation programs upon aging of hematopoietic stem cells. *Genome Research* 25, 1860-1872, doi:10.1101/gr.192237.115 (2015).

30 Yan, K. S. et al. Non-equivalence of Wnt and R-spondin ligands during Lgr5+ intestinal stem-cell self-renewal. *Nature* 545, 238-242, doi:10.1038/nature22313 (2017).

31 Garabedian, E. M., Roberts, L. J., McNevin, M. S. & Gordon, J. I. Examining the role of Paneth cells in the small intestine by lineage ablation in transgenic mice. *J Biol Chem* 272, 23729-23740 (1997).

32 Picelli, S. et al. Full-length RNA-seq from single cells using Smart-seq2. *Nature protocols* 9, 171-181, doi: 10.1038/nprot.2014.006 (2014).

33 van der Meer-van Kraaij, C. et al. Dietary modulation and structure prediction of rat mucosal pentraxin (Mptx) protein and loss of function in humans. *Genes & nutrition* 2, 275-285, doi:10.1007/s12263-007-0058-x (2007).

34 Du Clos, T. W. Pentraxins: structure, function, and role in inflammation. *ISRN inflammation* 2013, 379040, doi: 10.1155/2013/379040 (2013).

35 Katz, J. P. et al. The zinc-finger transcription factor Klf4 is required for terminal differentiation of goblet cells in the colon. *Development* 129, 2619-2628 (2002).

36 Duboc, H., Tache, Y. & Hofmann, A. F. The bile acid TGR5 membrane receptor: from basic research to clinical application. *Dig Liver Dis* 46, 302-312, doi:10.1016/j.dld.2013.10.021 (2014).

37 Overton, H. A., Fyfe, M. C. & Reynet, C. GPR119, a novel G protein-coupled receptor target for the treatment of type 2 diabetes and obesity. *Br J Pharmacol* 153 Suppl 1, 576-81, doi:10.1038/sj.bjp.0707529 (2008).

38 Kim, T. H. et al. Single-Cell Transcript Profiles Reveal Multilineage Priming in Early Progenitors Derived from Lgr5(+) Intestinal Stem Cells. *Cell Rep* 16, 2053-2060, doi:10.1016/j.celrep.2016.07.056 (2016).

39 Tetteh, P. W. et al. Replacement of Lost Lgr5-Positive Stem Cells through Plasticity of Their Enterocyte-Lineage Daughters. *Cell stem cell* 18, 203-213, doi:10.1016/j.stem.2016.01.001 (2016).

40 Coifman, R. R., et al. Geometric diffusions as a tool for harmonic analysis and structure definition of data: diffusion maps. *Proceedings of the National Academy of Sciences of the United States of America* 102, 7426-7431, doi:10.1073/pnas.0500334102 (2005).

41 Trapnell, C. et al. The dynamics and regulators of cell fate decisions are revealed by pseudotemporal ordering of single cells. *Nat Biotechnol* 32, 381-386, doi:10.1038/nbt.2859 (2014).

42 Bendall, S. C. et al. Single-cell trajectory detection uncovers progression and regulatory coordination in human B cell development. *Cell* 157, 714-725, doi: 10.1016/j.cell.2014.04.005 (2014).

43 Kohlnhofer, B. M., Thompson, C. A., Walker, E. M. & Battle, M. A. GATA4 regulates epithelial cell proliferation to control intestinal growth and development in mice. *Cell Mol Gastroenterol Hepatol* 2, 189-209, doi:10.1016/j.jcmgh.2015.11.010 (2016).

44 Basak, O. et al. Mapping early fate determination in Lgr5+ crypt stem cells using a novel Ki67-RFP allele. *EMBO J* 33, 2057-2068, doi:10.15252/embj.201488017 (2014).

45 Beuling, E. et al. GATA factors regulate proliferation, differentiation, and gene expression in small intestine of mature mice. *Gastroenterology* 140, 1219-1229 e1211-1212, doi:10.1053/j.gastro.2011.01.033 (2011).

46 Battle, M. A. et al. GATA4 is essential for jejunal function in mice. *Gastroenterology* 135, 1676-1686 e1671, doi: 10.1053/j.gastro.2008.07.074 (2008).

47 Sjolund, K., Sanden, G., Hakanson, R. & Sundler, F. Endocrine cells in human intestine: an immunocytochemical study. *Gastroenterology* 85, 1120-1130 (1983).

48 Cheng, H. & Leblond, C. P. Origin, differentiation and renewal of the four main epithelial cell types in the mouse small intestine. III. Entero-endocrine cells. *The American journal of anatomy* 141, 503-519, doi:10.1002/aja.1001410405 (1974).

49 Egerod, K. L. et al. A major lineage of enteroendocrine cells coexpress CCK, secretin, GIP, GLP-1, PYY, and neurotensin but not somatostatin. *Endocrinology* 153, 5782-5795, doi:10.1210/en.2012-1595 (2012).

50 Klok, M. D., Jakobsdottir, S. & Drent, M. L. The role of leptin and ghrelin in the regulation of food intake and body weight in humans: a review. *Obes Rev* 8, 21-34, doi:10.1111/j.1467-789X.2006.00270.x (2007).

51 Ichimura, A., Hirasawa, A., Hara, T. & Tsujimoto, G. Free fatty acid receptors act as nutrient sensors to regulate energy homeostasis. *Prostaglandins Other Lipid Mediat* 89, 82-88, doi:10.1016/j.prostaglandins.2009.05.003 (2009).

52 Karra, E., Chandarana, K. & Batterham, R. L. The role of peptide YY in appetite regulation and obesity. *J Physiol* 587, 19-25, doi:10.1113/jphysiol.2008.164269 (2009).

53 Basak, O. et al. Induced Quiescence of Lgr5+ Stem Cells in Intestinal Organoids Enables Differentiation of Hormone-Producing Enteroendocrine Cells. *Cell stem cell* 20, 177-190 e174, doi:10.1016/j.stem.2016.11.001 (2017).

54 Gershon, M. D. & Tack, J. The serotonin signaling system: from basic understanding to drug development for functional GI disorders. *Gastroenterology* 132, 397-414, doi:10.1053/j.gastro.2006.11.002 (2007).

55 Ramage, A. G. & Villalon, C. M. 5-hydroxytryptamine and cardiovascular regulation. *Trends in pharmacological sciences* 29, 472-481 (2008).

56 Reigstad, C. S. et al. Gut microbes promote colonic serotonin production through an effect of short-chain fatty acids on enterochromaffin cells. *FASEB J* 29, 1395-1403, doi:10.1096/fj.14-259598 (2015).

57 Ziegler, S. F. & Artis, D. Sensing the outside world: TSLP regulates barrier immunity. *Nat Immunol* 11, 289-293, doi:10.1038/ni.1852 (2010).

58 Terahara, K. et al. Comprehensive gene expression profiling of Peyer's patch M cells, villous M-like cells, and intestinal epithelial cells. *Journal of immunology* 180, 7840-7846 (2008).

59 Jang, M. H. et al. Intestinal villous M cells: an antigen entry site in the mucosal epithelium. *Proceedings of the National Academy of Sciences of the United States of America* 101, 6110-6115, doi:10.1073/pnas.0400969101 (2004).

60 Vassen, L., Okayama, T. & Moroy, T. Gfi1b:green fluorescent protein knock-in mice reveal a dynamic expression pattern of Gfi1b during hematopoiesis that is largely complementary to Gfi1. *Blood* 109, 2356-2364, doi: 10.1182/blood-2006-06-030031 (2007).

61 Coburn, B., Grassl, G. A. & Finlay, B. B. *Salmonella*, the host and disease: a brief review. *Immunology and cell biology* 85, 112-118, doi:10.1038/sj.icb.7100007 (2007).

62 Darwin, K. H. & Miller, V. L. Molecular basis of the interaction of *Salmonella* with the intestinal mucosa. *Clinical microbiology reviews* 12, 405-428 (1999).

63 Reynolds, L. A., Filbey, K. J. & Maizels, R. M. Immunity to the model intestinal helminth parasite Heligmosomoides polygyrus. *Seminars in immunopathology* 34, 829-846, doi:10.1007/s00281-012-0347-3 (2012).

64 Loonen, L. M. et al. REG3gamma-deficient mice have altered mucus distribution and increased mucosal inflammatory responses to the microbiota and enteric pathogens in the ileum. *Mucosal immunology* 7, 939-947, doi: 10.1038/mi.2013.109 (2014).

65 van Ampting, M. T. et al. Intestinally secreted C-type lectin Reg3b attenuates *salmonellosis* but not listeriosis in mice. *Infection and immunity* 80, 1115-1120, doi:10.1128/IAI.06165-11 (2012).

66 Rodenburg, W. et al. *Salmonella* induces prominent gene expression in the rat colon. *BMC Microbiol* 7, 84, doi: 10.1186/1471-2180-7-84 (2007).

67 Eckhardt, E. R. et al. Intestinal epithelial serum amyloid A modulates bacterial growth in vitro and pro-inflammatory responses in mouse experimental colitis. *BMC Gastroenterol* 10, 133, doi:10.1186/1471-230X-10-133 (2010).

68 Martinez Rodriguez, N. R. et al. Expansion of Paneth cell population in response to enteric Salmonella enterica serovar Typhimurium infection. *Infection and immunity* 80, 266-275, doi:10.1128/IAI.05638-11 (2012).

69 Artis, D. et al. RELMbeta/FIZZ2 is a goblet cell-specific immune-effector molecule in the gastrointestinal tract. *Proceedings of the National Academy of Sciences of the United States of America* 101, 13596-13600, doi:10.1073/pnas.0404034101 (2004).

70 Datta, R. et al. Identification of novel genes in intestinal tissue that are regulated after infection with an intestinal nematode parasite. *Infection and immunity* 73, 4025-4033, doi:10.1128/IAI.73.7.4025-4033.2005 (2005).

71 Birchenough, G. M., Johansson, M. E., Gustafsson, J. K., Bergstrom, J. H. & Hansson, G. C. New developments in goblet cell mucus secretion and function. *Mucosal immunology* 8, 712-719, doi:10.1038/mi.2015.32 (2015).

72 Young, R. L. et al. Expression of taste molecules in the upper gastrointestinal tract in humans with and without type 2 diabetes. *Gut* 58, 337-346, doi:10.1 136/gut.2008.148932 (2009).

73 Mukherjee, S. & Hooper, L. V. Antimicrobial defense of the intestine. *Immunity* 42, 28-39, doi:10.1016/j.immuni.2014.12.028 (2015).

74 Rubin, D. B. The Bayesian bootstrap. *The Annals of Statistics* 9, 130-134 (1981).

75 Kobayashi, A. et al. Identification of novel genes selectively expressed in the follicle-associated epithelium from the meta-analysis of transcriptomics data from multiple mouse cell and tissue populations. *DNA research: an*

76 Su, L. et al. Development of fatal intestinal inflammation in MyD88 deficient mice co-infected with helminth and bacterial enteropathogens. *PLoS Negl Trop Dis* 8, e2987, doi:10.1371/journal.pntd.0002987 (2014).

77 Schneider, C. A., Rasband, W. S. & Eliceiri, K. W. NIH Image to ImageJ: 25 years of image analysis. *Nat Methods* 9, 671-675 (2012).

78 Johnson, W. E., Li, C. & Rabinovic, A. Adjusting batch effects in microarray expression data using empirical Bayes methods. *Biostatistics (Oxford, England)* 8, 118-127, doi:10.1093/biostatistics/kxj037 (2007).

79 Leek, J. T., Johnson, W. E., Parker, H. S., Jaffe, A. E. & Storey, J. D. The sva package for removing batch effects and other unwanted variation in high-throughput experiments. *Bioinformatics* 28, 882-883, doi:10.1093/bioinformatics/bts034 (2012).

80 Brennecke, P. et al. Accounting for technical noise in single-cell RNA-seq experiments. *Nature Methods* 10, 1093-1095, doi:10.1038/nmeth.2645 (2013).

81 Langmead, B., Trapnell, C., Pop, M. & Salzberg, S. L. Ultrafast and memory-efficient alignment of short DNA sequences to the human genome. *Genome Biology, doi: 10.1 186/gb-2009-10-3-r25*) (2009).

82 Li, B. & Dewey, C. N. RSEM: accurate transcript quantification from RNA-Seq data with or without a reference genome. *BMC Bioinformatics* 12, 323, doi:10.1186/1471-2105-12-323 (2011).

83 Buja, A. & Eyuboglu, N. Remarks on Parallel Analysis. *Multivariate Behavioral Research* 27, 509-540, doi:10.1207/s15327906mbr2704_2 (1992).

84 van der Maaten, L. Accelerating t-SNE using Tree-Based Algorithms. *The Journal of Machine Learning Research* 15, 3221-3245 (2014).

85 van der Maaten, L. & Hinton, G. Visualizing Data using t-SNE. *The Journal of Machine Learning Research* 9, 2579-2605 (2008).

86 Zeisel, A. et al. Cell types in the mouse cortex and hippocampus revealed by single-cell RNA-seq. *Science* 347, 1138-1142, doi:10.1 126/science.aaa1934 (2015).

87 Haghverdi, L., Buettner, F. & Theis, F. J. Diffusion maps for high-dimensional single-cell analysis of differentiation data. *Bioinformatics* 31, 2989-2998, doi:10.1093/bioinformatics/btv325/-/DC1 (2015).

88 Ester, M., Kriegel, H. P., Sander, J. & Xu, X. A density-based algorithm for discovering clusters in large spatial databases with noise. Kdd (1996).

89 Levine, J. H. et al. Data-Driven Phenotypic Dissection of AML Reveals Progenitor-like Cells that Correlate with Prognosis. *Cell*, 1-15, doi:10.1016/j.cell.2015.05.047 (2015).

90 Rodriguez, A. & Laio, A. Machine learning. Clustering by fast search and find of density peaks. *Science* 344, 1492-1496, doi:10.1126/science.1242072 (2014).

91 Finak, G. et al. MAST: a flexible statistical framework for assessing transcriptional changes and characterizing heterogeneity in single-cell RNA sequencing data. *Genome Biol* 16, 278, doi:10.1186/s13059-015-0844-5 (2015).

92 Benjamini, Y. & Hochberg, Y. Controlling the False Discovery Rate: A Practical and Powerful Approach to Multiple Testing. *Journal of the Royal Statistical Society. Series B Methodological* 57, 289-300 (1995).

93 Zhang, H.-M. et al. AnimalTFDB: a comprehensive animal transcription factor database. *Nucleic Acids Research* 40, D144-149, doi:10.1093/nar/gkr965 (2012).

94 Ng, A., Eisenberg, J. M. & Heath, R. in *Proceedings of the* . . . (2011).

95 Young, M. D., Wakefield, M. J., Smyth, G. K. & Oshlack, A. Gene ontology analysis for RNA-seq: accounting for selection bias. *Genome Biology* 11, doi:10.1186/gb-2010-11-2-r14 (2010).

96 Barker, N. Adult intestinal stem cells: critical drivers of epithelial homeostasis and regeneration. Nat Rev Mol Cell Biol 15, 19-33, doi:10.1038/nrm3721 (2014).

97 Potten, C. S., Owen, G. & Booth, D. Intestinal stem cells protect their genome by selective segregation of template DNA strands. J Cell Sci 115, 2381-2388 (2002).

98 Tirosh, I. et al. Dissecting the multicellular ecosystem of metastatic melanoma by single-cell RNA-seq. Science 352, 189-196, doi:10.1126/science.aad0501 (2016).

99 Patel, A. P. et al. Single-cell RNA-seq highlights intra-tumoral heterogeneity in primary glioblastoma. Science 344, 1396-1401, doi:10.1126/science.1254257 (2014).

100 Hayami, S. et al. Overexpression of the JmjC histone demethylase KDM5B in human carcinogenesis: involvement in the proliferation of cancer cells through the E2F/RB pathway. Molecular *Cancer* 9, 59-14, doi: 10.1186/1476-4598-9-59 (2010).

101 Roesch, A. et al. A Temporarily Distinct Subpopulation of Slow-Cycling Melanoma Cells Is Required for Continuous Tumor Growth. Cell 141, 583-594, doi:10.1016/j.cell.2010.04.020 (2010).

102 Oki, T. et al. A novel cell-cycle-indicator, mVenus-β27K-, identifies quiescent cells and visualizes G0-G1 transition. Scientific Reports 4, 1-10, doi:10.1038/srep04012 (2014).

103 Munoz, J. et al. The Lgr5 intestinal stem cell signature: robust expression of proposed quiescent '+4' cell markers. The EMBO Journal 31, 3079-3091, doi:10.1038/emboj.2012.166 (2012).

104 Habib, N. et al. Div-Seq: Single-nucleus RNA-Seq reveals dynamics of rare adult newborn neurons. Science 353, 925-928, doi:10.1126/science.aad7038 (2016).

105 Kambayashi, T. & Laufer, T. M. Atypical MHC class II-expressing antigen presenting cells: can anything replace a dendritic cell? Nature reviews. Immunology 14, 719-730, doi:10.1038/nri3754 (2014).

106 Thelemann, C. et al. Interferon-gamma induces expression of MHC class II on intestinal epithelial cells and protects mice from colitis. PLoS One 9, e86844, doi: 10.1371/journal.pone.0086844 (2014).

107 Bland, P. MHC class II expression by the gut epithelium. Immunol Today 9, 174-178, doi:10.1016/0167-5699 (88)91293-5 (1988).

108 Salomon, P., Pizzimenti, A., Panja, A., Reisman, A. & Mayer, L. The expression and regulation of class II antigens in normal and inflammatory bowel disease peripheral blood monocytes and intestinal epithelium. Autoimmunity 9, 141-149 (1991).

109 Howie, D., Garcia Rueda, H., Brown, M. H. & Waldmann, H. Secreted and transmembrane 1A is a novel co-stimulatory ligand. PLoS One 8, e73610, doi:10.1371/journal.pone.0073610 (2013).

110 Madsen, L. et al. Mice lacking all conventional MHC class II genes. Proc Natl Acad Sci USA 96, 10338-10343 (1999).

111 Huch, M. et al. In vitro expansion of single Lgr5$^+$liver stem cells induced by Wnt-driven regeneration. Nature 494, 247-250, doi:10.1038/nature11826 (2013).

112 Boes, M. et al. T-cell engagement of dendritic cells rapidly rearranges MHC class II transport. Nature 418, 983-988, doi:10.1038/nature01004 (2002).

113 Noah, T. K., Donahue, B. & Shroyer, N. F. Intestinal development and differentiation. Exp Cell Res 317, 2702-2710, doi:10.1016/j.yexcr.2011.09.006 (2011).

114 van Es, J. H. et al. Notch/gamma-secretase inhibition turns proliferative cells in intestinal crypts and adenomas into goblet cells. Nature 435, 959-963, doi:10.1038/nature03659 (2005).

115 Saha, S. et al. Macrophage-derived extracellular vesicle-packaged WNTs rescue intestinal stem cells and enhance survival after radiation injury. Nat Commun 7, 13096, doi:10.1038/ncomms13096 (2016).

116 Lindemans, C. A. et al. Interleukin-22 promotes intestinal-stem-cell-mediated epithelial regeneration. Nature 528, 560-564, doi:10.1038/nature16460 (2015).

117 Aurora, A. B. & Olson, E. N. Immune modulation of stem cells and regeneration. Cell stem cell 15, 14-25, doi:10.1016/j.stem.2014.06.009 (2014).

118 Burzyn, D. et al. A special population of regulatory T cells potentiates muscle repair. Cell 155, 1282-1295, doi:10.1016/j.cell.2013.10.054 (2013).

119 Stappenbeck, T. S. & Miyoshi, H. The role of stromal stem cells in tissue regeneration and wound repair. Science 324, 1666-1669, doi:10.1126/science.1172687 (2009).

120 Griffin, A. J. & McSorley, S. J. Development of protective immunity to Salmonella, a mucosal pathogen with a systemic agenda. Mucosal Immunol 4, 371-382, doi:10.1038/mi.2011.2 (2011).

121 Pashine, A., John, B., Rath, S., George, A. & Bal, V. Th1 dominance in the immune response to live Salmonella typhimurium requires bacterial invasiveness but not persistence. Int Immunol 11, 481-489 (1999).

122 Sokol, C. L. et al. Basophils function as antigen-presenting cells for an allergen-induced T helper type 2 response. Nat Immunol 10, 713-720, doi:10.1038/ni.1738 (2009).

123 Nozaki, K. et al. Co-culture with intestinal epithelial organoids allows efficient expansion and motility analysis of intraepithelial lymphocytes. J Gastroenterol 51, 206-213, doi:10.1007/s00535-016-1170-8 (2016).

124 Jager, A., Dardalhon, V., Sobel, R. A., Bettelli, E. & Kuchroo, V. K. Th1, Th17, and Th9 effector cells induce experimental autoimmune encephalomyelitis with different pathological phenotypes. J Immunol 183, 7169-7177, doi:10.4049/jimmunol.0901906 (2009).

125 Sato, T. & Clevers, H. Growing self-organizing mini-guts from a single intestinal stem cell: mechanism and applications. Science 340, 1190-1194, doi:10.1126/science.1234852 (2013).

126 Farin, H. F. et al. Paneth cell extrusion and release of antimicrobial products is directly controlled by immune cell-derived IFN-gamma. J Exp Med 211, 1393-1405, doi:10.1084/jem.20130753 (2014).

127 Cordier, A. C. & Haumont, S. M. Development of thymus, parathyroids, and ultimo-branchial bodies in NMRI and nude mice. The American journal of anatomy 157, 227-263, doi:10.1002/aja.1001570303 (1980).

128 Mombaerts, P. et al. Mutations in T-cell antigen receptor genes alpha and beta block thymocyte development at different stages. Nature 360, 225-231, doi:10.1038/360225a0 (1992).

129 Kim, J. M., Rasmussen, J. P. & Rudensky, A. Y. Regulatory T cells prevent catastrophic autoimmunity throughout the lifespan of mice. Nat Immunol 8, 191-197, doi:10.1038/ni1428 (2007).

130 Liberzon, A. et al. Molecular signatures database (MSigDB) 3.0. Bioinformatics 27, 1739-1740, doi:10.1093/bioinformatics/btr260 (2011).

131 Ali, N. et al. Regulatory T Cells in Skin Facilitate Epithelial Stem Cell Differentiation. Cell 169, 1119-1129 e1111, doi:10.1016/j.cell.2017.05.002 (2017).

132 Hashimoto, K., Joshi, S. K. & Koni, P. A. A conditional null allele of the major histocompatibility IA-beta chain gene. Genesis 32, 152-153 (2002).

133 el Marjou, F. et al. Tissue-specific and inducible Cre-mediated recombination in the gut epithelium. Genesis 39, 186-193, doi:10.1002/gene.20042 (2004).

134 Ivanov, I I et al. Induction of intestinal Th17 cells by segmented filamentous bacteria. Cell 139, 485-498, doi:10.1016/j.cell.2009.09.033 (2009).

135 Tanoue, T., Atarashi, K. & Honda, K. Development and maintenance of intestinal regulatory T cells. Nature reviews. Immunology 16, 295-309, doi:10.1038/nri.2016.36 (2016).

136 Ritsma, L. et al. Intestinal crypt homeostasis revealed at single-stem-cell level by in vivo live imaging. Nature 507, 362-365, doi:10.1038/nature12972 (2014).

137 Snippert, H. J. et al. Intestinal crypt homeostasis results from neutral competition between symmetrically dividing Lgr5 stem cells. Cell 143, 134-144, doi:10.1016/j.cell.2010.09.016 (2010).

138 Buczacki, S. J. A. et al. Intestinal label-retaining cells are secretory precursors expressing Lgr5. Nature 495, 65-69, doi:10.1038/nature11965 (2013).

139 Sangiorgi, E. & Capecchi, M. R. Bmi1 is expressed in vivo in intestinal stem cells. Nature Genetics 40, 915-920, doi:10.1038/ng.165 (2008).

140 Shalek, A. K. et al. Single-cell RNA-seq reveals dynamic paracrine control of cellular variation [Supplementary Information]. Nature, 1-28, doi:10.1038/nature13437 (2014).

141 Su, L. et al. Coinfection with an intestinal helminth impairs host innate immunity against Salmonella enterica serovar Typhimurium and exacerbates intestinal inflammation in mice. Infect Immun 82, 3855-3866, doi:10.1128/IAI.02023-14 (2014).

142 Matsumoto, T. et al. Retinol Promotes In Vitro Growth of Proximal Colon Organoids through a Retinoic Acid-Independent Mechanism. PLoS One 11, e0162049, doi:10.1371/journal.pone.0162049 (2016).

143 Iwata, M. et al. Retinoic acid imprints gut-homing specificity on T cells. Immunity 21, 527-538, doi:10.1016/j.immuni.2004.08.011 (2004).

144 Esplugues, E. et al. Control of TH17 cells occurs in the small intestine. Nature 475, 514-518, doi:10.1038/nature10228 (2011).

145 Barriga, F. M. et al. Mex3a Marks a Slowly Dividing Subpopulation of Lgr5+Intestinal Stem Cells. Cell Stem Cell 20, 801-816 e807, doi:10.1016/j.stem.2017.02.007 (2017).

146 Worthington, J. J., Reimann, F. & Gribble, F. M. Enteroendocrine cells-sensory sentinels of the intestinal environment and orchestrators of mucosal immunity. Mucosal immunology, doi:10.1038/mi.2017.73 (2017).

147 Yan, K. S. et al. Intestinal Enteroendocrine Lineage Cells Possess Homeostatic and Injury-Inducible Stem Cell Activity. CellStem Cell21, 78-90 e76, doi:10.1016/j.stem.2017.06.014 (2017).

148 Gerbe, F. & Jay, P. Intestinal tuft cells: epithelial sentinels linking luminal cues to the immune system. Mucosal immunology 9, 1353-1359, doi:10.1038/mi.2016.68 (2016).

149 van der Flier, L. G., and Clevers, H. (2009). Stem cells, self-renewal, and differentiation in the intestinal epithelium. Annu Rev Physiol 71, 241-260.

150 Lei, N.Y., Jabaji, Z., Wang, J., Joshi, V. S., Brinkley, G. J., Khalil, H., Wang, F., Jaroszewicz, A., Pellegrini, M., Li, L., et al. (2014). Intestinal subepithelial myofibroblasts support the growth of intestinal epithelial stem cells. PLoS One 9, e84651.

151 Shale, M., Schiering, C., and Powrie, F. (2013). CD4(+) T-cell subsets in intestinal inflammation. Immunol Rev 252, 164-182.

152 Dombrowski, Y., O'Hagan, T., Dittmer, M., Penalva, R., Mayoral, S. R., Bankhead, P., Fleville, S., Eleftheriadis, G., Zhao, C., Naughton, M., et al. (2017). Regulatory T cells promote myelin regeneration in the central nervous system. Nat Neurosci 20, 674-680.

153 Arpaia, N., Green, J. A., Moltedo, B., Arvey, A., Hemmers, S., Yuan, S., Treuting, P. M., and Rudensky, A.Y. (2015). A Distinct Function of Regulatory T Cells in Tissue Protection. Cell 162, 1078-1089.

154. Ali, N., Zirak, B., Rodriguez, R. S., Pauli, M. L., Truong, H. A., Lai, K., Ahn, R., Corbin, K., Lowe, M. M., Scharschmidt, T. C., et al. (2017). Regulatory T Cells in Skin Facilitate Epithelial Stem Cell Differentiation. Cell 169, 1119-1129 e1111.

155. Kaser, A., Lee, A. H., Franke, A., Glickman, J. N., Zeissig, S., Tilg, H., Nieuwenhuis, E. E., Higgins, D. E., Schreiber, S., Glimcher, L. H., et al. (2008). XBP1 links ER stress to intestinal inflammation and confers genetic risk for human inflammatory bowel disease. Cell 134, 743-756.

156. Strober, W., and Ehrhardt, R. O. (1993). Chronic intestinal inflammation: an unexpected outcome in cytokine or T cell receptor mutant mice. Cell 75, 203-205.

157. Mombaerts, P., Mizoguchi, E., Grusby, M. J., Glimcher, L. H., Bhan, A. K., and Tonegawa, S. (1993). Spontaneous development of inflammatory bowel disease in T cell receptor mutant mice. Cell 75, 274-282.

158. Ramilowski, J. A., Goldberg, T., Harshbarger, J., Kloppmann, E., Lizio, M., Satagopam, V. P., Itoh, M., Kawaji, H., Carninci, P., Rost, B., et al. (2015). A draft network of ligand-receptor-mediated multicellular signalling in human. Nat Commun 6, 7866.

159. Beyaz, S., Mana, M. D., Roper, J., Kedrin, D., Saadatpour, A., Hong, S. J., Bauer-Rowe, K. E., Xifaras, M. E., Akkad, A., Arias, E., et al. (2016). High-fat diet enhances stemness and tumorigenicity of intestinal progenitors. Nature 531, 53-58.

160. Grun, D., Lyubimova, A., Kester, L., Wiebrands, K., Basak, O., Sasaki, N., Clevers, H., and van Oudenaarden, A. (2015). Single-cell messenger RNA sequencing reveals rare intestinal cell types. Nature, 1-23.

161 Erichson N. Benjamin, V. S., Brunton Steven L., Kutz J. Nathan (2016). Randomized Matrix Decompositions using R. arXiv preprint.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of modulating intestinal epithelial cell composition in an intestinal organoid culture comprising intestinal epithelial cells, the method comprising:
co-culturing the intestinal organoid with Th1, Th2, Th17, or regulatory T (Treg) cells in an amount sufficient to modify the intestinal epithelial cell composition, whereby the Th1, Th2, Th17, or Treg cells directly influence intestinal epithelial cell proliferation, differentiation, and/or maintenance; and
detecting intestinal epithelial cells after co-culturing the intestinal organoid culture with Th1, Th2, Th17, or regulatory T (Treg) cells, whereby the intestinal epithelial cell composition is monitored, and wherein detecting intestinal epithelial cells comprises performing single cell RNA-seq (scRNA-seq) on the intestinal organoid culture.

2. The method of claim 1, wherein the Th1, Th2, Th17, or Treg cells are added to the intestinal organoid culture in a ratio of 20 Th1, Th2, Th17, or Treg cells to each organoid in an intestinal organoid culture.

3. A method of modulating intestinal epithelial cell composition in an intestinal organoid culture comprising intestinal epithelial cells, the method comprising:
co-culturing the intestinal organoid with Th1 cells in an amount sufficient to modify the intestinal epithelial cell composition, whereby the Th1 cells directly influence intestinal epithelial cell proliferation, differentiation, and/or maintenance,
wherein expression of one or more anti-microbial peptides selected from the group consisting of Defa17, Defa24, Lyz1, Itln1, Mmp7, and Ang4 is increased in the intestinal organoid culture as compared to control organoids.

4. The method of claim 3, wherein tuft cells are decreased in the intestinal organoid culture as compared to control organoids.

5. The method of claim 3, wherein Paneth cells are increased in the intestinal organoid culture as compared to control organoids.

6. The method of claim 3, wherein the Th1 cells are added to the intestinal organoid culture in a ratio of 20 Th1 cells to each organoid in an intestinal organoid culture.

7. The method of claim 3, further comprising detecting intestinal epithelial cells after co-culturing the intestinal organoid culture with Th1 cells, wherein detecting intestinal epithelial cells comprises performing single cell RNA-seq (scRNA-seq) on the intestinal organoid culture.

8. A method of modulating intestinal epithelial cell composition in an intestinal organoid culture comprising intestinal epithelial cells, the method comprising:
co-culturing the intestinal organoid with Th1, Th2, or Th17 cells in an amount sufficient to modify the intestinal epithelial cell composition, whereby the Th1, Th2, or Th17 cells directly influence intestinal epithelial cell proliferation, differentiation, and/or maintenance,
wherein transit amplifying (TA) cells are increased in the intestinal organoid culture as compared to control organoids.

9. The method of claim 8, wherein stem cell markers selected from the group consisting of Lgr5, Ascl2 and Smoc2 are down-regulated in the intestinal organoid culture as compared to control organoids.

10. The method of claim 8, wherein the Th1, Th2, or Th17 cells are added to the intestinal organoid culture in a ratio of 20 Th1, Th2, or Th17 cells to each organoid in an intestinal organoid culture.

11. The method of claim 8, further comprising detecting intestinal epithelial cells after co-culturing the intestinal organoid culture with Th1, Th2, or Th17 cells, wherein detecting intestinal epithelial cells comprises performing single cell RNA-seq (scRNA-seq) on the intestinal organoid culture.

12. A method of modulating intestinal epithelial cell composition in an intestinal organoid culture comprising intestinal epithelial cells, the method comprising:
co-culturing the intestinal organoid with regulatory T (Treg) cells in an amount sufficient to modify the intestinal epithelial cell composition, whereby the regulatory T (Treg) cells directly influence intestinal epithelial cell proliferation, differentiation, and/or maintenance,
wherein stem cell genes selected from the group consisting of Soat1, Pdgfa and Glrx are increased in the intestinal organoid culture as compared to control organoids.

13. The method of claim 12, wherein stem cells are increased in the intestinal organoid culture as compared to control organoids.

14. The method of claim 12, wherein the Treg cells are added to the intestinal organoid culture in a ratio of 20 Treg cells to each organoid in an intestinal organoid culture.

15. The method of claim 12, further comprising detecting intestinal epithelial cells after co-culturing the intestinal organoid culture with Treg cells, wherein detecting intestinal epithelial cells comprises performing single cell RNA-seq (scRNA-seq) on the intestinal organoid culture.

16. A method of modulating intestinal epithelial cell composition in an intestinal organoid culture comprising intestinal epithelial cells, the method comprising:
co-culturing the intestinal organoid with Th2 cells in an amount sufficient to modify the intestinal epithelial cell composition, whereby the Th2 cells directly influence intestinal epithelial cell proliferation, differentiation, and/or maintenance,
Paneth cell gene expression is decreased in the intestinal organoid culture as compared to control organoids.

17. The method of claim 16, wherein the Th2 cells are added to the intestinal organoid culture in a ratio of 20 Th2 cells to each organoid in an intestinal organoid culture.

18. The method of claim 16, further comprising detecting intestinal epithelial cells after co-culturing the intestinal organoid culture with Th2 cells, wherein detecting intestinal epithelial cells comprises performing single cell RNA-seq (scRNA-seq) on the intestinal organoid culture.

* * * * *